US011773085B2

United States Patent
Zhou et al.

(10) Patent No.: US 11,773,085 B2
(45) Date of Patent: Oct. 3, 2023

(54) METHODS AND COMPOUNDS FOR TREATING DISORDERS

(71) Applicant: Foghorn Therapeutics Inc., Cambridge, MA (US)

(72) Inventors: Qianhe Zhou, Winchester, MA (US); Michael Bocker, Cambridge, MA (US); David Simon Millan, Stow, MA (US); Ho Man Chan, Carlisle, MA (US); Luis Soares, Cambridge, MA (US); Matthew Russell Netherton, Cambridge, MA (US); Sabine K. Ruppel, Cambridge, MA (US); Zhaoxia Yang, Belmont, MA (US); Jason T. Lowe, East Bridgewater, MA (US); Francois Brucelle, Belmont, MA (US)

(73) Assignee: Foghorn Therapeutics Inc., Cambridge, MA (US)

( * ) Notice: Subject to any disclaimer, the term of this patent is extended or adjusted under 35 U.S.C. 154(b) by 14 days.

(21) Appl. No.: 16/942,021

(22) Filed: Jul. 29, 2020

(65) Prior Publication Data
US 2021/0009568 A1    Jan. 14, 2021

Related U.S. Application Data

(63) Continuation of application No. PCT/US2019/015733, filed on Jan. 29, 2019.

(60) Provisional application No. 62/688,309, filed on Jun. 21, 2018, provisional application No. 62/653,285, filed on Apr. 5, 2018, provisional application No. 62/623,845, filed on Jan. 30, 2018.

(51) Int. Cl.
| | | |
|---|---|---|
| *A61P 35/00* | (2006.01) | |
| *A61K 31/551* | (2006.01) | |
| *C07D 519/00* | (2006.01) | |
| *C07D 403/14* | (2006.01) | |
| *A61K 9/16* | (2006.01) | |
| *A61K 45/06* | (2006.01) | |

(52) U.S. Cl.
CPC .......... *C07D 403/14* (2013.01); *A61K 9/1605* (2013.01); *A61K 45/06* (2013.01); *A61P 35/00* (2018.01)

(58) Field of Classification Search
CPC ...... A61P 35/00; A61K 31/551; C07D 519/00
See application file for complete search history.

(56) References Cited

U.S. PATENT DOCUMENTS

| | | |
|---|---|---|
| 5,858,358 A | 1/1999 | June et al. |
| 5,883,223 A | 3/1999 | Gray |
| 6,352,694 B1 | 3/2002 | June et al. |
| 6,534,055 B1 | 3/2003 | June et al. |
| 6,692,964 B1 | 2/2004 | June et al. |
| 6,797,514 B2 | 9/2004 | Berenson et al. |
| 6,867,041 B2 | 3/2005 | Berenson et al. |
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |
| 7,056,883 B2 | 6/2006 | Ito et al. |
| 7,067,318 B2 | 6/2006 | June et al. |
| 7,144,575 B2 | 12/2006 | June et al. |
| 7,172,869 B2 | 2/2007 | June et al. |
| 7,175,843 B2 | 2/2007 | June et al. |
| 7,205,103 B2 | 4/2007 | Emerson |
| 7,232,566 B2 | 6/2007 | June et al. |
| 9,271,978 B2 | 3/2016 | Liu et al. |
| 9,410,943 B2 | 8/2016 | Kadoch et al. |
| 10,105,420 B2 | 10/2018 | Kadoch et al. |
| 10,646,575 B2 | 5/2020 | Phillips et al. |
| 10,660,968 B2 | 5/2020 | Phillips et al. |
| 10,849,982 B2 | 12/2020 | Phillips et al. |
| 10,905,768 B1 | 2/2021 | Phillips et al. |
| 11,185,592 B2 | 11/2021 | Phillips et al. |
| 2005/0079512 A1 | 4/2005 | Emerson et al. |
| 2006/0121005 A1 | 6/2006 | Berenson et al. |
| 2011/0061116 A1 | 3/2011 | Haldar et al. |
| 2016/0058872 A1 | 3/2016 | Crew et al. |
| 2017/0014491 A1 | 1/2017 | Kadoch et al. |
| 2017/0050968 A1 | 2/2017 | Bennett et al. |
| 2017/0158709 A1 | 6/2017 | Boloor |
| 2018/0044335 A1 | 2/2018 | Martin et al. |
| 2018/0085465 A1 | 3/2018 | Bradner et al. |
| 2018/0187614 A1 | 7/2018 | Dudar |
| 2018/0213422 A1 | 7/2018 | Kazmi et al. |
| 2018/0215766 A1 | 8/2018 | Bair et al. |
| 2018/0215866 A1 | 8/2018 | Zhao et al. |
| 2019/0076539 A1 | 3/2019 | Phillips et al. |
| 2020/0140456 A1 | 5/2020 | Phillips et al. |

(Continued)

FOREIGN PATENT DOCUMENTS

| | | |
|---|---|---|
| CN | 108690020 A | 10/2018 |
| WO | WO-2017/197051 A1 | 11/2017 |

(Continued)

OTHER PUBLICATIONS

Crawford et al., "Inhibition of bromodomain-containing protein 9 for the prevention of epigenetically-defined drug resistance," Bioorg Med Chem Lett. 27(15):3534-41(2017).

(Continued)

*Primary Examiner* — Bruck Kifle

(74) *Attorney, Agent, or Firm* — Clark & Elbing LLP

(57) ABSTRACT

The present invention relates to methods and compositions for the treatment of BAF-related disorders such as cancers and viral infections.

4 Claims, 14 Drawing Sheets

Specification includes a Sequence Listing.

(56) References Cited

U.S. PATENT DOCUMENTS

| | | | |
|---|---|---|---|
| 2020/0206344 A1 | 7/2020 | Kadoch et al. | |
| 2021/0009568 A1 | 1/2021 | Zhou et al. | |
| 2021/0198256 A1 | 7/2021 | Nasveschuk et al. | |

FOREIGN PATENT DOCUMENTS

| | | |
|---|---|---|
| WO | WO-2017/197056 A1 | 11/2017 |
| WO | WO-2017/223452 A1 | 12/2017 |
| WO | WO-2018/177297 A1 | 10/2018 |
| WO | WO-2019/099868 A2 | 5/2019 |
| WO | WO-2020/051235 A1 | 3/2020 |
| WO | WO-2020/132561 A1 | 6/2020 |
| WO | WO-2020/160192 A1 | 8/2020 |
| WO | WO-2021/055295 A1 | 3/2021 |
| WO | WO-2021/178920 A1 | 9/2021 |

OTHER PUBLICATIONS

Hay et al., "Design and synthesis of potent and selective inhibitors of BRD7 and BRD9 bromodomains," Medchemcomm. 6:1381-86 (2015).

International Search Report and Written Opinion for International Patent Application No. PCT/US2019/015733, dated Jul. 1, 2019 (17 pages).

Kadoch et al., "Mammalian SWI/SNF chromatin remodeling complexes and cancer: Mechanistic insights gained from human genomics," Sci Adv. 1(5):e1500447 (2015) (17 pages).

Kadoch et al., "Proteomic and bioinformatic analysis of mammalian SWI/SNF complexes identifies extensive roles in human malignancy," Nat Genet. 45(6):592-601. (2013) (11 pages).

Martin et al., "Structure-Based Design of an in Vivo Active Selective BRD9 Inhibitor," J Med Chem. 59(10):4462-75 (2016).

Pan et al., "A major chromatin regulator determines resistance of tumor cells to T cell-mediated killing," Science. 359(6377):770-75 (2018) (11 pages).

Picaud et al., "9H-purine scaffold reveals induced-fit pocket plasticity of the BRD9 bromodomain," J Med Chem. 58(6):2718-36(2015).

Remillard et al., "Degradation of the BAF Complex Factor BRD9 by Heterobifunctional Ligands," Angew Chem Int Ed Engl. 56(21):5738-43 (2017) (7 pages).

Theodoulou et al., "Discovery of I-BRD9, a Selective Cell Active Chemical Probe for Bromodomain Containing Protein 9 Inhibition," J Med Chem. 59(4):1425-39 (2015).

Vangamudi et al., "The SMARCA2/4 ATPase Domain Surpasses the Bromodomain as a Drug Target in SWI/SNF-Mutant Cancers: Insights from cDNA Rescue and PFI-3 Inhibitor Studies," Cancer Res. 75(18):3865-78 (2015).

Zoppi et al., "Iterative Design and Optimization of Initially Inactive Proteolysis Targeting Chimeras (PROTACs) Identify VZ185 as a Potent, Fast, and Selective von Hippel-Lindau (VHL) Based Dual Degrader Probe of BRD9 and BRD7," J Med Chem. 62(2):699-726 (2019).

Kadoch et al, "Reversible Disruption of mSWI/SNF (BAF) Complexes by the SS18-SSX Oncogenic Fusion in Synovial Sarcoma" Cell 153:71-85 (2013).

Michael et al., "Abstract PR15: BRD9 defines a novel mammalian SWI/SNF (BAF) complex configuration which supports proliferation in AML.," Clin Cancer Res. 23(24): (2017).

McBride et al., "Disruption of mammalian SWI/SNF and polycomb complexes in human sarcomas: mechanisms and therapeutic opportunities." J Pathol. 244(5): 638-649 (2018).

Hohmann et al., "AF et al. Sensitivity and engineered resistance of myeloid leukemia cells to BRD9 inhibition.," Nat Cherm Biol. 12(9): 672-679 (2016).

Martin et al., "Structure-Based Design of an in Vivo Active Selective BRD9 Inhibitor," J Med Chem. 59(10):4462-4475 (2016).

Communication Pursuant to Rule 164(1) for European Patent Application 19746772.3, dated Oct. 7, 2021 (13 pages).

Extended European Search Report for European Application No. 19746772.3, dated Feb. 7, 2022 (15 pages).

International Search Report and Written Opinion for PCT/US2020/015746, dated May 18, 2020 (11 pages).

Remillard et al., "Degradation of the BAF Complex Factor BRD9 by Heterobifunctional Ligands," Angew Chem Int Ed Engl. 56(21 ):5738-5743 (2017) (14 pages).

Teuscher et al., "A Versatile Method to Determine the Cellular Bioavailability of Small-Molecule Inhibitors," J Med Chem. 60(1): 157-169 (2017).

Wang et al., "NMR Fragment Screening Hit Induces Plasticity of BRD7/9 Bromodomains," Chembiochem. 17(15):1456-63 (2016).

SYO1

HS-SY-II

ASKA

RD

HCT116

Calu6

METHODS AND COMPOUNDS FOR TREATING DISORDERS

BACKGROUND

Disorders can be affected by the BAF complex. BRD9 is a component of the BAF complex. The present invention relates to useful methods and compositions for the treatment of BAF-related disorders, such as cancer and infection.

SEQUENCE LISTING

The instant application contains a Sequence Listing which has been submitted electronically in ASCII format and is hereby incorporated by reference in its entirety. Said ASCII copy, created on Apr. 24, 2023, is named "51121-013004_Sequence_Listing_4_24_23_ST25" and is 99,535 bytes in size.

SUMMARY OF THE INVENTION

Bromodomain-containing protein 9 (BRD9) is a protein encoded by the BRD9 gene on chromosome 5. BRD9 is a component of the BAF (BRG1- or BRM-associated factors) complex, a SWI/SNF ATPase chromatin remodeling complex, and belongs to family IV of the bromodomain-containing proteins. BRD9 is present in several SWI/SNF ATPase chromatin remodeling complexes and is upregulated in multiple cancer cell lines. Accordingly, agents which reduce the levels and/or activity of BRD9 may provide new methods for the treatment of disease and disorders, such as cancer. The inventors have found that depleting BRD9 in cells results in the depletion of the SS18-SSX fusion protein in those cells. The SS18-SSX fusion protein has been detected in more than 95% of synovial sarcoma tumors and is often the only cytogenetic abnormality in synovial sarcoma. Thus, agents that degrade BRD9, e.g., antibodies, enzymes, polynucleotides, and compounds, are useful in the treatment of cancers related to BRD9 or SS18-SSX expression such as soft tissue sarcomas, e.g., synovial sarcoma.

The present disclosure features useful methods to treat cancer, e.g., in a subject in need thereof. In some embodiments, the methods described herein are useful in the treatment of disorders associated with BRD9 expression, e.g., adult soft tissue sarcomas. In some embodiments, the methods described herein are useful in the treatment of disorders associated with SS18-SSX fusion protein.

In one aspect, the invention features a method of treating adult soft tissue sarcoma in a subject in need thereof, the method including administering to the subject an effective amount of an agent that reduces the level and/or activity of BRD9 in the sarcoma.

In another aspect, the invention features a method of treating adult soft tissue sarcoma in a subject in need thereof, the method including administering to the subject an effective amount of an agent that reduces the level and/or activity of a BAF complex (e.g., GBAF) in the sarcoma.

In another aspect, the invention features a method of reducing tumor growth of an adult soft tissue sarcoma in a subject in need thereof, the method including administering to the subject an effective amount of an agent that reduces the level and/or activity of BRD9 in the tumor.

In another aspect, the invention features a method of inducing apoptosis in an adult soft tissue sarcoma cell, the method including contacting the cell with an effective amount of an agent that reduces the level and/or activity of BRD9 in the cell.

In another aspect, the invention features a method of reducing the level of BRD9 in an adult soft tissue sarcoma cell, the method including contacting the cell with an effective amount of an agent that reduces the level and/or activity of BRD9 in the cell.

In some embodiments of any of the above aspects, the adult soft tissue sarcoma cell is in a subject. In some embodiments, the subject or cell has been identified as expressing SS18-SSX fusion protein or BRD9 fusion protein.

In another aspect, the invention features a method of modulating the level of an SS18-SSX fusion protein, SS18 wild-type protein, or SSX wild-type protein in a cell or subject, the method including contacting the cell with an effective amount of an agent that reduces the level and/or activity of BRD9 in a cell or subject. In some embodiments, the cell is in a subject.

In another aspect, the invention features a method of treating a disorder related to an SS18-SSX fusion protein, SS18 wild-type protein, or SSX wild-type protein in a subject in need thereof, the method including administering to the subject an effective amount of an agent that reduces the level and/or activity of BRD9 in an SS18-SSX fusion protein-expressing cell in the subject.

In some embodiments of any of the above aspects, the effective amount of the agent reduces the level and/or activity of BRD9 by at least 5% (e.g., 6%, 7%, 8%, 8%, 10%, 15%, 20%, 25%, 30%, 35%, 40%, 45%, 50%, 55%, 60%, 65%, 70%, 75%, 80%, 85%, 90%, or 95%) as compared to a reference. In some embodiments, the effective amount of the agent that reduces the level and/or activity of BRD9 by at least 50% (e.g., 55%, 60%, 65%, 70%, 75%, 80%, 85%, 90%, or 95%) as compared to a reference. In some embodiments, the effective amount of the agent that reduces the level and/or activity of BRD9 by at least 90% (e.g., 91%, 92%, 93%, 94%, 95%, 96%, 97%, 98%, or 99%).

In some embodiments, the effective amount of the agent reduces the level and/or activity of BRD9 by at least 5% (e.g., 6%, 7%, 8%, 8%, 10%, 15%, 20%, 25%, 30%, 35%, 40%, 45%, 50%, 55%, 60%, 65%, 70%, 75%, 80%, 85%, 90%, or 95%) as compared to a reference for at least 12 hours (e.g., 14 hours, 16 hours, 18 hours, 20 hours, 22 hours, 24 hours, 30 hours, 36 hours, 48 hours, 72 hours, or more). In some embodiments, the effective amount of the agent that reduces the level and/or activity of BRD9 by at least 5% (e.g., 6%, 7%, 8%, 8%, 10%, 15%, 20%, 25%, 30%, 35%, 40%, 45%, 50%, 55%, 60%, 65%, 70%, 75%, 80%, 85%, 90%, or 95%) as compared to a reference for at least 4 days (e.g., 5 days, 6 days, 7 days, 14 days, 28 days, or more).

In some embodiments, the subject has cancer. In some embodiments, the cancer expresses SS18-SSX fusion protein and/or the cell or subject has been identified as expressing SS18-SSX fusion protein. In some embodiments, the disorder is synovial sarcoma or Ewing's sarcoma. In some embodiments, the disorder is synovial sarcoma.

In one aspect, the invention features a method of modulating the activity of a BAF complex in a cell or subject, the method including contacting the cell with an effective amount of an agent that reduces the level and/or activity of BRD9 in the cell or subject.

In another aspect, the invention features a method of increasing the level of BAF47 in a cell or subject, the method including contacting the cell with an effective amount of an agent that reduces the level and/or activity of BRD9 in the cell or subject.

In one aspect, the invention features a method of decreasing Wnt/β-catenin signaling in a cell or subject, the method including contacting the cell with an effective amount of an agent that reduces the level and/or activity of BRD9 in the cell or subject.

In one aspect, the invention features a method treating a disorder related to BAF47 in a subject in need thereof, the method including administering to the subject an effective amount of an agent that reduces the level and/or activity of BRD9 in the subject.

In some embodiments, the disorder related to BAF47 is a cancer or viral infection. In some embodiments, the cancer is a CD8+ T-cell lymphoma, endometrial carcinoma, ovarian carcinoma, bladder cancer, stomach cancer, pancreatic cancer, esophageal cancer, prostate cancer, renal cell carcinoma, melanoma, or colorectal cancer.

In some embodiments, the viral infection is an infection with a virus of the Retroviridae family, Hepadnaviridae family, Flaviviridae family, Adenoviridae family, Herpesviridae family, Papillomaviridae family, Parvoviridae family, Polyomaviridae family, Paramyxoviridae family, or Togaviridae family.

In an aspect, the invention features a method for treating cancer in a subject in need thereof, the method including administering to the subject an effective amount of an agent that reduces the level and/or activity of BRD9 in a cancer cell, wherein the cancer is a CD8+ T-cell lymphoma, endometrial carcinoma, ovarian carcinoma, bladder cancer, stomach cancer, pancreatic cancer, esophageal cancer, prostate cancer, renal cell carcinoma, melanoma, colorectal cancer, non-small cell lung cancer, stomach cancer, or breast cancer.

In an aspect, the invention features a method of reducing tumor growth of a cancer in a subject in need thereof, the method including administering to the subject an effective amount of an agent that reduces the level and/or activity of BRD9 in a tumor cell, wherein the cancer is a CD8+ T-cell lymphoma, endometrial carcinoma, ovarian carcinoma, bladder cancer, stomach cancer, pancreatic cancer, esophageal cancer, prostate cancer, renal cell carcinoma, melanoma, colorectal cancer, non-small cell lung cancer, stomach cancer, or breast cancer.

In one aspect, the invention features a method of inducing apoptosis in a cancer cell, the method including contacting the cell with an effective amount of an agent that reduces the level and/or activity of BRD9 in the cell, wherein the cancer is a CD8+ T-cell lymphoma, endometrial carcinoma, ovarian carcinoma, bladder cancer, stomach cancer, pancreatic cancer, esophageal cancer, prostate cancer, renal cell carcinoma, melanoma, colorectal cancer, non-small cell lung cancer, stomach cancer, or breast cancer.

In one aspect, the invention features a method of reducing the level of BRD9 in a cancer cell, the method including contacting the cell with an effective amount of an agent that reduces the level and/or activity of BRD9 in the cell, wherein the cancer is a CD8+ T-cell lymphoma, endometrial carcinoma, ovarian carcinoma, bladder cancer, stomach cancer, pancreatic cancer, esophageal cancer, prostate cancer, renal cell carcinoma, melanoma, colorectal cancer, non-small cell lung cancer, stomach cancer, or breast cancer.

In some embodiments of any of the above aspects, the cancer is a CD8+ T-cell lymphoma, endometrial carcinoma, ovarian carcinoma, bladder cancer, stomach cancer, pancreatic cancer, esophageal cancer, prostate cancer, renal cell carcinoma, melanoma, or colorectal cancer. In some embodiments, the cancer is non-small cell lung cancer, stomach cancer, or breast cancer.

In one aspect, the invention features a method of modulating the activity of a BRD9 fusion protein in a cell or subject, the method including contacting the cell with an effective amount of an agent that reduces the level and/or activity of BRD9 in the cell or subject.

In an aspect, the invention features a method of modulating the level of a BRD9 fusion protein in a cell or subject, the method including contacting the cell with an effective amount of an agent that reduces the level and/or activity of BRD9 in the cell or subject. In some embodiments, the cell is in a subject.

In an aspect, the invention features a method of treating a disorder related to a BRD9 fusion protein in a subject in need thereof, the method including administering to the subject an effective amount of an agent that reduces the level and/or activity of BRD9 in a BRD9 fusion protein-expressing cell.

In some embodiments of any of the above aspects, the subject has cancer. In some embodiments, the cancer expresses a BRD9 fusion protein and/or the cell or subject has been identified as expressing a BRD9 fusion protein. In some embodiments, the method further includes administering to the subject or contacting the cell with an anticancer therapy. In some embodiments, the anticancer therapy is a chemotherapeutic or cytotoxic agent or radiotherapy. In some embodiments, the chemotherapeutic or cytotoxic agent is doxorubicin or ifosfamide. In some embodiments, the anticancer therapy and the agent that reduces the level and/or activity of BRD9 in a cell are administered within 28 days of each other and each in an amount that together are effective to treat the subject. In some embodiments, the subject or cancer has been identified as having an elevated level of an SS18-SSX fusion protein or a BRD9 fusion protein as compared to a reference. In some embodiments, the subject or cancer has been identified as having a decreased level of SS18 wild-type protein or SSX wild-type protein as compared to a reference.

In one aspect, the invention features a method of treating a viral infection, the method including administering to the subject an effective amount of an agent that reduces the level and/or activity of BRD9 in a cell of the subject.

In some embodiments, the disorder is a viral infection is an infection with a virus of the Retroviridae family such as the lentiviruses (e.g., Human immunodeficiency virus (HIV) and deltaretroviruses (e.g., human T cell leukemia virus I (HTLV-1), human T cell leukemia virus II (HTLV-II)), Hepadnaviridae family (e.g., hepatitis B virus (HBV)), Flaviviridae family (e.g., hepatitis C virus (HCV)), Adenoviridae family (e.g., Human Adenovirus), Herpesviridae family (e.g., Human cytomegalovirus (HCMV), Epstein-Barr virus, herpes simplex virus 1 (HSV-1), herpes simplex virus 2 (HSV-2), human herpesvirus 6 (HHV-6), Herpesvitus K+, CMV, varicella-zoster virus), Papillomaviridae family (e.g., Human Papillomavirus (HPV, HPV E1)), Parvoviridae family (e.g., Parvovirus B19), Polyomaviridae family (e.g., JC virus and BK virus), Paramyxoviridae family (e.g., Measles virus), Togaviridae family (e.g., Rubella virus). In some embodiments, the disorder is Coffin Siris, Neurofibromatosis (e.g., NF-1, NF-2, or Schwannomatosis), or Multiple Meningioma. In some embodiments, the viral infection is an infection with a virus of the Retroviridae family, Hepadnaviridae family, Flaviviridae family, Adenoviridae family, Herpesviridae family, Papillomaviridae family, Parvoviridae family, Polyomaviridae family, Paramyxoviridae family, or Togaviridae family.

In some embodiments of any of the above aspects, the agent that reduces the level and/or activity of BRD9 in a cell is a small molecule compound, an antibody, an enzyme, and/or a polynucleotide. In some embodiments, the agent that reduces the level and/or activity of BRD9 in a cell is an enzyme. In some embodiments, the enzyme is a clustered regularly interspaced short palindromic repeats (CRISPR)-associated protein, a zinc finger nuclease (ZFN), a transcription activator-like effector nuclease (TALEN), or a meganuclease. In some embodiments, the CRISPR-associated protein is CRISPR-associated protein 9 (Cas9).

In some embodiments of any of the above aspects, the agent that reduces the level and/or activity of BRD9 in a cell is a polynucleotide. In some embodiments, the polynucleotide is an antisense nucleic acid, a short interfering RNA (siRNA), a short hairpin RNA (shRNA), a micro RNA (miRNA), a CRISPR/Cas 9 nucleotide (e.g., a guide RNA (gRNA)), or a ribozyme. In some embodiments, the polynucleotide has a sequence having at least 70% sequence identity (e.g., 70%, 75%, 80%, 85%, 86%, 87%, 88%, 89%, 90%, 91%, 92%, 93%, 94%, 95%, 96%, 97%, 98%, 99%, 99.9% identity, or more) to the nucleic acid sequence of any one of SEQ ID NOs: 3-202. In some embodiments, the polynucleotide has a sequence having at least 70% sequence identity (e.g., 70%, 75%, 80%, 85%, 86%, 87%, 88%, 89%, 90%, 91%, 92%, 93%, 94%, 95%, 96%, 97%, 98%, 99%, 99.9% identity, or more) to the nucleic acid sequence of any one of SEQ ID NOs: 3-139.

In some embodiments of any of the above aspects, the agent that reduces the level and/or activity of BRD9 in a cell is a small molecule compound, or a pharmaceutically acceptable salt thereof.

In some embodiments, the small molecule compound, or a pharmaceutically acceptable salt thereof is a degrader. In some embodiments, the degrader has the structure of Formula I:

A-L-B      Formula I wherein A is a BRD9 binding moiety; L is a linker; and B is a degradation moiety, or a pharmaceutically acceptable salt thereof. In some embodiments, the degradation moiety is a ubiquitin ligase moiety. In some embodiments, the ubiquitin ligase binding moiety includes Cereblon ligands, IAP (Inhibitors of Apoptosis) ligands, mouse double minute 2 homolog (MDM2), hydrophobic tag, or von Hippel-Lindau ligands, or derivatives or analogs thereof.

In some embodiments, the degradation moiety has the structure of Formula A-1:

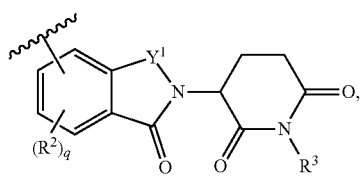

Formula A-1 where Y$^1$ is

each of R$^3$ and R$^4$ is, independently, H, optionally substituted C$_1$-C$_6$ alkyl, or optionally substituted C$_1$-C$_6$ heteroalkyl;

q is 0, 1, 2, 3, or 4; and each R$^2$ is, independently, halogen, optionally substituted C$_1$-C$_6$ alkyl, optionally substituted C$_1$-C$_6$ heteroalkyl, optionally substituted C$_3$-C$_{10}$ carbocyclyl, optionally substituted C$_2$-C$_9$ heterocyclyl, optionally substituted C$_6$-C$_{10}$ aryl, optionally substituted C$_2$-C$_9$ heteroaryl, optionally substituted C$_2$-C$_6$ alkenyl, optionally substituted C$_2$-C$_6$ heteroalkenyl, hydroxyl, thiol, or optionally substituted amino, or a pharmaceutically acceptable salt thereof.

In some embodiments, R$^3$ is H or optionally substituted C$_1$-C$_6$ alkyl.

In some embodiments, R$^3$ is H or CH$_3$. In some embodiments, R$^3$ is H. In some embodiments, R$^3$ is CH$_3$.

In some embodiments, Y$^1$ is

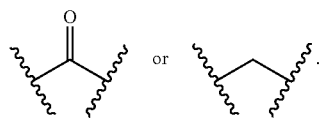

In some embodiments, Y$^1$ is

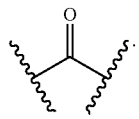

In some embodiments, R$^2$ is, independently, optionally substituted C$_1$-C$_6$ alkyl, optionally substituted C$_1$-C$_6$ heteroalkyl, hydroxyl, or optionally substituted amino.

In some embodiments, q is 0 or 1. In some embodiments, q is 0. In some embodiments, q is 1.

In some embodiments, the degradation moiety has the structure of Formula A-1a:

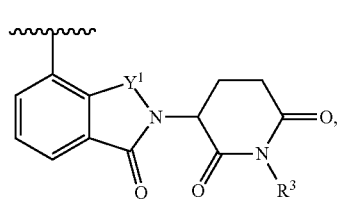

Formula A-1a or a pharmaceutically acceptable salt thereof.

In some embodiments, the degradation moiety has the structure of Formula A-1b:

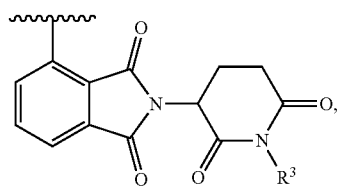

Formula A-1b or a pharmaceutically acceptable salt thereof.

In some embodiments, the degradation moiety has the structure of Formula A-1c:

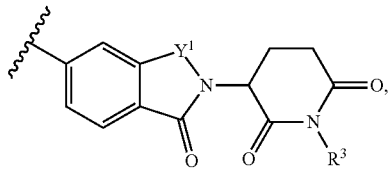

Formula A-1c or a pharmaceutically acceptable salt thereof.

In some embodiments, the degradation moiety has the structure of Formula A-1d:

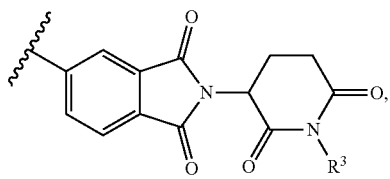

Formula A-1d or a pharmaceutically acceptable salt thereof.

In some embodiments, the degradation moiety has the structure:

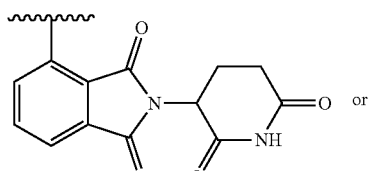

1a or

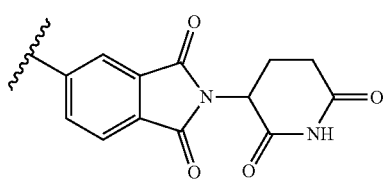

1b or is a derivative or an analog thereof.

In some embodiments, the degradation moiety has the structure of

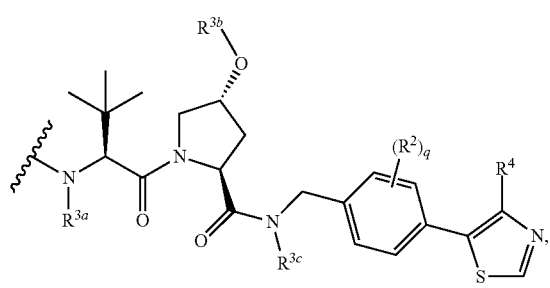

Formula B-1 where
q is 0, 1, 2, 3, or 4;
each $R^2$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxyl, thiol, or optionally substituted amino; each of $R^{3a}$, $R^{3b}$, and $R^{3c}$ is, independently, H, optionally substituted $C_1$-$C_6$ alkyl, or optionally substituted $C_1$-$C_6$ heteroalkyl; and $R^4$ is H, optionally substituted $C_1$-$C_6$ alkyl, or optionally substituted $C_1$-$C_6$ heteroalkyl, or a pharmaceutically acceptable salt thereof.

In some embodiments, each $R^2$ is, independently, optionally substituted $C_1$-$C_6$ alkyl, optionally substituted $C_1$-$C_6$ heteroalkyl, hydroxyl, or optionally substituted amino.

In some embodiments, q is 0 or 1.

In some embodiments, q is 0.

In some embodiments, each of $R^{3a}$, $R^{3b}$, and $R^{3c}$ is, independently, H or optionally substituted $C_1$-$C_6$ alkyl.

In some embodiments, $R^{3a}$ is H. In some embodiments, $R^{3b}$ is H. In some embodiments, $R^{3c}$ is H.

In some embodiments, the degradation moiety has the structure:

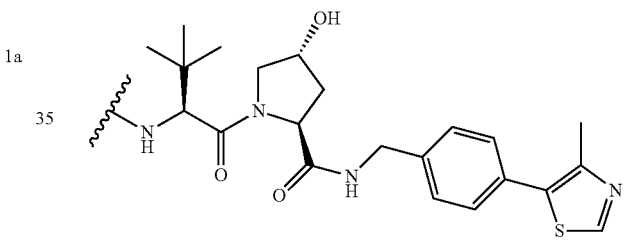

2a or is a derivative or an analog thereof.

In some embodiments, the linker has the structure of Formula II:

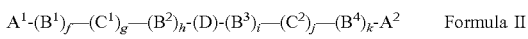

$$A^1-(B^1)_f-(C^1)_g-(B^2)_h-(D)-(B^3)_i-(C^2)_j-(B^4)_k-A^2 \quad \text{Formula II}$$

where
$A^1$ is a bond between the linker and A;
$A^2$ is a bond between B and the linker;
each of $B^1$, $B^2$, $B^3$, and $B^4$ is, independently, optionally substituted $C_1$-$C_2$ alkyl, optionally substituted $C_1$-$C_3$ heteroalkyl, O, S, S(O)$_2$, or NR$^N$;
each $R^N$ is, independently, H, optionally substituted $C_{1-4}$ alkyl, optionally substituted $C_{2-4}$ alkenyl, optionally substituted $C_{2-4}$ alkynyl, optionally substituted $C_{2-6}$ heterocyclyl, optionally substituted $C_{6-12}$ aryl, or optionally substituted $C_{1-7}$ heteroalkyl;
each of $C^1$ and $C^2$ is, independently, carbonyl, thiocarbonyl, sulphonyl, or phosphoryl; each of f, g, h, i, j, and k is, independently, 0 or 1; and
D is optionally substituted $C_{1-10}$ alkyl, optionally substituted $C_{2-10}$ alkenyl, optionally substituted $C_{2-10}$ alkynyl, optionally substituted $C_{2-6}$ heterocyclyl, optionally substituted $C_{6-12}$ aryl, optionally substituted $C_2$-$C_{10}$ polyethylene glycol, or optionally substituted $C_{1-10}$ heteroalkyl, or a chemical bond linking $A^1-(B^1)_f-(C^1)_g-(B^2)_h-$ to $-(B^3)_i-(C^2)_j-(B^4)_k-A^2$.

In some embodiments, each of B¹, B², B³, and B⁴ is, independently, optionally substituted $C_1$-$C_4$ alkyl, optionally substituted $C_1$-$C_4$ heteroalkyl, or $NR^N$.

In some embodiments, each $R^N$ is, independently, H or optionally substituted $C_{1-4}$ alkyl. In some embodiments, each $R^N$ is, independently, H or $CH_3$.

In some embodiments, each of B¹ and B⁴ is, independently,

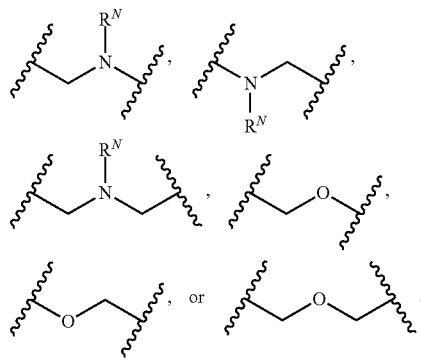

In some embodiments, B¹ is

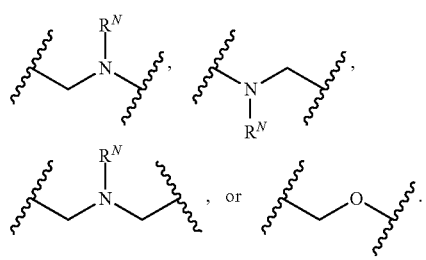

In some embodiments, each of C¹ and C² is, independently,

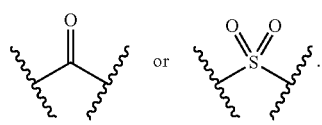

In some embodiments, C¹ is

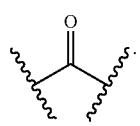 [SMILES: *C(*)=O]

In some embodiments, B² is $NR^N$.

In some embodiments, B² is optionally substituted $C_1$-$C_4$ alkyl.

In some embodiments, f is 0. In some embodiments, f is 1.

In some embodiments, g is 0. In some embodiments, g is 1.

In some embodiments, h is 0. In some embodiments, h is 1.

In some embodiments, i is 0. In some embodiments, i is 1.

In some embodiments, j is 0. In some embodiments, j is 1.

In some embodiments, k is 0. In some embodiments, k is 1.

In some embodiments, the linker has the structure of

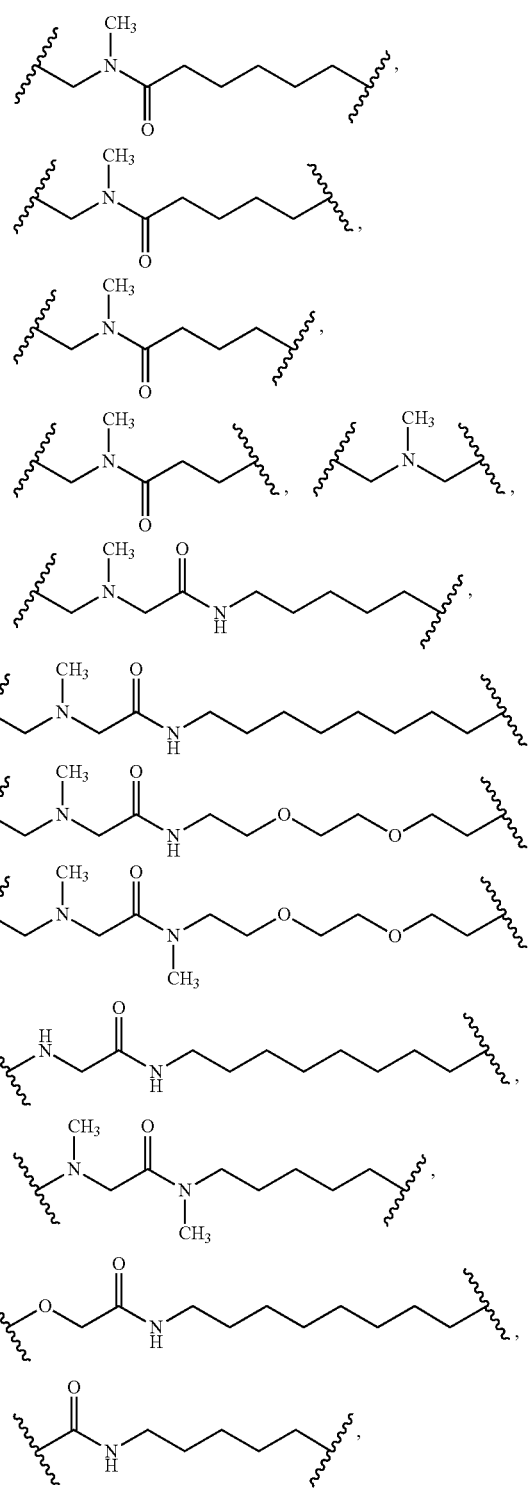

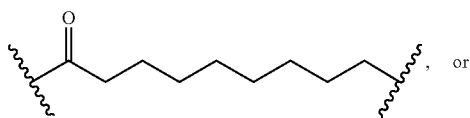, or

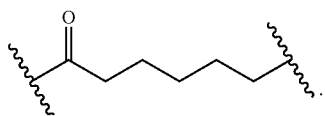.

In some embodiments, the BRD9 binding moiety includes the structure of Formula E-a:

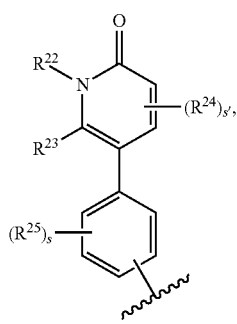

Formula E-a where $R^{22}$ is H, optionally substituted $C_1$-$C_6$ alkyl, or optionally substituted $C_1$-$C_6$ heteroalkyl;

$R^{23}$ is H, halogen, optionally substituted $C_1$-$C_6$ alkyl, or optionally substituted $C_6$-$C_{10}$ aryl;

s' is 0, 1, or 2;

each $R^{24}$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_9$ heteroalkenyl, hydroxyl, thiol, or optionally substituted amino, or two $R^{24}$ combine with the carbon atoms to which they are attached to form an optionally substituted $C_6$-$C_{10}$ aryl or optionally substituted $C_2$-$C_9$ heteroaryl;

s is 0, 1, 2, 3, or 4; and each $R^{25}$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxyl, thiol, or optionally substituted amino, or a pharmaceutically acceptable salt thereof.

In some embodiments, the BRD9 binding moiety includes the structure of Formula E-b:

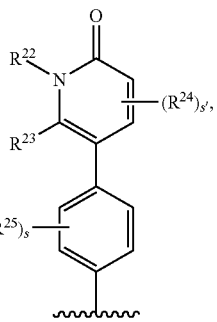

Formula E-b or a pharmaceutically acceptable salt thereof.

In some embodiments, the BRD9 binding moiety includes the structure Formula E-1a:

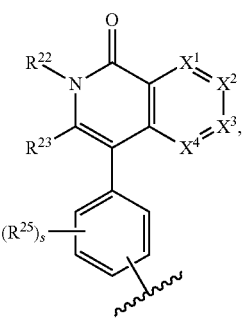

Formula E-1a where $R^{22}$ is H, optionally substituted $C_1$-$C_6$ alkyl, or optionally substituted $C_1$-$C_6$ heteroalkyl;

$R^{23}$ is H, halogen, optionally substituted $C_1$-$C_6$ alkyl, or optionally substituted $C_6$-$C_{10}$ aryl;

s is 0, 1, 2, 3, or 4;

each $R^{25}$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxyl, thiol, or optionally substituted amino;

$X^1$ is N or $CR^{24a}$;

$X^2$ is N or $CR^{24b}$;

$X^3$ is N or $CR^{24c}$;

$X^4$ is N or $CR^{24d}$; and each of $R^{24a}$, $R^{24b}$, $R^{24c}$, and $R^{24d}$ is, independently, H, halogen, hydroxyl, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxyl, thiol, or optionally substituted amino, or a pharmaceutically acceptable salt thereof.

In some embodiments, the BRD9 binding moiety includes the structure of Formula E-1b:

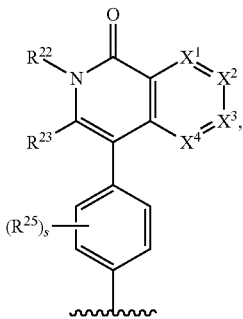

Formula E-1b or a pharmaceutically acceptable salt thereof.

In some embodiments, the BRD9 binding moiety includes the structure of Formula E-2a:

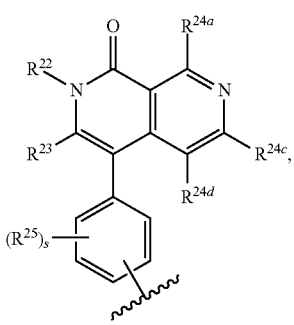

Formula E-2a or a pharmaceutically acceptable salt thereof.

In some embodiments, the BRD9 binding moiety includes the structure of Formula E-2b:

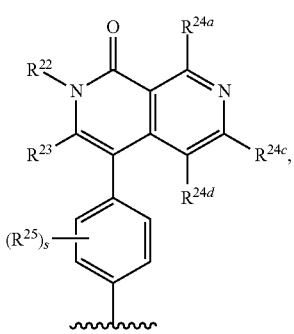

Formula E-2b or a pharmaceutically acceptable salt thereof.

In some embodiments, $R^{22}$ is H, optionally substituted $C_1$-$C_6$ alkyl, or optionally substituted $C_3$-$C_6$ carbocyclyl.

In some embodiments, $R^{22}$ is H or $CH_3$.

In some embodiments, $R^{23}$ is H or optionally substituted $C_1$-$C_6$ alkyl.

In some embodiments, $R^{23}$ is H.

In some embodiments, s is 0, 1, or 2. In some embodiments, s is 1 or 2. In some embodiments, s is 1. In some embodiments, s is 2.

In some embodiments, each $R^{25}$ is, independently, halogen, optionally substituted $C_1$-$C_6$ alkyl, or optionally substituted $C_1$-$C_6$ heteroalkyl.

In some embodiments, each $R^{25}$ is, independently, optionally substituted $C_1$-$C_6$ alkyl or optionally substituted $C_1$-$C_6$ heteroalkyl.

In some embodiments, each $R^{25}$ is, independently, F,

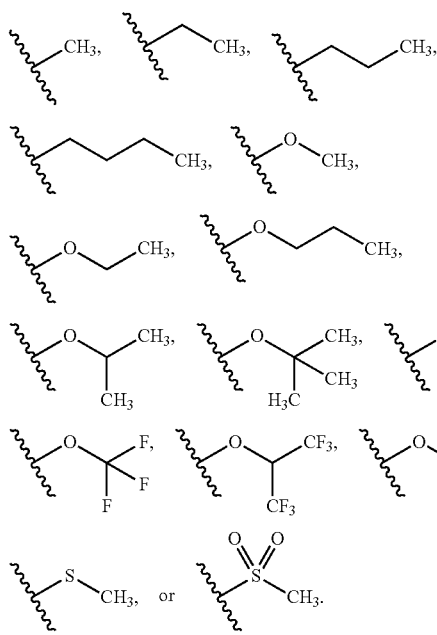

In some embodiments, each $R^{25}$ is, independently,

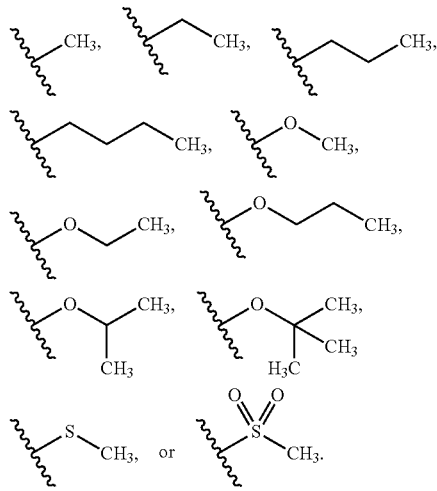

In some embodiments, s' is 1.

In some embodiments, each of $R^{24a}$, $R^{24b}$, $R^{24c}$, and $R^{24d}$ is, independently, optionally substituted $C_1$-$C_6$ alkyl, optionally substituted $C_1$-$C_6$ heteroalkyl, or optionally substituted amino.

In some embodiments, each of $R^{24a}$, $R^{24b}$, $R^{24c}$, and $R^{24d}$ is, independently, —$NH_2$,

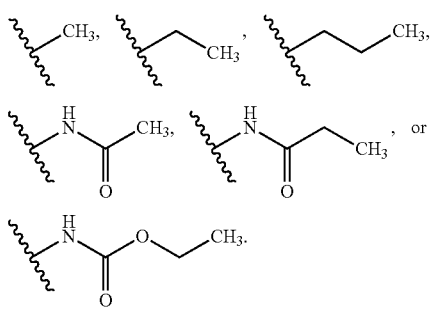

In some embodiments, the BRD9 binding moiety includes the structure of Formula F-a:

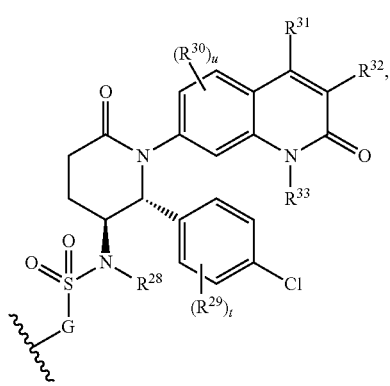

Formula F-a where each of $R^{28}$ and $R^{33}$ is, independently, H, optionally substituted $C_1$-$C_6$ alkyl, or optionally substituted $C_1$-$C_6$ heteroalkyl;

t is 0, 1, 2, 3, or 4;

each $R^{29}$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxyl, thiol, or optionally substituted amino;

u is 0, 1, 2, 3, or 4;

each $R^{30}$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxyl, thiol, or optionally substituted amino;

each of $R^{31}$ and $R^{32}$ is, independently, selected form the group consisting of H, halogen, optionally substituted $C_1$-$C_6$ alkyl, or optionally substituted $C_6$-$C_{10}$ aryl; and G is optionally substituted $C_1$-$C_6$ alkylene, optionally substituted $C_6$-$C_{10}$ arylene, or optionally substituted $C_3$-$C_6$ carbocyclylene, or a pharmaceutically acceptable salt thereof.

In some embodiments, the BRD9 binding moiety includes the structure of Formula G:

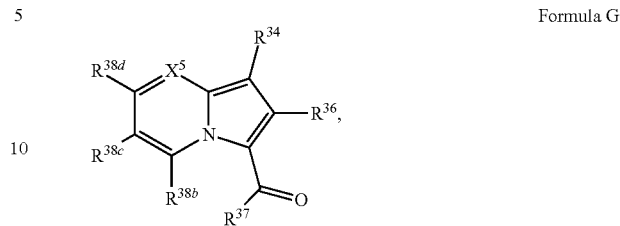

Formula G where $R^{34}$ is optionally substituted $C_6$-$C_{10}$ aryl or $C_2$-$C_9$ heteroaryl;

$R^{36}$ is H, halogen, optionally substituted $C_1$-$C_6$ alkyl, or optionally substituted $C_6$-$C_{10}$ aryl;

$R^{37}$ is H, optionally substituted $C_1$-$C_6$ alkyl, or optionally substituted $C_6$-$C_{10}$ aryl;

$X^5$ is $CR^{38a}$ or N;

each of $R^{38a}$, $R^{38b}$, and $R^{38c}$ is, independently, H, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxyl, thiol, or optionally substituted amino; and $R^{38d}$ is hydrogen or —$NR^{39}R^{40}$; and each of $R^{39}$ and $R^{40}$ is, independently, H, optionally substituted $C_1$-$C_6$ alkyl, or optionally substituted $C_1$-$C_6$ heteroalkyl, or $R^{39}$ and $R^{40}$ combine to form an optionally substituted $C_2$-$C_9$ heterocyclyl, where at least one of $R^{34}$, $R^{39}$, or $R^{40}$ includes a bond to the linker, or a pharmaceutically acceptable salt thereof.

In some embodiments, the BRD9 binding moiety includes the structure of Formula G-1:

Formula G-1 where each of $R^{34a}$, $R^{34b}$, and $R^{34c}$ is, independently, H, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxyl, thiol, or optionally substituted amino;

each $R^{35a}$ and $R^{35b}$ is, independently, H, halogen, optionally substituted $C_1$-$C_6$ alkyl, or optionally substituted $C_6$-$C_{10}$ aryl;

$R^{36}$ is H, halogen, optionally substituted $C_1$-$C_6$ alkyl, or optionally substituted $C_6$-$C_{10}$ aryl;

$R^{37}$ is H, optionally substituted $C_1$-$C_6$ alkyl, or optionally substituted $C_6$-$C_{10}$ aryl;

each $R^{38a}$, $R^{38b}$, and $R^{38c}$ is, independently, H, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxyl, thiol, or optionally substituted amino; and $R^{38d}$ is hydrogen or —$NR^{39}R^{40}$; and each $R^{39}$ and $R^{40}$ is, independently, H, optionally substituted $C_1$-$C_6$ alkyl, or optionally substituted $C_1$-$C_6$ heteroalkyl, or $R^{39}$ and $R^{40}$ combine to form an optionally substituted $C_2$-$C_9$ heterocyclyl, where at least one of $R^{34}$, $R^{39}$, or $R^{40}$ includes a bond to the linker, or a pharmaceutically acceptable salt thereof.

In some embodiments, the BRD9 binding moiety includes the structure of Formula H-a:

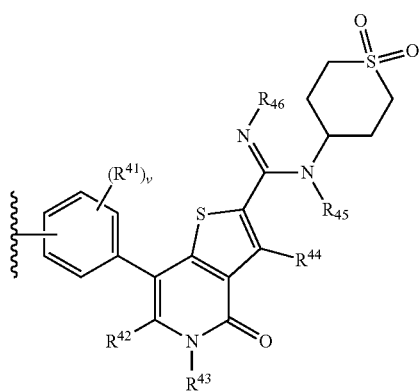

Formula H-a where v is 0, 1, 2, 3, or 4;

each $R^{41}$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxyl, thiol, or optionally substituted amino;

$R^{42}$ is H, halogen, optionally substituted $C_1$-$C_6$ alkyl, or optionally substituted $C_6$-$C_{10}$ aryl;

$R^{44}$ is H, halogen, optionally substituted $C_1$-$C_6$ alkyl, or optionally substituted $C_6$-$C_{10}$ aryl; and each $R^{43}$, $R^{45}$, and $R^{46}$ is, independently, H, optionally substituted $C_1$-$C_6$ alkyl, or optionally substituted $C_1$-$C_6$ heteroalkyl, or a pharmaceutically acceptable salt thereof.

In some embodiments, the BRD9 binding moiety includes the structure of Formula J-a:

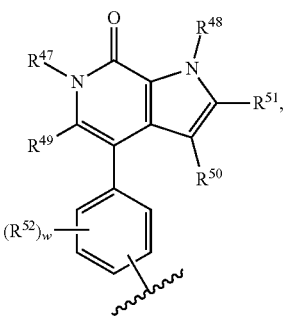

Formula J-a where each of $R^{47}$ and $R^{48}$ is, independently, H, optionally substituted $C_1$-$C_6$ alkyl, or optionally substituted $C_1$-$C_6$ heteroalkyl;

each of $R^{49}$, $R^{50}$, and $R^{51}$ is, independently, H, halogen, optionally substituted $C_1$-$C_6$ alkyl, or optionally substituted $C_6$-$C_{10}$ aryl;

w is 0, 1, 2, 3, or 4; and each $R^{52}$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxyl, thiol, or optionally substituted amino, or a pharmaceutically acceptable salt thereof.

In some embodiments, the BRD9 binding moiety includes the structure of Formula J-b:

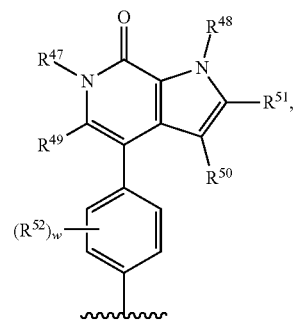

Formula J-b or a pharmaceutically acceptable salt thereof.

In some embodiments, the BRD9 binding moiety includes the structure of Formula E-3:

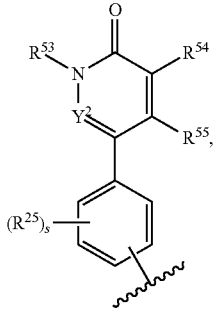

Formula E-3 where $Y^2$ is N or $CR^{23}$;

$R^{23}$ is H, halogen, optionally substituted $C_1$-$C_6$ alkyl, or optionally substituted $C_6$-$C_{10}$ aryl;

s is 0, 1, 2, 3, or 4;

each $R^{25}$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxyl, thiol, or optionally substituted amino;

$R^{53}$ is H, optionally substituted $C_1$-$C_6$ alkyl, optionally substituted $C_1$-$C_6$ heteroalkyl, or optionally substituted $C_3$-$C_{10}$ carbocyclyl;

$R^{54}$ is H or optionally substituted $C_2$-$C_9$ heteroaryl; and $R^{55}$ is H or $NR^a$, where $R^a$ is H, optionally substituted $C_1$-$C_6$ alkyl, optionally substituted $C_1$-$C_6$ heteroalkyl, or optionally substituted $C_3$-$C_{10}$ carbocyclyl, where if $R^{53}$ is H and $R^{54}$ is H, then $R^{55}$ is $NR^a$; if $R^{54}$ is H and $R^{55}$ is H, then $R^{53}$ is optionally substituted $C_3$-$C_{10}$ carbocyclyl; and if $R^{53}$ is H and $R^{55}$ is H, then $R^{54}$ is optionally substituted $C_2$-$C_9$ heteroaryl, or a pharmaceutically acceptable salt thereof.

In some embodiments, the BRD9 binding moiety includes the structure of Formula E-3a:

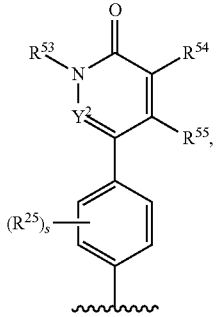

Formula E-3a or a pharmaceutically acceptable salt thereof.

In some embodiments, the BRD9 binding moiety includes the structure of Formula E-4:

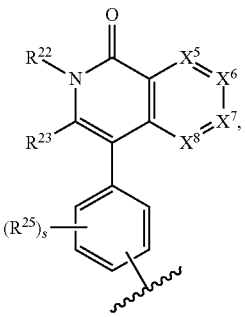

Formula E-4 where $R^{22}$ is H, optionally substituted $C_1$-$C_6$ alkyl, or optionally substituted $C_1$-$C_6$ heteroalkyl;

$R^{23}$ is H, halogen, optionally substituted $C_1$-$C_6$ alkyl, or optionally substituted $C_6$-$C_{10}$ aryl;

s is 0, 1, 2, 3, or 4;

each $R^{25}$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxyl, thiol, or optionally substituted amino;

$X^5$ is N or $CR^{56a}$;

$X^6$ is N or $CR^{56b}$;

$X^7$ is N or $CR^{56c}$;

$X^6$ is N or $CR^{56d}$; and each of $R^{56a}$, $R^{56b}$, $R^{56c}$, and $R^{56d}$ is, independently, H, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxyl, thiol, optionally substituted sulfonamide, or optionally substituted amino, or a pharmaceutically acceptable salt thereof.

In some embodiments, $X^7$ is N or CH. In some embodiments, $X^8$ is N or CH.

In some embodiments, the BRD9 binding moiety includes the structure of Formula E-4a:

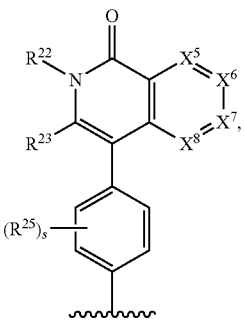

Formula E-4a or a pharmaceutically acceptable salt thereof.

In some embodiments, the BRD9 binding moiety includes the structure of Formula G-2:

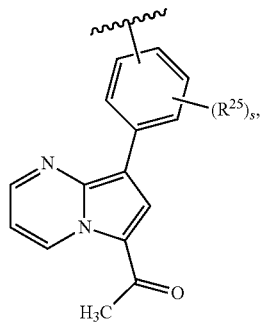

Formula G-2 where
s is 0, 1, 2, 3, or 4; and
each $R^{25}$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxyl, thiol, or optionally substituted amino, or a pharmaceutically acceptable salt thereof.

In some embodiments, the BRD9 binding moiety includes the structure of Formula G-2a:

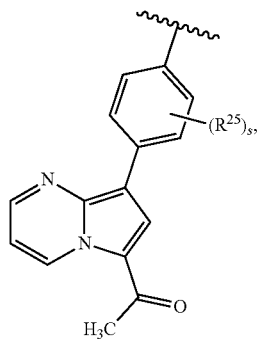

Formula G-2a or a pharmaceutically acceptable salt thereof.

In some embodiments, the BRD9 binding moiety includes the structure of Formula G-3:

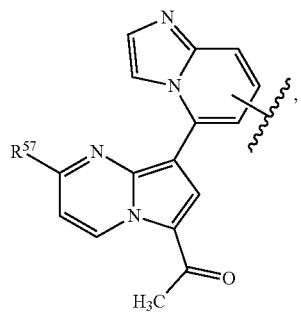

Formula G-3 where $R^{57}$ is optionally substituted $C_2$-$C_{10}$ heterocyclyl, or a pharmaceutically acceptable salt thereof.

In some embodiments, the BRD9 binding moiety includes the structure of Formula J-1:

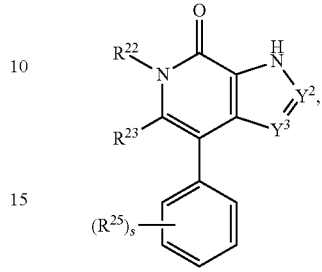

Formula J-1 where
$R^{22}$ is H, optionally substituted $C_1$-$C_6$ alkyl, or optionally substituted $C_1$-$C_6$ heteroalkyl;
$R^{23}$ is H, halogen, optionally substituted $C_1$-$C_6$ alkyl, or optionally substituted $C_6$-$C_{10}$ aryl;
s is 0, 1, 2, 3, or 4;
each $R^{25}$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_{6-10}$ aryl, optionally substituted $C_2$-$C_9$ heteroaryl, optionally substituted $C_2$-$C_6$ alkenyl, optionally substituted $C_2$-$C_6$ heteroalkenyl, hydroxyl, thiol, or optionally substituted amino;
$Y^2$ is N or $CR^{56a}$;
$Y^3$ is N or $CR^{58b}$; and
each of $R^{58a}$ and $R^{58b}$ is, independently, H or optionally substituted $C_1$-$C_6$ alkyl, or a pharmaceutically acceptable salt thereof.

In another aspect, the disclosure features a compound having the structure of Formula K-1, Formula K-2, Formula M-2, Formula M-3, or Formula O-1:

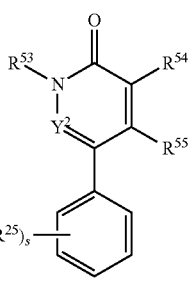

Formula K-1

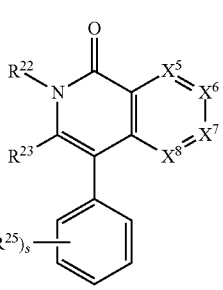

Formula K-2

-continued

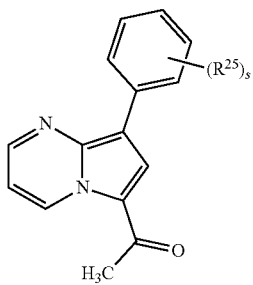

Formula M-2

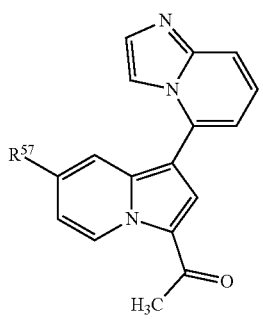

Formula M-3

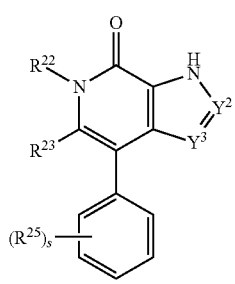

Formula O-1 where $Y^2$ is N or $CR^{23}$;

$R^{22}$ is H, optionally substituted $C_1$-$C_6$ alkyl, or optionally substituted $C_1$-$C_6$ heteroalkyl;

$R^{23}$ is H, halogen, optionally substituted $C_1$-$C_6$ alkyl, or optionally substituted $C_6$-$C_{10}$ aryl;

s is 0, 1, 2, 3, or 4;

each $R^{25}$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxyl, thiol, or optionally substituted amino;

$R^{53}$ is H, optionally substituted $C_1$-$C_6$ alkyl, optionally substituted $C_1$-$C_6$ heteroalkyl, or optionally substituted $C_3$-$C_{10}$ carbocyclyl;

$R^{54}$ is H or optionally substituted $C_2$-$C_9$ heteroaryl;

$R^{55}$ is H or $NR^a$, where $R^a$ is H, optionally substituted $C_1$-$C_6$ alkyl, optionally substituted $C_1$-$C_6$ heteroalkyl, or optionally substituted $C_3$-$C_{10}$ carbocyclyl;

$X^5$ is N or $CR^{56a}$;

$X^6$ is N or $CR^{56b}$;

each of $X^7$ and $X^8$ is, independently, N or CH;

each of $R^{56a}$ and $R^{56b}$ is, independently, H or $NR^a$, where each $R^a$ is H, optionally substituted $C_1$-$C_6$ alkyl, optionally substituted $C_1$-$C_6$ heteroalkyl, or optionally substituted $C_3$-$C_{10}$ carbocyclyl;

$R^{57}$ is optionally substituted $C_2$-$C_{10}$ heterocyclyl;

$Y^2$ is N or $CR^{58a}$;

$Y^3$ is N or $CR^{58b}$; and each of $R^{58a}$ and $R^{58b}$ is, independently, H or optionally substituted $C_1$-$C_6$ alkyl, where if $R^{53}$ is H and $R^{54}$ is H, then $R^{55}$ is $NR^a$; if $R^{54}$ is H and $R^{55}$ is H, then $R^{53}$ is optionally substituted $C_3$-$C_{10}$ carbocyclyl; and if $R^{53}$ is H and $R^{55}$ is H, then $R^{54}$ is optionally substituted $C_2$-$C_9$ heteroaryl, or a pharmaceutically acceptable salt thereof.

In some embodiments, the compound has the structure of Formula K-1.

In some embodiments, the compound has the structure of Formula K-2.

In some embodiments, the compound has the structure of Formula M-2.

In some embodiments, the compound has the structure of Formula M-3.

In some embodiments, the compound has the structure of Formula O-1.

In some embodiments, s is 0, 1, or 2.

In some embodiments, the compound has the structure of compounds B1-B65 in Table 1. In some embodiments, the compound has the structure of compounds B1, B3-B13, B16-B22, and B28-B67 in Table 1.

TABLE 1

Compounds B1-B68 of the Disclosure

| Compound No. | Structure |
|---|---|
| B1 | 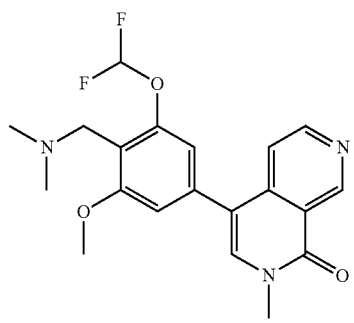 [SMILES: COc1cc(-c2cn(C)c(=O)c3cnccc23)cc(OC(F)F)c1CN(C)C] |

TABLE 1-continued

Compounds B1-B68 of the Disclosure

| Compound No. | Structure |
|---|---|
| B2 | (structure) |
| B3 | (structure) |
| B4 | (structure) |
| B5 | (structure) |

TABLE 1-continued

Compounds B1-B68 of the Disclosure

| Compound No. | Structure |
| --- | --- |
| B6 | 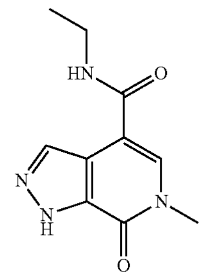 [SMILES: CCNC(=O)c1cn(C)c(=O)c2[nH]ncc12] |
| B7 | 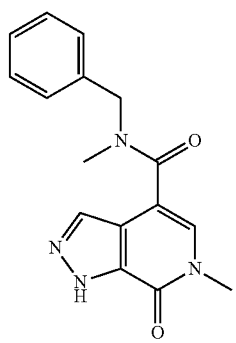 [SMILES: CN(Cc1ccccc1)C(=O)c1cn(C)c(=O)c2[nH]ncc12] |
| B8 | 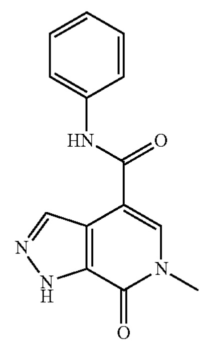 [SMILES: Cn1cc(C(=O)Nc2ccccc2)c2cn[nH]c2c1=O] |
| B9 | 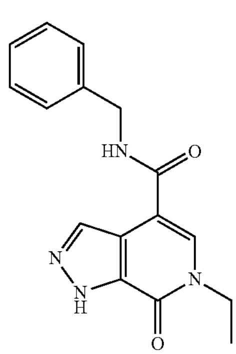 [SMILES: CCn1cc(C(=O)NCc2ccccc2)c2cn[nH]c2c1=O] |

TABLE 1-continued
Compounds B1-B68 of the Disclosure
| Compound No. | Structure |
| --- | --- |
| B10 | 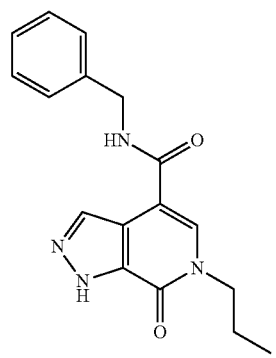 [SMILES: CCCn1cc(C(=O)NCc2ccccc2)c2cn[nH]c2c1=O] |
| B11 | 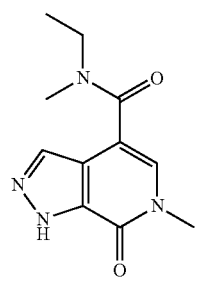 [SMILES: CCN(C)C(=O)c1cn(C)c(=O)c2[nH]ncc12] |
| B12 | 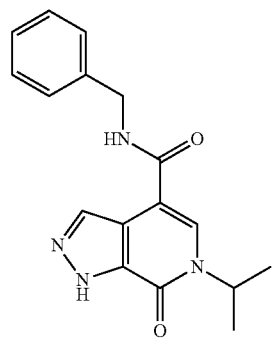 [SMILES: CC(C)n1cc(C(=O)NCc2ccccc2)c2cn[nH]c2c1=O] |
| B13 | 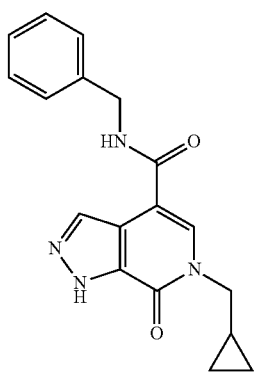 [SMILES: O=C(NCc1ccccc1)c1cn(CC2CC2)c(=O)c2[nH]ncc12] |

TABLE 1-continued
Compounds B1-B68 of the Disclosure
| Compound No. | Structure |
| --- | --- |
| B14 | 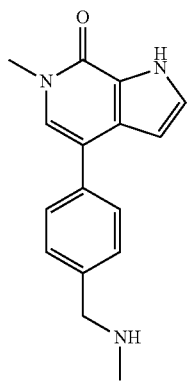 [SMILES: CNCc1ccc(-c2cn(C)c(=O)c3[nH]ccc23)cc1] |
| B15 | 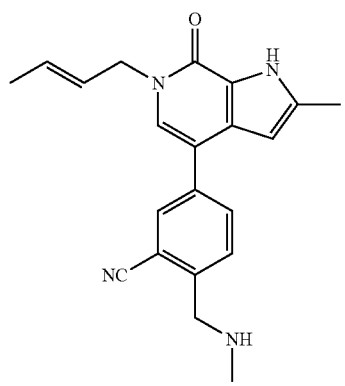 [SMILES: C/C=C/Cn1cc(-c2ccc(CNC)c(C#N)c2)c2cc(C)[nH]c2c1=O] |
| B16 | 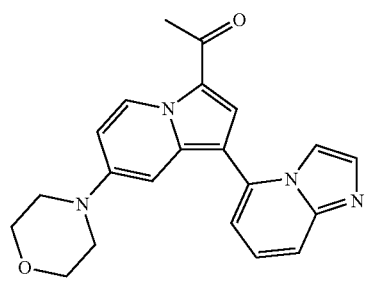 [SMILES: CC(=O)c1cc(-c2cccc3nccn23)c2cc(N3CCOCC3)ccn12] |
| B17 | 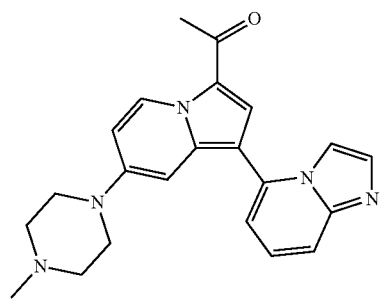 [SMILES: CC(=O)c1cc(-c2cccc3nccn23)c2cc(N3CCN(C)CC3)ccn12] |

TABLE 1-continued
Compounds B1-B68 of the Disclosure
| Compound No. | Structure |
|---|---|
| B18 | 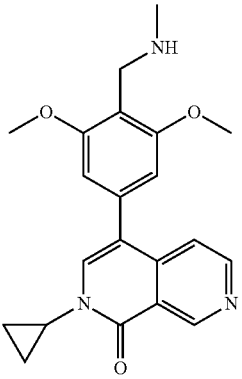 [SMILES: CNCc1c(OC)cc(-c2cn(C3CC3)c(=O)c3cnccc23)cc1OC] |
| B19 | 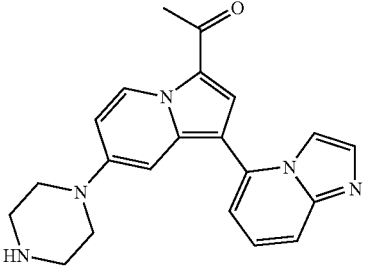 [SMILES: CC(=O)c1cc(-c2cccc3nccn23)c2cc(N3CCNCC3)ccn12] |
| B20 | 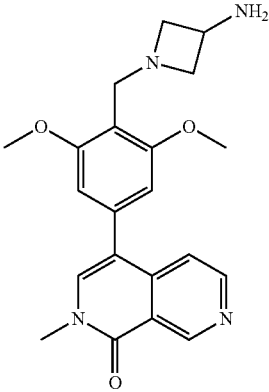 [SMILES: COc1cc(-c2cn(C)c(=O)c3cnccc23)cc(OC)c1CN1CC(N)C1] |
| B21 | 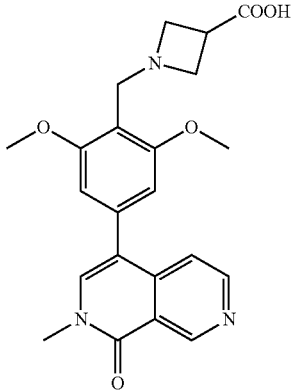 [SMILES: COc1cc(-c2cn(C)c(=O)c3cnccc23)cc(OC)c1CN1CC(C(=O)O)C1] |

TABLE 1-continued

Compounds B1-B68 of the Disclosure

| Compound No. | Structure |
| --- | --- |
| B22 | 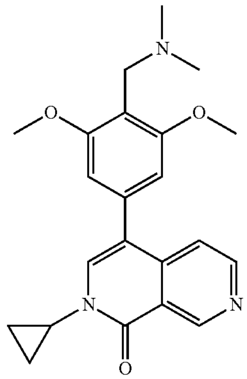 [SMILES: COc1cc(-c2cn(C3CC3)c(=O)c3cnccc23)cc(OC)c1CN(C)C] |
| B23 | 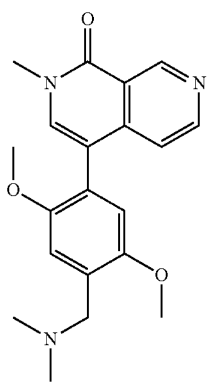 [SMILES: COc1cc(-c2cn(C)c(=O)c3cnccc23)c(OC)cc1CN(C)C] |
| B24 | 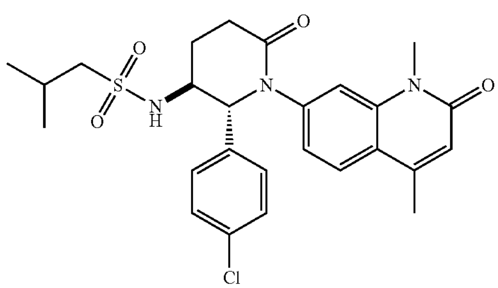 [SMILES: Cc1cc(=O)n(C)c2cc(N3C(=O)CC[C@H](NS(=O)(=O)CC(C)C)[C@H]3c3ccc(Cl)cc3)ccc12] |
| B25 | 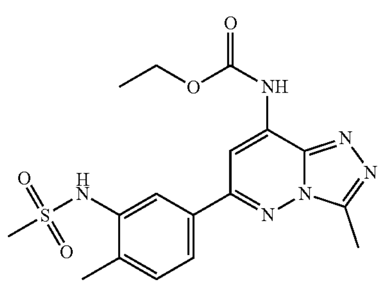 [SMILES: CCOC(=O)Nc1cc(-c2ccc(C)c(NS(C)(=O)=O)c2)nn2c(C)nnc12] |
| B26 | 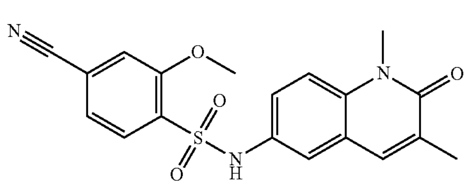 [SMILES: COc1cc(C#N)ccc1S(=O)(=O)Nc1ccc2c(c1)cc(C)c(=O)n2C] |

TABLE 1-continued

Compounds B1-B68 of the Disclosure

| Compound No. | Structure |
|---|---|
| B27 | 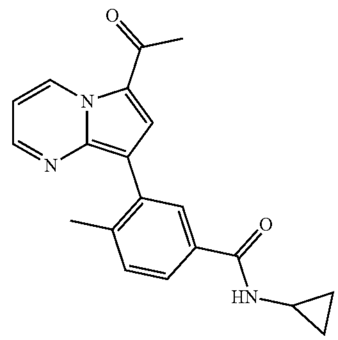 [SMILES: CC(=O)c1cc(-c2cc(C(=O)NC3CC3)ccc2C)c2ncccn12] |
| B28 | 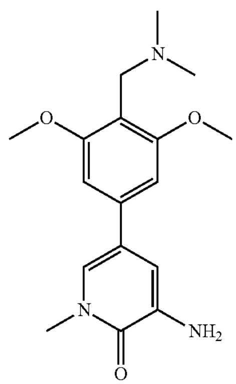 |
| B29 | 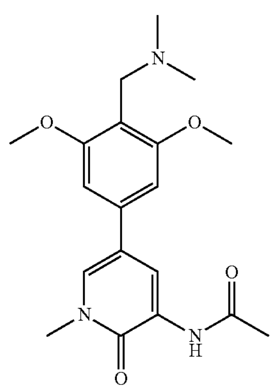 [SMILES: COc1cc(-c2cc(NC(C)=O)c(=O)n(C)c2)cc(OC)c1CN(C)C] |
| B30 | 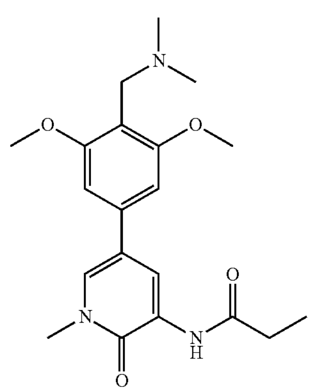 [SMILES: CCC(=O)Nc1cc(-c2cc(OC)c(CN(C)C)c(OC)c2)cn(C)c1=O] |

TABLE 1-continued

Compounds B1-B68 of the Disclosure

| Compound No. | Structure |
| --- | --- |
| B31 | 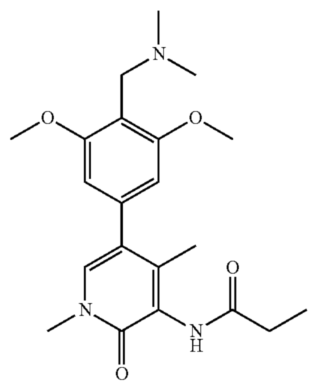 [SMILES: CCC(=O)Nc1c(C)c(-c2cc(OC)c(CN(C)C)c(OC)c2)cn(C)c1=O] |
| B32 | 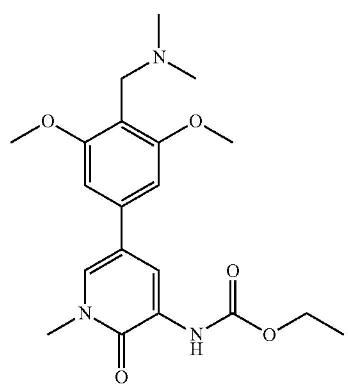 [SMILES: CCOC(=O)Nc1cc(-c2cc(OC)c(CN(C)C)c(OC)c2)cn(C)c1=O] |
| B33 | 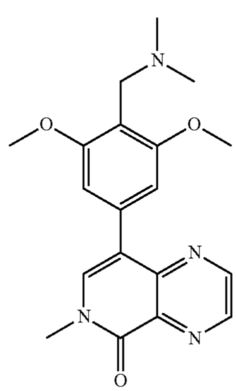 [SMILES: COc1cc(-c2cn(C)c(=O)c3nccnc23)cc(OC)c1CN(C)C] |

TABLE 1-continued
Compounds B1-B68 of the Disclosure
| Compound No. | Structure |
|---|---|
| B34 | 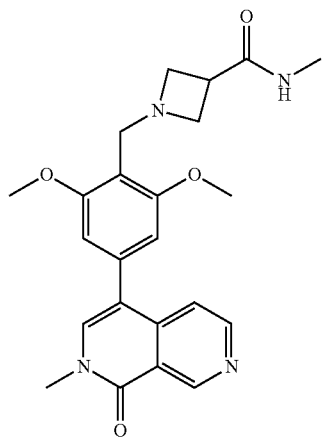 |
| B35 | 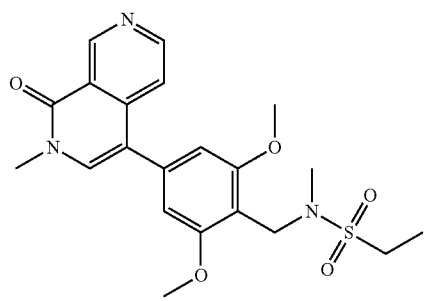 [SMILES: CCS(=O)(=O)N(C)Cc1c(OC)cc(-c2cn(C)c(=O)c3cnccc23)cc1OC] |
| B36 | 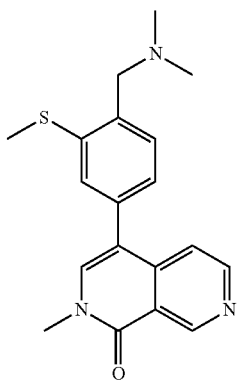 [SMILES: CSc1cc(-c2cn(C)c(=O)c3cnccc23)ccc1CN(C)C] |
| B37 | 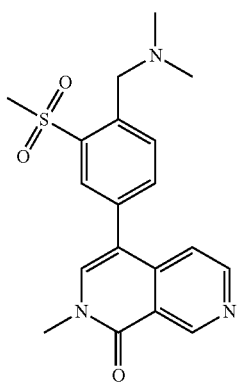 [SMILES: CN(C)Cc1ccc(-c2cn(C)c(=O)c3cnccc23)cc1S(C)(=O)=O] |

TABLE 1-continued

Compounds B1-B68 of the Disclosure

| Compound No. | Structure |
|---|---|
| B38 | 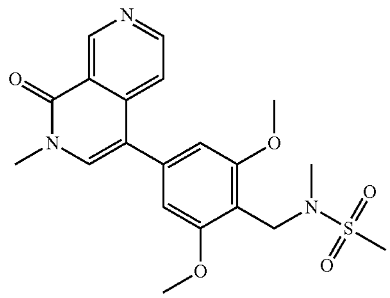 |
| B39 | 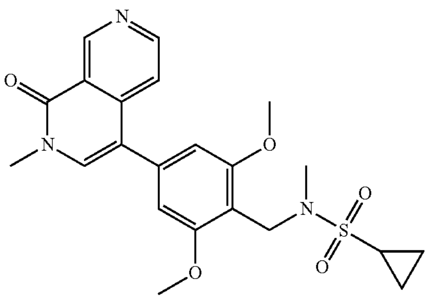 [SMILES: COc1cc(-c2cn(C)c(=O)c3cnccc23)cc(OC)c1CN(C)S(=O)(=O)C1CC1] |
| B40 | 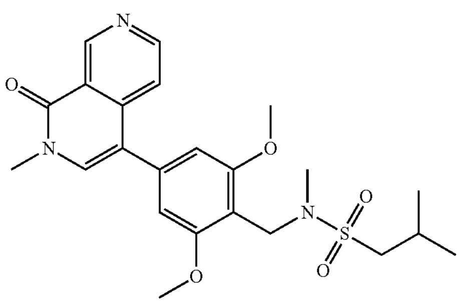 [SMILES: COc1cc(-c2cn(C)c(=O)c3cnccc23)cc(OC)c1CN(C)S(=O)(=O)CC(C)C] |
| B41 | 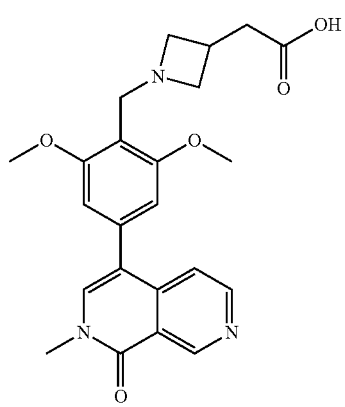 [SMILES: COc1cc(-c2cn(C)c(=O)c3cnccc23)cc(OC)c1CN1CC(CC(=O)O)C1] |

TABLE 1-continued

Compounds B1-B68 of the Disclosure

| Compound No. | Structure |
| --- | --- |
| B42 | 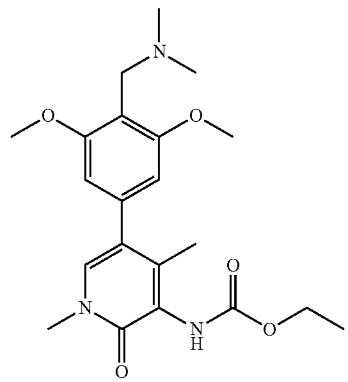 [SMILES: CCOC(=O)Nc1c(C)c(-c2cc(OC)c(CN(C)C)c(OC)c2)cn(C)c1=O] |
| B43 | 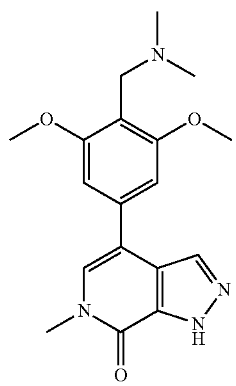 |
| B44 | 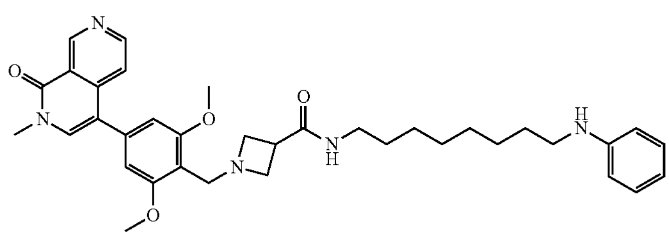 [SMILES: COc1cc(-c2cn(C)c(=O)c3cnccc23)cc(OC)c1CN1CC(C(=O)NCCCCCCCCNc2ccccc2)C1] |
| B45 | 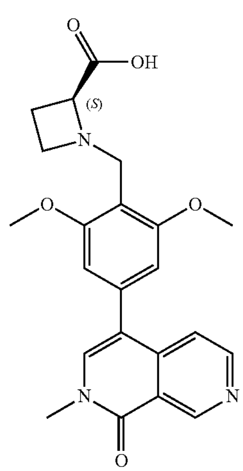 |

TABLE 1-continued
Compounds B1-B68 of the Disclosure
| Compound No. | Structure |
|---|---|
| B46 | 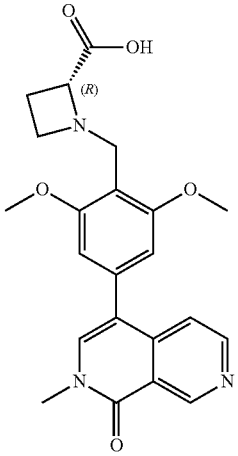 |
| B47 | 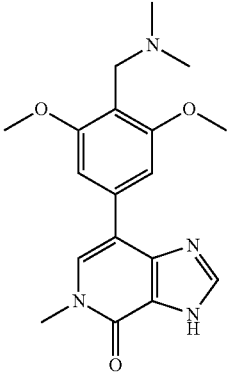 |
| B48 | 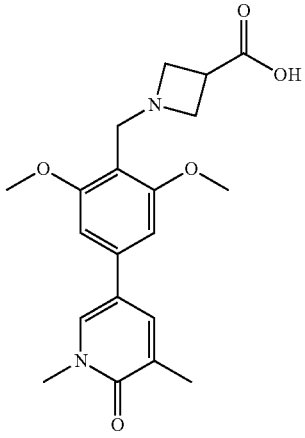 [SMILES: COc1cc(-c2cc(C)c(=O)n(C)c2)cc(OC)c1CN1CC(C(=O)O)C1] |
| B49 | 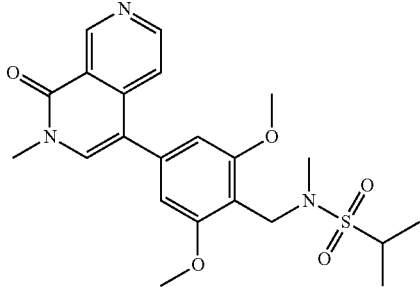 [SMILES: COc1cc(-c2cn(C)c(=O)c3cnccc23)cc(OC)c1CN(C)S(=O)(=O)C(C)C] |

TABLE 1-continued
Compounds B1-B68 of the Disclosure
| Compound No. | Structure |
|---|---|
| B50 | 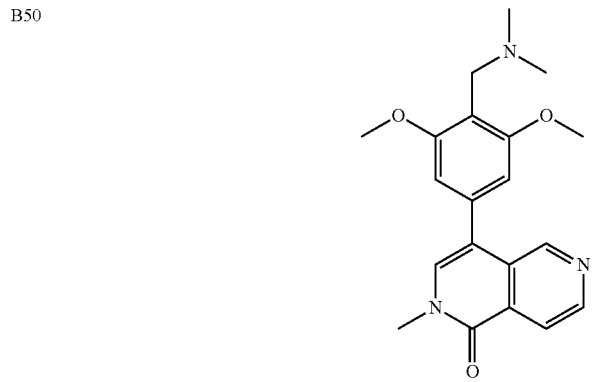 |
| B51 | 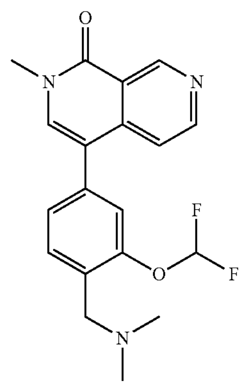 [SMILES: CN(C)Cc1ccc(-c2cn(C)c(=O)c3cnccc23)cc1OC(F)F] |
| B52 | 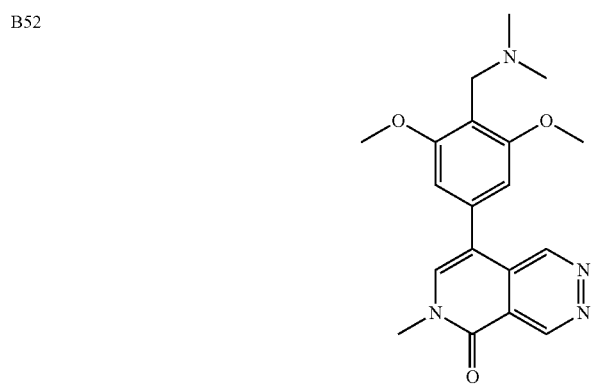 |
| B53 | 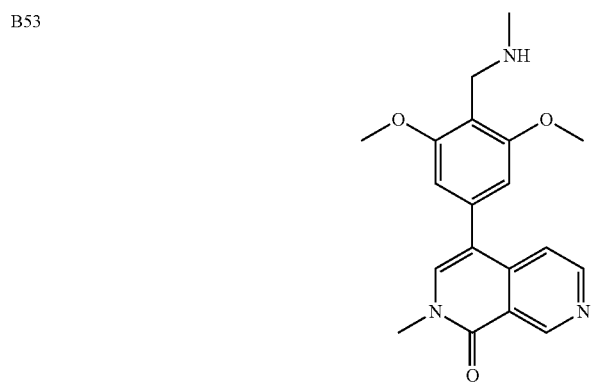 |

TABLE 1-continued
Compounds B1-B68 of the Disclosure
| Compound No. | Structure |
| --- | --- |
| B54 | 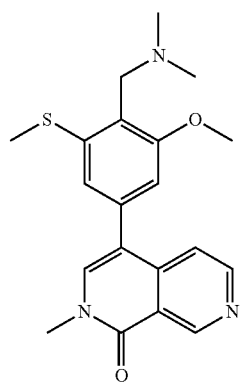 [SMILES: COc1cc(-c2cn(C)c(=O)c3cnccc23)cc(SC)c1CN(C)C] |
| B55 | 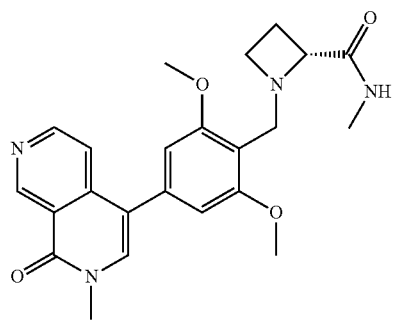 [SMILES: CNC(=O)[C@H]1CCN1Cc1c(OC)cc(-c2cn(C)c(=O)c3cnccc23)cc1OC] |
| B56 | 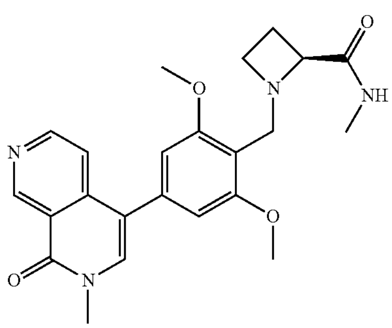 [SMILES: CNC(=O)[C@@H]1CCN1Cc1c(OC)cc(-c2cn(C)c(=O)c3cnccc23)cc1OC] |
| B57 | 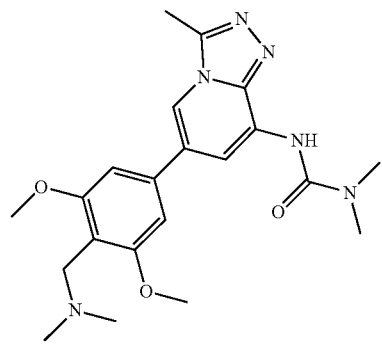 |

TABLE 1-continued

Compounds B1-B68 of the Disclosure

| Compound No. | Structure |
|---|---|
| B58 | 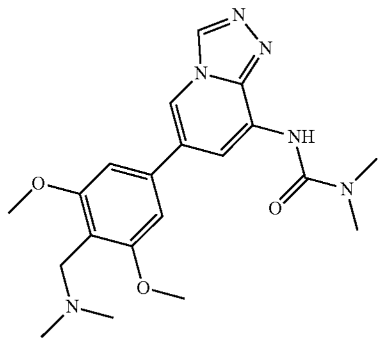 |
| B59 | 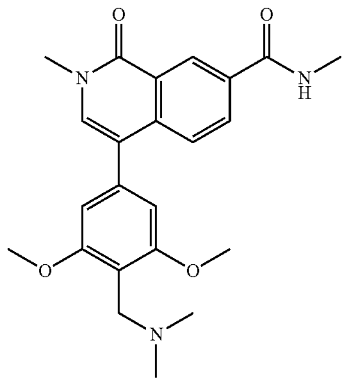 |
| B60 | 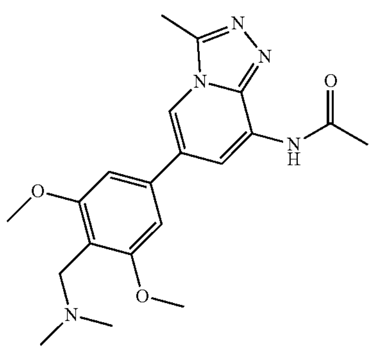 [SMILES: COc1cc(-c2cc(NC(C)=O)c3nnc(C)n3c2)cc(OC)c1CN(C)C] |
| B61 | 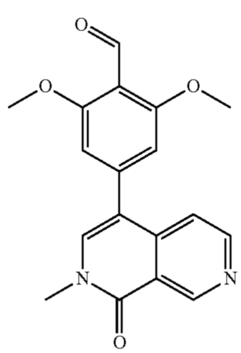 [SMILES: COc1cc(-c2cn(C)c(=O)c3cnccc23)cc(OC)c1C=O] |

TABLE 1-continued

Compounds B1-B68 of the Disclosure

| Compound No. | Structure |
| --- | --- |
| B62 | 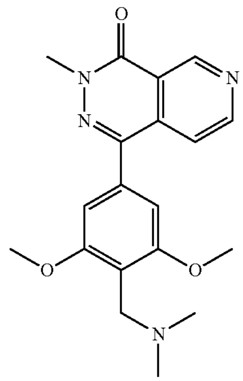 [SMILES: COc1cc(-c2nn(C)c(=O)c3cnccc23)cc(OC)c1CN(C)C] |
| B63 | 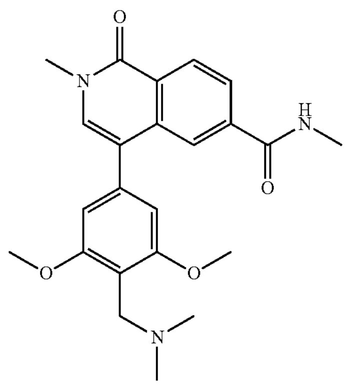 |
| B64 | 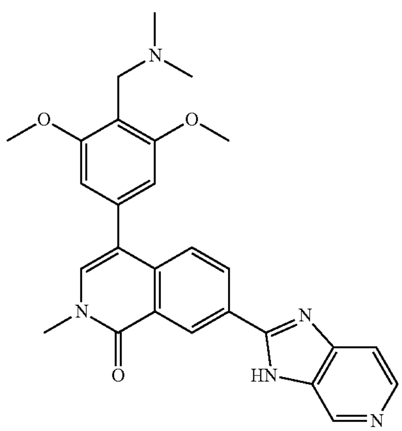 [SMILES: COc1cc(-c2cn(C)c(=O)c3cc(-c4nc5ccncc5[nH]4)ccc23)cc(OC)c1CN(C)C] |
| B65 | 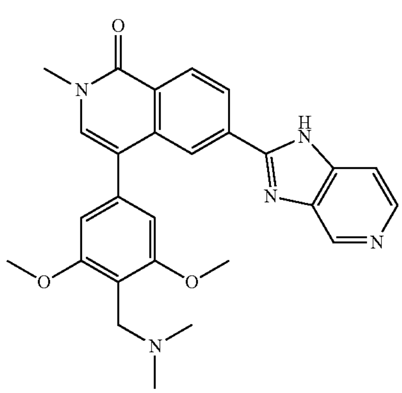 [SMILES: COc1cc(-c2cn(C)c(=O)c3ccc(-c4nc5cnccc5[nH]4)cc23)cc(OC)c1CN(C)C] |

TABLE 1-continued

Compounds B1-B68 of the Disclosure

| Compound No. | Structure |
|---|---|
| B66 | 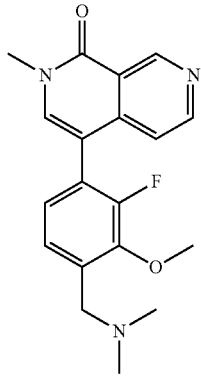 [SMILES: COc1c(CN(C)C)ccc(-c2cn(C)c(=O)c3cnccc23)c1F] |
| B67 | 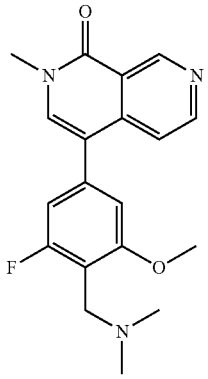 [SMILES: COc1cc(-c2cn(C)c(=O)c3cnccc23)cc(F)c1CN(C)C] |
| B68 | 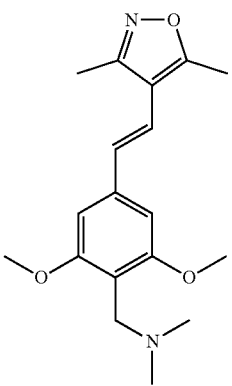 |

In another aspect, the disclosure features a pharmaceutical composition including any of the foregoing compounds and a pharmaceutically acceptable excipient.

In yet another aspect, the disclosure features a method of treating a cancer in a subject in need thereof, the method including administering to the subject an effective amount of any of the foregoing compounds or any of the foregoing pharmaceutical compositions.

In another aspect, the disclosure features a method of treating a cancer related to BRD9 inhibition in a subject in need thereof, the method including administering to the subject an effective amount of any of the foregoing compounds or any of the foregoing pharmaceutical compositions.

In yet another aspect, the disclosure features a compound having the structure of Formula I:

A-L-B      Formula I, where

L is a linker;

B is a degradation moiety; and

A has the structure of Formula E-3, Formula E-4, Formula G-2, Formula G-3, or Formula E-5:

Formula E-3

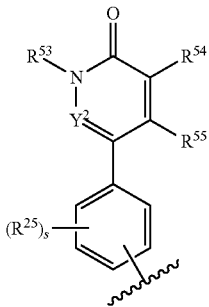

Formula E-4

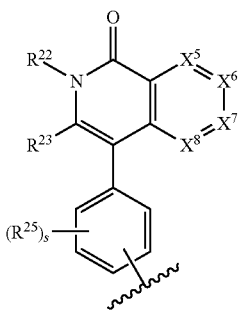

Formula G-2

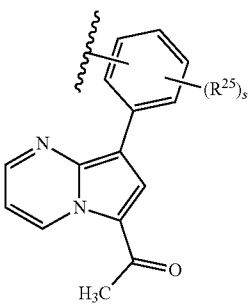

Formula G-3

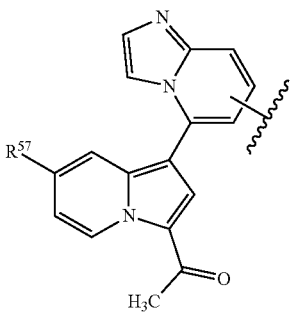

Formula E-5

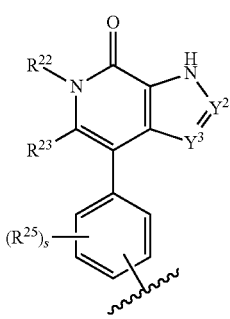

where $Y^2$ is N or $CR^{23}$;

$R^{22}$ is H, optionally substituted $C_1$-$C_6$ alkyl, or optionally substituted $C_1$-$C_6$ heteroalkyl;

$R^{23}$ is H, halogen, optionally substituted $C_1$-$C_6$ alkyl, or optionally substituted $C_6$-$C_{10}$ aryl;

s is 0, 1, 2, 3, or 4;

each $R^{25}$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxyl, thiol, or optionally substituted amino;

$R^{53}$ is H, optionally substituted $C_1$-$C_6$ alkyl, optionally substituted $C_1$-$C_6$ heteroalkyl, or optionally substituted $C_3$-$C_{10}$ carbocyclyl;

$R^{54}$ is H or optionally substituted $C_2$-$C_9$ heteroaryl;

$R^{55}$ is H or $NR^a$, where $R^a$ is H, optionally substituted $C_1$-$C_6$ alkyl, optionally substituted $C_1$-$C_6$ heteroalkyl, or optionally substituted $C_3$-$C_{10}$ carbocyclyl;

each of $X^5$ and $X^6$ is, independently, N or $CR^{56}$;

each of $X^7$ and $X^8$ is, independently, N or CH;

each $R^{56}$ is, independently, H or $NR^a$, where $R^a$ is H, optionally substituted $C_1$-$C_6$ alkyl, optionally substituted $C_1$-$C_6$ heteroalkyl, or optionally substituted $C_3$-$C_{10}$ carbocyclyl;

$R^{57}$ is optionally substituted $C_2$-$C_{10}$ heterocyclyl;

each of $Y^2$ and $Y^3$ is, independently, N or $CR^{58}$; and each $R^{58}$ is, independently, H or optionally substituted $C_1$-$C_6$ alkyl, where if $R^{53}$ is H and $R^{54}$ is H, then $R^{55}$ is $NR^a$; if $R^{54}$ is H and $R^{55}$ is H, then $R^{53}$ is optionally substituted $C_3$-$C_{10}$ carbocyclyl; and if $R^{53}$ is H and $R^{55}$ is H, then $R^{54}$ is optionally substituted $C_2$-$C_9$ heteroaryl, or a pharmaceutically acceptable salt thereof.

In some embodiments, A has the structure of Formula E-3.

In some embodiments, A has the structure of Formula E-4.

In some embodiments, A has the structure of Formula G-2.

In some embodiments, A has the structure of Formula G-3.

In some embodiments, A has the structure of Formula E-5.

In some embodiments, s is 0, 1, or 2.

In some embodiments, the degradation moiety is a ubiquitin ligase binding moiety.

In some embodiments, the ubiquitin ligase binding moiety includes Cereblon ligands, IAP (Inhibitors of Apoptosis) ligands, mouse double minute 2 homolog (MDM2), or von Hippel-Lindau ligands, or derivatives or analogs thereof.

In some embodiments, the degradation moiety has the structure of Formula A-1:

Formula A-1

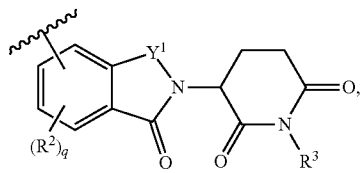

where
Y¹ is

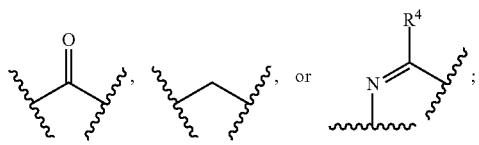

R³ and R⁴ are, independently, H, optionally substituted $C_1$-$C_6$ alkyl, or optionally substituted $C_1$-$C_6$ heteroalkyl;

q is 0, 1, 2, 3, or 4; and each R² is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxyl, thiol, or optionally substituted amino, or a pharmaceutically acceptable salt thereof.

In some embodiments, R³ is H or optionally substituted $C_1$-$C_6$ alkyl.

In some embodiments, R³ is H or $CH_3$. In some embodiments, R³ is H. In some embodiments, R³ is CH.

In some embodiments, Y¹ is

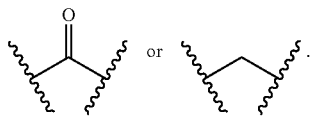

In some embodiments, Y¹ is

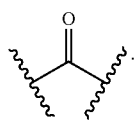

In some embodiments, each R² is, independently, optionally substituted $C_1$-$C_6$ alkyl, optionally substituted $C_1$-$C_6$ heteroalkyl, hydroxyl, or optionally substituted amino.

In some embodiments, q is 0 or 1. In some embodiments, q is 0.

In some embodiments, the structure of Formula A-1 has the structure of Formula A-1a:

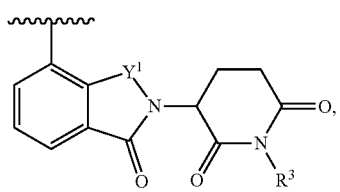

Formula A-1a or a pharmaceutically acceptable salt thereof.

In some embodiments, the structure of Formula A-1 has the structure of Formula A-1b:

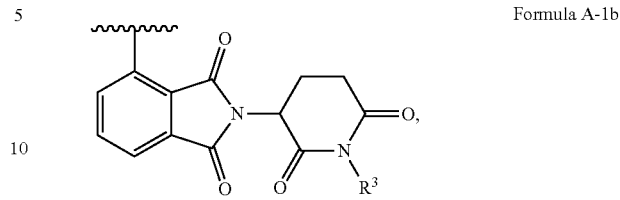

Formula A-1b or a pharmaceutically acceptable salt thereof.

In some embodiments, the structure of Formula A-1c has the structure of Formula A-1c:

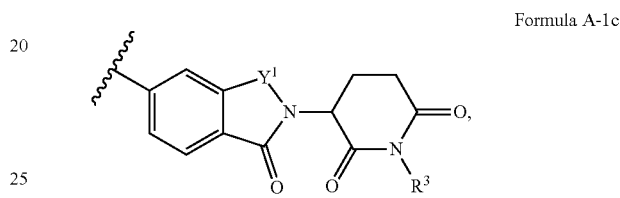

Formula A-1c or a pharmaceutically acceptable salt thereof.

In some embodiments, the structure of Formula A-1 has the structure of Formula A-1d:

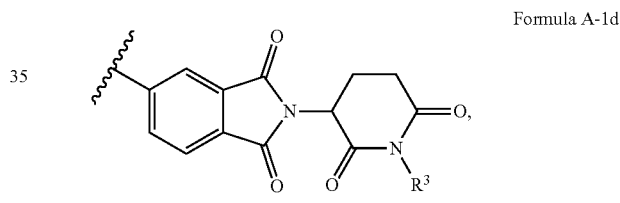

Formula A-1d or a pharmaceutically acceptable salt thereof.

In some embodiments, the degradation moiety has the structure:

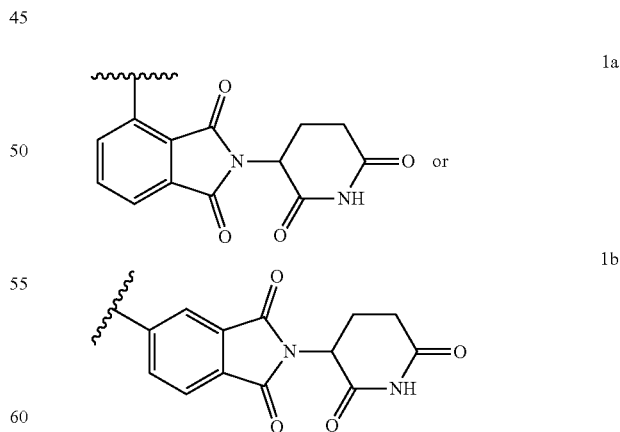

1a

1b or is a derivative or an analog thereof.

In some embodiments, the linker has the structure of Formula II:

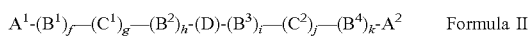

Formula II where $A^1$ is a bond between the linker and A;

$A^2$ is a bond between B and the linker;

each of $B^1$, $B^2$, $B^3$, and $B^4$ is, independently, optionally substituted $C_1$-$C_2$ alkyl, optionally substituted $C_1$-$C_3$ heteroalkyl, O, S, $S(O)_2$, or $NR^N$;

$R^N$ is H, optionally substituted $C_{1-4}$ alkyl, optionally substituted $C_{2-4}$ alkenyl, optionally substituted $C_{2-4}$ alkynyl, optionally substituted $C_{2-6}$ heterocyclyl, optionally substituted $C_{6-12}$ aryl, or optionally substituted $C_{1-7}$ heteroalkyl;

each of $C^1$ and $C^2$ is, independently, carbonyl, thiocarbonyl, sulphonyl, or phosphoryl;

f, g, h, l, j, and k are each, independently, 0 or 1; and

D is optionally substituted $C_{1-10}$ alkyl, optionally substituted $C_{2-10}$ alkenyl, optionally substituted $C_{2-10}$ alkynyl, optionally substituted $C_{2-6}$ heterocyclyl, optionally substituted $C_{6-12}$ aryl, optionally substituted $C_2$-$C_{10}$ polyethylene glycol, or optionally substituted $C_{1-10}$ heteroalkyl, or a chemical bond linking $A^1$-$(B^1)_f$—$(C^1)_g$—$(B^2)_h$— to —$(B^3)$—$(C^2)$—$(B^4)_k$-$A^2$.

In some embodiments, each of $B^1$, $B^2$, $B^3$, and $B^4$ is, independently, optionally substituted $C_1$-$C_4$ alkyl, optionally substituted $C_1$-$C_4$ heteroalkyl, or $NR^N$.

In some embodiments, $R^N$ is H or optionally substituted $C_{1-4}$ alkyl.

In some embodiments, $R^N$ is H or $CH_3$.

In some embodiments, each of $B^1$ and $B^4$ is, independently,

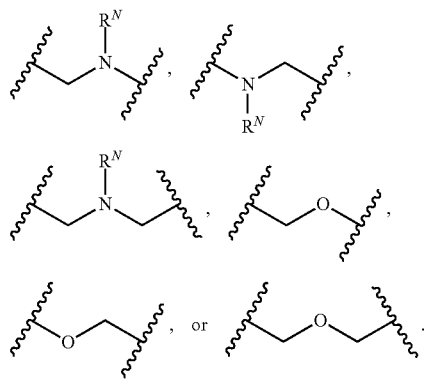

In some embodiments, $B^1$ is

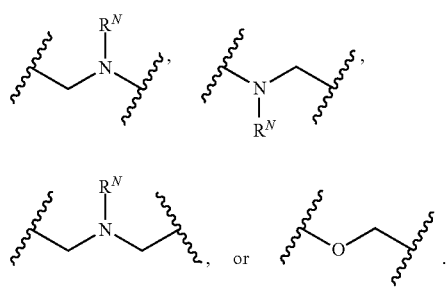

In some embodiments, each of $C^1$ and $C^2$ is, independently,

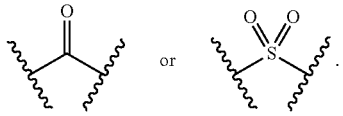

In some embodiments, $C^1$ is

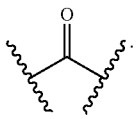 [SMILES: *C(*)=O]

In some embodiments, $B^2$ is $NR^N$.

In some embodiments, $B^2$ is optionally substituted $C_1$-$C_4$ alkyl.

In some embodiments, f is 0. In some embodiments, f is 1.

In some embodiments, g is 0. In some embodiments, g is 1.

In some embodiments, h is 0. In some embodiments, h is 1.

In some embodiments, i is 0. In some embodiments, i is 1.

In some embodiments, j is 0. In some embodiments, j is 1.

In some embodiments, k is 0. In some embodiments, k is 1.

In some embodiments, the linker has the structure of

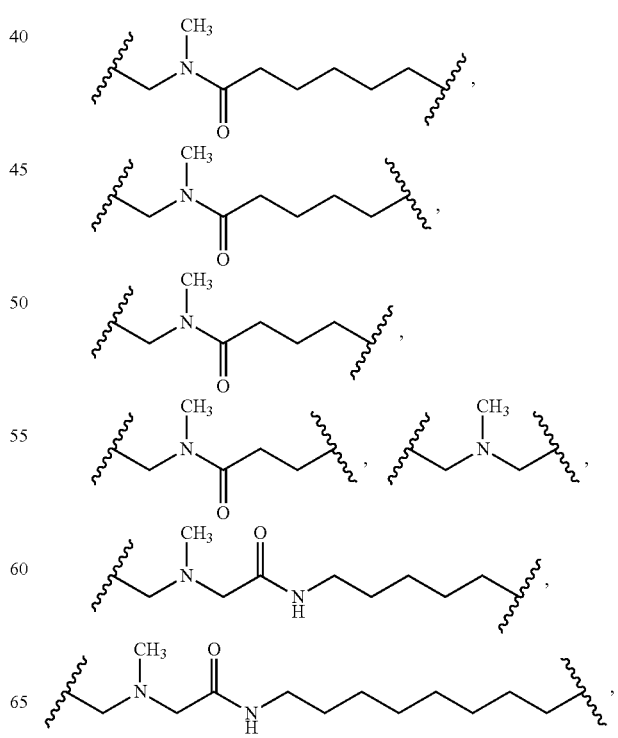

-continued
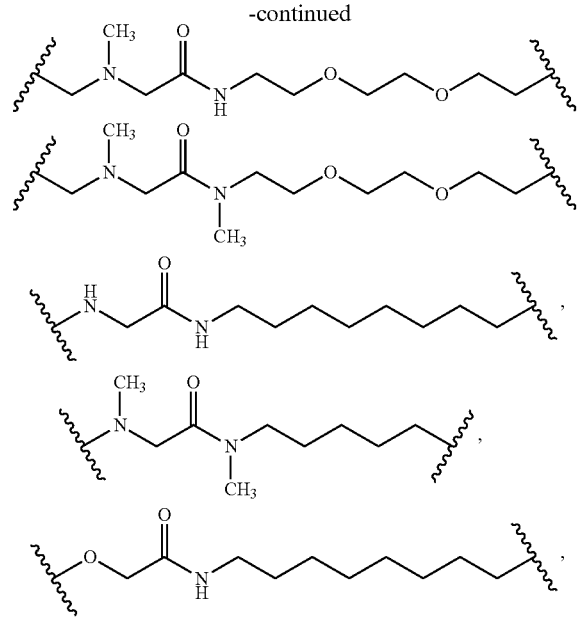
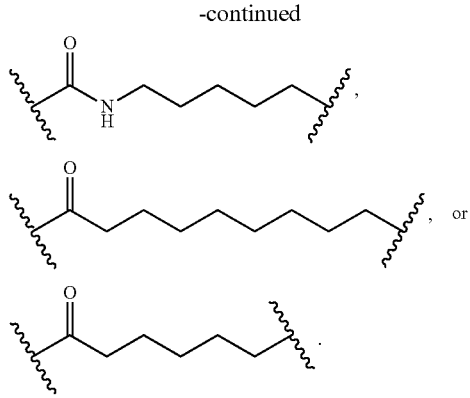
In some embodiments, the compound has the structure of any of compounds D1-D20 in Table 2. In some embodiments, the compound has the structure of any of compounds D1-D17 in Table 2. In some embodiments, the compound has the structure of any of compounds D18-D20 in Table 2.
TABLE 2
Compounds D1-D20 of the Disclosure
| Compound No. | Structure |
|---|---|
| D1 | 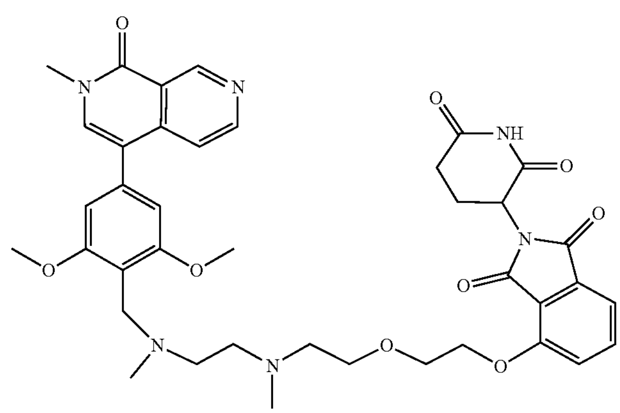 [SMILES: COc1cc(-c2cn(C)c(=O)c3cnccc23)cc(OC)c1CN(C)CCN(C)CCOCCOc1cccc2c1C(=O)N(C1CCC(=O)NC1=O)C2=O] |
| D2 | 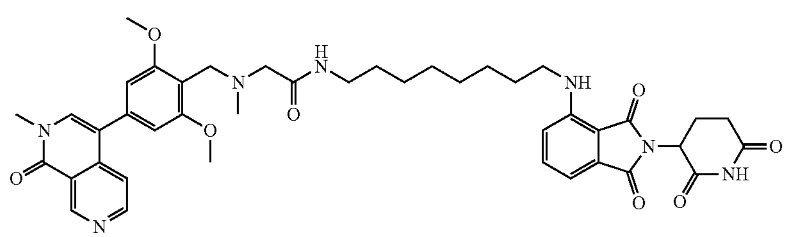 [SMILES: COc1cc(-c2cn(C)c(=O)c3cnccc23)cc(OC)c1CN(C)CC(=O)NCCCCCCCCNc1cccc2c1C(=O)N(C1CCC(=O)NC1=O)C2=O] |

TABLE 2-continued

Compounds D1-D20 of the Disclosure

| Compound No. | Structure |
|---|---|
| D3 | 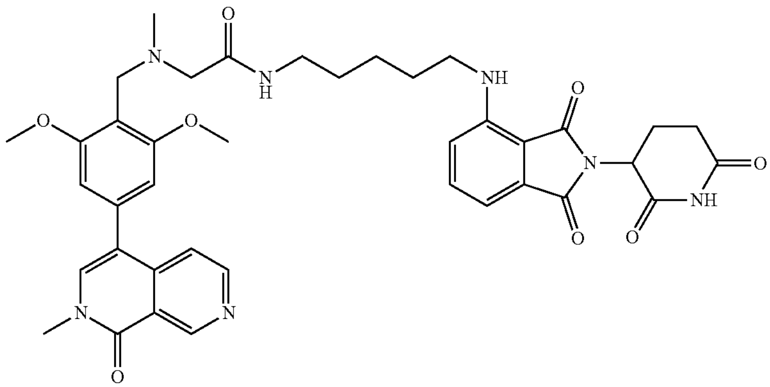 [SMILES: COc1cc(-c2cn(C)c(=O)c3cnccc23)cc(OC)c1CN(C)CC(=O)NCCCCCNc1cccc2c1C(=O)N(C1CCC(=O)NC1=O)C2=O] |
| D4 | 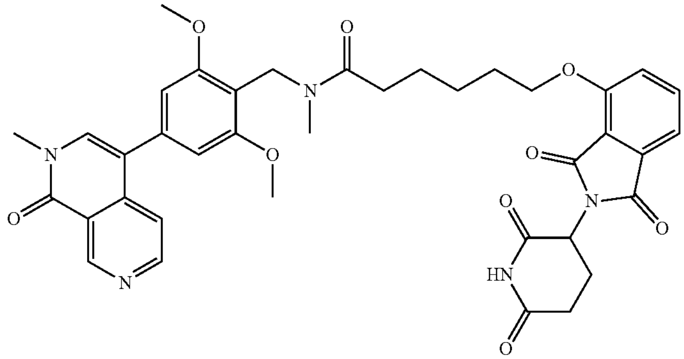 [SMILES: COc1cc(-c2cn(C)c(=O)c3cnccc23)cc(OC)c1CN(C)C(=O)CCCCCOc1cccc2c1C(=O)N(C1CCC(=O)NC1=O)C2=O] |
| D5 | 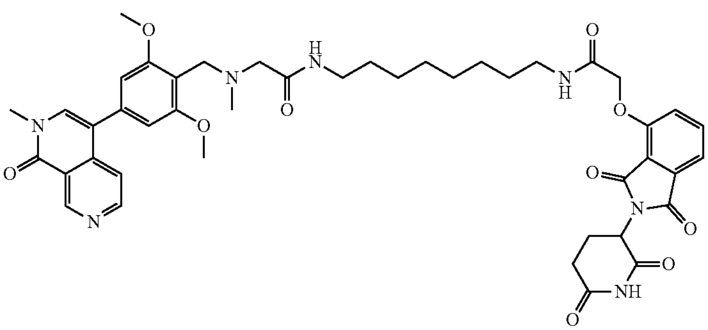 [SMILES: COc1cc(-c2cn(C)c(=O)c3cnccc23)cc(OC)c1CN(C)CC(=O)NCCCCCCCCNC(=O)COc1cccc2c1C(=O)N(C1CCC(=O)NC1=O)C2=O] |
| D6 | 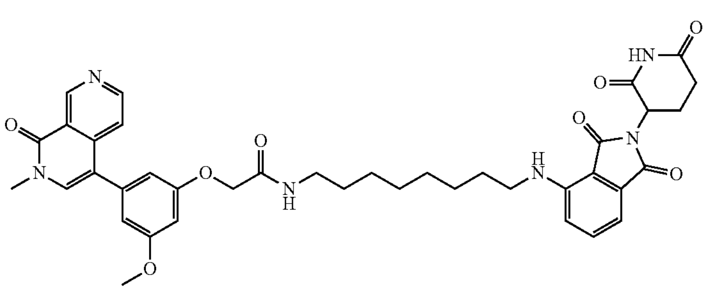 [SMILES: COc1cc(OCC(=O)NCCCCCCCCNc2cccc3c2C(=O)N(C2CCC(=O)NC2=O)C3=O)cc(-c2cn(C)c(=O)c3cnccc23)c1] |

TABLE 2-continued

Compounds D1-D20 of the Disclosure

| Compound No. | Structure |
|---|---|
| D7 | 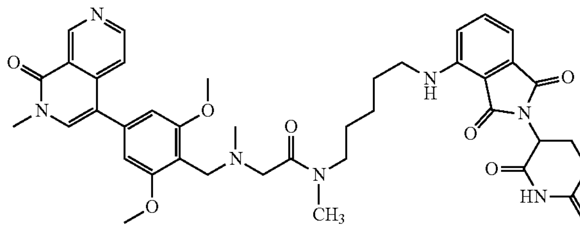 |
| D8 | 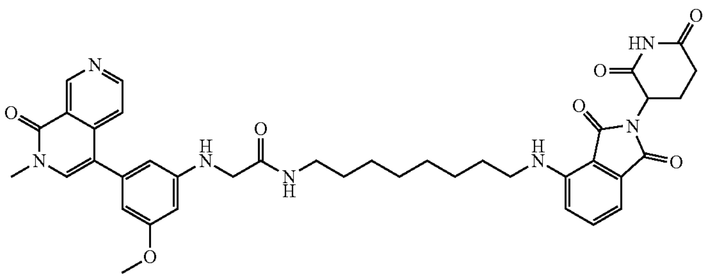 [SMILES: COc1cc(NCC(=O)NCCCCCCCCNc2cccc3c2C(=O)N(C2CCC(=O)NC2=O)C3=O)cc(-c2cn(C)c(=O)c3cnccc23)c1] |
| D9 | 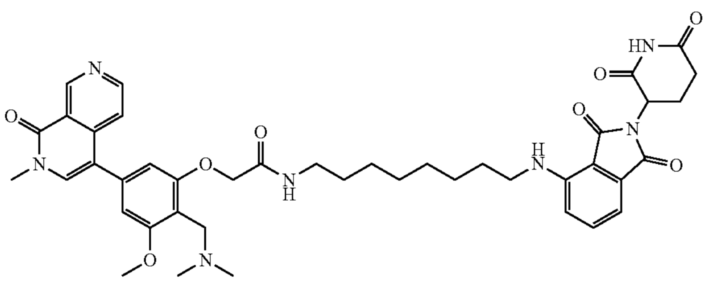 [SMILES: COc1cc(-c2cn(C)c(=O)c3cnccc23)cc(OCC(=O)NCCCCCCCCNc2cccc3c2C(=O)N(C2CCC(=O)NC2=O)C3=O)c1CN(C)C] |
| D10 | 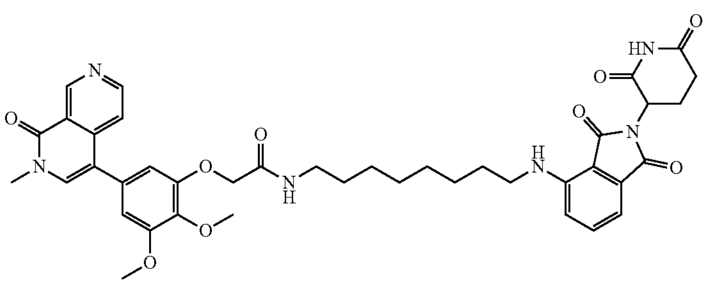 [SMILES: COc1cc(-c2cn(C)c(=O)c3cnccc23)cc(OCC(=O)NCCCCCCCCNc2cccc3c2C(=O)N(C2CCC(=O)NC2=O)C3=O)c1OC] |
| D11 | 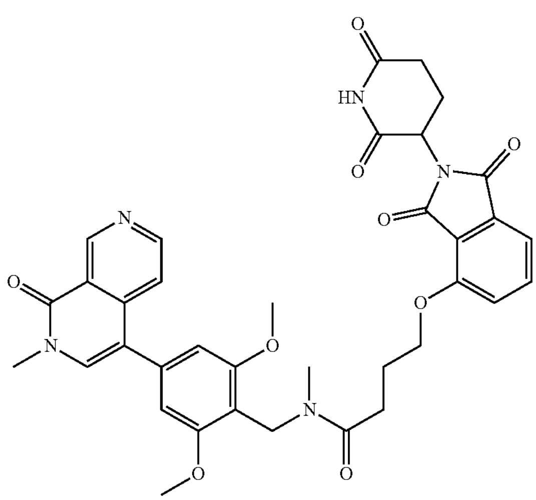 [SMILES: COc1cc(-c2cn(C)c(=O)c3cnccc23)cc(OC)c1CN(C)C(=O)CCCOc1cccc2c1C(=O)N(C1CCC(=O)NC1=O)C2=O] |

TABLE 2-continued
Compounds D1-D20 of the Disclosure
| Compound No. | Structure |
| --- | --- |
| D12 | 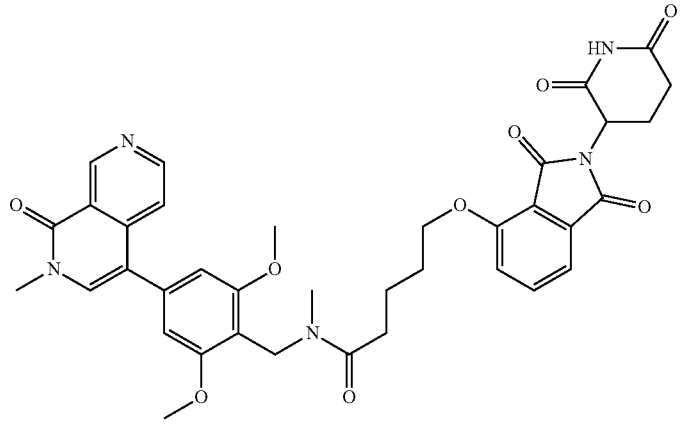 [SMILES: COc1cc(-c2cn(C)c(=O)c3cnccc23)cc(OC)c1CN(C)C(=O)CCCCOc1cccc2c1C(=O)N(C1CCC(=O)NC1=O)C2=O] |
| D13 | 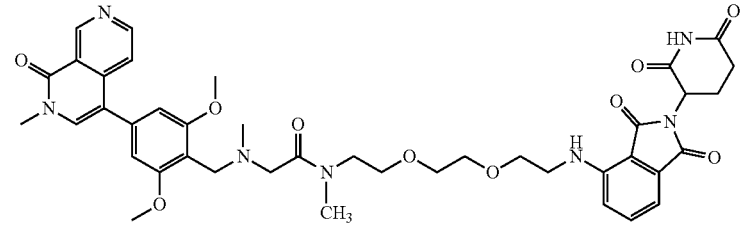 [SMILES: COc1cc(-c2cn(C)c(=O)c3cnccc23)cc(OC)c1CN(C)CC(=O)N(C)CCOCCOCCNc1cccc2c1C(=O)N(C1CCC(=O)NC1=O)C2=O] |
| D14 | 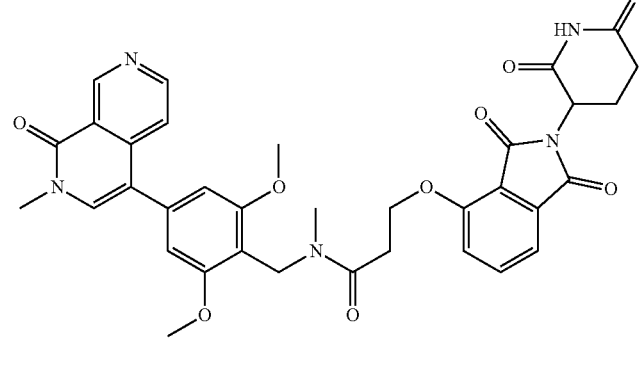 |
| D15 | 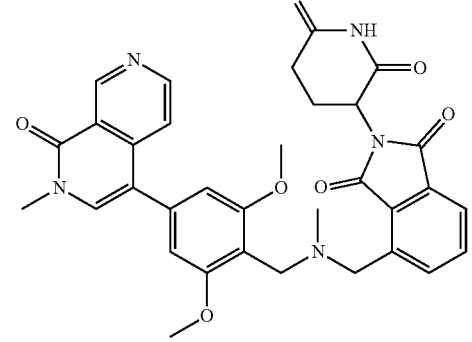 |

TABLE 2-continued

Compounds D1-D20 of the Disclosure

| Compound No. | Structure |
| --- | --- |
| D16 | 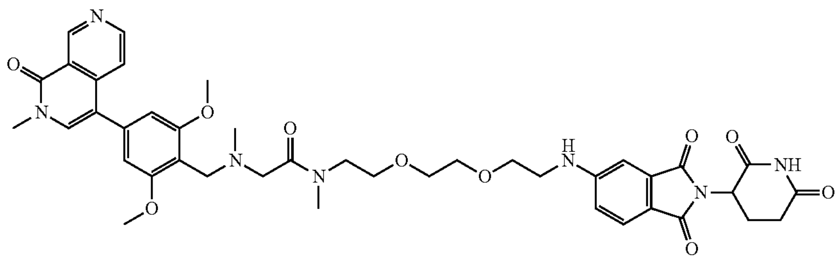 [SMILES: COc1cc(-c2cn(C)c(=O)c3cnccc23)cc(OC)c1CN(C)CC(=O)N(C)CCOCCOCCNc1ccc2c(c1)C(=O)N(C1CCC(=O)NC1=O)C2=O] |
| D17 | 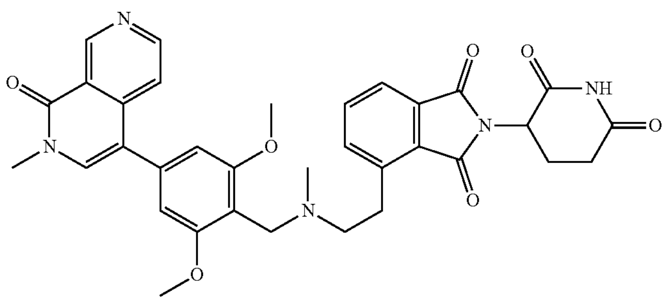 [SMILES: COc1cc(-c2cn(C)c(=O)c3cnccc23)cc(OC)c1CN(C)CCc1cccc2c1C(=O)N(C1CCC(=O)NC1=O)C2=O] |
| D18 | 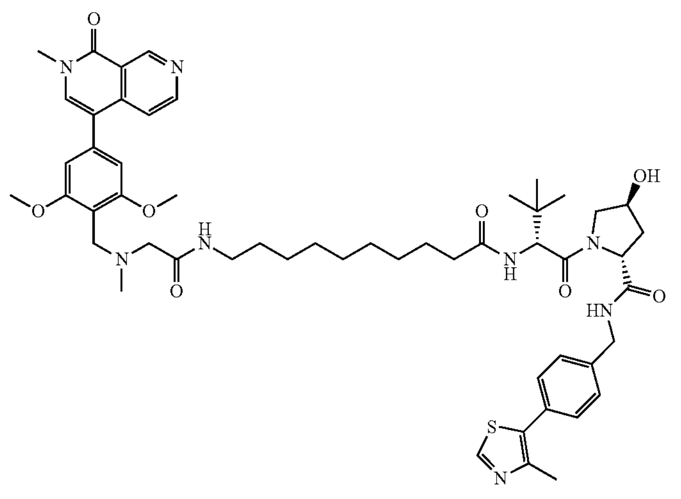 [SMILES: COc1cc(-c2cn(C)c(=O)c3cnccc23)cc(OC)c1CN(C)CC(=O)NCCCCCCCCCC(=O)N[C@@H](C(=O)N1C[C@@H](O)C[C@@H]1C(=O)NCc1ccc(-c2scnc2C)cc1)C(C)(C)C] |
| D19 | 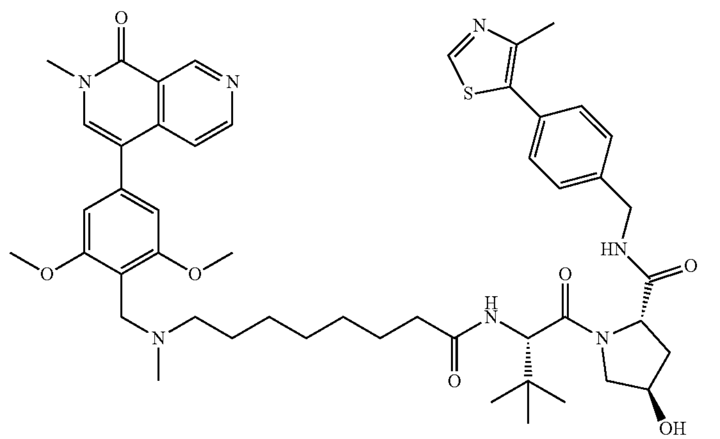 [SMILES: COc1cc(-c2cn(C)c(=O)c3cnccc23)cc(OC)c1CN(C)CCOCCOCC(=O)N[C@H](C(=O)N1C[C@H](O)C[C@H]1C(=O)NCc1ccc(-c2scnc2C)cc1)C(C)(C)C] |

TABLE 2-continued

Compounds D1-D20 of the Disclosure

| Compound No. | Structure |
|---|---|
| D20 | 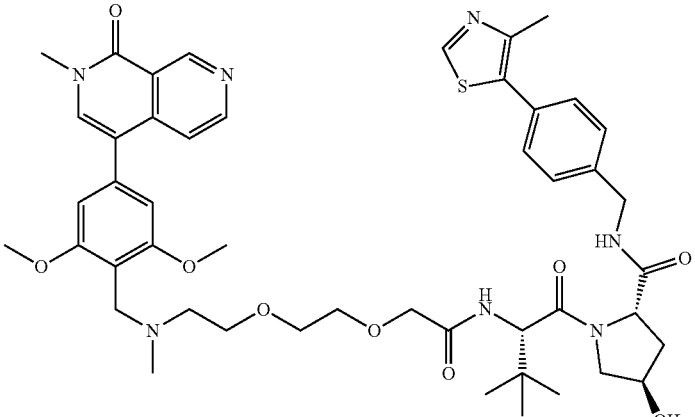 |

In another aspect, the disclosure features a pharmaceutical composition including any of the foregoing compounds and a pharmaceutically acceptable excipient.

In yet another aspect, the disclosure features a method of treating a cancer in a subject in need thereof, the method including administering to the subject an effective amount of any of the foregoing compounds or any of the foregoing pharmaceutical compositions.

In another aspect, the disclosure features a method of treating a cancer related to BRD9 inhibition in a subject in need thereof, the method including administering to the subject an effective amount of any of the foregoing compounds or any of the foregoing pharmaceutical compositions.

In some embodiments, the cancer is a CD8+ T-cell lymphoma, endometrial carcinoma, ovarian carcinoma, bladder cancer, stomach cancer, pancreatic cancer, esophageal cancer, prostate cancer, renal cell carcinoma, melanoma, colorectal cancer, non-small cell lung cancer, stomach cancer, or breast cancer.

Chemical Terms

For any of the following chemical definitions, a number following an atomic symbol indicates that total number of atoms of that element that are present in a particular chemical moiety. As will be understood, other atoms, such as hydrogen atoms, or substituent groups, as described herein, may be present, as necessary, to satisfy the valences of the atoms. For example, an unsubstituted $C_2$ alkyl group has the formula —$CH_2CH_3$. When used with the groups defined herein, a reference to the number of carbon atoms includes the divalent carbon in acetal and ketal groups but does not include the carbonyl carbon in acyl, ester, carbonate, or carbamate groups. A reference to the number of oxygen, nitrogen, or sulfur atoms in a heteroaryl group only includes those atoms that form a part of a heterocyclic ring.

The term "acyl," as used herein, represents a hydrogen or an alkyl group that is attached to a parent molecular group through a carbonyl group, as defined herein, and is exemplified by formyl (i.e., a carboxyaldehyde group), acetyl, trifluoroacetyl, propionyl, and butanoyl. Exemplary unsubstituted acyl groups include from 1 to 6, from 1 to 11, or from 1 to 21 carbons.

The term "alkyl," as used herein, refers to a branched or straight-chain monovalent saturated aliphatic hydrocarbon radical of 1 to 20 carbon atoms (e.g., 1 to 16 carbon atoms, 1 to 10 carbon atoms, or 1 to 6 carbon atoms).

An alkylene is a divalent alkyl group. The term "alkenyl," as used herein, alone or in combination with other groups, refers to a straight chain or branched hydrocarbon residue having a carbon-carbon double bond and having 2 to 20 carbon atoms (e.g., 2 to 16 carbon atoms, 2 to 10 carbon atoms, 2 to 6, or 2 carbon atoms).

The term "alkynyl," as used herein, alone or in combination with other groups, refers to a straight chain or branched hydrocarbon residue having a carbon-carbon triple bond and having 2 to 20 carbon atoms (e.g., 2 to 16 carbon atoms, 2 to 10 carbon atoms, 2 to 6, or 2 carbon atoms).

The term "amino," as used herein, represents —$N(R^{N1})_2$, wherein each $R^{N1}$ is, independently, H, OH, $NO_2$, $N(R^{N2})_2$, $SO_2OR^{N2}$, $SO_2R^{N2}$, $SOR^{N2}$, an N-protecting group, alkyl, alkoxy, aryl, arylalkyl, cycloalkyl, acyl (e.g., acetyl, trifluoroacetyl, or others described herein), wherein each of these recited $R^{N1}$ groups can be optionally substituted; or two $R^{N1}$ combine to form an alkylene or heteroalkylene, and wherein each $R^{N2}$ is, independently, H, alkyl, or aryl. The amino groups of the compounds described herein can be an unsubstituted amino (i.e., —$NH_2$) or a substituted amino (i.e., —$N(R^{N1})_2$).

The term "aryl," as used herein, refers to an aromatic mono- or polycarbocyclic radical of 6 to 12 carbon atoms having at least one aromatic ring. Examples of such groups include, but are not limited to, phenyl, naphthyl, 1,2,3,4-tetrahydronaphthyl, 1,2-dihydronaphthyl, indanyl, and 1H-indenyl.

The term "arylalkyl," as used herein, represents an alkyl group substituted with an aryl group.

Exemplary unsubstituted arylalkyl groups are from 7 to 30 carbons (e.g., from 7 to 16 or from 7 to 20 carbons, such as $C_1$-$C_6$ alkyl $C_6$-$C_{10}$ aryl, $C_1$-$C_{20}$ alkyl $C_{6-10}$ aryl, or $C_1$-$C_{20}$ alkyl $C_6$-$C_{10}$ aryl), such as, benzyl and phenethyl. In some embodiments, the alkyl and the aryl each can be further substituted with 1, 2, 3, or 4 substituent groups as defined herein for the respective groups.

The term "azido," as used herein, represents a —$N_3$ group.

The term "bridged cyclyl," as used herein, refers to a bridged polycyclic group of 5 to 20 atoms, containing from 1 to 3 bridges. Bridged cyclyl includes bridged carbocyclyl (e.g., norbornyl) and bridged heterocyclyl (e.g., 1,4-diazabicyclo[2.2.2]octane).

The term "cyano," as used herein, represents a —CN group.

The term "carbocyclyl," as used herein, refers to a non-aromatic $C_3$-$C_{12}$ monocyclic or polycyclic (e.g., bicyclic or tricyclic) structure in which the rings are formed by carbon atoms. Carbocyclyl structures include cycloalkyl groups and unsaturated carbocyclyl radicals. Polycyclic carbocyclyl includes spirocyclic carbocyclyl, bridged carbocyclyl, and fused carbocyclyl.

The term "cycloalkyl," as used herein, refers to a saturated, non-aromatic, monovalent mono- or polycarbocyclic radical of 3 to 10, preferably 3 to 6 carbon atoms. This term is further exemplified by radicals such as cyclopropyl, cyclobutyl, cyclopentyl, cyclohexyl, cycloheptyl, norbornyl, and adamantyl.

The term "halogen," as used herein, means a fluorine (fluoro), chlorine (chloro), bromine (bromo), or iodine (iodo) radical.

The term "heteroalkyl," as used herein, refers to an alkyl group, as defined herein, in which one or more of the constituent carbon atoms have been replaced by nitrogen, oxygen, or sulfur. In some embodiments, the heteroalkyl group can be further substituted with 1, 2, 3, or 4 substituent groups as described herein for alkyl groups. Examples of heteroalkyl groups are an "alkoxy" which, as used herein, refers alkyl-O— (e.g., methoxy and ethoxy). A heteroalkylene is a divalent heteroalkyl group. The term "heteroalkenyl," as used herein, refers to an alkenyl group, as defined herein, in which one or more of the constituent carbon atoms have been replaced by nitrogen, oxygen, or sulfur. In some embodiments, the heteroalkenyl group can be further substituted with 1, 2, 3, or 4 substituent groups as described herein for alkenyl groups. Examples of heteroalkenyl groups are an "alkenoxy" which, as used herein, refers alkenyl-O—. A heteroalkenylene is a divalent heteroalkenyl group. The term "heteroalkynyl," as used herein, refers to an alkynyl group, as defined herein, in which one or more of the constituent carbon atoms have been replaced by nitrogen, oxygen, or sulfur. In some embodiments, the heteroalkynyl group can be further substituted with 1, 2, 3, or 4 substituent groups as described herein for alkynyl groups.

Examples of heteroalkynyl groups are an "alkynoxy" which, as used herein, refers alkynyl-O—. A heteroalkynylene is a divalent heteroalkynyl group.

The term "heteroaryl," as used herein, refers to an aromatic monocyclic or polycyclic structure of 5 to 12 atoms having at least one aromatic ring containing 1, 2, or 3 ring atoms selected from nitrogen, oxygen, and sulfur, with the remaining ring atoms being carbon. One or two ring carbon atoms of the heteroaryl group may be replaced with a carbonyl group. Examples of heteroaryl groups are pyridyl, pyrazoyl, benzooxazolyl, benzoimidazolyl, benzothiazolyl, imidazolyl, oxaxolyl, and thiazolyl.

The term "heteroarylalkyl," as used herein, represents an alkyl group substituted with a heteroaryl group. Exemplary unsubstituted heteroarylalkyl groups are from 7 to 30 carbons (e.g., from 7 to 16 or from 7 to 20 carbons, such as $C_1$-$C_6$ alkyl $C_2$-$C_9$ heteroaryl, $C_1$-$C_{10}$ alkyl $C_2$-$C_9$ heteroaryl, or $C_1$-$C_{20}$ alkyl $C_2$-$C_9$ heteroaryl). In some embodiments, the alkyl and the heteroaryl each can be further substituted with 1, 2, 3, or 4 substituent groups as defined herein for the respective groups.

The term "heterocyclyl," as used herein, refers a monocyclic or polycyclic (e.g., bicyclic or tricyclic) structure having 3 to 12 atoms having at least one ring containing 1, 2, 3, or 4 ring atoms selected from N, O or S, wherein no ring is aromatic. Polycyclic heterocyclyl includes spirocyclic heterocyclyl, bridged heterocyclyl, and fused heterocyclyl. Examples of heterocyclyl groups include, but are not limited to, morpholinyl, thiomorpholinyl, furyl, piperazinyl, piperidinyl, pyranyl, pyrrolidinyl, tetrahydropyranyl, tetrahydrofuranyl, and 1,3-dioxanyl.

The term "heterocyclylalkyl," as used herein, represents an alkyl group substituted with a heterocyclyl group. Exemplary unsubstituted heterocyclylalkyl groups are from 7 to 30 carbons (e.g., from 7 to 16 or from 7 to 20 carbons, such as $C_1$-$C_6$ alkyl $C_2$-$C_9$ heterocyclyl, $C_1$-$C_{10}$ alkyl $C_2$-$C_9$ heterocyclyl, or $C_1$-$C_{20}$ alkyl $C_2$-$C_9$ heterocyclyl). In some embodiments, the alkyl and the heterocyclyl each can be further substituted with 1, 2, 3, or 4 substituent groups as defined herein for the respective groups.

The term "hydroxyalkyl," as used herein, represents alkyl group substituted with an —OH group.

The term "hydroxyl," as used herein, represents an —OH group.

The term "N-protecting group," as used herein, represents those groups intended to protect an amino group against undesirable reactions during synthetic procedures. Commonly used N-protecting groups are disclosed in Greene, "Protective Groups in Organic Synthesis," 3rd Edition (John Wiley & Sons, New York, 1999). N-protecting groups include, but are not limited to, acyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected D, L, or D, L-amino acids such as alanine, leucine, and phenylalanine; sulfonyl-containing groups such as benzenesulfonyl, and p-toluenesulfonyl; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, and phenylthiocarbonyl, arylalkyl groups such as benzyl, triphenylmethyl, and benzyloxymethyl, and silyl groups, such as trimethylsilyl. Preferred N-protecting groups are alloc, formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "nitro," as used herein, represents an —NO$_2$ group.

The term "thiol," as used herein, represents an —SH group.

The alkyl, alkenyl, alkynyl, heteroalkyl, heteroalkenyl, heteroalkynyl, carbocyclyl (e.g., cycloalkyl), aryl, heteroaryl, and heterocyclyl groups may be substituted or unsubstituted. When substituted, there will generally be 1 to 4 substituents present, unless otherwise specified. Substituents include, for example: alkyl (e.g., unsubstituted and substituted, where the substituents include any group described herein, e.g., aryl, halo, hydroxyl), aryl (e.g., substituted and unsubstituted phenyl), carbocylyl (e.g., substituted and unsubstituted cycloalkyl), halogen (e.g., fluoro), hydroxyl, heteroalkyl (e.g., substituted and unsubstituted methoxy, ethoxy, or thioalkoxy), heteroaryl, heterocyclyl, amino (e.g., $NH_2$ or mono- or dialkyl amino), azido, cyano, nitro, or thiol. Aryl, carbocyclyl (e.g., cycloalkyl), heteroaryl, and heterocyclyl groups may also be substituted with alkyl (unsubstituted and substituted such as arylalkyl (e.g., substituted and unsubstituted benzyl)).

Compounds described herein can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates, or mixtures of diastereoisomeric racemates. The optically active forms can be obtained for example by resolution of the racemates, by asymmetric synthesis or asymmetric chromatography (chromatography with a chiral adsorbent or eluant). That is, certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms and represent the configuration of substituents around one or more chiral carbon atoms. Enantiomers of a compound can be prepared, for example, by separating an enantiomer from a racemate using one or more well-known techniques and methods, such as, for example, chiral chromatography and separation methods based thereon. The appropriate technique and/or method for separating an enantiomer of a compound described herein from a racemic mixture can be readily determined by those of skill in the art. "Racemate" or "racemic mixture" means a compound containing two enantiomers, wherein such mixtures exhibit no optical activity; i.e., they do not rotate the plane of polarized light. "Geometric isomer" means isomers that differ in the orientation of substituent atoms in relationship to a carbon-carbon double bond, to a cycloalkyl ring, or to a bridged bicyclic system.

Atoms (other than H) on each side of a carbon-carbon double bond may be in an E (substituents are on 25 opposite sides of the carbon-carbon double bond) or Z (substituents are oriented on the same side) configuration. "R," "S," "S*," "R*," "E," "Z," "cis," and "trans," indicate configurations relative to the core molecule. Certain of the disclosed compounds may exist in atropisomeric forms. Atropisomers are stereoisomers resulting from hindered rotation about single bonds where the steric strain barrier to rotation is high enough to allow for the isolation of the conformers. The compounds described herein may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide 35 of each of the isomers of an isomeric pair using an optically pure acid, amine or alcohol (followed by chromatographic separation and removal of the chiral auxiliary), or resolving an isomeric mixture of either a starting material or a final product using various well known chromatographic methods. When the stereochemistry of a disclosed compound is named or depicted by structure, the named or depicted stereoisomer is at least 60%, 70%, 80%, 90%, 99%, or 99.9% by weight relative to the other stereoisomers. When a single enantiomer is named or depicted by structure, the depicted or named enantiomer is at least 60%, 70%, 80%, 90%, 99%, or 99.9% by weight optically pure. When a single diastereomer is named or depicted by structure, the depicted or named diastereomer is at least 60%, 70%, 80%, 90%, 99%, or 99.9% by weight pure. Percent optical purity is the ratio of the weight of the enantiomer or over the weight of the enantiomer plus the weight of its optical isomer. Diastereomeric purity by weight is the ratio of the weight of one diastereomer or over the weight of all the diastereomers. When the stereochemistry of a disclosed compound is named or depicted by structure, the named or depicted stereoisomer is at least 60%, 70%, 80%, 90%, 99%, or 99.9% by mole fraction pure relative to the other stereoisomers. When a single enantiomer is named or depicted by structure, the depicted or named enantiomer is at least 60%, 70%, 80%, 90%, 99%, or 99.9% by mole fraction pure. When a single diastereomer is named or depicted by structure, the depicted or named diastereomer is at least 60%, 70%, 80%, 90%, 99%, or 99.9% by mole fraction pure. Percent purity by mole fraction is the ratio of the moles of the enantiomer or over the moles of the enantiomer plus the moles of its optical isomer. Similarly, percent purity by moles fraction is the ratio of the moles of the diastereomer or over the moles of the diastereomer plus the moles of its isomer. When a disclosed compound is named or depicted by structure without indicating the stereochemistry, and the compound has at least one chiral center, it is to be understood that the name or structure encompasses either enantiomer of the compound free from the corresponding optical isomer, a racemic mixture of the compound, or mixtures enriched in one enantiomer relative to its corresponding optical isomer. When a disclosed compound is named or depicted by structure without indicating the stereochemistry and has two or more chiral centers, it is to be understood that the name or structure encompasses a diastereomer free of other diastereomers, a number of diastereomers free from other diastereomeric pairs, mixtures of diastereomers, mixtures of diastereomeric pairs, mixtures of diastereomers in which one diastereomer is enriched relative to the other diastereomer(s), or mixtures of diastereomers in which one or more diastereomer is enriched relative to the other diastereomers. The invention embraces all of these forms.

Unless otherwise defined, all technical and scientific terms used herein have the same meaning as commonly understood by one of ordinary skill in the art to which this invention belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Definitions

In this application, unless otherwise clear from context, (i) the term "a" may be understood to mean "at least one"; (ii) the term "or" may be understood to mean "and/or"; and (iii) the terms "including" and "including" may be understood to encompass itemized components or steps whether presented by themselves or together with one or more additional components or steps.

As used herein, the terms "about" and "approximately" refer to a value that is within 10% above or below the value being described. For example, the term "about 5 nM" indicates a range of from 4.5 to 5.5 nM.

As used herein, the term "administration" refers to the administration of a composition (e.g., a compound or a preparation that includes a compound as described herein) to a subject or system. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intratumoral, intravenous, intraventricular, mucosal, nasal, oral, rectal, subcutaneous, sublingual, topical, tracheal (including by intratracheal instillation), transdermal, vaginal, and vitreal.

As used herein, the term "adult soft tissue sarcoma" refers to a sarcoma that develops in the soft tissues of the body, typically in adolescent and adult subjects (e.g., subjects who are at least 10 years old, 11 years old, 12 years old, 13 years old, 14 years old, 15 years old, 16 years old, 17 years old, 18 years old, or 19 years old). Non-limiting examples of adult soft tissue sarcoma include, but are not limited to, synovial sarcoma, fibrosarcoma, malignant fibrous histiocytoma, dermatofibrosarcoma, liposarcoma, leiomyosarcoma, hemangiosarcoma, Kaposi's sarcoma, lymphangiosarcoma, malignant peripheral nerve sheath tumor/neurofibrosarcoma, extraskeletal chondrosarcoma, extraskeletal osteosarcoma, extraskeletal myxoid chondrosarcoma, and extraskeletal mesenchymal.

As used herein, the term "BAF complex" refers to the BRG1- or HRBM-associated factors complex in a human cell.

As used herein, the terms "GBAF complex" and "GBAF" refer to a SWI/SNF ATPase chromatin remodeling complex in a human cell. GBAF complex subunits may include, but are not limited to, ACTB, ACTL6A, ACTL6B, BICRA, BICRAL, BRD9, SMARCA2, SMARCA4, SMARCC1, SMARCD1, SMARCD2, SMARCD3, and SS18. The term "cancer" refers to a condition caused by the proliferation of malignant neoplastic cells, such as tumors, neoplasms, carcinomas, sarcomas, leukemias, and lymphomas.

As used herein, a "combination therapy" or "administered in combination" means that two (or more) different agents or treatments are administered to a subject as part of a defined treatment regimen for a particular disease or condition. The treatment regimen defines the doses and periodicity of administration of each agent such that the effects of the separate agents on the subject overlap. In some embodiments, the delivery of the two or more agents is simultaneous or concurrent and the agents may be co-formulated. In some embodiments, the two or more agents are not co-formulated and are administered in a sequential manner as part of a prescribed regimen. In some embodiments, administration of two or more agents or treatments in combination is such that the reduction in a symptom, or other parameter related to the disorder is greater than what would be observed with one agent or treatment delivered alone or in the absence of the other. The effect of the two treatments can be partially additive, wholly additive, or greater than additive (e.g., synergistic). Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination may be administered by intravenous injection while a second therapeutic agent of the combination may be administered orally.

As used herein, the term "BRD9" refers to bromodomain-containing protein 9, a component of the BAF (BRG1- or BRM-associated factors) complex, a SWI/SNF ATPase chromatin remodeling complex, and belongs to family IV of the bromodomain-containing proteins. BRD9 is encoded by the BRD9 gene, the nucleic acid sequence of which is set forth in SEQ ID NO: 1. The term "BRD9" also refers to natural variants of the wild-type BRD9 protein, such as proteins having at least 85% identity (e.g., 85%, 86%, 87%, 88%, 89%, 90%, 91%, 92%, 93%, 94%, 95%, 96%, 97%, 98%, 99%, 99.9% identity, or more) to the amino acid sequence of wild-type BRD9, which is set forth in SEQ ID NO: 2.

As used herein, the term "degrader" refers to a small molecule compound including a degradation moiety, wherein the compound interacts with a protein (e.g., BRD9) in a way which results in degradation of the protein, e.g., binding of the compound results in at least 5% reduction of the level of the protein, e.g., in a cell or subject.

As used herein, the term "degradation moiety" refers to a moiety whose binding results in degradation of a protein, e.g., BRD9. In one example, the moiety binds to a protease or a ubiquitin ligase that metabolizes the protein, e.g., BRD9.

By "determining the level of a protein" is meant the detection of a protein, or an mRNA encoding the protein, by methods known in the art either directly or indirectly. "Directly determining" means performing a process (e.g., performing an assay or test on a sample or "analyzing a sample" as that term is defined herein) to obtain the physical entity or value. "Indirectly determining" refers to receiving the physical entity or value from another party or source (e.g., a third-party laboratory that directly acquired the physical entity or value). Methods to measure protein level generally include, but are not limited to, western blotting, immunoblotting, enzyme-linked immunosorbent assay (ELISA), radioimmunoassay (RIA), immunoprecipitation, immunofluorescence, surface plasmon resonance, chemiluminescence, fluorescent polarization, phosphorescence, immunohistochemical analysis, matrix-assisted laser desorption/ionization time-of-flight (MALDI-TOF) mass spectrometry, liquid chromatography (LC)-mass spectrometry, microcytometry, microscopy, fluorescence activated cell sorting (FACS), and flow cytometry, as well as assays based on a property of a protein including, but not limited to, enzymatic activity or interaction with other protein partners. Methods to measure mRNA levels are known in the art.

By "modulating the activity of a BAF complex," is meant altering the level of an activity related to a BAF complex (e.g., GBAF), or a related downstream effect. The activity level of a BAF complex may be measured using any method known in the art, e.g., the methods described in Kadoch et al, Cell 153:71-85 (2013), the methods of which are herein incorporated by reference.

By "reducing the activity of BRD9," is meant decreasing the level of an activity related to an BRD9, or a related downstream effect. A non-limiting example of inhibition of an activity of BRD9 is decreasing the level of a BAF complex (e.g., GBAF) in a cell. The activity level of BRD9 may be measured using any method known in the art. In some embodiments, an agent which reduces the activity of BRD9 is a small molecule BRD9 inhibitor. In some embodiments, an agent which reduces the activity of BRD9 is a small molecule BRD9 degrader.

By "reducing the level of BRD9," is meant decreasing the level of BRD9 in a cell or subject. The level of BRD9 may be measured using any method known in the art.

By "level" is meant a level of a protein, or mRNA encoding the protein, as compared to a reference. The reference can be any useful reference, as defined herein. By a "decreased level" or an "increased level" of a protein is meant a decrease or increase in protein level, as compared to a reference (e.g., a decrease or an increase by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 150%, about 200%, about 300%, about 400%, about 500%, or more; a decrease or an increase of more than about 10%, about 15%, about 20%, about 50%, about 75%, about 100%, or about 200%, as compared to a reference; a decrease or an increase by less than about 0.01-fold, about 0.02-fold, about 0.1-fold, about 0.3-fold, about 0.5-fold, about 0.8-fold, or less; or an increase by more than about 1.2-fold, about 1.4-fold, about 1.5-fold, about 1.8-fold, about 2.0-fold, about 3.0-fold, about 3.5-fold, about 4.5-fold, about 5.0-fold, about 10-fold, about 15-fold, about 20-fold, about 30-fold, about 40-fold, about 50-fold, about 100-fold, about 1000-fold, or more). A level of a protein may be expressed in mass/vol (e.g., g/dL, mg/mL, μg/mL, ng/mL) or percentage relative to total protein or mRNA in a sample.

As used herein, the term "inhibitor" refers to any agent which reduces the level and/or activity of a protein (e.g., BRD9). Non-limiting examples of inhibitors include small molecule inhibitors, degraders, antibodies, enzymes, or polynucleotides (e.g., siRNA).

As used herein, the terms "effective amount," "therapeutically effective amount," and "a sufficient amount" of an agent that reduces the level and/or activity of BRD9 (e.g., in a cell or a subject) described herein refer to a quantity sufficient to, when administered to the subject, including a human, effect beneficial or desired results, including clinical results, and, as such, an "effective amount" or synonym thereto depends on the context in which it is being applied. For example, in the context of treating cancer, it is an amount of the agent that reduces the level and/or activity of BRD9 sufficient to achieve a treatment response as compared to the response obtained without administration of the agent that reduces the level and/or activity of BRD9. The amount of a given agent that reduces the level and/or activity of BRD9 described herein that will correspond to such an amount will vary depending upon various factors, such as the given agent, the pharmaceutical formulation, the route of administration, the type of disease or disorder, the identity of the subject (e.g., age, sex, and/or weight) or host being treated, and the like, but can nevertheless be routinely determined by one of skill in the art. Also, as used herein, a "therapeutically effective amount" of an agent that reduces the level and/or activity of BRD9 of the present disclosure is an amount which results in a beneficial or desired result in a subject as compared to a control. As defined herein, a therapeutically effective amount of an agent that reduces the level and/or activity of BRD9 of the present disclosure may be readily determined by one of ordinary skill by routine methods known in the art. Dosage regimen may be adjusted to provide the optimum therapeutic response.

The term "inhibitory RNA agent" refers to an RNA, or analog thereof, having sufficient sequence complementarity to a target RNA to direct RNA interference. Examples also include a DNA that can be used to make the RNA. RNA interference (RNAi) refers to a sequence-specific or selective process by which a target molecule (e.g., a target gene, protein, or RNA) is down-regulated. Generally, an interfering RNA ("iRNA") is a double-stranded short-interfering RNA (siRNA), short hairpin RNA (shRNA), or single-stranded micro-RNA (miRNA) that results in catalytic degradation of specific mRNAs, and also can be used to lower or inhibit gene expression.

The terms "short interfering RNA" and "siRNA" (also known as "small interfering RNAs") refer to an RNA agent, preferably a double-stranded agent, of about 10-50 nucleotides in length, the strands optionally having overhanging ends comprising, for example 1, 2 or 3 overhanging nucleotides (or nucleotide analogs), which is capable of directing or mediating RNA interference. Naturally-occurring siRNAs are generated from longer dsRNA molecules (e.g., >25 nucleotides in length) by a cell's RNAi machinery (e.g., Dicer or a homolog thereof).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region.

The terms "miRNA" and "microRNA" refer to an RNA agent, preferably a single-stranded agent, of about 10-50 nucleotides in length, preferably between about 15-25 nucleotides in length, which is capable of directing or mediating RNA interference. Naturally-occurring miRNAs are generated from stem-loop precursor RNAs (i.e., pre-miRNAs) by Dicer. The term "Dicer" as used herein, includes Dicer as well as any Dicer ortholog or homolog capable of processing dsRNA structures into siRNAs, miRNAs, siRNA-like or miRNA-like molecules. The term microRNA ("miRNA") is used interchangeably with the term "small temporal RNA" ("stRNA") based on the fact that naturally-occurring miRNAs have been found to be expressed in a temporal fashion (e.g., during development).

The term "antisense," as used herein, refers to a nucleic acid comprising a polynucleotide that is sufficiently complementary to all or a portion of a gene, primary transcript, or processed mRNA, so as to interfere with expression of the endogenous gene (e.g., BRD9). "Complementary" polynucleotides are those that are capable of base pairing according to the standard Watson-Crick complementarity rules.

Specifically, purines will base pair with pyrimidines to form a combination of guanine paired with cytosine (G:C) and adenine paired with either thymine (A:T) in the case of DNA, or adenine paired with uracil (A:U) in the case of RNA. It is understood that two polynucleotides may hybridize to each other even if they are not completely complementary to each other, provided that each has at least one region that is substantially complementary to the other.

The term "antisense nucleic acid" includes single-stranded RNA as well as double-stranded DNA expression cassettes that can be transcribed to produce an antisense RNA. "Active" antisense nucleic acids are antisense RNA molecules that are capable of selectively hybridizing with a primary transcript or mRNA encoding a polypeptide having at least 80% sequence identity (e.g., 80%, 85%, 86%, 87%, 88%, 89%, 90%, 91%, 92%, 93%, 94%, 95%, 96%, 97%, 98%, 99%, 99.9% identity, or more) with the targeted polypeptide sequence (e.g., a BRD9 polypeptide sequence). The antisense nucleic acid can be complementary to an entire coding strand, or to only a portion thereof. In some embodiments, an antisense nucleic acid molecule is antisense to a "coding region" of the coding strand of a nucleotide sequence. The term "coding region" refers to the region of the nucleotide sequence comprising codons that are translated into amino acid residues. In some embodiments, the antisense nucleic acid molecule is antisense to a "noncoding region" of the coding strand of a nucleotide sequence. The term "noncoding region" refers to 5' and 3' sequences that flank the coding region that are not translated into amino acids (i.e., also referred to as 5' and 3' untranslated regions). The antisense nucleic acid molecule can be complementary to the entire coding region of mRNA, or can be antisense to only a portion of the coding or noncoding region of an mRNA. For example, the antisense oligonucleotide can be complementary to the region surrounding the translation start site. An antisense oligonucleotide can be, for example, about 5, 10, 15, 20, 25, 30, 35, 40, 45, or 50 nucleotides in length.

"Percent (%) sequence identity" with respect to a reference polynucleotide or polypeptide sequence is defined as the percentage of nucleic acids or amino acids in a candidate sequence that are identical to the nucleic acids or amino acids in the reference polynucleotide or polypeptide sequence, after aligning the sequences and introducing gaps, if necessary, to achieve the maximum percent sequence identity. Alignment for purposes of determining percent nucleic acid or amino acid sequence identity can be achieved in various ways that are within the capabilities of one of skill in the art, for example, using publicly available computer software such as BLAST, BLAST-2, or Megalign software. Those skilled in the art can determine appropriate parameters for aligning sequences, including any algorithms needed to achieve maximal alignment over the full length of the sequences being compared.

For example, percent sequence identity values may be generated using the sequence comparison computer program BLAST. As an illustration, the percent sequence identity of a given nucleic acid or amino acid sequence, A, to, with, or against a given nucleic acid or amino acid sequence, B, (which can alternatively be phrased as a given nucleic acid or amino acid sequence, A that has a certain percent sequence identity to, with, or against a given nucleic acid or amino acid sequence, B) is calculated as follows:

100 multiplied by (the fraction X/Y)

where X is the number of nucleotides or amino acids scored as identical matches by a sequence alignment program (e.g., BLAST) in that program's alignment of A and B, and where Y is the total number of nucleic acids in B. It will be appreciated that where the length of nucleic acid or amino acid sequence A is not equal to the length of nucleic acid or amino acid sequence B, the percent sequence identity of A to B will not equal the percent sequence identity of B to A.

The term "pharmaceutical composition," as used herein, represents a composition containing a compound described herein formulated with a pharmaceutically acceptable excipient, and manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other pharmaceutically acceptable formulation.

A "pharmaceutically acceptable excipient," as used herein, refers any ingredient other than the compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

As used herein, the term "pharmaceutically acceptable salt" means any pharmaceutically acceptable salt of the compound of any of the compounds described herein. For example, pharmaceutically acceptable salts of any of the compounds described herein include those that are within the scope of sound medical judgment, suitable for use in contact with the tissues of humans and animals without undue toxicity, irritation, allergic response and are commensurate with a reasonable benefit/risk ratio. Pharmaceutically acceptable salts are well known in the art. For example, pharmaceutically acceptable salts are described in: Berge et al., J. Pharmaceutical Sciences 66:1-19, 1977 and in Pharmaceutical Salts: Properties, Selection, and Use, (Eds. P. H. Stahl and C. G. Wermuth), Wiley-VCH, 2008. The salts can be prepared in situ during the final isolation and purification of the compounds described herein or separately by reacting a free base group with a suitable organic acid.

The compounds described herein may have ionizable groups so as to be capable of preparation as pharmaceutically acceptable salts. These salts may be acid addition salts involving inorganic or organic acids or the salts may, in the case of acidic forms of the compounds described herein, be prepared from inorganic or organic bases. Frequently, the compounds are prepared or used as pharmaceutically acceptable salts prepared as addition products of pharmaceutically acceptable acids or bases. Suitable pharmaceutically acceptable acids and bases and methods for preparation of the appropriate salts are well-known in the art. Salts may be prepared from pharmaceutically acceptable non-toxic acids and bases including inorganic and organic acids and bases. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, and valerate salts. Representative alkali or alkaline earth metal salts include sodium, lithium, potassium, calcium, and magnesium, as well as nontoxic ammonium, quaternary ammonium, and amine cations, including, but not limited to ammonium, tetramethylammonium, tetraethylammonium, methylamine, dimethylamine, trimethylamine, triethylamine, and ethylamine.

By a "reference" is meant any useful reference used to compare protein or mRNA levels. The reference can be any sample, standard, standard curve, or level that is used for comparison purposes. The reference can be a normal reference sample or a reference standard or level. A "reference sample" can be, for example, a control, e.g., a predetermined negative control value such as a "normal control" or a prior sample taken from the same subject; a sample from a normal healthy subject, such as a normal cell or normal tissue; a sample (e.g., a cell or tissue) from a subject not having a disease; a sample from a subject that is diagnosed with a disease, but not yet treated with a compound described herein; a sample from a subject that has been treated by a compound described herein; or a sample of a purified protein (e.g., any described herein) at a known normal concentration. By "reference standard or level" is meant a value or number derived from a reference sample. A "normal control value" is a pre-determined value indicative of non-disease state, e.g., a value expected in a healthy control subject. Typically, a normal control value is expressed as a range ("between X and Y"), a high threshold ("no higher than X"), or a low threshold ("no lower than X"). A subject having a measured value within the normal control value for a particular biomarker is typically referred to as "within normal limits" for that biomarker. A normal reference standard or level can be a value or number derived from a normal subject not having a disease or disorder (e.g., cancer); a subject that has been treated with a compound described herein. In preferred embodiments, the reference sample, standard, or level is matched to the sample subject sample by at least one of the following criteria: age, weight, sex, disease stage, and overall health. A standard curve of levels of a purified protein, e.g., any described herein, within the normal reference range can also be used as a reference.

As used herein, the term "subject" refers to any organism to which a composition in accordance with the invention may be administered, e.g., for experimental, diagnostic, prophylactic, and/or therapeutic purposes. Typical subjects include any animal (e.g., mammals such as mice, rats, rabbits, non-human primates, and humans). A subject may seek or be in need of treatment, require treatment, be receiving treatment, be receiving treatment in the future, or be a human or animal who is under care by a trained professional for a particular disease or condition.

As used herein, the terms "treat," "treated," or "treating" mean both therapeutic treatment and prophylactic or preventative measures wherein the object is to prevent or slow down (lessen) an undesired physiological condition, disorder, or disease, or obtain beneficial or desired clinical results. Beneficial or desired clinical results include, but are not limited to, alleviation of symptoms; diminishment of the extent of a condition, disorder, or disease; stabilized (i.e., not worsening) state of condition, disorder, or disease; delay in onset or slowing of condition, disorder, or disease progression; amelioration of the condition, disorder, or disease state or remission (whether partial or total), whether detectable or undetectable; an amelioration of at least one measurable physical parameter, not necessarily discernible by the patient; or enhancement or improvement of condition, disorder, or disease. Treatment includes eliciting a clinically significant response without excessive levels of side effects. Treatment also includes prolonging survival as compared to expected survival if not receiving treatment.

As used herein, the terms "variant" and "derivative" are used interchangeably and refer to naturally-occurring, synthetic, and semi-synthetic analogues of a compound, peptide, protein, or other substance described herein. A variant or derivative of a compound, peptide, protein, or other substance described herein may retain or improve upon the biological activity of the original material.

The details of one or more embodiments of the invention are set forth in the description below. Other features, objects, and advantages of the invention will be apparent from the description and from the claims.

DETAILED DESCRIPTION

Figure 1:
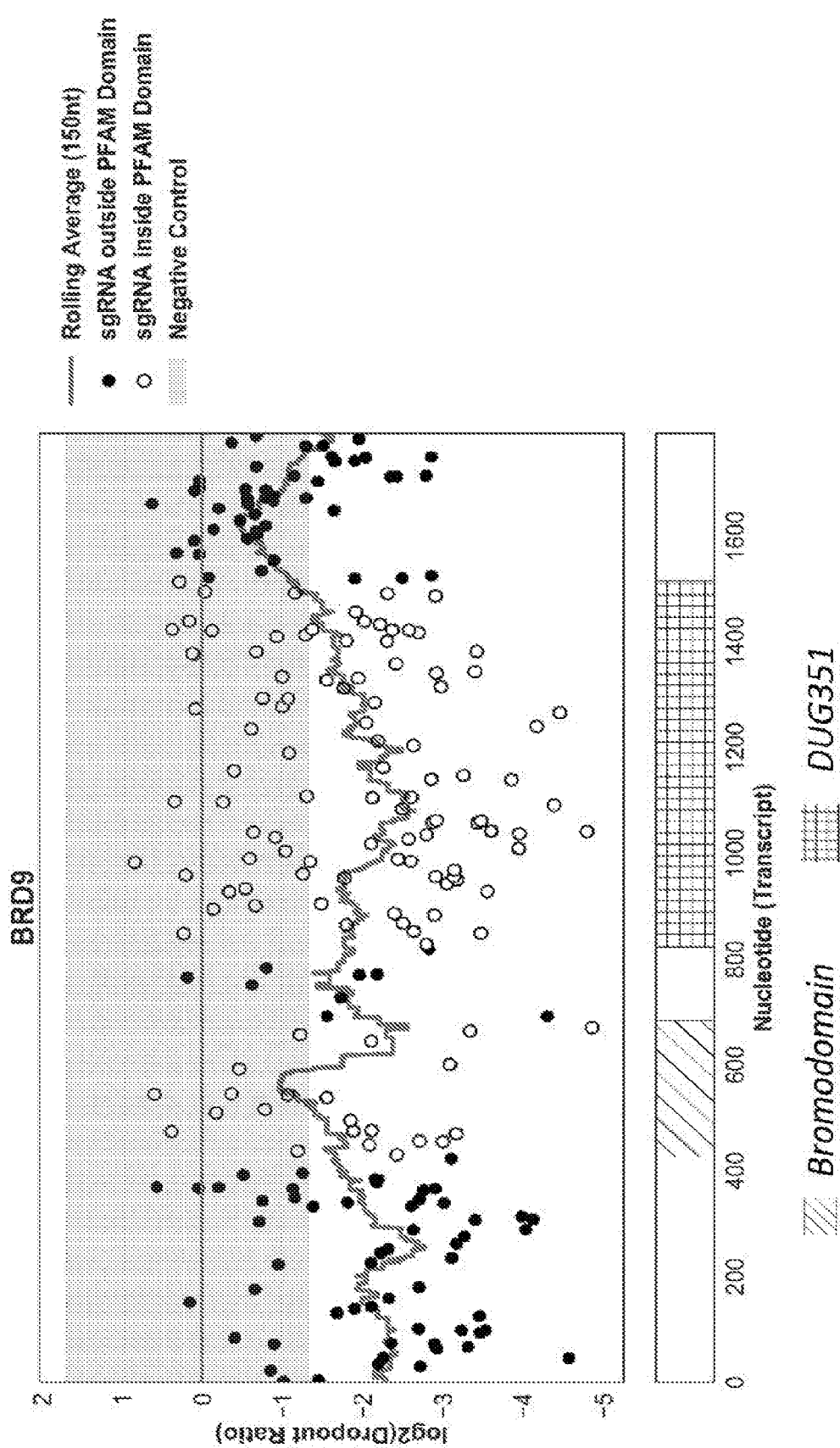
FIG. 1 is a series of graphs illustrating the effect of specific guide RNA (sgRNA) targeting of the BRD9 BAF complex subunit on synovial sarcoma cell growth. The Y-axis indicated the dropout ratio. The X-axis indicates the nucleotide position of the BRD9 gene. The grey box indicates the range of the negative control sgRNAs in the screen. The SYO1 cell line carries SS18-SSX2 fusion protein. The breakpoint joining the N-terminal region of SS18 to the C-terminal region of SSX2 are indicated by the black lines in their respective panel. The linear protein sequence is show with BRD9 PFAM domains annotated from the PFAM database.

The present inventors have found that depletion of BRD9 in cancer cells results in the depletion of the SS18-SSX fusion protein and further inhibits the proliferation of the cancer cells.

Accordingly, the invention features methods and compositions useful for the inhibition of the activity of the SS18-SSX fusion proteins, e.g., for the treatment of cancer such as adult soft tissue sarcomas. The invention further features methods and compositions useful for inhibition of the activity of the BRD9 protein, e.g., for the treatment of cancer such as adult soft tissue sarcomas, e.g., in a subject in need thereof. Exemplary methods are described herein.

Compounds

Agents described herein that reduce the level and/or activity of BRD9 in a cell may be an antibody, a protein (such as an enzyme), a polynucleotide, or a small molecule compound. The agents reduce the level of an activity related to BRD9, or a related downstream effect, or reduce the level of BRD9 in a cell or subject.

Small Molecule Compounds

In some embodiments of the invention, the agent that reduces the level and/or activity of BRD9 in a cell is a small molecule compound. In some embodiments, the small molecule compound is a structure of Formula I:

A-L-B          Formula I where A is a BRD9 binding moiety; L is a linker; and B is a degradation moiety, or a pharmaceutically acceptable salt thereof. In some embodiments, the degradation moiety is a ubiquitin ligase moiety. In some embodiments, the ubiquitin ligase binding moiety includes Cereblon ligands, IAP (Inhibitors of Apoptosis) ligands, mouse double minute 2 homolog (MDM2), hydrophobic tag, or von Hippel-Lindau ligands, or derivatives or analogs thereof.

Pharmaceutical Uses

The compounds described herein are useful in the methods of the invention and, while not bound by theory, are believed to exert their desirable effects through their ability to modulate the level, status, and/or activity of a BAF complex, e.g., by inhibiting the activity or level of the BRD9 protein in a cell within the BAF complex in a mammal.

An aspect of the present invention relates to methods of treating disorders related to BRD9 such as cancer in a subject in need thereof. In some embodiments, the compound is administered in an amount and for a time effective to result in one of (or more, e.g., two or more, three or more, four or more of): (a) reduced tumor size, (b) reduced rate of tumor growth, (c) increased tumor cell death (d) reduced tumor progression, (e) reduced number of metastases, (f) reduced rate of metastasis, (g) decreased tumor recurrence (h) increased survival of subject, and (i) increased progression free survival of a subject.

Treating cancer can result in a reduction in size or volume of a tumor. For example, after treatment, tumor size is reduced by 5% or greater (e.g., 10%, 20%, 30%, 40%, 50%, 60%, 70%, 80%, 90%, or greater) relative to its size prior to treatment. Size of a tumor may be measured by any reproducible means of measurement. For example, the size of a tumor may be measured as a diameter of the tumor.

Treating cancer may further result in a decrease in number of tumors. For example, after treatment, tumor number is reduced by 5% or greater (e.g., 10%, 20%, 30%, 40%, 50%, 60%, 70%, 80%, 90%, or greater) relative to number prior to treatment. Number of tumors may be measured by any reproducible means of measurement, e.g., the number of tumors may be measured by counting tumors visible to the naked eye or at a specified magnification (e.g., 2×, 3×, 4×, 5×, 10×, or 50×).

Treating cancer can result in a decrease in number of metastatic nodules in other tissues or organs distant from the primary tumor site. For example, after treatment, the number of metastatic nodules is reduced by 5% or greater (e.g., 10%, 20%, 30%, 40%, 50%, 60%, 70%, 80%, 90% or greater) relative to number prior to treatment. The number of metastatic nodules may be measured by any reproducible means of measurement. For example, the number of metastatic nodules may be measured by counting metastatic nodules visible to the naked eye or at a specified magnification (e.g., 2×, 10×, or 50×).

Treating cancer can result in an increase in average survival time of a population of subjects treated according to the present invention in comparison to a population of untreated subjects. For example, the average survival time is increased by more than 30 days (more than 60 days, 90 days, or 120 days). An increase in average survival time of a population may be measured by any reproducible means. An increase in average survival time of a population may be measured, for example, by calculating for a population the average length of survival following initiation of treatment with the compound described herein. An increase in average survival time of a population may also be measured, for example, by calculating for a population the average length of survival following completion of a first round of treatment with a pharmaceutically acceptable salt of a compound described herein.

Treating cancer can also result in a decrease in the mortality rate of a population of treated subjects in comparison to an untreated population. For example, the mortality rate is decreased by more than 2% (e.g., more than 5%, 10%, or 25%). A decrease in the mortality rate of a population of treated subjects may be measured by any reproducible means, for example, by calculating for a population the average number of disease-related deaths per unit time following initiation of treatment with a pharmaceutically acceptable salt of a compound described herein. A decrease in the mortality rate of a population may also be measured, for example, by calculating for a population the average number of disease-related deaths per unit time following completion of a first round of treatment with a pharmaceutically acceptable salt of a compound described herein.

Combination Therapies

A method of the invention can be used alone or in combination with an additional therapeutic agent, e.g., other agents that treat cancer or symptoms associated therewith, or in combination with other types of therapies to treat cancer. In combination treatments, the dosages of one or more of the therapeutic compounds may be reduced from standard dosages when administered alone. For example, doses may be determined empirically from drug combinations and permutations or may be deduced by isobolographic analysis (e.g., Black et al., Neurology 65:S3-S6 (2005)). In this case, dosages of the compounds when combined should provide a therapeutic effect.

In some embodiments, the second therapeutic agent is a chemotherapeutic agent (e.g., a cytotoxic agent or other chemical compound useful in the treatment of cancer). These include alkylating agents, antimetabolites, folic acid analogs, pyrimidine analogs, purine analogs and related inhibitors, vinca alkaloids, epipodopyyllotoxins, antibiotics, L-Asparaginase, topoisomerase inhibitors, interferons, platinum coordination complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analog. Also included is 5-fluorouracil (5-FU), leucovorin (LV), irenotecan, oxaliplatin, capecitabine, paclitaxel, and doxetaxel. Non-limiting examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, Chem. Intl. Ed Engl. 33:183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin, including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE®, cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DMFO); retinoids such as retinoic acid; capecitabine; and pharmaceutically acceptable salts, acids or derivatives of any of the above. Two or more chemotherapeutic agents can be used in a cocktail to be administered in combination with the first therapeutic agent described herein. Suitable dosing regimens of combination chemotherapies are known in the art and described in, for example, Saltz et al., *Proc. Am. Soc. Clin. Onco.* 18:233a (1999), and Douillard et al., *Lancet* 355(9209):1041-1047 (2000).

In some embodiments, the second therapeutic agent is a therapeutic agent which is a biologic such a cytokine (e.g., interferon or an interleukin (e.g., IL-2)) used in cancer treatment. In some embodiments the biologic is an anti-angiogenic agent, such as an anti-VEGF agent, e.g., bevacizumab (AVASTIN®). In some embodiments the biologic is an immunoglobulin-based biologic, e.g., a monoclonal antibody (e.g., a humanized antibody, a fully human antibody, an Fc fusion protein or a functional fragment thereof) that agonizes a target to stimulate an anti-cancer response, or antagonizes an antigen important for cancer. Such agents include RITUXAN (rituximab); ZENAPAX® (daclizumab); SIMULECT® (basiliximab); SYNAGIS® (palivizumab); REMICADE® (infliximab); HERCEPTIN® (trastuzumab); MYLOTARG® (gemtuzumab ozogamicin); CAMPATH® (alemtuzumab); ZEVALIN® (ibritumomab tiuxetan); HUMIRA® (adalimumab); XOLAIR® (omalizumab); BEXXAR® (tositumomab-I-131); RAPTIVA® (efalizumab); ERBITUX® (cetuximab); AVASTIN® (bevacizumab); TYSABRI® (natalizumab); ACTEMRA® (tocilizumab); VECTIBIX® (panitumumab); LUCENTIS® (ranibizumab); SOLIRIS® (eculizumab); CIMZIA® (certolizumab pegol); SIMPONI® (golimumab); ILARIS® (canakinumab); STELARA® (ustekinumab); ARZERRA® (ofatumumab); PROLIA® (denosumab); NUMAX® (motavizumab); ABTHRAX® (raxibacumab); BENLYSTA® (belimumab); YERVOY® (ipilimumab); ADCETRIS® (brentuximab vedotin); PERJETA® (pertuzumab); KADCYLA® (ado-trastuzumab emtansine); and GAZYVA® (obinutuzumab). Also included are antibody-drug conjugates.

The second agent may be a therapeutic agent which is a non-drug treatment. For example, the second therapeutic agent is radiation therapy, cryotherapy, hyperthermia, and/or surgical excision of tumor tissue.

The second agent may be a checkpoint inhibitor. In one embodiment, the inhibitor of checkpoint is an inhibitory antibody (e.g., a monospecific antibody such as a monoclonal antibody). The antibody may be, e.g., humanized or fully human. In some embodiments, the inhibitor of checkpoint is a fusion protein, e.g., an Fc-receptor fusion protein. In some embodiments, the inhibitor of checkpoint is an agent, such as an antibody, that interacts with a checkpoint protein. In some embodiments, the inhibitor of checkpoint is an agent, such as an antibody, that interacts with the ligand of a checkpoint protein. In some embodiments, the inhibitor of checkpoint is an inhibitor (e.g., an inhibitory antibody or small molecule inhibitor) of CTLA-4 (e.g., an anti-CTLA4 antibody or fusion a protein such as ipilimumab/YERVOY® or tremelimumab). In some embodiments, the inhibitor of checkpoint is an inhibitor (e.g., an inhibitory antibody or small molecule inhibitor) of PD-1 (e.g., nivolumab/OPDIVO®; pembrolizumab/KEYTRUDA®; pidilizumab/CT-011). In some embodiments, the inhibitor of checkpoint is an inhibitor (e.g., an inhibitory antibody or small molecule inhibitor) of PDL1 (e.g., MPDL3280A/RG7446; MEDI4736; MSB0010718C; BMS 936559). In some embodiments, the inhibitor of checkpoint is an inhibitor (e.g., an inhibitory antibody or Fc fusion or small molecule inhibitor) of PDL2 (e.g., a PDL2/Ig fusion protein such as AMP 224). In some embodiments, the inhibitor of checkpoint is an inhibitor (e.g., an inhibitory antibody or small molecule inhibitor) of B7-H3 (e.g., MGA271), B7-H4, BTLA, HVEM, TIM3, GAL9, LAG3, VISTA, KIR, 2B4, CD160, CGEN-15049, CHK 1, CHK2, A2aR, B-7 family ligands, or a combination thereof.

In some embodiments, the anti-cancer therapy is a T cell adoptive transfer (ACT) therapy. In some embodiments, the T cell is an activated T cell. The T cell may be modified to express a chimeric antigen receptor (CAR). CAR modified T (CAR-T) cells can be generated by any method known in the art. For example, the CAR-T cells can be generated by introducing a suitable expression vector encoding the CAR to a T cell. Prior to expansion and genetic modification of the T cells, a source of T cells is obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In some embodiments, the T cell is an autologous T cell. Whether prior to or after genetic modification of the T cells to express a desirable protein (e.g., a CAR), the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

In any of the combination embodiments described herein, the first and second therapeutic agents are administered simultaneously or sequentially, in either order. The first therapeutic agent may be administered immediately, up to 1 hour, up to 2 hours, up to 3 hours, up to 4 hours, up to 5 hours, up to 6 hours, up to 7 hours, up to, 8 hours, up to 9 hours, up to 10 hours, up to 11 hours, up to 12 hours, up to 13 hours, 14 hours, up to hours 16, up to 17 hours, up 18 hours, up to 19 hours up to 20 hours, up to 21 hours, up to 22 hours, up to 23 hours up to 24 hours or up to 1-7, 1-14, 1-21 or 1-30 days before or after the second therapeutic agent.

Pharmaceutical Compositions

The pharmaceutical compositions described herein are preferably formulated into pharmaceutical compositions for administration to human subjects in a biologically compatible form suitable for administration in vivo.

The compounds described herein may be used in the form of the free base, in the form of salts, solvates, and as prodrugs. All forms are within the methods described herein. In accordance with the methods of the invention, the described compounds or salts, solvates, or prodrugs thereof may be administered to a patient in a variety of forms depending on the selected route of administration, as will be understood by those skilled in the art. The compounds described herein may be administered, for example, by oral, parenteral, buccal, sublingual, nasal, rectal, patch, pump, intratumoral, or transdermal administration and the pharmaceutical compositions formulated accordingly. Parenteral administration includes intravenous, intraperitoneal, subcutaneous, intramuscular, transepithelial, nasal, intrapulmonary, intrathecal, rectal, and topical modes of administration. Parenteral administration may be by continuous infusion over a selected period of time.

A compound described herein may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, a compound described herein may be incorporated with an excipient and used in the form of ingestible tablets, buccal tablets, troches, capsules, elixirs, suspensions, syrups, and wafers. A compound described herein may also be administered parenterally. Solutions of a compound described herein can be prepared in water suitably mixed with a surfactant, such as hydroxypropylcellulose.

Dispersions can also be prepared in glycerol, liquid polyethylene glycols, DMSO, and mixtures thereof with or without alcohol, and in oils. Under ordinary conditions of storage and use, these preparations may contain a preservative to prevent the growth of microorganisms. Conventional procedures and ingredients for the selection and preparation of suitable formulations are described, for example, in Remington's Pharmaceutical Sciences (2012, 22nd ed.) and in The United States Pharmacopeia: The National Formulary (USP 41 NF36), published in 2018. The pharmaceutical forms suitable for injectable use include sterile aqueous solutions or dispersions and sterile powders for the extemporaneous preparation of sterile injectable solutions or dispersions. In all cases the form must be sterile and must be fluid to the extent that may be easily administered via syringe. Compositions for nasal administration may conveniently be formulated as aerosols, drops, gels, and powders. Aerosol formulations typically include a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device, such as a single dose nasal inhaler or an aerosol dispenser fitted with a metering valve which is intended for disposal after use. Where the dosage form includes an aerosol dispenser, it will contain a propellant, which can be a compressed gas, such as compressed air or an organic propellant, such as fluorochlorohydrocarbon. The aerosol dosage forms can also take the form of a pump-atomizer. Compositions suitable for buccal or sublingual administration include tablets, lozenges, and pastilles, where the active ingredient is formulated with a carrier, such as sugar, acacia, tragacanth, gelatin, and glycerine. Compositions for rectal administration are conveniently in the form of suppositories containing a conventional suppository base, such as cocoa butter. A compound described herein may be administered intratumorally, for example, as an intratumoral injection. Intratumoral injection is injection directly into the tumor vasculature and is specifically contemplated for discrete, solid, accessible tumors. Local, regional, or systemic administration also may be appropriate. A compound described herein may advantageously be contacted by administering an injection or multiple injections to the tumor, spaced for example, at approximately, 1 cm intervals. In the case of surgical intervention, the present invention may be used preoperatively, such as to render an inoperable tumor subject to resection. Continuous administration also may be applied where appropriate, for example, by implanting a catheter into a tumor or into tumor vasculature.

The compounds described herein may be administered to an animal, e.g., a human, alone or in combination with pharmaceutically acceptable carriers, as noted herein, the proportion of which is determined by the solubility and chemical nature of the compound, chosen route of administration, and standard pharmaceutical practice.

Dosages

The dosage of the compounds described herein, and/or compositions including a compound described herein, can vary depending on many factors, such as the pharmacodynamic properties of the compound; the mode of administration; the age, health, and weight of the recipient; the nature and extent of the symptoms; the frequency of the treatment, and the type of concurrent treatment, if any; and the clearance rate of the compound in the animal to be treated. One of skill in the art can determine the appropriate dosage based on the above factors. The compounds described herein may be administered initially in a suitable dosage that may be adjusted as required, depending on the clinical response. In general, satisfactory results may be obtained when the compounds described herein are administered to a human at a daily dosage of, for example, between 0.05 mg and 3000 mg (measured as the solid form). Dose ranges include, for example, between 10-1000 mg (e.g., 50-800 mg). In some embodiments, 50, 100, 150, 200, 250, 300, 350, 400, 450, 500, 550, 600, 650, 700, 750, 800, 850, 900, 950, or 1000 mg of the compound is administered.

Alternatively, the dosage amount can be calculated using the body weight of the patient. For example, the dose of a compound, or pharmaceutical composition thereof, administered to a patient may range from 0.1-50 mg/kg (e.g., 0.25-25 mg/kg). In exemplary, non-limiting embodiments, the dose may range from 0.5-5.0 mg/kg (e.g., 0.5, 1.0, 1.5, 2.0, 2.5, 3.0, 3.5, 4.0, 4.5, or 5.0 mg/kg) or from 5.0-20 mg/kg (e.g., 5.5, 6.0, 6.5, 7.0, 7.5, 8.0, 8.5, 9.0, 9.5, 10, 11, 12, 13, 14, 15, 16, 17, 18, 19, or 20 mg/kg).

Kits

The invention also features kits including (a) a pharmaceutical composition including an agent that reduces the level and/or activity of BRD9 in a cell or subject described herein, and (b) a package insert with instructions to perform any of the methods described herein. In some embodiments, the kit includes (a) a pharmaceutical composition including an agent that reduces the level and/or activity of BRD9 in a cell or subject described herein, (b) an additional therapeutic agent (e.g., an anti-cancer agent), and (c) a package insert with instructions to perform any of the methods described herein.

EXAMPLES

Example 1—High Density Tiling sgRNA Screen Against Human BAF Complex Subunits in Synovial Sarcoma Cell Line SYO1

The following example shows that BRD9 sgRNA inhibits cell growth in synovial sarcoma cells.

Procedure:

To perform high density sgRNA tiling screen, an sgRNA library against BAF complex subunits was custom synthesized at Cellecta (Mountain View, Calif.). Sequences of DNA encoding the BRD9-targeting sgRNAs used in this screen are listed in Table 3. Negative and positive control sgRNA were included in the library. Negative controls consisted of 200 sgRNAs that do not target human genome. The positive controls are sgRNAs targeting essential genes (CDC16, GTF2B, HSPA5, HSPA9, PAFAHIB1, PCNA, POLR2L, RPL9, and SF3A3). DNA sequences encoding all positive and negative control sgRNAs are listed in Table 4. Procedures for virus production, cell infection, and performing the sgRNA screen were previously described (Tsherniak et al, Cell 170:564-576 (2017); Munoz et al, Cancer Discovery 6:900-913 (2016)). For each sgRNA, 50 counts were added to the sequencing counts and for each time point the resulting counts were normalized to the total number of counts. The log 2 of the ratio between the counts (defined as dropout ratio) at day 24 and day 1 post-infection was calculated. For negative control sgRNAs, the 2.5 and 97.5 percentile of the log 2 dropout ratio of all non-targeting sgRNAs was calculated and considered as background (grey box in the graph). Protein domains were obtained from PFAM regions defined for the UNIPROT identifier: Q9H8M2.

Results:

As shown in FIG. 1, targeted inhibition of the GBAF complex component BRD9 by sgRNA resulted in growth inhibition of the SYO1 synovial sarcoma cell line. sgRNAs against other components of the BAF complexes resulted in increased proliferation of cells, inhibition of cell growth, or had no effect on SYO1 cells. These data show that targeting various subunits of the GBAF complex represents a therapeutic strategy for the treatment of synovial sarcoma.

TABLE 3

BRD9 sgRNA Library

| SEQ ID NO | Nucleic Acid Sequence |
|---|---|
| 203 | CAAGAAGCACAAGAAGCACA |
| 204 | CTTGTGCTTCTTGCCCATGG |
| 205 | CTTCTTGTGCTTCTTGCCCA |
| 206 | ACAAGAAGCACAAGGCCGAG |
| 207 | CTCGTAGGACGAGCGCCACT |
| 208 | CGAGTGGCGCTCGTCCTACG |
| 209 | GAGTGGCGCTCGTCCTACGA |
| 210 | AGGCTTCTCCAGGGGCTTGT |
| 211 | AGATTATGCCGACAAGCCCC |
| 212 | ACCTTCAGGACTAGCTTTAG |
| 213 | AGCTTTAGAGGCTTCTCCAG |
| 214 | CTAGCTTTAGAGGCTTCTCC |
| 215 | TAGCTTTAGAGGCTTCTCCA |
| 216 | CTAAAGCTAGTCCTGAAGGT |
| 217 | GCCTCTAAAGCTAGTCCTGA |
| 218 | CTTCACTTCCTCCGACCTTC |
| 219 | AAGCTAGTCCTGAAGGTCGG |
| 220 | AGTGAAGTGACTGAACTCTC |
| 221 | GTGACTGAACTCTCAGGATC |
| 222 | ATAGTAACTGGAGTCGTGGC |
| 223 | CATCATAGTAACTGGAGTCG |
| 224 | TGACCTGTCATCATAGTAAC |
| 225 | ACTCCAGTTACTATGATGAC |
| 226 | CTTTGTGCCTCTCTCGCTCA |
| 227 | GGTCAGACCATGAGCGAGAG |
| 228 | GAAGAAGAAGAAGTCCGAGA |
| 229 | GTCCAGATGCTTCTCCTTCT |
| 230 | GTCCGAGAAGGAGAAGCATC |
| 231 | GGAGAAGCATCTGGACGATG |
| 232 | TGAGGAAAGAAGGAAGCGAA |
| 233 | ATCTGGACGATGAGGAAAGA |
| 234 | AGAAGAAGCGGAAGCGAGAG |
| 235 | GAAGAAGCGGAAGCGAGAGA |
| 236 | CCGCCCAGGAAGAGAAGAAG |
| 237 | AGAGAGGGAGCACTGTGACA |
| 238 | AGGGAGCACTGTGACACGGA |
| 239 | GAGGGAGCACTGTGACACGG |
| 240 | GCACTGTGACACGGAGGGAG |
| 241 | GAGGCTGACGACTTTGATCC |
| 242 | AGGCTGACGACTTTGATCCT |
| 243 | TCCACCTCCACCTTCTTCCC |
| 244 | CGACTTTGATCCTGGGAAGA |
| 245 | CTTTGATCCTGGGAAGAAGG |
| 246 | TGATCCTGGGAAGAAGGTGG |
| 247 | TCCTGGGAAGAAGGTGGAGG |
| 248 | CGGACTGGCCGATCTGGGGG |
| 249 | ACGCTCGGACTGGCCGATCT |
| 250 | AGGTGGAGCCGCCCCCAGAT |
| 251 | CGCTCGGACTGGCCGATCTG |
| 252 | GCTCGGACTGGCCGATCTGG |
| 253 | CACGCTCGGACTGGCCGATC |
| 254 | TGTGTCCGGCACGCTCGGAC |
| 255 | CTGGCTGTGTCCGGCACGCT |
| 256 | ATCGGCCAGTCCGAGCGTGC |
| 257 | CACCCTTGCCTGGCTGTGTC |
| 258 | CGAGCGTGCCGGACACAGCC |
| 259 | TGTTCCAGGAGTTGCTGAAT |
| 260 | CACACCTATTCAGCAACTCC |
| 261 | GCTGGCGGAGGAAGTGTTCC |
| 262 | TTTACCTCTGAAGCTGGCGG |
| 263 | CCCCGGTTTACCTCTGAAGC |
| 264 | ACTTCCTCCGCCAGCTTCAG |
| 265 | CAGGAAAAGCAAAAATCCA |
| 266 | GCTTTCAGAAAAGATCCCCA |
| 267 | AGGAAAAGCAAAAATCCAT |
| 268 | GGAAAAGCAAAAATCCATG |
| 269 | GGAGCAATTGCATCCGTGAC |
| 270 | GTCACGGATGCAATTGCTCC |
| 271 | TTTATTATCATTGAATATCC |
| 272 | AATGATAATAAAACATCCCA |
| 273 | ATAAAACATCCCATGGATTT |
| 274 | TTCATGGTGCCAAAATCCAT |
| 275 | TTTCATGGTGCCAAAATCCA |
| 276 | TAATGAATACAAGTCAGTTA |
| 277 | CAAGTCAGTTACGGAATTTA |

TABLE 3-continued

BRD9 sgRNA Library

| SEQ ID NO | Nucleic Acid Sequence |
|---|---|
| 278 | ATAATGCAATGACATACAAT |
| 279 | AACTTGTAGTACACGGTATC |
| 280 | CTTCGCCAACTTGTAGTACA |
| 281 | AGATACCGTGTACTACAAGT |
| 282 | GCGAAGAAGATCCTTCACGC |
| 283 | TCATCTTAAAGCCTGCGTGA |
| 284 | TTCTCAGCAGGCAGCTCTTT |
| 285 | CAATGAAGATACAGCTGTTG |
| 286 | ACTGGTACAACTTCAGGGAC |
| 287 | CTTGTACTGGTACAACTTCA |
| 288 | ACTTGTACTGGTACAACTTC |
| 289 | TTGGCAGTTTCTACTTGTAC |
| 290 | TACCTGATAACTTCTCTACT |
| 291 | AGCCGAGTAGAGAAGTTATC |
| 292 | AGCTGCATGTTTGAGCCTGA |
| 293 | GCTGCATGTTTGAGCCTGAA |
| 294 | AAGCTGCAGGCATTCCCTTC |
| 295 | GGTACTGTCCGTCAAGCTGC |
| 296 | AGGGAATGCCTGCAGCTTGA |
| 297 | CTTGACGGACAGTACCGCAG |
| 298 | CGCCAGCACGTGCTCCTCTG |
| 299 | TACCGCAGAGGAGCACGTGC |
| 300 | AGAGGAGCACGTGCTGGCGC |
| 301 | GGAGCACGTGCTGGCGCTGG |
| 302 | AGCACGCAGCTGACGAAGCT |
| 303 | GCACGCAGCTGACGAAGCTC |
| 304 | CAGCTGACGAAGCTCGGGAC |
| 305 | AAGCTCGGGACAGGATCAAC |
| 306 | CCTTGCCGCCTGGGAGGAAC |
| 307 | AGGATCAACCGGTTCCTCCC |
| 308 | ATCAACCGGTTCCTCCCAGG |
| 309 | GCACTACCTTGCCGCCTGGG |
| 310 | AGAGCACTACCTTGCCGCCT |
| 311 | CCGGTTCCTCCCAGGCGGCA |
| 312 | TCCTCTTCAGATAGCCCATC |
| 313 | ATGGGCTATCTGAAGAGGAA |
| 314 | GGGCTATCTGAAGAGGAACG |
| 315 | TGGGCTATCTGAAGAGGAAC |
| 316 | TATCTGAAGAGGAACGGGGA |
| 317 | ATCTGAAGAGGAACGGGGAC |
| 318 | TGTTGACCACGCTGTAGAGC |
| 319 | GCTCTACAGCGTGGTCAACA |
| 320 | CGGGAGCCTGCTCTACAGCG |
| 321 | CGTGGTCAACACGGCCGAGC |
| 322 | CCCACCATCAGCGTCCGGCT |
| 323 | ACGGCCGAGCCGGACGCTGA |
| 324 | GGGCACCCACCATCAGCGTC |
| 325 | GCCGAGCCGGACGCTGATGG |
| 326 | CCATGTCCGTGTTGCAGAGG |
| 327 | CCGAGCCGGACGCTGATGGT |
| 328 | CGAGCTCAAGTCCACCGGGT |
| 329 | GCGAGCTCAAGTCCACCGGG |
| 330 | AGAGCGAGCTCAAGTCCACC |
| 331 | GAGAGCGAGCTCAAGTCCAC |
| 332 | GAAGCCTGGGAGTAGCTTAC |
| 333 | CTCTCCAGTAAGCTACTCCC |
| 334 | AGCCCAGCGTGGTGAAGCCT |
| 335 | AAGCCCAGCGTGGTGAAGCC |
| 336 | ACTCCCAGGCTTCACCACGC |
| 337 | CTCCCAGGCTTCACCACGCT |
| 338 | CTCGTCTTTGAAGCCCAGCG |
| 339 | CACTGGAGAGAAAGGTGACT |
| 340 | GCACTGGAGAGAAAGGTGAC |
| 341 | AGTAGTGGCACTGGAGAGAA |
| 342 | CGAAAGCGCAGTAGTGGCAC |
| 343 | CTGCATCGAAAGCGCAGTAG |
| 344 | ATGCAGAATAATTCAGTATT |
| 345 | AGTATTTGGCGACTTGAAGT |
| 346 | CGACTTGAAGTCGGACGAGA |
| 347 | GAGCTGCTCTACTCAGCCTA |
| 348 | CACGCCTGTCTCATCTCCGT |
| 349 | TCAGCCTACGGAGATGAGAC |
| 350 | CAGGCGTGCAGTGTGCGCTG |
| 351 | CCGCGGCCCCTCTAGCCTGC |
| 352 | CATCCTTCACAAACTCCTGC |

TABLE 3-continued

BRD9 sgRNA Library

| SEQ ID NO | Nucleic Acid Sequence |
|---|---|
| 353 | TAGCCTGCAGGAGTTTGTGA |
| 354 | CAGGAGTTTGTGAAGGATGC |
| 355 | AGGAGTTTGTGAAGGATGCT |
| 356 | TGGGAGCTACAGCAAGAAAG |
| 357 | GAGCTACAGCAAGAAAGTGG |
| 358 | GAAAGTGGTGGACGACCTCC |
| 359 | CGCCTGTGATCTGGTCCAGG |
| 360 | CTCCGCCTGTGATCTGGTCC |
| 361 | GACCTCCTGGACCAGATCAC |
| 362 | CTCCTGGACCAGATCACAGG |
| 363 | GCTGGAAGAGCGTCCTAGAG |
| 364 | TGCAGCCCACCTGCTTCAGC |
| 365 | GACGCTCTTCCAGCTGAAGC |
| 366 | CTCTTCCAGCTGAAGCAGGT |
| 367 | GCTCTTCCAGCTGAAGCAGG |
| 368 | CCTCCAGATGAAGCCAAGGT |
| 369 | GCTTCATCTGGAGGCTTCAT |
| 370 | GGCTTCATCTGGAGGCTTCA |
| 371 | CTTACCTTGGCTTCATCTGG |
| 372 | AAACTTACCTTGGCTTCATC |
| 373 | GAAGCCTCCAGATGAAGCCA |
| 374 | TCCTAGGGTGTCCCCAACCT |
| 375 | CCTAGGGTGTCCCCAACCTG |
| 376 | GTGTCTGTCTCCACAGGTTG |
| 377 | TGTGTCTGTCTCCACAGGTT |
| 378 | CCACAGGTTGGGGACACCCT |
| 379 | AGAGCTGCTGCTGTCTCCTA |
| 380 | CAGAGCTGCTGCTGTCTCCT |
| 381 | AGACAGCAGCAGCTCTGTTC |
| 382 | ATCCACAGAAACGTCGGGAT |
| 383 | GAGATATCCACAGAAACGTC |
| 384 | GGAGATATCCACAGAAACGT |
| 385 | GTCCTATCCCGACGTTTCTG |
| 386 | TCTCCATGCTCAGCTCTCTG |
| 387 | CTCACCCAGAGAGCTGAGCA |
| 388 | ATCTCCATGCTCAGCTCTCT |
| 389 | TATCTCCATGCTCAGCTCTC |
| 390 | ATGTCCTGTTTACACAGGGA |
| 391 | TTACACAGGGAAGGTGAAGA |
| 392 | AGTTCAAATGGCTGTCGTCA |
| 393 | TGACGACAGCCATTTGAACT |
| 394 | AAGTTCAAATGGCTGTCGTC |
| 395 | TCGTCTCATCCAAGTTCAAA |
| 396 | TGAGACGACGAAGCTCCTGC |
| 397 | GTGCTTCGTGCAGGTCCTGC |
| 398 | GCAGGACCTGCACGAAGCAC |
| 399 | GCTCCGCCTGTGCTTCGTGC |
| 400 | GGACCTGCACGAAGCACAGG |
| 401 | CACGAAGCACAGGCGGAGCG |
| 402 | AGGCGGAGCGCGGCGGCTCT |
| 403 | AGGGAGCTGAGGTTGGACGA |
| 404 | GTTGGACAGGGAGCTGAGGT |
| 405 | AGGCGTTGGACAGGGAGCT |
| 406 | CCCTCTCGGAGGCGTTGGAC |
| 407 | CCTCTCGGAGGCGTTGGACA |
| 408 | CTGGTCCCTCTCGGAGGCGT |
| 409 | CCCTGTCCAACGCCTCCGAG |
| 410 | CCTGTCCAACGCCTCCGAGA |
| 411 | GTGGTGCTGGTCCCTCTCGG |
| 412 | CAGGTGGTGCTGGTCCCTCT |
| 413 | GCATCTCACCCAGGTGGTGC |
| 414 | CGAGAGGGACCAGCACCACC |
| 415 | GAGAGGGACCAGCACCACCT |
| 416 | GTGGGGGCATCTCACCCAGG |
| 417 | CCCCGACACTCAGGCGAGAA |
| 418 | TCCCCGACACTCAGGCGAGA |
| 419 | AGCCCTTCTCGCCTGAGTGT |
| 420 | CTGGCTGCTCCCCGACACTC |
| 421 | CCCTTCTCGCCTGAGTGTCG |
| 422 | GCCCTTCTCGCCTGAGTGTC |
| 423 | TAGGGGTCGTGGGTGACGTC |
| 424 | AAGAAACTCATAGGGGTCGT |
| 425 | GAAGAAACTCATAGGGGTCG |
| 426 | GAGACTGAAGAAACTCATAG |
| 427 | GGAGACTGAAGAAACTCATA |

TABLE 3-continued

BRD9 sgRNA Library

| SEQ ID NO | Nucleic Acid Sequence |
|---|---|
| 428 | TGGAGACTGAAGAAACTCAT |
| 429 | TCTTCAGTCTCCAGAGCCTG |
| 430 | TTGGCAGAGGCCGCAGGCTC |
| 431 | TAGGTCTTGGCAGAGGCCGC |
| 432 | CTAGAGTTAGGTCTTGGCAG |
| 433 | GGTGGTCTAGAGTTAGGTCT |

TABLE 4

Control sgRNA Library

| SEQ ID NO. | gRNA Label | Gene | Nucleic Acid Sequence |
|---|---|---|---|
| 434 | 1\|sg_Non_Targeting_Human_0001\|Non_Targeting_Human | Non_Targeting_Human | GTAGCGAACGTGTCCGGCGT |
| 435 | 1\|sg_Non_Targeting_Human_0002\|Non_Targeting_Human | Non_Targeting_Human | GACCGGAACGATCTCGCGTA |
| 436 | 1\|sg_Non_Targeting_Human_0003\|Non_Targeting_Human | Non_Targeting_Human | GGCAGTCGTTCGGTTGATAT |
| 437 | 1\|sg_Non_Targeting_Human_0004\|Non_TargctingHuman | Non_Targeting_Human | GCTTGAGCACATACGCGAAT |
| 438 | 1\|sg_Non_Targeting_Human_0005\|Non_Targeting_Human | Non_Targeting_Human | GTGGTAGAATAACGTATTAC |
| 439 | 1\|sg_Non_Targeting_Human_0006\|Non_Targeting_Human | Non_Targeting_Human | GTCATACATGGATAAGGCTA |
| 440 | 1\|sg_Non_Targeting_Human_0007\|Non_Targeting_Human | Non_Targeting_Human | GATACACGAAGCATCACTAG |
| 441 | 1\|sg_Non_Targeting_Human_0008\|Non_TargctingHuman | Non_Targeting_Human | GAACGTTGGCACTACTTCAC |
| 442 | 1\|sg_Non_Targeting_Human_0009\|Non_Targeting_Human | Non_Targeting_Human | GATCCATGTAATGCGTTCGA |
| 443 | 1\|sg_Non_Targeting_Human_0010\|Non_Targeting_Human | Non_Targeting_Human | GTCGTGAAGTGCATTCGATC |
| 444 | 1\|sg_Non_Targeting_Human_0011\|Non_Targeting_Human | Non_Targeting_Human | GTTCGACTCGCGTGACCGTA |
| 445 | 1\|sg_Non_Targeting_Human_0012\|Non_Targeting_Human | Non_Targeting_Human | GAATCTACCGCAGCGGTTCG |
| 446 | 1\|sg_Non_Targeting_Human_0013\|Non_Targeting_Human | Non_Targeting_Human | GAAGTGACGTCGATTCGATA |
| 447 | 1\|sg_Non_Targeting_Human_0014\|Non_Targeting_Human | Non_Targeting_Human | GCGGTGTATGACAACCGCCG |
| 448 | 1\|sg_Non_Targeting_Human_0015\|Non_Targeting_Human | Non_Targeting_Human | GTACCGCGCCTGAAGTTCGC |
| 449 | 1\|sg_Non_Targeting_Human_0016\|Non_Targeting_Human | Non_Targeting_Human | GCAGCTCGTGTGTCGTACTC |
| 450 | 1\|sg_Non_Targeting_Human_0017\|Non_Targeting_Human | Non_Targeting_Human | GCGCCTTAAGAGTACTCATC |
| 451 | 1\|sg_Non_Targeting_Human_0018\|Non_Targeting_Human | Non_Targeting_Human | GAGTGTCGTCGTTGCTCCTA |
| 452 | 1\|sg_Non_Targeting_Human_00019\|Non_Targeting_Human | Non_Targeting_Human | GCAGCTCGACCTCAAGCCGT |

TABLE 4 -continued

Control sgRNA Library

| SEQ ID NO. | gRNA Label | Gene | Nucleic Acid Sequence |
|---|---|---|---|
| 453 | 1\|sg_Non_Targeting_Human_0020\|Non_Targeting_Human | Non_Targeting_Human | GTATCCTGACCTACGCGCTG |
| 454 | 1\|sg_Non_Targeting_Human_0021\|Non_Targeting_Human | Non_Targeting_Human | GTGTATCTCAGCACGCTAAC |
| 455 | 1\|sg_Non_Targeting_Human_0022\|Non_Targeting_Human | Non_Targeting_Human | GTCGTCATACAACGGCAACG |
| 456 | 1\|sg_Non_Targeting_Human_0023\|Non_Targeting_Human | Non_Targeting_Human | GTCGTGCGCTTCCGGCGGTA |
| 457 | 1\|sg_Non_Targeting_Human_0024\|Non_Targeting_Human | Non_Targeting_Human | GCGGTCCTCAGTAAGCGCGT |
| 458 | 1\|sg_Non_Targeting_Human_0025\|Non_Targeting_Human | Non_Targeting_Human | GCTCTGCTGCGGAAGGATTC |
| 459 | 1\|sg_Non_Targeting_Human_0026\|Non_TargetingHuman | Non_Targeting_Human | GCATGGAGGAGCGTCGCAGA |
| 460 | 1\|sg_Non_Targeting_Human_0027\|Non_Targeting_Human | Non_Targeting_Human | GTAGCGCGCGTAGGAGTGGC |
| 461 | 1\|sg_Non_Targeting_Human_0028\|Non_Targeting_Human | Non_Targeting_Human | GATCACCTGCATTCGTACAC |
| 462 | 1\|sg_Non_Targeting_Human_0029\|Non_Targeting_Human | Non_Targeting_Human | GCACACCTAGATATCGAATG |
| 463 | 1\|sg_Non_Targeting_Human_0030\|Non_Targeting_Human | Non_Targeting_Human | GTTGATCAACGCGCTTCGCG |
| 464 | 1\|sg_Non_Targeting_Human_0031\|Non_Targeting_Human | Non_Targeting_Human | GCGTCTCACTCACTCCATCG |
| 465 | 1\|sg_Non_Targeting_Human_0032\|Non_Targeting_Human | Non_Targeting_Human | GCCGACCAACGTCAGCGGTA |
| 466 | 1\|sg_Non_Targeting_Human_0033\|Non_Targeting_Human | Non_Targeting_Human | GGATACGGTGCGTCAATCTA |
| 467 | 1\|sg_Non_Targeting_Human_0034\|Non_Targeting_Human | Non_Targeting_Human | GAATCCAGTGGCGGCGACAA |
| 468 | 1\|sg_Non_Targeting_Human_0035\|Non_Targeting_Human | Non_Targeting_Human | GCACTGTCAGTGCAACGATA |
| 469 | 1\|sg_Non_Targeting_Human_0036\|Non_Targeting_Human | Non_Targeting_Human | GCGATCCTCAAGTATGCTCA |
| 470 | 1\|sg_Non_Targeting_Human_0037\|Non_Targeting_Human | Non_Targeting_Human | GCTAATATCGACACGGCCGC |
| 471 | 1\|sg_Non_Targeting_Human_0038\|Non_Targeting_Human | Non_Targeting_Human | GGAGATGCATCGAAGTCGAT |
| 472 | 1\|sg_Non_Targeting_Human_0039\|Non_Targeting_Human | Non_Targeting_Human | GGATGCACTCCATCTCGTCT |
| 473 | 1\|sg_Non_Targeting_Human_0040\|Non_Targeting_Human | Non_Targeting_Human | GTGCCGAGTAATAACGCGAG |
| 474 | 1\|sg_Non_Targeting_Human_0041\|Non_Targeting_Human | Non_Targeting_Human | GAGATTCCGATGTAACGTAC |
| 475 | 1\|sg_Non_Targeting_Human_0042\|Non_Targeting_Human | Non_Targeting_Human | GTCGTCACGAGCAGGATTGC |
| 476 | 1\|sg_Non_Targeting_Human_0043\|Non_Targeting_Human | Non_Targeting_Human | GCGTTAGTCACTTAGCTCGA |

TABLE 4 -continued

Control sgRNA Library

| SEQ ID NO. | gRNA Label | Gene | Nucleic Acid Sequence |
|---|---|---|---|
| 477 | 1\|sg_Non_Targeting_Human_0044\|Non_Targeting_Human | Non_Targeting_Human | GTTCACACGGTGTCGGATAG |
| 478 | 1\|sg_Non_Targeting_Human_0045\|Non_Targeting_Human | Non_Targeting_Human | GGATAGGTGACCTTAGTACG |
| 479 | 1\|sg_Non_Targeting_Human_0046\|Non_Targeting_Human | Non_Targeting_Human | GTATGAGTCAAGCTAATGCG |
| 480 | 1\|sg_Non_Targeting_Human_0047\|Non_Targeting_Human | Non_Targeting_Human | GCAACTATTGGAATACGTGA |
| 481 | 1\|sg_Non_Targeting_Human_0048\|Non_Targeting_Human | Non_Targeting_Human | GTTACCTTCGCTCGTCTATA |
| 482 | 1\|sg_Non_Targeting_Human_0049\|Non_Targeting_Human | Non_Targeting_Human | GTACCGAGCACCACAGGCCG |
| 483 | 1\|sg_Non_Targeting_Human_0050\|Non_Targeting_Human | Non_Targeting_Human | GTCAGCCATCGGATAGAGAT |
| 484 | 1\|sg_Non_Targeting_Human_0051\|Non_Targeting_Human | Non_Targeting_Human | GTACGGCACTCCTAGCCGCT |
| 485 | 1\|sg_Non_Targeting_Human_0052\|Non_Targeting_Human | Non_Targeting_Human | GGTCCTGTCGTATGCTTGCA |
| 486 | 1\|sg_Non_Targeting_Human_0053\|Non_Targeting_Human | Non_Targeting_Human | GCCGCAATATATGCGGTAAG |
| 487 | 1\|sg_Non_Targeting_Human_0054\|Non_Targeting_Human | Non_Targeting_Human | GCGCACGTATAATCCTGCGT |
| 488 | 1\|sg_Non_Targeting_Human_0055\|Non_Targeting_Human | Non_Targeting_Human | GTGCACAACACGATCCACGA |
| 489 | 1\|sg_Non_Targeting_Human_0056\|Non_Targeting_Human | Non_Targeting_Human | GCACAATGTTGACGTAAGTG |
| 490 | 1\|sg_Non_Targeting_Human_0057\|Non_Targeting_Human | Non_Targeting_Human | GTAAGATGCTGCTCACCGTG |
| 491 | 1\|sg_Non_Targeting_Human_0058\|Non_Targeting_Human | Non_Targeting_Human | GTCGGTGATCCAACGTATCG |
| 492 | 1\|sg_Non_Targeting_Human_0059\|Non_Targeting_Human | Non_Targeting_Human | GAGCTAGTAGGACGCAAGAC |
| 493 | 1\|sg_Non_Targeting_Human_0060\|Non_Targeting_Human | Non_Targeting_Human | GTACGTGGAAGCTTGTGGCC |
| 494 | 1\|sg_Non_Targeting_Human_0061\|Non_Targeting_Human | Non_Targeting_Human | GAGAACTGCCAGTTCTCGAT |
| 495 | 1\|sg_Non_Targeting_Human_0062\|Non_Targeting_Human | Non_Targeting_Human | GCCATTCGGCGCGGCACTTC |
| 496 | 1\|sg_Non_Targeting_Human_0063\|Non_Targeting_Human | Non_Targeting_Human | GCACACGACCAATCCGCTTC |
| 497 | 1\|sg_Non_Targeting_Human_0064\|Non_Targeting_Human | Non_Targeting_Human | GAGGTGATCGATTAAGTACA |
| 498 | 1\|sg_Non_Targeting_Human_0065\|Non_Targeting_Human | Non_Targeting_Human | GTCACTCGCAGACGCCTAAC |
| 499 | 1\|sg_Non_Targeting_Human_0066\|Non_Targeting_Human | Non_Targeting_Human | GCGCTACGGAATCATACGTT |
| 500 | 1\|sg_Non_Targeting_Human_0067\|Non_Targeting_Human | Non_Targeting_Human | GGTAGGACCTCACGGCGCGC |

TABLE 4 -continued

Control sgRNA Library

| SEQ ID NO. | gRNA Label | Gene | Nucleic Acid Sequence |
|---|---|---|---|
| 501 | 1\|sg_Non_Targeting_Human_0068\|Non_Targeting_Human | Non_Targeting_Human | GAACTGCATCTTGTTGTAGT |
| 502 | 1\|sg_Non_Targeting_Human_0069\|Non_Targeting_Human | Non_Targeting_Human | GATCCTGATCCGGCGGCGCG |
| 503 | 1\|sg_Non_Targeting_Human_0070\|Non_Targeting_Human | Non_Targeting_Human | GGTATGCGCGATCCTGAGTT |
| 504 | 1\|sg_Non_Targeting_Human_0071\|Non_Targeting_Human | Non_Targeting_Human | GCGGAGCTAGAGAGCGGTCA |
| 505 | 1\|sg_Non_Targeting_Human_0072\|Non_Targeting_Human | Non_Targeting_Human | GAATGGCAATTACGGCTGAT |
| 506 | 1\|sg_Non_Targeting_Human_0073\|Non_Targeting_Human | Non_Targeting_Human | GTATGGTGAGTAGTCGCTTG |
| 507 | 1\|sg_Non_Targeting_Human_0074\|Non_Targeting_Human | Non_Targeting_Human | GTGTAATTGCGTCTAGTCGG |
| 508 | 1\|sg_Non_Targeting_Human_0075\|Non_Targeting_Human | Non_Targeting_Human | GGTCCTGGCGAGGAGCCTTG |
| 509 | 1\|sg_Non_Targeting_Human_0076\|Non_Targeting_Human | Non_Targeting_Human | GAAGATAAGTCGCTGTCTCG |
| 510 | 1\|sg_Non_Targeting_Human_0077\|Non_Targeting_Human | Non_Targeting_Human | GTCGGCGTTCTGTTGTGACT |
| 511 | 1\|sg_Non_Targeting_Human_0078\|Non_Targeting_Human | Non_Targeting_Human | GAGGCAAGCCGTTAGGTGTA |
| 512 | 1\|sg_Non_Targeting_Human_0079\|Non_Targeting_Human | Non_Targeting_Human | GCGGATCCAGATCTCATTCG |
| 513 | 1\|sg_Non_Targeting_Human_0080\|Non_Targeting_Human | Non_Targeting_Human | GGAACATAGGAGCACGTAGT |
| 514 | 1\|sg_Non_Targeting_Human_0081\|Non_Targeting_Human | Non_Targeting_Human | GTCATCATTATGGCGTAAGG |
| 515 | 1\|sg_Non_Targeting_Human_0082\|Non_Targeting_Human | Non_Targeting_Human | GCGACTAGCGCCATGAGCGG |
| 516 | 1\|sg_Non_Targeting_Human_0083\|Non_Targeting_Human | Non_Targeting_Human | GGCGAAGTTCGACATGACAC |
| 517 | 1\|sg_Non_Targeting_Human_0084\|Non_Targeting_Human | Non_Targeting_Human | GCTGTCGTGTGGAGGCTATG |
| 518 | 1\|sg_Non_Targeting_Human_0085\|Non_Targeting_Human | Non_Targeting_Human | GCGGAGAGCATTGACCTCAT |
| 519 | 1\|sg_Non_Targeting_Human_0086\|Non_Targeting_Human | Non_Targeting_Human | GACTAATGGACCAAGTCAGT |
| 520 | 1\|sg_Non_Targeting_Human_0087\|Non_Targeting_Human | Non_Targeting_Human | GCGGATTAGAGGTAATGCGG |
| 521 | 1\|sg_Non_Targeting_Human_0088\|Non_Targeting_Human | Non_Targeting_Human | GCCGACGGCAATCAGTACGC |
| 522 | 1\|sg_Non_Targeting_Human_0089\|Non_Targeting_Human | Non_Targeting_Human | GTAACCTCTCGAGCGATAGA |
| 523 | 1\|sg_Non_Targeting_Human_0090\|Non_Targeting_Human | Non_Targeting_Human | GACTTGTATGTGGCTTACGG |
| 524 | 1\|sg_Non_Targeting_Human_0091\|Non_Targeting_Human | Non_Targeting_Human | GTCACTGTGGTCGAACATGT |

TABLE 4 -continued

Control sgRNA Library

| SEQ ID NO. | gRNA Label | Gene | Nucleic Acid Sequence |
|---|---|---|---|
| 525 | 1\|sg_Non_Targeting_Human_0092\|Non_Targeting_Human | Non_Targeting_Human | GTACTCCAATCCGCGATGAC |
| 526 | 1\|sg_Non_Targeting_Human_0093\|Non_Targeting_Human | Non_Targeting_Human | GCGTTGGCACGATGTTACGG |
| 527 | 1\|sg_Non_Targeting_Human_0094\|Non_Targeting_Human | Non_Targeting_Human | GAACCAGCCGGCTAGTATGA |
| 528 | 1\|sg_Non_Targeting_Human_0095\|Non_Targeting_Human | Non_Targeting_Human | GTATACTAGCTAACCACACG |
| 529 | 1\|sg_Non_Targeting_Human_0096\|Non_Targeting_Human | Non_Targeting_Human | GAATCGGAATAGTTGATTCG |
| 530 | 1\|sg_Non_Targeting_Human_0097\|Non_Targeting_Human | Non_Targeting_Human | GAGCACTTGCATGAGGCGGT |
| 531 | 1\|sg_Non_Targeting_Human_0098\|Non_Targeting_Human | Non_Targeting_Human | GAACGGCGATGAAGCCAGCC |
| 532 | 1\|sg_Non_Targeting_Human_0099\|Non_Targeting_Human | Non_Targeting_Human | GCAACCGAGATGAGAGGTTC |
| 533 | 1\|sg_Non_Targeting_Human_0100\|Non_Targeting_Human | Non_Targeting_Human | GCAAGATCAATATGCGTGAT |
| 534 | 1\|sg_Non_Targeting_Human_GA_0101\|Non_Targeting_Human | Non_Targeting_Human | ACGGAGGCTAAGCGTCGCAA |
| 535 | 1\|sg_Non_Targeting_Human_GA_0102\|Non_Targeting_Human | Non_Targeting_Human | CGCTTCCGCGGCCCGTTCAA |
| 536 | 1\|Non_Targeting_Human_GA_0103\|Non_Targeting_Human | Non_Targeting_Human | ATCGTTTCCGCTTAACGGCG |
| 537 | 1\|sg_Non_Targeting_Human_GA_0104\|Non_Targeting_Human | Non_Targeting_Human | GTAGGCGCGCCGCTCTCTAC |
| 538 | 1\|sg_Non_Targeting_Human_GA_0105\|Non_Targeting_Human | Non_Targeting_Human | CCATATCGGGGCGAGACATG |
| 539 | 1\|sg_Non_Targeting_Human_GA_0106\|Non_Targeting_Human | Non_Targeting_Human | TACTAACGCCGCTCCTACAG |
| 540 | 1\|sg_Non_Targeting_Human_GA_0107\|Non_Targeting_Human | Non_Targeting_Human | TGAGGATCATGTCGAGCGCC |
| 541 | 1\|sg_Non_Targeting_Human_GA_0108\|Non_Targeting_Human | Non_Targeting_Human | GGGCCCGCATAGGATATCGC |
| 542 | 1\|sg_Non_Targeting_Human_GA_0109\|Non_Targeting_Human | Non_Targeting_Human | TAGACAACCGCGGAGAATGC |
| 543 | 1\|sg_Non_Targeting_Human_GA_0110\|Non_Targeting_Human | Non_Targeting_Human | ACGGGCGGCTATCGCTGACT |
| 544 | 1\|sg_Non_Targeting_Human_GA_0111\|Non_Targeting_Human | Non_Targeting_Human | CGCGGAAATTTTACCGACGA |
| 545 | 1\|sg_Non_Targeting_Human_GA_0112\|Non_Targeting_Human | Non_Targeting_Human | CTTACAATCGTCGGTCCAAT |
| 546 | 1\|sg_Non_Targeting_Human_GA_0113\|Non_Targeting_Human | Non_Targeting_Human | GCGTGCGTCCCGGGTTACCC |
| 547 | 1\|sg_Non_Targeting_Human_GA_0114\|Non_Targeting_Human | Non_Targeting_Human | CGGAGTAACAAGCGGACGGA |
| 548 | 1\|sg_Non_Targeting_Human_GA_0115\|Non_Targeting_Human | Non_Targeting_Human | CGAGTGTTATACGCACCGTT |

TABLE 4 -continued

Control sqRNA Library

| SEQ ID NO. | gRNA Label | Gene | Nucleic Acid Sequence |
|---|---|---|---|
| 549 | 1\|sg_Non_Targeting_Human_GA_0116\|Non_Targeting_Human | Non_Targeting_Human | CGACTAACCGGAAACTTTTT |
| 550 | 1\|sg_Non_Targeting_Human_GA_0117\|Non_Targeting_Human | Non_Targeting_Human | CAACGGGTTCTCCCGGCTAC |
| 551 | 1\|sg_Non_Targeting_Human_GA_0118\|Non_Targeting_Human | Non_Targeting_Human | CAGGAGTCGCCGATACGCGT |
| 552 | 1\|sg_Non_Targeting_Human_GA_0119\|Non_Targeting_Human | Non_Targeting_Human | TTCACGTCGTCTCGCGACCA |
| 553 | 1\|sg_Non_Targeting_Human_GA_0120\|Non_Targeting_Human | Non_Targeting_Human | GTGTCGGATTCCGCCGCTTA |
| 554 | 1\|sg_Non_Targeting_Human_GA_0121\|Non_Targeting_Human | Non_Targeting_Human | CACGAACTCACACCGCGCGA |
| 555 | 1\|sg_Non_Targeting_Human_GA_0122\|Non_Targeting_Human | Non_Targeting_Human | CGCTAGTACGCTCCTCTATA |
| 556 | 1\|sg_Non_Targeting_Human_GA_0123\|Non_Targeting_Human | Non_Targeting_Human | TCGCGCTTGGGTTATACGCT |
| 557 | 1\|sg_Non_Targeting_Human_GA_0124\|Non_Targeting_Human | Non_Targeting_Human | CTATCTCGAGTGGTAATGCG |
| 558 | 1\|sg_Non_Targeting_Human_GA_0125\|Non_Targeting_Human | Non_Targeting_Human | AATCGACTCGAACTTCGTGT |
| 559 | 1\|sg_Non_Targeting_Human_GA_0126\|Non_Targeting_Human | Non_Targeting_Human | CCCGATGGACTATACCGAAC |
| 560 | 1\|sg_Non_Targeting_Human_GA_0127\|Non_Targeting_Human | Non_Targeting_Human | ACGTTCGAGTACGACCAGCT |
| 561 | 1\|sg_Non_Targeting_Human_GA_0128\|Non_Targeting_Human | Non_Targeting_Human | CGCGACGACTCAACCTAGTC |
| 562 | 1\|sg_Non_Targeting_Human_GA_0129\|Non_Targeting_Human | Non_Targeting_Human | GGTCACCGATCGAGAGCTAG |
| 563 | 1\|sg_Non_Targeting_Human_GA_0130\|Non_Targeting_Human | Non_Targeting_Human | CTCAACCGACCGTATGGTCA |
| 564 | 1\|sg_Non_Targeting_Human_GA_0131\|Non_Targeting_Human | Non_Targeting_Human | CGTATTCGACTCTCAACGCG |
| 565 | 1\|sg_Non_Targeting_Human_GA_0132\|Non_Targeting_Human | Non_Targeting_Human | CTAGCCGCCCAGATCGAGCC |
| 566 | 1\|sg_Non_Targeting_Human_GA_0133\|Non_Targeting_Human | Non_Targeting_Human | GAATCGACCGACACTAATGT |
| 567 | 1\|sg_Non_Targeting_Human_GA_0134\|Non_Targeting_Human | Non_Targeting_Human | ACTTCAGTTCGGCGTAGTCA |
| 568 | 1\|sg_Non_Targeting_Human_GA_0135\|Non_Targeting_Human | Non_Targeting_Human | GTGCGATGTCGCTTCAACGT |
| 569 | 1\|sg_Non_Targeting_Human_GA_0136\|Non_Targeting_Human | Non_Targeting_Human | CGCCTAATTTCCGGATCAAT |
| 570 | 1\|sg_Non_Targeting_Human_GA_0137\|Non_Targeting_Human | Non_Targeting_Human | CGTGGCCGGAACCGTCATAG |
| 571 | 1\|sg_Non_Targeting_Human_GA_0138\|Non_Targeting_Human | Non_Targeting_Human | ACCCTCCGAATCGTAACGGA |
| 572 | 1\|sg_Non_Targeting_Human_GA_0139\|Non_Targeting_Human | Non_Targeting_Human | AAACGGTACGACAGCGTGTG |

TABLE 4 -continued

Control sgRNA Library

| SEQ ID NO. | gRNA Label | Gene | Nucleic Acid Sequence |
|---|---|---|---|
| 573 | 1\|sg_Non_Targeting_Human_GA_0140\|Non_Targeting_Human | Non_Targeting_Human | ACATAGTCGACGGCTCGATT |
| 574 | 1\|sg_Non_Targeting_Human_GA_0141\|Non_Targeting_Human | Non_Targeting_Human | GATGGCGCTTCAGTCGTCGG |
| 575 | 1\|sg_Non_Targeting_Human_GA_0142\|Non_Targeting_Human | Non_Targeting_Human | ATAATCCGGAAACGCTCGAC |
| 576 | 1\|sg_Non_Targeting_Human_GA_0143\|Non_Targeting_Human | Non_Targeting_Human | CGCCGGGCTGACAATTAACG |
| 577 | 1\|sg_Non_Targeting_Human_GA_0144\|Non_Targeting_Human | Non_Targeting_Human | CGTCGCCATATGCCGGTGGC |
| 578 | 1\|sg_Non_Targeting_Human_GA_0145\|Non_Targeting_Human | Non_Targeting_Human | CGGGCCTATAACACCATCGA |
| 579 | 1\|sg_Non_Targeting_Human_GA_0146\|Non_Targeting_Human | Non_Targeting_Human | CGCCGTTCCGAGATACTTGA |
| 580 | 1\|sg_Non_Targeting_Human_GA_0147\|Non_Targeting_Human | Non_Targeting_Human | CGGGACGTCGCGAAAATGTA |
| 581 | 1\|sg_Non_Targeting_Human_GA_0148\|Non_Targeting_Human | Non_Targeting_Human | TCGGCATACGGGACACACGC |
| 582 | 1\|sg_Non_Targeting_Human_GA_0149\|Non_Targeting_Human | Non_Targeting_Human | AGCTCCATCGCCGCGATAAT |
| 583 | 1\|sg_Non_Targeting_Human_GA_0150\|Non_Targeting_Human | Non_Targeting_Human | ATCGTATCATCAGCTAGCGC |
| 584 | 1\|sg_Non_Targeting_Human_GA_0151\|Non_Targeting_Human | Non_Targeting_Human | TCGATCGAGGTTGCATTCGG |
| 585 | 1\|sg_Non_Targeting_Human_GA_0152\|Non_Targeting_Human | Non_Targeting_Human | CTCGACAGTTCGTCCCGAGC |
| 586 | 1\|sg_Non_Targeting_Human_GA_0153\|Non_Targeting_Human | Non_Targeting_Human | CGGTAGTATTAATCGCTGAC |
| 587 | 1\|sg_Non_Targeting_Human_GA_0154\|Non_TargetingHuman | Non_Targeting_Human | TGAACGCGTGTTTCCTTGCA |
| 588 | 1\|sg_Non_Targeting_Human_GA_0155\|Non_Targeting_Human | Non_Targeting_Human | CGACGCTAGGTAACGTAGAG |
| 589 | 1\|sg_Non_Targeting_Human_GA0156\|NonTargetingHuman | Non_Targeting_Human | CATTGTTGAGCGGGCGCGCT |
| 590 | 1\|sg_Non_Targeting_Human_GA_0157\|Non_Targeting_Human | Non_Targeting_Human | CCGCTATTGAAACCGCCCAC |
| 591 | 1\|sg_Non_Targeting_Human_GA_0158\|Non_Targeting_Human | Non_Targeting_Human | AGACACGTCACCGGTCAAAA |
| 592 | 1\|sg_Non_Targeting_Human_GA_0159\|Non_Targeting_Human | Non_Targeting_Human | TTTACGATCTAGCGGCGTAG |
| 593 | 1\|sg_Non_Targeting_Human_GA0160\|NonTargetingHuman | Non_Targeting_Human | TTCGCACGATTGCACCTTGG |
| 594 | 1\|sg_Non_Targeting_Human_GA_0161\|Non_Targeting_Human | Non_Targeting_Human | GGTTAGAGACTAGGCGCGCG |
| 595 | 1\|sg_Non_Targeting_Human_GA_0162\|Non_Targeting_Human | Non_Targeting_Human | CCTCCGTGCTAACGCGGACG |
| 596 | 1\|sg_Non_Targeting_Human_GA_0163\|Non_Targeting_Human | Non_Targeting_Human | TTATCGCGTAGTGCTGACGT |

TABLE 4 -continued

Control sqRNA Library

| SEQ ID NO. | gRNA Label | Gene | Nucleic Acid Sequence |
|---|---|---|---|
| 597 | 1\|sg_Non_Targeting_Human_GA0164\|NonTargetingHuman | Non_Targeting_Human | TACGCTTGCGTTTAGCGTCC |
| 598 | 1\|sg_Non_Targeting_Human_GA_0165\|Non_Targeting_Human | Non_Targeting_Human | CGCGGCCCACGCGTCATCGC |
| 599 | 1\|sg_Non_Targeting_Human_GA_0166\|Non_Targeting_Human | Non_Targeting_Human | AGCTCGCCATGTCGGTTCTC |
| 600 | 1\|sg_Non_Targeting_Human_GA_0167\|Non_Targeting_Human | Non_Targeting_Human | AACTAGCCCGAGCAGCTTCG |
| 601 | 1\|sg_Non_Targeting_Human_GA_0168\|Non_Targeting_Human | Non_Targeting_Human | CGCAAGGTGTCGGTAACCCT |
| 602 | 1\|sg_Non_Targeting_Human_GA_0169\|Non_Targeting_Human | Non_Targeting_Human | CTTCGACGCCATCGTGCTCA |
| 603 | 1\|sg_Non_Targeting_Human_GA_0170\|Non_Targeting_Human | Non_Targeting_Human | TCCTGGATACCGCGTGGTTA |
| 604 | 1\|sg_Non_Targeting_Human_GA_0171\|Non_Targeting_Human | Non_Targeting_Human | ATAGCCGCCGCTCATTACTT |
| 605 | 1\|sg_Non_Targeting_Human_GA_0172\|Non_Targeting_Human | Non_Targeting_Human | GTCGTCCGGGATTACAAAAT |
| 606 | 1\|sg_Non_Targeting_Human_GA_0173\|Non_Targeting_Human | Non_Targeting_Human | TAATGCTGCACACGCCGAAT |
| 607 | 1\|sg_Non_Targeting_Human_GA_0174\|Non_Targeting_Human | Non_Targeting_Human | TATCGCTTCCGATTAGTCCG |
| 608 | 1\|sg_Non_Targeting_Human_GA_0175\|Non_Targeting_Human | Non_Targeting_Human | GTACCATACCGCGTACCCTT |
| 609 | 1\|sg_Non_Targeting_Human_GA_0176\|Non_Targeting_Human | Non_Targeting_Human | TAAGATCCGCGGGTGGCAAC |
| 610 | 1\|sg_Non_Targeting_Human_GA_0177\|Non_Targeting_Human | Non_Targeting_Human | GTAGACGTCGTGAGCTTCAC |
| 611 | 1\|sg_Non_Targeting_Human_GA_0178\|Non_Targeting_Human | Non_Targeting_Human | TCGCGGACATAGGGCTCTAA |
| 612 | 1\|sg_Non_Targeting_Human_GA_0179\|NonTargetingHuman | Non_Targeting_Human | AGCGCAGATAGCGCGTATCA |
| 613 | 1\|sg_Non_Targeting_Human_GA_0180\|Non_Targeting_Human | Non_Targeting_Human | GTTCGCTTCGTAACGAGGAA |
| 614 | 1\|sg_Non_Targeting_Human_GA_0181\|Non_Targeting_Human | Non_Targeting_Human | GACCCCCGATAACTTTTGAC |
| 615 | 1\|sg_Non_Targeting_Human_GA_0182\|Non_Targeting_Human | Non_Targeting_Human | ACGTCCATACTGTCGGCTAC |
| 616 | 1\|sg_Non_Targeting_Human_GA_0183\|Non_Targeting_Human | Non_Targeting_Human | GTACCATTGCCGGCTCCCTA |
| 617 | 1\|sg_Non_Targeting_Human_GA_0184\|Non_Targeting_Human | Non_Targeting_Human | TGGTTCCGTAGGTCGGTATA |
| 618 | 1\|sg_Non_Targeting_Human_GA_0185\|Non_Targeting_Human | Non_Targeting_Human | TCTGGCTTGACACGACCGTT |
| 619 | 1\|sg_Non_Targeting_Human_GA_0186\|Non_Targeting_Human | Non_Targeting_Human | CGCTAGGTCCGGTAAGTGCG |
| 620 | 1\|sg_Non_Targeting_Human_GA_0187\|Non_Targeting_Human | Non_Targeting_Human | AGCACGTAATGTCCGTGGAT |

TABLE 4 -continued

Control sgRNA Library

| SEQ ID NO. | gRNA Label | Gene | Nucleic Acid Sequence |
|---|---|---|---|
| 621 | 1\|sg_Non_Targeting_Human_GA_0188\|Non_Targeting_Human | Non_Targeting_Human | AAGGCGCGCGAATGTGGCAG |
| 622 | 1\|sg_Non_Targeting_Human_GA_0189\|Non_Targeting_Human | Non_Targeting_Human | ACTGCGGAGCGCCCAATATC |
| 623 | 1\|sg_Non_Targeting_Human_GA_0190\|Non_Targeting_Human | Non_Targeting_Human | CGTCGAGTGCTCGAACTCCA |
| 624 | 1\|sg_Non_Targeting_Human_GA_0191\|Non_Targeting_Human | Non_Targeting_Human | TCGCAGCGGCGTGGGATCGG |
| 625 | 1\|sg_Non_Targeting_Human_GA_0192\|Non_Targeting_Human | Non_Targeting_Human | ATCTGTCCTAATTCGGATCG |
| 626 | 1\|sg_Non_Targeting_Human_GA_0193\|Non_Targeting_Human | Non_Targeting_Human | TGCGGCGTAATGCTTGAAAG |
| 627 | 1\|sg_Non_Targeting_Human_GA_0194\|Non_Targeting_Human | Non_Targeting_Human | CGAACTTAATCCCGTGGCAA |
| 628 | 1\|sg_Non_Targeting_Human_GA_0195\|Non_Targeting_Human | Non_Targeting_Human | GCCGTGTTGCTGGATACGCC |
| 629 | 1\|sg_Non_Targeting_Human_GA_0196\|Non_Targeting_Human | Non_Targeting_Human | TACCCTCCGGATACGGACTG |
| 630 | 1\|sg_Non_Targeting_Human_GA_0197\|Non_Targeting_Human | Non_Targeting_Human | CCGTTGGACTATGGCGGGTC |
| 631 | 1\|sg_Non_Targeting_Human_GA_0198\|Non_Targeting_Human | Non_Targeting_Human | GTACGGGCGATCATCCACA |
| 632 | 1\|sg_Non_Targeting_Human_GA_0199\|Non_Targeting_Human | Non_Targeting_Human | AAGAGTAGTAGACGCCCGGG |
| 633 | 1\|sg_Non_Targeting_Human_GA_0200\|Non_Targeting_Human | Non_Targeting_Human | AAGAGCGAATCGATTTCGTG |
| 634 | 3\|sg_hCDC16_CC_1\|CDC16 | CDC16 | TCAACACCAGTGCCTGACGG |
| 635 | 3\|sg_hCDC16_CC_2\|CDC16 | CDC16 | AAAGTAGCTTCACTCTCTCG |
| 636 | 3\|sg_hCDC16_CC_3\|CDC16 | CDC16 | GAGCCAACCAATAGATGTCC |
| 637 | 3\|sg_hCDC16_CC_4\|CDC16 | CDC16 | GCGCCGCCATGAACCTAGAG |
| 638 | 3\|sg_hGTF2B_CC_1\|GTF2B | GTF2B | ACAAAGGTTGGAACAGAACC |
| 639 | 3\|sg_hGTF2B_CC_2\|GTF2B | GTF2B | GGTGACCGGGTTATTGATGT |
| 640 | 3\|sg_hGTF2B_CC_3\|GTF2B | GTF2B | TTAGTGGAGGACTACAGAGC |
| 641 | 3\|sg_hGTF2B_CC_4\|GTF2B | GTF2B | ACATATAGCCCGTAAAGCTG |
| 642 | 3\|sg_hHSPA5_CC_1\|HSPA5 | HSPA5 | CGTTGGCGATGATCTCCACG |
| 643 | 3\|sg_hHSPA5_CC_2\|HSPA5 | HSPA5 | TGGCCIIIICTACCTCGCGC |
| 644 | 3\|sg_hHSPA5_CC_3\|HSPA5 | HSPA5 | AATGGAGATACTCATCTGGG |
| 645 | 3\|sg_hHSPA5CC_4\|HSPA5 | HSPA5 | GAAGCCCGTCCAGAAAGTGT |
| 646 | 3\|sg_hHSPA9_CC_1\|HSPA9 | HSPA9 | CAATCTGAGGAACTCCACGA |
| 647 | 3\|sg_hHSPA9_CC_2\|HSPA9 | HSPA9 | AGGCTGCGGCGCCCACGAGA |
| 648 | 3\|sg_hHSPA9_CC_3\|HSPA9 | HSPA9 | ACTTTGACCAGGCCTTGCTA |
| 649 | 3\|sg_hHSPA9_CC_4\|HSPA9 | HSPA9 | ACCTTCCATAACTGCCACGC |
| 650 | 3\|sg_hPAFAH1_B1_CC_1\|PAFAH1B1 | PAFAH1B1 | CGAGGCGTACATACCCAAGG |

TABLE 4 -continued

Control sgRNA Library

| SEQ ID NO. | gRNA Label | Gene | Nucleic Acid Sequence |
|---|---|---|---|
| 651 | 3\|sg_hPAFAH1_B1_CC_2\|PAFAH1B1 | PAFAH1B1 | ATGGTACGGCCAAATCAAGA |
| 652 | 3\|sg_hPAFAH1_B1_CC_3\|PAFAH1B1 | PAFAH1B1 | TCTTGTAATCCCATACGCGT |
| 653 | 3\|sg_hPAFAH1_B1_CC_4\|PAFAH1B1 | PAFAH1B1 | ATTCACAGGACACAGAGAAT |
| 654 | 3\|sg_hPCNA_CC_1\|PCNA | PCNA | CCAGGGCTCCATCCTCAAGA |
| 655 | 3\|sg_hPCNA_CC_2\|PCNA | PCNA | TGAGCTGCACCAAAGAGACG |
| 656 | 3\|sg_hPCNA_CC_3\|PCNA | PCNA | ATGTCTGCAGATGTACCCCT |
| 657 | 3\|sg_hPCNA_CC_4\|PCNA | PCNA | CGAAGATAACGCGGATACCT |
| 658 | 3\|sg_hPOLR2L_CC_1\|POLR2L | POLR2L | GCTGCAGGCCGAGTACACCG |
| 659 | 3\|sg_hPOLR2L_CC_2\|POLR2L | POLR2L | ACAAGTGGGAGGCTTACCTG |
| 660 | 3\|sg_hPOLR2L_CC_3\|POLR2L | POLR2L | GCAGCGTACAGGGATGATCA |
| 661 | 3\|sg_hPOLR2L_CC_4\|POLR2L | POLR2L | GCAGTAGCGCTTCAGGCCCA |
| 662 | 3\|sg_hRPL9_CC_1\|RPL9 | RPL9 | CAAATGGTGGGGTAACAGAA |
| 663 | 3\|sg_hRPL9_CC_2\|RPL9 | RPL9 | GAAAGGAACTGGCTACCGTT |
| 664 | 3\|sg_hRPL9_CC_3\|RPL9 | RPL9 | AGGGCTTCCGTTACAAGATG |
| 665 | 3\|sg_hRPL9_CC_4\|RPL9 | RPL9 | GAACAAGCAACACCTAAAAG |
| 666 | 3\|sg_hSF3A3_CC_1\|SF3A3 | SF3A3 | TGAGGAGAAGGAACGGCTCA |
| 667 | 3\|sg_hSF3A3_CC_2\|SF3A3 | SF3A3 | GGAAGAATGCAGAGTATAAG |
| 668 | 3\|sg_hSF3A3CC3\|SF3A3 | SF3A3 | GGAATTTGAGGAACTCCTGA |
| 669 | 3\|sg_hSF3A3_CC_4\|SF3A3 | SF3A3 | GCTCACCGGCCATCCAGGAA |
| 670 | 3\|sg_hSF3B3_CC_1\|SF3B3 | SF3B3 | ACTGGCCAGGAACGATGCGA |
| 671 | 3\|sg_hSF3B3_CC_2\|SF3B3 | SF3B3 | GCAGCTCCAAGATCTTCCCA |
| 672 | 3\|sg_hSF3B3CC3\|SF3B3 | SF3B3 | GAATGAGTACACAGAACGGA |
| 673 | 3\|sg_hSF3B3_CC_4\|SF3B3 | SF3B3 | GGAGCAGGACAAGGTCGGGG |

Example 2—BRD9 Degrader Depletes BRD9 Protein

The following example demonstrates the depletion of the BRD9 protein in synovial sarcoma cells treated with a BRD9 degrader.

Procedure:

Cells were treated with DMSO or the BRD9 degrader, Compound 1 (also known as dBRD9, see Remillard et al, *Angew. Chem. Int. Ed. Engl.* 56(21):5738-5743 (2017); see structure of compound 1 below), for indicated doses and timepoints.

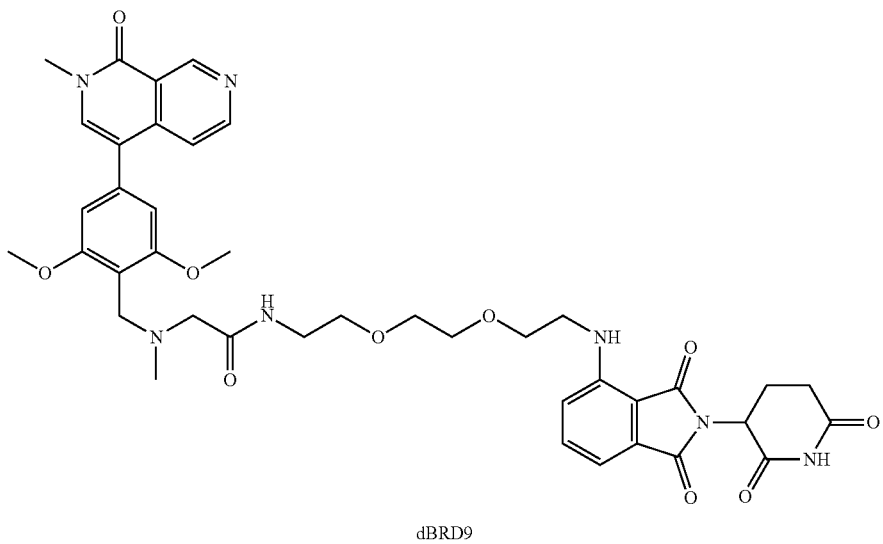

(compound 1)

dBRD9

Whole cell extracts were fractionated by SDS-PAGE and transferred to a polyvinylidene difluoride membrane using a transfer apparatus according to the manufacturer's protocols (Bio-Rad). After incubation with 5% nonfat milk in TBST (10 mM Tris, pH 8.0, 150 mM NaCl, 0.5% Tween 20) for 60 min, the membrane was incubated with antibodies against BRD9 (1:1,000, Bethyl laboratory A303-781A), GAPDH (1:5,000, Cell Signaling Technology), and/or MBP (1:1,000, BioRad) overnight at 4° C.

Figure 2:
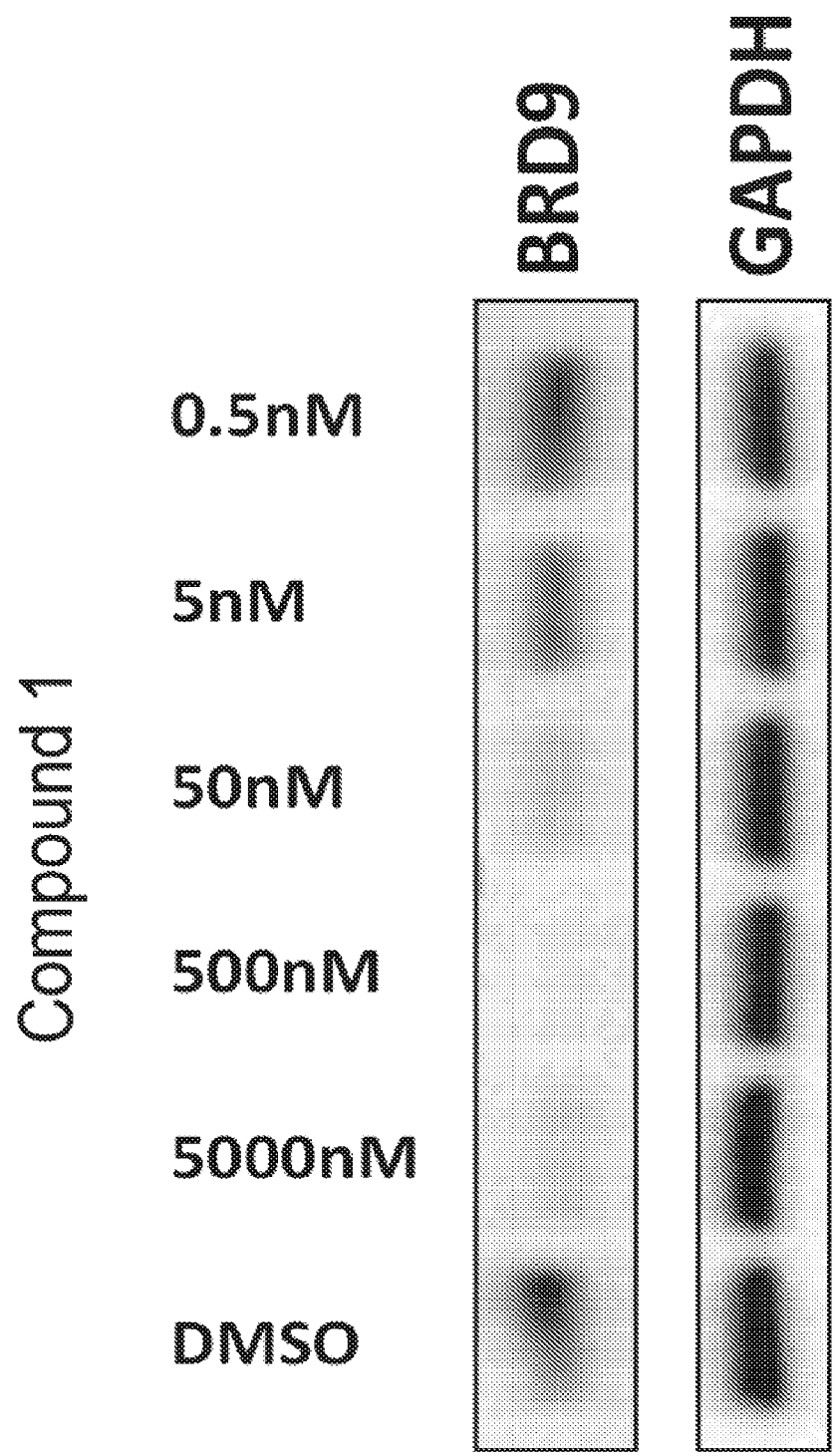
FIG. 2 is an image illustrating dose dependent depletion of BRD9 levels in a synovial sarcoma cell line (SYO1) in the presence of a BRD9 degrader.
Figure 3:
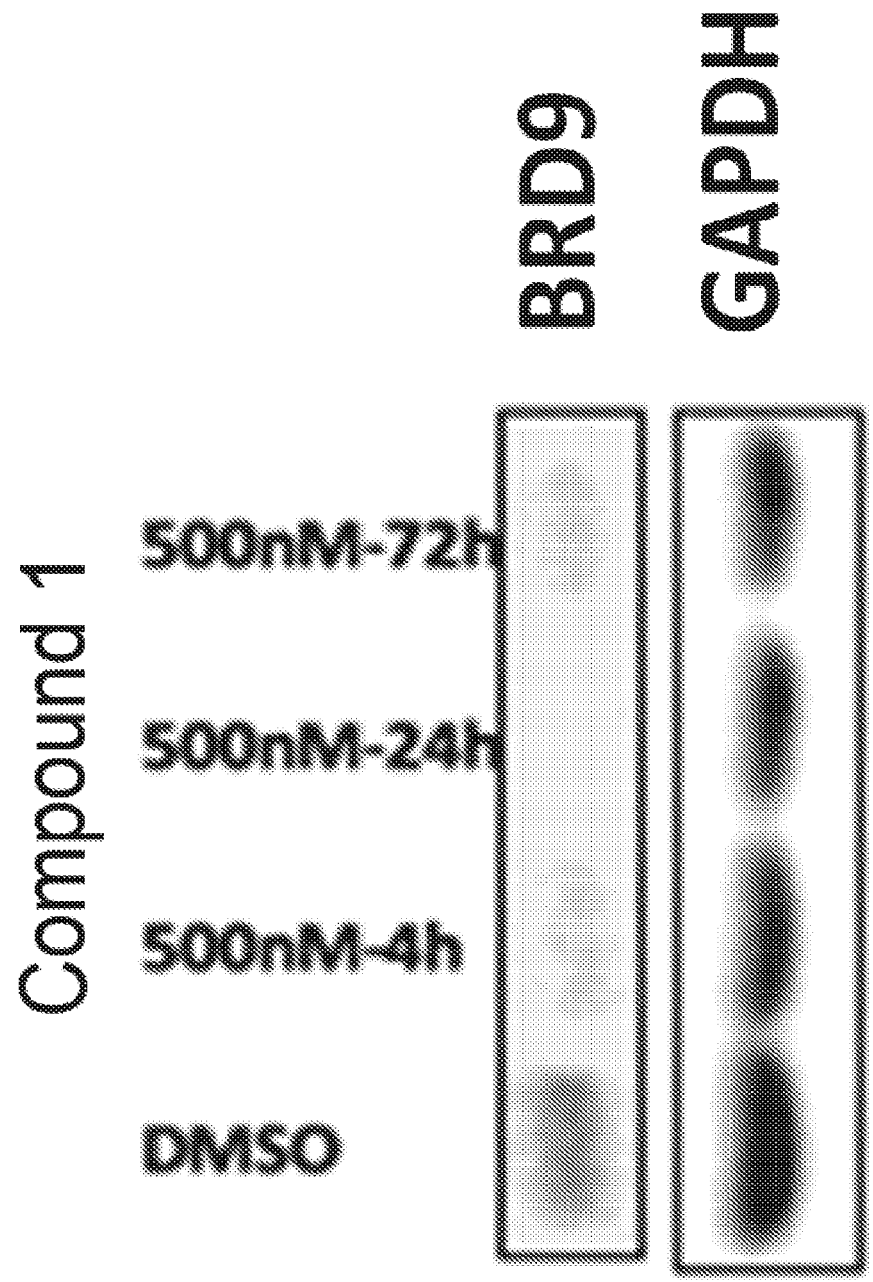
FIG. 3 is an image illustrating sustained suppression of BRD9 levels in a synovial sarcoma cell line (SYO1) in the presence of a BRD9 degrader over 72 hours.
Figure 4:
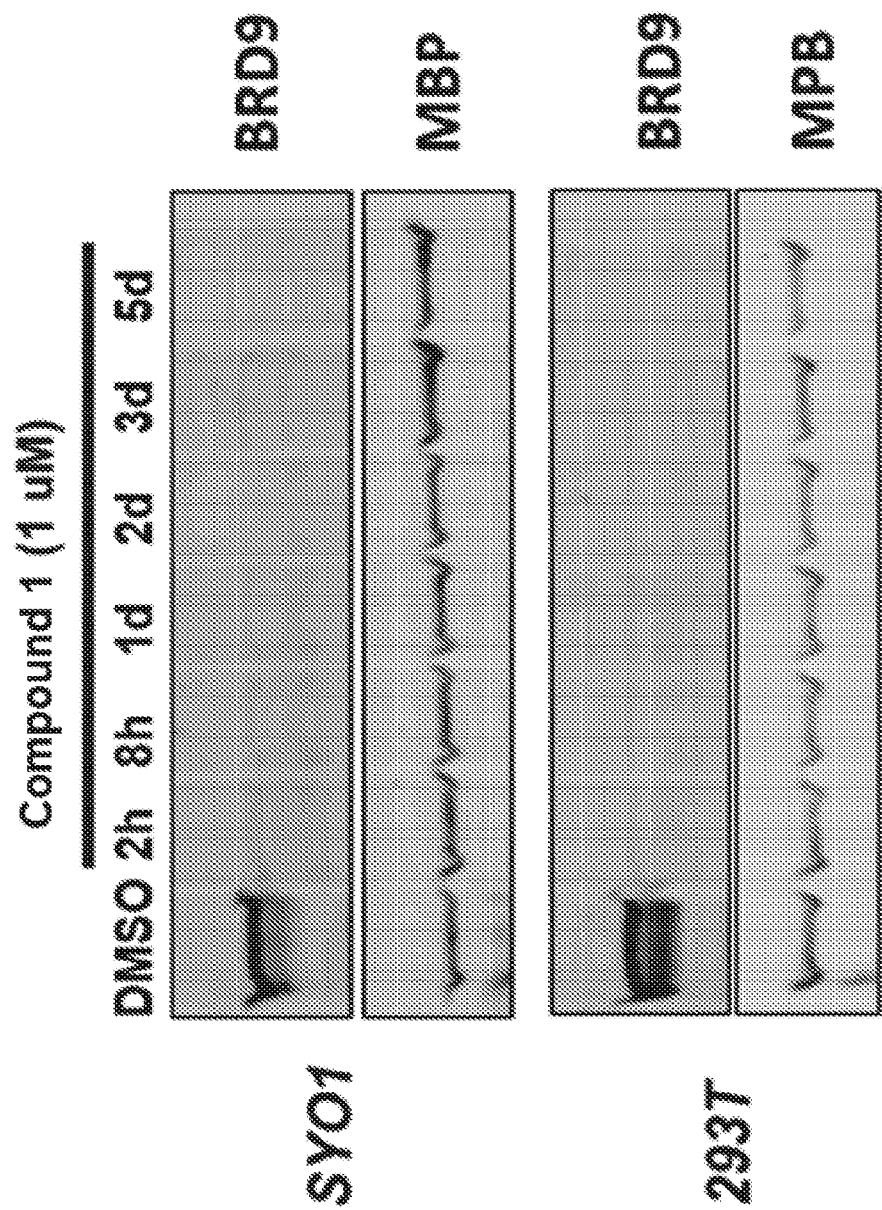
FIG. 4 is an image illustrating sustained suppression of BRD9 levels in two cell lines (293T and SYO1) in the presence of a BRD9 degrader over 5 days.

Membranes were washed three times for 10 min and incubated with anti-mouse or anti-rabbit antibodies conjugated with either horseradish peroxidase (HRP, FIGS. 2-3) or IRDye (FIG. 4, 1:20,000, LI-COR) for at least 1 h. Blots were washed with TBST three times and developed with either the ECL system according to the manufacturer's protocols (FIGS. 2-3) or scanned on an Odyssey CLx Imaging system (FIG. 4).

Results:

Treatment of SYO1 synovial sarcoma cells with the BRD9 degrader Compound 1 results in dose dependent (FIG. 2) and time dependent (FIG. 3) depletion of BRD9 in the cells. Further, as shown in FIG. 4, the depletion of BRD9 by Compound 1 is replicated in a non-synovial sarcoma cell line (293T) and may be sustained for at least 5 days.

Example 3—Inhibition of Growth of Synovial Cell Lines by BRD9 Inhibitors and BRD9 Degraders The following example demonstrates that BRD9 degraders and inhibitors selectively inhibit growth of synovial sarcoma cells.

Figure 5:
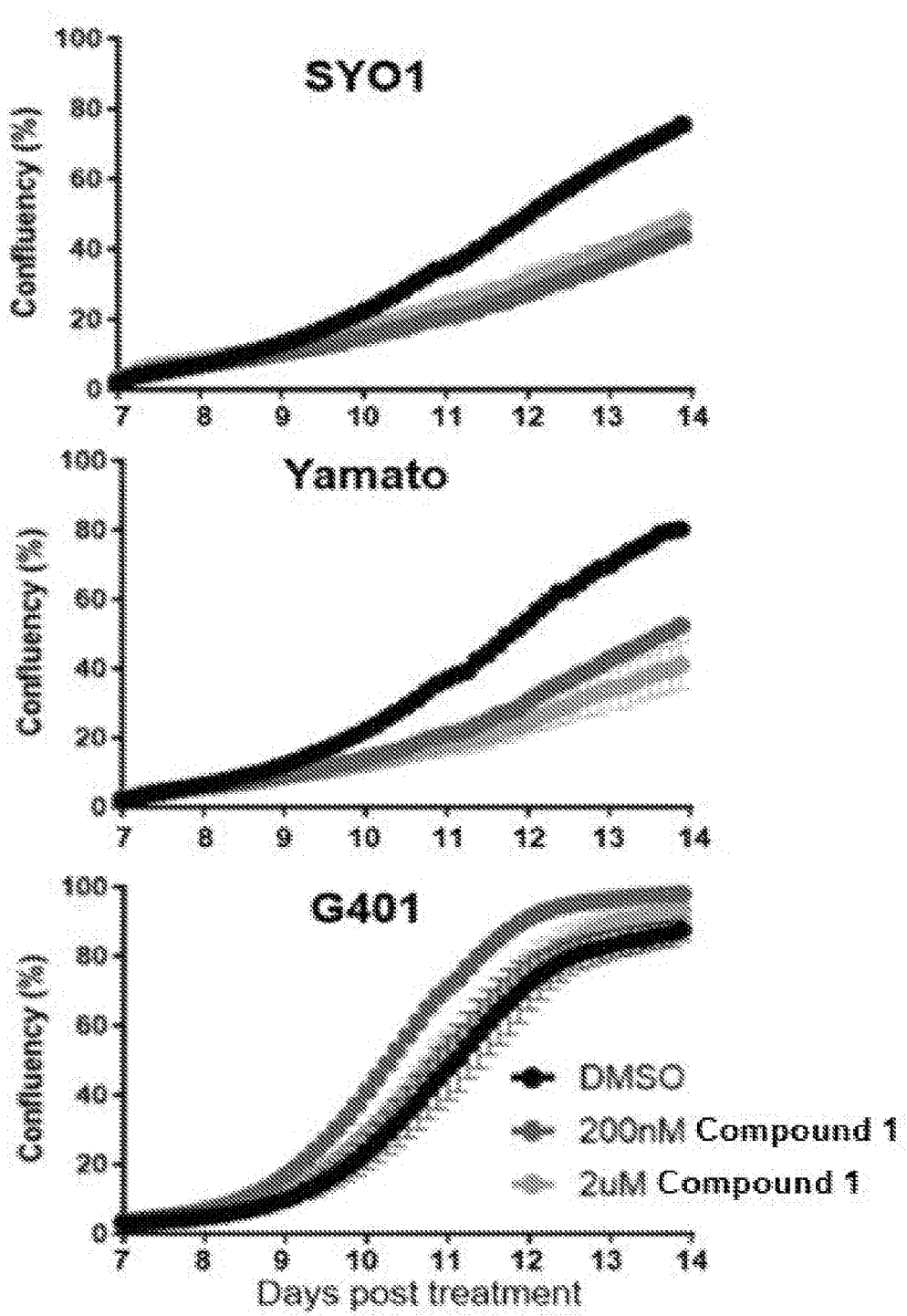
FIG. 5 is an image illustrating sustained suppression of BRD9 levels in three synovial sarcoma cell lines (293T, SYO1, and Yamato) in the presence of a BRD9 degrader over 7 days compared to the levels in cells treated with CRISPR reagents.

Procedures:

Cells were treated with DMSO or the BRD9 degrader, Compound 1, at indicated concentrations, and proliferation was monitored from day 7 to day 14 by measuring confluency over time using an IncuCyte live cell analysis system (FIG. 5). Growth medium and compounds were refreshed every 3-4 days.

Cells were seeded into 12-well plates and treated with DMSO, 1 µM BRD9 inhibitor, Compound 2 (also known as BI-7273, see Martin et al, J Med Chem. 59(10):4462-4475 (2016); see structure of compound 2 below), or 1 µM BRD9 degrader, Compound 1.

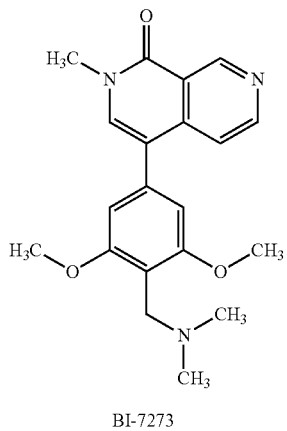

(compound 2)

BI-7273

The number of cells was optimized for each cell line. Growth medium and compounds were refreshed every 3-5 days. SYO1, Yamato, A549, 293T and HS-SY-II cells were fixed and stained at day 11. ASKA cells were fixed and stained at day 23. Staining was done by incubation with crystal violet solution (0.5 g Crystal Violet, 27 ml 37% Formaldehyde, 100 mL 10×PBS, 10 mL Methanol, 863 dH20 to 1 L) for 30 min followed by 3× washes with water and drying the plates for at least 24 h at room temperature. Subsequently plates were scanned on an Odyssey CLx Imaging system (FIG. 6).

Figure 7:
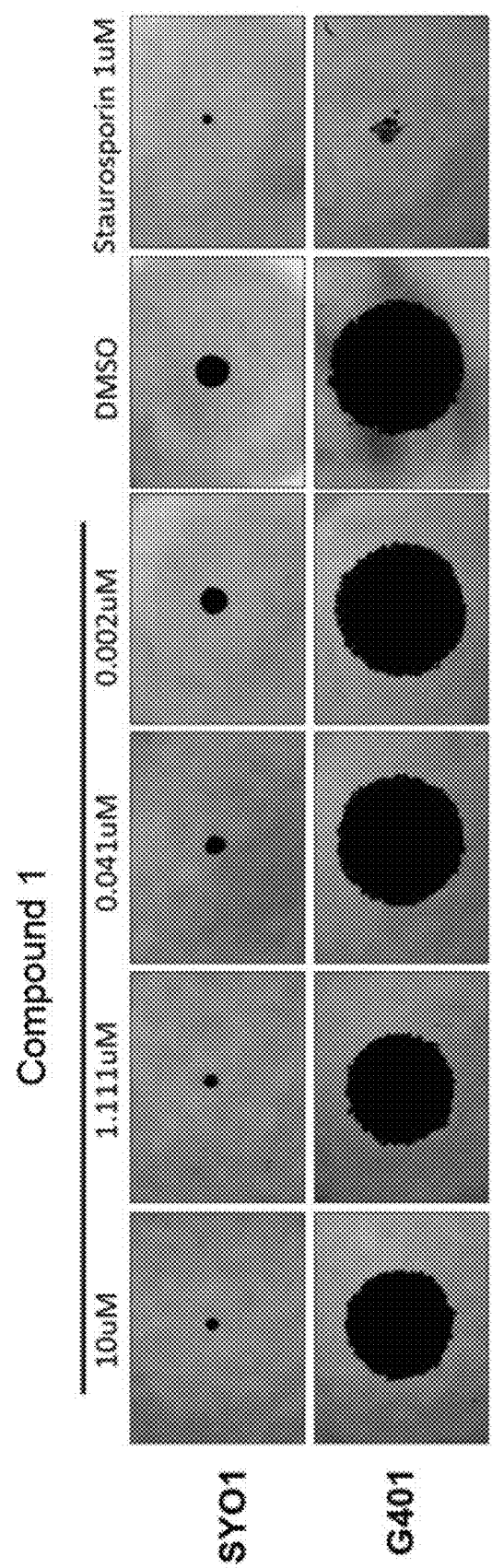
FIG. 7 is an image illustrating the effect on cell growth of two cell lines (SYO1 and G401) in the presence of a BRD9 degrader.

Cells were seeded into 96-well ultra low cluster plate (Costar, #7007) in 200 µL complete media and treated at day 2 with DMSO, Staurosporin, or BRD9 degarder, Compound 1, at indicated doses (FIG. 7). Media and compounds were changed every 5 d and cell colonies were imaged at day 14.

Figure 6:
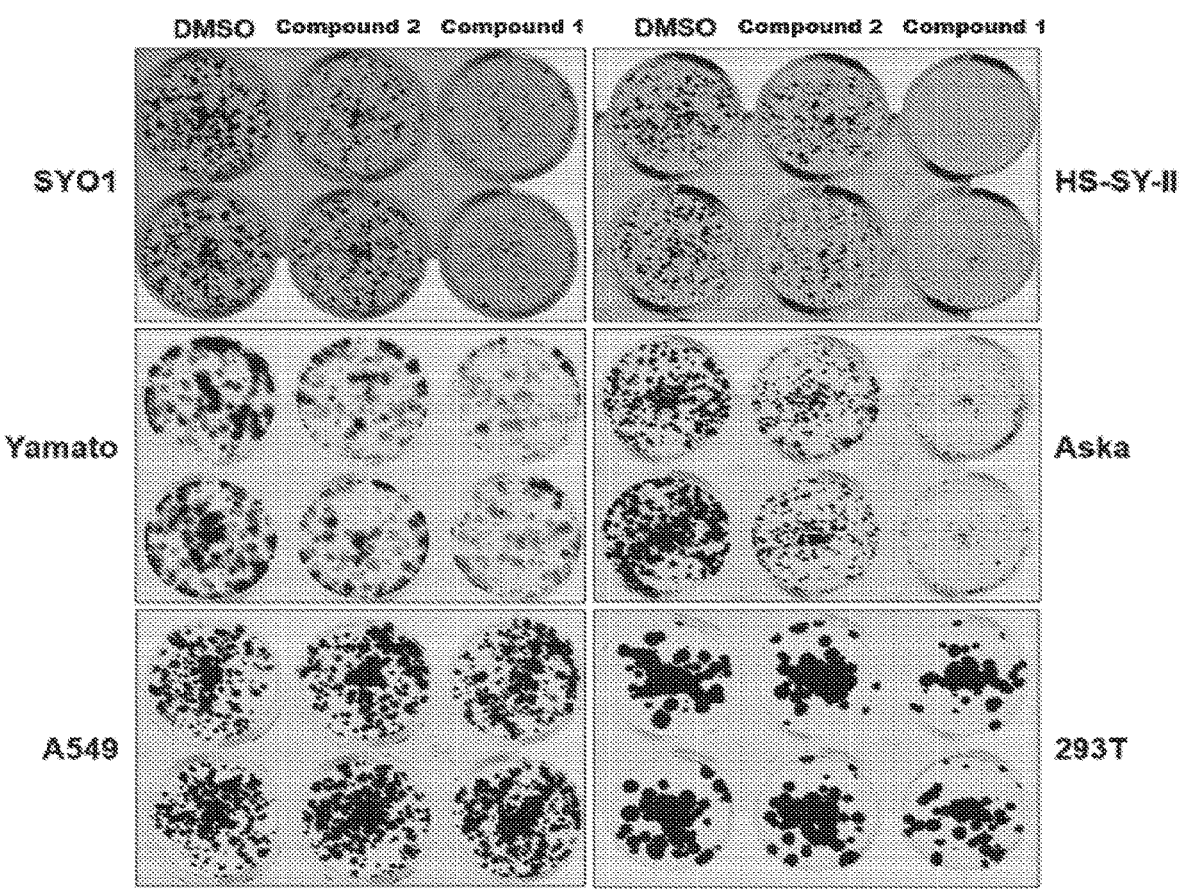
FIG. 6 is an image illustrating the effect on cell growth of six cell lines (SYO1, Yamato, A549, HS-SY-II, ASKA, and 293T) in the presence of a BRD9 degrader and a BRD9 inhibitor.

Results:

As shown in FIGS. 5, 6, and 7, treatment of synovial sarcoma cell lines (SYO1, Yamato, HS-SY-II, and ASKA) with a BRD9 inhibitor, Compound 2, or a BRD9 degrader, Compound 1, results in inhibition of the growth of the cells, but does not result in inhibition of the growth of non-synovial control cancer cell lines (293T, A549, G401).

Example 4—Selective Inhibition of Growth of Synovial Cell Lines by BRD9 Degraders and BRD9 Binders The following example demonstrates that BRD9 degraders and binders selectively inhibit growth of synovial sarcoma cells.

Procedure:

Cells were seeded into 6-well or 12-well plates and were treated daily with a BRD9 degrader (Compound 1), a bromo-domain BRD9 binder (Compound 2), E3 ligase binder (lenalidomide), DMSO, or staurosporin (positive control for cell killing), at indicated concentrations. The number of cells was optimized for each cell line. Growth media was refreshed every 5 days. By day 14, medium was removed, cells were washed with PBS, and stained using 500 μL of 0.005% (w/v) crystal violet solution in 25% (v/v) methanol for at least 1 hour at room temperature. Subsequently plates were scanned on an Odyssey CLx Imaging system.

Figure 8:
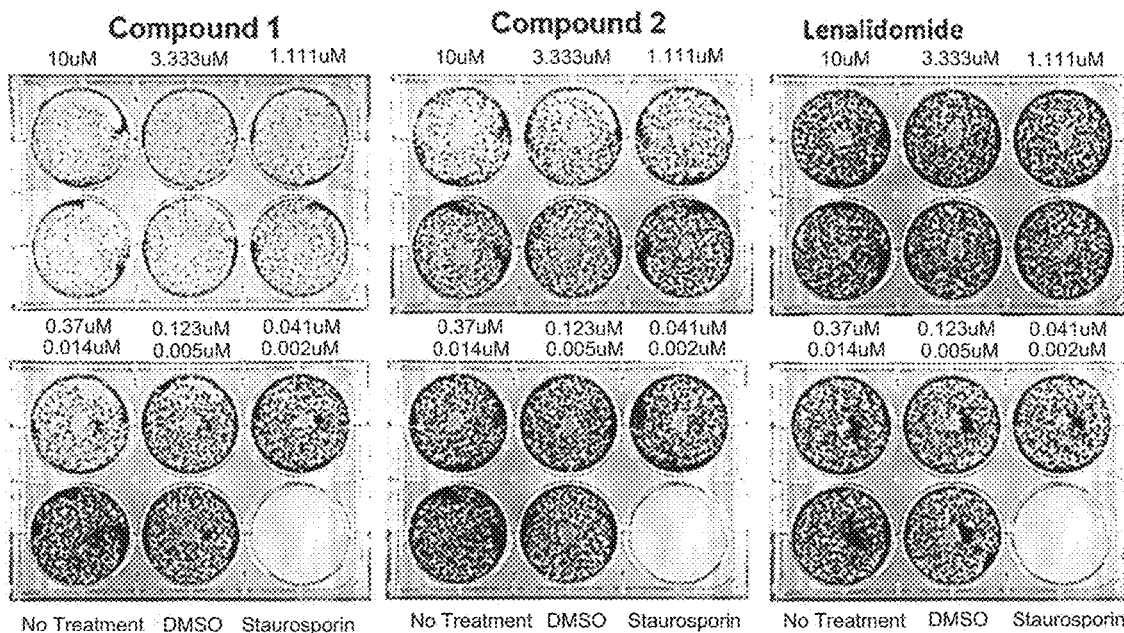
FIG. 8 is an image illustrating the effect on cell growth of three synovial sarcoma cell lines (SYO1, HS-SY-II, and ASKA) in the presence of a BRD9 degrader, BRD9 binder and E3 ligase binder.
Figure 8:
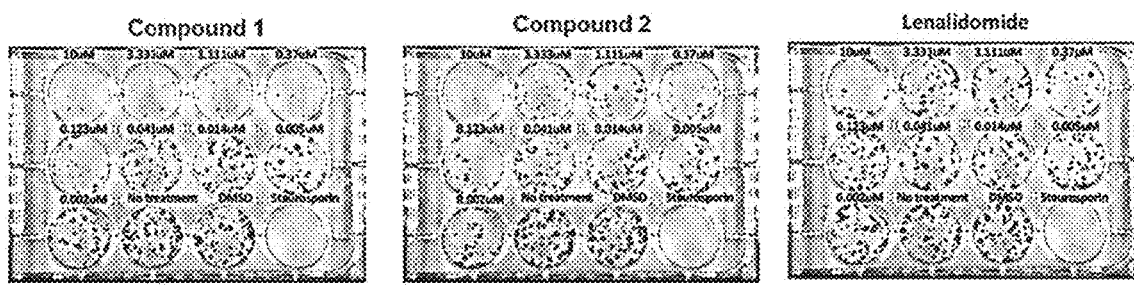
Figure 8:
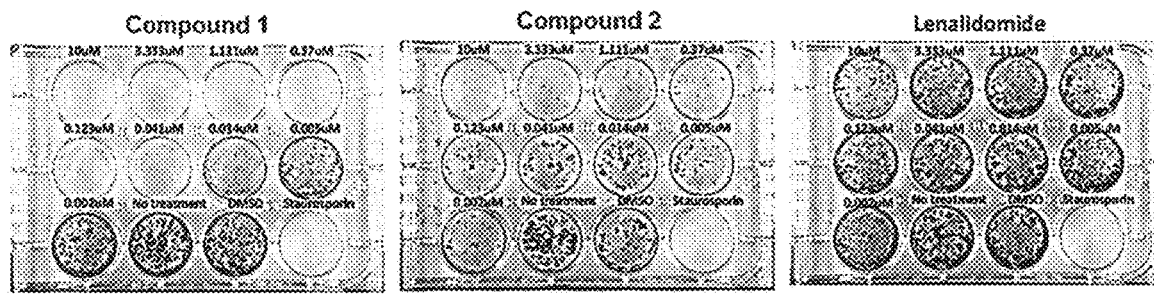
Figure 9:
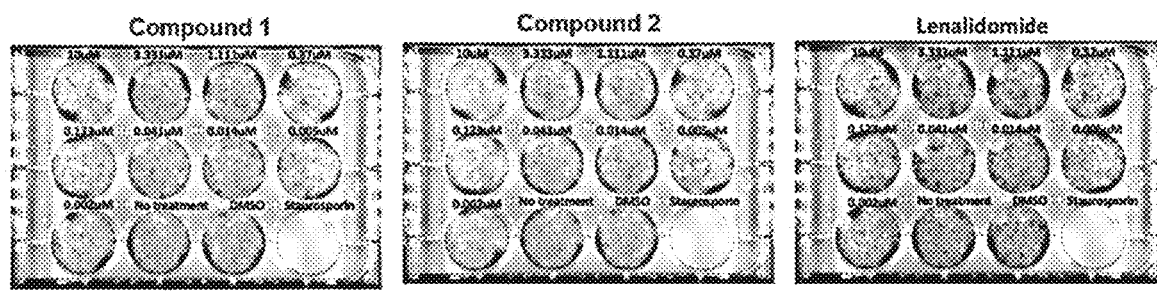
FIG. 9 is an image illustrating the effect on cell growth of three non-synovial sarcoma cell lines (RD, HCT116, and Calu6) in the presence of a BRD9 degrader, BRD9 binder and E3 ligase binder.
Figure 9:
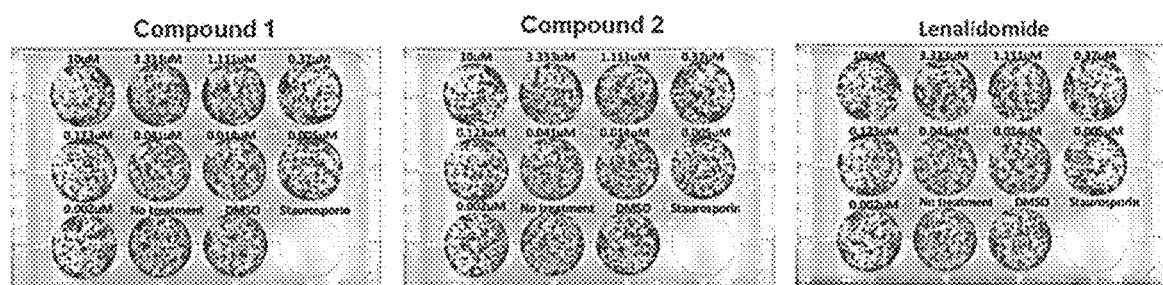
Figure 9:
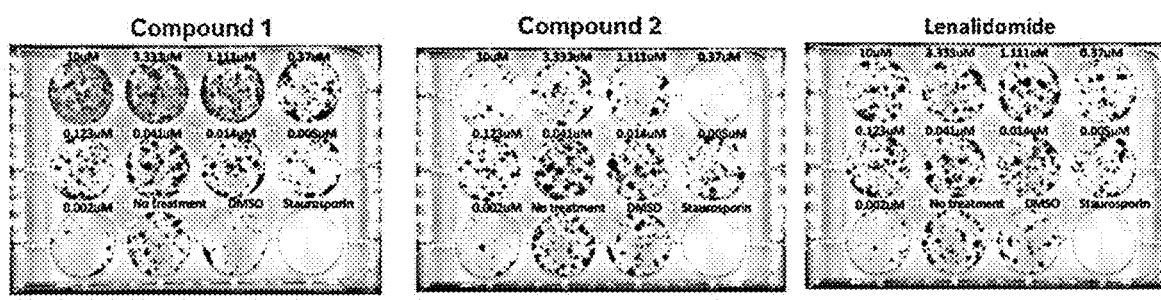
Figure 10:
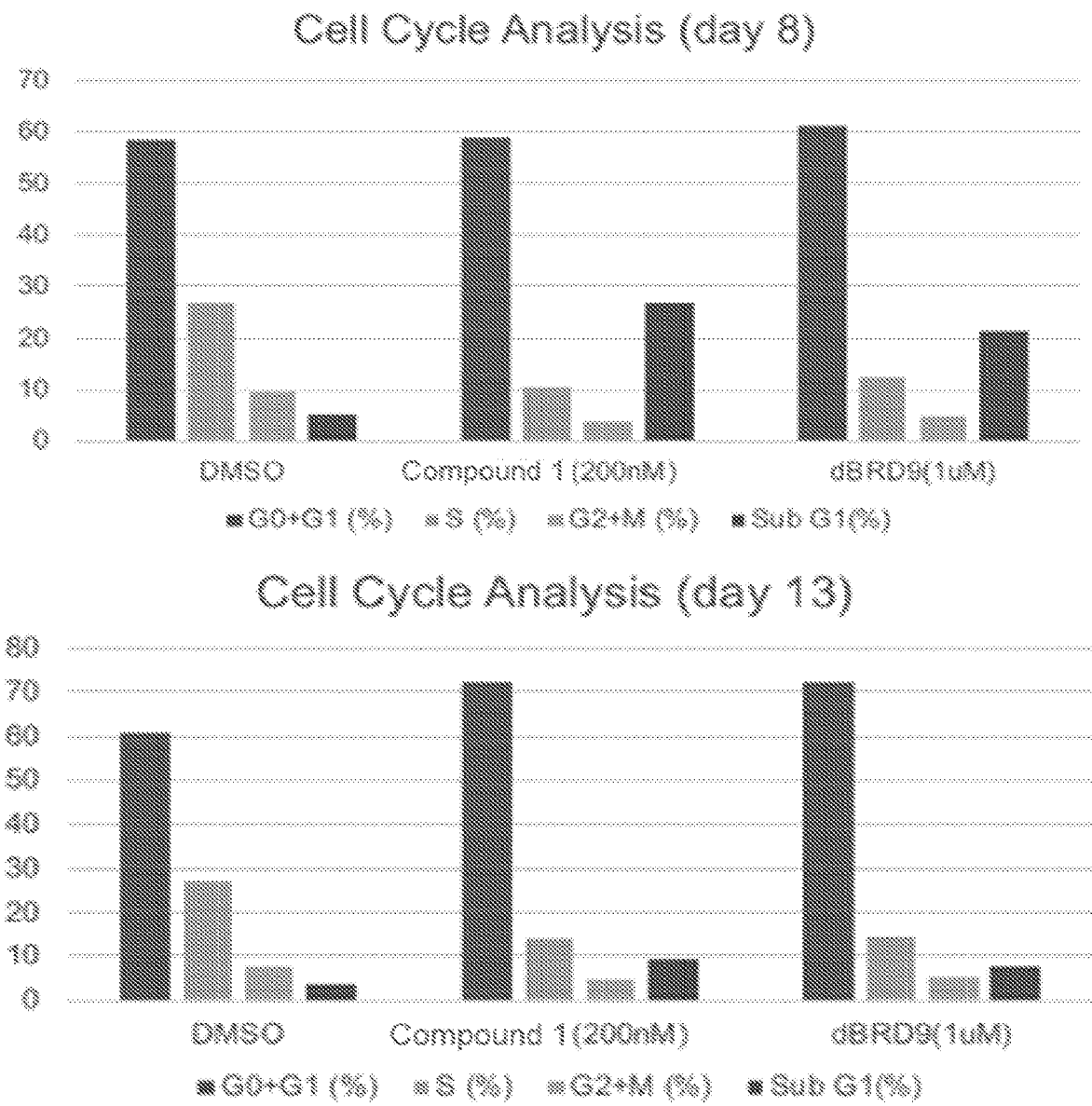
FIG. 10 is a graph illustrating the percentage of SYO1 in various cell cycle phases following treatment with DMSO, Compound 1 at 200 nM, or Compound 1 at 1 µM for 8 or 13 days.
Figure 11:
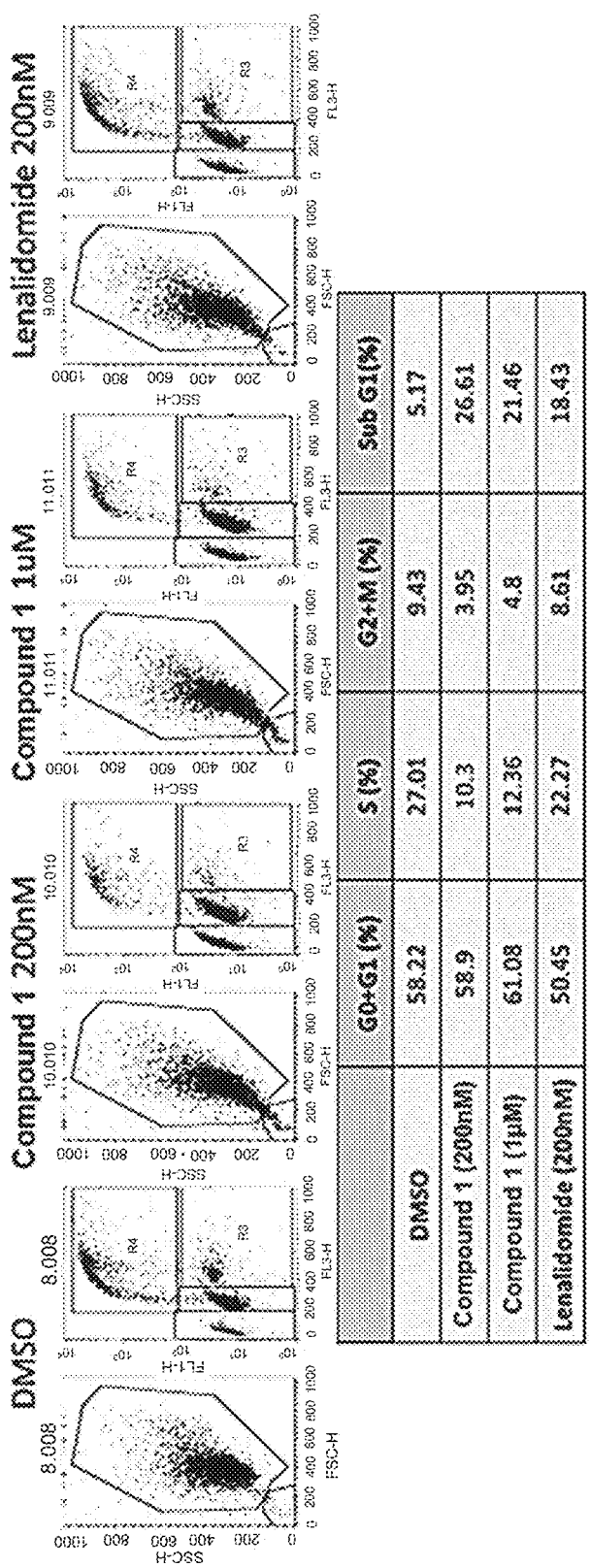
FIG. 11 is a series of contour plots illustrating the percentage of SYO1 cells in various cell cycle phases following treatment with DMSO, Compound 1 at 200 nM, Compound 1 at 1 µM, or lenalidomide at 200 nM for 8 days. Numerical values corresponding to each contour plot are found in the table below.
Figure 12:
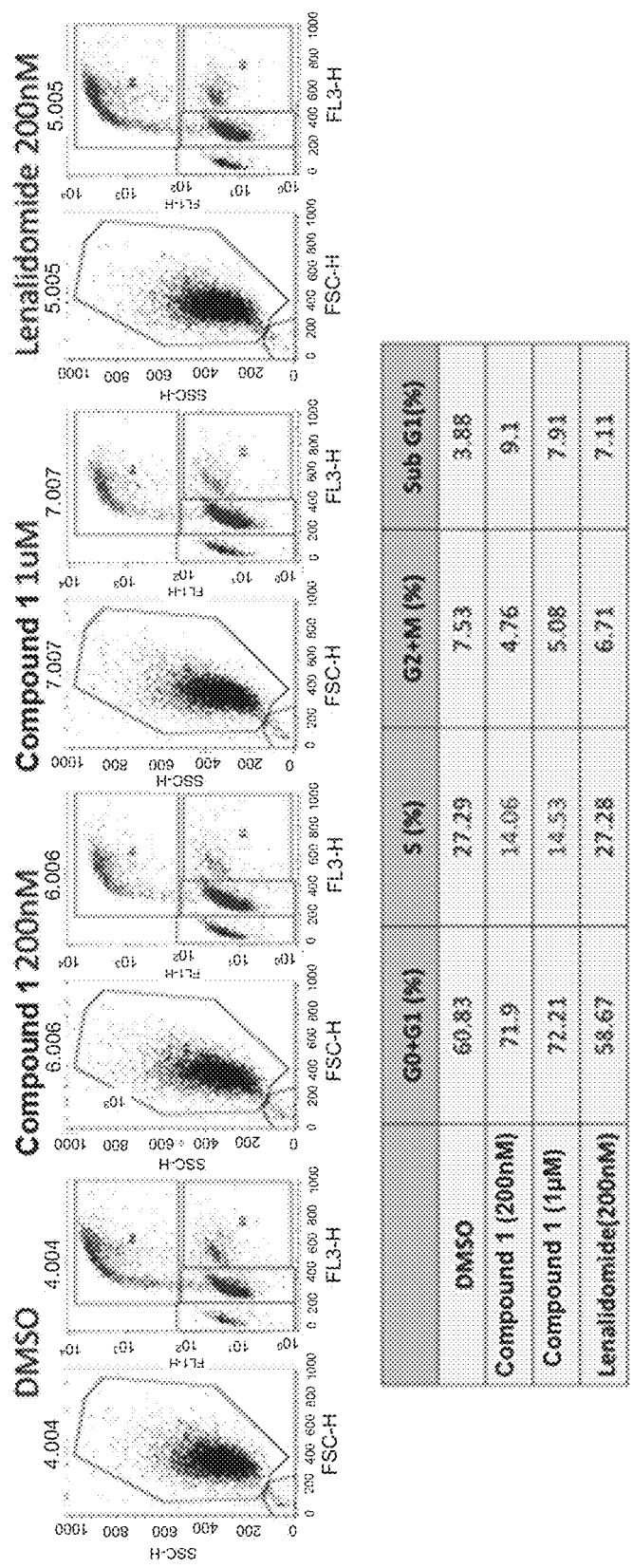
FIG. 12 is a series of contour plots illustrating the percentage of SYO1 cells in various cell cycle phases following treatment with DMSO, Compound 1 at 200 nM, Compound 1 at 1 µM, or lenalidomide at 200 nM for 13 days. Numerical values corresponding to each contour plot are found in the table below.
Figure 13:
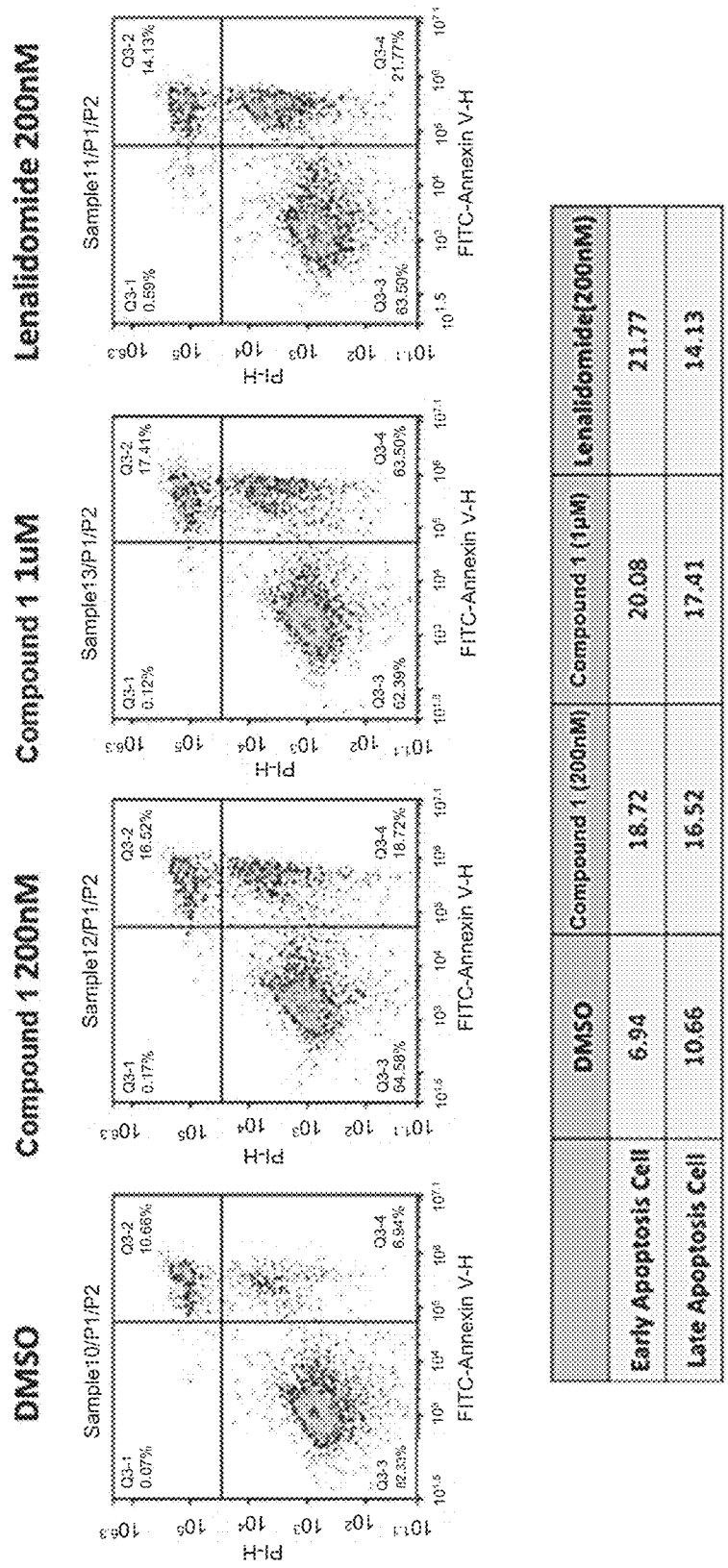
FIG. 13 is a series of contour plots illustrating the percentage of early- and late-apoptotic SYO1 cells following treatment with DMSO, Compound 1 at 200 nM, Compound 1 at 1 µM, or lenalidomide at 200 nM for 8 days. Numerical values corresponding to each contour plot are found in the table below.

Results:

As shown in FIGS. 8 and 9, treatment of synovial sarcoma cell lines (SYO1, HS-SY-II, and ASKA) with Compound 1 or Compound 2 resulted in inhibition of the growth of the cells, but did not result in inhibition of the growth of non-synovial control cancer cell lines (RD, HCT116, and Calu6). Overall, Compound 1 showed most significant growth inhibition in all synovial cell lines.

Example 5—Inhibition of Cell Growth in Synovial Sarcoma Cells

The following example shows that BRD9 degraders inhibit cell growth and induce apoptosis in synovial sarcoma cells.

Procedure:

SYO1 cells were treated for 8 or 13 days with DMSO, a BRD9 degrader (Compound 1) at 200 nM or 1 μM, or an E3 ligase binder (lenalidomide) at 200 nM. Compounds were refreshed every 5 days. Cell cycle analysis was performed using the Click-iT™ Plus EdU Flow Cytometry Assay (Invitrogen). The apoptosis assay was performed using the Annexin V-FITC Apoptosis Detection Kit (Sigma A9210). Assays were performed according to the manufacturer's protocol.

Results:

As shown in FIGS. 10-13, treatment with Compound 1 for 8 or 13 days resulted in reduced numbers of cells in the S-phase of the cell cycle as compared to DMSO and lenalidomide.

Treatment with Compound 1 for 8 days also resulted in increased numbers of early- and late-apoptotic cells as compared to DMSO controls.

Example 6—Composition for SS18-SSX1-BAF

The following example shows the identification of BRD9 as a component of SS18-SSX containing BAF complexes.

Procedure:

A stable 293T cell line expressing HA-SS18SSX1 was generated using lentiviral integration. SS18-SSX1 containing BAF complexes were subject to affinity purification and subsequent mass spectrometry analysis revealed SS18-SSX1 interacting proteins.

Figure 14:
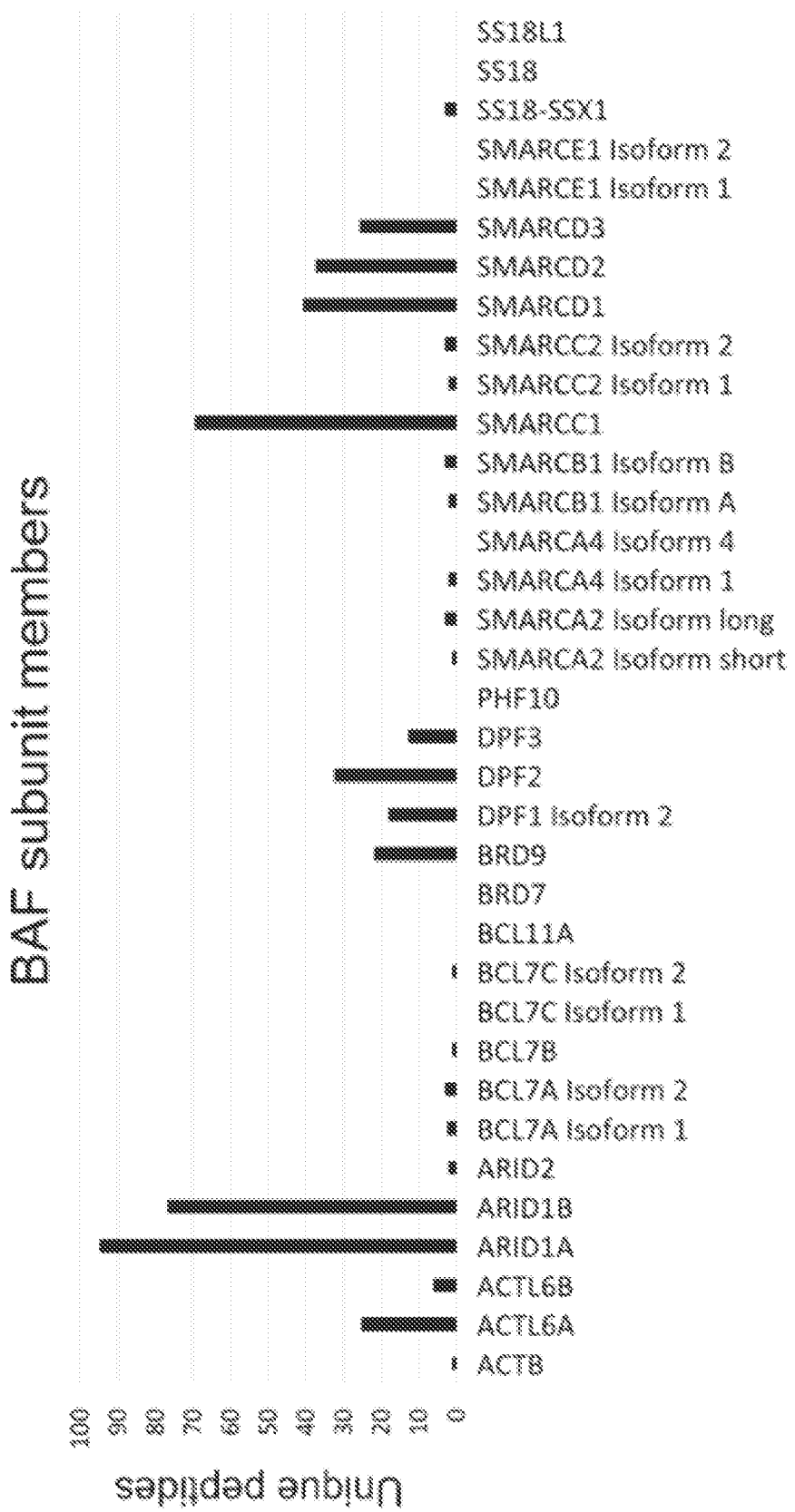
FIG. 14 is a graph illustrating the proteins present in BAF complexes including the SS18-SSX fusion protein.

Results:

As shown in FIG. 14, BAF complexes including the SS18-SSX fusion protein also included BRD9. More than 5 unique peptides were identified for ARID1A (95 peptides), ARID1B (77 peptides), SMARCC1 (69 peptides), SMARCD1 (41 peptides), SMARCD2 (37 peptides), DPF2 (32 peptides), SMARCD3 (26 peptides), ACTL6A (25 peptides), BRD9 (22 peptides), DPF1 Isoform 2 (18 peptides), DPF3 (13 peptides), and ACTL6B (6 peptides).

Example 7—Preparation of 1-(1-[imidazo[1,2-a]pyridin-5-yl]-7-(morpholin-4-yl)indolizin-3-yl)ethan-1-one (Compound B16)

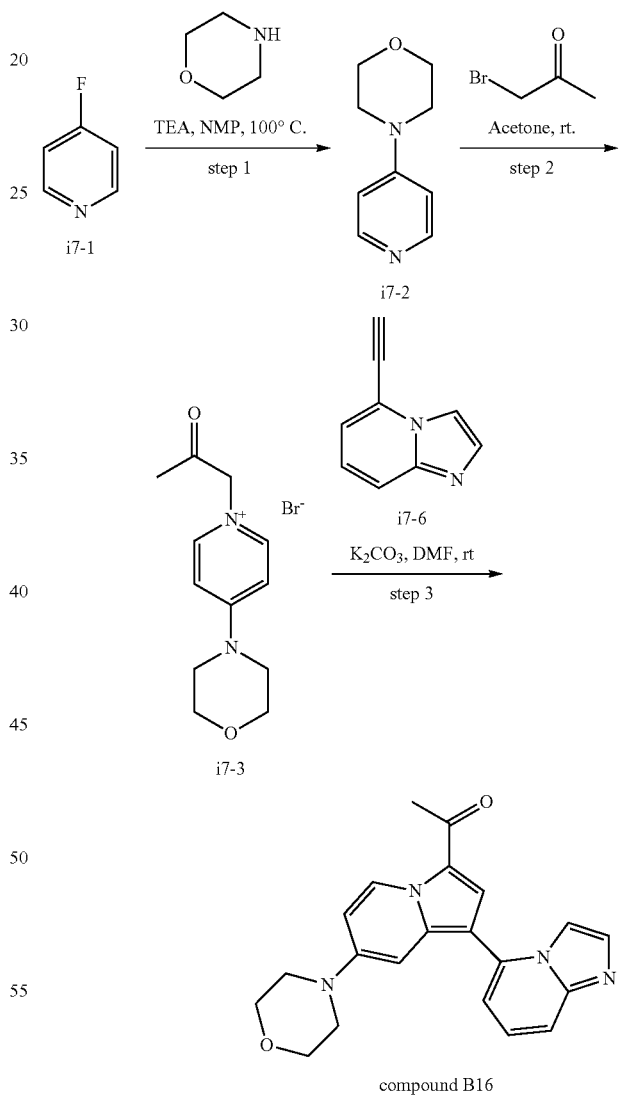

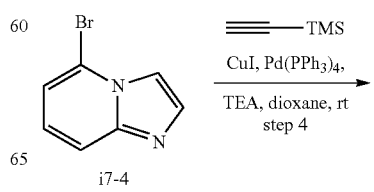

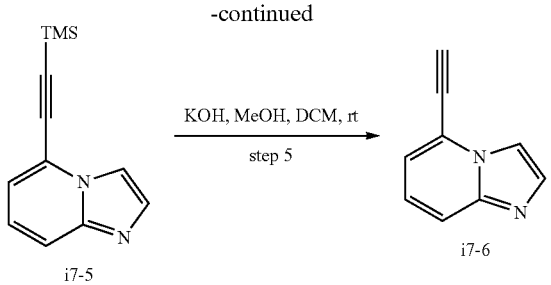

Step 1: Preparation of 4-(pyridin-4-yl)morpholine (i7-2)

To the solution of 4-chloropyridine (1 g, 8.807 mmol, 1 equiv) in toluene (25 mL) was added morpholine (920.79 mg, 10.569 mmol, 1.2 equiv), Pd(OAC)$_2$ (197.74 mg, 0.881 mmol, 0.1 equiv), BINAP (1.10 g, 1.761 mmol, 0.2 equiv), and tert-BuONa (2.54 g, 26.422 mmol, 3 equiv). The resulting solution was stirred at 110° C. for 12 hours under nitrogen atmosphere. The resulting solution was concentrated. The residue was purified by Flash column chromatography with EtOAc/PE (0-100%), to give compound 4-(pyridin-4-yl)morpholine (600 mg, 41.49%) as yellow solid. LCMS (ESI) m/z: [M+H]+=165.

Step 2: Preparation of 4-(morpholin-4-yl)-1-(2-oxopropyl)pyridin-1-ium bromide (i7-3)

1-bromopropan-2-one (275.27 mg, 2.010 mmol, 1.1 equiv) was added slowly to a solution of 4-(pyridin-4-yl)morpholine (300 mg, 1.827 mmol, 1 equiv) in ACN (5 mL), and the resulting mixture was stirred at room temperature for 3 hour. The solid was collected by filtration, washed, and dried in vacuo to give pure 4-(morpholin-4-yl)-1-(2-oxopropyl)pyridin-1-ium bromide (181 mg, 32.89%). LCMS (ESI) m/z: [M+H]+=221.

Step 3: Preparation of 1-(1-[imidazo[1,2-a]pyridin-5-yl]-7-(morpholin-4-yl)indolizin-3-yl)ethan-1-one (Compound B16)

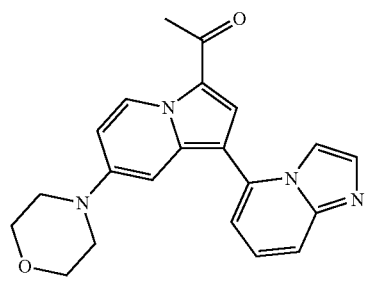

compound B16

To the solution of 4-(morpholin-4-yl)-1-(2-oxopropyl)pyridin-1-ium bromide (181 mg, 0.601 mmol, 1 equiv) in DMF (5 mL) was added 5-ethynylimidazo[1,2-a]pyridine (256.30 mg, 1.803 mmol, 3 equiv) K$_2$CO$_3$ (249.17 mg, 1.803 mmol, 3 equiv). The resulting solution was stirred at 90° C. for 3 hours. The resulting solution was concentrated. The residue was purified by reverse flash chromatography (conditions: column, C18 silica gel; mobile phase, MeOH in water, 10% to 100% gradient in 45 minutes; detector, UV 254 nm). This resulted in 1-(1-[imidazo[1,2-a]pyridin-5-yl]-7-(morpholin-4-yl)indolizin-3-yl)ethan-1-one (105.7 mg, 46.51%) as a yellow solid. $^1$H NMR (300 MHz, DMSO-d6) δ9.66 (d, 1H), 8.19 (d, 1H), 8.11 (d, 2H), 8.03-7.85 (m, 2H), 7.57 (d, 1H), 7.21-7.12 (m, 1H), 6.72 (d, 1H), 3.72 (t, 4H), 3.29 (d, 4H), 2.52 (s, 3H). LCMS (ESI) m/z: [M+H]+=361.10.

Step 4: Preparation of 5-[2-(trimethylsilyl)ethynyl]imidazo[1,2-a]pyridine (i7-5)

To the solution of 5-bromoimidazo[1,2-a]pyridine (2 g, 10.150 mmol, 1 equiv) in dioxane (30 mL) was added ethynyltrimethylsilane (1196.38 g, 12.181 mmol, 1.2 equiv), CuI (386.63 mg, 2.030 mmol, 0.2 equiv), Pd(PPh$_3$)$_4$ (1172.95 g, 1.015 mmol, 0.1 equiv), and TEA (3081.38 g, 30.451 mmol, 3.0 equiv).

The resulting solution was stirred at room temperature for 3 hours under nitrogen atmosphere. The resulting solution was concentrated. The residue was purified by Flash column chromatography with EtOAc/PE (0100%), to give compound 5-[2-(trimethylsilyl)ethynyl]imidazo[1,2-a]pyridine (1.13 g, 51.94%) as yellow solid. LCMS (ESI) m/z: [M+H]+=215.

Step 5: Preparation of 5-ethynyimidazo[1,2-a]pyridine (i7-6)

To the solution of 5-[2-(trimethylsilyl)ethynyl]imidazo[1,2-a]pyridine (1.127 g, 5.258 mmol, 1 equiv) in MeOH (20 mL), DCM (10 mL) was added NaOH (420.60 mg, 10.516 mmol, 2 equiv). The resulting solution was stirred at room temperature for 1 hour. The resulting solution was concentrated. The residue was purified by Flash column chromatography with EtOAc/PE (0100%), to give compound 5-ethynylimidazo[1,2-a]pyridine (578 mg, 77.33%) as yellow solid. LCMS (ESI) m/z: [M+H]+=143.

Example 8—Preparation of 1-(1-[imidazo[1,2-a]pyridin-5-yl]-7-(4-methylpiperazin-1-yl)indolizin-3-yl)ethan-1-one (Compound B17)

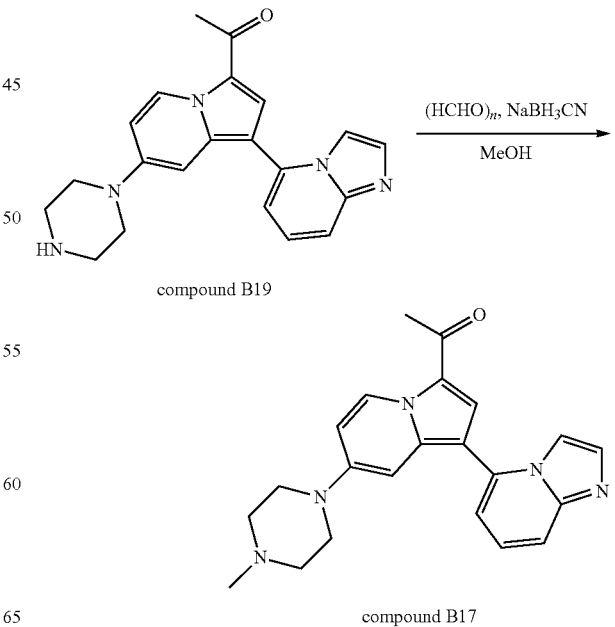

compound B19 compound B17

To a stirred mixture of 1-(1-[imidazo[1,2-a]pyridin-5-yl]-7-(piperazin-1-yl)indolizin-3-yl)ethan-1-one (50 mg, 0.139 mmol, 1 equiv) and (HCHO)$_n$ (21.07 mg, 0.696 mmol, 5 equiv) in MeOH (2 mL) was added NaBH$_3$CN (17.48 mg, 0.278 mmol, 2 equiv) in portions, and the resulting mixture was stirred for 2 hours at room temperature. The reaction mixture was then concentrated under reduced pressure. The crude product (50 mg) was purified by Prep-HPLC (conditions: X Bridge Shield RP18 OBD Column, 19*250 mm, 10 μm; mobile phase, Water (10 mmol NH$_4$HCO$_3$) and ACN (35% Phase B up to 68% in 8 minutes); Detector, UV). This resulted in 1-(1-[imidazo[1,2-a]pyridin-5-yl]-7-(4-methylpiperazin-1-yl)indolizin-3-yl)ethan-1-one (19.5 mg, 37.54%) as a yellow solid. $^1$H NMR (300 MHz, DMSO-d6) δ 9.64 (d, J=8.0 Hz, 1H), 8.06 (s, 1H), 7.81 (s, 1H), 7.66-7.52 (m, 2H), 7.35 (dd, J=9.1, 6.9 Hz, 1H), 7.12 (dd, J=7.9, 2.6 Hz, 1H), 7.03 (d, J=6.7 Hz, 1H), 6.60 (d, J=2.5 Hz, 1H), 3.27 (t, J=5.0 Hz, 4H), 2.55 (s, 3H), 2.42 (t, J=5.1 Hz, 4H), 2.21 (s, 3H). LCMS (ESI) m/z: [M+H]+=374.10.

Example 9—Preparation of 2-cyclopropyl-4-[3,5-dimethoxy-4-[(methylamino)methyl]phenyl]-2,7-naphthyridin-1-one (Compound B18)

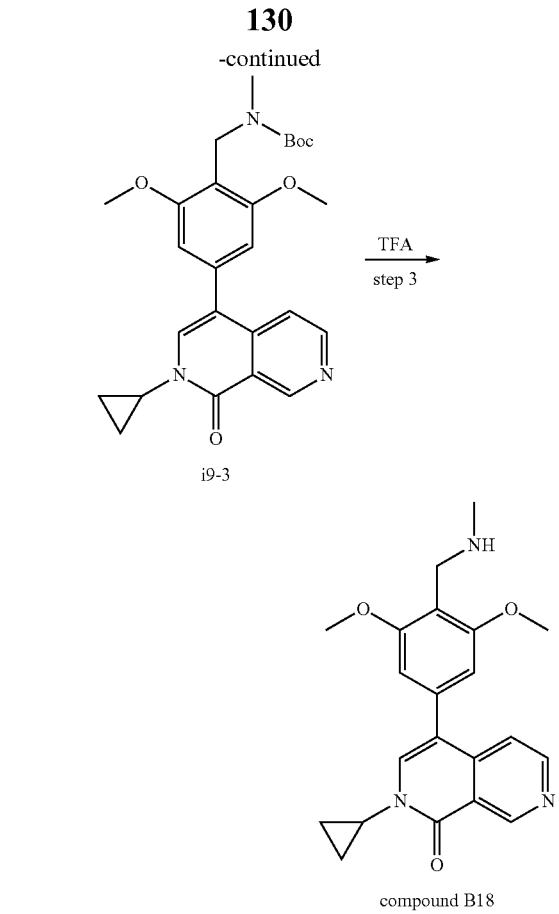

Step 1: Preparation of 4-bromo-2-cyclopropyl-2,7-naphthyridin-1-one (i9-2)

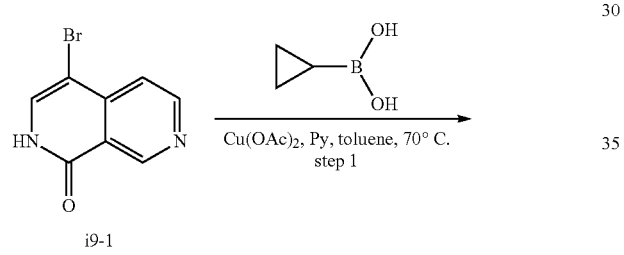

To a solution of 4-bromo-2H-2,7-naphthyridin-1-one (400.00 mg, 1.777 mmol, 1.00 equiv), cyclopropylboronic acid (229.02 mg, 2.666 mmol, 1.5 equiv) and pyridine (281.19 mg, 3.555 mmol, 2.00 equiv) in toluene (20.00 mL) was added CU(OAc)$_2$ (645.68 mg, 3.555 mmol, 2.00 equiv). The resulting mixture was stirred at 70 degrees C. for 16 hours. The solvent was removed under reduced pressure, and the residue was purified by chromatography on silica gel eluted with MeOH/DCM from 0% to 10% to give 4-bromo-2-cyclopropyl-2,7-naphthyridin-1-one (260 mg, 55.18%) as a brown solid. LCMS (ESI) m/z: [M+H]$^+$=265.

Step 2: Preparation of N-[[4-(2-cyclopropyl-1-oxo-2,7-naphthyridin-4-yl)-2,6-dimethoxyphenyl]methyl]-N-methylcarbamate (i9-3)

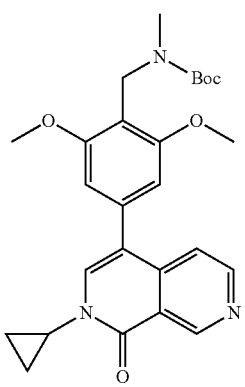

i9-3

To a solution of 4-bromo-2-cyclopropyl-2,7-naphthyridin-1-one (260.00 mg, 0.981 mmol, 1.00 equiv) and tert-butyl N-[[2,6-dimethoxy-4-(4,4,5,5-tetramethyl-1,3,2-dioxaborolan-2-yl)phenyl]methyl]-N-methylcarbamate (439.41 mg, 1.079 mmol, 1.10 equiv) in DMF (5.00 mL) was added Pd(dppf)Cl$_2$ (71.76 mg, 0.098 mmol, 0.10 equiv) and Na$_2$CO$_3$ (207.89 mg, 1.961 mmol, 2.00 equiv). After stirring at 100 degrees C. for 1 hour under nitrogen atmosphere, water (100 mL) was added, and the mixture was extracted with EtOAc (50 mL×4). The organic layer was washed with water (2×30 mL) and saturated brine (1×30 mL), then dried over anhydrous sodium sulfate, filtered, and concentrated to give crude product, which was purified by chromatography on silica gel eluted with PE/EA from 0% to 80% to give tert-butyl N-[[4-(2-cyclopropyl-1-oxo-2,7-naphthyridin-4-yl)-2,6-dimethoxyphenyl]methyl]-N-methylcarbamate (140 mg, 30.66%) as a brown solid. LCMS (ESI) m/z: [M+H]$^+$=466.

Step 3: Preparation of 2-cyclopropyl-4-[3,5-dimethoxy-4-[(methylamino)methyl]phenyl]-2,7-naphthyridin-1-one (Compound B18)

compound B18

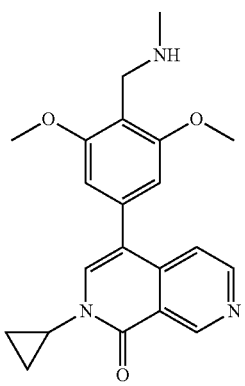

To a solution of tert-butyl N-[[4-(2-cyclopropyl-1-oxo-2,7-naphthyridin-4-yl)-2,6-dimethoxyphenyl]methyl]-N-methylcarbamate (140.00 mg, 0.301 mmol, 1.00 equiv) in DCM (1.00 mL) was added TFA (1.00 mL). The resulting mixture was stirred at room temperature for 1 hour. The solvent was removed under reduced pressure. The crude product was purified by Prep-HPLC (conditions: XBridge Shield RP18 OBD Column, 5 um, 19*150 mm; Mobile Phase A: Water (10 mmol/L NH$_4$HCO$_3$), Mobile Phase B: ACN; Flow rate: 25 mL/min; Gradient: 17% B to 23% B in 8 min; 254 nm; Rt: 6.2 min) to afford 2-cyclopropyl-4-[3,5-dimethoxy-4-[(methylamino)methyl]phenyl]-2,7-naphthyridin-1-one (45.1 mg, 41.04%) as a white solid. $^1$H NMR (300 MHz, DMSO-d6) δ 9.44 (s, 1H), 8.72 (d, J=5.7 Hz, 1H), 7.59 (s, 1H), 7.51 (d, J=5.7 Hz, 1H), 6.73 (s, 2H), 3.82 (s, 6H), 3.72 (s, 2H), 3.46-3.38 (m, 1H), 2.28 (s, 3H), 1.10-0.97 (m, 4H). LCMS (ESI) m/z: [M+H]$^+$=366.25.

Example 10—Preparation of 1-(1-[imidazo[1,2-a]pyridin-5-yl]-7-(piperazin-1-yl)indolizin-3-yl)ethan-1-one (Compound B19)

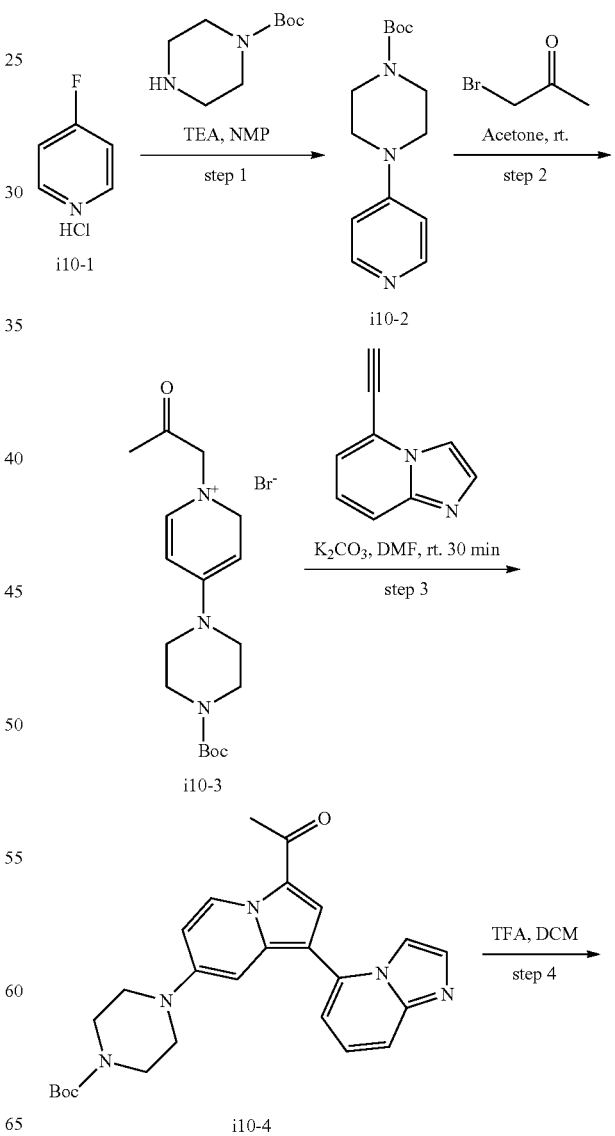

Step 1: Preparation of tert-butyl-4-(pyridin-4-yl)piperazine-1-carboxylate (i10-2)

To a stirred mixture of 4-fluoropyridine hydrochloride (4.78 g, 35.792 mmol, 1 equiv) and tert-butylpiperazine-1-carboxylate (8.00 g, 42.950 mmol, 1.2 equiv) in NMP (25 mL) was added TEA (10.87 g, 107.376 mmol, 3 equiv) at room temperature. The mixture was stirred for 3 hours at 100 degrees C. To the mixture was added EA (50 mL) and washed with water (3×20 mL). The organic layer was dried over anhydrous sodium sulfate and concentrated under vacuum, and the crude product was used in the next step directly without further purification. LCMS (ESI) m/z: [M+H]+=264.2.

Step 2: Preparation of 4-[4-[(tert-butoxy)carbonyl]piperazin-1-yl]-1-(2-oxopropyl)pyridin-1-ium bromide (i10-3)

A mixture of tert-butyl 4-(pyridin-4-yl)piperazine-1-carboxylate (526 mg, 1.997 mmol, 1 equiv) and 1-bromopropan-2-one (820.79 mg, 5.992 mmol, 3.00 equiv) in acetone (10 mL) was stirred for 3 hours at room temperature. The precipitated solids were collected by filtration and washed with acetone (3×5 mL), and the crude product was used in the next step directly without further purification. LCMS (ESI) m/z: [M+H]+=322.

Step 3: Preparation of tert-butyl-4-(3-acetyl-1-[imidazo[1,2-a]pyridin-5-yl]indolizin-7-yl)piperazine-1-carboxylate (i10-4)

To a stirred mixture of 4-[4-[(tert-butoxy)carbonyl]piperazin-1-yl]-1-(2-oxopropyl)pyridin-1-ium bromide (1 g, 2.498 mmol, 1 equiv) and 5-ethynylimidazo[1,2-a]pyridine (0.43 g, 2.998 mmol, 1.2 equiv) in DMF (16 mL) was added K$_2$CO$_3$ (0.69 g, 4.996 mmol, 2 equiv), and the resulting mixture was stirred for 15 hours at room temperature. The resulting mixture was diluted with water and extracted with EtOAc (2×20 mL). The organic layers were washed with water (3×10 mL) and dried over anhydrous sodium sulfate. After filtration, the filtrate was concentrated under reduced pressure. The residue was purified by Prep-TLC to afford tert-butyl 4-(3-acetyl-1-[imidazo[1,2-a]pyridin-5-yl]indolizin-7-yl)piperazine-1-carboxylate (178 mg, 14.27%). LCMS (ESI) m/z: [M+H]+=460.

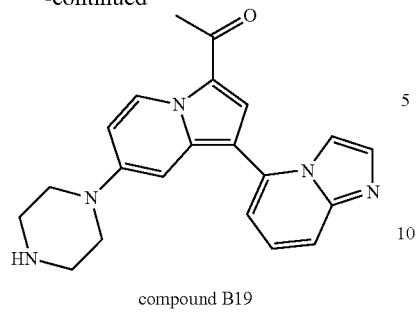

compound B19

Step 4: Preparation of 1-(1-[imidazo[1,2-a]pyridin-5-yl]-7-(piperazin-1-yl)indolizin-3-yl)ethan-1-one (Compound B19)

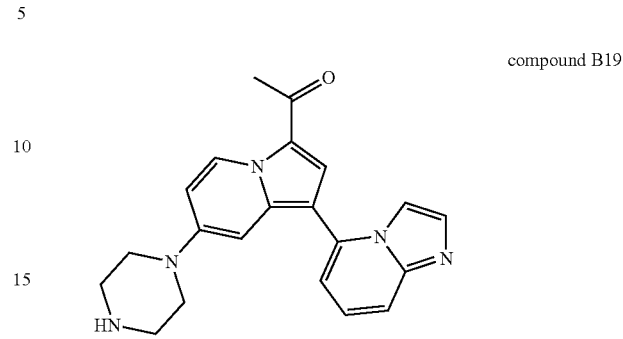

compound B19

To a stirred solution of tert-butyl 4-(3-acetyl-1-[imidazo[1,2-a]pyridin-5-yl]indolizin-7-yl)piperazine-1-carboxylate (60 mg, 0.131 mmol, 1 equiv) in DCM (5 mL) was added TFA (3.00 mL, 40.389 mmol, 309.35 equiv). The resulting mixture was stirred for 2 hours at room temperature, and then was concentrated under reduced pressure. The crude product was purified by Prep-HPLC (conditions: X Bridge Shield RP18 OBD Column, 5 μm, 19*150 mm; mobile phase, Water (0.05% NH$_3$H$_2$O) and ACN (35% Phase B up to 58% in 8 minutes); Detector, UV). This resulted in 1-(1-[imidazo[1,2-a]pyridin-5-yl]-7-(piperazin-1-yl)indolizin-3-yl)ethan-1-one (43.6 mg, 30.06%) as a white solid. $^1$H NMR (400 MHz, Methanol-d4) δ 9.81 (d, J=7.8 Hz, 1H), 8.18-8.03 (m, 4H), 7.92 (d, J=8.9 Hz, 1H), 7.63 (d, J=7.3 Hz, 1H), 7.12 (d, J=8.0, 1H), 6.87 (s, 1H), 3.69-3.61 (m, 4H), 3.42-3.29 (m, 4H), 2.61 (d, J=1.5 Hz, 3H). LCMS (ESI) m/z: [M+H]+=360.05.

Example 11—Preparation of 4-[4-[(3-aminoazetidin-1-yl)methyl]-3,5-dimethoxyphenyl]-2-methyl-1,2-dihydro-2,7-naphthyridin-1-one (Compound B20)

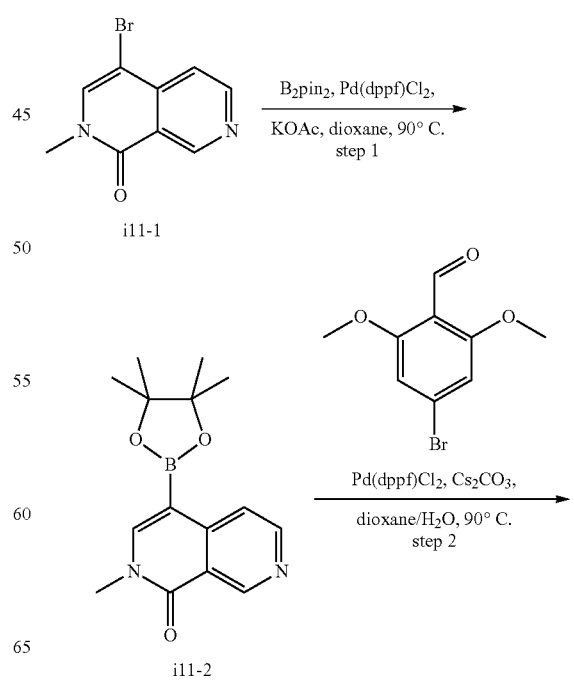

-continued

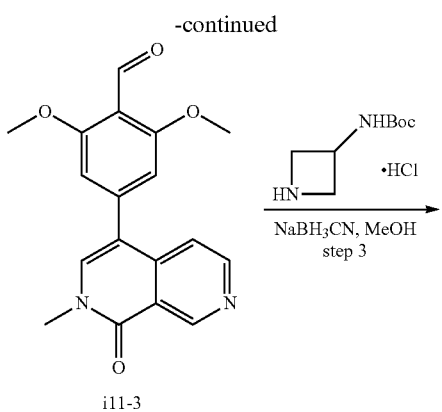

i11-3

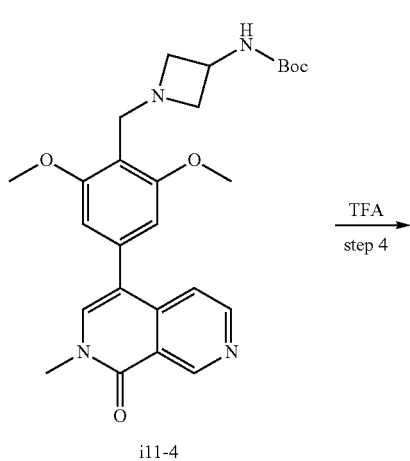

i11-4

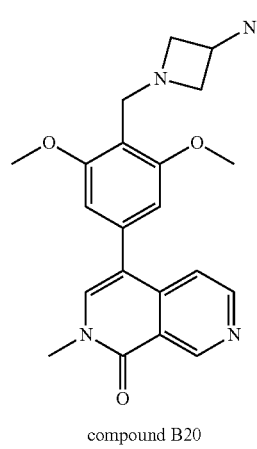

compound B20

Step 1: Preparation of 2-methyl-4-(4,4,5,5-tetramethyl-1,3,2-dioxaborolan-2-yl)-1,2-dihydro-2,7-naphthyridin-1-one (i11-2)

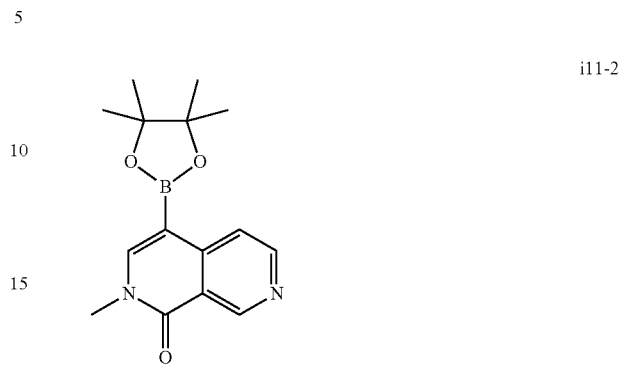

i11-2

To the solution of 4-bromo-2-methyl-1,2-dihydro-2,7-naphthyridin-1-one (2.7 g, 11.294 mmol, 1 equiv) in dioxane (15 mL) was added 4,4,5,5-tetramethyl-2-(4,4,5,5-tetramethyl-1,3,2-dioxaborolan-2-yl)-1,3,2-dioxaborolane (3.44 g, 13.552 mmol, 1.2 equiv), Pd(dppf)Cl$_2$ (0.83 g, 1.129 mmol, 0.1 equiv), and AcOK (3.33 g, 33.881 mmol, 3 equiv). The resulting solution was stirred at 90° C. for 2 hours under nitrogen atmosphere. The resulting solution was concentrated. The residue was purified by Flash column chromatography with EtOAc/PE (0-100%) to give compound 2-methyl-4-(4,4,5,5-tetramethyl-1,3,2-dioxaborolan-2-yl)-1,2-dihydro-2,7-naphthyridin-1-one (1.62 g, 50.13%) as light yellow solid. LCMS (ESI) m/z: [M+H]+=287.

Step 2: Preparation of 2,6-dimethoxy-4-(2-methyl-1-oxo-1,2-dihydro-2,7-naphthyridin-4-yl)benzaldehyde (i11-3)

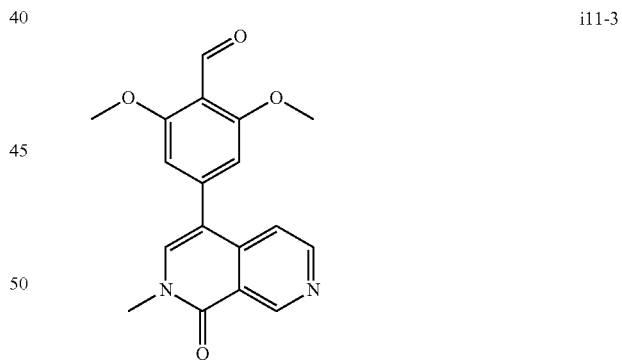

i11-3

To the solution of 2-methyl-4-(4,4,5,5-tetramethyl-1,3,2-dioxaborolan-2-yl)-1,2-dihydro-2,7-naphthyridin-1-one (1.62 g, 5.662 mmol, 1 equiv) in dioxane (30 mL) was added 4-bromo-2,6-dimethoxybenzaldehyde (1.39 g, 5.662 mmol, 1 equiv), Pd(dppf)Cl$_2$ (414.26 mg, 0.566 mmol, 0.1 equiv), Cs$_2$CO$_3$ (5.53 g, 16.985 mmol, 3 equiv), and H$_2$O (3 mL). The resulting solution was stirred at 90° C. for 2 hours under nitrogen atmosphere. The resulting solution was concentrated. The residue was purified by Flash column chromatography with EtOAc/PE (0100%) to give compound 2,6-dimethoxy-4-(2-methyl-1-oxo-1,2-dihydro-2,7-naphthyridin-4-yl)benzaldehyde (1.02 g, 55.55%) as yellow solid. LCMS (ESI) m/z: [M+H]+=325.

Step 3: Preparation of tert-butyl N-(1-[[2,6-dimethoxy-4-(2-methyl-1-oxo-1,2-dihydro-2,7-naphthyridin-4-yl)phenyl]methyl]azetidin-3-yl)carbamate (i11-4)

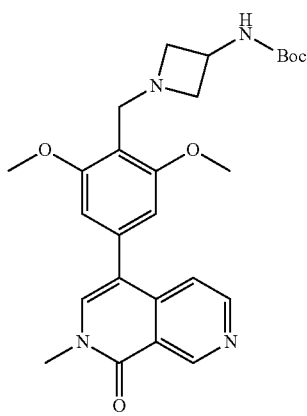

i11-4

To a stirred solution of 2,6-dimethoxy-4-(2-methyl-1-oxo-1,2-dihydro-2,7-naphthyridin-4-yl)benzaldehyde (450.00 mg, 1.387 mmol, 1.00 equiv) in MeOH (10.00 mL) was added NaBH$_3$CN (261.57 mg, 4.162 mmol, 3.00 equiv), tert-butyl N-(azetidin-3-yl)carbamate hydrochloride (347.46 mg, 1.665 mmol, 1.20 equiv). The resulting mixture was stirred for 1 hour at room temperature. The residue was purified by Flash column chromatography with EtOAc/PE (0100%) to afford tert-butyl N-(1-[[2,6-dimethoxy-4-(2-methyl-1-oxo-1,2-dihydro-2,7-naphthyridin-4-yl)phenyl]methyl]azetidin-3-yl)carbamate (475 mg, 71.24%) as a light yellow solid. LCMS (ESI) m/z: [M+H]$^+$=481.

Step 4: Preparation of 4-[4-[(3-aminoazetidin-1-yl)methyl]-3,5-dimethoxyphenyl]-2-methyl-1,2-dihydro-2,7-naphthyridin-1-one (Compound B20)

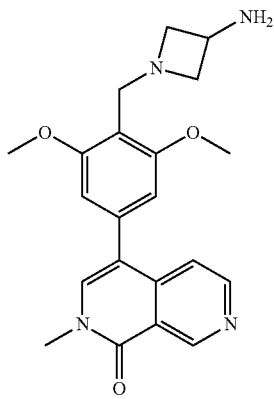

compound B20

To the solution of tert-butyl N-(1-[[2,6-dimethoxy-4-(2-methyl-1-oxo-2,7-naphthyridin-4-yl)phenyl]methyl]azetidin-3-yl)carbamate (50.00 mg, 0.104 mmol, 1.00 equiv) in DCM (2.00 mL) was added TFA (2.00 mL, 26.926 mmol, 258.79 equiv). The resulting solution was stirred at room temperature for 1 hour. The resulting solution was concentrated. The crude product was purified by Prep-HPLC (conditions: XSelect CSH Prep C18 OBD Column, 5 um, 19*150 mm; Mobile Phase A: Water (0.1% FA), Mobile Phase B: ACN; Flow rate: 25 mL/min; Gradient: 35% B to 65% B in 8 min; 254 nm; Rt: 7.38 min) to afford 4-[4-[(3-aminoazetidin-1-yl)methyl]-3,5-dimethoxyphenyl]-2-methyl-2,7-naphthyridin-1-one (9.8 mg, 24.76%) as a yellow solid. $^1$H NMR (400 MHz, MeOD) δ 9.57 (s, 1H), 8.70 (d, 1H), 7.87 (s, 1H), 7.72 (d, 1H), 6.88 (s, 2H), 4.63 (s, 2H), 4.54 (t, 2H), 4.45 (t, 2H), 4.38 (d, 1H), 3.98 (d, 6H), 3.73 (d, 3H), 2.69 (s, 1H). LCMS (ESI) m/z: [M+H]+=381.25.

Example 12—Preparation of 1-[[2,6-dimethoxy-4-(2-methyl-1-oxo-1,2-dihydro-2,7-naphthyridin-4-yl)phenyl]methyl]azetidine-3-carboxylic acid (Compound B21)

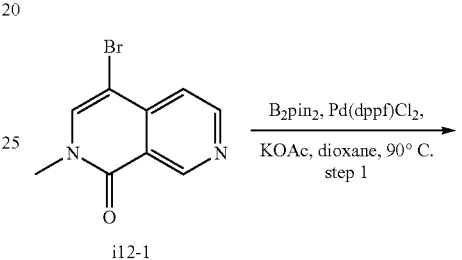

i12-1

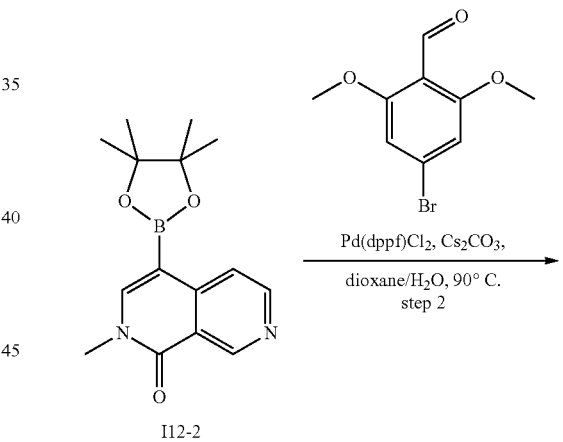

I12-2

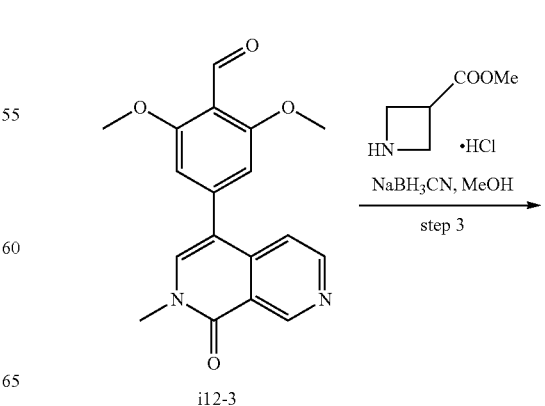

i12-3

-continued

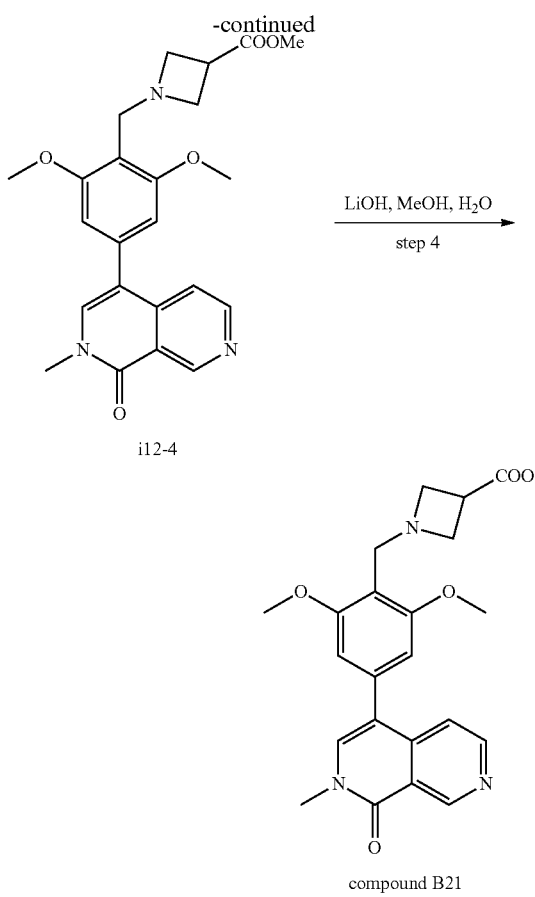

i12-4 compound B21

Step 1: Preparation of 2-methyl-4-(4,4,5,5-tetramethyl-1,3,2-dioxaborolan-2-yl)-1,2-dihydro-2,7-naphthyridin-1-one (i12-2)

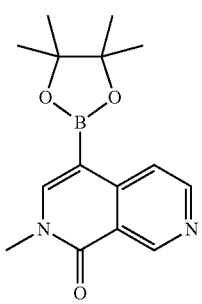

To the solution of 4-bromo-2-methyl-1,2-dihydro-2,7-naphthyridin-1-one (2.7 g, 11.294 mmol, 1 equiv) in dioxane (15 mL) was added 4,4,5,5-tetramethyl-2-(4,4,5,5-tetramethyl-1,3,2-dioxaborolan-2-yl)-1,3,2-dioxaborolane (3.44 g, 13.552 mmol, 1.2 equiv), Pd(dppf)Cl₂ (0.83 g, 1.129 mmol, 0.1 equiv), and AcOK (3.33 g, 33.881 mmol, 3 equiv). The resulting solution was stirred at 90° C. for 2 hours under nitrogen atmosphere. The resulting solution was concentrated. The residue was purified by Flash column chromatography with EtOAc/PE (0-100%) to give compound 2-methyl-4-(4,4,5,5-tetramethyl-1,3,2-dioxaborolan-2-yl)-1,2-dihydro-2,7-naphthyridin-1-one (1.62 g, 50.13%) as light yellow solid. LCMS (ESI) m/z: [M+H]⁺=287.

Step 2: Preparation of 2,6-dimethoxy-4-(2-methyl-1-oxo-1,2-dihydro-2,7-naphthyridin-4-yl)benzaldehyde (i12-3)

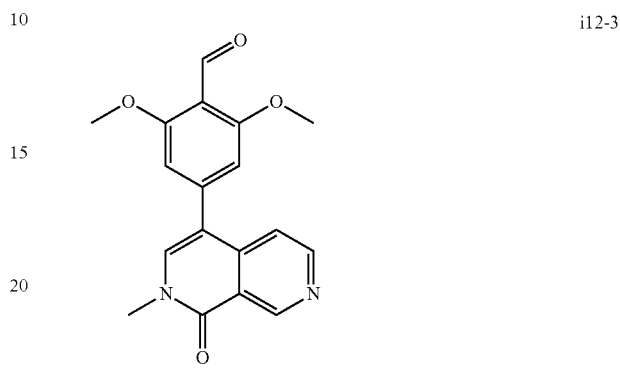

To the solution of 2-methyl-4-(4,4,5,5-tetramethyl-1,3,2-dioxaborolan-2-yl)-1,2-dihydro-2,7-naphthyridin-1-one (1.62 g, 5.662 mmol, 1 equiv) in dioxane (30 mL) was added 4-bromo-2,6-dimethoxybenzaldehyde (1.39 g, 5.662 mmol, 1 equiv), Pd(dppf)Cl₂ (414.26 mg, 0.566 mmol, 0.1 equiv), and Cs₂CO₃ (5.53 g, 16.985 mmol, 3 equiv), H₂O (3 mL). The resulting solution was stirred at 90° C. for 2 hours under nitrogen atmosphere. The resulting solution was concentrated. The residue was purified by Flash column chromatography with EtOAc/PE (0-100%) to give compound 2,6-dimethoxy-4-(2-methyl-1-oxo-1,2-dihydro-2,7-naphthyridin-4-yl)benzaldehyde (1.02 g, 55.55%) as yellow solid. LCMS (ESI) m/z: [M+H]+=325.

Step 3: Preparation of methyl 1-[[2,6-dimethoxy-4-(2-methyl-1-oxo-1,2-dihydro-2,7-naphthyridin-4-yl)phenyl]methyl]azetidine-3-carboxylate (i12-4)

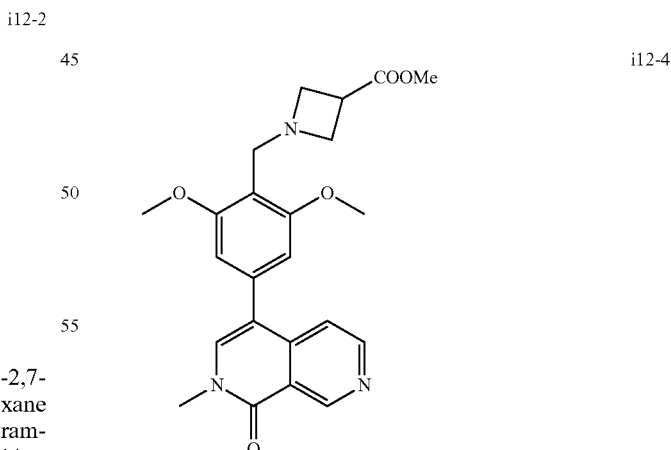

To a stirred solution of 2,6-dimethoxy-4-(2-methyl-1-oxo-1,2-dihydro-2,7-naphthyridin-4-yl)benzaldehyde (600.00 mg, 1.850 mmol, 1.00 equiv) in DCM (15.00 mL) was added methyl azetidine-3-carboxylate hydrochloride (336.52 mg, 2.220 mmol, 1.20 equiv) and NaBH₃CN (348.76 mg, 5.550 mmol, 3.00 equiv). The resulting mixture was stirred for 1 hour at room temperature. The residue was purified by Flash column chromatography with EtOAc/PE (0-100%) to afford methyl 1-[[2,6-dimethoxy-4-(2-methyl-1-oxo-1,2-dihydro-2,7-naphthyridin-4-yl)phenyl]methyl]azetidine-3-carboxylate (800 mg, 102.12%) as a light yellow solid. LCMS (ESI) m/z: [M+H]+=424.

Step 4: Preparation of 1-[[2,6-dimethoxy-4-(2-methyl-1-oxo-1,2-dihydro-2,7-naphthyridin-4-yl)phenyl]methyl]azetidine-3-carboxylic acid (Compound B21)

Example 13—Preparation of 2-cyclopropyl-4-[4-[(dimethylamino)methyl]-3,5-dimethoxyphenyl]-2,7-naphthyridin-1-one (Compound B22)

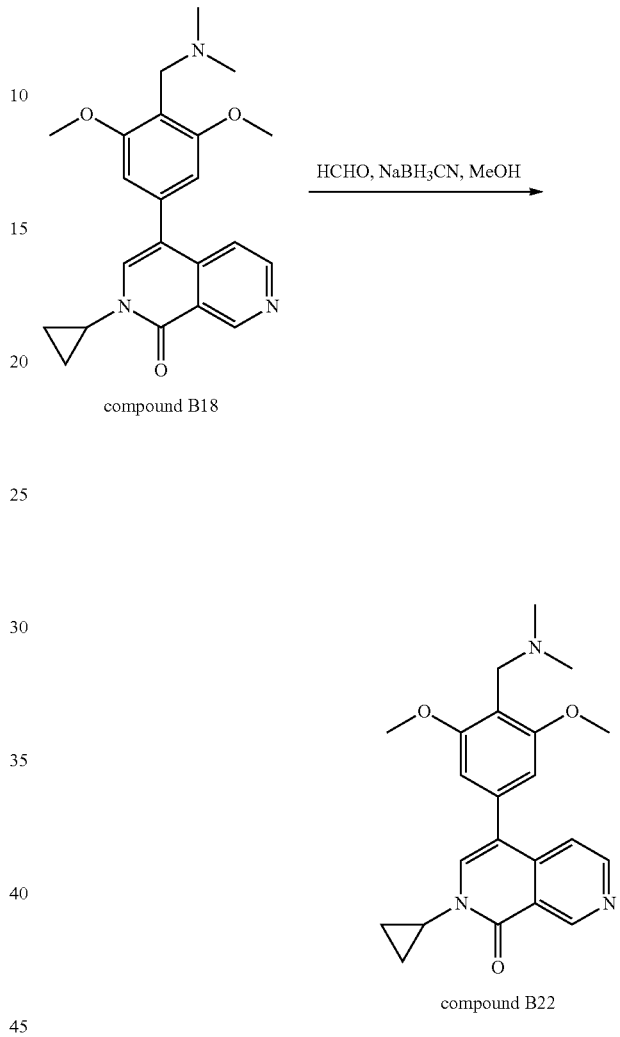

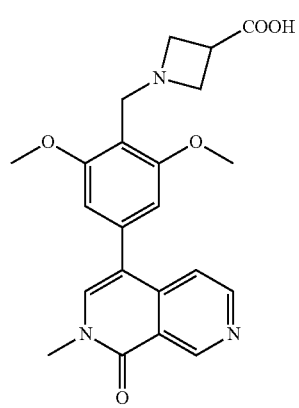

To the solution of methyl 1-[[2,6-dimethoxy-4-(2-methyl-1-oxo-1,2-dihydro-2,7-naphthyridin-4-yl)phenyl]methyl]azetidine-3-carboxylate (50 mg, 0.118 mmol, 1 equiv) in MeOH (10 mL, 0.312 mmol, 2.64 equiv) was added LiOH (28.28 mg, 1.181 mmol, 10 equiv). The resulting solution was stirred at room temperature for 12 hours. The resulting solution was concentrated. The crude product was purified by Prep-HPLC (conditions: SunFire C18 OBD Prep Column, 19 mm×250 mm; Mobile Phase A: Water (0.1% FA), Mobile Phase B: ACN; Flow rate: 25 mL/min; Gradient: 4% B to 4% B in 2 min; 254 nm; Rt: 9.83 min) to afford 1-[[2,6-dimethoxy-4-(2-methyl-1-oxo-1,2-dihydro-2,7-naphthyridin-4-yl)phenyl]methyl]azetidine-3-carboxylic acid (8.6 mg, 16.91%) as a yellow solid. $^1$H NMR (400 MHz, MeOD) δ 9.55 (s, 1H), 8.70 (d, 1H), 7.80 (s, 1H), 7.64 (d, 1H), 6.88 (d, 2H), 4.56 (s, 2H), 4.39 (d, 4H), 3.99 (d, 6H), 3.72 (d, 4H). LCMS (ESI) m/z: [M+H]$^+$=410.10.

To a solution of 2-cyclopropyl-4-[3,5-dimethoxy-4-[(methylamino)methyl]phenyl]-2,7-naphthyridin-1-one (40.00 mg, 0.109 mmol, 1.00 equiv) and a solution of formaldehyde in water (0.20 mL, 37%) was added NaBH$_3$CN (20.64 mg, 0.328 mmol, 3.00 equiv). The resulting mixture was stirred at room temperature for 1 hour. The solvent was removed under reduced pressure. The crude product was purified by Prep-HPLC (conditions: XSelect CSH Prep C18 OBD Column, 5 um, 19*150 mm; Mobile Phase A: Water (0.1% FA), Mobile Phase B: ACN; Flow rate: 25 mL/min; Gradient: 32% B to 68% B in 8 min; 254 nm; Rt: 7.38 min) to afford 2-cyclopropyl-4-[4-[(dimethylamino)methyl]-3,5-dimethoxyphenyl]-2,7-naphthyridin-1-one (10 mg, 24.08%) as a white solid. $^1$H NMR (400 MHz, Methanol-d4) δ 9.53 (s, 1H), 8.68 (d, J=5.7 Hz, 1H), 8.57 (s, 1H), 7.66 (s, 1H), 7.58 (d, J=5.7 Hz, 1H), 6.81 (s, 2H), 4.07 (s, 2H), 3.93 (s, 6H), 3.43 (s, 1H), 3.33 (s, 3H), 2.63 (s, 6H), 1.19 (t, J=6.8 Hz, 2H), 1.08-1.00 (m, 2H). LCMS (ESI) m/z: [M+H]$^+$=380.25.

Example 14—Preparation of 3-amino-5-(4-((dimethylamino)methyl)-3,5-dimethoxyphenyl)-1-methylpyridin-2(1H)-one (Compound B28)

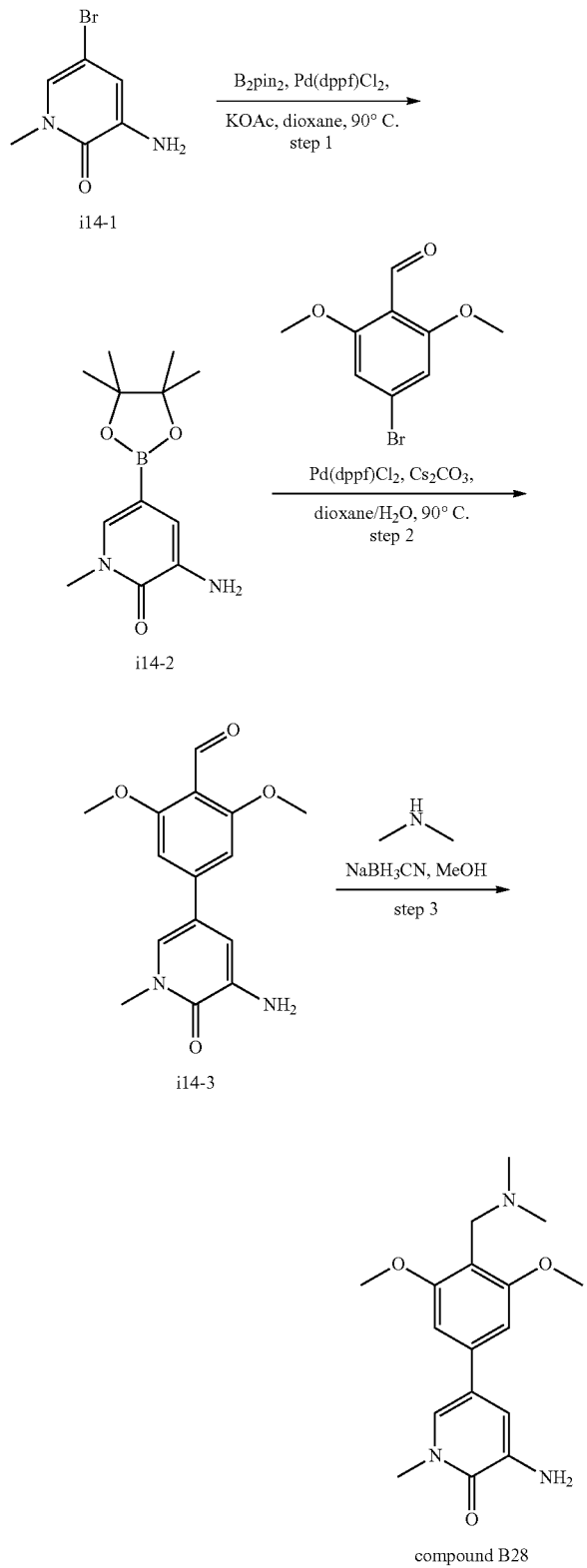

Step 1: Preparation of 3-amino-1-methyl-5-(4,4,5,5-tetramethyl-1,3,2-dioxaborolan-2-yl)-1,2-dihydropyridin-2-one (i14-2)

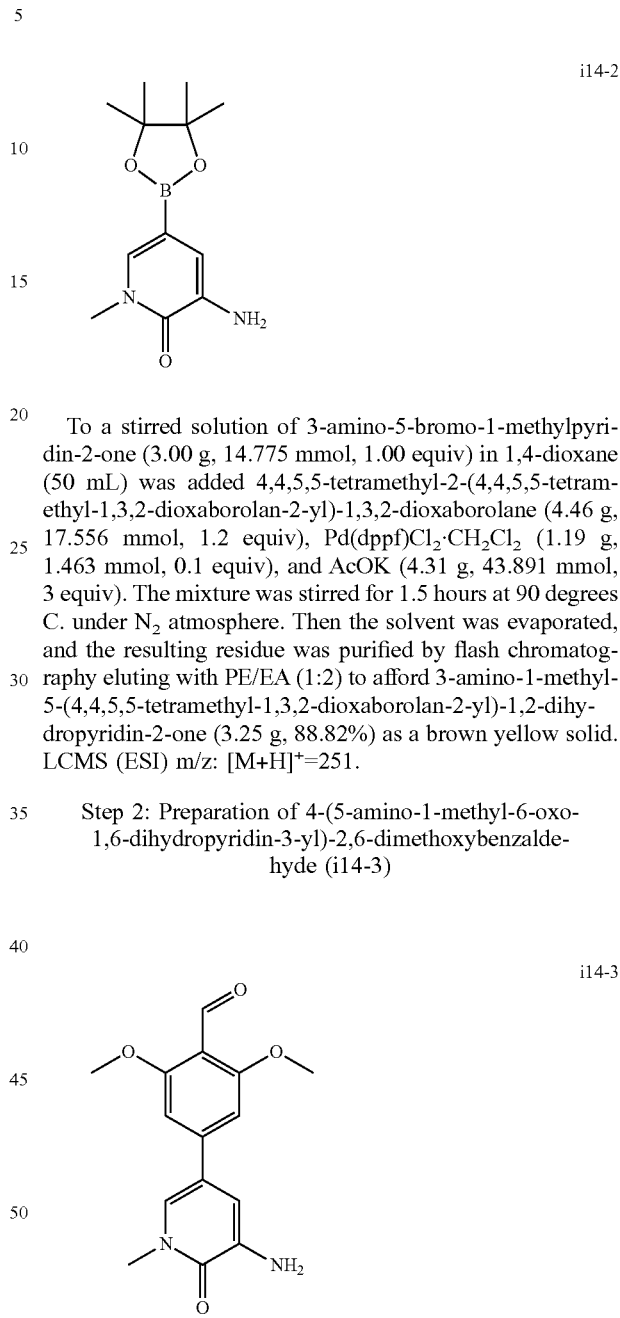

To a stirred solution of 3-amino-5-bromo-1-methylpyridin-2-one (3.00 g, 14.775 mmol, 1.00 equiv) in 1,4-dioxane (50 mL) was added 4,4,5,5-tetramethyl-2-(4,4,5,5-tetramethyl-1,3,2-dioxaborolan-2-yl)-1,3,2-dioxaborolane (4.46 g, 17.556 mmol, 1.2 equiv), Pd(dppf)Cl$_2$·CH$_2$Cl$_2$ (1.19 g, 1.463 mmol, 0.1 equiv), and AcOK (4.31 g, 43.891 mmol, 3 equiv). The mixture was stirred for 1.5 hours at 90 degrees C. under N$_2$ atmosphere. Then the solvent was evaporated, and the resulting residue was purified by flash chromatography eluting with PE/EA (1:2) to afford 3-amino-1-methyl-5-(4,4,5,5-tetramethyl-1,3,2-dioxaborolan-2-yl)-1,2-dihydropyridin-2-one (3.25 g, 88.82%) as a brown yellow solid. LCMS (ESI) m/z: [M+H]$^+$=251.

Step 2: Preparation of 4-(5-amino-1-methyl-6-oxo-1,6-dihydropyridin-3-yl)-2,6-dimethoxybenzaldehyde (i14-3)

To a stirred solution of 3-amino-1-methyl-5-(4,4,5,5-tetramethyl-1,3,2-dioxaborolan-2-yl)-1,2-dihydropyridin-2-one (3.69 g, 14.754 mmol, 1 equiv) in 1,4-dioxane (80 mL) and H$_2$O (8 mL) was added 4-bromo-2,6-dimethoxybenzaldehyde (3.25 g, 13.278 mmol, 0.90 equiv), Pd(dppf)Cl$_2$·CH$_2$Cl$_2$ (1.20 g, 1.475 mmol, 0.1 equiv), and Cs$_2$CO$_3$ (14.42 g, 44.261 mmol, 3 equiv). The solution was stirred for 1 hour at 90 degrees C. under N$_2$ atmosphere. Then the mixture was diluted with water and extracted with EtOAc, and the combined organic layer was concentrated. The residue was purified by silica gel chromatography eluting with PE/EtOAc (1:3) to afford 4-(5-amino-1-methyl-6-oxo- 1,6-dihydropyridin-3-yl)-2,6-dimethoxybenzaldehyde (3.0 g, 70.53%) as a brown solid. LCMS (ESI) m/z: [M+H]$^+$=289.

Step 3: Preparation of 3-amino-5-(4-((dimethyl-amino)methyl)-3,5-dimethoxyphenyl)-1-methylpyridin-2(1H)-one (Compound B28)

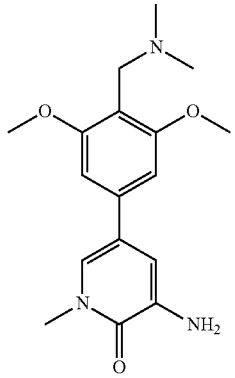

compound B28

To a stirred solution of dimethylamine hydrochloride (1.22 g, 14.984 mmol, 1.5 equiv) in MeOH (50 mL) was added 4-(5-amino-1-methyl-6-oxo-1,6-dihydropyridin-3-yl)-2,6-dimethoxybenzaldehyde (2.88 g, 9.989 mmol, 1 equiv). After 30 minutes of stirring, NaBH$_3$CN (1.26 g, 19.979 mmol, 2 equiv) was added in portions, and the mixture was stirred for 1 hour at 25 degrees C. Then MeOH was evaporated, and the residue was purified by Prep-HPLC (conditions: XSelect CSH Prep C18 OBD Column, 5 um, 19*150 mm; Mobile Phase A: Water (0.1% FA), Mobile Phase B: ACN; Flow rate: 25 mL/min; Gradient: 5% B to 22% B in 8 min; 254 nm; Rt: 7.52 min). This resulted in 3-amino-5-[4-[(dimethylamino)methyl]-3,5-dimethoxyphenyl]-1-methyl-1,2-dihydropyridin-2-one (500 mg, 15.75%) as light green salt. $^1$H NMR (300 MHz, Methanol-d4) δ 8.56 (s, 1H), 7.39 (d, J=2.2 Hz, 1H), 7.06 (d, J=2.3 Hz, 1H), 6.84 (s, 2H), 4.22 (s, 2H), 3.97 (s, 6H), 3.67 (s, 3H), 2.76 (s, 6H). LCMS (ESI) m/z: [M+H]$^+$=318.15.

Example 15—Preparation of N-(5-[4-[(dimethyl-amino)methyl]-3,5-dimethoxyphenyl]-1-methyl-2-oxo-1,2-dihydropyridin-3-yl)acetamide (Compound B29)

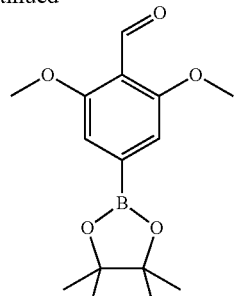

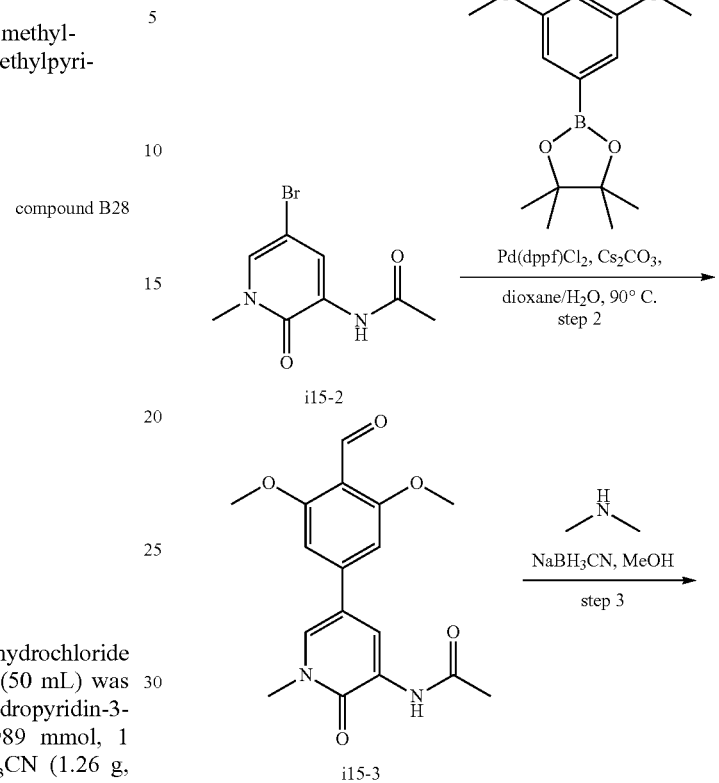

compound B29

Step 1: preparation of N-(5-bromo-1-methyl-2-oxo-1,2-dihydropyridin-3-yl)acetamide (i15-2)

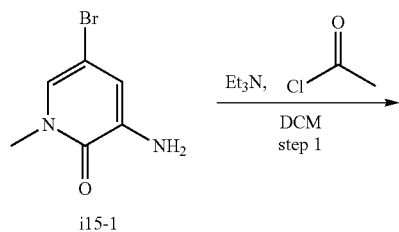

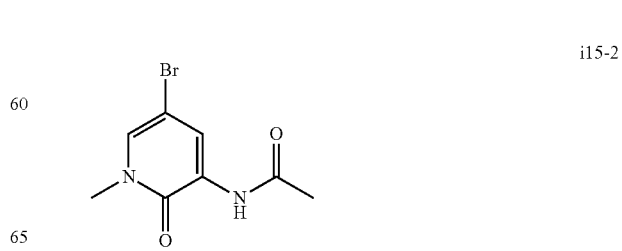

To a stirred solution of 3-amino-5-bromo-1-methyl-1,2-dihydropyridin-2-one (406.08 mg, 2.000 mmol, 1 equiv) and Et₃N (1619.05 mg, 16.000 mmol, 8 equiv) in DCM (5 mL) was added acetyl chloride (628.00 mg, 8.00 mmol, 4 equiv) dropwise at 0 degrees C. The mixture was stirred for 1 hour at room temperature. Then the solvent was evaporated, and the residue was purified by flash chromatography, eluted with EtOAc/PE (0-100%) to give the N-(5-bromo-1-methyl-2-oxo-1,2-dihydropyridin-3-yl)acetamide (487 mg, 99.36%). LCMS (ESI) m/z: [M+H]⁺=245.

Step 2: Preparation of N-[5-(4-formyl-3,5-dimethoxyphenyl)-1-methylidene-2-oxo-1,2-dihydro-1lambda4-pyridin-3-yl]acetamide (i15-3)

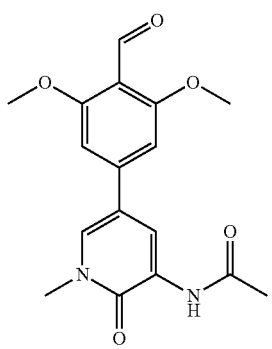

i15-3

To a stirred solution of 2,6-dimethoxy-4-(4,4,5,5-tetramethyl-1,3,2-dioxaborolan-2-yl)benzaldehyde (292 mg, 1.000 mmol, 1 equiv), and N-(5-bromo-1-methyl-2-oxo-1,2-dihydropyridin-3-yl)acetamide (244.96 mg, 1.000 mmol, 1 equiv) in 1,4-dioxane (5 mL) and H₂O (0.5 mL) was added Pd(dppf)Cl₂·CH₂Cl₂ (81.62 mg, 0.100 mmol, 0.1 equiv) and Cs₂CO₃ (976.99 mg, 2.999 mmol, 3 equiv). The mixture was reacted for 1 hour at 90 degrees C. under N₂ atmosphere. After cooling, the mixture was concentrated, and the residue was purified by flash chromatography, eluted with EtOAc/PE (0-10%) to afford N-[5-(4-formyl-3,5-dimethoxyphenyl)-1-methylidene-2-oxo-1,2-dihydro-1lambda4-pyridin-3-yl]acetamide (280 mg, 85.06%) as a white solid. LCMS (ESI) m/z: [M+H]⁺=331.

Step 3: Preparation of N-(5-[4-[(dimethylamino)methyl]-3,5-dimethoxyphenyl]-1-methyl-2-oxo-1,2-dihydropyridin-3-yl)acetamide (Compound B29)

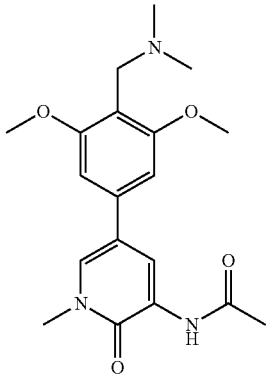

compound B29

To a stirred solution of dimethylamine hydrochloride (98.73 mg, 1.211 mmol, 1.6 equiv) in MeOH (5 mL) was added N-[5-(4-formyl-3,5-dimethoxyphenyl)-1-methyl-2-oxo-1,2-dihydropyridin-3-yl]acetamide (250 mg, 0.757 mmol, 1 equiv). The mixture was stirred for 30 minutes at 25 degrees C. Then NaBH₃CN (95.12 mg, 1.514 mmol, 2 equiv) was added in portions, and the reaction mixture was stirred for another 1 hour at 25 degrees C. The mixture was quenched with addition of water and extracted with DCM. The organic layer was concentrated, and the residue was purified by Prep-HPLC (conditions: XSelect CSH Prep C18 OBD Column, 5 um, 19*150 mm; Mobile Phase A: Water (0.1% FA), Mobile Phase B: ACN; Flow rate: 25 mL/min; Gradient: 12% B to 25% B in 8 min; 254 nm; Rt: 5.68 min), to give N-(5-[4-[(dimethylamino)methyl]-3,5-dimethoxyphenyl]-1-methyl-2-oxo-1,2-dihydropyridin-3-yl)acetamide (26.4 mg, 9.32%) as white solid. ¹H NMR (300 MHz, Methanol-d4) δ 8.69 (d, J=2.5 Hz, 1H), 8.56 (s, 0.3H, FA), 7.81 (d, J=2.5 Hz, 1H), 6.88 (s, 2H), 4.23 (s, 2H), 3.99 (s, 6H), 3.72 (s, 3H), 2.77 (s, 6H), 2.25 (s, 3H). LCMS (ESI) m/z: [M+H]⁺=360.25.

Example 16—Preparation of N-(5-[4-[(dimethylamino)methyl]-3,5-dimethoxyphenyl]-1-methyl-2-oxo-1,2-dihydropyridin-3-yl)propanamide (Compound B30)

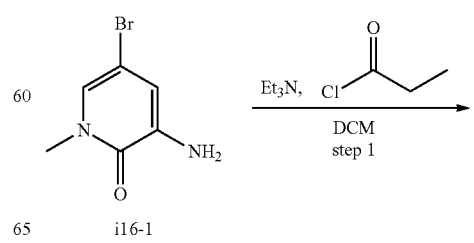

i16-1

Step 2: Preparation of N-(5-[4-[(dimethylamino)methyl]-3,5-dimethoxyphenyl]-1-methyl-2-oxo-1,2-dihydropyridin-3-yl)propanamide (Compound B30)

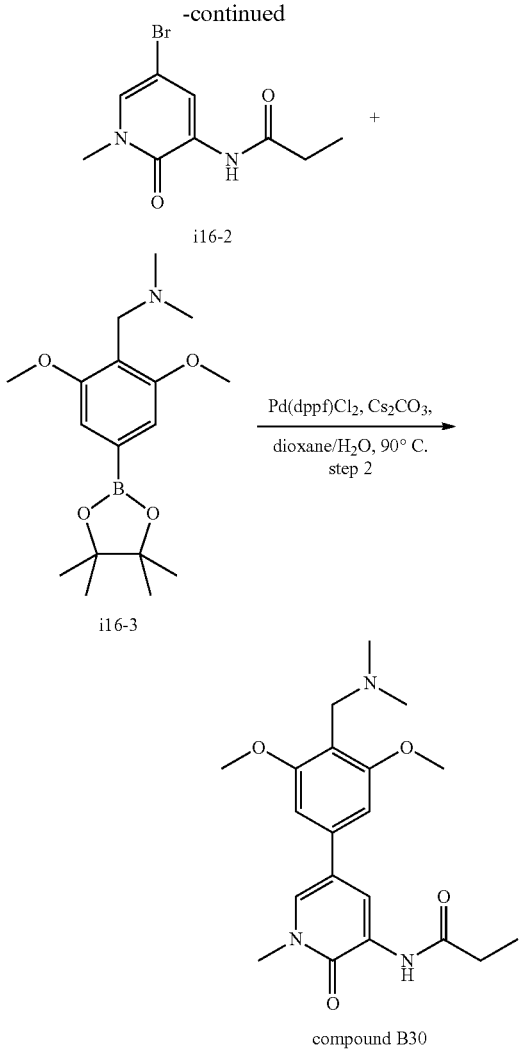

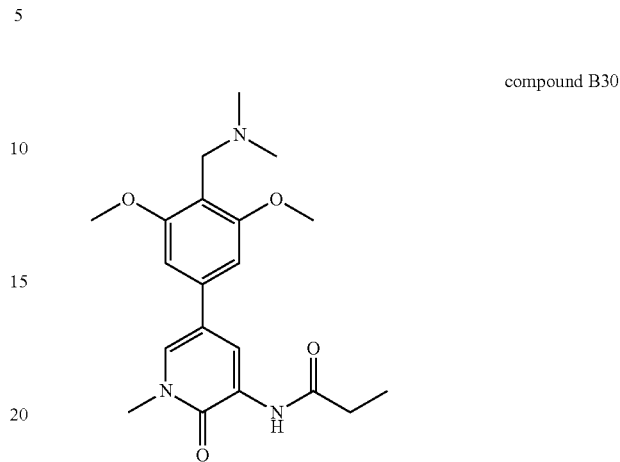

To a solution of N-(5-bromo-1-methyl-2-oxo-1,2-dihydropyridin-3-yl)propanamide (100 mg, 0.386 mmol, 1 equiv) and [[2,6-dimethoxy-4-(4,4,5,5-tetramethyl-1,3,2-dioxaborolan-2-yl)phenyl]methyl]dimethylamine (123.97 mg, 0.386 mmol, 1 equiv) in 1,4-dioxane (3 mL) and H$_2$O (0.3 mL) was added Cs$_2$CO$_3$ (377.25 mg, 1.158 mmol, 3 equiv) and Pd(dppf)Cl$_2$·CH$_2$Cl$_2$ (31.52 mg, 0.039 mmol, 0.1 equiv). The mixture was stirred for 1 hour at 90 degrees C. under N$_2$ atmosphere. After the solvent was evaporated, the mixture was purified by flash chromatography, eluted with DCM/MeOH (0-10%) to afford 270 mg of crude product, which was further purified by Prep-HPLC (conditions: XSelect CSH Prep C18 OBD Column, 5 um, 19*150 mm; Mobile Phase A: Water (0.1% FA), Mobile Phase B: ACN; Flow rate: 25 mL/min; Gradient: 12% B to 22% B in 8 min; 254 nm; Rt: 4.95 min) to afford N-(5-[4-[(dimethylamino)methyl]-3,5-dimethoxyphenyl]-1-methyl-2-oxo-1,2-dihydropyridin-3-yl)propanamide (26 mg, 18.04%) as a white solid. $^1$H NMR (300 MHz, Chloroform-d) 12.14 (s, 1H), 8.73 (d, J=2.4 Hz, 1H), 8.48 (s, 1H), 7.26 (d, J=2.5 Hz, 1H), 6.64 (s, 2H), 4.29 (s, 2H), 3.92 (s, 6H), 3.72 (s, 3H), 2.80 (s, 6H), 2.51 (q, J=7.5 Hz, 2H), 1.28 (t, J=7.5 Hz, 3H). LCMS (ESI) m/z: [M+H]$^+$=374.40.

Example 17—Preparation of N-(5-[4-[(dimethylamino)methyl]-3,5-dimethoxyphenyl]-1,4-dimethyl-2-oxo-1,2-dihydropyridin-3-yl)propanamide (Compound B31)

Step 1: preparation of N-(5-bromo-1-methyl-2-oxopyridin-3-yl)propanamide (i16-2)

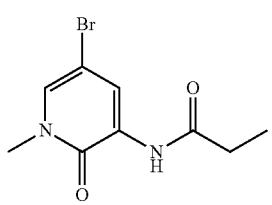

To a stirred solution of 3-amino-5-bromo-1-methylpyridin-2-one (150.00 mg, 0.738 mmol, 1.00 equiv) and Et$_3$N (300 mg, 2.95 mmol, 4 equiv) in DCM (3.00 mL) was added propanoyl chloride (348.60 mg, 3.69 mmol, 5 equiv) dropwise at 0 degrees C., and the solution was stirred for 1 hour. Then the solvent was evaporated, and the residue was purified by silica gel column chromatography, eluted with EtOAc/PE (0-100%) to afford N-(5-bromo-1-methyl-2-oxopyridin-3-yl)propanamide (168 mg, 87.77%) as a purple solid. LCMS (ESI) m/z: [M+H]+=259.

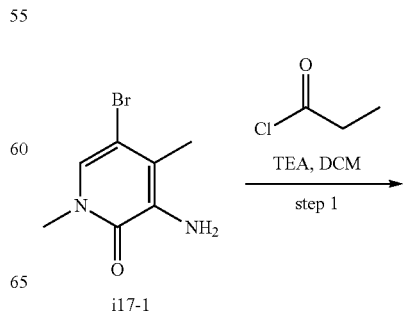

Step 2: Preparation of N-(5-[4-[(dimethylamino)methyl]-3,5-dimethoxyphenyl]-1,4-dimethyl-2-oxo-1,2-dihydropyridin-3-yl)propanamide (Compound B35)

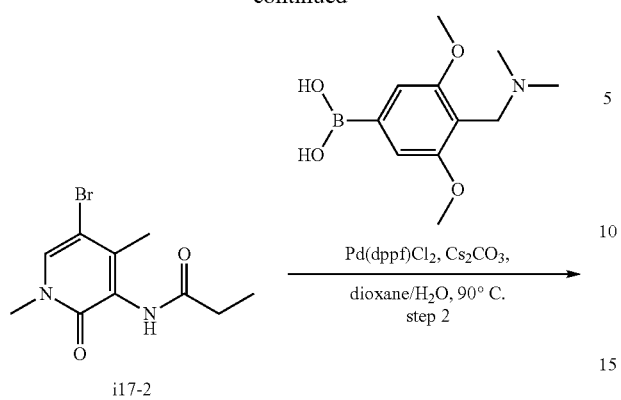

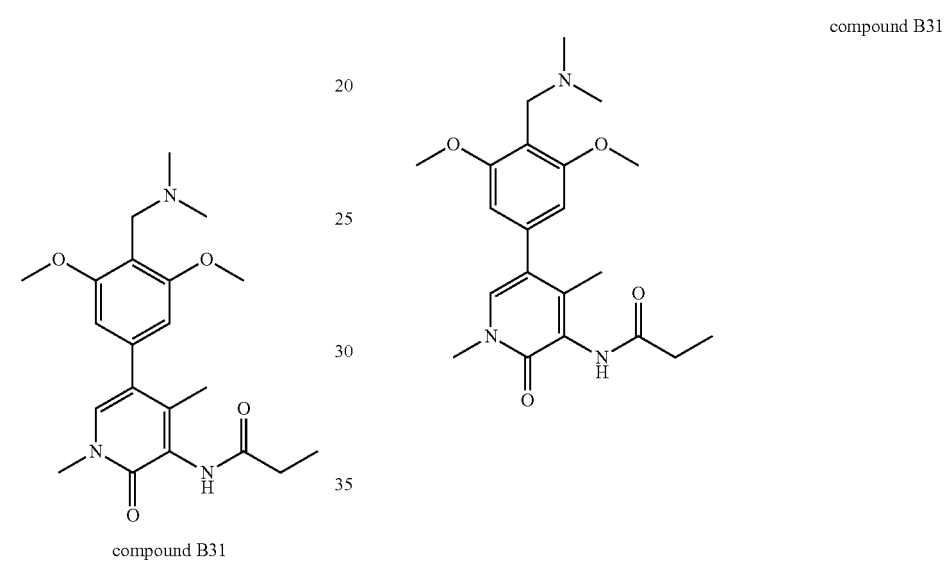

compound B31

Step 1: Preparation of N-(5-bromo-1,4-dimethyl-2-oxo-1,2-dihydropyridin-3-yl)propanamide (i17-2)

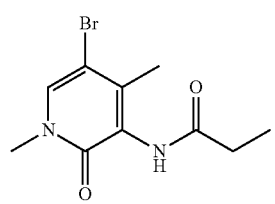

i17-2

To a solution of 5-bromo-1,4-dimethyl-2-oxo-1,2-dihydropyridin-3-aminium (400 mg, 1.83 mmol, 1.0 eq.) and TEA (742.43 mg, 7.34 mmol, 4.0 eq.) in DCM (5 mL) was added propanoyl chloride (186.68 mg, 2.02 mmol, 1.1 eq.) at 0° C. The resulting solution was stirred at room temperature for 16 hours. The mixture was concentrated under reduced pressure. The residue was purified by silica gel column chromatography, eluted with $CH_2Cl_2$/MeOH (10:1) to afford N-(5-bromo-1,4-dimethyl-2-oxo-1,2-dihydropyridin-3-yl)propanamide (460 mg, 73%) as a yellow solid. LCMS (ESI) m/z: $[M+H]^+$=273.1.

To a solution of N-(5-bromo-1,4-dimethyl-2-oxo-1,2-dihydropyridin-3-yl)propanamide (100 mg, 0.37 mmol, 1.0 eq.) and [4-[(dimethylamino)methyl]-3,5-dimethoxyphenyl] boronic acid (87.53 mg, 0.37 mmol, 1.0 eq.) in dioxane (2.5 mL) and $H_2O$ (0.5 mL) was added $Cs_2CO_3$ (238.58 mg, 0.73 mmol, 2.0 eq.) and Pd(dppf)$Cl_2$·$CH_2Cl_2$ (29.90 mg, 0.037 mmol, 0.1 eq.). The resulting solution was stirred at 90 degree C. for 1 hour (under $N_2$ atmosphere). LCMS indicated that the reaction was completed. The mixture was allowed to cool down to room temperature. The resulting mixture was diluted water (30 mL) and extracted with EtOAc (30 mL×2). After dry over $Na_2SO_4$, the filtrate was concentrated in vacuo. The crude product was purified by Prep-HPLC (conditions: Xselect CSH F-Phenyl OBD Column 19*150 mm 5 umn; Mobile Phase A: Water (0.1% FA), Mobile Phase B: EtOH-HPLC; Flow rate: 25 mL/min; Gradient: 5% B to 11% B in 10 min; 220 nm; Rt: 7.60 min) to afford fomate of N-(5-[4-[(dimethylamino)methyl]-3,5-dimethoxyphenyl]-1,4-dimethyl-2-oxo-1,2-dihydropyridinyl)propanamide (8.6 mg, 6%) as light brown solid. $^1$H NMR (400 MHz, Methanol-d4) δ 8.56 (s, 1H), 7.59 (s, 1H), 6.77 (s, 2H), 4.36 (s, 2H), 3.96 (s, 6H), 3.64 (s, 3H), 3.33 (s, 5H), 2.87 (s, 6H), 2.51 (q, J=7.7 Hz, 2H), 2.06 (s, 3H), 1.26 (t, J=7.6 Hz, 3H). LCMS (ESI) m/z: $[M+H]^+$=388.35.

Example 18—Preparation of N-(5-[4-[(dimethylamino)methyl]-3,5-dimethoxyphenyl]-1-methyl-2-oxo-1,2-dihydropyridin-3-yl)acetamide (Compound B32)

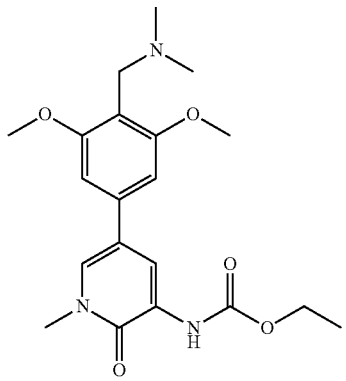

compound B32

Compound B32 was prepared in a similar manner as described for compound B42. N-(5-[4-[(dimethylamino)methyl]-3,5-dimethoxyphenyl]-1-methyl-2-oxo-1,2-dihydropyridin-3-yl)acetamide (40 mg, 27.27%) was obtained as a white solid. $^1$H NMR (300 MHz, Chloroform-d) δ 8.64 (s, 0.35H, FA), 8.34 (d, J=2.3 Hz, 1H), 7.88 (s, 1H), 7.20 (d, J=2.4 Hz, 1H), 6.64 (s, 2H), 4.26 (q, J=7.1 Hz, 2H), 4.16 (s, 2H), 3.92 (s, 6H), 3.71 (s, 3H), 2.67 (s, 6H), 1.35 (t, J=7.1 Hz, 3H). LCMS (ESI) m/z: [M+H]$^+$=390.20.

Example 19—Preparation of 8-[4-[(dimethylamino)methyl]-3,5-dimethoxyphenyl]-6-methylpyrido[3,4-b]pyrazin-5-one (Compound B33)

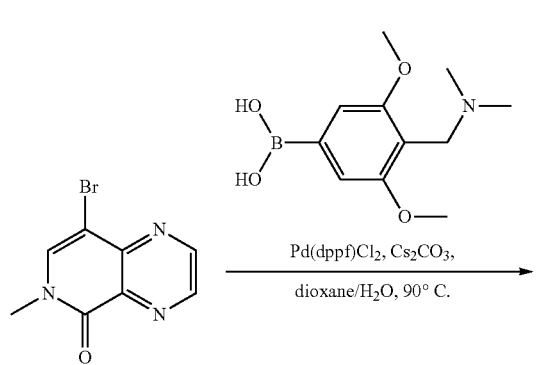

-continued

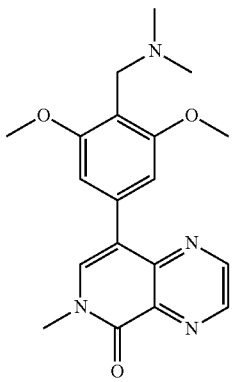

compound B33

To a stirred mixture of 8-bromo-6-methylpyrido[3,4-b]pyrazin-5-one (81.0 mg, 0.34 mmol, 1.0 equiv) and 4-[(dimethylamino)methyl]-3,5-dimethoxyphenylboronic acid (96.80 mg, 0.41 mmol, 1.2 equiv) in 1,4-dioxane (4 mL) and H$_2$O (1 mL) was added Pd(dppf)Cl$_2$ (49.38 mg, 0.067 mmol, 0.2 equiv) and Cs$_2$CO$_3$ (274.84 mg, 0.84 mmol, 2.5 equiv), and the reaction was stirred at 90 degrees C. under nitrogen atmosphere. After completion of the reaction, the mixture was allowed to cool down to room temperature. The reaction was diluted with water (25 mL) and extracted with EtOAc (3×20 mL). The filtrate was concentrated under reduced pressure. The crude product was purified by Prep-HPLC (conditions: Xselect CSH F-Phenyl OBD Column 19*150 mm 5 μm; Mobile Phase A: Water (0.1% FA), Mobile Phase B: ACN; Flow rate: 25 mL/minute; Gradient: 6% B to 10% B in 6 minutes; 220 nm; R$_T$: 4.37 minutes) to afford formate of 8-[4-[(dimethylamino)methyl]-3,5-dimethoxyphenyl]-6-methylpyrido[3,4-b]pyrazin-5-one (15.1 mg, 12.54%) as a yellow solid. $^1$H NMR (400 MHz, Methanol-d4) δ 8.98 (s, 1H), 8.87 (s, 1H), 8.58 (s, 0.75H, FA), 7.97 (s, 1H), 7.02 (d, J=1.6 Hz, 2H), 4.30 (s, 2H), 3.96 (d, J=1.5 Hz, 6H), 3.79 (s, 3H), 2.82 (s, 6H). LCMS (ESI) m/z: [M+H]$^+$=355.4.

Example 20—Preparation of 1-[[2,6-dimethoxy-4-(2-methyl-1-oxo-1,2-dihydro-2,7-naphthyridin-4-yl)phenyl]methyl]-N-methylazetidine-3-carboxamide formic acid (Compound B34 formic acid)

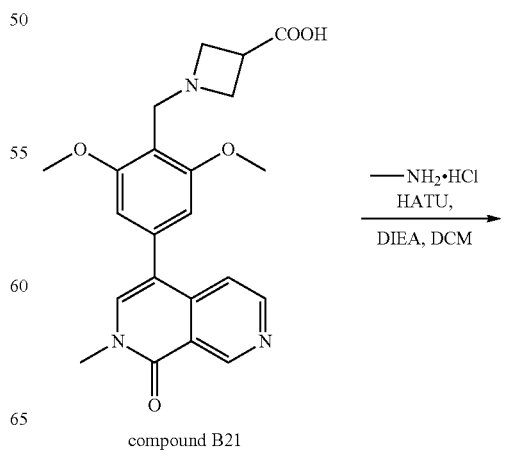

compound B21

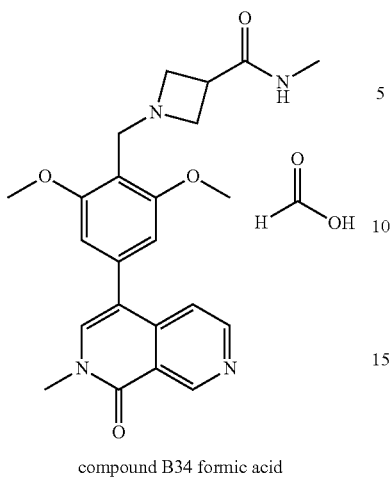

compound B34 formic acid

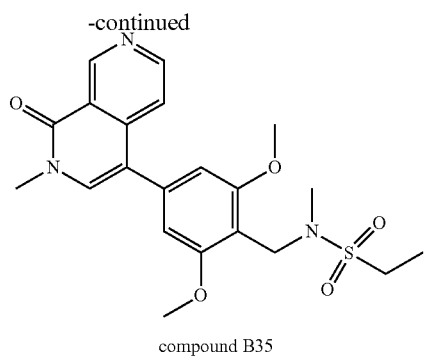

compound B35

To a stirred mixture of 4-[3,5-dimethoxy-4-[(methylamino)methyl]phenyl]-2-methyl-1,2-dihydro-2,7-naphthyridin-1-one (65 mg, 1.0 equiv) and TEA (58.29 mg, 3.0 equiv) in DCM (1 mL) was added propane-2-sulfonyl chloride (37.2 mg, 1.5 equiv). The mixture was stirred at 25 degrees C. for 2 hours. The resulting mixture was concentrated under vacuum. The crude product was purified by Prep-HPLC (conditions: XBridge Shield RP18 OBD Column, 5 μm, 19*150 mm; Mobile Phase A: Water (0.05% NH$_3$H$_2$O), Mobile Phase B: ACN; Flow rate: 25 mL/minute; Gradient: 27% B to 46% B in 8 minutes; 220 nm; R$_T$: 7.8 minutes) to afford N-[[2,6-dimethoxy-4-(2-methyl-1-oxo-1,2-dihydro-2,7-naphthyridin-4-yl)phenyl]methyl]-N-methylethane-1-sulfonamide (8.4 mg, 10%) as a white solid. $^1$H NMR (400 MHz, Methanol-d4) δ 9.54 (d, J=0.9 Hz, 1H), 8.69 (d, J=5.8 Hz, 1H), 7.77 (s, 1H), 7.65 (dd, J=5.8, 1.0 Hz, 1H), 6.79 (s, 2H), 4.52 (s, 2H), 3.91 (s, 6H), 3.72 (s, 3H), 3.17 (q, J=7.3 Hz, 2H), 2.77 (s, 3H), 1.34 (q, J=8.4, 7.9 Hz, 3H). LCMS (ESI) m/z: [M+H]$^+$=432.25.

To a stirred mixture of 1-[[2,6-dimethoxy-4-(2-methyl-1-oxo-1,2-dihydro-2,7-naphthyridin-4-yl)phenyl]methyl]azetidine-3-carboxylic acid (127.87 mg, 0.24 mmol, 1.0 equiv) and DIEA (189.43 mg, 1.47 mmol, 6.0 equiv) in DCM (3 mL) was added methanamine hydrochloride (19.79 mg, 0.29 mmol, 1.20 equiv). The mixture was stirred at room temperature for 5 minutes, then HATU (139.32 mg, 0.37 mmol, 1.50 equiv) was added. The mixture was stirred for another 2 hours at room temperature. The residue was directly purified by Prep-HPLC (conditions: Xselect CSH F-Phenyl OBD Column 19*150 mm 5 μm; Mobile Phase A: Water (0.1% FA), Mobile Phase B: ACN; Flow rate: 25 mL/minute; Gradient: 7% B to 7% B in 7 minutes; 220 nm; R$_T$: 5.17 minutes) to afford 1-[[2,6-dimethoxy-4-(2-methyl-1-oxo-1,2-dihydro-2,7-naphthyridin-4-yl)phenyl]methyl]-N-methylazetidine-3-carboxamide formic acid (13.7 mg, 11%) as a yellow solid. $^1$H NMR (400 MHz, Methanol-d4) δ 9.54 (s, 1H), 8.69 (d, J=5.8 Hz, 1H), 8.55 (brs, 1.3H, FA), 7.77 (s, 1H), 7.62 (d, J=5.8 Hz, 1H), 6.86 (s, 2H), 4.45 (s, 2H), 4.24-4.16 (m, 4H), 3.97 (s, 6H), 3.72 (s, 3H), 3.56 (p, J=7.9 Hz, 1H), 2.79 (s, 3H). LCMS (ESI) m/z: [M+H]$^+$=423.25.

Example 21—Preparation of N-[[2,6-dimethoxy-4-(2-methyl-1-oxo-1,2-dihydro-2,7-naphthyridin-4-yl)phenyl]methyl]-N-methylethane-1-sulfonamide (Compound B35)

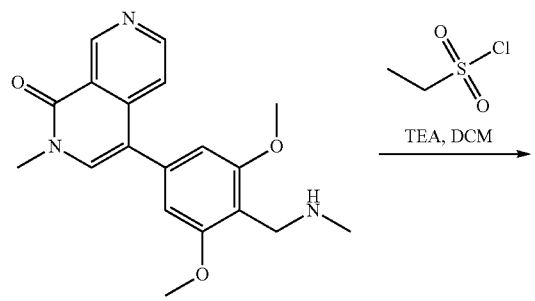

Example 22—Preparation of 4-[4-[(dimethylamino)methyl]-3-(methylsulfanyl)phenyl]-2-methyl-1,2-dihydro-2,7-naphthyridin-1-one (Compound B36)

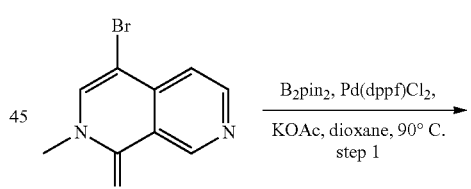

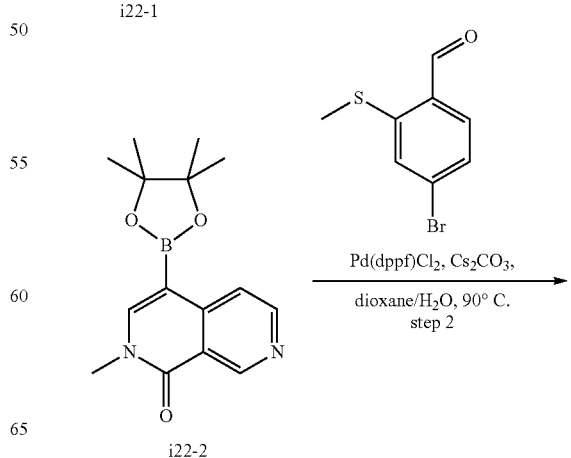

-continued

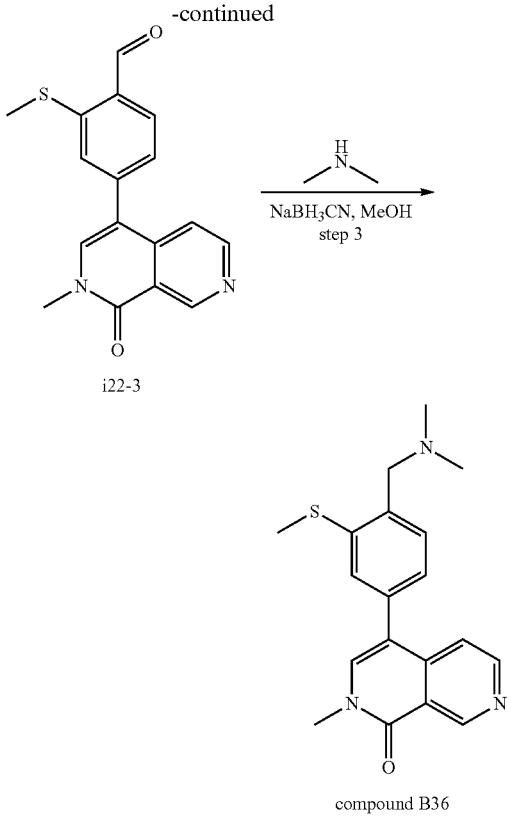

Step 1: Preparation of 2-methyl-4-(4,4,5,5-tetramethyl-1,3,2-dioxaborolan-2-yl)-1,2-dihydro-2,7-naphthyridin-1-one (i22-2)

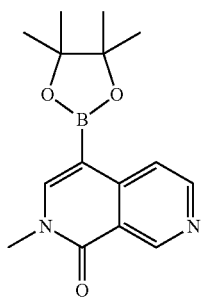

To a solution of 4-bromo-2-methyl-1,2-dihydro-2,7-naphthyridin-1-one (239 mg, 1.000 mmol, 1 equiv) and 4,4,5,5-tetramethyl-2-(4,4,5,5-tetramethyl-1,3,2-dioxaborolan-2-yl)-1,3,2-dioxaborolane (380.80 mg, 1.500 mmol, 1.5 equiv) in dioxane (3.00 mL) was added CH₃COOK (294.34 mg, 2.999 mmol, 3 equiv) and Pd(dppf)Cl₂ (36.57 mg, 0.050 mmol, 0.05 equiv). The resulting solution was stirred at 80 degree C. for 1 hour. The resulting mixture was concentrated under reduced pressure. The residue was applied onto a silica gel column with ethyl acetate/petroleum ether (1:1). This resulted in 2-methyl-4-(4,4,5,5-tetramethyl-1,3,2-dioxaborolan-2-yl)-1,2-dihydro-2,7-naphthyridin-1-one (228 mg, 79.71%) as a white solid. LCMS (ESI) m/z: [M+H]+=287.1.

Step 2: Preparation of 4-(2-methyl-1-oxo-1,2-dihydro-2,7-naphthyridin-4-yl)-2-(methylsulfanyl)benzaldehyde (i22-3)

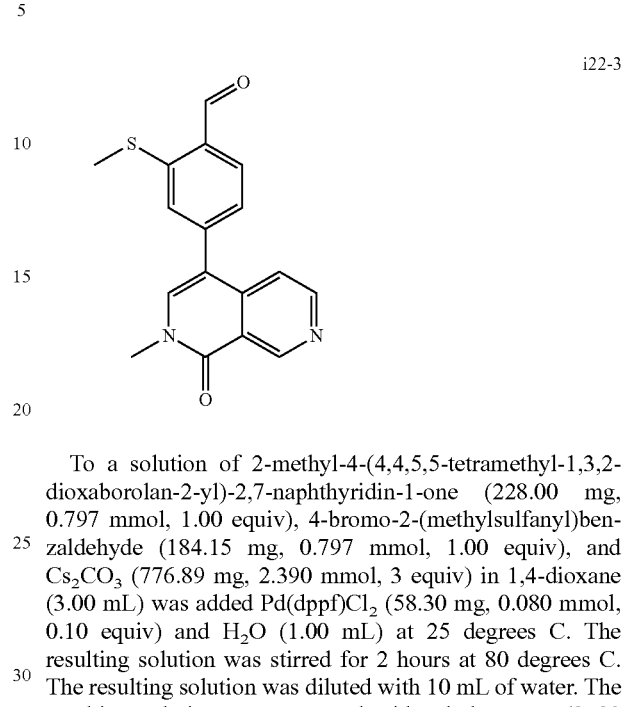

To a solution of 2-methyl-4-(4,4,5,5-tetramethyl-1,3,2-dioxaborolan-2-yl)-2,7-naphthyridin-1-one (228.00 mg, 0.797 mmol, 1.00 equiv), 4-bromo-2-(methylsulfanyl)benzaldehyde (184.15 mg, 0.797 mmol, 1.00 equiv), and Cs₂CO₃ (776.89 mg, 2.390 mmol, 3 equiv) in 1,4-dioxane (3.00 mL) was added Pd(dppf)Cl₂ (58.30 mg, 0.080 mmol, 0.10 equiv) and H₂O (1.00 mL) at 25 degrees C. The resulting solution was stirred for 2 hours at 80 degrees C. The resulting solution was diluted with 10 mL of water. The resulting solution was extracted with ethyl acetate (2×20 mL) and the organic layers combined and dried over anhydrous sodium sulfate and concentrated. The residue was applied onto a silica gel column with ethyl acetate/petroleum ether (1:1). This resulted in 4-(2-methyl-1-oxo-2,7-naphthyridin-4-yl)-2-(methylsulfanyl)benzaldehyde (200 mg, 80.87%) as a yellow solid. LCMS (ESI) m/z: [M+H]+=311.1.

Step 3: Preparation of 4-[4-[(dimethylamino)methyl]-3-(methylsulfanyl)phenyl]-2-methyl-2,7-naphthyridin-1-one (Compound B36)

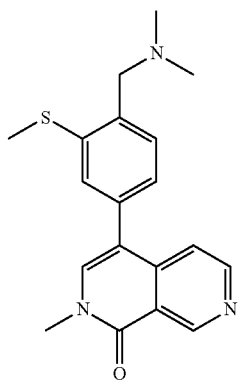

To a solution of 4-(2-methyl-1-oxo-2,7-naphthyridin-4-yl)-2-(methylsulfanyl)benzaldehyde (200.00 mg, 0.644 mmol, 1.00 equiv) and dimethylamine (34.86 mg, 0.773 mmol, 1.20 equiv) in MeOH (3.00 mL) was added NaBH₃CN (80.99 mg, 1.289 mmol, 2.00 equiv) at 0 degrees C. The resulting solution was stirred for 1 hours at 0 degrees C. The resulting solution was diluted with 10 mL of water and extracted with ethyl acetate (2×20 mL), and the organic layers combined and dried over anhydrous sodium sulfate and concentrated. The crude product was purified by Prep-HPLC (conditions: Atlantis HILIC OBD Column, 19 mm×150 mm; mobile phase, Water (0.1% FA) and ACN (hold 5% Phase B in 2 minutes, up to 17% in 8 minutes); Detector, UV). This resulted in 4-[4-[(dimethylamino) methyl]-3-(methylsulfanyl)phenyl]-2-methyl-2,7-naphthyridin-1-one (150 mg, 68.57%) as a white solid. $^1$H NMR (400 MHz, Methanol-d4) δ 9.54 (s, 1H), 8.68 (d, J=5.8 Hz, 1H), 7.73 (s, 1H), 7.56 (d, J=5.7 Hz, 1H), 7.48 (d, J=7.8 Hz, 1H), 7.39 (d, J=1.7 Hz, 1H), 7.26 (dd, J=7.8, 1.7 Hz, 1H), 3.71 (s, 3H), 3.64 (s, 2H), 2.52 (s, 3H), 2.33 (s, 6H). LCMS (ESI) m/z: [M+H]+=340.20.

Example 23—Preparation of 4-[4-[(dimethylamino) methyl]-3-methanesulfonylphenyl]-2-methyl-2,7-naphthyridin-1-one (Compound B37)

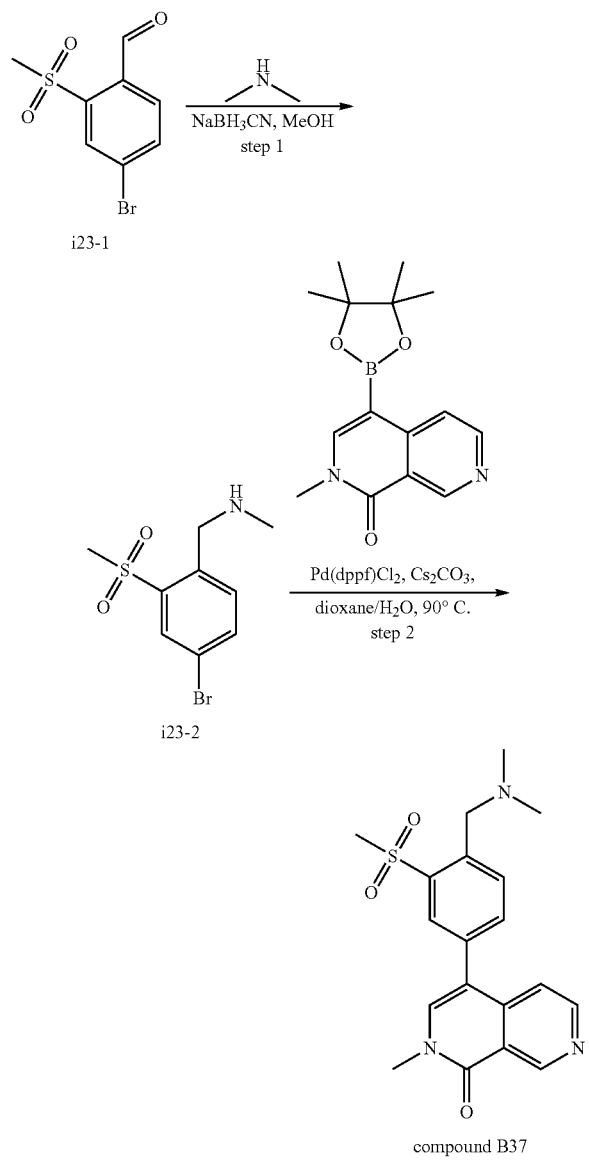

compound B37

Step 1: Preparation of [(4-bromo-2-methanesulfonylphenyl)methyl]dimethylamine (i23-2)

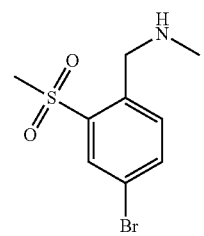

i23-2

To a solution of 4-bromo-2-methanesulfonylbenzaldehyde (263 mg, 1.000 mmol, 1 equiv) and dimethylamine (135.20 mg, 2.999 mmol, 3 equiv) in MeOH (3.00 mL) was added NaBH$_3$CN (125.63 mg, 1.999 mmol, 2 equiv) at 0 degrees C. The resulting solution was stirred for 1 hour at 0 degrees C. The resulting solution was diluted with 10 mL of water. The resulting solution was extracted with ethyl acetate (2×20 mL), and the organic layers combined, dried over anhydrous sodium sulfate, and concentrated. The residue was applied onto a silica gel column with ethyl acetate/petroleum ether (0-50%). This resulted in [(4-bromo-2-methanesulfonylphenyl)methyl]dimethylamine (175 mg, 59.92%) as a yellow solid.

LCMS (ESI) m/z: [M+H]+=278.0.

Step 2: Preparation of 4-[4-[(dimethylamino) methyl]-3-methanesulfonylphenyl]-2-methyl-1,2-dihydro-2,7-naphthyridin-1-one (Compound B37)

To a solution of [(4-bromo-2-methanesulfonylphenyl) methyl]dimethylamine (175 mg, 0.599 mmol, 1.00 equiv) and 2-methyl-4-(4,4,5,5-tetramethyl-1,3,2-dioxaborolan-2-yl)-2,7-naphthyridin-1-one (205.65 mg, 0.719 mmol, 1.20 equiv) in 1,4-dioxane (3.00 mL) was added Cs$_2$CO$_3$ (585.43 mg, 1.797 mmol, 3.00 equiv), Pd(dppf)Cl$_2$ (43.82 mg, 0.060 mmol, 0.10 equiv), and H$_2$O (1.00 mL) at 25 degrees C. The resulting solution was stirred for 2 hours at 80 degrees C. The resulting solution was diluted with 10 mL of water and extracted with ethyl acetate (2×20 mL), and the organic layers combined and dried over anhydrous sodium sulfate and concentrated. The crude product was purified by Prep-HPLC (conditions: Atlantis HILIC OBD Column, 19 mm×250 mm, mobile phase, Water (0.1% FA) and ACN (hold 5% Phase B in 2 minutes, up to 17% in 8 minutes); Detector, UV). This resulted in 4-[4-[(dimethylamino)methyl]-3-methanesulfonylphenyl]-2-methyl-2,7-naphthyridin-1-one (120 mg, 53.94%) as a white solid. $^1$H NMR (400 MHz, Methanol-d4) δ 9.55 (s, 1H), 8.71 (d, J=5.7 Hz, 1H), 8.16 (d, J=1.9 Hz, 1H), 7.80 (d, J=9.0 Hz, 2H), 7.72 (d, J=7.8 Hz, 1H), 7.53 (d, J=5.8 Hz, 1H), 3.96 (s, 2H), 3.72 (s, 3H), 3.47 (s, 3H), 2.33 (s, 6H). LCMS (ESI) m/z: [M+H]+=372.10.

Example 24—Preparation N-[[2,6-dimethoxy-4-(2-methyl-1-oxo-2,7-naphthyridin-4-yl)phenyl]methyl]-N-methylmethanesulfonamide (Compound B38)

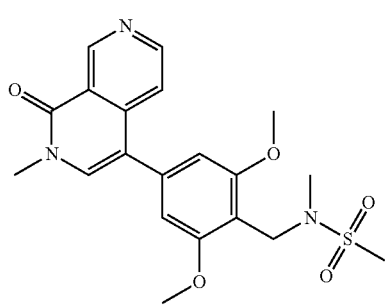

compound B38

Compound B38 was prepared in a similar manner as described for compound B35. N-[[2,6-dimethoxy-4-(2-methyl-1-oxo-2,7-naphthyridin-4-yl)phenyl]methyl]-N-methylmethane sulfonamide (14.2 mg, 16%) was obtained as a white solid. $^1$H NMR (400 MHz, Methanol-d4) δ 9.57 (s, 1H), 8.70 (d, J=6.1 Hz, 1H), 7.90 (s, 1H), 7.79 (d, J=6.2 Hz, 1H), 6.80 (s, 2H), 4.50 (s, 2H), 3.92 (s, 6H), 3.74 (s, 3H), 2.94 (s, 3H), 2.75 (s, 3H). LCMS (ESI) m/z: [M+H]+=418.10.

Example 25—Preparation of N-[[2,6-dimethoxy-4-(2-methy-1-oxo-2,7-naphthyridin-4-yl)phenyl]methyl]-N-methyl cyclopropanesulfonamide (Compound B39)

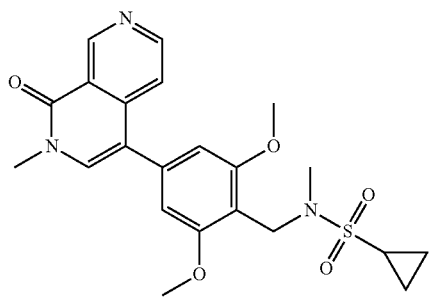

compound B39

Compound B39 was prepared in a similar manner as described for compound B35. N-[[2,6-dimethoxy-4-(2-methyl-1-oxo-2,7-naphthyridin-4-yl)phenyl]methyl]-N-methylcyclopropanesufonamide (14.2 mg, 31%) was obtained as a white solid. $^1$H NMR (400 MHz, Methanol-d4) δ 9.54 (d, J=0.9 Hz, 1H), 8.70 (d, J=5.7 Hz, 1H), 7.77 (s, 1H), 7.65 (d, J=5.6 Hz, 1H), 6.79 (s, 2H), 4.54 (s, 2H), 3.91 (s, 6H), 3.72 (s, 3H), 3.29 (s, 1H), 2.77 (s, 3H), 1.14-1.05 (m, 4H). LCMS (ESI) m/z: [M+H]+=444.20.

Example 26—Preparation of N-[[2,6-dimethoxy-4-(2-methyl-1-oxo-2,7-naphthyridin-4-yl)phenyl]methyl]-N,2-dim ethylpropane-1-sulfonamide (Compound B40)

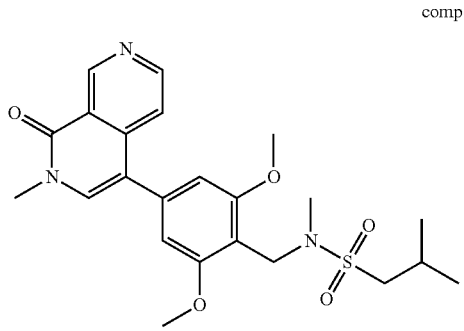

compound B40

Compound B40 was prepared in a similar manner as described for compound B35. N-[[2,6-dimethoxy-4-(2-methyl-1-oxo-2,7-naphthyridin-4-yl)phenyl]methyl]-N,2-dimethylpropane-1-sulfonamide (10.3 mg, 8%) was obtained as a white solid. $^1$H NMR (400 MHz, Methanol-d4) δ 9.54 (d, J=0.9 Hz, 1H), 8.69 (d, J=5.8 Hz, 1H), 7.77 (s, 1H), 7.65 (dd, J=5.8, 0.9 Hz, 1H), 6.79 (s, 2H), 4.52 (s, 2H), 3.91 (s, 6H), 3.72 (s, 3H), 2.99 (d, J=6.5 Hz, 2H), 2.76 (s, 3H), 2.26 (hept, J=6.6 Hz, 1H), 1.14 (d, J=6.7 Hz, 6H). LCMS (ESI) m/z: [M+H]+=460.15.

Example 27—Preparation of 2-(1-[[2,6-dimethoxy-4-(2-methyl-1-oxo-1,2-dihydro-2,7-naphthyridin-4-yl)phenyl]methyl]azetidin-3-yl)acetic acid formic acid (Compound B41 Formic Acid)

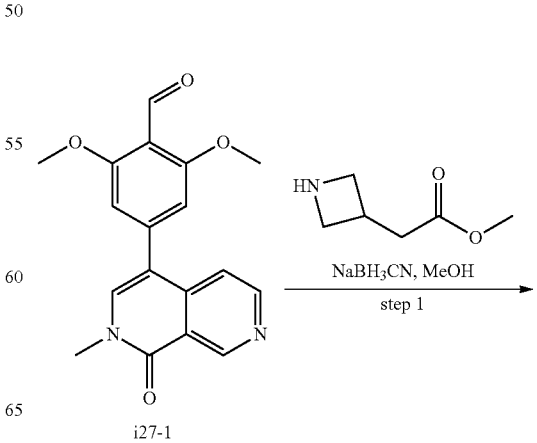

i27-1 flash silica chromatography, elution gradient 0 to 10% MeOH in DCM. Pure fractions were evaporated to dryness to afford methyl 2-(1-[[2,6-dimethoxy-4-(2-methyl-1-oxo-2,7-naphthyridin-4-yl)phenyl]methyl]azetidin-3-yl)acetate (110 mg, 81.55%) as a brown solid. LCMS (ESI) m/z: [M+H]$^+$=438.

Step 2: Preparation of 2-(1-[[2,6-dimethoxy-4-(2-methyl-1-oxo-1,2-dihydro-2,7-naphthyridin-4-yl)phenyl]methyl]azetidin-3-yl)acetic acid formic acid (Compound B41 Formic Acid)

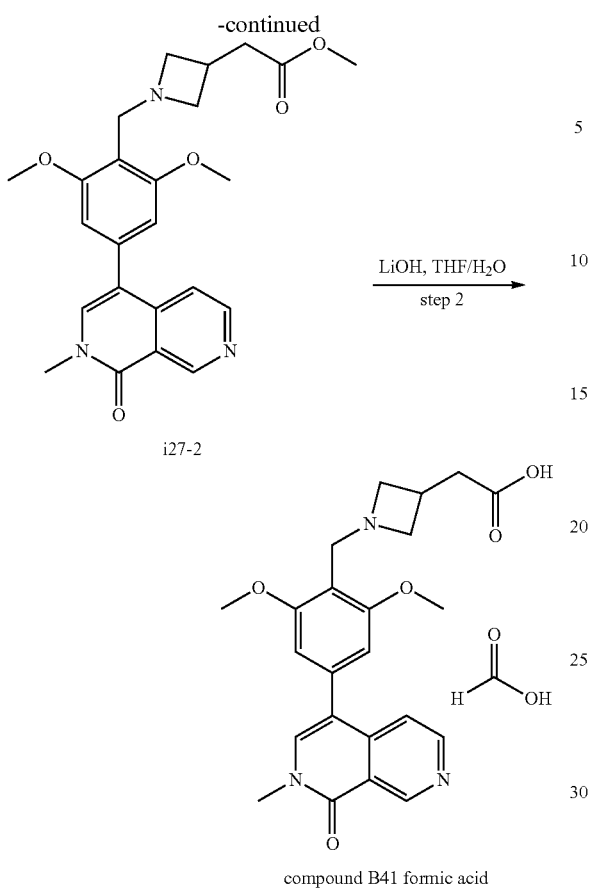

Step 1: Preparation of 2-(1-[[2,6-dimethoxy-4-(2-methyl-1-oxo-2,7-naphthyridin-4-yl)phenyl]methyl]azetidin-3-yl)acetate (i27-2)

To a solution of 2,6-dimethoxy-4-(2-methyl-1-oxo-2,7-naphthyridin-4-yl)benzaldehyde (100.00 mg, 0.308 mmol, 1.00 equiv) and methyl 2-(azetidin-3-yl)acetate; trifluoroacetic acid (82.48 mg, 0.339 mmol, 1.10 equiv) in MeOH (3.00 mL) was added NaBH$_3$CN (38.75 mg, 0.617 mmol, 2.00 equiv). The resulting mixture was stirred at room temperature for 16 hours. The mixture was concentrated under reduced pressure. The crude product was purified by To a solution of methyl 2-(1-[[2,6-dimethoxy-4-(2-methyl-1-oxo-1,2-dihydro-2,7-naphthyridin-4-yl)phenyl]methyl]azetidin-3-yl)acetate (120 mg, 0.274 mmol, 1 equiv) in MeOH (5 mL) and H$_2$O (1 mL) was added LiOH (65.69 mg, 2.743 mmol, 10 equiv). The resulting mixture was stirred at room temperature for 3 hours. The solvent was removed under reduced pressure, the residue was dissolved in water (10 mL). The mixture was acidified to pH 3 with 1 N HCl (aq.). The solvent was removed under reduced pressure. The crude product was purified by preparative HPLC (conditions: XSelect CSH Prep C18 OBD Column, 5 um, 19*150 mm; Mobile Phase A: Water (0.1% FA), Mobile Phase B: ACN; Flow rate: 25 mL/min; Gradient: 5% B to 35% B in 8 min; 254 nm; Rt: 7.25 min). Fractions containing the desired compound were evaporated to dryness to afford 2-(1-[[2,6-dimethoxy-4-(2-methyl-1-oxo-1,2-dihydro-2,7-naphthyridin-4-yl)phenyl]methyl]azetidin-3-yl)acetic acid formic acid (8.1 mg, 6.16%) as an off-white solid. $^1$H NMR (400 MHz, DMSO-d6) δ 9.44 (s, 1H), 8.72 (d, J=5.6 Hz, 1H), 8.26 (s, 0.67H, FA), 7.86 (s, 1H), 7.56 (d, J=5.6 Hz, 1H), 6.79 (d, J=11.8 Hz, 0H), 6.74 (s, 2H), 4.36 (dd, J=8.8, 7.1 Hz, 1H), 4.04 (dd, J 8.8, 5.8 Hz, 1H), 3.90 (s, 6H), 3.76 (s, 2H), 3.60 (s, 3H), 2.72 (p, J 7.0 Hz, 1H), 2.65-2.52 (m, 3H), 2.28 (dd, J=17.3, 6.4 Hz, 1H). LCMS (ESI) m/z: [M+H]+=424.25.

Example 28—Preparation ethyl N-(5-[4-[(dimethylamino)methyl]-3,5-dimethoxyphenyl]-1,4-dimethyl-2-oxo-1,2-dihydropyridin-3-yl)carbamate (Compound B42)

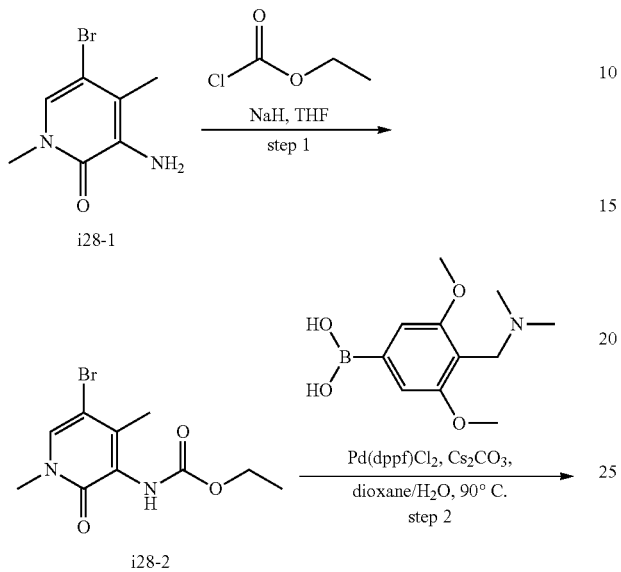

i28-1 i28-2 compound B42

Step 1: Preparation of N-(5-bromo-1,4-dimethyl-2-oxo-1,2-dihydropyridin-3-yl)propanamide (i28-2)

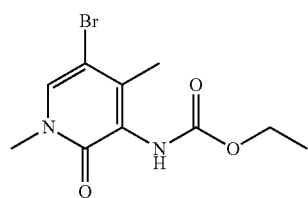

i28-2

To a solution of 3-amino-5-bromo-1,4-dimethylpyridin-2-one (300.00 mg, 1.382 mmol, 1.00 equiv) in THF (3.00 mL) was added NaH (66.33 mg, 2.764 mmol, 2 equiv) and ethyl chloroformate (179.98 mg, 1.658 mmol, 1.2 equiv). The resulting solution was stirred for 1 hour at room temperature. Then the reaction was quenched with saturated NH$_4$Cl (aq.) and purified by silica gel column chromatography, eluted with PE/EtOAc (5:1) to afford ethyl N-(5-bromo-1,4-dimethyl-2-oxopyridin-3-yl)carbamate (287 mg, 71.82%). LCMS (ESI) m/z: [M+H]+=289.1.

Step 2: Preparation of ethyl N-(5-[4-[(dimethylamino) methyl]-3,5-dimethoxyphenyl]-1,4-dimethyl-2-oxo-1,2-dihydropyridin-3-yl)carbamate (Compound B42)

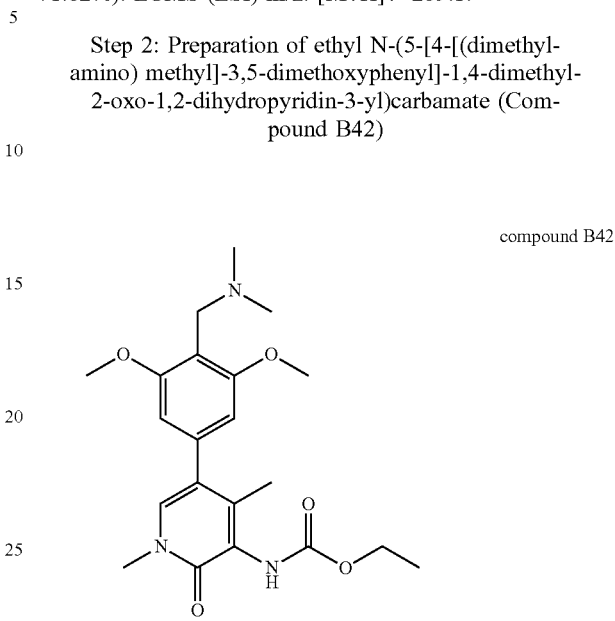

compound B42

To a solution of ethyl N-(5-bromo-1,4-dimethyl-2-oxo-1,2-dihydropyridin-3-yl)carbamate (25 mg, 0.086 mmol, 1 equiv) and [4-[(dimethylamino)methyl]-3,5-dimethoxyphenyl]boronic acid (20.67 mg, 0.086 mmol, 1 equiv) in solvent dioxane (2 mL) and H$_2$O (0.5 mL) was added Cs$_2$CO$_3$ (84.52 mg, 0.259 mmol, 3 equiv) and Pd(dppf)Cl$_2$ (9.49 mg, 0.013 mmol, 0.15 equiv). The resulting solution was stirred at 90 degree C. for 2 hours (under N$_2$ atmosphere). The crude product (140 mg) was purified by Prep-HPLC (conditions: X Bridge Shield RP18 OBD Column, 5 um, 19*150 mm; Mobile Phase A: Water (0.05% NH$_3$H$_2$O), Mobile Phase B: ACN; Flow rate: 25 mL/min; Gradient: 30% B to 65% B in 8 minutes; 220 nm; Rt: 8.2 minutes) to afford ethyl N-(5-[4-[(dimethylamino)methyl]-3,5-dimethoxyphenyl]-1,4-dimethyl-2-oxo-1,2-dihydropyridin-3-yl)carbamate (9.1 mg, 4.46%) as a light brown solid. $^1$H NMR (300 MHz, Methanol-d4) δ 7.56 (s, 1H), 6.65 (s, 2H), 4.21 (q, J=7.1 Hz, 2H), 3.88 (s, 6H), 3.79 (s, 2H), 3.64 (s, 3H), 2.41 (s, 6H), 2.12 (s, 3H), 1.32 (t, J=7.1 Hz, 3H). LCMS (ESI) m/z: [M+H]+=404.3.

Example 29—Preparation of 4-(4-((dimethyllamino)methyl)-3,5-dimethoxyphenyl)-6-methyl-1,6-dihydro-7H-pyrazolo[3,4-c]pyridin-7-one (Compound B43)

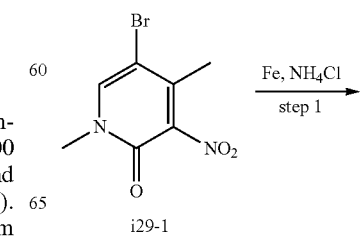

i29-1

-continued

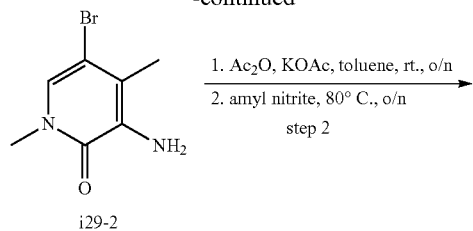

1. Ac₂O, KOAc, toluene, rt., o/n
2. amyl nitrite, 80° C., o/n
step 2

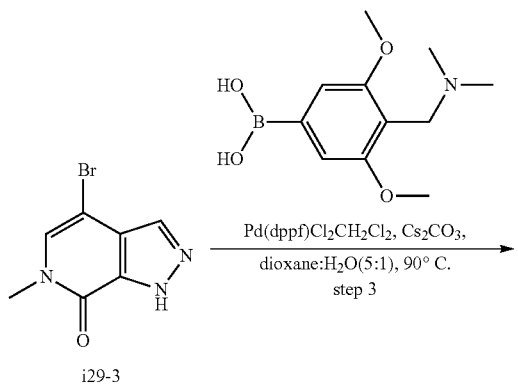

Pd(dppf)Cl₂CH₂Cl₂, Cs₂CO₃,
dioxane:H₂O(5:1), 90° C.
step 3 compound B43

Step 1: Preparation of 3-amino-5-bromo-1,4-dimethylpyridin-2(1H)-one (i29-2)

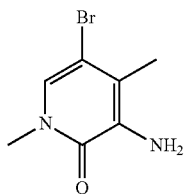

To a stirred mixture of NH₄Cl (17.3 g, 323.42 mmol, 10.0 equiv) in H₂O/EtOH (1/1, 400 mL) was added 5-bromo-1,4-dimethyl-3-nitro-1,2-dihydropyridin-2-one (8.0 g, 32.38 mmol, 1.0 equiv) and Fe (18.1 g, 324.11 mmol, 10.0 equiv) at room temperature. The mixture was stirred at rt. for 2 hours, the solid was filtered off. The filtrate was diluted with water (100 mL) and extracted with ethyl acetate (200 mL×2). The organic layers were combined and washed with saturated NaCl (aq.), dried over with anhydrous Na₂SO₄. After filtration, the filtrate was concentrated under reduced pressure. This resulted in 6.56 g (93%) 3-amino-5-bromo-1,4-dimethyl-pyridin-2(1H)-one as a red solid that was used directly without further purification. LCMS (ESI) m/z: [M+H]⁺=217.

Step 2: Preparation of 4-bromo-6-methyl-1,6-dihydro-7H-pyrazolo[3,4-c]pyridin-7-one (i29-3)

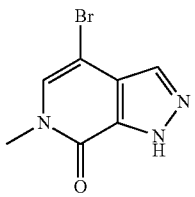

To a solution of acetyl acetate (2.82 g, 27.62 mmol, 3.0 equiv) in toluene (50 mL) was added KOAc (1.01 g, 11.11 mmol, 1.20 equiv) at 25 degrees C. After stirring for 24 hours, to the yellow mixture was added 3-methylbutyl nitrite (174.86 mg, 1.49 mmol, 1.50 equiv), the resulting mixture was stirred at 110 degrees C. for another 18 hours. Then it was allowed to cool down and mixture was concentrated under vacuum, the residue was purified by silica gel column chromatography (EtOAc/PE from 1/2 to 1/1). This resulted in 1.15 g (38%) of 4-bromo-6-methyl-1,6-dihydro-7H-pyrazolo [3,4-c]pyridin-7-one as a yellow solid. LCMS (ESI) m/z: [M+H]⁺=228.

Step 3: Preparation of 4-(4-((dimethyllamino)methyl)-3,5-dimethoxyphenyl)-6-methyl-1,6-dihydro-7H-pyrazolo [3,4-c] pyridin-7-one (Compound B43)

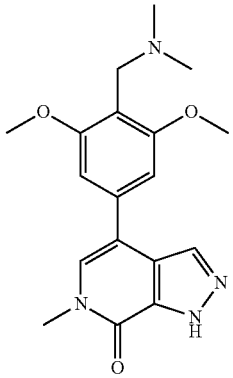

compound B43

To a stirred mixture of 4-bromo-6-methyl-1H,6H,7H-pyrazolo[3,4-c]pyridin-7-one (220.34 mg, 0.97 mmol, 1.10 equiv) and [4-[(dimethylamino)methyl]-3,5-dimethoxyphenyl]boronic acid (210 mg, 0.88 mmol, 1.0 equiv) in dioxane (5 mL) and H₂O (1 mL), was added Cs₂CO₃ (858.57 mg, 2.64 mmol, 3.0 equiv) and Pd(dppf)Cl₂·CH₂Cl₂ (107.6 mg, 0.13 mmol, 0.15 equiv) at 25 degrees C. The resulting mixture was heated to 90 degrees C. under nitrogen atmosphere. After 16 hours, it was cooled down and diluted with water (10 mL), then extracted with ethyl acetate (20 mL×2). The organic layers were combined and washed with saturated NaCl (aq.), dried over with anhydrous $Na_2SO_4$. After filtration, the filtrate was concentrated under reduced pressure, then the crude product was purified by preparative-HPLC Column (XBridge Shield RP18 OBD Column, 5 um, 19*150 mm; Mobile Phase A: Water (0.1% FA), Mobile Phase B: MeOH-HPLC; Flow rate: 25 mL/min; Gradient: 5% B to 35% B in 8 min; 254 nm; Rt: 3.87 min). This resulted in 19.1 mg (3%) formate of 4-(4-((dimethyllamino) methyl)-3,5-dimethoxyphenyl)-6-methyl-1,6-dihydro-7H-pyrazolo[3,4-c]pyridin-7-one as a yellow solid. $^1$H NMR (300 MHz, Methanol-d4) δ 8.51 (s, 1H, FA), 8.16 (s, 1H), 7.51 (s, 1H), 7.02 (s, 2H), 4.40 (s, 2H), 4.03 (s, 6H), 3.74 (s, 3H), 2.90 (s, 6H). LCMS (ESI) m/z: [M+H]$^+$=343.3.

Example 30—Preparation of 1-[[2,6-dimethoxy-4-(2-methyl-1-oxo-1,2-dihydro-2,7-naphthyridin-4-yl) phenyl] methyl]-N-[8-(phenylamino)octyl]azetidine-3-carboxamide (Compound B44)

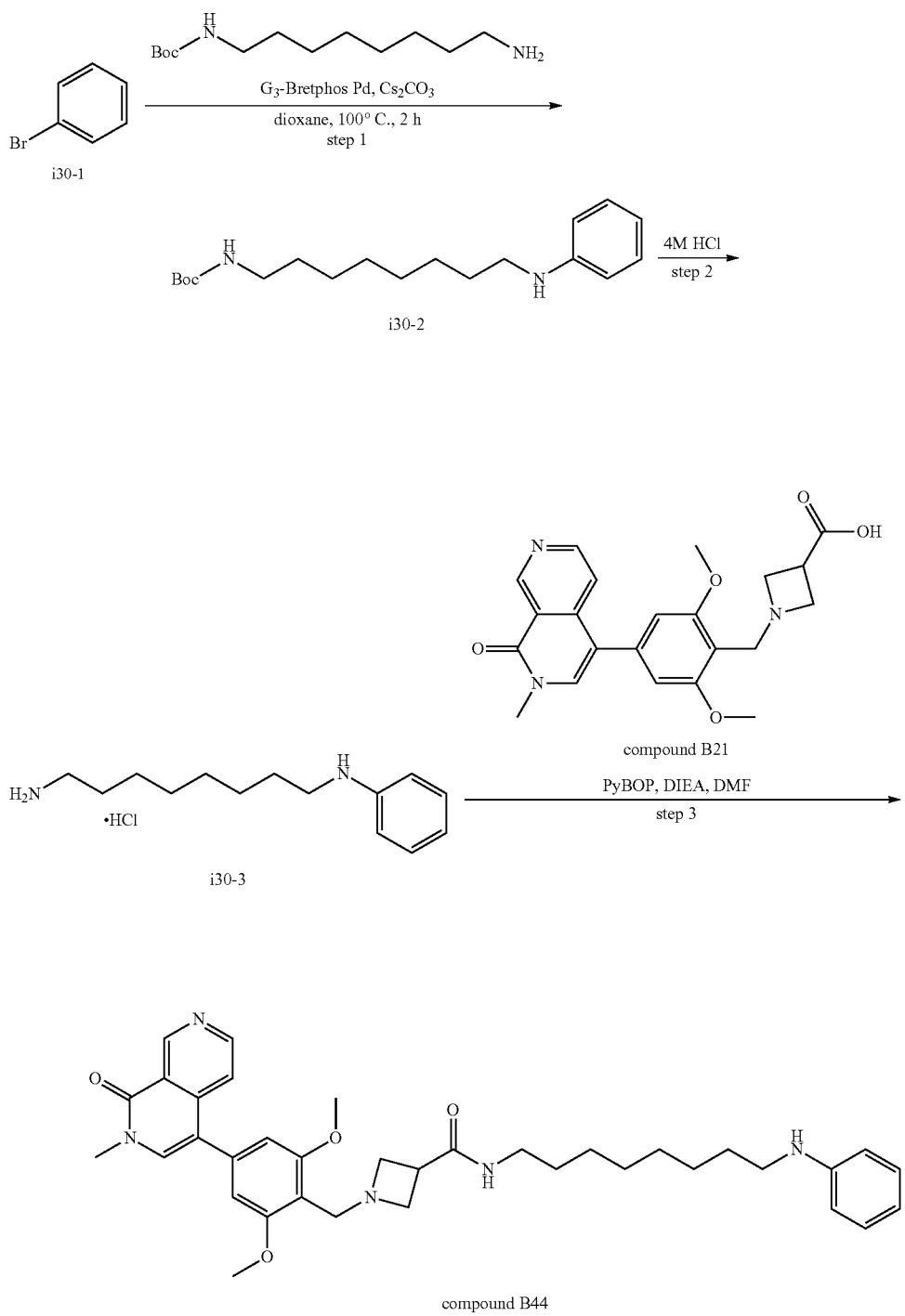

compound B44

Step 1: Preparation of tert-butyl (8-(phenylamino)octyl)carbamate (i30-2)

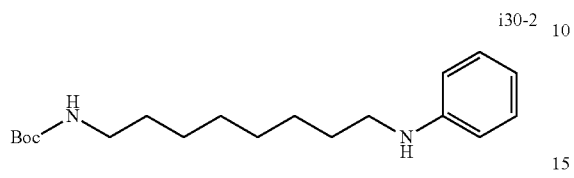

To a stirred mixture of bromobenzene (25.42 mg, 0.162 mmol, 0.23 equiv) and tert-butyl N-(8-aminooctyl)carbamate (172.05 mg, 0.70 mmol, 1.0 equiv) in dioxane was added Cs$_2$CO$_3$ (314.26 mg, 0.97 mmol, 1.37 equiv) and G$_3$-Bretphos Pd (53.63 mg, 0.063 mmol, 0.09 equiv). The mixture was stirred at 100 degrees C. for 2 h under nitrogen atmosphere. After cooling, the mixture was diluted with water (20 mL) and extracted with DCM (30 mL×3). The organic layers were combined and dried over anhydrous sodium sulfate, filtered and concentrated to give a crude product. The residue was purified by silica gel column chromatography, eluted with (PE/EtOAc 10:1) to afford tert-butyl N-[8-(phenylamino)octyl]carbamate (150 mg, 53%) as an off-white solid. LCMS (ESI) m/z: [M+H]$^+$=321.

Step 2: Preparation of N1-phenyloctane-1,8-diamine (i30-3)

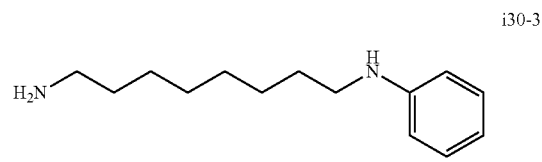 [SMILES: NCCCCCCCCNc1ccccc1]

To a solution of tert-butyl N-[8-(phenylamino)octyl]carbamate (110.0 mg, 0.34 mmol, 1.0 equiv) in DCM (8 mL) was added TFA (2 mL), and the mixture was stirred 2 h at room temperature. Then it was concentrated under reduced pressure to afford N1-phenyloctane-1,8-diamine (105 mg, 95%) as a yellow solid, that was used directly without further purification. LCMS (ESI) m/z: [M+H]$^+$=221.

Step 4: 1-(2,6-dimethoxy-4-(2-methyl-1-oxo-1,2-dihydro-2,7-naphthyridin-4-yl)benzyl)-N-(8-(phenylamino)octyl)azetidine-3-carboxamide (Compound B44)

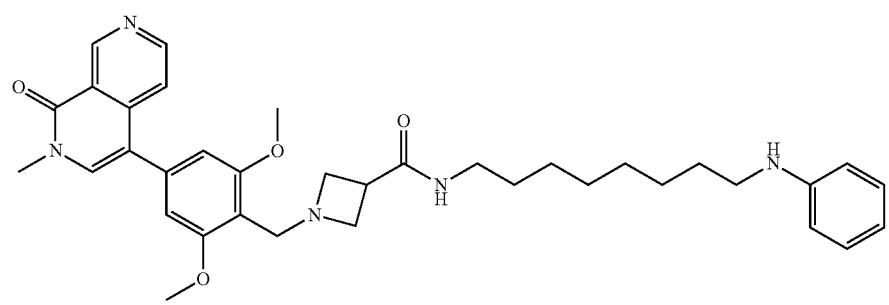

compound B44

To a stirred solution of 1-[[2,6-dimethoxy-4-(2-methyl-1-oxo-1,2-dihydro-2,7-naphthyridin-4-yl) phenyl]methyl]azetidine-3-carboxylic acid (95 mg, 0.23 mmol, 1.0 equiv) and N1-phenyloctane-1,8-diamine (102.26 mg, 0.46 mmol, 2.0 equiv) in DMF (2 mL), was added EDCI (53.38 mg, 0.278 mmol, 1.20 equiv) and HOBT (37.62 mg, 0.278 mmol, 1.20 equiv). The resulting mixture was stirred at room temperature under nitrogen atmosphere. The reaction was quenched by the addition of water (5 mL) and extracted with DCM (30 mL×3). The organic layers were combined and dried over anhydrous sodium sulfate, filtered and concentrated to give a crude product. The crude product was purified by Prep-HPLC (conditions: XBridge Shield RP18 OBD Column, 5 um, 19*150 mm; Mobile Phase A: Water (0.05% $NH_3$—$H_2O$), Mobile Phase B: ACN; Flow rate: 25 mL/min; Gradient: 49% B to 69% B in 8 min; 220 nm; Rt: 7.8 min) to afford 1-[[2,6-dimethoxy-4-(2-methyl-1-oxo-1,2-dihydro-2,7-naphthyridin-4-yl)phenyl]methyl]-N-[8-(phenylamino)octyl]azetidine-3-carboxamide (6.0 mg, 4%) as a light yellow solid. $^1$H NMR (400 MHz, Methanol-d4) δ 9.53 (s, 1H), 8.68 (d, J=5.8 Hz, 1H), 7.73 (s, 1H), 7.63 (d, J=5.8 Hz, 1H), 7.09 (t, J=7.8 Hz, 2H), 6.74 (s, 2H), 6.66-6.56 (m, 3H), 3.88 (s, 6H), 3.80 (s, 2H), 3.71 (s, 3H), 3.50 (d, J=8.0 Hz, 4H), 3.19 (dt, J=11.1, 7.6 Hz, 3H), 3.06 (t, J=7.2 Hz, 2H), 1.61 (p, J=7.1 Hz, 2H), 1.51 (q, J=6.9 Hz, 2H), 1.46-1.37 (m, 2H), 1.37-1.28 (m, 8H). LCMS (ESI) m/z: [M+H]+=612.50.

Example 31—Preparation of (2S)-1-[[2,6-dimethoxy-4-(2-methyl-1-oxo-2,7-naphthyridin-4-yl) phenyl]methyl] azetidine-2-carboxylic acid (Compound B45)

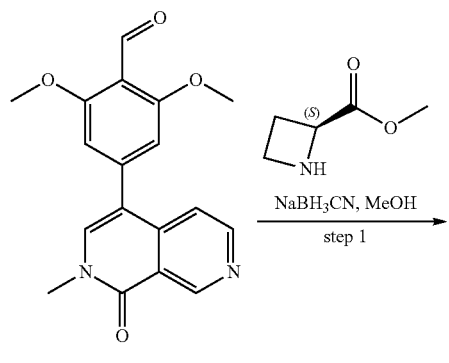

i31-1

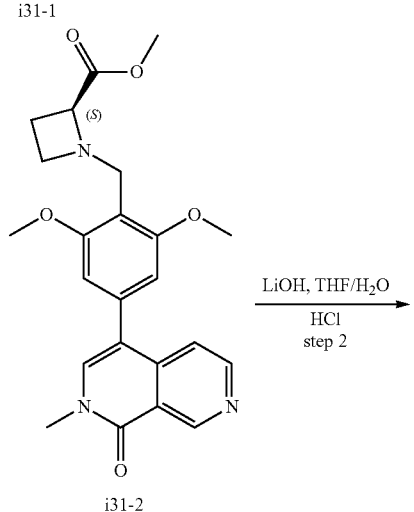

i31-2

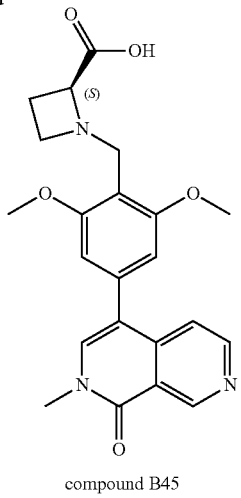

compound B45

Step 1: Preparation of methyl(2S)-1-[[2,6-dimethoxy-4-(2-methy-1-oxo-1,2-dihydro-2,7-naphthyridin-4-yl)phenyl]methyl]azetidine-2-carboxylate (i31-2)

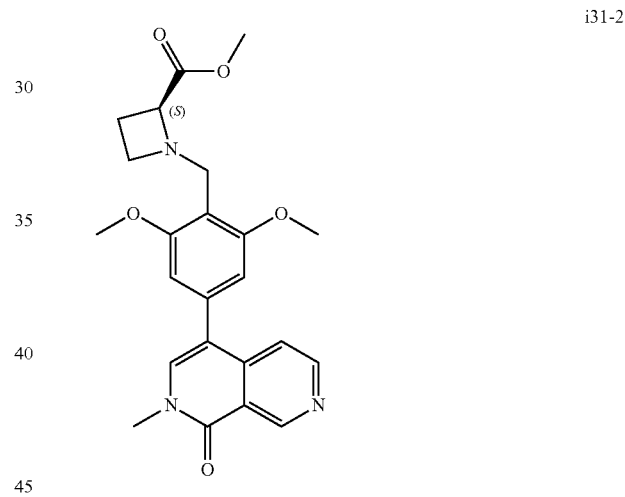

i31-2

To a solution of 2,6-dimethoxy-4-(2-methyl-1-oxo-1,2-dihydro-2,7-naphthyridin-4-yl)benzaldehyde (40.00 mg, 0.123 mmol, 1.00 equiv) and methyl (2S)-azetidine-2-carboxylate (15.62 mg, 0.136 mmol, 1.10 equiv) in MeOH (3.00 mL) was added $Et_3N$ (14.98 mg, 0.148 mmol, 1.20 equiv) and $NaBH_3CN$ (23.25 mg, 0.370 mmol, 3.00 equiv) at 0° C. The resulting solution was stirred for 1 hour at 0° C. The resulting solution was diluted with 10 mL of water. The resulting solution was extracted with ethyl acetate (2×20 mL) and the organic layers combined and dried over anhydrous sodium sulfate and concentrated. The residue was applied onto a silica gel column with $CH_2Cl_2$/MeOH (50:1), which resulted in 42 mg (80.42%) of methyl (2S)-1-[[2,6-dimethoxy-4-(2-methyl-1-oxo-1,2-dihydro-2,7-naphthyridin-4-yl)phenyl]methyl]azetidine-2-carboxylate as a yellow solid. LCMS (ESI) m/z: [M+H]+=423.2.

Step 2: Preparation of (2S)-1-[[2,6-dimethoxy-4-(2-methy-1-oxo-2,7-naphthyridin-4-yl)phenyl]methyl]azetidine-2-carboxylic acid (Compound B45)

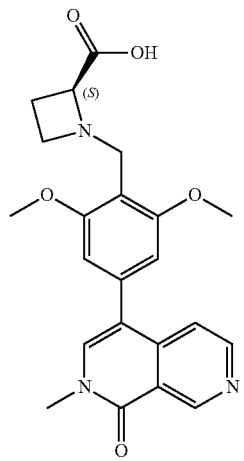

compound B45

To a solution of methyl (2S)-1-[[2,6-dimethoxy-4-(2-methyl-1-oxo-2,7-naphthyridin-4-yl)phenyl]methyl]azetidine-2-carboxylate (42 mg, 0.099 mmol, 1.00 equiv) in THF (1.50 mL) was added LiOH (11.88 mg, 0.496 mmol, 5.00 equiv) and H$_2$O (1.00 mL) at 0° C. The resulting solution was stirred for 2 hours at 25° C. The resulting solution was diluted with 10 mL of water. Then HCl (6 M) (0.50 mL, 16.456 mmol, 165.92 equiv) was added, and the resulting solution was extracted with ethyl acetate (2×20 mL). The organic layers combined and dried over anhydrous sodium sulfate and concentrated. The crude product was purified by Prep-HPLC (conditions: Atlantis HILIC OBD Column, 19 mm×250 mm; mobile phase, Water (0.1% FA) and ACN (hold 5% Phase B in 2 minutes, up to 17% in 8 minutes); Detector, uv). This resulted in 25 mg (61.65%) (2S)-1-[[2,6-dimethoxy-4-(2-methyl-1-oxo-2,7-naphthyridin-4-yl)phenyl]methyl]azetidine-2-carboxylic acid as a white solid. $^1$H NMR (400 MHz, Methanol-d4) δ 9.55 (s, 1H), 8.69 (d, J=5.8 Hz, 1H), 7.82 (s, 1H), 7.66 (d, J=5.8 Hz, 1H), 6.85 (s, 2H), 5.00 (t, J=9.5 Hz, 1H), 4.53 (s, 2H), 4.14 (q, J=9.6 Hz, 1H), 3.98 (s, 7H), 3.72 (s, 3H), 2.72 (d, J=10.6 Hz, 1H), 2.61 (q, J=10.1 Hz, 1H). LCMS (ESI) m/z: [M+H]$^+$=410.15

Example 32—Preparation of 1-[[2,6-dimethoxy-4-(2-methyl-1-oxo-1,2-dihydro-2,7-naphthyridin-4-yl)phenyl]methyl]azetidine-3-carboxylic acid (Compound B46)

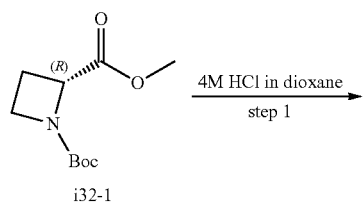

i32-1

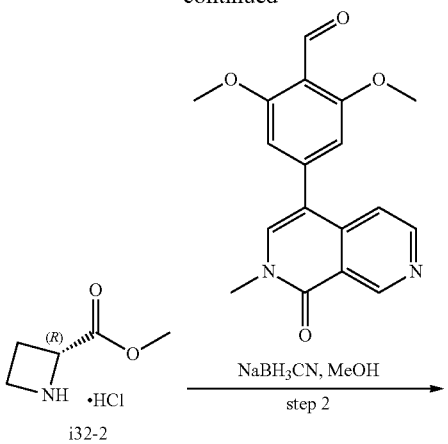

i32-2

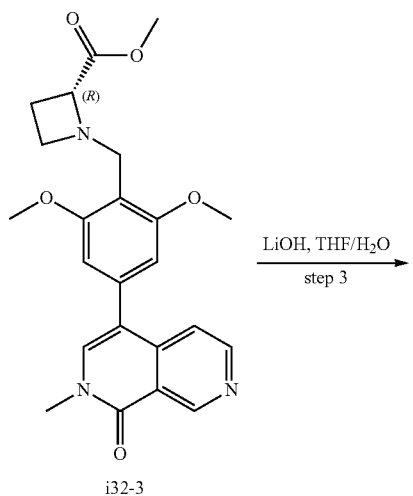

i32-3

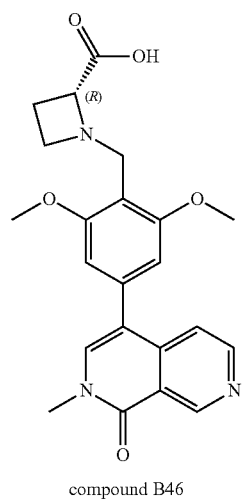

compound B46

Step 1: preparation of methyl (2R)-azetidine-2-carboxylate hydrochloride (i32-2)

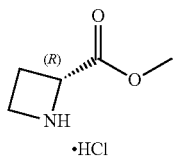

i32-2

A mixture of 1-tert-butyl 2-methyl (2R)-azetidine-1,2-dicarboxylate (40.30 mg, 0.187 mmol, 1.00 equiv) and HCl (4M) in 1,4-dioxane (3.00 mL) was stirred at room temperature for 1 hour. Then the solvent was evaporated, and the result crude methyl (2R)-azetidine-2-carboxylate hydrochloride was used directly in the next step without further purification. LCMS (ESI) m/z: [M+H]+=116.

Step 2: Preparation of methyl(2R)-1-[[2,6-dimethoxy-4-(2-methyl-1-oxo-2,7-naphthyridin-4-yl)phenyl]methyl]azetidine-2-carboxylate (i32-3)

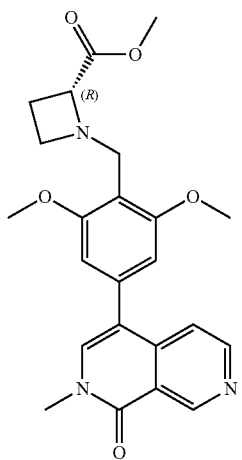

i32-3

To a stirred solution of methyl (2R)-azetidine-2-carboxylate hydrochloride (28.23 mg, 0.186 mmol, 1.00 equiv) and Et₃N (37.69 mg, 0.372 mmol, 2 equiv) in MeOH (2.00 mL) was added 2,6-dimethoxy-4-(2-methyl-1-oxo-2,7-naphthyridin-4-yl)benzaldehyde (60.40 mg, 0.186 mmol, 1.00 equiv), and the mixture was stirred for 0.5 hours before NaBH₃CN (23.41 mg, 0.372 mmol, 2 equiv) was added in portions at room temperature under ambient atmosphere. Then the reaction was quenched by the addition of water (10 mL) at 0° C., and the mixture extracted with EtOAc (20 mL×2). The organic layer was dried over anhydrous sodium sulfate, filtered, and concentrated to give crude product that was purified by chromatography on silica gel, eluted with MeOH/DCM (0-10%) to afford methyl (2R)-1-[[2,6-dimethoxy-4-(2-methyl-1-oxo-2,7-naphthyridin-4-yl)phenyl]methyl]azetidine-2-carboxylate (68 mg, 86.23%) as a yellow solid. LCMS (ESI) m/z: [M+H]+=424.

Step 3: Preparation of 1-[[2,6-dimethoxy-4-(2-methyl-1-oxo-1,2-dihydro-2,7-naphthyridin-4-yl)phenyl]methyl]azetidine-3-carboxylic acid (Compound B46)

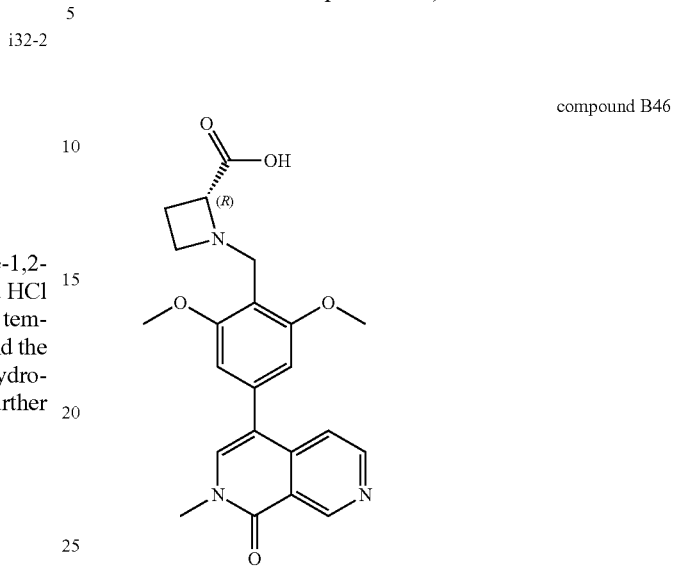

compound B46

To a stirred solution of methyl 1-[[2,6-dimethoxy-4-(2-methyl-1-oxo-1,2-dihydro-2,7-naphthyridin-4-yl)phenyl]methyl]azetidine-3-carboxylate (840 mg, 1.984 mmol, 1 equiv) in the mixed solvent of THF (4 mL) and H₂O (2 mL) was added LiOH (475.04 mg, 19.836 mmol, 10.00 equiv), and the solution was stirred for 1 hour at ambient atmosphere. The mixture was purified by reverse phase flash to get a crude product, and the result residue was further purified by Prep-HPLC (conditions: XSelect CSH Prep C18 OBD Column, 5 μm, 19*150 mm; Mobile Phase A: Water (0.1% FA), Mobile Phase B: ACN; Flow rate: 25 mL/min; Gradient: 38% B to 58% B in 8 minutes; 254 nm; Rt: 7.35 minutes) to afford 1-[[2,6-dimethoxy-4-(2-methyl-1-oxo-1,2-dihydro-2,7-naphthyridin-4-yl)phenyl]methyl]azetidine-3-carboxylic acid (421 mg, 51.84%) as a light yellow semi-solid. ¹H NMR (300 MHz, Methanol-d4) δ 9.62 (s, 1H), 8.72 (d, J=6.4 Hz, 1H), 8.08 (s, 1H), 7.92 (d, J=6.3 Hz, 1H), 6.88 (s, 2H), 5.18 (t, J=9.7 Hz, 1H), 4.56 (s, 2H), 4.19 (q, J 9.6 Hz, 1H), 3.98 (s, 7H), 3.75 (s, 3H), 2.72-2.59 (m, 2H). LCMS (ESI) m/z: [M+H]+=410.20.

Example 33—Preparation of 7-[4-[(dimethylamino)methyl]-3,5-dimethoxyphenyl]-5-methyl-3H-imidazo[4,5-c]pyridin-4-one formic acid (Compound B47 Formic Acid)

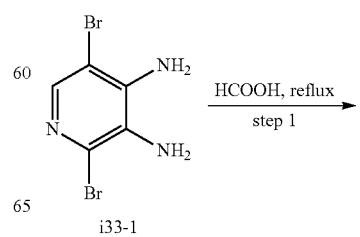

i33-1

-continued

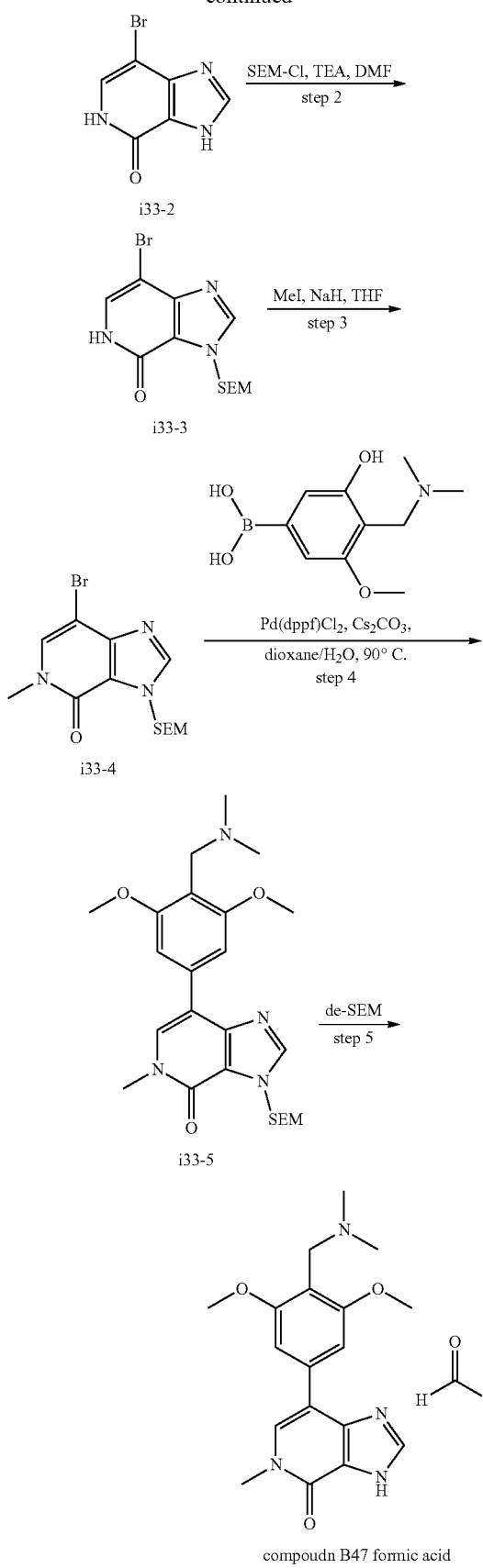

Step 1: Preparation of 7-bromo-3,5-dihydro-4H-imidazo[4,5-c]pyridin-4-one (i33-2)

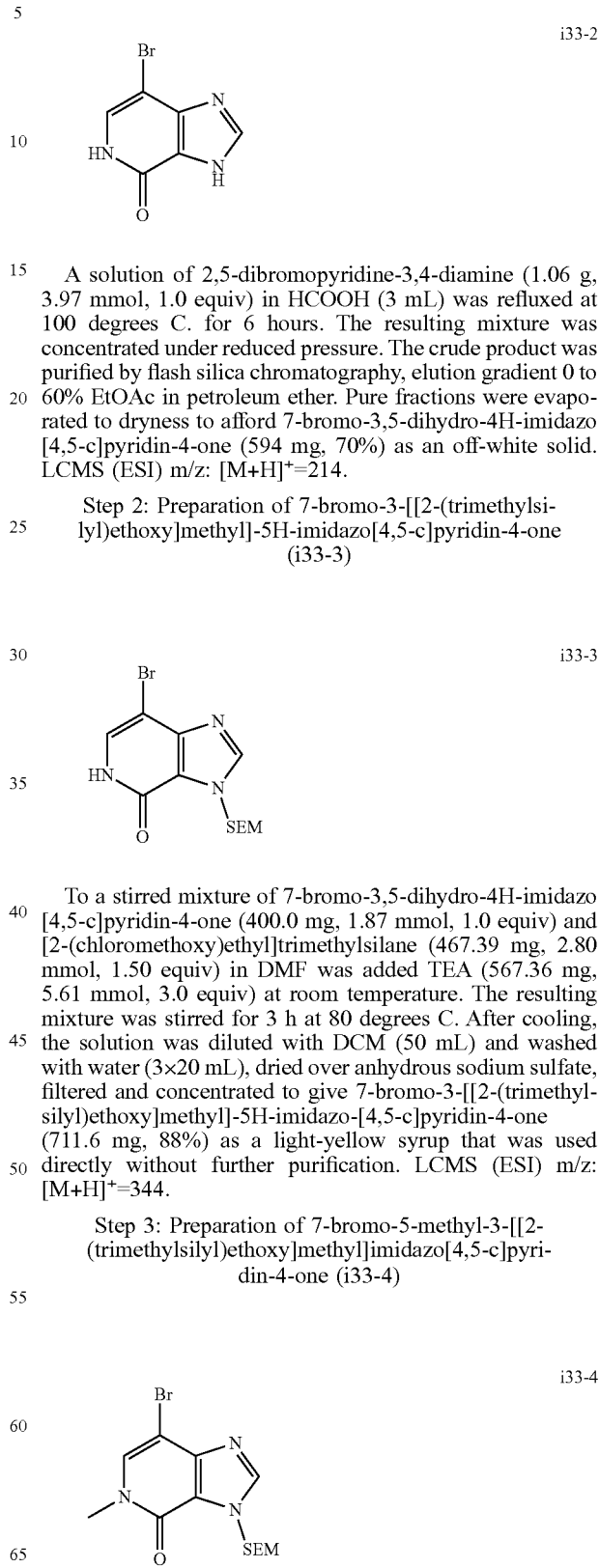

A solution of 2,5-dibromopyridine-3,4-diamine (1.06 g, 3.97 mmol, 1.0 equiv) in HCOOH (3 mL) was refluxed at 100 degrees C. for 6 hours. The resulting mixture was concentrated under reduced pressure. The crude product was purified by flash silica chromatography, elution gradient 0 to 60% EtOAc in petroleum ether. Pure fractions were evaporated to dryness to afford 7-bromo-3,5-dihydro-4H-imidazo[4,5-c]pyridin-4-one (594 mg, 70%) as an off-white solid. LCMS (ESI) m/z: $[M+H]^+=214$.

Step 2: Preparation of 7-bromo-3-[[2-(trimethylsilyl)ethoxy]methyl]-5H-imidazo[4,5-c]pyridin-4-one (i33-3)

To a stirred mixture of 7-bromo-3,5-dihydro-4H-imidazo[4,5-c]pyridin-4-one (400.0 mg, 1.87 mmol, 1.0 equiv) and [2-(chloromethoxy)ethyl]trimethylsilane (467.39 mg, 2.80 mmol, 1.50 equiv) in DMF was added TEA (567.36 mg, 5.61 mmol, 3.0 equiv) at room temperature. The resulting mixture was stirred for 3 h at 80 degrees C. After cooling, the solution was diluted with DCM (50 mL) and washed with water (3×20 mL), dried over anhydrous sodium sulfate, filtered and concentrated to give 7-bromo-3-[[2-(trimethylsilyl)ethoxy]methyl]-5H-imidazo-[4,5-c]pyridin-4-one (711.6 mg, 88%) as a light-yellow syrup that was used directly without further purification. LCMS (ESI) m/z: $[M+H]^+=344$.

Step 3: Preparation of 7-bromo-5-methyl-3-[[2-(trimethylsilyl)ethoxy]methyl]imidazo[4,5-c]pyridin-4-one (i33-4)

A mixture of 7-bromo-3-[[2-(trimethylsilyl)ethoxy]methyl]-5H-imidazo[4,5-c]pyridin-4-one (643.0 mg, 1.87 mmol, 1.0 equiv) in THF (10.0 mL) was cooled to 0 degrees C., then NaH (53.78 mg, 2.24 mmol, 1.20 equiv) was added in portions. The mixture was stirred for 20 min, and then CH$_3$I (795.27 mg, 5.60 mmol, 3.0 equiv) was added. After stirring for 1 h at room temperature under nitrogen atmosphere, the reaction was quenched with water (100 mL) and the mixture extracted with EA (4×100 mL). The organic layers were combined and dried over anhydrous sodium sulfate, filtered and concentrated to give 7-bromo-5-methyl-3-[[2-(trimethylsilyl)ethoxy]methyl]imidazo[4,5-c]pyridin-4-one (660 mg, 83%) as a brown-yellow syrup, that was used directly without further purification. LCMS (ESI) m/z: [M+H]$^+$=358.

Step 4: Preparation of 7-[4-[(dimethylamino)methyl]-3,5-dimethoxyphenyl]-5-methyl-3-[[2-(trimethylsilyl) ethoxy]methyl]imidazo[4,5-c]pyridin-4-one (i33-5)

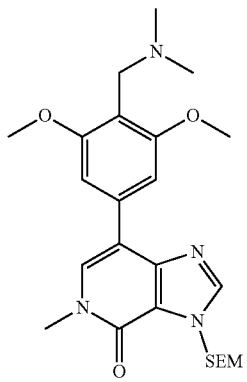

i33-5

To a solution of 7-bromo-5-methyl-3-[[2-(trimethylsilyl)ethoxy]methyl]imidazo[4,5-c]pyridin-4-one (200.0 mg, 0.56 mmol, 1.0 equiv) and 4-[(dimethylamino)methyl]-3,5-dimethoxyphenylboronic acid (160.14 mg, 0.67 mmol, 1.20 equiv) in dioxane (10 mL) and H$_2$O (2 mL) was added Cs$_2$CO$_3$ (545.59 mg, 1.68 mmol, 3.0 equiv) and Pd(dppf)Cl$_2$·CH$_2$Cl$_2$ (40.84 mg, 0.056 mmol, 0.10 equiv). The mixture was stirred for 2 hours at 90 degrees C. under a nitrogen atmosphere. After cooling, the mixture was diluted with water (20 mL) and extracted with EtOAc (30 mL×3). The organic layers were combined and dried over anhydrous sodium sulfate, filtered and concentrated to give a crude product. The crude product was purified by flash silica chromatography, elution gradient 0 to 7% CH$_3$OH in CH$_2$Cl$_2$. Pure fractions were evaporated to dryness to afford 7-[4-[(dimethylamino)methyl]-3,5-dimethoxyphenyl]-5-methyl-3-[[2-(trimethylsilyl)ethoxy]methyl]imidazo[4,5-c]pyridin-4-one (140 mg, 53%). LCMS (ESI) m/z: [M+H]$^+$=473

Step 5: Preparation of 7-[4-[(dimethylamino)methyl]-3,5-dimethoxyphenyl]-5-methyl-3H-imidazo[4,5-c]pyridin-4-one formic acid (Compound B47 Formic Acid)

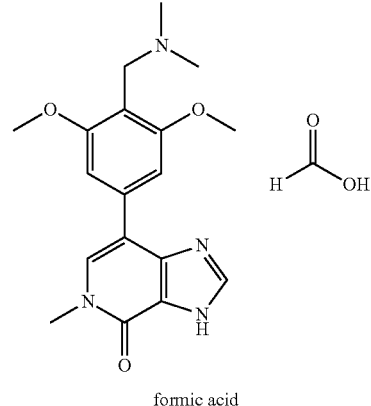

compoudn B47 formic acid

A mixture of 7-[4-[(dimethylamino)methyl]-3,5-dimethoxyphenyl]-5-methyl-3-[[2-(trimethylsilyl)ethoxy]methyl]imidazo[4,5-c]pyridin-4-one (120.0 mg, 0.25 mmol, 1.0 equiv) in 2M HCl-1,4-dioxane (5 mL) was stirred for 2 hours at 70 degrees C. After cooling, the mixture was concentrated under reduced pressure. The crude product was purified by Prep-HPLC with the following conditions Column: SunFire C18 OBD Prep Column, 100 Å, 5 μm, 19 mm×250 mm; Mobile Phase A: Water (0.1% FA), Mobile Phase B: ACN; Flow rate: 25 mL/min; Gradient: 7% B to 26% B in 8 min; 254 nm; Rt: 6.25 min. to afford formate of 26 mg (25%) of 7-[4-[(dimethylamino)methyl]-3,5-dimethoxyphenyl]-5-methyl-3H-imidazo [4,5-c]pyridin-4-one as a white solid. $^1$H NMR (400 MHz, Methanol-d4) δ 8.55 (s, 1H), 8.24 (s, 1H), 7.78 (s, 1H), 7.20 (s, 2H), 4.39 (s, 2H), 4.03 (s, 6H), 3.77 (s, 3H), 2.89 (s, 6H). LCMS (ESI) m/z: [M+H]+=343.15.

Example 34—Preparation of 1-[[4-(1,5-dimethyl-6-oxopyridin-3-yl)-2,6-dimethoxyphenyl]methyl]azetidine-3-carboxylic acid (Compound B48)

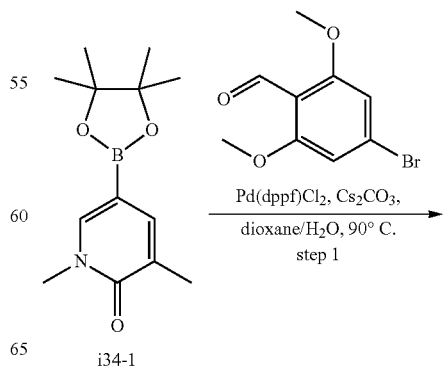

i34-1

183
-continued

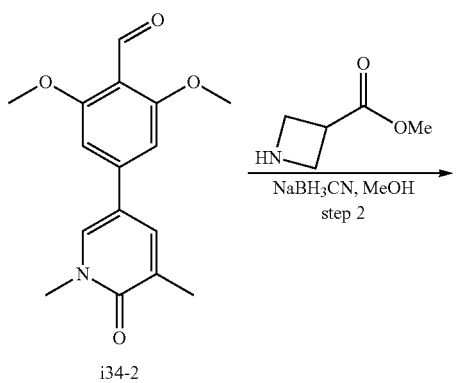

i34-2

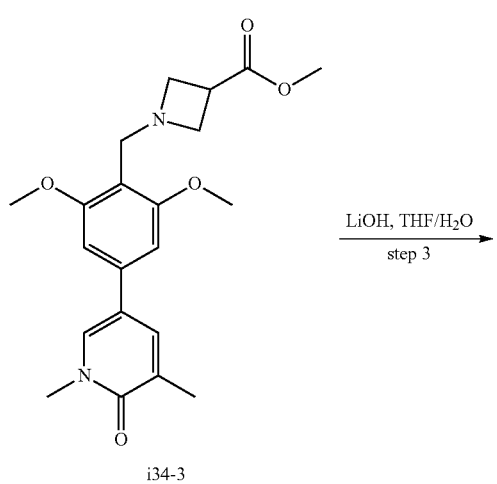

i34-3 compound B48

184

Step 1: Preparation of 4-(1,5-dimethyl-6-oxopyridin-3-yl)-2,6-dimethoxybenzaldehyde (i34-2)

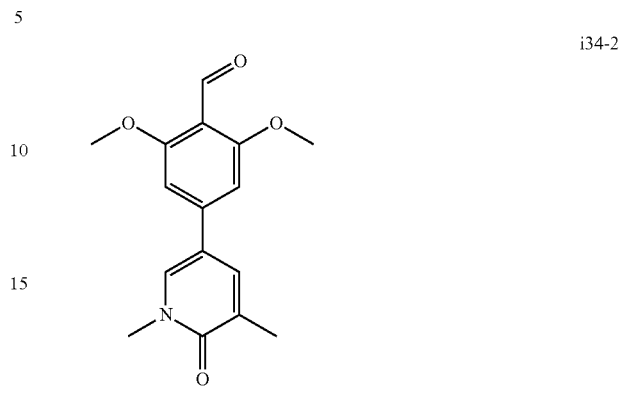

i34-2

To a stirred solution of 1,3-dimethyl-5-(4,4,5,5-tetramethyl-1,3,2-dioxaborolan-2-yl)pyridin-2-one (430 mg, 1.73 mmol, 1.0 equiv) and 4-bromo-2,6-dimethoxybenzaldehyde (634.52 mg, 2.59 mmol, 1.50 equiv) in 1,4-dioxane (25 mL)/$H_2O$ (5 mL), was added Pd(dppf)$Cl_2$ (126.3 mg, 0.17 mmol, 0.10 equiv) and $Cs_2CO_3$ (1124.78 mg, 3.45 mmol, 2.0 equiv). The resulting solution was stirred at 90 degrees C. for 2 h under nitrogen atmosphere. Then the mixture was allowed to cool down to room temperature, the mixture was diluted with water (25 mL) and extracted with EtOAc (3×25 mL). The organic layers were combined and dried over anhydrous sodium sulfate, filtered and concentrated to give a crude product. The residue was purified by silica gel column chromatography, eluted with $CH_2Cl_2$/MeOH (20:1) to afford 4-(1,5-dimethyl-6-oxopyridin-3-yl)-2,6-dimethoxybenzaldehyde (313 mg, 51.42%) as an off-white solid. LCMS (ESI) m/z: $[M+H]^+$=288

Step 2: Preparation of methyl 1-[[4-(1,5-dimethyl-6-oxopyridin-3-yl)-2,6-dimethoxyphenyl]methyl]azetidine-3-carboxylate (i34-3)

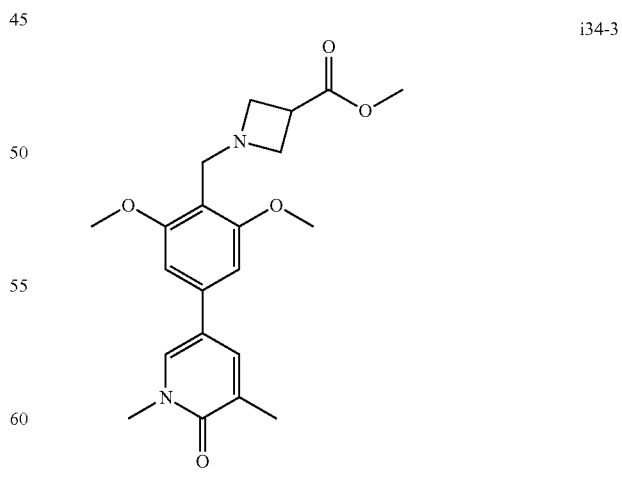

i34-3

To a stirred mixture of 4-(1,5-dimethyl-6-oxopyridin-3-yl)-2,6-dimethoxybenzaldehyde (313.00 mg, 1.09 mmol, 1.0 equiv) and methyl azetidine-3-carboxylate (188.14 mg, 1.63 mmol, 1.50 equiv) in MeOH was added $NaBH_3CN$ (136.92 mg, 2.18 mmol, 2.0 equiv), the mixture was stirred at room temperature under nitrogen atmosphere. Then the mixture was diluted with water (25 mL) and extracted with EtOAc (3×25 mL). The organic layers were combined and dried over anhydrous sodium sulfate, filtered and concentrated to give a crude product. The residue was purified by silica gel column chromatography, eluted with CHCl₃/MeOH (10:1) to afford methyl 1-[[4-(1,5-dimethyl-6-oxopyridin-3-yl)-2,6-dimethoxyphenyl] methyl]-azetidine-3-carboxylate (172.5 mg, 35%) as a off-white solid. LCMS (ESI) m/z: [M+H]⁺=386.4

Step 3: Preparation of 1-[[4-(1,5-dimethyl-6-oxopyridin-3-yl)-2,6-dimethoxyphenyl]methyl]azetidine-3-carboxylic acid (Compound B48)

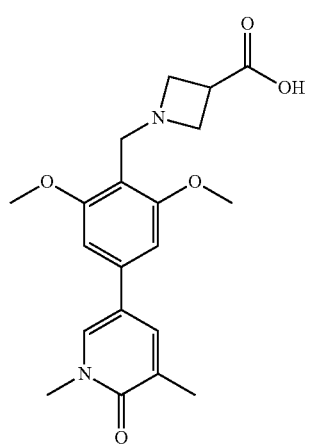

compound B48

A mixture of methyl 1-[[4-(1,5-dimethyl-6-oxopyridin-3-yl)-2,6-dimethoxyphenyl]methyl]azetidine-3-carboxylate (169.0 mg, 0.48 mmol, 1.0 equiv) and LiOH (52.36 mg, 2.19 mmol, 5.0 equiv) in THF (3 mL) and H₂O (3 mL) was stirred for 1 h at room temperature. Then the mixture was acidified with 12 N HCl until pH 4. The mixture was extracted with DCM (30 mL×3), dried over anhydrous sodium sulfate, filtered and concentrated to give the crude product which was purified by Prep-HPLC with the following conditions (Column: SunFire C18 OBD Prep Column, 100 Å, 5 μm, 19 mm×250 mm; Mobile Phase A: Water (0.1% FA), Mobile Phase B: ACN; Flow rate: 25 mL/min; Gradient: 7% B to 24% B in 8 min; 254 nm; Rt: 7.85 min) to afford 1-[[4-(1, 5-dimethyl-6-oxopyridin-3-yl)-2,6-dimethoxyphenyl] methyl]azetidine-3-carboxylic acid (48 mg, 29%) as a white solid. ¹H NMR (400 MHz, Methanol-d4) δ 7.98 (d, J=2.5 Hz, 1H), 7.84 (s, 1H), 6.91 (s, 2H), 4.48 (s, 2H), 4.30 (d, J=9.8 Hz, 4H), 4.01 (s, 6H), 3.69 (s, 3H), 3.59 (s, 1H), 2.23 (s, 3H). LCMS (ESI) m/z: [M+H]⁺=373.20.

Example 35—Preparation of N-[[2,6-dimethoxy-4-(2-methyl-1-oxo-2,7-naphthyridin-4-yl)phenyl] methyl]-N-methyl propane-2-sulfonamide (Compound B49)

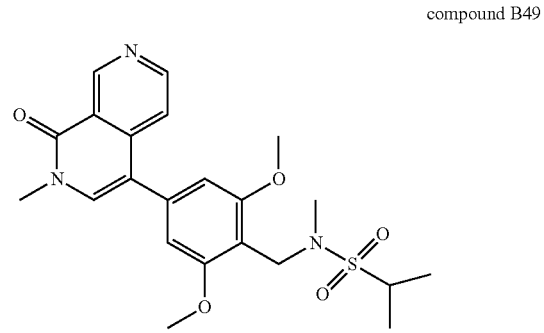 [SMILES: COc1cc(-c2cn(C)c(=O)c3cnccc23)cc(OC)c1CN(C)S(=O)(=O)C(C)C]

compound B49

Compound B49 was prepared in a similar manner as described for compound B35. N-[[2,6-dimethoxy-4-(2-methyl-1-oxo-2,7-naphthyridin-4-yl) phenyl] methyl]-N-methylpropane-2-sulfonamide (19.1 mg, 9%) was obtained as a white solid. ¹H NMR (400 MHz, Methanol-d4) δ 9.56 (s, 1H), 8.70 (d, J=5.9 Hz, 1H), 7.85 (s, 1H), 7.72 (d, J=6.0 Hz, 1H), 6.80 (s, 2H), 4.53 (s, 2H), 3.91 (s, 6H), 3.73 (s, 3H), 3.62-3.49 (m, 1H), 2.77 (s, 3H), 1.35 (d, J=6.8 Hz, 6H). LCMS (ESI) m/z: [M+H]⁺=446.25.

Example 36—Preparation of 4-(4-((dimethylamino)methyl)-3,5-dimethoxyphenyl)-2methyl-2,6-naphthyridin-1(2H)-one (Compound B50)

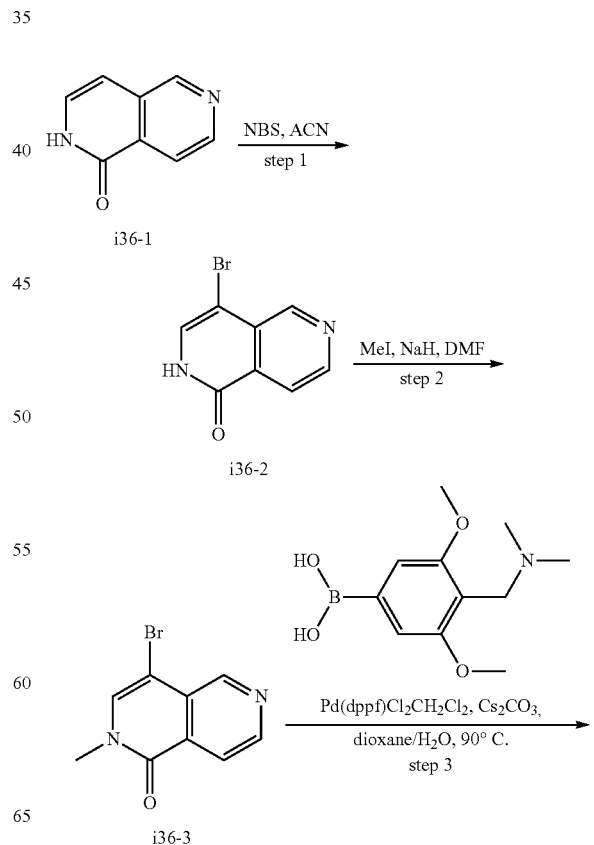

-continued

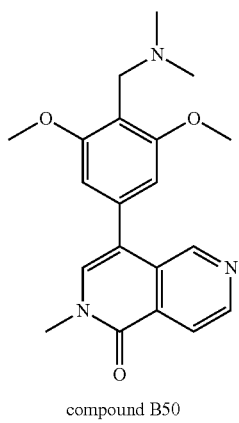

compound B50

Step 1: Preparation of
4-bromo-2,6-naphthyridin-1(2H)-one (i36-2)

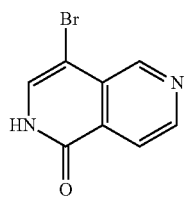

i36-2

To a stirred solution of 1,2-dihydro-2,6-naphthyridin-1-one (500 mg, 3.421 mmol, 1.00 equiv) in CH$_3$CN (10 mL) was added 1-bromopyrrolidine-2,5-dione (669.81 mg, 3.763 mmol, 1.10 equiv) at room temperature. The resulting mixture was stirred for 3 hours at room temperature. The mixture was concentrated under vacuum. The residue was purified by flash silica gel column chromatography, eluted with ethyl acetate/petroleum ether from 50% to 100%. This resulted in 4-bromo-2,6-naphthyridin-1(2H)-one (760 mg, 99.08%) of as a yellow solid. LCMS (ESI) m/z: [M+H]$^+$=225.

Step 2: Preparation of 4-bromo-2-methyl-2,6-naphthyridin-1(2H)-one (i36-3)

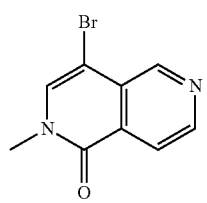

i36-3

To a stirred solution of 4-bromo-2,6-naphthyridin-1(2H)-one (396.0 mg, 1.76 mmol, 1.0 equiv) in DMF (6 mL) was added NaH (59.12 mg, 2.464 mmol, 1.40 equiv) at 0 degrees C. After 10 minutes of stirring, iodomethane (499.53 mg, 3.519 mmol, 2.00 equiv) was added to the solution. The solution was stirred at 25 degrees C. for 10 hours. Then water (50 mL) was added, and the reaction mixture was then extracted with DCM (50 mL×3). The combined organic layers were washed with saturated brine (30 mL×2), dried over anhydrous sodium sulfate, filtered, and concentrated to give 331 mg of crude product. This material was used directly in the next step without further purification. LCMS (ESI) m/z: [M+H]$^+$=239.

Step 3: Preparation of 4-(4-((dimethylamino) methyl)-3,5-dimethoxyphenyl)-2-methyl-2,6-naphthyridin-1 (2H)-one (Compound B50)

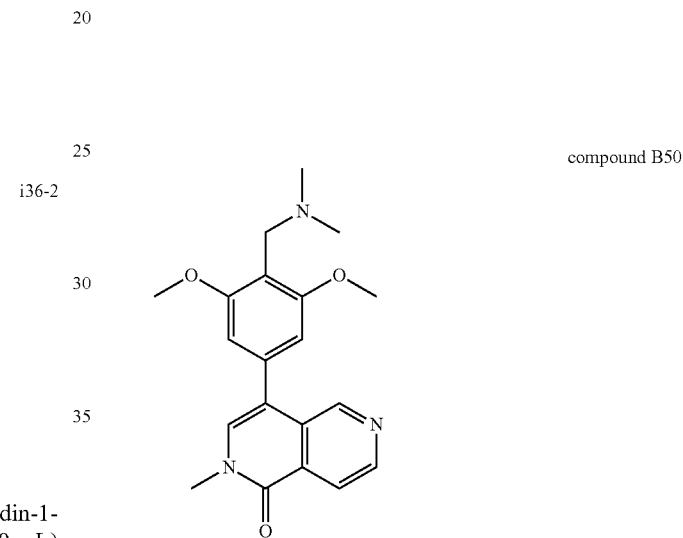

compound B50

To a stirred mixture of 4-bromo-2-methyl-1,2-dihydro-2,6-naphthyridin-1-one (80.30 mg, 0.336 mmol, 1.10 equiv) and [4-[(dimethylamino)methyl]-3,5-dimethoxyphenyl]boronic acid (73 mg, 0.305 mmol, 1.00 equiv) in dioxane (5 mL) and H$_2$O (1 mL) was added Cs$_2$CO$_3$ (298.45 mg, 0.916 mmol, 3.00 equiv) and Pd(dppf)Cl$_2$·CH$_2$Cl$_2$ (37.40 mg, 0.046 mmol, 0.15 equiv). The resulting reaction mixture was stirred for 5 hours at 90 degrees C. under N$_2$ atmosphere. The reaction mixture was concentrated under reduced pressure, and then the residue was diluted with DCM (100 mL) and filtered through a short pad of Celite. The solvent was evaporated and the crude product was purified by preparative HPLC (conditions: XBridge Shield RP18 OBD Column, 5 um, 19*150 mm; Mobile Phase A: Water (10 mmol/L NH$_4$HCO$_3$), Mobile Phase B: ACN; Flow rate: 25 mL/min; Gradient: 35% B to 75% B in 8 minutes; 220 nm; Rt: 7.9 minutes). This resulted in 4-(4-((dimethylamino) methyl)-3,5-dimethoxyphenyl)-2-methyl-2,6-naphthyridin-1 (2H)-one (9.6 mg, 8.90%) as a yellow solid. $^1$H NMR (300 MHz, Methanol-d4) δ 9.02 (s, 1H), 8.69 (d, J=5.3 Hz, 1H), 8.28 (d, J=5.4 Hz, 1H), 7.60 (s, 1H), 6.81 (s, 2H), 3.89 (s, 6H), 3.74 (d, J=4.1 Hz, 5H), 2.36 (s, 6H). LCMS (ESI) m/z: [M+H]$^+$=354.15.

Example 37—Preparation of 4-(3-(difluoromethoxy)-4-((dimethylamino)methyl)phenyl)-2-methyl-2,7-naphthyridin-1(2H)-one (Compound B51)

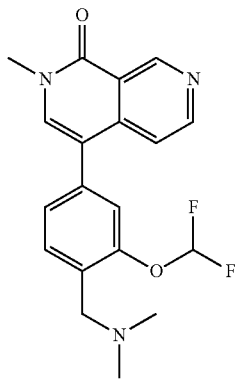

compound B51

Compound B51 was prepared in a similar manner as described for compound B50. $^1$H NMR (400 MHz, DMSO-$d_6$) δ 9.43 (d, J=0.9 Hz, 1H), 8.71 (d, J=5.6 Hz, 1H), 7.85 (s, 1H), 7.56 (d, J=7.9 Hz, 1H), 7.45 (dd, J=5.6, 0.9 Hz, 1H), 7.34 (dd, J=7.8, 1.7 Hz, 1H), 7.28-7.24 (m, 1H), 3.57 (s, 3H), 3.47 (s, 2H), 2.19 (s, 6H). LCMS (ESI) m/z: [M+H]$^+$=360.2.

Example 38—Preparation of 8-[4-[(dimethylamino)methyl]-3,5-dimethoxyphenyl]-6-methyl-5H,6H-pyrido[3,4-d]pyridazin-5-one (Compound B52)

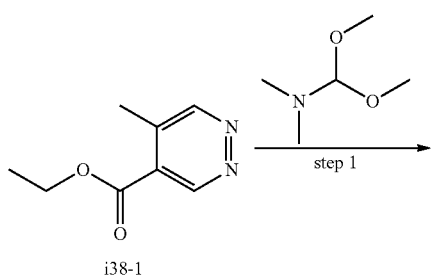

i38-1

CH$_3$NH$_2$, EtOH, reflux
step 2

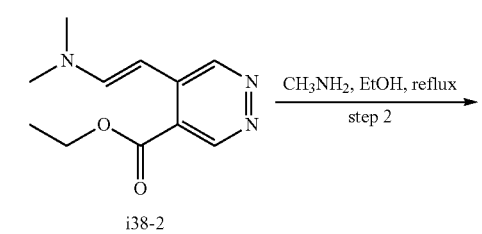

i38-2

NBS, DMF
step 3

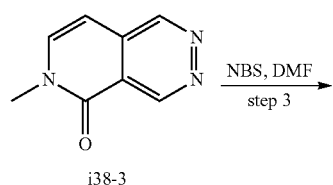

i38-3

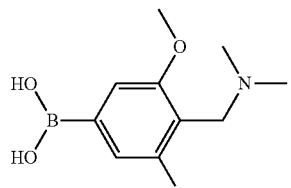

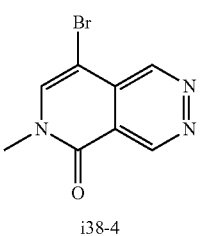

i38-4

Pd(dppf)Cl$_2$, Cs$_2$CO$_3$,
dioxane/H$_2$O, 90° C.
step 4

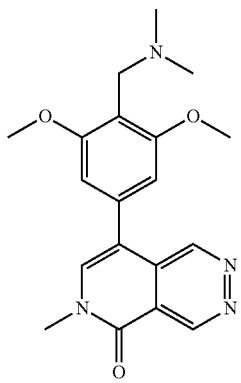

compound B52

Step 1: Preparation of ethyl 5-[(E)-2-(dimethylamino)ethenyl]pyridazine-4-carboxylate (i38-2)

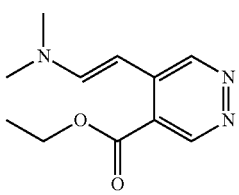

i38-2

A mixture of ethyl 5-methylpyridazine-4-carboxylate (200.0 mg, 1.20 mmol, 1.0 equiv) in (dimethoxymethyl)dimethylamine (5.00 mL) was stirred at 80 degrees C. for 3 hours. After completion of the reaction, the solvent was removed under reduced pressure to afford ethyl 5-[(E)-2-(dimethylamino)ethenyl]pyridazine-4-carboxylate (320 mg) as a black solid. The crude was not further purification and directly used in next step. LCMS (ESI) m/z: [M+H]$^+$=222.1.

191

Step 3: Preparation of
6-methylpyrido[3,4-d]pyridazin-5-one (i38-3)

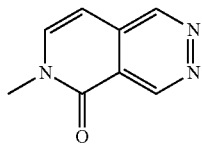

i38-3

To a stirred mixture of ethyl 5-[(E)-2-(dimethylamino)ethenyl]pyridazine-4-carboxylate (300.0 mg, 1.36 mmol, 1.0 equiv) in EtOH (5 mL) was added methanamine hydrochloride (915.48 mg, 1.56 mmol, 10.0 equiv). The reaction was stirred for 3 hours at 75 degrees C. After cooling, the solvent was removed under reduced pressure, and the residue was purified by silica gel column chromatography eluted with DCM/MeOH (20:1) to give 6-methylpyrido[3,4-d]pyridazin-5-one (200 mg, 91%) as a brown solid. LCMS (ESI) m/z: [M+H]$^+$=162.2.

Step 4: Preparation of 8-bromo-6-methylpyrido[3,4-d]pyridazin-5-one (i38-4)

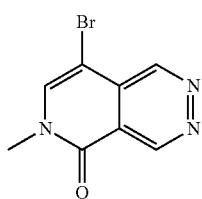

i38-4

To a stirred mixture of 6-methylpyrido[3,4-d]pyridazin-5-one (170.0 mg, 1.06 mmol, 1.0 equiv) in DMF (1 mL) was added NBS (226.42 mg, 1.27 mmol, 1.2 equiv). The reaction was stirred room temperature for 2 hours. The reaction mixture was diluted with EA (50 mL), washed with water (3×30 mL) and saturated brine (1×30 mL). The organic layer was dried over Na$_2$SO$_4$, filtered and evaporated to afford crude product. The residue was purified by silica gel column chromatography, eluted with DCM/MeOH (10:1) to afford 8-bromo-6-methylpyrido[3,4-d]pyridazin-5-one (82 mg, 32%) as a brown solid. LCMS (ESI) m/z: [M+H]$^+$=240.1.

192

Step 4: Preparation of 8-[4-[(dimethylamino)methyl]-3,5-dimethoxyphenyl]-6-methyl-5H,6H-pyrido[3,4-d]pyridazin-5-one (Compound B52)

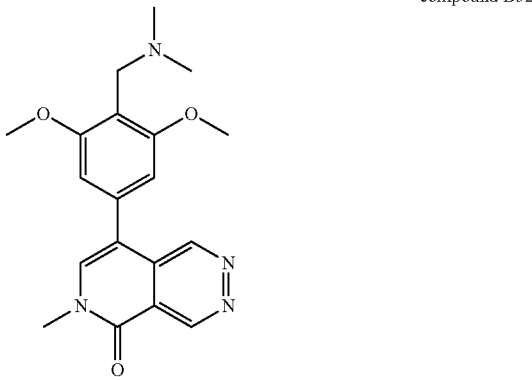

compound B52

To a solution of 8-bromo-6-methyl-5H,6H-pyrido[3,4-d]pyridazin-5-one (60.0 mg, 0.25 mmol, 1.0 equiv), [4-[(dimethylamino)methyl]-3,5-dimethoxyphenyl] boronic acid (59.76 mg, 0.25 mmol, 1.0 equiv), Cs$_2$CO$_3$ (162.87 mg, 0.5 mmol, 2.0 equiv) in dioxane (3 mL) and H$_2$O (0.8 mL) was added Pd(dppf)Cl$_2$ (18.29 mg, 0.025 mmol, 0.1 equiv). The resulting mixture was stirred at 90 degrees C. for 1 hour under nitrogen atmosphere. After cooling, the solvent was removed under reduced pressure. The residue was purified by chromatography on silica gel eluted with DCM/MeOH (20:1) to give the crude product. The crude product was further purified by Prep-HPLC (conditions: XBridge Shield RP18 OBD Column, 5 µm, 19*150 mm; Mobile Phase A: Water (10 mmol/L NH$_4$HCO$_3$), Mobile Phase B: ACN; Flow rate: 25 mL/minute; Gradient: 17% B to 47% B in 8 minutes; 220 nm; Rt: 7.8 minutes) to afford 8-[4-[(dimethylamino)methyl]-3,5-dimethoxyphenyl]-6-methyl-5H,6H-pyrido[3,4-d]pyridazin-5-one (17.3 mg, 19.5%) as an off-white solid. $^1$H NMR (300 MHz, DMSO-d6) δ 9.72 (d, J=1.4 Hz, 1H), 9.51 (d, J=1.4 Hz, 1H), 8.18 (s, 1H), 6.81 (s, 2H), 3.82 (s, 6H), 3.66 (s, 3H), 3.47 (s, 2H), 2.14 (s, 6H). LCMS (ESI) m/z: [M+H]$^+$=355.20.

Example 39—Preparation of 4-[3,5-dimethoxy-4-[(methylamino)methyl]phenyl]-2-methyl-1,2-dihydro-2,7-naphthyridin-1-one (Compound B53)

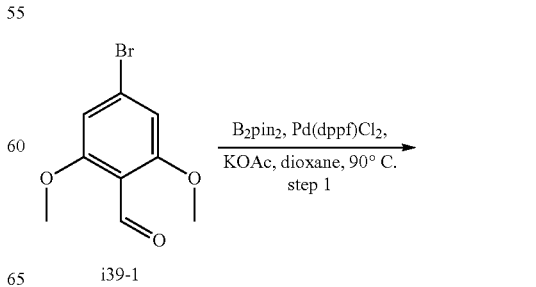

i39-1

-continued

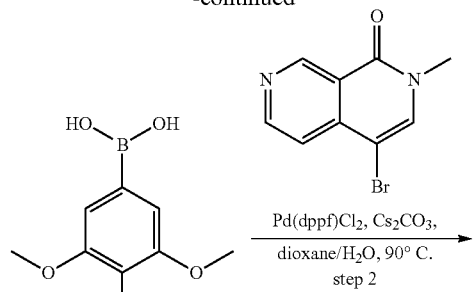

i39-2

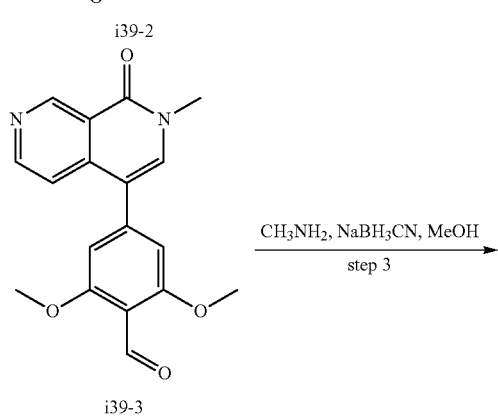

i39-3

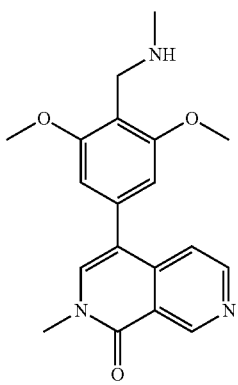

compound B53

Step 1: Preparation of (4-formyl-3,5-dimethoxyphenyl)boronic acid (i39-2)

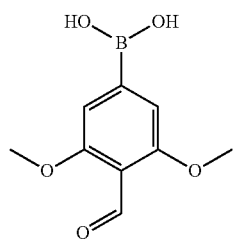

i39-2

To a solution of 4-bromo-2,6-dimethoxybenzaldehyde (4.00 g, 16.322 mmol, 1.00 equiv) and KOAc (4.81 g, 48.965 mmol, 3.00 equiv) in 1,4-dioxane (30.00 ml) was added Bis(pinacolato)diboron (4.97 g, 19.586 mmol, 1.20 equiv) and Pd(dppf)Cl$_2$·CH$_2$Cl$_2$ (1.33 g, 1.632 mmol, 0.10 equiv). The resulting solution was stirred for 3 hours at 90° C. The solids were filtered out. The resulting mixture was concentrated. This resulted in 2.5 g (72.94%) of (4-formyl-3,5-dimethoxyphenyl)boronic acid as a brown solid.

Step 2: Preparation of 2,6-dimethoxy-4-(2-methyl-1-oxo-1,2-dihydro-2,7-naphthyridin-4-yl)benzaldehyde (i39-3)

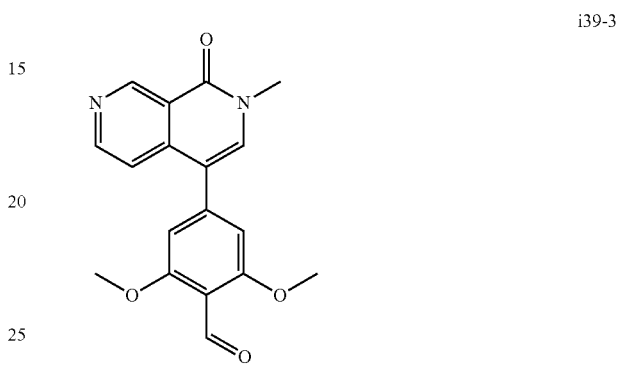

i39-3

To a solution of (4-formyl-3,5-dimethoxyphenyl)boronic acid (2.80 g, 13.334 mmol, 1.00 equiv), 4-bromo-2-methyl-1,2-dihydro-2,7-naphthyridin-1-one (4.78 g, 20.001 mmol, 1.50 equiv), and Cs$_2$CO$_3$ (13.03 g, 40.002 mmol, 3 equiv) in 1,4-dioxane (17.50 mL, 198.599 mmol, 15.49 equiv) was added Pd(dppf)Cl$_2$·CH$_2$Cl$_2$ (1.09 g, 1.333 mmol, 0.1 equiv) and H$_2$O (3.50 mL, 194.276 mmol, 14.57 equiv). The resulting solution was stirred for 2 hours at 80° C. The resulting solution was diluted with 20 mL of water. The resulting solution was extracted with ethyl acetate (2×20 mL) and the organic layers combined and dried over anhydrous sodium sulfate and concentrated. The residue was applied onto a silica gel column with dichloromethane/methanol (2:1). This resulted in 3 g (69.37%) of 2,6-dimethoxy-4-(2-methyl-1-oxo-1,2-dihydro-2,7-naphthyridin-4-yl)benzaldehyde as a yellow solid.

Step 3: Preparation of 4-[3,5-dimethoxy-4-[(methylamino)methyl]phenyl]-2-methyl-1,2-dihydro-2,7-naphthyridin-1-one (Compound B53)

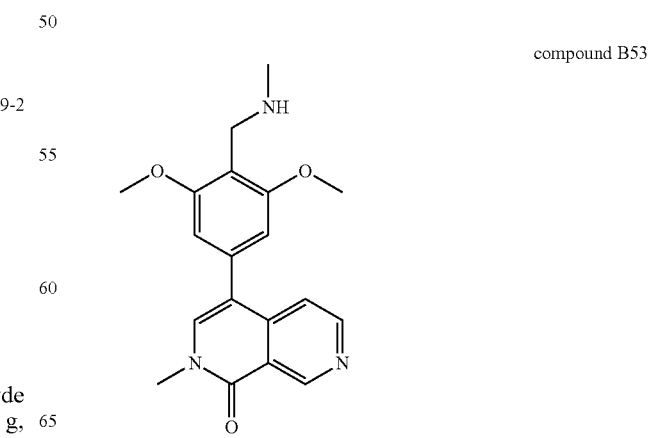

compound B53

To a solution of 2,6-dimethoxy-4-(2-methyl-1-oxo-1,2-dihydro-2,7-naphthyridin-4-yl)benzaldehyde (200.00 mg, 0.617 mmol, 1.00 equiv) in MeOH (5.00 mL) was added methylamine (28.73 mg, 0.925 mmol, 1.50 equiv) at 25° C. and the reaction mixture was stirred for 10 minutes. Then NaBH₃CN (116.25 mg, 1.850 mmol, 3.00 equiv) was added to the reaction mixture. The resulting solution was stirred for 1 hour at 25° C. The resulting mixture was concentrated. The crude product was purified by Prep-HPLC (conditions: XBridge Prep C18 OBD Column, 5 µm, 19*150 mm; mobile phase, Water (0.1% FA) and ACN (hold 5% Phase B in 2 minutes, up to 26% in 8 minutes); Detector, uv). This resulted in 70 mg (33.45%) of 4-[3,5-dimethoxy-4-[(methylamino)methyl]phenyl]-2-methyl-1,2-dihydro-2,7-naphthyridin-1-one as a white solid. $^1$H NMR (400 MHz, Methanol-d4) δ 9.55 (s, 1H), 8.69 (d, J=5.8 Hz, 1H), 8.54 (s, 1H), 7.78 (s, 1H), 7.61 (dd, J=5.7, 0.9 Hz, 1H), 6.87 (s, 2H), 4.33 (s, 2H), 3.97 (s, 6H), 3.72 (s, 3H), 2.74 (s, 3H). LCMS (ESI) m/z: [M+H]⁺=340.4.

Example 40—Preparation of 4-[4-[(dimethylamino)methyl]-3-methoxy-5-(methylsulfanyl)phenyl]-2-methyl-1,2-dihydro-2,7-naphthyridin-1-one (Compound B54)

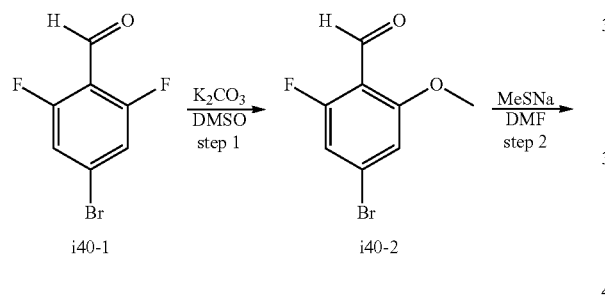

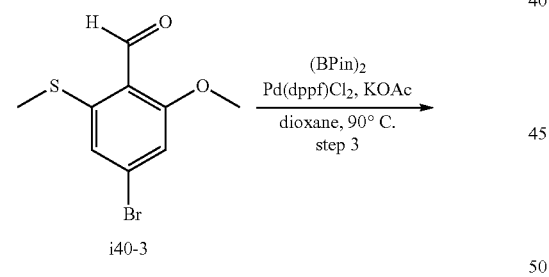

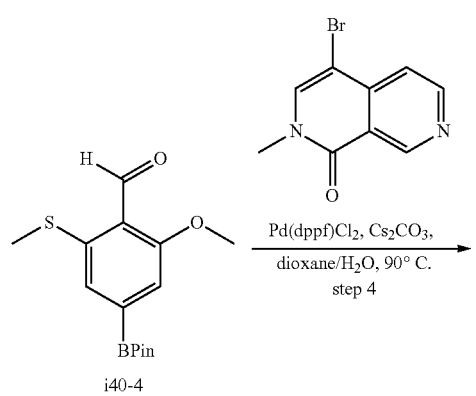

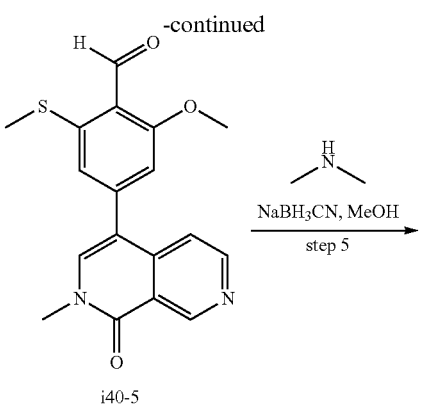

i40-5

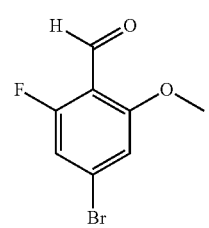

compound B54

Step 1: Preparation of 4-bromo-2-fluoro-6-methoxybenzaldehyde (i40-2)

i40-2

To the solution of 4-bromo-2,6-difluorobenzaldehyde (5.00 g, 22.624 mmol, 1.00 equiv) in MeOH (43.00 mL) was added sodium methoxide (1.83 g, 33.936 mmol, 1.5 equiv). The resulting solution was stirred at 65° C. for 12 hours. The resulting solution was concentrated. The residue was purified by silica gel column chromatography, eluted with PE/EtOAc (1:1) to afford 4-bromo-2-fluoro-6-methoxybenzaldehyde (2.87 g, 54.44%) as a light yellow solid. LCMS (ESI) m/z: [M+H]+=233.

Step 2: Preparation of 4-bromo-2-methoxy-6-(methylsulfanyl)benzaldehyde (i40-3)

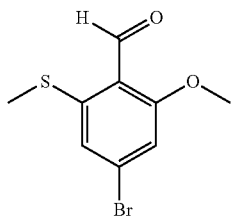

i40-3

To the solution of 4-bromo-2-fluoro-6-methoxybenzaldehyde (1.00 g, 4.291 mmol, 1.00 equiv) in DMSO (20.00 mL) was added (methylsulfanyl)sodium (0.45 g, 6.437 mmol, 1.50 equiv). The resulting solution was stirred at room temperature for 12 hours. The reaction was quenched with water at room temperature. The resulting mixture was extracted with EtOAc (3×75 mL). The combined organic layers were washed with water (3×75 mL) and dried over anhydrous $Na_2SO_4$. After filtration, the filtrate was concentrated under reduced pressure. The residue was purified by silica gel column chromatography, eluted with PE/EtOAc (1:1) to afford 4-bromo-2-methoxy-6-(methylsulfanyl)benzaldehyde (988 mg, 88.17%) as a light yellow solid. LCMS (ESI) m/z: [M+H]+=261.

Step 3: Preparation of 2-methoxy-6-(methylsulfanyl)-4-(4,4,5,5-tetramethyl-1,3,2-dioxaborolan-2-yl)benzaldehyde (i40-4)

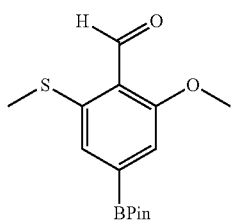

i40-4

To the solution of 4-bromo-2-methoxy-6-(methylsulfanyl)benzaldehyde (400.00 mg, 1.532 mmol, 1.00 equiv) in dioxane (15.00 mL) was added KOAc (451.00 mg, 4.595 mmol, 3 equiv), Pd(dppf)Cl$_2$ (112.08 mg, 0.153 mmol, 0.1 equiv), and 4,4,4',4',5,5,5',5'-octamethyl-2,2'-bi-1,3,2-dioxaborolane. The resulting solution was stirred at 90° C. for 6 hours under nitrogen atmosphere. The resulting mixture was filtered, the filter cake was washed with EtOAc (3×15 mL). The filtrate was concentrated under reduced pressure. This resulted in crude 2-methoxy-6-(methylsulfanyl)-4-(4,4,5,5-tetramethyl-1,3,2-dioxaborolan-2-yl)benzaldehyde (300 mg, 63.55%) as a light yellow oil, that was used directly without further purification. LCMS (ESI) m/z: [M+H]+=309.

Step 4: Preparation of 2-methoxy-4-(2-methyl-1-oxo-2,7-naphthyridin-4-yl)-6-methylsulfanyl)benzaldehyde (i40-5)

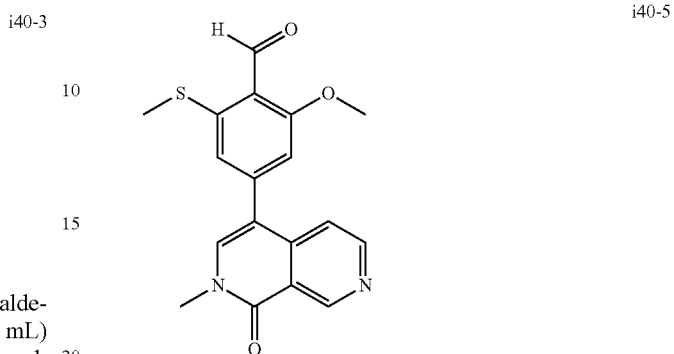

i40-5

To the solution of 4-bromo-2-methyl-2,7-naphthyridin-1-one (442.15 mg, 1.849 mmol, 1.2 equiv) and 2-methoxy-6-(methylsulfanyl)-4-(4,4,5,5-tetramethyl-1,3,2-dioxaborolan-2-yl)benzaldehyde in dioxane (15.00 mL) was added H$_2$O (1.50 mL), Pd(dppf)Cl$_2$ (112.77 mg, 0.154 mmol, 0.1 equiv), and Cs$_2$CO$_3$ (1.51 g, 4.624 mmol, 3 equiv). The resulting solution was stirred at 90° C. for 3 hours. The crude was concentrated under reduced pressure. The residue was purified by silica gel column chromatography, eluted with CH$_2$Cl$_2$/MeOH (10:1) to afford 2-methoxy-4-(2-methyl-1-oxo-2,7-naphthyridin-4-yl)-6-(methylsulfanyl)benz aldehyde (70 mg, 13.34%) as a light yellow solid. LCMS (ESI) m/z: [M+H]+=341.

Step 5: Preparation of 4-[4-[(dimethylamino)methyl]-3-methoxy-5-(methylsulfanyl)phenyl]-2-methyl-1,2-dihydro-2,7-naphthyridin-1-one (Compound B54)

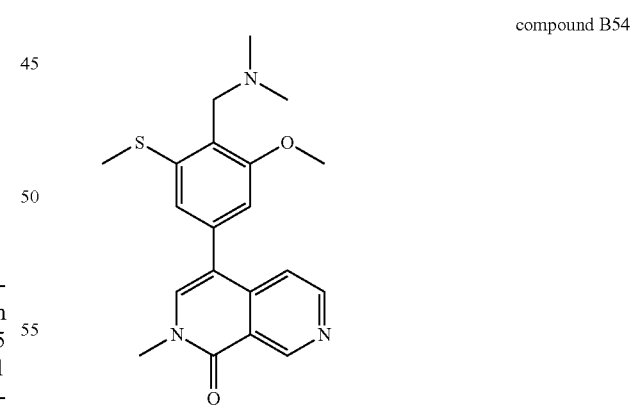

compound B54

To the solution of 2-methoxy-4-(2-methyl-1-oxo-1,2-dihydro-2,7-naphthyridin-4-yl)-6-(methylsulfanyl)benzaldehyde (70 mg, 0.206 mmol, 1 equiv) in MeOH (2 mL) was added dimethylamine (13.91 mg, 0.308 mmol, 1.5 equiv) and NaBH$_3$CN (38.77 mg, 0.617 mmol, 3 equiv). The resulting solution was stirred at room temperature for 1 hour. The resulting solution was concentrated. The crude product was purified by Prep-HPLC (conditions: SunFire C18 OBD Prep Column, 100 mm, 5 μm, 19 mm×250 mm; Mobile Phase A: Water (0.1% FA), Mobile Phase B: ACN; Flow rate: 25 mL/minute; Gradient: 9% B to 15% B in 8 minutes; 254 nm; Rt: 8.68 minutes) to afford 4-[4-[(dimethylamino)methyl]-3-methoxy-5-(methylsulfanyl)phenyl]-2-methyl-1,2-dihydro-2,7-naphthyridin-1-one as a white solid. $^1$H NMR (300 MHz, MeOD) δ 9.54 (d, 1H), 8.69 (d, 1H), 7.75 (s, 1H), 7.60 (dd, 1H), 7.02 (d, 1H), 6.92 (d, 1H), 3.89 (s, 3H), 3.73 (d, 5H), 2.51 (s, 3H), 2.34 (s, 6H). LCMS (ESI) m/z: [M+H]+=370.20.

Example 41—Preparation of (2R)-1-[[2,6-dimethoxy-4-(2-methyl-1-oxo-1,2-dihydro-2,7-naphthyridin-4-yl)phenyl]methyl]-N-methylazetidine-2-carboxamide (Compound B55)

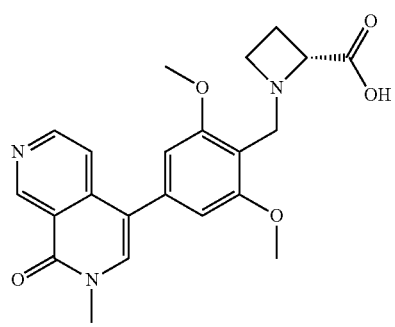

compound B46

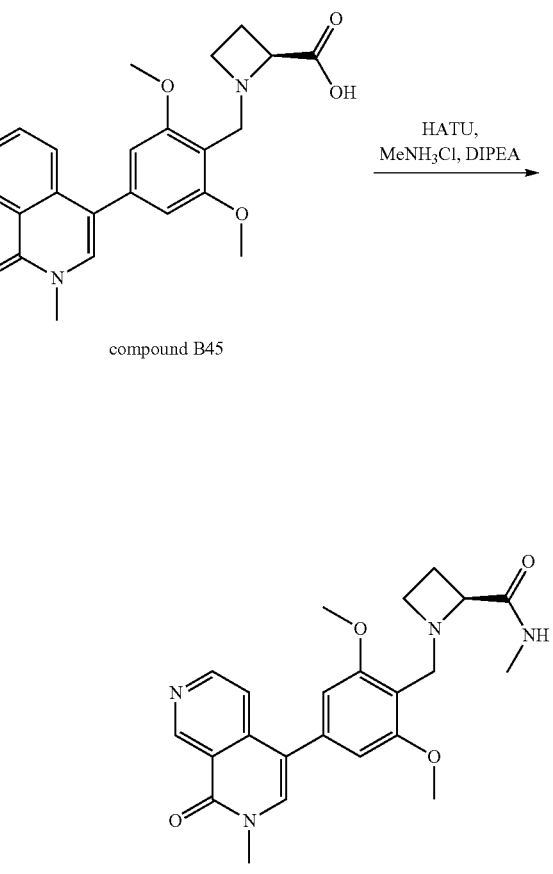

compound B55

To a stirred solution of (2R)-1-[[2,6-dimethoxy-4-(2-methyl-1-oxo-1,2-dihydro-2,7-naphthyridin-4-yl)phenyl]methyl]azetidine-2-carboxylic acid (40.9 mg, 0.100 mmol, 1.00 equiv) and DIPEA (64.6 mg, 0.499 mmol, 5.00 equiv) in DMF (0.5 mL) was added HATU (76 mg, 0.200 mmol, 2.00 equiv) and methylamine (12.4 mg, 0.400 mmol, 4 equiv). The solution was stirred for 2 hours at room temperature. The resulting mixture was purified directly by Prep-HPLC (conditions: XBridge Shield RP18 OBD Column, 5 μm, 19*150 mm; Mobile Phase A: Water (0.05% NH$_3$H$_2$O), Mobile Phase B: ACN; Flow rate: 25 mL/minute; Gradient: 45% B to 75% B in 8 minutes; 220 nm; Rt: 8.2 minutes) to afford (2R)-1-[[2,6-dimethoxy-4-(2-methyl-1-oxo-1,2-dihydro-2,7-naphthyridin-4-yl)phenyl]methyl]-N-methylazetidine-2-carboxamide (6 mg) as a white solid. $^1$H NMR (300 MHz, Methanol-d4) δ 9.53 (s, 1H), 8.69 (d, J=5.8 Hz, 1H), 7.74 (s, 1H), 7.61 (dd, J=5.8, 0.9 Hz, 1H), 6.75 (s, 2H), 3.89 (s, 6H), 3.94-3.80 (m, 1H), 3.78-3.66 (m, 1H), 3.72 (s, 4H), 3.31-3.14 (m, 2H), 2.76 (s, 3H), 2.31-2.20 (m, 1H), 2.07-1.89 (m, 1H). LCMS (ESI) m/z: [M+H]+=423.15.

Example 42—Preparation of (2S)-1-[[2,6-dimethoxy-4-(2-methyl-1-oxo-2,7-naphthyridin-4-yl)phenyl]methyl]-N-methylazetidine-2-carboxamide (Compound B56)

compound B45 compound B56

To a solution of (2S)-1-[[2,6-dimethoxy-4-(2-methyl-1-oxo-2,7-naphthyridin-4-yl)phenyl]methyl] azetidine-2-carboxylic acid (40 mg, 0.098 mmol, 1.00 equiv) in DMF (2.00 mL) was added methylamine hydrochloride (7.92 mg, 0.117 mmol, 1.20 equiv), HATU (74.29 mg, 0.195 mmol, 2.00 equiv), and DIEA (37.88 mg, 0.293 mmol, 3.00 equiv) at 0° C. The resulting solution was stirred for 2 hours at 25° C. The resulting solution was diluted with 10 mL of water. The resulting solution was extracted with ethyl acetate (2×20 mL) and the organic layers combined and dried over anhydrous sodium sulfate and concentrated. The crude product was purified by Prep-HPLC (conditions: Atlantis HILIC OBD Column, 19 mm×250 mm; mobile phase, Water (0.1% FA) and ACN (hold 5% Phase B in 2 minutes, up to 17% in 8 minutes); Detector, uv). This resulted in 30 mg (72.68%) (2S)-1-[[2,6-dimethoxy-4-(2-methyl-1-oxo-2,7-naphthyridin-4-yl)phenyl]methyl]-N-methylazetidine-2-carboxamide as a yellow solid. $^1$H NMR (400 MHz, Methanol-d4) δ 9.59 (s, 1H), 8.71 (d, J=6.1 Hz, 1H), 7.93 (s, 1H), 7.77 (dd, J=6.1, 0.8 Hz, 1H), 6.86 (s, 2H), 5.01 (t, J=9.3 Hz, 1H), 4.51 (d, J=1.6 Hz, 2H), 4.20 (q, J=9.6 Hz, 1H), 4.03 (t, J=9.4 Hz, 1H), 3.98 (s, 6H), 3.74 (s, 3H), 2.78 (s, 3H), 2.74-2.61 (m, 1H), 2.61-2.46 (m, 1H). LCMS (ESI) m/z: [M+H]$^+$=423.20.

Example 43—Preparation of 1-(6-[4-[(dimethylamino)methyl]-3,5-dimethoxyphenyl]-3-methyl-[1,2,4]triazolo[4,3-a]pyridin-8-yl)-3,3-dimethylurea (Compound B57)

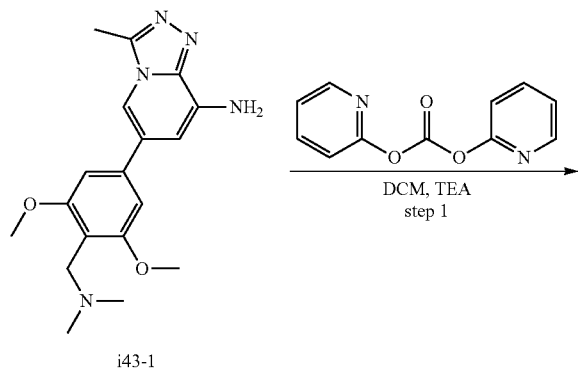

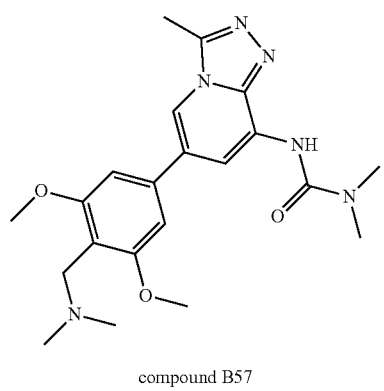

Step 1: Preparation of [(4-[8-isocyanato-3-methyl-[1,2,4]triazolo[4,3-a]pyridin-6-yl]-2,6-dimethoxyphenyl) methyl]dimethylamine (i43-2)

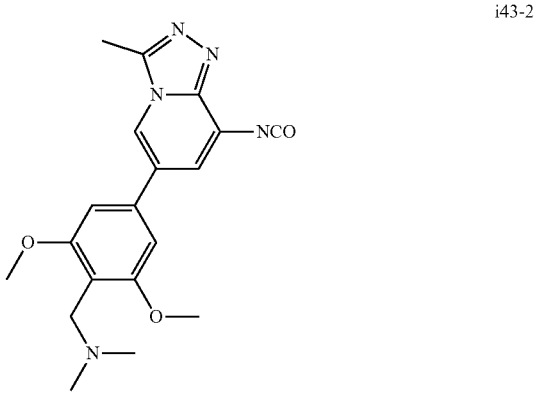

To a solution of 6-[4-[(dimethylamino)methyl]-3,5-dimethoxyphenyl]-3-methyl-[1,2,4]triazolo[4,3-a]pyridin-8-amine (50.00 mg, 0.146 mmol, 1.00 equiv) and TEA (44.46 mg, 0.439 mmol, 3.00 equiv) in DCM (5.00 mL) was added bis(pyridin-2-yl) carbonate (31.66 mg, 0.146 mmol, 1.00 equiv) at 25° C. The resulting solution was stirred for 1 overnight at 25° C. The resulting mixture was concentrated. This resulted in 30 mg (55.76%) of [(4-[8-isocyanato-3-methyl-[1,2,4]triazolo[4,3-a]pyridin-6-yl]-2,6-dimethoxyphenyl)methyl]dimethylamine as a brown crude solid.

Step 2: Preparation of 1-(6-[4-[(dimethylamino)methyl]-3,5-dimethoxyphenyl]-3-methyl-[1,2,4]triazolo[4,3-a]pyridin-8-yl)-3,3-dimethylurea (Compound B57)

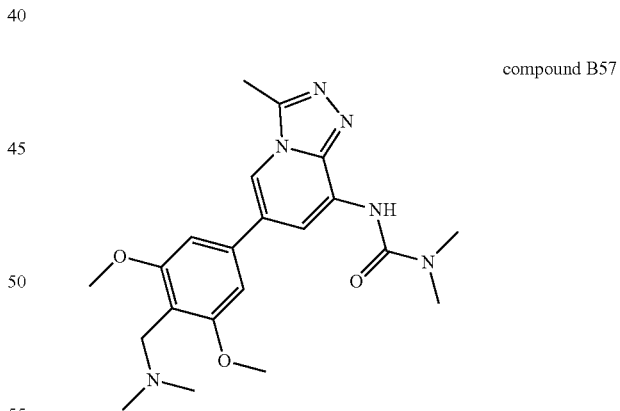

To a solution of [(4-[8-isocyanato-3-methyl-[1,2,4]triazolo[4,3-a]pyridin-6-yl]-2,6-dimethoxyphenyl) methyl]dimethylamine (20.00 mg, 0.054 mmol, 1.00 equiv) in THF (5.00 mL) was added dimethylamine (2.45 mg, 0.054 mmol, 1.00 equiv) and NaH (3.92 mg, 0.163 mmol, 3.00 equiv). The resulting solution was stirred for 2 hours at 25° C. The reaction was then quenched by the addition of 2 mL of MeOH. The resulting mixture was concentrated. The crude product was purified by Prep-HPLC (conditions: XSelect CSH Prep C18 OBD Column, 19*250 mm, 5 μm; mobile phase, Water (0.1% FA) and ACN (hold 5% Phase B in 2 minutes, up to 22% in 6 minutes); Detector, UV). This resulted in 2 mg (8.91%) of 1-(6-[4-[(dimethylamino)methyl]-3,5-dimethoxyphenyl]-3-methyl-[1,2,4]triazolo[4,3-a]pyridin-8-yl)-3,3-dimethylurea as a brown solid. $^1$H NMR (400 MHz, Methanol-d4) δ 8.56 (s, 1.3H, FA), 8.29 (d, J=1.4 Hz, 1H), 8.23 (d, J=1.4 Hz, 1H), 7.08 (s, 2H), 4.23 (s, 2H), 4.03 (s, 6H), 3.18 (s, 6H), 2.86 (s, 3H), 2.75 (s, 6H). LCMS (ESI) m/z: [M+H]$^+$=413.30.

Example 44—Preparation Preparation of 1-(6-[4-[(dimethylamino)methyl]-3,5-dimethoxyphenyl]-[1,2,4]triazolo[4,3-a]pyridin-8-yl)-3,3-dimethylurea (Compound B58)

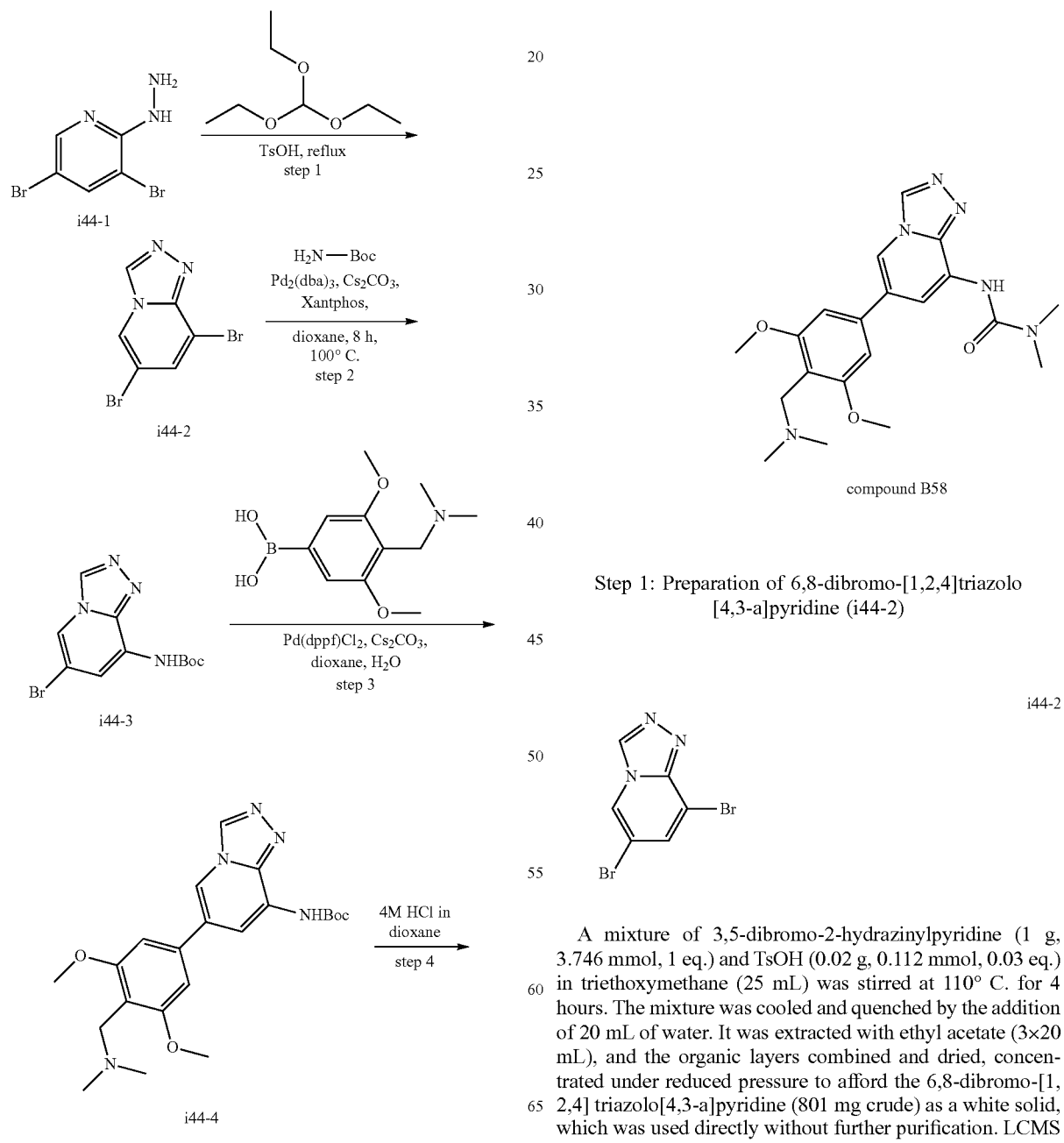

Step 1: Preparation of 6,8-dibromo-[1,2,4]triazolo[4,3-a]pyridine (i44-2)

A mixture of 3,5-dibromo-2-hydrazinylpyridine (1 g, 3.746 mmol, 1 eq.) and TsOH (0.02 g, 0.112 mmol, 0.03 eq.) in triethoxymethane (25 mL) was stirred at 110° C. for 4 hours. The mixture was cooled and quenched by the addition of 20 mL of water. It was extracted with ethyl acetate (3×20 mL), and the organic layers combined and dried, concentrated under reduced pressure to afford the 6,8-dibromo-[1,2,4]triazolo[4,3-a]pyridine (801 mg crude) as a white solid, which was used directly without further purification. LCMS (ESI) m/z: [M+H]+=277.

Step 2: Preparation of tert-butyl N-[6-bromo-[1,2,4]triazolo[4,3-a]pyridin-8-yl]carbamate (i44-3)

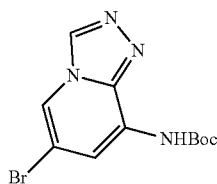

i44-3

To a solution of 6,8-dibromo-[1,2,4]triazolo[4,3-a]pyridine (800 mg, 2.889 mmol, 1 eq.) and tert-butyl carbamate (507.65 mg, 4.333 mmol, 1.5 eq.) in dioxane (16 mL) was added Pd$_2$(dba)$_3$ (132.27 mg, 0.144 mmol, 0.05 eq.), Cs$_2$CO$_3$ (1882.54 mg, 5.778 mmol, 2.0 eq.), and XantPhos (250.74 mg, 0.433 mmol, 0.15 eq.). The resulting solution was stirred for 8 hours at 100° C. under a nitrogen atmosphere. The reaction was then quenched by the addition of 20 mL of water and extracted with ethyl acetate (3×30 mL), and the organic layers were combined and dried over anhydrous sodium sulfate. The residue was applied onto a silica gel column with dichloromethane/methanol (10:1) to afford tert-butyl (6-bromo-[1,2,4]triazolo[4,3-a] pyridin-8-yl)carbamate (400 mg, 44.0%) as a gray solid. LCMS (ESI) m/z: [M+H]+=315.

Step 3: Preparation of tert-butyl N-(6-[4-[(dimethylamino)methyl]-3,5-dimethoxyphenyl]-[1,2,4]triazolo[4,3-a] pyridin-8-yl) carbamate (i44-4)

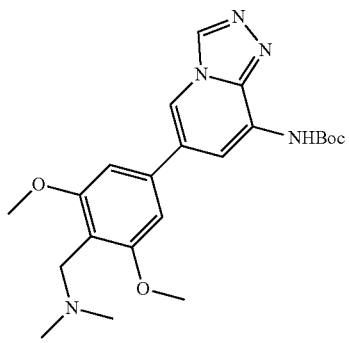

i44-4

To a solution of tert-butyl (6-bromo-[1,2,4]triazolo[4,3-a]pyridin-8-yl)carbamate (400 mg, 1.277 mmol, 1 eq.) and [4-[(dimethylamino)methyl]-3,5-dimethoxyphenyl]boronic acid (244.31 mg, 1.022 mmol, 0.8 eq.) in H$_2$O (2.00 mL) and dioxane (8.00 mL) was added PdCl$_2$(dppf) (93.46 mg, 0.128 mmol, 0.1 eq.) and Cs$_2$CO$_3$ (832.35 mg, 2.555 mmol, 2.0 eq.). The resulting solution was stirred for 13 hours at 80° C. under a nitrogen atmosphere. The reaction was cooled and then quenched by the addition of 20 mL of water and extracted with ethyl acetate (3×20 mL). The organic layer was dried over anhydrous sodium sulfate and concentrated. The residue was applied onto a silica gel column with dichloromethane/methanol (5:1) to afford tert-butyl (6-(4-((dimethylamino)methyl)-3,5-dimethoxyphenyl)-[1,2,4]triazolo[4,3-a]pyridin-8-yl)carbamate (216 mg, 16.8%) as a gray solid. LCMS (ESI) m/z: [M+H]+=428.

Step 4: Preparation of 6-[4-[(dimethylamino)methyl]-3,5-dimethoxyphenyl]-[1,2,4]triazolo[4,3-a]pyridin-8-amine (i44-5)

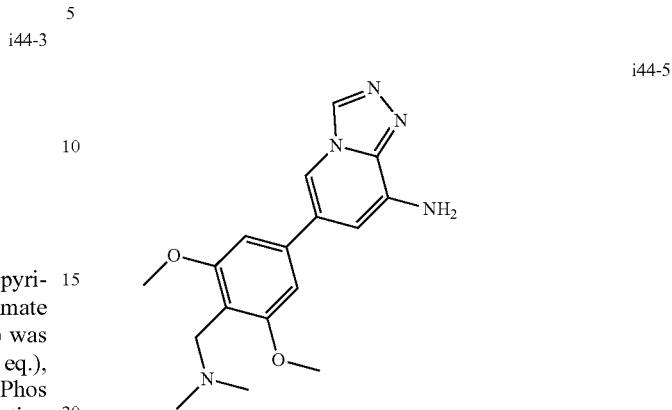

i44-5

A solution of tert-butyl (6-(4-((dimethylamino)methyl)-3,5-dimethoxyphenyl)-[1,2,4]triazolo[4,3-a]pyridin-8-yl)carbamate (216 mg, 1 equiv) in HCl (4 M) in 1,4-dioxane (8 mL) was stirred for 4 hours at room temperature. The resulting mixture was concentrated to afford 6-[4-[(dimethylamino)methyl]-3,5-dimethoxyphenyl]-[1,2,4]triazolo[4,3-a]pyridin-8-amine (120 mg, 73.7%) as a gray solid, which was used directly without further purification. LCMS (ESI) m/z: [M+H]+=328.

Step 5: Preparation of 1-(6-[4-[(dimethylamino)methyl]-3,5-dimethoxyphenyl]-[1,2,4]triazolo[4,3-a]pyridin-8-yl)-3,3-dimethylurea (Compound B58)

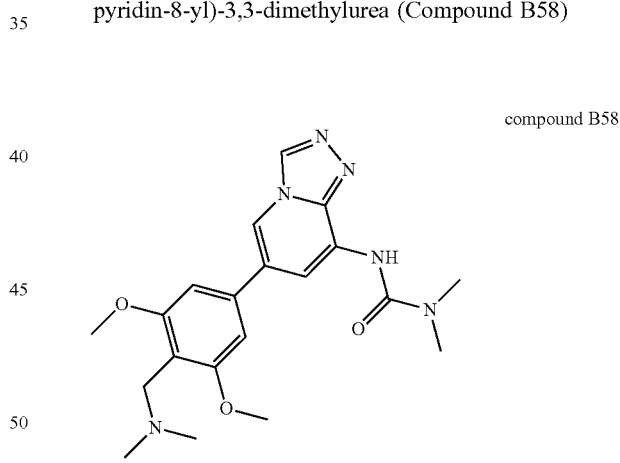

compound B58

To a solution of 6-[4-[(dimethylamino)methyl]-3,5-dimethoxyphenyl]-[1,2,4]triazolo[4,3-a]pyridin-8-amine (120 mg, 0.367 mmol, 1 equiv) in pyridine (5 mL, 62.118 mmol, 169.47 equiv) was added dimethylcarbamic chloride (78.83 mg, 0.733 mmol, 2.0 equiv) The resulting solution was stirred for 2 hours at 80° C. The mixture was cooled and concentrated, the crude product was purified by Prep-HPLC (conditions: Atlantis HILIC OBD Column 19*150 mm*5 μm; mobile phase, Phase A: Water (0.05% TFA) Phase B: MeOH-HPLC; Detector, uv: 254/220 nm). This resulted in 14 mg (9.59%) of 1-(6-[4-[(dimethylamino)methyl]-3,5-dimethoxyphenyl]-[1,2,4]triazolo[4,3-a]pyridine-8-yl)-3,3-dimethylurea as a grey solid. $^1$H NMR (400 MHz, Methanol-d4) δ 8.75 (d, J=2.0 Hz, 1H), 8.49 (s, 1H), 8.42 (d, J=2.0 Hz, 1H), 7.09 (s, 2H), 4.42 (s, 2H), 4.05 (s, 6H), 3.23 (q, J=7.3 Hz, 1H), 3.13 (s, 6H), 2.91 (s, 6H). LCMS (ESI) m/z: [M+H]⁺=399.1.

Example 45—Preparation of 4-[4-[(dimethylamino)methyl]-3,5-dimethoxyphenyl]-N,2-dimethyl-1-oxoisoquinoline-7-carboxamide (Compound B59)

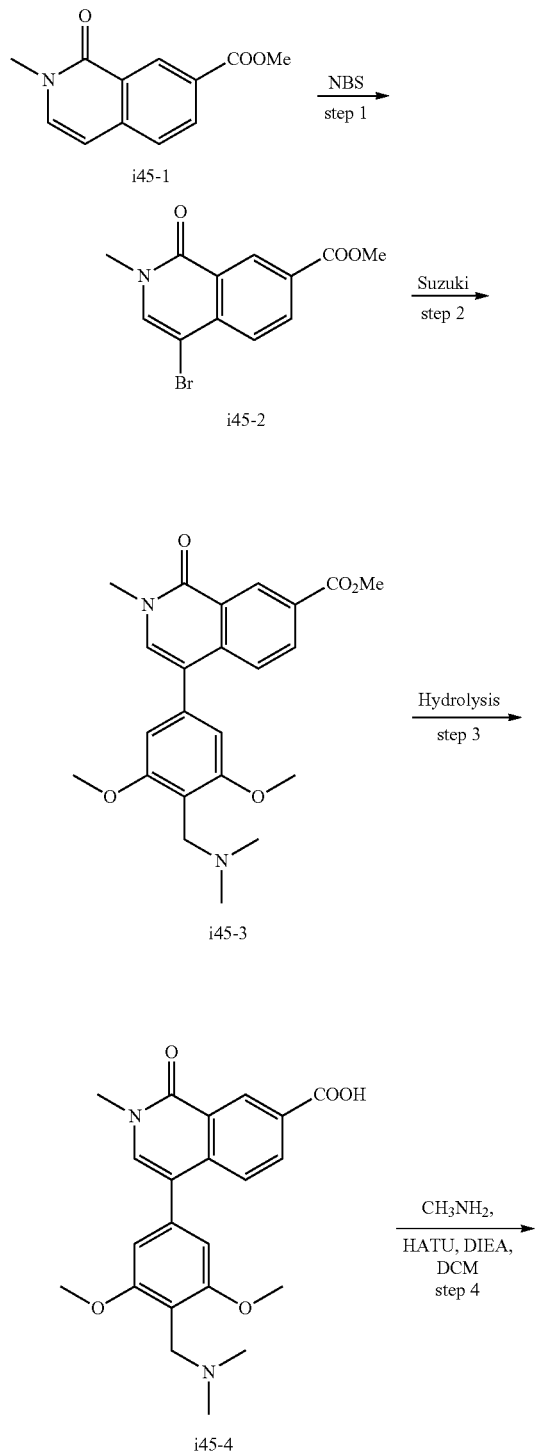

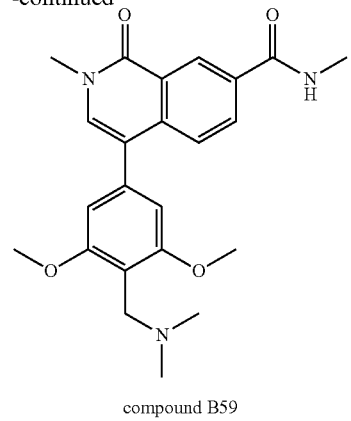

compound B59

Step 1: Preparation of methyl 4-bromo-2-methyl-1-oxoisoquinoline-7-carboxylate (i45-2)

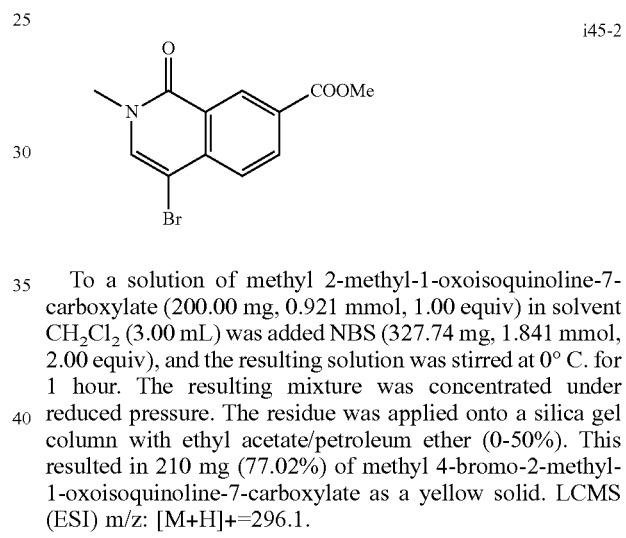

To a solution of methyl 2-methyl-1-oxoisoquinoline-7-carboxylate (200.00 mg, 0.921 mmol, 1.00 equiv) in solvent CH₂Cl₂ (3.00 mL) was added NBS (327.74 mg, 1.841 mmol, 2.00 equiv), and the resulting solution was stirred at 0° C. for 1 hour. The resulting mixture was concentrated under reduced pressure. The residue was applied onto a silica gel column with ethyl acetate/petroleum ether (0-50%). This resulted in 210 mg (77.02%) of methyl 4-bromo-2-methyl-1-oxoisoquinoline-7-carboxylate as a yellow solid. LCMS (ESI) m/z: [M+H]+=296.1.

Step 2: Preparation of methyl 4-[4-[(dimethylamino)methyl]-3,5-dimethoxyphenyl]-2-methyl-1-oxoisoquinoline-7-carboxylate (i45-3)

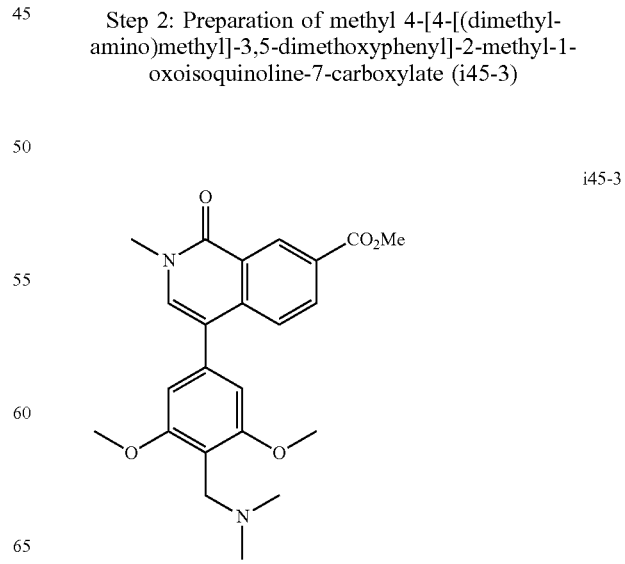

To a solution of methyl 4-bromo-2-methyl-1-oxoisoquinoline-7-carboxylate (210.00 mg, 0.709 mmol, 1.00 equiv), 4-[(dimethylamino)methyl]-3,5-dimethoxyphenylboronic acid (203.46 mg, 0.851 mmol, 1.20 equiv), and $Cs_2CO_3$ (693.19 mg, 2.128 mmol, 3.00 equiv) in 1,4-dioxane (3.00 mL) was added Pd(dppf)Cl$_2$ (51.89 mg, 0.071 mmol, 0.10 equiv) and H$_2$O (1.00 mL) at 25° C. The resulting solution was stirred for 2 hours at 80° C. The resulting solution was diluted with 10 mL of water. The resulting solution was extracted with ethyl acetate (2×20 mL) and the organic layers combined and dried over anhydrous sodium sulfate and concentrated. The residue was applied onto a silica gel column with ethyl acetate/petroleum ether (0-100%). This resulted in 195 mg (66.99%) of methyl 4-[4-[(dimethylamino)methyl]-3,5-dimethoxyphenyl]-2-methyl-1-oxoisoquinoline-7-carboxylate as a yellow solid. LCMS (ESI) m/z: [M+H]+=411.2.

Step 3: Preparation of 4-[4-[(dimethylamino)methyl]-3,5-dimethoxyphenyl]-2-methyl-1-oxoisoquinoline-7-carboxylic acid (i45-4)

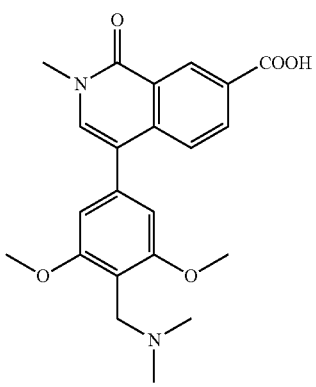

i45-4

To a solution of methyl methyl 4-[4-[(dimethylamino)methyl]-3,5-dimethoxyphenyl]-2-methyl-1-oxoisoquinoline-7-carboxylate (195.00 mg, 0.475 mmol, 1.00 equiv) in Hydrochloric acid 37% solution in water (3.00 mL) at 25° C. The resulting solution was stirred for 2 hours at 90° C. The resulting mixture was concentrated under vacuum. This resulted in 185 mg (98.23%) of 4-[4-[(dimethylamino)methyl]-3,5-dimethoxyphenyl]-2-methyl-1-oxoisoquinoline-7-carboxylic acid as a yellow solid, that was used directly without further purification. LCMS (ESI) m/z: [M+H]+=397.1.

Step 4: Preparation of 4-[4-[(dimethylamino)methyl]-3,5-dimethoxyphenyl]-N,2-dimethyl-1-oxoisoquinoline-7-carboxamide (Compound B59)

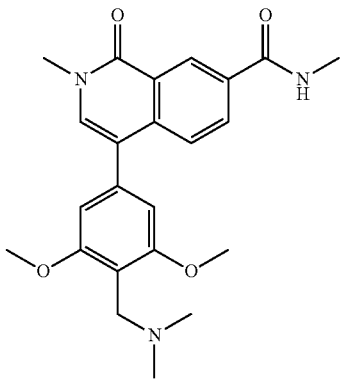

compound B59

To a solution of 4-[4-[(dimethylamino)methyl]-3,5-dimethoxyphenyl]-2-methyl-1-oxoisoquinoline-7-carboxylic acid (180 mg, 0.454 mmol, 1.00 equiv) in CH$_2$Cl$_2$ (3.00 mL) was added HATU (345.28 mg, 0.908 mmol, 2.00 equiv). After that, CH$_3$NH$_2$ (28.20 mg, 0.908 mmol, 2.00 equiv) and DIEA (293.41 mg, 2.270 mmol, 5.00 equiv) was added at 0° C. The resulting solution was stirred for 2 hours at 25° C. The resulting solution was diluted with 10 mL of water and extracted with ethyl acetate (2×20 mL) and the organic layers combined and dried over anhydrous sodium sulfate and concentrated. The crude product was purified by Prep-HPLC (conditions: Atlantis HILIC OBD Column, 19 mm×250 mm; mobile phase, Water (0.1% FA) and ACN (hold 5% Phase B in 2 minutes, up to 17% in 8 minutes); Detector, uv). This resulted in 150 mg (80.65%) 4-[4-[(dimethylamino)methyl]-3,5-dimethoxyphenyl]-N,2-dimethyl-1-oxoisoquinoline-7-carboxamide as a yellow solid. $^1$H NMR (400 MHz, Methanol-d4) δ 8.89 (d, J=2.0 Hz, 1H), 8.12 (dd, J=8.6, 2.1 Hz, 1H), 7.75 (d, J=8.6 Hz, 1H), 7.57 (s, 1H), 6.88 (s, 2H), 4.44 (s, 2H), 3.97 (s, 6H), 3.71 (s, 3H), 2.98 (s, 3H), 2.93 (s, 6H). LCMS (ESI) m/z: [M+H]+=410.30.

Example 46—Preparation of N-(6-[4-[(dimethylamino)methyl]-3,5-dimethoxyphenyl]-3-methyl-[1,2,4]triazolo[4,3-a]pyridin-8-yl)acetamide (Compound B60)

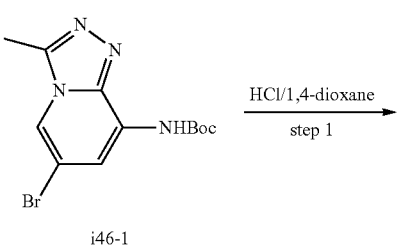

i46-1

Step 2: Preparation of N-[6-bromo-3-methyl-[1,2,4]triazolo[4,3-a]pyridin-8-yl]acetamide (i46-3)

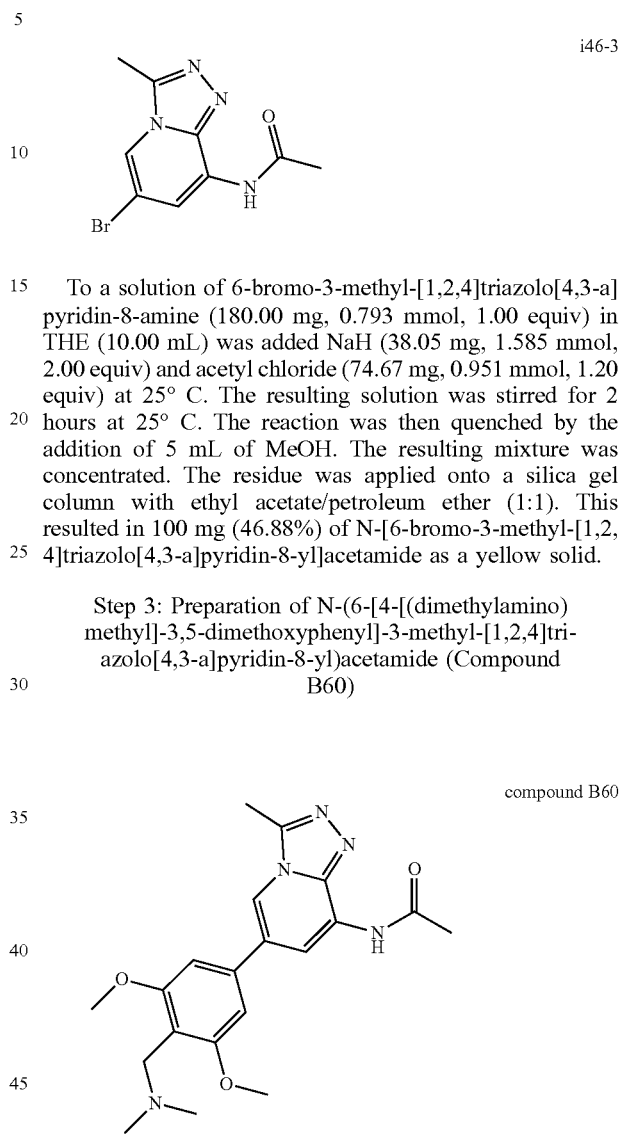

To a solution of 6-bromo-3-methyl-[1,2,4]triazolo[4,3-a]pyridin-8-amine (180.00 mg, 0.793 mmol, 1.00 equiv) in THF (10.00 mL) was added NaH (38.05 mg, 1.585 mmol, 2.00 equiv) and acetyl chloride (74.67 mg, 0.951 mmol, 1.20 equiv) at 25° C. The resulting solution was stirred for 2 hours at 25° C. The reaction was then quenched by the addition of 5 mL of MeOH. The resulting mixture was concentrated. The residue was applied onto a silica gel column with ethyl acetate/petroleum ether (1:1). This resulted in 100 mg (46.88%) of N-[6-bromo-3-methyl-[1,2,4]triazolo[4,3-a]pyridin-8-yl]acetamide as a yellow solid.

Step 3: Preparation of N-(6-[4-[(dimethylamino)methyl]-3,5-dimethoxyphenyl]-3-methyl-[1,2,4]triazolo[4,3-a]pyridin-8-yl)acetamide (Compound B60)

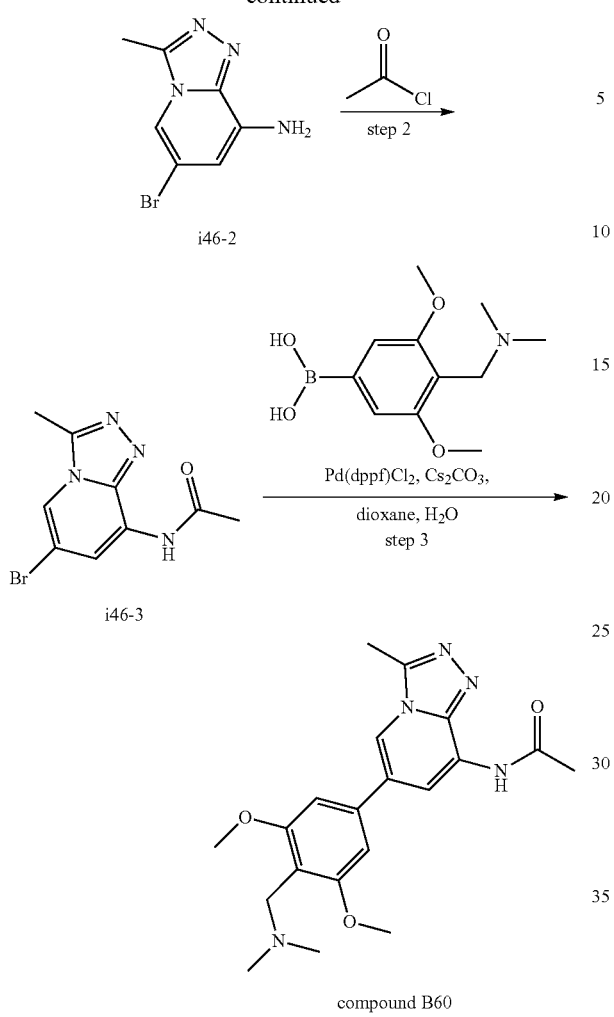

compound B60

Step 1: Preparation of 6-bromo-3-methyl-[1,2,4]triazolo[4,3-a]pyridin-8-amine (i46-2)

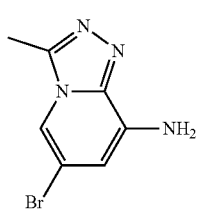

Into a 50-mL round-bottom flask, was placed tert-butyl N-[6-bromo-3-methyl-[1,2,4]triazolo[4,3-a]pyridin-8-yl]carbamate (300.00 mg, 0.917 mmol, 1.00 equiv), HCl (gas) in 1,4-dioxane (7.50 mL, 205.696 mmol, 269.20 equiv). The resulting solution was stirred for 2 hours at 25° C. The resulting mixture was concentrated. This resulted in 180 mg (86.46%) of 6-bromo-3-methyl-[1,2,4]triazolo[4,3-a]pyridin-8-amine as a white solid.

To a solution of N-[6-bromo-3-methyl-[1,2,4]triazolo[4,3-a]pyridin-8-yl]acetamide (60.00 mg, 0.223 mmol, 1.00 equiv), [4-[(dimethylamino)methyl]-3,5-dimethoxyphenyl]boronic acid (53.31 mg, 0.223 mmol, 1.00 equiv), and $Cs_2CO_3$ (145.29 mg, 0.446 mmol, 2.00 equiv) in 1,4-dioxane (5.00 mL) was added Pd(dppf)Cl2 $CH_2Cl_2$ (18.21 mg, 0.022 mmol, 0.10 equiv) and $H_2O$ (1.00 mL) at 25° C. The resulting solution was stirred for 2 hours at 80° C. The resulting solution was diluted with 10 mL of water. The resulting solution was extracted with ethyl acetate (2×20 mL) and the organic layers were combined and dried over anhydrous sodium sulfate and concentrated. The crude product was purified by Prep-HPLC (conditions: SunFire C18 OBD Prep Column, 19 mm×250 mm; mobile phase, Water (0.1% FA (formic acid)) and ACN (hold 5% Phase B in 2 minutes, up to 17% in 8 minutes); Detector, uv). This resulted in 10.3 mg (12.05%) of N-(6-[4-[(dimethylamino)methyl]-3,5-dimethoxyphenyl]-3-methyl-[1,2,4]triazolo[4,3-a]pyridin-8-yl)acetamide as a brown semi-solid. $^1$H NMR (400 MHz, Methanol-d4) δ 8.55 (s, 1H, FA), 8.48 (d, J=1.4 Hz, 1H), 8.35 (d, J=1.5 Hz, 1H), 7.08 (s, 2H), 4.38 (s, 2H), 4.05 (s, 6H), 2.88 (s, 6H), 2.85 (s, 3H), 2.33 (s, 3H). LCMS (ESI) m/z: [M+H]$^+$=384.25.

Example 47—Preparation of 2,6-dimethoxy-4-(2-methyl-1-oxo-1,2-dihydro-2,7-naphthyridin-4-yl)benzaldehyde (Compound B61)

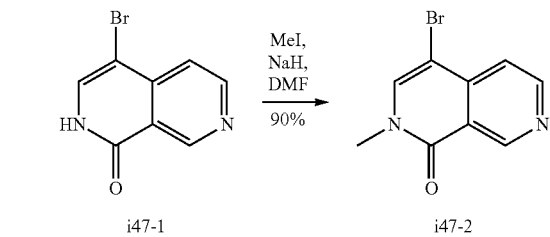

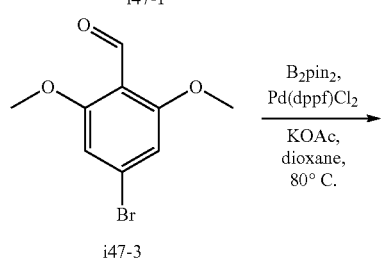

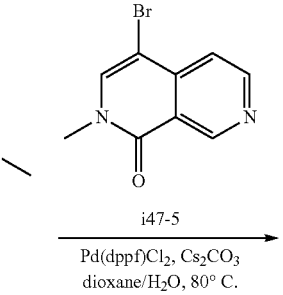

Step 1: Preparation of 4-bromo-2-methyl-2,7-naphthyridin-1(2H)-one (i47-2)

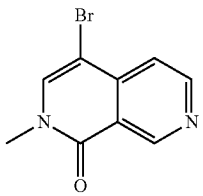

To a solution of 4-bromo-1,2-dihydro-2,7-naphthyridin-1-one (20.00 g, 88.871 mmol, 1 equiv) in DMF (150 mL) was added NaH (8.80 g, 60%, 222.178 mmol, 2.5 equiv) in portions at 0° C., and the resulting mixture was stirred at 0° C. for 30 minutes. Then CH$_3$I (1.90 g, 133.307 mmol, 1.5 equiv) was added dropwise. The resulting mixture was stirred at 0° C. for 1 hour. The mixture was poured into ice water (200 mL) and stirred for 30 minutes. The mixture was filtered and the solid was dried to afford 4-bromo-2-methyl-2,7-naphthyridin-1(2H)-one (20.00 g, 94.13%) as light grey solid. LCMS (ESI, m/z): [M+H]$^+$=239.1, [M+H+2]$^+$=241.1.

Step 2: Preparation of 2,6-dimethoxy-4-(2-methyl-1-oxo-1,2-dihydro-2,7-naphthyridin-4-yl)benzaldehyde (Compound B61)

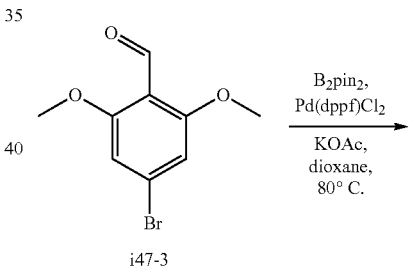

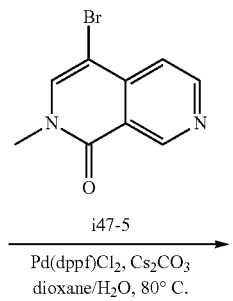

-continued

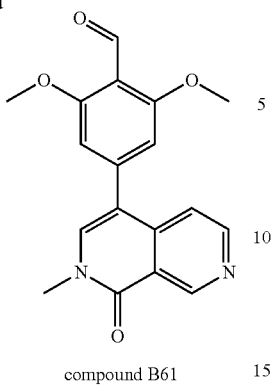

compound B61

To a solution of 4-bromo-2,6-dimethoxybenzaldehyde (5.00 g, 20.402 mmol, 1 equiv) in 1,4-dioxane (300 mL) was added 4,4,5,5-tetramethyl-2-(4,4,5,5-tetramethyl-1,3,2-dioxaborolan-2-yl)-1,3,2-dioxaborolane (6.22 g, 24.483 mmol, 1.2 equiv), Pd(dppf)Cl₂ (298.57 mg, 0.408 mmol, 0.02 equiv), and KOAc (4.00 g, 40.804 mmol, 2 equiv) at 25° C. The resulting mixture was stirred at 80° C. for 1 hour under N₂ atmosphere. The mixture was cooled to 60° C. Then 4-bromo-2-methyl-1,2-dihydro-2,7-naphthyridin-1-one (4.91 g, 20.538 mmol, 1 equiv), Cs₂CO₃ (13.38 g, 41.076 mmol, 2 equiv), Pd(dppf)Cl₂ (298.57 mg, 0.408 mmol, 0.02 equiv), and water (60 mL) were added. The resulting mixture was stirred at 80° C. for 1 hour. The mixture was filtered and activated charcoal (5 g) was added to the filtrate and refluxed at 100° C. for 1 hour. The mixture was filtered and concentrated to get crude product, which was slurried in EA, EtOH, and water respectively to afford light brown solid. This solid was dissolved in DCM and MeOH (200 mL, v/v=20/1), and then precipitated with EA (200 mL) dropwise under stirring. The solid was filtered and dried to afford 2,6-dimethoxy-4-(2-methyl-1-oxo-1,2-dihydro-2,7-naphthyridin-4-yl)benzaldehyde (2.3 g, 34.63%) as light grey solid. LCMS (ESI, m/z): [M+H]⁺=325.2. ¹H NMR (300 MHz, DMSO) δ 10.41 (s, 1H), 9.46 (s, 1H), 8.74 (d, J=5.7 Hz, 1H), 7.99 (s, 1H), 7.64 (d, J=5.7 Hz, 1H), 6.85 (s, 2H), 3.89 (s, 6H), 3.62 (s, 3H).

Example 48—Preparation of 1-(4-((dimethylamino)methyl)-3,5-dimethoxyphenyl)-3-methylpyrido[3,4-d]pyridazin-4(3H)-one 2,2,2-trifluoroacetate (Compound B62)

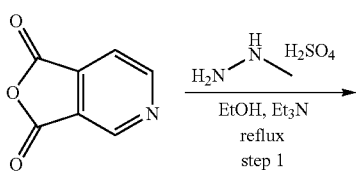

i48-1

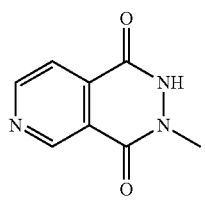

i48-2

-continued

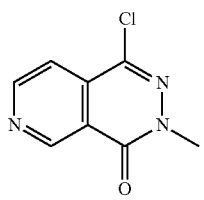

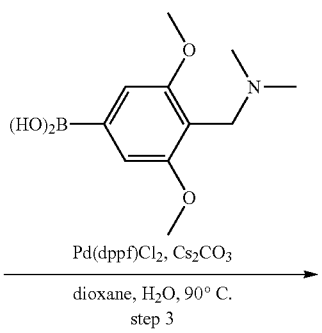

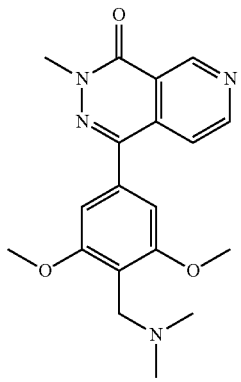

compound B62

Step 1: Preparation of 3-methyl-2,3-dihydropyrido[3,4-d]pyridazine-1,4-dione (i48-2)

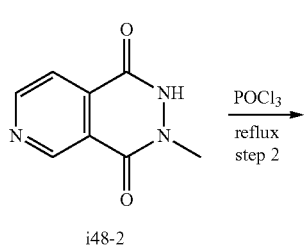

i48-2

To a stirred mixture of furo[3,4-c]pyridine-1,3-dione (2.00 g, 13.413 mmol, 1.00 equiv) and methylhydrazine sulfate (5.80 g, 40.240 mmol, 3 equiv) in EtOH (20.00 mL) was added Et₃N (8.14 g, 80.480 mmol, 6.00 equiv), the resulting solution was stirred at 80 degrees C. under nitrogen atmosphere for 10 hours. Then the resulting mixture was concentrated under reduced pressure to give 4.2 g of crude product. This material was used directly in the next step without further purification. LCMS (ESI) m/z: [M+H]⁺=178.

Step 2: Preparation of N 1-chloro-3-methylpyrido[3,4-d]pyridazin-4(3H)-one (i48-3)

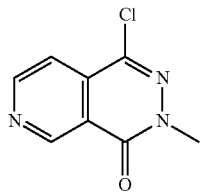

i48-3

Into POCl₃ (20.00 mL, 214.567 mmol, 9.05 equiv) was added 3-methyl-2H-pyrido[3,4-d]pyridazine-1,4-dione (4.20 g, 23.707 mmol, 1.00 equiv), and then it was stirred for 8 h at 105 degrees C. under nitrogen atmosphere. The resulting mixture was concentrated to remove POCl₃, then neutralized with the saturated solution of NaHCO₃ (200 mL), extracted with EA (300 mL×3). The combined organic layers were washed with the solution of saturated NaCl, dried over anhydrous Na₂SO₄. After filtration, the filtrate was concentrated under reduced pressure, then purified by flash chromatography (ethyl acetate/petroleum ether from 1:4 to 1:1). This resulted-chloro-3-methylpyrido[3,4-d]pyridazin-4(3H)-one. This material was used directly in the next step without further purification. LCMS (ESI) m/z: [M+H]⁺=196.

Step 3: Preparation of 1-(4-((dimethylamino)methyl)-3,5-dimethoxyphenyl)-3-methylpyrido[3,4-d]pyridazin-4(3H)-one 2,2,2-trifluoroacetate (PH-FOG-P3-B87)

compound B62

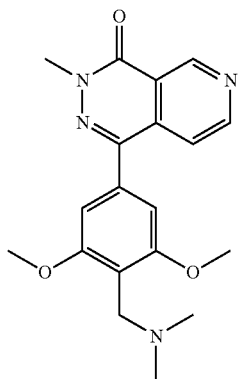

Into a stirred mixture of 1-chloro-3-methyl-3H,4H-pyrido[3,4-d]pyridazin-4-one (150.00 mg, 0.767 mmol, 1.00 equiv) and [4-[(dimethylamino)methyl]-3,5-dimethoxyphenyl]boronic acid (275.00 mg, 1.150 mmol, 1.50 equiv) in dioxane (5.00 mL) and H₂O (0.50 mL) was added Pd(dppf)Cl₂·CH₂Cl₂ (62.62 mg, 0.077 mmol, 0.10 equiv) and Cs₂CO₃ (999.40 mg, 3.067 mmol, 4.00 equiv) at 25 degrees C. under N₂ atmosphere. Then the reaction was stirred at 90 degrees C. for 12 h. The resulting mixture was extracted with EtOAc (2×40 mL). The combined organic layers were washed with saturated NaCl solution, dried over anhydrous Na₂SO₄. After filtration, the filtrate was concentrated under reduced pressure. The crude product was purified by Prep-HPLC (conditions: Sunfire C18 OBD Prep Column, 5 um, 19 mm*250 mm; Mobile Phase A: Water (0.05% TFA), Mobile Phase B: ACN; Flow rate: 25 mL/min; Gradient: 2% B to 2% B in 2 min; 254 nm; Rt: 13.78 min). This resulted in 20.3 mg (5.57%) of 1-(4-((dimethylamino)methyl)-3,5-dimethoxyphenyl)-3-methylpyrido[3,4-d]pyridazin-4(3H) as a white solid. ¹H NMR (300 MHz, Methanol-d4) δ 9.66 (s, 1H), 8.99 (d, J=5.6 Hz, 1H), 7.79 (d, J=5.6 Hz, 1H), 7.04 (s, 2H), 4.46 (s, 2H), 4.00 (s, 6H), 3.93 (s, 3H), 2.94 (s, 6H). LCMS (ESI) m/z: [M+H]⁺=355.15.

Example 49—Preparation of 4-(4-((dimethylamino)methyl)-3,5-dimethoxyphenyl)-N,2-dimethyl-1-oxo-12-dihydroisoquinoline-6-carboxamide (Compound B63)

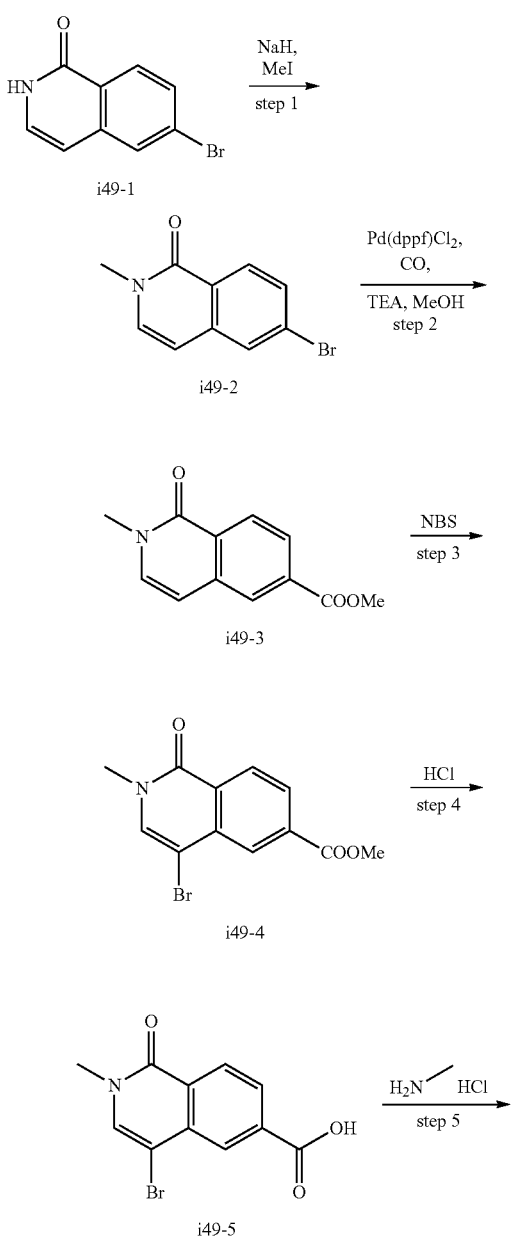

219

-continued

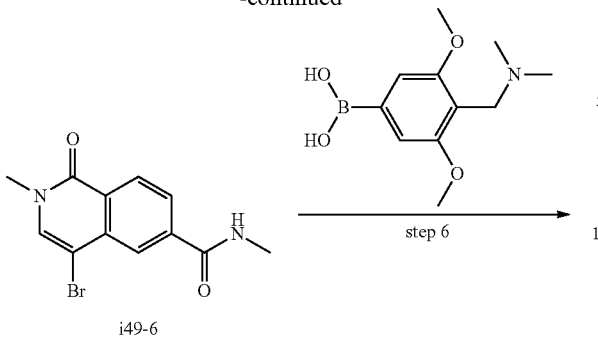

i49-6

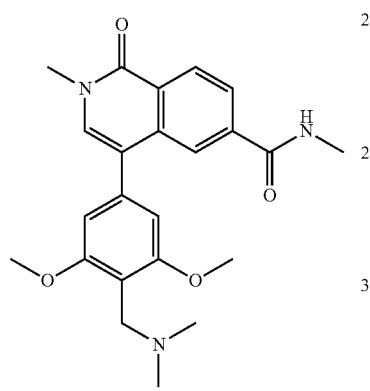

compound B63

Step 1: Preparation of 6-bromo-3-methyl-[1,2,4]triazolo[4,3-a]pyridin-8-amine (i49-2)

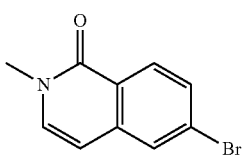

i49-2

To a solution of 6-bromo-2H-isoquinolin-1-one (5.0 g, 22.316 mmol, 1.00 equiv) in DMF was added sodium hydride (60% in oil, 803.3 mg) at 0° C. The mixture was stirred for 15 minutes. MeI (9.5 g, 66.947 m mol, 3.00 equiv) was added, and the mixture was allowed to warm to room temperature and stirred for additional 1 hour. The reaction mixture was quenched by water and extracted with DCM (3×100 mL). The DCM layer was concentrated under vacuum. This resulted in 6-bromo-2-methylisoquinolin-1-one as a white solid (6.45 g, crude) that was used directly without further purification. LCMS (ESI) m/z: [M+H]+=238.

220

Step 2: Preparation of methyl 2-methyl-1-oxo-1,2-dihydroisoquinoline-6-carboxylate (i49-3)

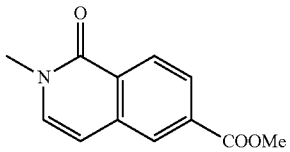

i49-3

To a solution of 6-bromo-2-methylisoquinolin-1-one (1 g, 4.200 mmol, 1.00 equiv) and PdCl$_2$(dppf) (307.3 mg, 0.420 m mol, 0.10 equiv) in MeOH (9 mL) was added Et$_3$N (7.00 mL, 50.361 mmol, 11.99 equiv) in a pressure tank. The mixture was purged with nitrogen for 20 minutes and then was pressurized to 50 atm with carbon monoxide. The mixture was then stirred at 100° C. for 15 hours. The reaction mixture was cooled to room temperature and filtered to remove insoluble solids. The resulting mixture was concentrated under vacuum. The residue was purified by silica gel column chromatography, eluted with PE (petroleum ether)/EtOAc (ethyl acetate) (2:1) to afford methyl 2-methyl-1-oxoisoquinoline-6-carboxylate as yellow solid (501 mg, 55%). LCMS (ESI) m/z: [M+H]+=218.

Step 3: Preparation of methyl 4-bromo-2-methyl-1-oxo-1,2-dihydroisoquinoline-6-carboxylate (i49-4)

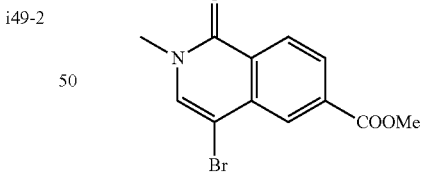

i49-4

To a stirred solution of methyl 2-methyl-1-oxoisoquinoline-6-carboxylate (200 mg, 0.921 mmol, 1.00 equiv) in THF (10 mL) was added NBS (245.8 mg, 1.381 mmol, 1.50 equiv) in portions over 25 minutes at 0° C. The resulting mixture was stirred for additional 2 hours at room temperature. The resulting mixture was diluted with 10 mL of water and extracted with EtOAc (3×30 mL). The combined organic layers were washed with saturated NaCl (20 mL) and dried over anhydrous Na$_2$SO$_4$. After filtration, the filtrate was concentrated under reduced pressure. The crude product (161 mg) was used in the next step directly without further purification.

Step 4: Preparation of 4-bromo-2-methyl-1-oxo-1,2-dihydroisoquinoline-6-carboxylic acid (i49-5)

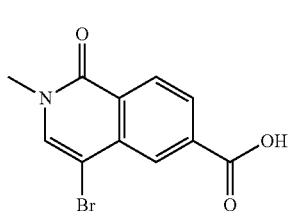

i49-5

A solution of methyl 4-bromo-2-methyl-1-oxoisoquinoline-6-carboxylate (161 mg, 0.544 mmol, 1.00 equiv) in conc. HCl (5 mL) was stirred for 4 hours at 100° C. The resulting mixture was concentrated under vacuum. The crude product (177 mg) was used in the next step directly without further purification. LCMS (ESI) m/z: [M+H]+=283.

Step 5: Preparation of 4-bromo-N,2-dimethyl-1-oxo-1,2-dihydroisoquinoline-6-carboxamide (i49-6)

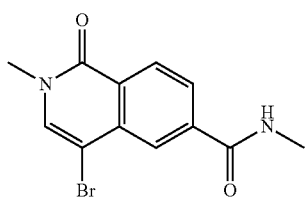

i49-6

A solution of 4-bromo-2-methyl-1-oxoisoquinoline-6-carboxylic acid (85 mg, 0.301 mmol, 1.00 equiv) in DMF was treated with HATU (137.5 mg, 0.362 mmol, 1.20 equiv) for 30 minutes at room temperature followed by the addition of DIEA (194.7 mg, 1.507 mmol, 5.00 equiv) and methylamine (9.4 mg, 0.301 mmol, 1.00 equiv) at room temperature. The resulting mixture was stirred for 2 hours at room temperature under nitrogen atmosphere. The resulting mixture was concentrated under reduced pressure. The residue was purified by silica gel column chromatography, eluted with CH$_2$Cl$_2$/MeOH (10:1) to afford 4-bromo-N,2-dimethyl-1-oxoisoquinoline-6-carboxamide (81 mg, 91%) as a white solid. LCMS (ESI) m/z: [M+H]+=296.

Step 6: Preparation of 4-(4-((dimethylamino)methyl)-3,5-dimethoxyphenyl)-N,2-dimethyl-1-oxo-1,2-dihydroisoquinoline-6-carboxamide (Compound B63)

compound B63

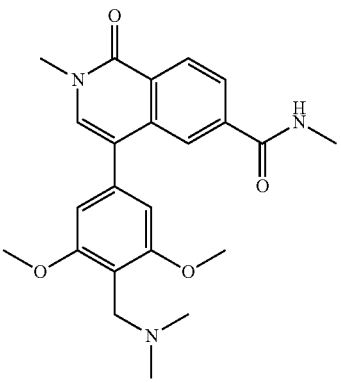

To a solution of 4-bromo-N,2-dimethyl-1-oxo-1,2-dihydroisoquinoline-6-carboxamide (80 mg, 0.271 mmol, 1.00 equiv) and [4-[(dimethylamino)methyl]-3,5-dimethoxyphenyl]boronic acid (97.2 mg, 0.407 mmol, 1.50 equiv) in dioxane (2 mL) and water (0.4 mL) was added Cs$_2$CO$_3$ (264.95 mg, 0.813 mmol, 3.00 e.q.) and Pd(dppf)Cl$_2$ (19.8 mg, 0.027 mmol, 0.10 equiv). After stirring for 2 hours at 75° C. under nitrogen atmosphere, the resulting mixture was concentrated under reduced pressure. The residue was purified by silica gel column chromatography and eluted with CH$_2$Cl$_2$/MeOH (5:1). The crude product was further purified by Prep-HPLC (conditions: Atlantis HILIC OBD Column 19*150 mm*5 μm; mobile phase, Phase A: Water (10 mmol/L NH$_4$HCO$_3$); Phase B: ACN, Gradient; Detector, uv 254/220 nm). This gave 4-[4-[(dimethylamino)methyl]-3,5-dimethoxyphenyl]-N,2-dimethyl-1-oxo-1,2-dihydroisoquinoline-6-carboxamide (10.1 mg, 9.1%) as a yellow solid. $^1$H NMR (300 MHz, DMSO-d6) δ 8.64 (d, J=4.9 Hz, 1H), 8.38 (d, J=8.4 Hz, 1H), 8.13 (d, J=1.6 Hz, 1H), 7.93 (dd, J=8.4, 1.7 Hz, 1H), 7.65 (s, 1H), 6.73 (s, 2H), 3.79 (s, 6H), 3.60 (s, 3H), 3.47 (s, 2H), 2.78 (d, J=4.5 Hz, 3H), 2.15 (s, 6H).

LCMS (ESI) m/z: [M+H]+=410.20.

Example 50—Preparation of 4-[4-[(dimethylamino)methyl]-3,5-dimethoxyphenyl]-7-[1H-imidazo[4,5-c]pyridin-2-yl]-2-methylisoquinolin-1-one (Compound B64)

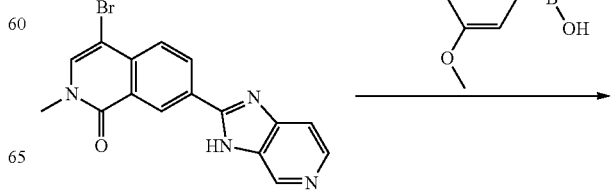

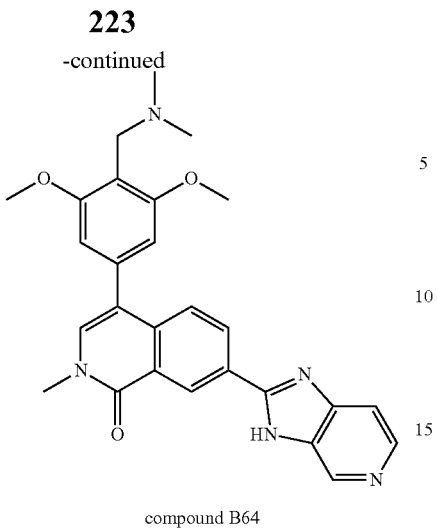

compound B64

To a solution of 4-bromo-7-[3H-imidazo[4,5-c]pyridin-2-yl]-2-methylisoquinolin-1-one (80.00 mg, 0.225 mmol, 1.00 equiv) and [[2,6-dimethoxy-4-(4,4,5,5-tetramethyl-1,3,2-dioxaborolan-2-yl)phenyl]methyl]dimethylamine (108.52 mg, 0.338 mmol, 1.5 equiv) in mixed DMF (3.00 mL) and H$_2$O (0.30 mL) was added Cs$_2$CO$_3$ (220.15 mg, 0.676 mmol, 3 equiv) and Pd(dppf)Cl$_2$·CH$_2$Cl$_2$ (18.39 mg, 0.023 mmol, 0.10 equiv). After stirring for 2 hours at 90° C. under a nitrogen atmosphere, the resulting mixture was concentrated under reduced pressure. The residue was purified by silica gel column chromatography, eluted with CH$_2$Cl$_2$/MeOH (12:1) to afford a crude product. The crude product was further purified by Prep-HPLC (conditions: XSelect CSH Prep C18 OBD Column, 5 μm, 19*150 mm; Mobile Phase A: Water (10 mmol/L NH$_4$HCO$_3$), Mobile Phase B: ACN; Flow rate: 25 mL/minute; Gradient: 40% B to 55% B in 8 minutes; 254/220 nm; Rt (retention time): 6.50 minutes) to afford 4-[4-[(dimethylamino)methyl]-3,5-dimethoxyphenyl]-7-[1H-imidazo[4,5-c]pyridin-2-yl]-2-methylisoquinolin-1-one (7 mg, 6.62%) as a grey solid. $^1$H NMR (300 MHz, Methanol-d4) δ 9.21 (d, J=2.0 Hz, 1H), 8.91 (d, J=1.0 Hz, 1H), 8.48 (dd, J=8.6, 2.0 Hz, 1H), 8.32 (d, J=5.8 Hz, 1H), 7.86 (d, J=8.6 Hz, 1H), 7.68 (dd, J=5.8, 1.0 Hz, 1H), 7.55 (s, 1H), 6.80 (s, 2H), 3.91 (s, 6H), 3.76 (d, J=18.1 Hz, 5H), 2.41 (s, 6H). LCMS (ESI) m/z: [M+H]+=470.20.

Example 51—Preparation of 4-(4-((dimethylamino)methyl)-3,5-dimethoxyphenyl)-6-(1H-imidazo[4,5-c]pyridin-2-yl)-2-methylisoquinolin-1(2H)-one (Compound B65)

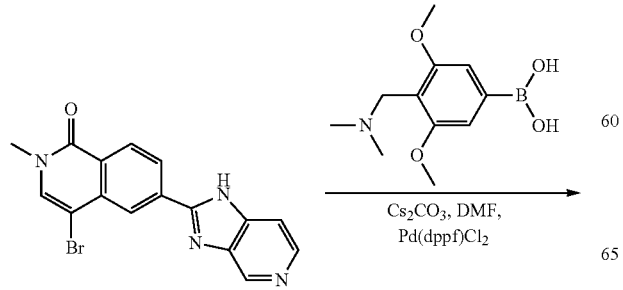

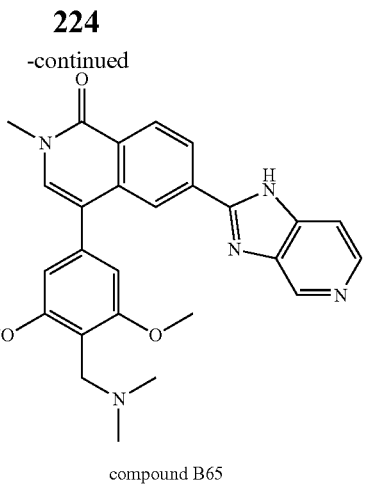

compound B65

To a solution of 4-bromo-6-[1H-imidazo[4,5-c]pyridin-2-yl]-2-methylisoquinolin-1-one (100.00 mg, 0.282 m mol, 1.00 e.q.) and 4-[(dimethylamino)methyl]-3,5-dimethoxyphenylboronic acid (100.96 mg, 0.422 mmol, 1.50 e.q.) in DMF (2 mL) and water (0.4 mL), was added Cs$_2$CO$_3$ (275.19 mg, 0.845 mmol, 3.00 e.q.) and Pd(dppf)Cl$_2$ (20.60 mg, 0.028 mmol, 0.10 e.q.). After stirring for 2 h at 80 degrees C. under a nitrogen atmosphere, the resulting mixture was concentrated under reduced pressure. The residue was purified by silica gel column chromatography, eluted with CH$_2$Cl$_2$/MeOH (5:1). The crude product was purified by Prep-HPLC with the following conditions (2 #SHI-MADZU (HPLC-01)): Column, Atlantis HILIC OBD Column, 19 mm×250 mm×5 um; mobile phase, Water (0.1% FA) and ACN (hold 5% Phase B in 5 min, up to 10% in 10.5 min); Detector, uv, 254. This resulted in 5.0 mg (11.35%) of to afford 4-[4-[(dimethylamino)methyl]-3,5-dimethoxyphenyl]-6-[1H-imidazo[4,5-c]pyridin-2-yl]-2-methy-isoquinolin-1-one as a yellow solid. $^1$H NMR (300 MHz, Methanol-d4) δ 8.90 (s, 1H), 8.64 (d, J=8.5 Hz, 1H), 8.59 (s, 1H), 8.55 (br s, 1H, FA), 8.33 (d, J=6.5 Hz, 2H), 7.70 (d, J=5.9 Hz, 1H), 7.58 (s, 1H), 6.96 (s, 2H), 4.44 (s, 2H), 3.99 (s, 6H), 3.75 (s, 3H), 2.95 (s, 6H). LCMS (ESI) m/z: [M+H]+ =470.45.

Example 52—Preparation of 4-(4-((dimethylamino)methyl)-2-fluoro-3-methoxyphenyl)-2-methyl-2,7-naphthyridin-1(2H)-one (Compound B66)

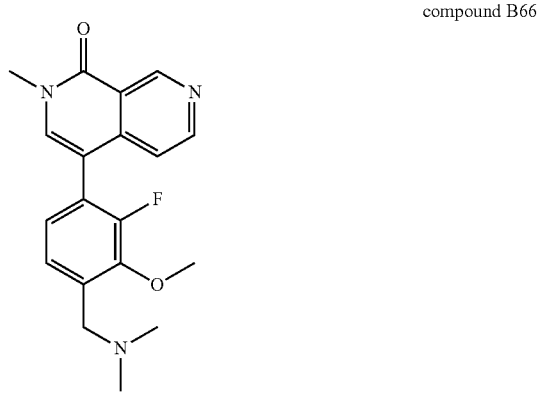

compound B66

Compound B66 was prepared in a similar manner as described for compound B50. $^1$H NMR (400 MHz, DMSO-$d_6$) δ 9.42 (d, J=0.8 Hz, 1H), 8.69 (d, J=5.7 Hz, 1H), 7.88 (s, 1H), 7.28 (dd, J=8.0, 1.2 Hz, 1H), 7.19-7.09 (m, 2H), 3.86 (d, J=1.2 Hz, 3H), 3.57 (s, 3H), 3.48 (s, 2H), 2.20 (s, 6H). LCMS (ESI) m/z: [M+H]+=342.2.

Preparation of 4-(4-((dimethylamino)methyl)-3-fluoro-5-methoxyphenyl)-2-methyl-2,7-naphthyridin-1(2H)-one (Compound B67)

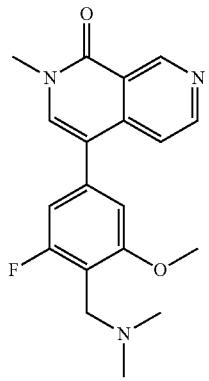

compound B67

Compound B67 was prepared in a similar manner as described for compound B50. $^1$H NMR (400 MHz, DMSO-$d_6$) δ 9.42 (d, J=0.9 Hz, 1H), 8.71 (d, J=5.7 Hz, 1H), 7.89 (s, 1H), 7.52 (dd, J=5.7, 0.9 Hz, 1H), 6.94 (d, J=1.8 Hz, 1H), 6.90 (dd, J=10.0, 1.5 Hz, 1H), 3.84 (s, 3H), 3.57 (s, 4H), 3.48 (d, J=1.8 Hz, 2H), 2.15 (s, 6H). LCMS (ESI) m/z: [M+H]+=342.2.

Example 53—Preparation of 4-[2-(2-[[2-([[2,6-dimethoxy-4-(2-methyl-1-oxo-2,7-naphthyridin-4-yl)(methyl)amino)ethyl](methyl)amino]ethoxy)ethoxy]-2-(2,6-dioxopiperidin-3-yl)isoindole-1,3-dione formic acid (Compound D1 Formic Acid)

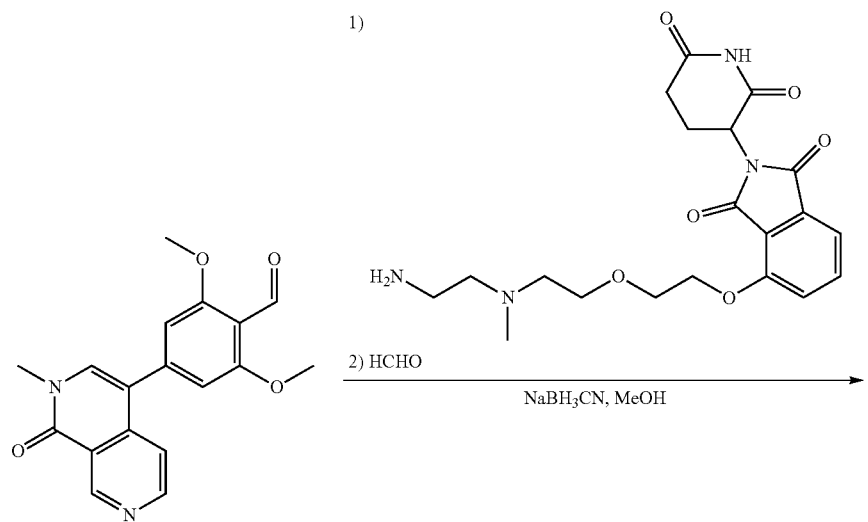

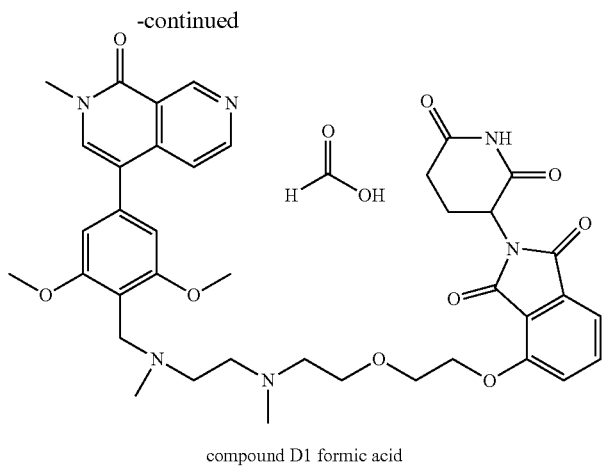

compound D1 formic acid

A solution of 2,6-dimethoxy-4-(2-methyl-1-oxo-2,7-naphthyridin-4-yl)benzaldehyde (30.00 mg, 0.092 mmol, 1.00 equiv) and 4-(2-[2-[(2-aminoethyl)(methyl)amino]ethoxy]ethoxy)-2-(2,6-dioxopiperidin-3-yl)isoindole-1,3-dione (38.71 mg, 0.093 mmol, 1.00 equiv) in MeOH (1 mL) was stirred for 3 hours at room temperature under nitrogen atmosphere. To the above mixture was added NaBH$_3$CN (11.63 mg, 0.185 mmol, 2.00 equiv) and stirred for 1 h at room temperature under nitrogen atmosphere. Then HCHO (27.77 mg, 0.925 mmol, 10.00 equiv) was added. After 1 hour. The above mixture was added NaBH$_3$CN (11.63 mg, 0.185 mmol, 2.00 equiv) and stirred for 1 h at room temperature under nitrogen atmosphere. The crude product (30 mg) was purified by Prep-HPLC (conditions: SunFire Prep C18 OBD Column, 19×150 mm 5 μm 10 nm; Mobile Phase A: Water (0.1% FA), Mobile Phase B: ACN: Flow rate: 25 mL/min: Gradient: 7 B to 17 B in 12 min; 254/220 nm; R$_T$: 7.68 minutes) to afford 4-[2-(2-[[2-([[2,6-dimethoxy-4-(2-methyl-1-oxo-2,7-naphthyridin-4-yl)phenyl]methyl](methyl)amino)ethyl](methyl)amino]ethoxy)ethoxy]-2-(2,6-dioxopiperidin-3-yl)isoindole-1,3-dione; formic acid (10.1 mg) as a white solid. $^1$H NMR (400 MHz, Methanol-d4) δ 2.03-2.14 (1H, m), 2.42 (3H, s), 2.60-2.77 (3H, m), 2.82 (6H, d), 2.96 (5H, s), 3.28 (3H, s), 3.70 (3H, s), 3.80 (2H, s), 3.93 (8H, s), 4.34 (4H, d), 5.04-5.13 (1H, m), 6.79 (2H, s), 7.31-7.38 (2H, m), 7.57 (1H, d), 7.66 (1H, t), 7.73 (1H, s), 8.44 (1H, s), 8.66 (1H, d), 9.52 (1H, s). LCMS (ESI) m/z: [M+H]+=741.45.

Example 54—Preparation of 2-([[2,6-dimethoxy-4-(2-methyl-1-oxo-1,2-dihydro-2,7-naphthyridin-4-yl)phenyl]methyl](methyl)amino)-N-(8-[[2-(2,6-dioxopiperidin-3-yl)-1,3-dioxo-2,3-dihydro-1H-isoindol-4-yl]amino]octyl)acetamide formic acid (Compound D2 Formic Acid)

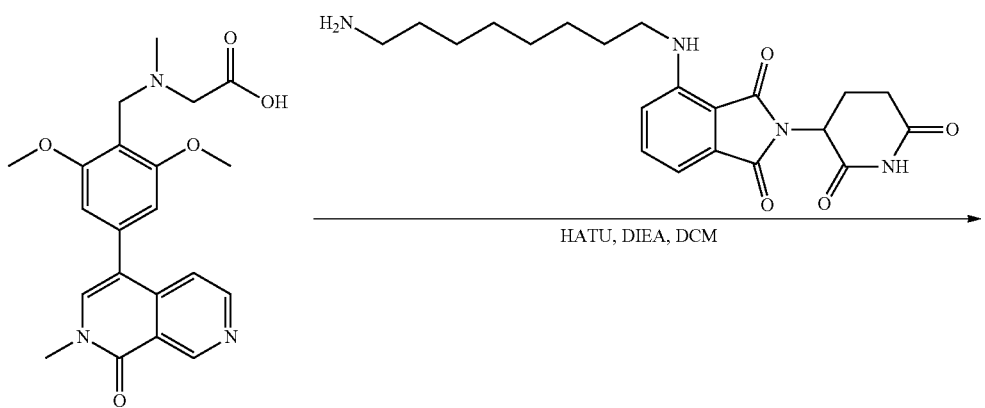

HATU, DIEA, DCM

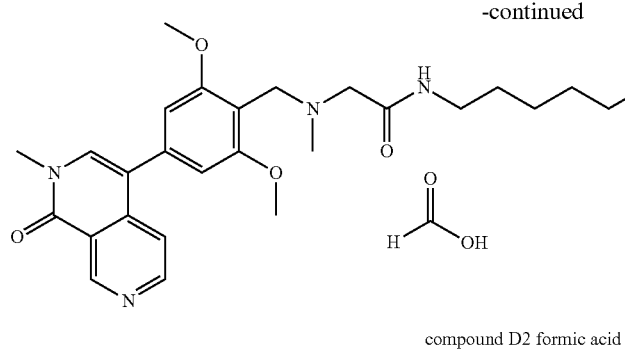

compound D2 formic acid

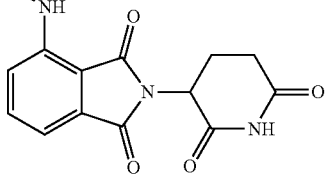

To the solution of 2-([[2,6-dimethoxy-4-(2-methyl-1-oxo-1,2-dihydro-2,7-naphthyridin-4-yl)phenyl]methyl](methyl)amino)acetic acid (40 mg, 0.101 mmol, 1 equiv) in DCM (2 mL) was added 4-[(8-aminooctyl)amino]-2-(2,6-dioxopiperidin-3-yl)-2,3-dihydro-1H-isoindole-1,3-dione (48.37 mg, 0.121 mmol, 1.2 equiv), HATU (57.40 mg, 0.151 mmol, 1.5 equiv), and DIEA (39.02 mg, 0.302 mmol, 3 equiv). The resulting solution was stirred at room temperature for 1 hour. The mixture was concentrated. The crude product was purified by Prep-HPLC (conditions: XSelect CSH Prep C18 OBD Column, 5 um, 19*150 mm; Mobile Phase A: Water (0.1% FA), Mobile Phase B: ACN; Flow rate: 25 mL/min; Gradient: 15% B to 40% B in 8 min; 254 nm; Rt: 7.04 min) to afford 2-([[2,6-dimethoxy-4-(2-methyl-1-oxo-1,2-dihydro-2,7-naphthyridin-4-yl)phenyl]methyl](methyl)amino)-N-(8-[[2-(2,6-dioxopiperidin-3-yl)-1,3-dioxo-2,3-dihydro-1H-isoindol-4-yl]amino]octyl)acetamide formic acid (14.9 mg, 17.13%) as a yellow solid. $^1$H NMR (400 MHz, Methanol-d4) δ 9.51 (d, J=0.8 Hz, 1H), 8.67 (d, J=5.7 Hz, 1H), 7.73 (s, 1H), 7.62 (d, J=5.7 Hz, 1H), 7.52 (dd, J=8.6, 7.1 Hz, 1H), 6.99 (dd, J=12.1, 7.8 Hz, 2H), 6.76 (s, 2H), 5.05 (dd, J=12.4, 5.5 Hz, 1H), 3.90 (s, 6H), 3.81 (s, 2H), 3.69 (s, 3H), 3.24 (dt, J=9.7, 7.0 Hz, 4H), 3.14 (s, 2H), 2.87 (ddd, J=19.0, 14.1, 5.2 Hz, 1H), 2.81-2.64 (m, 2H), 2.38 (s, 3H), 2.17-2.07 (m, 1H), 1.59 (q, J=6.9 Hz, 2H), 1.53 (d, J=7.3 Hz, 2H), 1.36 (s, 8H). LCMS (ESI) m/z: [M+H]$^+$=780.40.

Example 55—Preparation of 2-([[2,6-dimethoxy-4-(2-methyl-1-oxo-1,2-dihydro-2,7-naphthyridin-4-yl)phenyl]methyl](methyl)amino)-N-(5-[[2-(2,6-dioxopiperidin-3-yl)-1,3-dioxo-2,3-dihydro-1H-isoindol-4-yl]amino]pentyl)acetamide formic acid (Compound D3 Formic Acid)

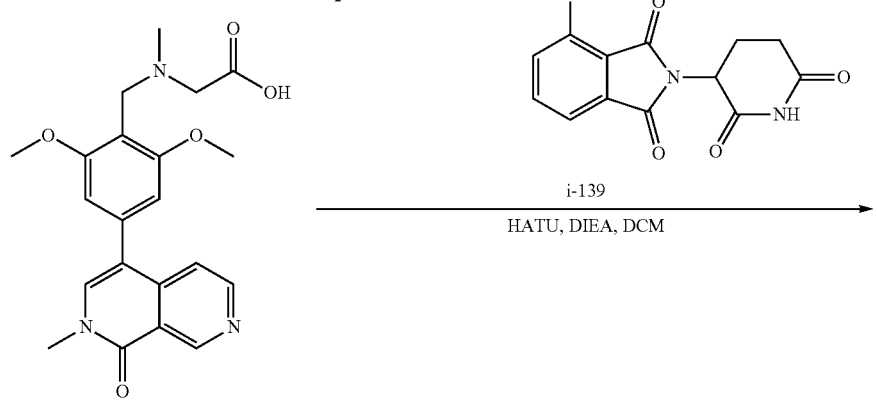

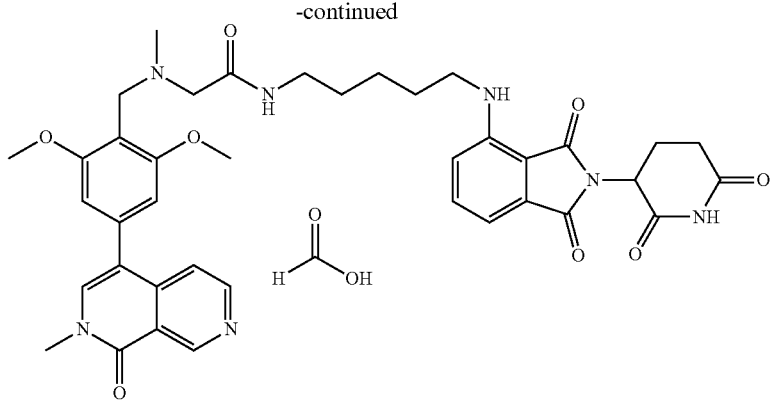

compound D3 formic acid

To the solution of 2-([[2,6-dimethoxy-4-(2-methyl-1-oxo-1,2-dihydro-2,7-naphthyridin-4-yl)phenyl]methyl](methyl)amino)acetic acid (40 mg, 0.101 mmol, 1 equiv) in DCM (2 mL) was added 4-[(5-aminopentyl)amino]-2-(2,6-dioxopiperidin-3-yl)-2,3-dihydro-1H-isoindole-1,3-dione (43.29 mg, 0.121 mmol, 1.2 equiv), HATU (57.40 mg, 0.151 mmol, 1.5 equiv), and DIEA (39.02 mg, 0.302 mmol, 3 equiv). The resulting solution was stirred at room temperature for 1 hour. The mixture was concentrated. The crude product was purified by Prep-HPLC (conditions: XSelect CSH Prep C18 OBD Column, 5 um, 19*150 mm; Mobile Phase A: Water (0.1% FA), Mobile Phase B: ACN; Flow rate: 25 mL/min; Gradient: 12% B to 30% B in 8 min; 254 nm; Rt: 7.15 min) to afford 2-([[2,6-dimethoxy-4-(2-methyl-1-oxo-1,2-dihydro-2,7-naphthyridin-4-yl)phenyl]methyl](methyl)amino)-N-(5-[[2-(2,6-dioxopiperidin-3-yl)-1,3-dioxo-2,3-dihydro-1H-isoindol-4-yl]amino]pentyl)acetamide formic acid (15.2 mg, 18.44%) as a yellow solid. $^1$H NMR (400 MHz, Methanol-d4) δ 9.49 (d, J=0.9 Hz, 1H), 8.67 (d, J=5.7 Hz, 1H), 7.72 (s, 1H), 7.63 (d, J=5.7 Hz, 1H), 7.46 (dd, J=8.5, 7.1 Hz, 1H), 6.96 (dd, J=12.3, 7.8 Hz, 2H), 6.75 (s, 2H), 5.04 (dd, J=12.4, 5.4 Hz, 1H), 3.89 (s, 6H), 3.78 (s, 2H), 3.69 (s, 3H), 3.27 (q, J=6.5 Hz, 4H), 3.13 (s, 2H), 2.87 (ddd, J=18.8, 14.1, 5.2 Hz, 1H), 2.81-2.63 (m, 2H), 2.38 (s, 3H), 2.17-2.09 (m, 1H), 1.67 (p, J=7.0 Hz, 2H), 1.58 (p, J=6.8 Hz, 2H), 1.45 (q, J=8.0 Hz, 2H). LCMS (ESI) m/z: [M+H]$^+$=738.30.

Example 56—Preparation of N-[[2,6-dimethoxy-4-(2-methyl-1-oxo-1,2-dihydro-2,7-naphthyridin-4-yl)phenyl]methyl]-6-[[2-(2,6-dioxopiperidin-3-yl)-1,3-dioxo-2,3-dihydro-1H-isoindol-4-yl]oxy]-N-methylhexanamide (Compound D4)

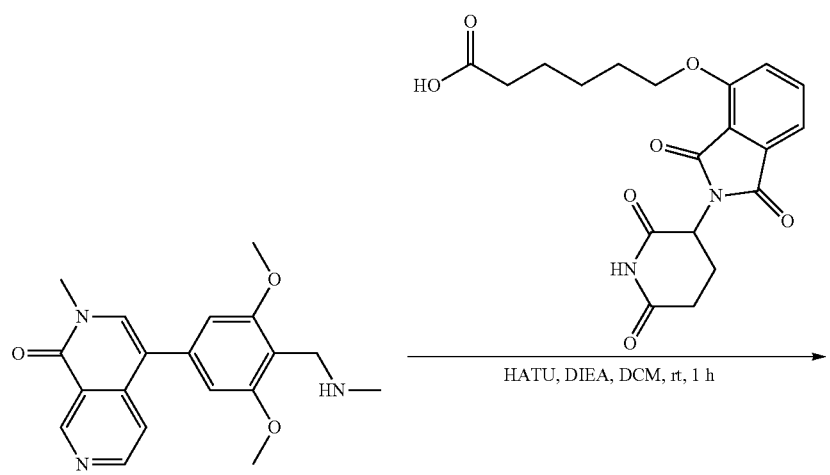

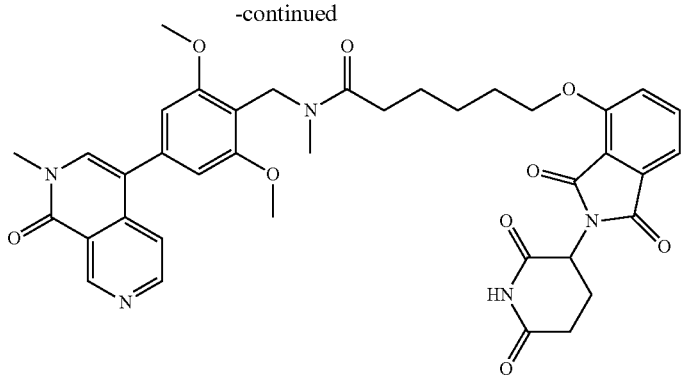

compound D4

To a solution of 6-[[2-(2,6-dioxopiperidin-3-yl)-1,3-dioxo-2,3-dihydro-1H-isoindol-4-yl]oxy]hexanoic acid (50.00 mg, 0.13 mmol, 1 eq.) and DIPEA (49.92 mg, 0.39 mmol, 3 eq.) in DCM (2 mL) was added PyBOP (100.49 mg, 0.19 mmol, 1.5 eq.) and 4-[3,5-dimethoxy-4-[(methylamino)methyl]phenyl]-2-methyl-1,2-dihydro-2,7-naphthyridin-1-one (43.69 mg, 0.13 mmol, 1.00 eq.). The resulting solution was stirred at room temperature for 1 hour. The solution was concentrated. The crude product was purified by Prep-HPLC (conditions: X Select CSH Prep C18 OBD Column, 5 um, 19*150 mm; Mobile Phase A: Water (0.1% FA), Mobile Phase B: ACN; Flow rate: 25 mL/min; Gradient: 15% B to 32% B in 8 min; 254 nm; Rt: 6.45 min) to afford N-[[2,6-dimethoxy-4-(2-methyl-1-oxo-1,2-dihydro-2,7-naphthyridin-4-yl)phenyl]methyl]-6-[[2-(2,6-dioxopiperidin-3-yl)-1,3-dioxo-2,3-dihydro-1H-isoindol-4-yl]oxy]-N-methylhexanamide (8.4 mg, 9.16%) as a yellow solid. $^1$H NMR (400 MHz, Methanol-d4) δ 9.54 (d, J=7.5 Hz, 1H), 8.71-8.64 (m, 1H), 7.84 (d, J=5.5 Hz, 1H), 7.79-7.70 (m, 1H), 7.74-7.63 (m, 1H), 7.47-7.33 (m, 2H), 6.76 (d, J=15.9 Hz, 2H), 5.08 (dd, J=12.5, 5.5 Hz, 1H), 4.76 (s, 1H), 4.69 (d, J=6.7 Hz, 1H), 4.24 (dt, J=11.6, 6.1 Hz, 2H), 3.89 (d, J=16.9 Hz, 6H), 3.71 (d, J=9.7 Hz, 3H), 2.88 (s, 3H), 2.70 (td, J=16.0, 14.2, 6.7 Hz, 4H), 2.11 (s, 1H), 1.90 (dt, J=14.7, 7.6 Hz, 2H), 1.80-1.57 (m, 4H). LCMS (ESI) m/z: [M+H]$^+$=710.30.

Example 57—Preparation of N-[8-[2-([[2,6-dimethoxy-4-(2-methyl-1-oxo-1,2-dihydro-2,7-naphthyridin-4-yl)phenyl]methyl](methyl)amino)acetamido]octyl]-2-[[2-(2,6-dioxopiperidin-3-yl)-1,3-dioxo-2,3-dihydro-1H-isoindol-4-yl]oxy]acetamide
(Compound D5)

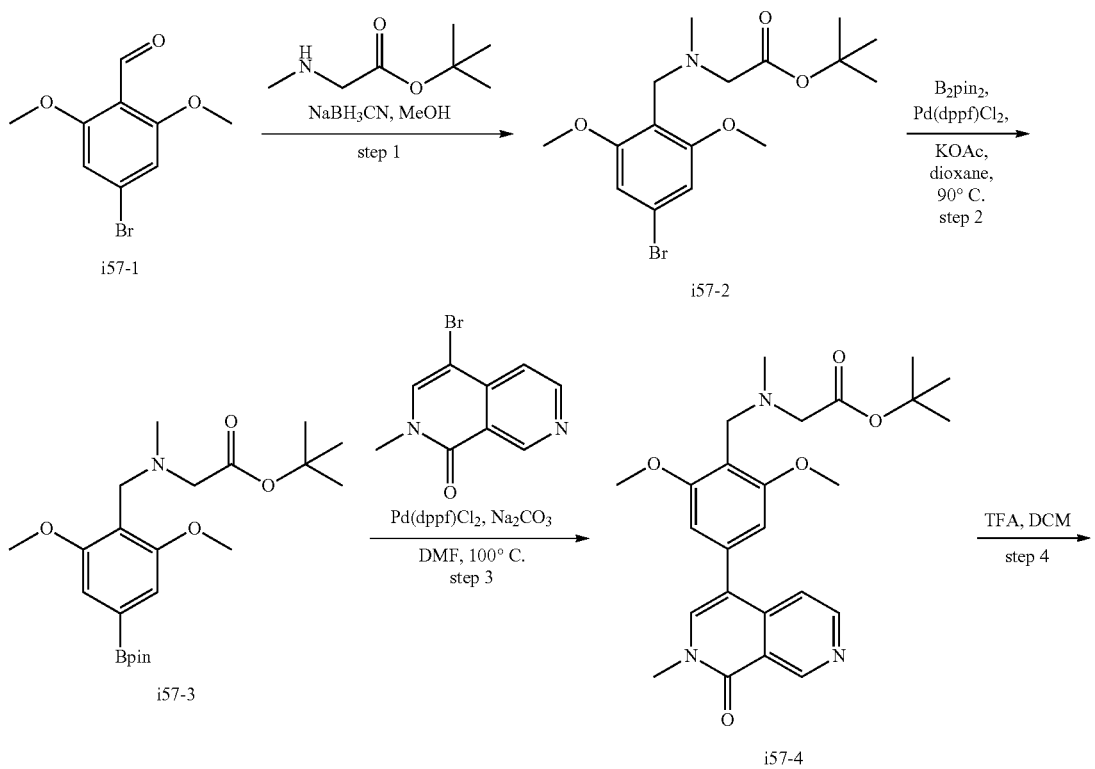

-continued

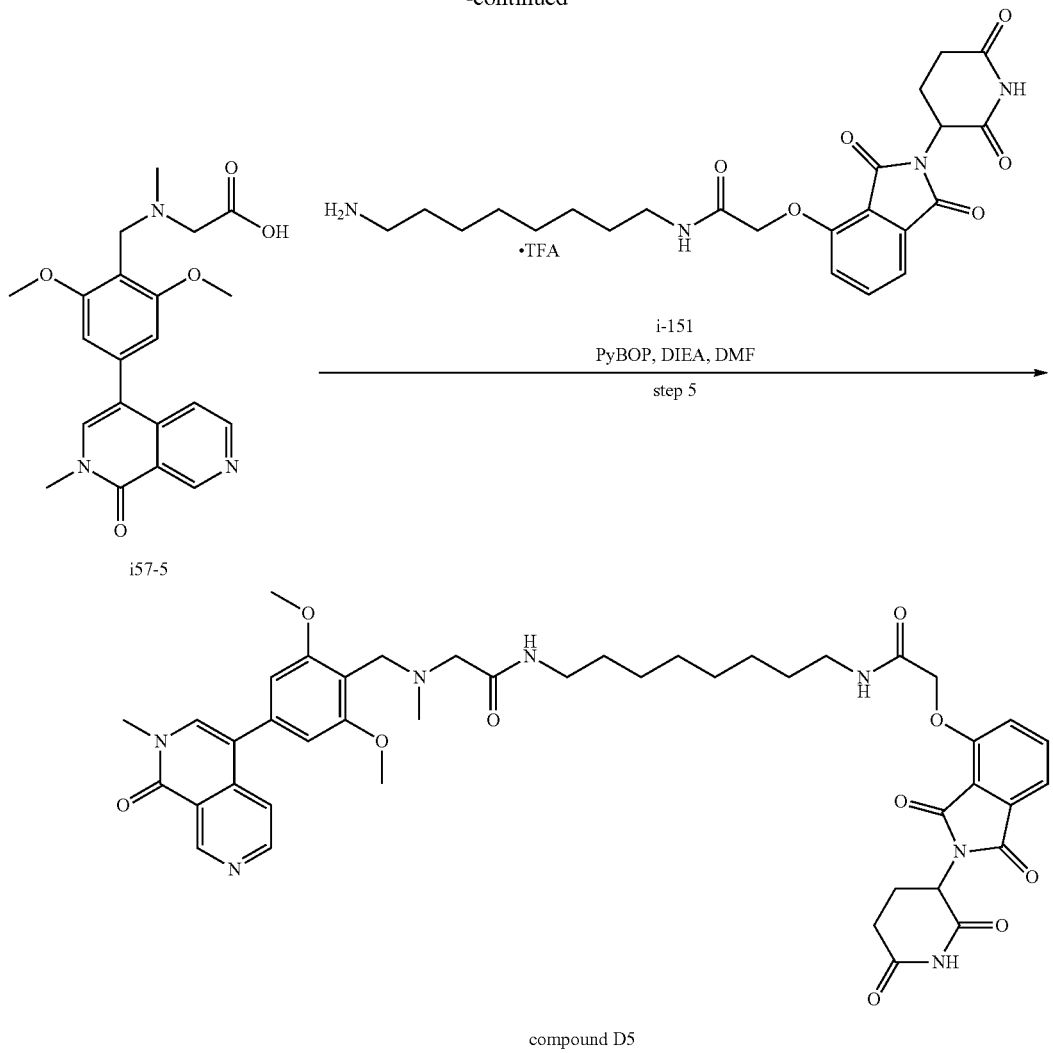

i-151
PyBOP, DIEA, DMF
step 5 compound D5

Step 1: preparation of tert-butyl 2-[[(4-bromo-2,6-dimethoxyphenyl)methyl](methyl)amino]acetate (i57-2)

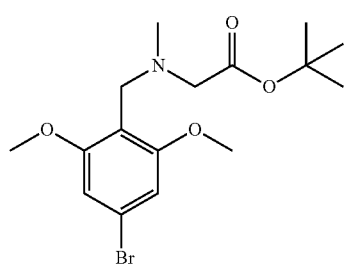

i57-2

To a stirred solution of tert-butyl 2-(methylamino)acetate hydrochloride (5.93 g, 32.643 mmol, 1.60 equiv) in MeOH (60 mL) was added 4-bromo-2,6-dimethoxybenzaldehyde (5 g, 20.402 mmol, 1 equiv), and the mixture was stirred for 30 minutes before NaBH$_3$CN (2.56 g, 40.737 mmol, 2.00 equiv) was added in portions. The resulting solution was stirred for another 3 hours at 25 degrees C. Then the mixture was concentrated. The residue was purified by silica gel column chromatography, eluted with EA/PE (1:1) to afford tert-butyl 2-[[(4-bromo-2,6-dimethoxyphenyl)methyl](methyl)amino]acetate (4.97 g, 65.09%) as a white solid. LCMS (ESI) m/z: [M+H]$^+$=374.

Step 2: Preparation of tert-butyl 2-([[2,6-dimethoxy-4-(4,4,5,5-tetramethyl-1,3,2-dioxaborolan-2-yl)phenyl]methyl] (methyl)amino)acetate (i57-3)

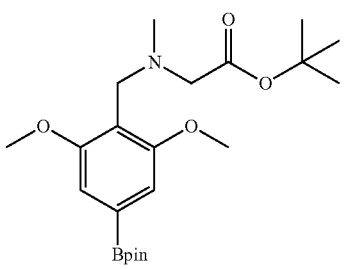

i57-3

To a stirred solution of tert-butyl 2-[[(4-bromo-2,6-dimethoxyphenyl)methyl](methyl)amino] acetate (4.5 g, 12.023 mmol, 1 equiv) and Pd(dppf)Cl$_2$·CH$_2$Cl$_2$ (981.87 mg, 1.202 mmol, 0.1 equiv) in 1,4-dioxane (60 mL) was added AcOK (3.6 g, 36.681 mmol, 3.05 equiv) and 4,4,5,5-tetramethyl-2-(4,4,5,5-tetramethyl-1,3,2-dioxaborolan-2-yl)-1,3,2-dioxaborol-ane (3.7 g, 14.570 mmol, 1.21 equiv). The mixture was stirred at 90 degrees C. under N$_2$ atmosphere for 3 hours. Then the reaction was cooled to room temperature and filtered. The filter cake was washed with EtOAc, and the filtrate was concentrated. The residue was used directly in the next step. LCMS (ESI) m/z: [M+H]$^+$=422.

Step 3: Preparation of tert-butyl 2-([[2,6-dimethoxy-4-(2-methyl-1-oxo-1,2-dihydro-2,7-naphthyridin-4-yl) phenyl]methyl](methyl)amino)acetate (i57-4)

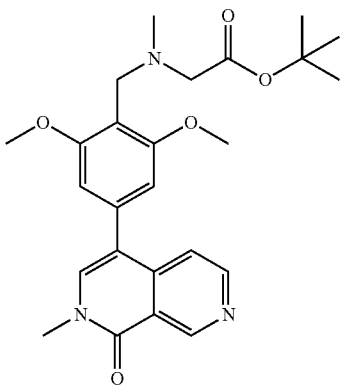

i57-4

To a stirred solution of tert-butyl 2-([[2,6-dimethoxy-4-(4,4,5,5-tetramethyl-1,3,2-dioxaborolan-2-yl)phenyl] methyl](methyl)amino)acetate (7.28 g, 17.278 mmol, 1 equiv) and Pd(dppf)Cl$_2$·CH$_2$Cl$_2$ (1.41 g, 1.728 mmol, 0.1 equiv) in 1,4-dioxane (80 mL)/H$_2$O (4 mL) was added Cs$_2$CO$_3$ (16.89 g, 51.835 mmol, 3 equiv) and 4-bromo-2-methyl-1,2-dihydro-2,7-naph-thyridin-1-one (4.13 g, 17.278 mmol, 1 equiv). The resulting mixture was stirred at 90 degrees C. under N$_2$ atmosphere for 3.5 hours. The resulting solution was concentrated, and the residue was purified by silica gel column chromatography, eluted with DCM/MeOH (0-10%) to afford tert-butyl 2-([[2,6-dimethoxy-4-(2-methyl-1-oxo-1,2-dihydro-2,7-naphthyridin-4-yl)phenyl] methyl](methyl)amino)acetate (4.43 g, 56.53%) as a yellow solid. LCMS (ESI) m/z: [M+H]$^+$=454.

Step 4: Preparation of 2-([[2,6-dimethoxy-4-(2-methyl-1-oxo-1,2-dihydro-2,7-naphthyridin-4-yl) phenyl]methyl] (methyl)amino)acetic acid (i57-5)

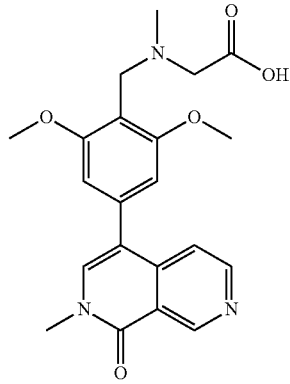

i57-5

A mixture of tert-butyl 2-([[2,6-dimethoxy-4-(2-methyl-1-oxo-1,2-dihydro-2,7-naphthyridin-4-yl)phenyl]methyl] (methyl)amino)acetate (4.23 g, 9.327 mmol, 1 equiv) in TFA (17 mL) and DCM (50 mL) was stirred for 17 hours at 25 degrees C. The resulting solution was concentrated, and the residue was purified by reverse flash chromatography (conditions: column, C18 silica gel; mobile phase, MeCN in water (0.1% FA), 10% to 50% gradient in 10 min; detector, UV 254 nm, to afford the 2-([[2,6-dimethoxy-4-(2-methyl-1-oxo-1,2-dihydro-2,7-naphthyridin-4-yl)phenyl]methyl] (methyl)amino)acetic acid (3.20 g, 86.48%) as a yellow solid. LCMS (ESI) m/z: [M+H]$^+$=398.

Step 5: Preparation of N-[8-[2-([[2,6-dimethoxy-4-(2-methyl-1-oxo-1,2-dihydro-2,7-naphthyridin-4-yl) phenyl]methyl](methyl)amino)acetamido]octyl]-2-[[2-(2,6-dioxopiperidin-3-yl)-1,3-dioxo-2,3-dihydro-1H-isoindol-4-yl]oxy]acetamide (Compound D5)

compound D5

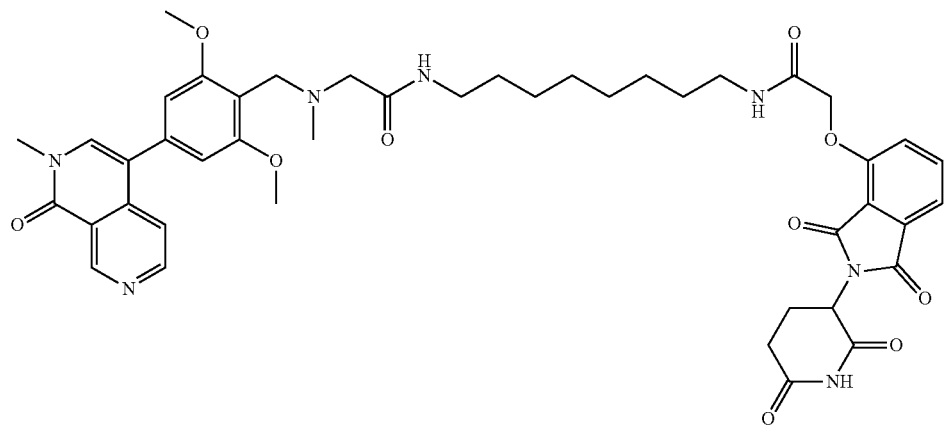

To a solution of 2-([[2,6-dimethoxy-4-(2-methyl-1-oxo-1,2-dihydro-2,7-naphthyridin-4-yl)phenyl]methyl](methyl)amino)acetic acid (20.82 mg, 0.052 mmol, 1 equiv) in DMF (1 mL) was added DIEA (20.32 mg, 0.157 mmol, 3 equiv), PyBOP (29.89 mg, 0.079 mmol, 1.50 equiv), and N-(8-aminooctyl)-2-[[2-(2,6-dioxopiperidin-3-yl)-1,3-dioxo-2,3-dihydro-1H-isoindol-4-yl]oxy]acetamide trifluoro-acetic acid (30 mg, 0.052 mmol, 1 equiv). The mixture was stirred for 2 hours at room temperature under ambient atmosphere. The resulting solution was purified by Prep-HPLC (conditions: XSelect CSH Prep C18 OBD Column, 5 um, 19*150 mm; Mobile Phase A: Water (0.1% FA), Mobile Phase B: ACN; Flow rate: 25 mL/min; Gradient: 20% B to 55% B in 8 min; 254 nm; Rt: 5.75 min) to afford N-[8-[2-([[2,6-dimethoxy-4-(2-methyl-1-oxo-1,2-dihydro-2,7-naphthyridin-4-yl)phenyl]methyl](methyl)amino)acetamido]octyl]-2-[[2-(2,6-dioxopiperidin-3-yl)-1,3-dioxo-2,3-dihydro-1H-isoindol-4-yl]oxy]acetamide (24.6 mg, 56.03%) as a white solid. $^1$H NMR (300 MHz, Methanol-d4) δ 9.50 (s, 1H), 8.68 (d, J=5.7 Hz, 1H), 7.87-7.72 (m, 2H), 7.63 (d, J=5.8 Hz, 1H), 7.54 (d, J=7.4 Hz, 1H), 7.41 (d, J=8.4 Hz, 1H), 6.79 (s, 2H), 5.13 (dd, J=12.4, 5.4 Hz, 1H), 4.73 (s, 2H), 3.92 (s, 8H), 3.70 (s, 3H), 3.29-3.20 (m, 6H), 2.93-2.71 (m, 3H), 2.50 (s, 3H), 2.120-2.10 (m, 1H), 1.52 (d, J=8.2 Hz, 4H), 1.32 (s, 8H). LCMS (ESI) m/z: [M+H]$^+$=838.35.

Example 58—Preparation of N-(8-((2-(2,6-dioxopiperidin-3-yl)-1,3-dioxoisoindolin-4-yl)amino)octyl)-2-(3-methoxy-5-(2-methyl-1-oxo-1,2-dihydro-2,7-naphthyridin-4-yl)phenoxy)acetamide (Compound 06)

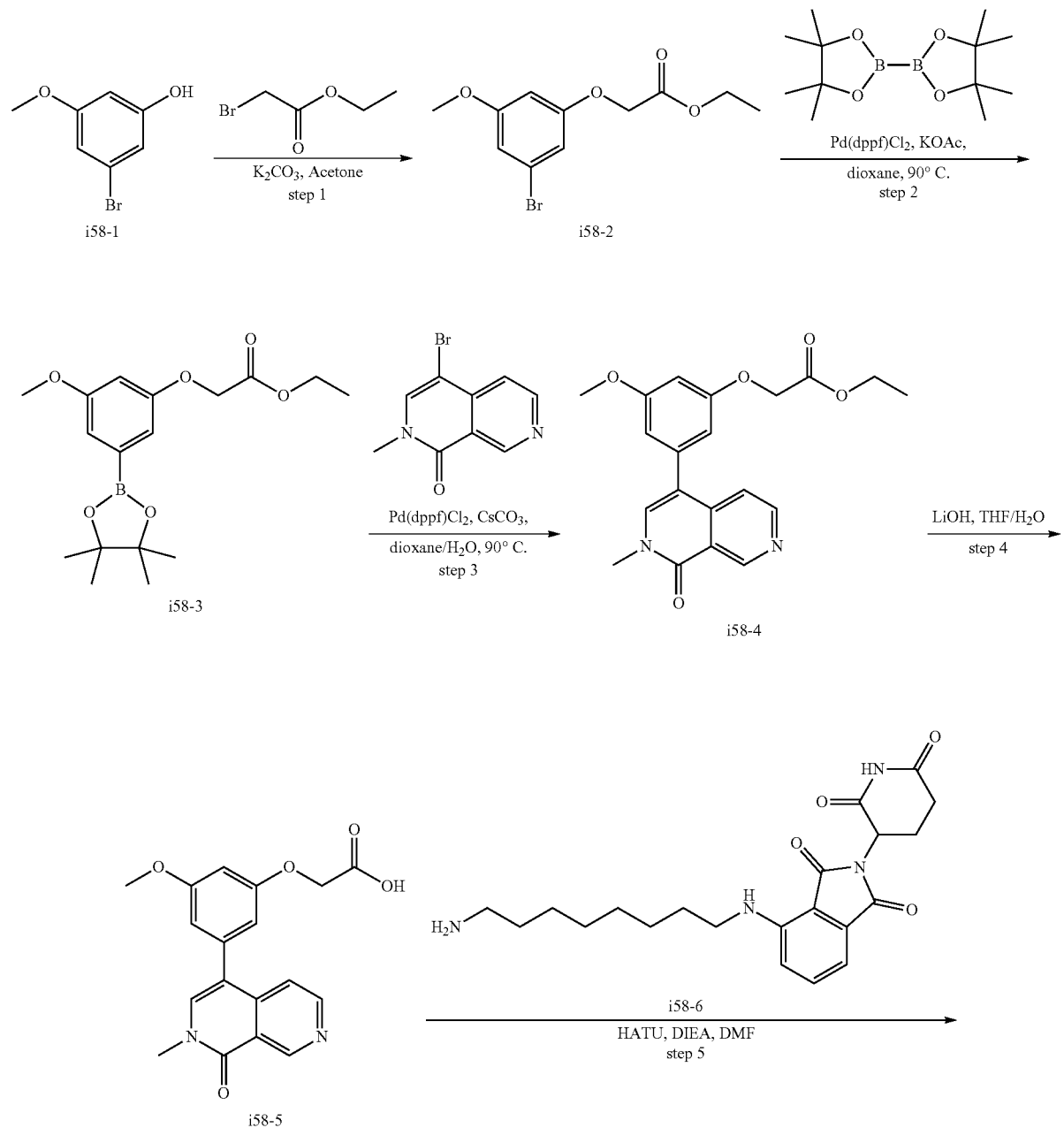

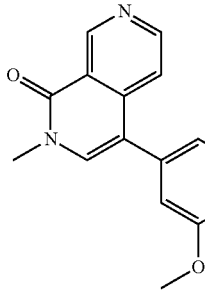

compound D6

Step 1: Preparation of ethyl 2-(3-bromo-5-methoxyphenoxy)acetate (i58-2)

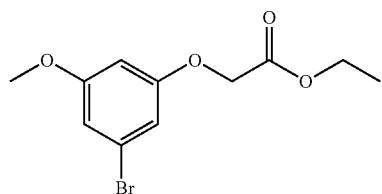

i58-2

To a solution of 3-bromo-5-methoxyphenol (1 g, 4.925 mmol, 1 equiv) and ethyl 2-bromoacetate (0.99 g, 5.928 mmol, 1.20 equiv) in acetone (10 mL, 136.021 mmol, 27.62 equiv) was added $K_2CO_3$ (1.36 g, 9.851 mmol, 2 equiv), and the resulting solution was stirred at 25° C. for 1 hour. After filtration, the filtrate was concentrated under reduced pressure. The residue was purified by silica gel column chromatography, eluted with EA/PE (1:4) to afford methyl 2-(3-bromo-5-methoxyphenoxy)acetate (1.23 g, 90.78%) as a colorless liquid. LCMS (ESI) m/z: [M+H]+=289.

Step 2: Preparation of ethyl 2-(3-methoxy-5-(4,4,5,5-tetramethyl-1,3,2-dioxaborolan-2-yl)phenoxy) acetate (i58-3)

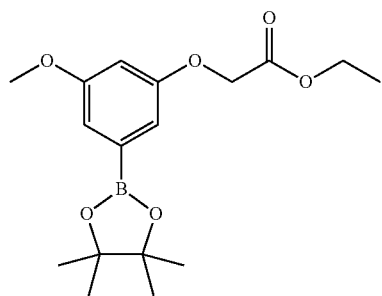

i58-3

To a solution of ethyl 2-(3-bromo-5-methoxyphenoxy)acetate (630 mg, 2.179 mmol, 1 equiv) and 4,4,5,5-tetramethyl-2-(4,4,5,5-tetramethyl-1,3,2-dioxaborolan-2-yl)-1,3,2-dioxaborolane (664.00 mg, 2.615 mmol, 1.2 equiv) in dioxane (6 mL) was added Pd(dppf)Cl₂ (159.44 mg, 0.218 mmol, 0.1 equiv) and KOAC (427.70 mg, 4.358 mmol, 2 equiv. The resulting solution was stirred at 90° C. for 2 hours (under $N_2$ atmosphere). After filtration, the filtrate was concentrated under reduced pressure. The residue was purified by silica gel column chromatography, eluted with EA/PE (1:4) to afford ethyl 2-[3-methoxy-5-(4,4,5,5-tetramethyl-1,3,2-dioxaborolan-2-yl)phenoxy]acetate (550 mg, 78.0%) as an off-white solid. LCMS (ESI) m/z: [M+H]+=337.

Step 3: Preparation of ethyl 2-(3-methoxy-5-(2-methyl-1-oxo-1,2-dihydro-2,7-naphthyridin-4-yl) phenoxy) acetate (i58-4)

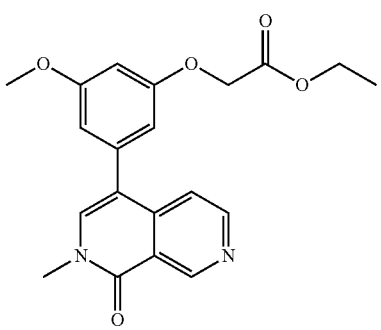

i58-4

To a solution of ethyl 2-[3-methoxy-5-(4,4,5,5-tetramethyl-1,3,2-dioxaborolan-2-yl)phenoxy]acetate (550 mg, 1.636 mmol, 1.40 equiv) and 4-bromo-2-methyl-1,2-dihydro-2,7-naphthyridin-1-one (280 mg, 1.171 mmol, 1 equiv) in dioxane (16 mL) and H₂O (4 mL) was added Cs₂CO₃ (763.20 mg, 2.342 mmol, 2 equiv) and Pd(dppf)Cl₂ (85.70 mg, 0.117 mmol, 0.1 equiv), and the resulting solution was stirred at 80° C. for 1 hour (under $N_2$ atmosphere). After filtration, the filtrate was concentrated under reduced pressure. The residue was purified by silica gel column chromatography, eluted with EA/PE (60:40) to afford ethyl 2-[3-methoxy-5-(2-methyl-1-oxo-1,2-dihydro-2,7-naphthyridin-4-yl)phenoxy]acetate (303 mg, 70.23%) as a brown solid. LCMS (ESI) m/z: [M+H]+=369.

Step 4: Preparation of 2-(3-methoxy-5-(2-methyl-1-oxo-1,2-dihydro-2,7-naphthyridin-4-yl)phenoxy) acetic acid (i58-5)

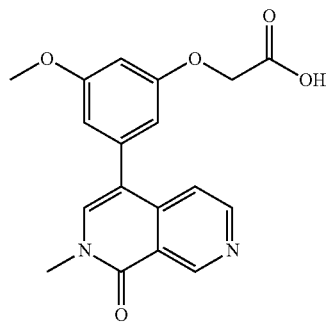

i58-5

A solution of ethyl 2-[3-methoxy-5-(2-methyl-1-oxo-1,2-dihydro-2,7-naphthyridin-4-yl)phenoxy]acetate (50 mg) in HCl (12 M, 2 mL) was stirred at 90° C. for 40 minutes. The resulting mixture was cooled and was concentrated under reduced pressure to give 2-[3-methoxy-5-(2-methyl-1-oxo-1,2-dihydro-2,7-naphthyridin-4-yl)phenoxy]acetic acid (86.8 mg) as an off-white solid, which was used directly without further purification. LCMS (ESI) m/z: [M+H]+=341.

Step 5: Preparation of N-(8-((2-(2,6-dioxopiperidin-3-yl)-1,3-dioxoisoindolin-4-yl)amino)octyl)-2-(3-methoxy-5-(2-methyl-1-oxo-1,2-dihydro-2,7-naphthyridin-4-yl)phenoxy)acetamide (Compound D6)

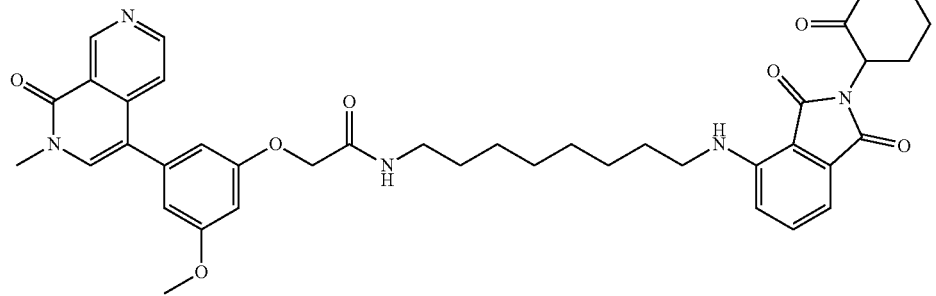

compound D6

To a solution of 2-[3-methoxy-5-(2-methyl-1-oxo-1,2-dihydro-2,7-naphthyridin-4-yl)phenoxy]acetic acid (42.49 mg, 0.125 mmol, 1.00 equiv) and 4-[(8-aminooctyl)amino]-2-(2,6-dioxopiperidin-3-yl)-2,3-dihydro-1H-isoindole-1,3-dione (50 mg, 0.125 mmol, 1 equiv) in DMF (2 mL) was added HATU (71.21 mg, 0.187 mmol, 1.50 equiv) and DIEA (96.82 mg, 0.749 mmol, 6.00 equiv). The resulting solution was stirred at 25° C. for 1 hour. The crude product was purified by Prep-HPLC (conditions: XBridge Prep C18 OBD Column, 5 μm, 19*150 mm; mobile phase, Water (0.1% FA) and ACN; Detector, uv 254 nm) to give N-(8-[[2-(2,6-dioxopiperidin-3-yl)-1,3-dioxo-2,3-dihydro-1H-isoindol-4-yl]amino]octyl)-2-[3-methoxy-5-(2-methyl-1-oxo-1,2-dihydro-2,7-naphthyridin-4-yl)phenoxy]acetamide (36 mg, 39.89%) as a yellow solid. 1H NMR (300 MHz, DMSO-d6) δ 11.10 (s, 1H), 9.46 (s, 1H), 8.72 (d, J=5.8 Hz, 1H), 8.08 (t, J=5.8 Hz, 1H), 7.88 (d, J=2.3 Hz, 1H), 7.57 (dd, J=8.6, 7.0 Hz, 2H), 7.08 (d, J=8.6 Hz, 1H), 7.01 (d, J=7.0 Hz, 1H), 6.64 (q, J=1.8 Hz, 3H), 6.51 (s, 1H), 5.05 (dd, J=12.8, 5.4 Hz, 1H), 4.52 (s, 2H), 3.80 (s, 3H), 3.59 (s, 3H), 3.27 (d, J=5.8 Hz, 2H), 3.12 (q, J=6.6 Hz, 2H), 2.98-2.80 (m, 1H), 2.65-2.52 (m, 2H), 2.11-1.98 (m, 1H), 1.55 (t, J=7.0 Hz, 2H), 1.40 (d, J=6.5 Hz, 2H), 1.24 (t, J=7.4 Hz, 8H); LCMS (ESI) m/z: [M+H]+=723.15.

Example 59—Preparation of 2-([[2,6-dimethoxy-4-(2-methyl-1-oxo-1,2-dihydro-2,7-naphthyridin-4-yl)phenyl]methyl](methyl)amino)-N-(5-[[2-(2,6-dioxopiperidin-3-yl)-1,3-dioxo-2,3-dihydro-1H-isoindol-4-yl]amino]pentyl)-N-methylacetamide formic acid (Compound D7 Formic Acid)
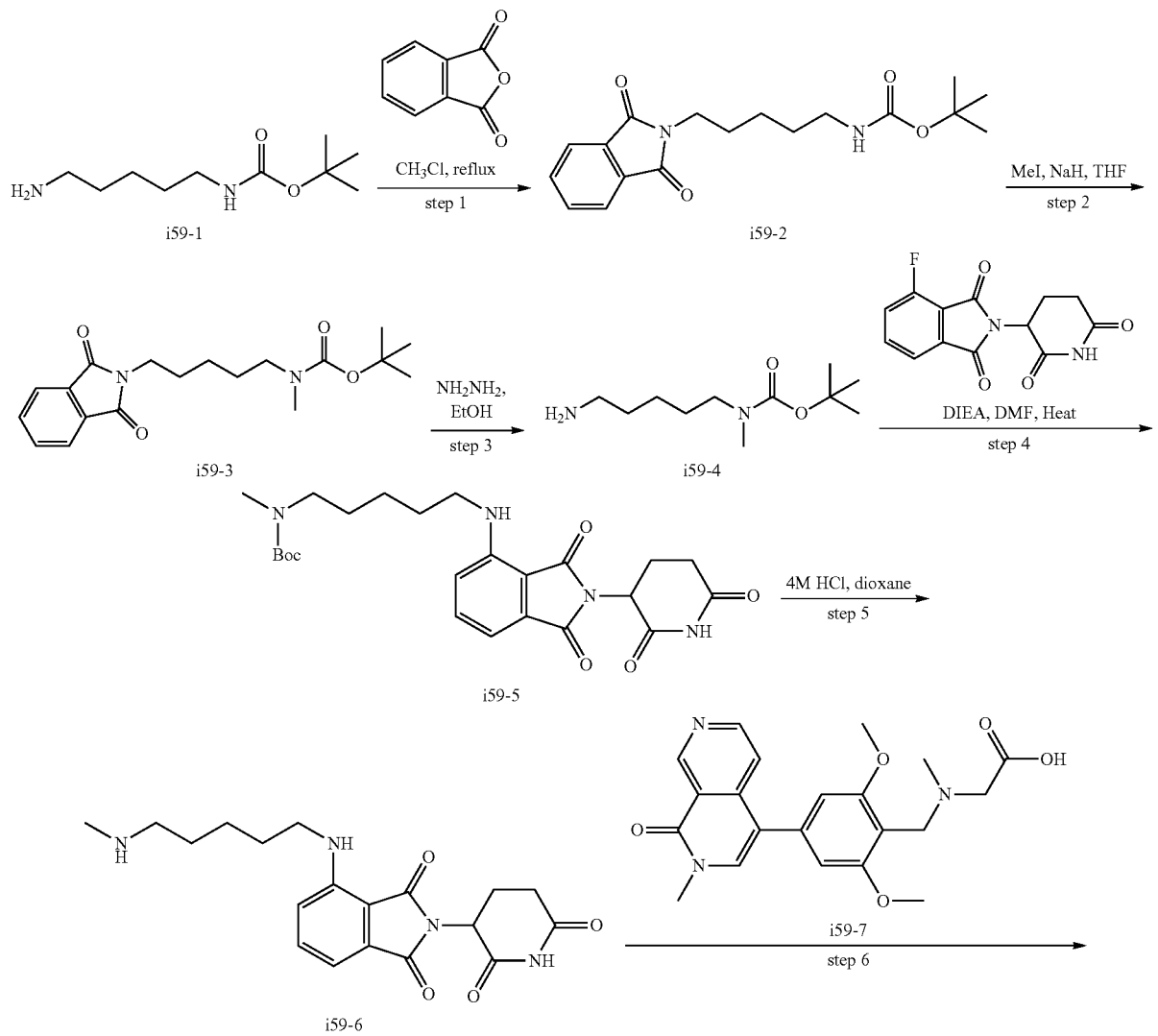
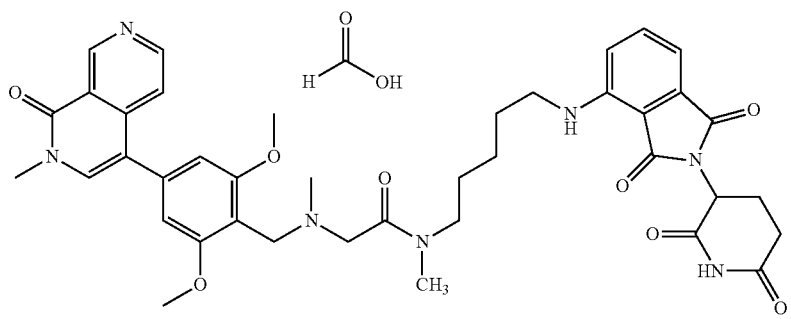
compound D7 formic acid Step 1: Preparation of tert-butyl N-[5-(1,3-dioxoisoindol-2-yl)pentyl]carbamate (i59-2)

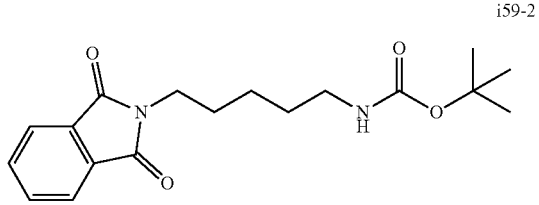 [SMILES: CC(C)(C)OC(=O)NCCCCCN1C(=O)c2ccccc2C1=O]

i59-2

A mixture of tert-butyl N-(5-aminopentyl)carbamate (4.00 g, 19.773 mmol, 1.00 equiv) and phthalic anhydride (3.22 g, 21.750 mmol, 1.1 equiv) in toluene (50.00 mL, 469.945 mmol, 23.77 equiv) was stirred at reflux for 3 hours. The solvent was removed under reduced pressure, and the crude product was purified by flash silica chromatography, elution gradient 0 to 40% EtOAc in petroleum ether. Pure fractions were evaporated to dryness to afford tert-butyl N-[5-(1,3-dioxoisoindol-2-yl)pentyl]carbamate (5.8 g, 88.25%) as a white solid. LCMS (ESI) m/z: $[M+H]^+$=333.

Step 2: Preparation of tert-butyl N-[5-(1,3-dioxoisoindol-2-yl)pentyl]-N-methylcarbamate (i59-3)

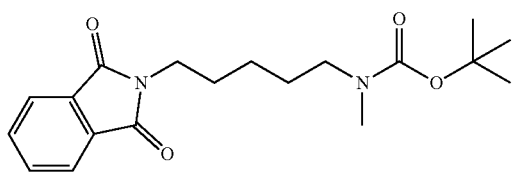

i59-3

To a solution of tert-butyl N-[5-(1,3-dioxoisoindol-2-yl)pentyl]carbamate (2.00 g, 6.017 mmol, 1.00 equiv) in DMF (30.00 mL) was added NaH (0.48 g, 12.034 mmol, 2.00 equiv, 60%) at 0° C., the resulting mixture was stirred at 0° C. for 30 minutes, and methyl iodide (1.28 g, 9 mmol, 1.50 equiv) was added to the reaction mixture at 0° C. After stirring at room temperature for 16 hours, and the reaction was quenched by the addition of water (50 mL) at 0° C. The mixture was extracted with EtOAc (100 mL×4). The organic layer was washed with water (100 mL) and saturated brine (100 mL), and then dried over anhydrous sodium sulfate, filtered, and concentrated to give crude product that was purified by flash silica chromatography, elution gradient 0 to 60% EtOAc in petroleum ether. Pure fractions were evaporated to dryness to afford tert-butyl N-[5-(1,3-dioxoisoindol-2-yl)pentyl]-N-methylcarbamate (1.8 g, 86.36%) as a colorless oil. LCMS (ESI) m/z: $[M+H]^+$=347.

Step 3: Preparation of tert-butyl N-(5-aminopentyl)-N-methylcarbamate (i59-4)

i59-4

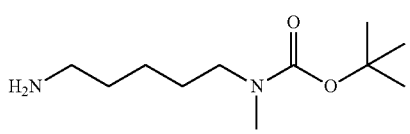

A mixture of tert-butyl N-[5-(1,3-dioxoisoindol-2-yl)pentyl]-N-methylcarbamate (1.00 g, 2.887 mmol, 1.00 equiv) and $NH_2NH_2 \cdot H_2O$ (0.36 g, 0.006 mmol, 2.00 equiv, 80%) in EtOH (10.00 mL) was stirred at reflux for 1 hour. The solid was filtered out, and the filtrate was concentrated under reduced pressure to afford tert-butyl N-(5-aminopentyl)-N-methylcarbamate (372 mg, 59.57%) as a yellow oil that was used directly without further purification. LCMS (ESI) m/z: $[M+H]^+$=217.

Step 4: Preparation of N-(5-[[2-(2,6-dioxopiperidin-3-yl)-1,3-dioxoisoindol-4-yl]amino]pentyl)-N-methylcarbamate (i59-5)

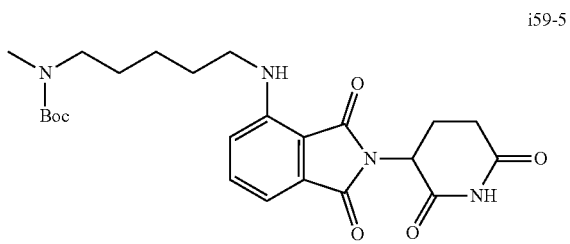 [SMILES: CN(CCCCCNc1cccc2c1C(=O)N(C1CCC(=O)NC1=O)C2=O)C(=O)OC(C)(C)C]

i59-5

To a solution of tert-butyl N-(5-aminopentyl)-N-methylcarbamate (215.37 mg, 0.996 mmol, 1.10 equiv) and 2-(2,6-dioxopiperidin-3-yl)-4-fluoroisoindole-1,3-dione (250.00 mg, 0.905 mmol, 1.00 equiv) in NMP (3.00 mL) was added DIEA (233.95 mg, 1.810 mmol, 2.00 equiv). The resulting mixture was stirred at 90° C. for 4 hours. The reaction mixture was diluted with EA (50 mL). The resulting mixture was washed with water (3×30 mL) and saturated brine (30 mL). The organic layer was dried over $Na_2SO_4$, filtered, and evaporated to afford crude product. The crude product was purified by flash silica chromatography, elution gradient 0 to 75% EtOAc in petroleum ether. Pure fractions were evaporated to dryness to afford tert-butyl N-(5-[[2-(2,6-dioxopiperidin-3-yl)-1,3-dioxoisoindol-4-yl]amino]pentyl)-N-methylcarbamate (198 mg, 46.30%) as a yellow oil. LCMS (ESI) m/z: $[M+H]^+$=473.

Step 5: Preparation of 2-(2,6-dioxopiperidin-3-yl)-4-[[5-(methylamino)pentyl]amino]isoindole-1,3-dione (i59-6)

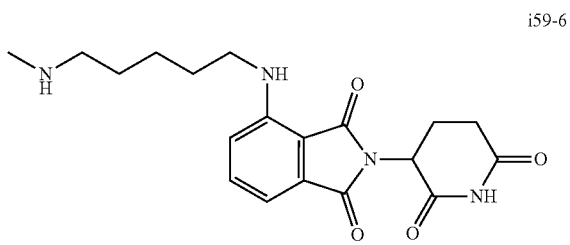 [SMILES: CNCCCCCNc1cccc2c1C(=O)N(C1CCC(=O)NC1=O)C2=O]

i59-6

A solution of tert-butyl N-(5-[[2-(2,6-dioxopiperidin-3-yl)-1,3-dioxoisoindol-4-yl]amino]pentyl)-N-methylcarbamate (198.00 mg) in a solution of HCl in 1,4-dioxane (5.00 mL, 4 M) was stirred at room temperature for 1 hour. The solvent was removed under reduced pressure to afford 2-(2,6-dioxopiperidin-3-yl)-4-[[5-(methylamino)pentyl]amino]isoindole-1,3-dione (153 mg, 97.8%) as a yellow solid that was used directly without further purification. LCMS (ESI) m/z: $[M+H]^+$=373.

Step 6: Preparation of 2-([[2,6-dimethoxy-4-(2-methyl-1-oxo-1,2-dihydro-2,7-naphthyridin-4-yl)phenyl]methyl](methyl)amino)-N-(5-[[2-(2,6-dioxopiperidin-3-yl)-1,3-dioxo-2,3-dihydro-1H-isoindol-4-yl]amino]pentyl)-N-methylacetamide formic acid (Compound D7 Formic Acid)

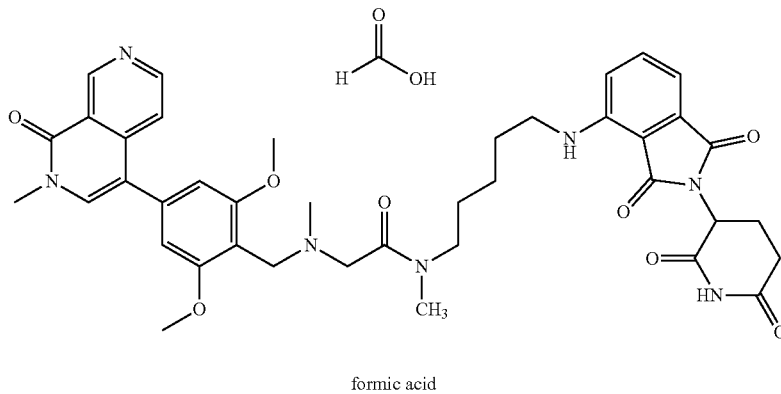

compound D7 formic acid

To a solution of 2-(2,6-dioxopiperidin-3-yl)-4-[[5-(methylamino)pentyl]amino]-2,3-dihydro-1H-isoindole-1,3-dione (60.00 mg, 0.161 mmol, 1.00 equiv), 2-([[2,6-dimethoxy-4-(2-methyl-1-oxo-1,2-dihydro-2,7-naphthyridin-4-yl)phenyl]methyl](methyl)amino)acetic acid (64.03 mg, 0.161 mmol, 1.00 equiv), and DIEA (41.64 mg, 0.322 mmol, 2.00 equiv) in DMF (1.00 mL) was added HATU (91.89 mg, 0.242 mmol, 1.50 equiv). The resulting mixture was stirred at room temperature for 16 hours. The crude product (mg) was purified by Prep-HPLC (conditions: XBridge Shield RP18 OBD Column, 5 μm, 19*150 mm; Mobile Phase A: Water (0.1% FA), Mobile Phase B: ACN; Flow rate: 25 mL/minute; Gradient: 10% B to 40% B in 8 minutes; 254/220 nm; $R_t$: 7.32 minutes) to afford 2-([[2,6-dimethoxy-4-(2-methyl-1-oxo-1,2-dihydro-2,7-naphthyridin-4-yl)phenyl]methyl](methyl)amino)-N-(5-[[2-(2,6-dioxopiperidin-3-yl)-1,3-dioxo-2,3-dihydro-1H-isoindol-4-yl]amino]pentyl)-N-methylacetamide formic acid (99.4 mg) as a yellow solid. $^1$H NMR (400 MHz, Methanol-d4) δ 9.51 (s, 0.5H), 9.41 (s, 0.5H), 8.67 (dd, J=14.1, 5.7 Hz, 1H), 8.55 (s, 0.28H, FA), 7.74 (d, J=15.6 Hz, 1H), 7.63 (dd, J=18.0, 5.8, 1H), 7.51 (dd, J=8.6, 7.1 Hz, 0.5H), 7.30 (dd, J=8.5, 7.1 Hz, 0.5H), 7.00 (dd, J=7.9, 3.5 Hz, 1H), 6.92 (d, J=7.0 Hz, 1H), 6.78 (d, J=17.9 Hz, 2H), 5.05 (dd, J=12.8, 5.6, 1H), 4.23 (s, 1H), 3.91 (d, J=5.4 Hz, 8H), 3.86 (s, 1.5H), 3.70 (s, 1.5H), 3.61 (s, 2H), 3.49-3.41 (m, 1H), 3.30 (s, 1H), 3.13 (d, J=6.8 Hz, 1H), 3.02 (s, 1.5H), 2.93 (s, 1.5H), 2.89-2.80 (m, 1H), 2.80-2.71 (m, 4H), 2.54 (s, 2H), 2.12 (td, J=8.0, 2.7 Hz, 1H), 1.76-1.53 (m, 4H), 1.45 (q, J=8.1 Hz, 1H), 1.22 (d, J=7.9 Hz, 1H). LCMS (ESI) m/z: [M+H]$^+$=752.20.

Example 60—Preparation of 2-cyclopropyl-4-[3,5-dimethoxy-4-[(methylamino)methyl]phenyl]-2,7-naphthyridin-1-one (Compound D8)

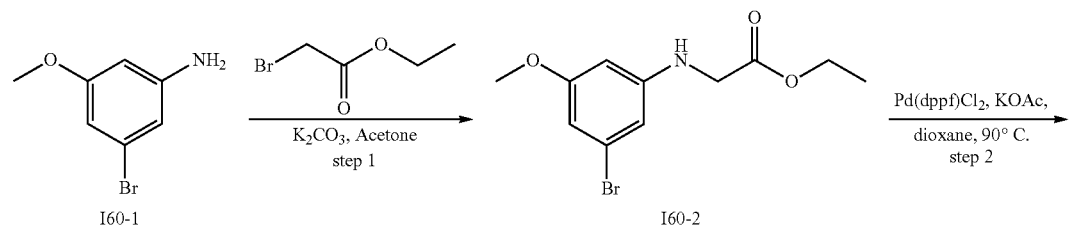

251

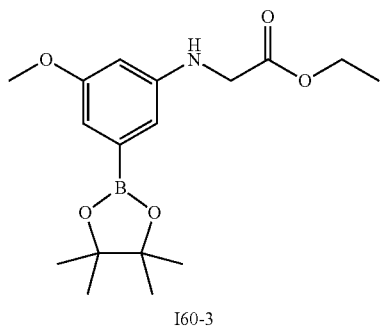

I60-3

252

-continued

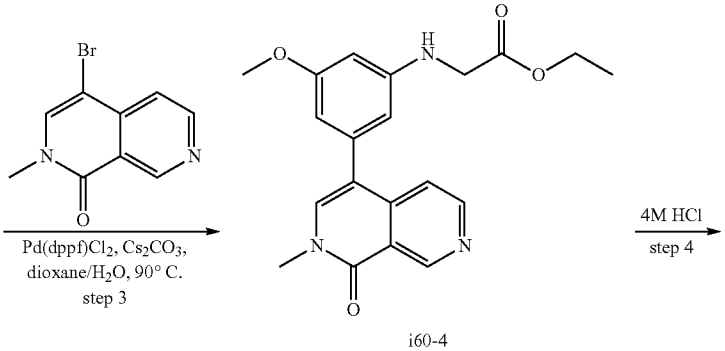

i60-4

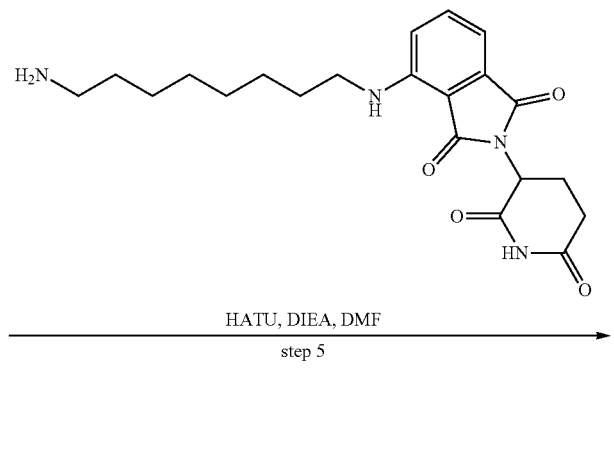

I60-5

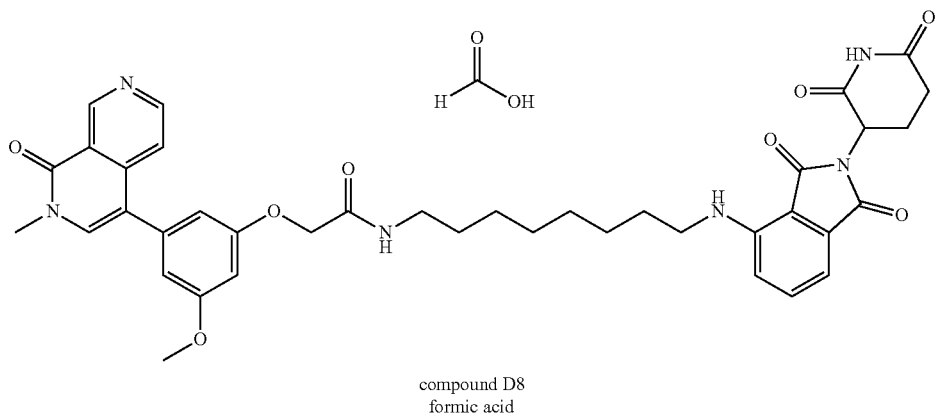

compound D8
formic acid

Step 1: Preparation of ethyl 2-[(3-bromo-5-methoxyphenyl)amino]acetate (i60-2)

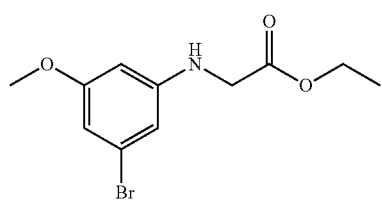

I60-2

To a solution of 3-bromo-5-methoxyaniline (5.00 g, 24.746 mmol, 1.00 equiv) and $K_2CO_3$ (5.13 g, 37.119 mmol, 1.50 equiv) in acetone (100.00 mL) was added ethyl bromoacetate (4.96 g, 29.695 mmol, 1.20 equiv). The resulting mixture was stirred at reflux for 3 days. The reaction mixture was filtered, and the filtrate was evaporated to afford crude product. The crude product was purified by flash silica chromatography, elution gradient 0 to 30% EtOAc in petroleum ether. Pure fractions were evaporated to dryness to afford ethyl 2-[(3-bromo-5-methoxyphenyl)amino]acetate (1.8 g, 25.24%) as a yellow gum. LCMS (ESI) m/z: [M+H]+=288.

Step 2: Preparation of 2-[[3-methoxy-5-(4,4,5,5-tetramethyl-1,3,2-dioxaborolan-2-yl)phenyl]amino]acetate (i60-3)

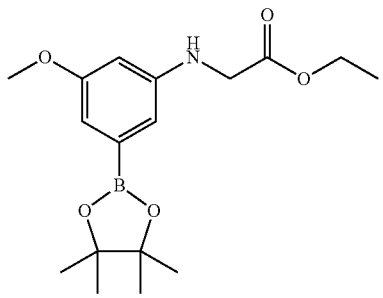

i60-3

To a solution of bis(pinacolato)diboron (528.78 mg, 2.082 mmol, 1.2 equiv), ethyl 2-[(3-bromo-5-methoxyphenyl)amino]acetate (500.00 mg, 1.735 mmol, 1.00 equiv) and KOAc (340.61 mg, 3.471 mmol, 2 equiv) in dioxane (10.00 mL) was added Pd(dppf)Cl$_2$ (126.97 mg, 0.174 mmol, 0.1 equiv). The resulting mixture was stirred at 90° C. for 2 hours under a nitrogen atmosphere. The resulting mixture was diluted with ethyl acetate (100 mL), washed with water (3×100 mL) and saturated brine (100 mL). The organic layer was dried over Na$_2$SO$_4$, filtered, and evaporated to afford crude product. The crude product was purified by flash silica chromatography, elution gradient 0 to 50% EtOAc in petroleum ether. Pure fractions were evaporated to dryness to afford ethyl 2-[[3-methoxy-5-(4,4,5,5-tetramethyl-1,3,2-dioxaborolan-2-yl)phenyl]amino]acetate (365 mg, 62.75%) as a yellow gum. LCMS (ESI) m/z: [M+H]+=336.

Step 3: Preparation of 2-[[3-methoxy-5-(2-methyl-1-oxo-2,7-naphthyridin-4-yl)phenyl]amino]acetate (i60-4)

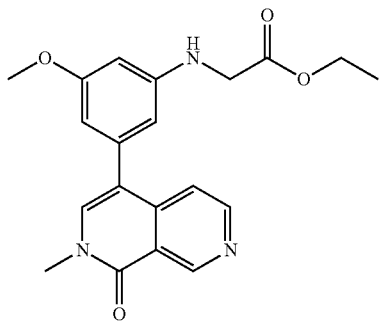

i60-4

To a solution of ethyl 2-[[3-methoxy-5-(4,4,5,5-tetramethyl-1,3,2-dioxaborolan-2-yl)phenyl]amino]acetate (100.00 mg, 0.298 mmol, 1.00 equiv), 4-bromo-2-methyl-2,7-naphthyridin-1-one (71.32 mg, 0.298 mmol, 1.00 equiv) and Cs$_2$CO$_3$ (194.40 mg, 0.597 mmol, 2.00 equiv) in dioxane (4.00 mL) and H$_2$O (1.00 mL) was added Pd(dppf)Cl$_2$ (21.83 mg, 0.030 mmol, 0.10 equiv). The resulting mixture was stirred at 80° C. for 2 hours under a nitrogen atmosphere. The reaction mixture was diluted with EA (100 mL) and washed with water (3×100 mL) and saturated brine (100 mL) The organic layer was dried over Na$_2$SO$_4$, filtered, and evaporated to afford crude product. The crude product was purified by flash silica chromatography, elution gradient 0 to 80% EtOAc in petroleum ether. Pure fractions were evaporated to dryness to afford ethyl 2-[[3-methoxy-5-(2-methyl-1-oxo-2,7-naphthyridin-4-yl)phenyl]amino]acetate (70 mg, 63.87%) as a brown solid. LCMS (ESI) m/z: [M+H]+=368.

Step 4: Preparation of [[3-methoxy-5-(2-methyl-1-oxo-2,7-naphthyridin-4-yl)phenyl]amino]acetic acid (i60-5)

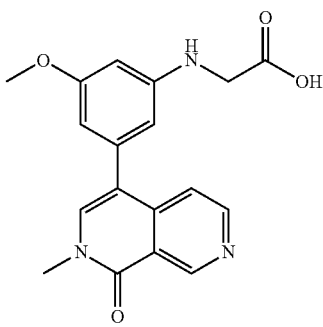

i60-5

Ethyl 2-[[3-methoxy-5-(2-methyl-1-oxo-2,7-naphthyridin-4-yl)phenyl]amino]acetate (70.00 mg, 0.191 mmol, 1.00 equiv) was added to a solution of HCl in water (2.00 mL, 12 N). The resulting mixture was stirred at 90° C. for 1 hour. The solvent was removed to afford [[3-methoxy-5-(2-methyl-1-oxo-2,7-naphthyridin-4-yl)phenyl]amino]acetic acid (65 mg) as a brown solid that was used directly without further purification. LCMS (ESI) m/z: [M+H]+=340.

Step 5: Preparation of N-(8-[[2-(2,6-dioxopiperidin-3-yl)-1,3-dioxo-2,3-dihydro-1H-isoindol-4-yl]amino]octyl)-2-[[3-methoxy-5-(2-methyl-1-oxo-1,2-dihydro-2,7-naphthyridin-4-yl)phenyl]amino]acetamide formic acid (Compound D8 Formic Acid)

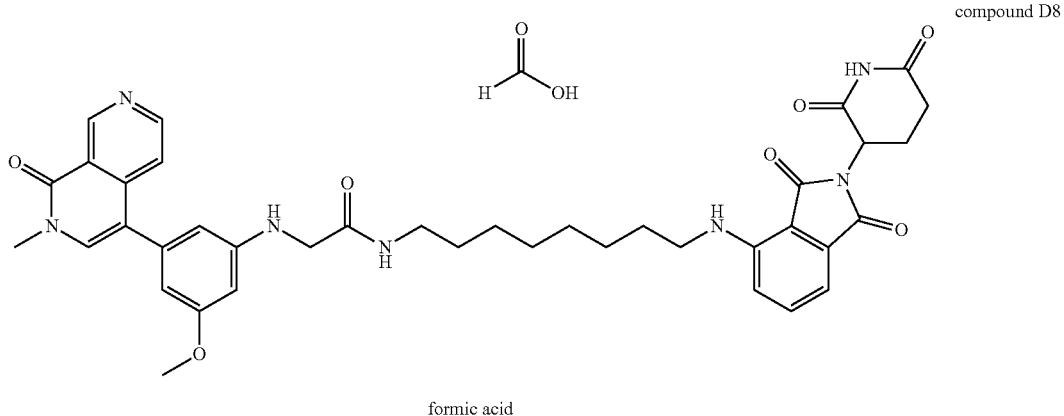 [SMILES: COc1cc(NCC(=O)NCCCCCCCCNc2cccc3c2C(=O)N(C2CCC(=O)NC2=O)C3=O)cc(-c2cn(C)c(=O)c3cnccc23)c1 ; O=CO]

compound D8 formic acid

To a solution of 2-[[3-methoxy-5-(2-methyl-1-oxo-1,2-dihydro-2,7-naphthyridin-4-yl)phenyl]amino]acetic acid (65.00 mg, 0.192 mmol, 1.00 equiv), 4-[(8-aminooctyl)amino]-2-(2,6-dioxopiperidin-3-yl)-2,3-dihydro-1H-isoindole-1,3-dione (76.71 mg, 0.192 mmol, 1.00 equiv) and DIEA (49.51 mg, 0.383 mmol, 2.00 equiv) in DMF (1.00 mL, 12.922 mmol, 67.46 equiv) was added HATU (109.25 mg, 0.287 mmol, 1.50 equiv). The resulting mixture was stirred at room temperature for 16 hours. The crude product was purified by Prep-HPLC (conditions: XBridge Shield RP18 OBD Column 30*150 mm, 5 μm; Mobile Phase A: Water (0.1% FA), Mobile Phase B: ACN; Flow rate: 40 mL/minute; Gradient: 18% B to 18% B in 2 minutes; 254/220 nm; Rt: 11.43 minutes) to afford N-(8-[[2-(2,6-dioxopiperidin-3-yl)-1,3-dioxo-2,3-dihydro-1H-isoindol-4-yl]amino]octyl)-2-[[3-methoxy-5-(2-methyl-1-oxo-1,2-dihydro-2,7-naphthyridin-4-yl)phenyl]amino]acetamide formic acid (36.8 mg) as a yellow solid. $^1$H NMR (400 MHz, Methanol-d4) δ 9.49 (d, J=0.8 Hz, 1H), 8.64 (d, J=5.9 Hz, 1H), 7.94 (t, J=6.0 Hz, 1H), 7.73-7.67 (m, 2H), 7.51 (dd, J=8.6, 7.1 Hz, 1H), 6.99 (s, 1H), 6.99 (dd, J=16.0, 7.8 Hz, 2H), 6.36 (t, J=1.8 Hz, 1H), 6.26 (d, J=1.8 Hz, 2H), 5.06 (dd, J=12.5, 5.4 Hz, 1H), 3.79 (d, J=7.7 Hz, 5H), 3.67 (s, 3H), 3.24 (dt, J=8.4, 6.5 Hz, 4H), 2.87 (ddd, J=17.7, 14.1, 5.0 Hz, 1H), 2.81-2.64 (m, 2H), 2.17-2.07 (m, 1H), 1.60 (p, J=7.0 Hz, 2H), 1.47 (d, J=13.8 Hz, 2H), 1.34 (d, J=7.2 Hz, 2H), 1.25 (s, 6H). LCMS (ESI) m/z: [M+H]$^+$=722.30.

Example 61—Preparation of 2-(2-((dimethylamino)methyl)-3-methoxy-5-(2-methyl-1-oxo-1,2-dihydro-2,7-naphthyridin-4-yl)phenoxy)-N-(8-((2-(2,6-dioxopiperidin-3-yl)-1,3-dioxoisoindolin-4-yl)amino)octyl)acetamide (Compound D9)

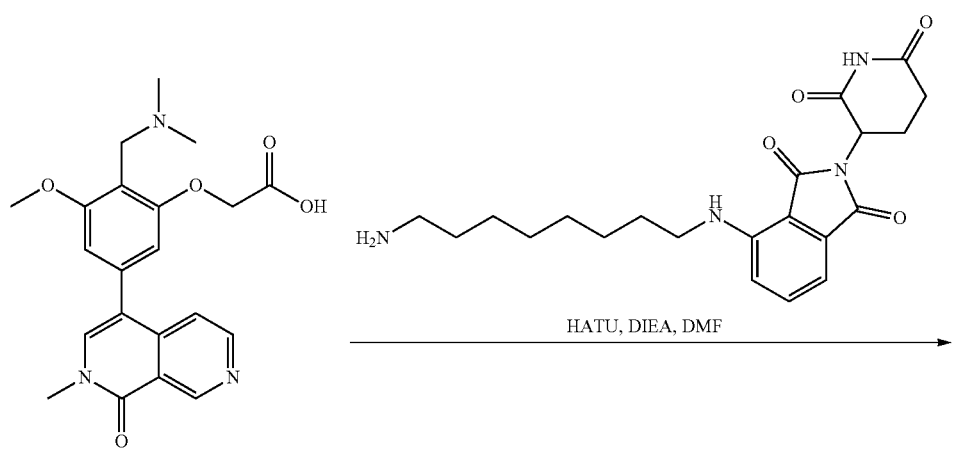

HATU, DIEA, DMF

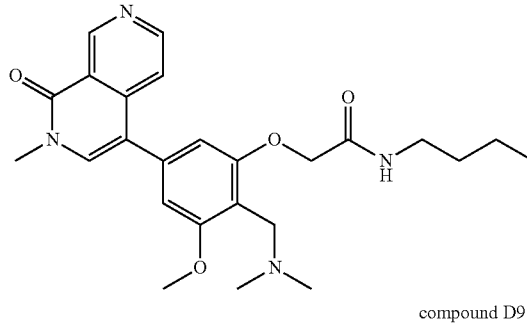

compound D9

Compound D9 was prepared in a similar manner as described for compound D8. 2-(2-((dimethylamino)methyl)-3-methoxy-5-(2-methyl-1-oxo-1,2-dihydro-2,7-naphthyridin-4-yl)phenoxy)-N-(8-((2-(2,6-dioxopiperidin-3-yl)-1,3-dioxoisoindolin-4-yl)amino)octyl)acetamide (17.8 mg, 11.3%) was obtained as a yellow solid. $^{1}$H NMR (400 MHz, Methanol-d4) δ 9.52 (s, 1H), 8.67 (d, J=5.8 Hz, 1H), 8.56 (s, 0.83H, FA), 7.75 (s, 1H), 7.60-7.50 (m, 2H), 7.02 (dd, J=9.5, 7.8 Hz, 2H), 6.90 (d, J=1.3 Hz, 1H), 6.78 (d, J=1.3 Hz, 1H), 5.06 (dd, J=12.5, 5.4 Hz, 1H), 4.81 (s, 2H), 4.29 (s, 2H), 3.96 (s, 3H), 3.68 (s, 3H), 3.27 (dt, J=14.0, 6.9 Hz, 4H), 2.87-2.65 (m, 9H), 2.12 (dtd, J=13.0, 5.0, 2.3 Hz, 1H), 1.61 (p, J=6.9 Hz, 2H), 1.48 (t, J=6.9 Hz, 2H), 1.37 (t, J=7.6 Hz, 2H), 1.27 (d, J=3.8 Hz, 6H). LCMS (ESI) m/z: [M+H]+=780.40.

Example 62—Preparation of 2-(2,3-dimethoxy-5-(2-methyl-1-oxo-1,2-dihydro-2,7-naphthyridin-4-yl)phenoxy)-N-(8-((2-(2,6-dioxopiperidin-3-yl)-1,3-dioxoisoindolin-4-yl)amino)octyl)acetamide (Compound D10)

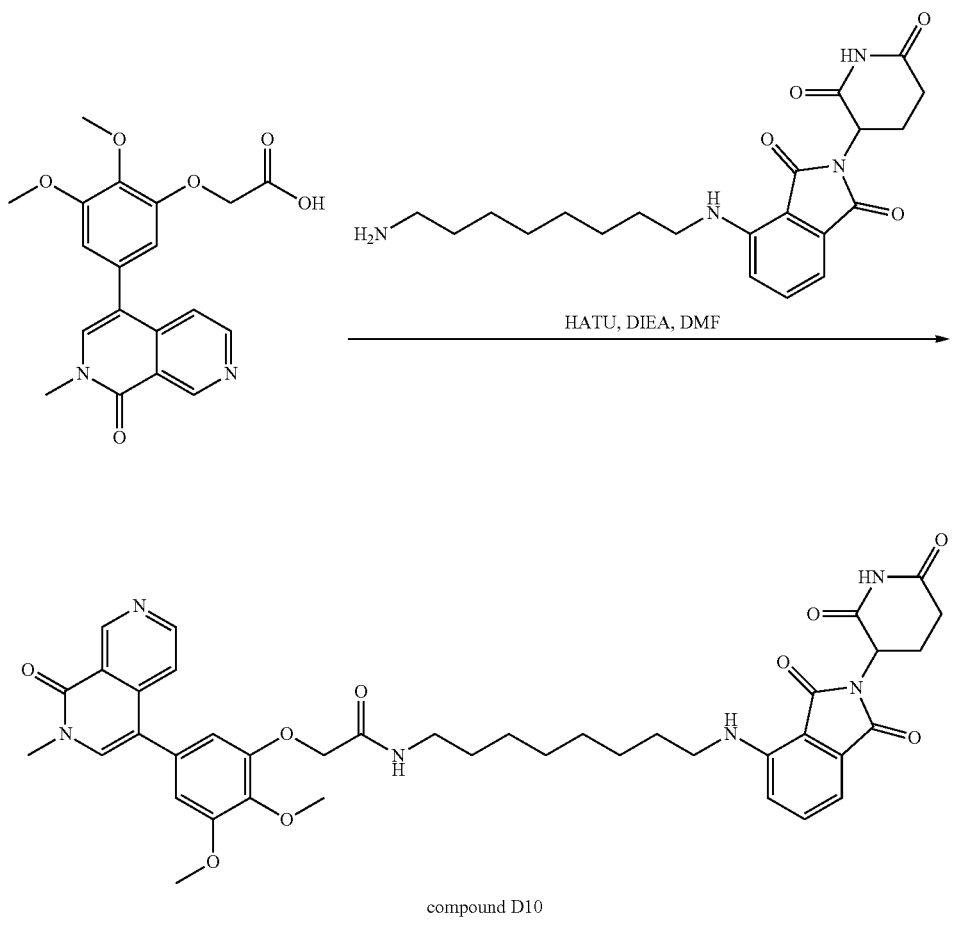

compound D10

Compound D10 was prepared in a similar manner as described for compound D8. 2-(2,3-dimethoxy-5-(2-methyl-1-oxo-1,2-dihydro-2,7-naphthyridin-4-yl)phenoxy)-N-(8-((2-(2,6-dioxopiperidin-3-yl)-1,3-dioxoisoindolin-4-yl)amino)octyl)acetamide (32.7 mg, 32.17%) was obtained as a yellow solid. $^1$H NMR (400 MHz, Methanol-d4) δ 9.51 (s, 1H), 8.67 (d, J=5.9 Hz, 1H), 7.73 (s, 1H), 7.63 (d, J=5.9 Hz, 1H), 7.53 (dd, J=8.6, 7.1 Hz, 1H), 7.00 (dd, J=12.0, 7.8 Hz, 2H), 6.85 (d, J=1.9 Hz, 1H), 6.77 (d, J=1.9 Hz, 1H), 5.06 (dd, J=12.5, 5.4 Hz, 1H), 4.62 (s, 2H), 3.92 (d, J=2.9 Hz, 6H), 3.68 (s, 3H), 3.28 (q, J=6.9 Hz, 4H), 2.92-2.65 (m, 3H), 2.16-2.03 (m, 1H), 1.62 (p, J=6.9 Hz, 2H), 1.53 (t, J=7.0 Hz, 2H), 1.38 (d, J=8.0 Hz, 2H), 1.31 (s, 8H). LCMS (ESI) m/z: [M+H]+=753.35.

Example 63—Preparation of N-[[2,6-dimethoxy-4-(2-methyl-1-oxo-1,2-dihydro-2,7-naphthyridin-4-yl)phenyl]methyl]-4-[[2-(2,6-dioxopiperidin-3-yl)-1,3-dioxo-2,3-dihydro-1H-isoindol-4-yl]oxy]-N-methylbutanamide (Compound D11)

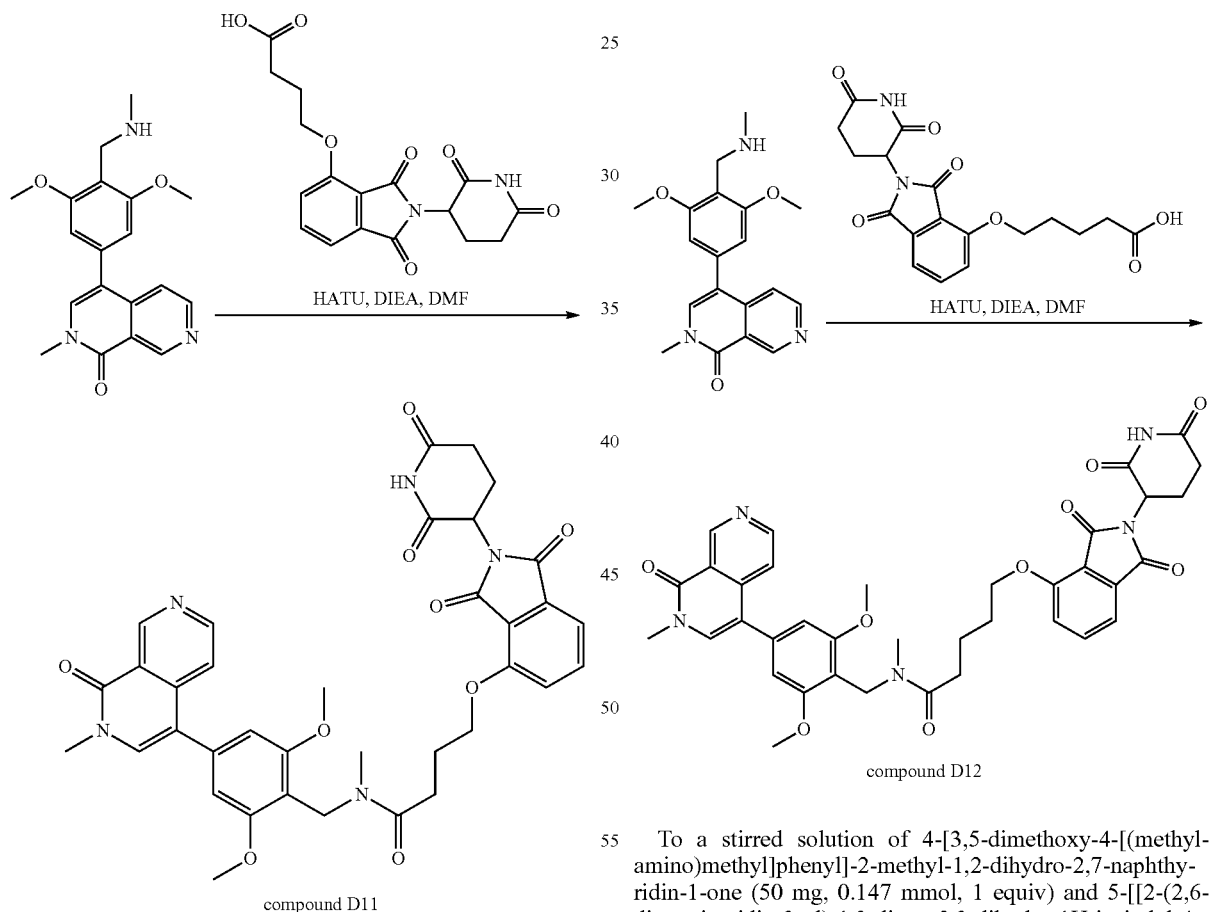

compound D11

To a solution of 4-[3,5-dimethoxy-4-[(methylamino)methyl]phenyl]-2-methyl-1,2-dihydro-2,7-naphthyridin-1-one (50 mg, 0.147 mmol, 1 equiv) and 4-[[2-(2,6-dioxopiperidin-3-yl)-1,3-dioxo-2,3-dihydro-1H-isoindol-4-yl]oxy]butanoic acid (53.08 mg, 0.147 mmol, 1 equiv) in DMF (1 mL) was added DIEA (38.08 mg, 0.295 mmol, 2 equiv). The resulting mixture was stirred for 10 minutes at 25° C. Then HATU (84.02 mg, 0.221 mmol, 1.5 equiv) was added to the reaction mixture. The resulting solution was stirred for 2 hours at 25° C. The crude product was purified by Prep-HPLC (conditions: SunFire C18 OBD Prep Column, 19 mm×250 mm; mobile phase, Water (0.1% FA) and ACN (24% Phase B up to 48% in 8 minutes); Detector, uv). This resulted in 27 mg (26.88%) of N-[[2,6-dimethoxy-4-(2-methyl-1-oxo-1,2-dihydro-2,7-naphthyridin-4-yl)phenyl]methyl]-4-[[2-(2,6-dioxopiperidin-3-yl)-1,3-dioxo-2,3-dihydro-1H-isoindol-4-yl]oxy]-N-methylbutanamide as a white solid. $^1$H NMR (400 MHz, Methanol-d4) δ 9.54 (s, 1H), 8.69 (d, J=6.0 Hz, 1H), 7.84-7.74 (m, 2H), 7.67 (s, 1H), 7.54-7.41 (m, 2H), 6.77 (s, 1H), 6.72 (s, 1H), 5.13-5.02 (m, 1H), 4.76 (dd, J=10.7, 2.5 Hz, 2H), 4.33 (dt, J=19.9, 5.9 Hz, 2H), 3.85 (d, J=17.8 Hz, 6H), 3.71 (d, J=12.1 Hz, 4H), 3.06-2.97 (m, 1H), 2.89 (s, 2H), 2.80 (s, 3H), 2.74-2.59 (m, 3H), 2.27-2.13 (m, 3H). LCMS (ESI) m/z: [M+H]+=682.25.

Example 64—Preparation of N-[[2,6-dimethoxy-4-(2-methyl-1-oxo-1,2-dihydro-2,7-naphthyridin-4-yl)phenyl]methyl]-5-[[2-(2,6-dioxopiperidin-3-yl)-1,3-dioxo-2,3-dihydro-1H-isoindol-4-yl]oxy]-N-methylpentanamide (Compound D12)

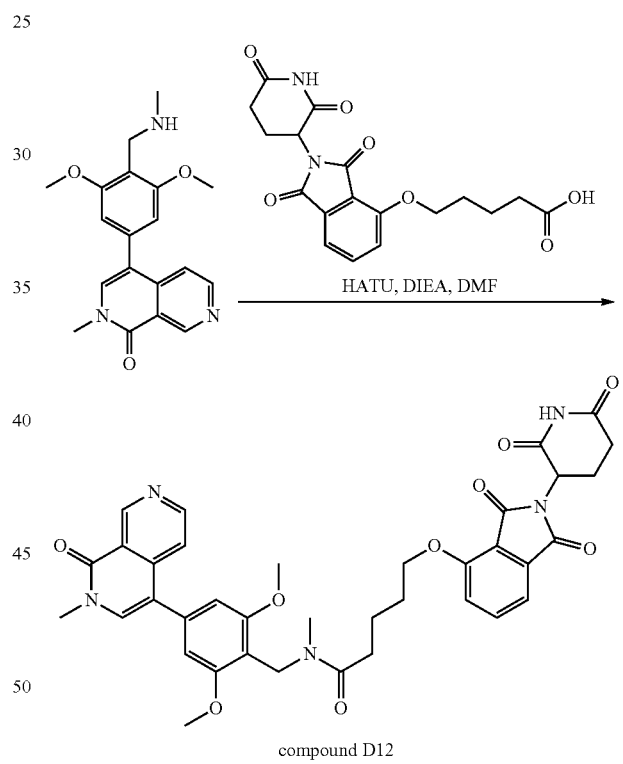

compound D12

To a stirred solution of 4-[3,5-dimethoxy-4-[(methylamino)methyl]phenyl]-2-methyl-1,2-dihydro-2,7-naphthyridin-1-one (50 mg, 0.147 mmol, 1 equiv) and 5-[[2-(2,6-dioxopiperidin-3-yl)-1,3-dioxo-2,3-dihydro-1H-isoindol-4-yl]oxy]pentanoic acid (55.15 mg, 0.147 mmol, 1 equiv) in DMF (2 mL) was added DIEA (57.12 mg, 0.442 mmol, 3 equiv) at 25° C. The resulting mixture was stirred for 10 minutes at 25° C. Then HATU (84.02 mg, 0.221 mmol, 1.5 equiv) was added to the reaction mixture. The resulting solution was stirred for 2 hours at 25° C. The crude product was purified by Prep-HPLC (conditions: SunFire C18 OBD Prep Column, 19 mm×250 mm; mobile phase, Water (0.1% FA) and ACN (24% Phase B up to 53% in 8 minutes);

Detector, uv). This resulted in 48.1 mg (46.9%) of N-[[2,6-dimethoxy-4-(2-methyl-1-oxo-1,2-dihydro-2,7-naphthyridin-4-yl)phenyl]methyl]-5-[[2-(2,6-dioxopiperidin-3-yl)-1,3-dioxo-2,3-dihydro-1H-isoindol-4-yl]oxy]-N-methylpentanamide as a white solid. $^1$H NMR (400 MHz, Methanol-d4) δ 9.55 (s, 1H), 8.71-8.64 (m, 1H), 7.85-7.71 (m, 3H), 7.45 (dd, J=9.6, 7.9 Hz, 2H), 6.76 (d, J=9.2 Hz, 2H), 5.05 (dd, J=12.6, 5.7 Hz, 1H), 4.74 (d, J=16.1 Hz, 2H), 4.30 (q, J=6.8, 6.2 Hz, 2H), 3.86 (s, 6H), 3.72 (dd, J=2.7, 1.1 Hz, 3H), 2.85 (s, 2H), 2.84 (d, J=40.1 Hz, 4H), 2.76-2.52 (m, 2H), 2.08-1.87 (m, 5H). LCMS (ESI) m/z: [M+H]+=696.4.

Example 65—Preparation of 2-((2,6-dimethoxy-4-(2-methyl-1-oxo-1,2-dihydro-2,7-naphthyridin-4-yl)benzyl)(methyl)amino)-N-(2-(2-(2-((2-(2,6-dioxopiperidin-3-yl)-1,3-dioxoisoindolin-4-yl)amino)ethoxy)ethoxy)ethyl)-N-methylacetamide (Compound D13)

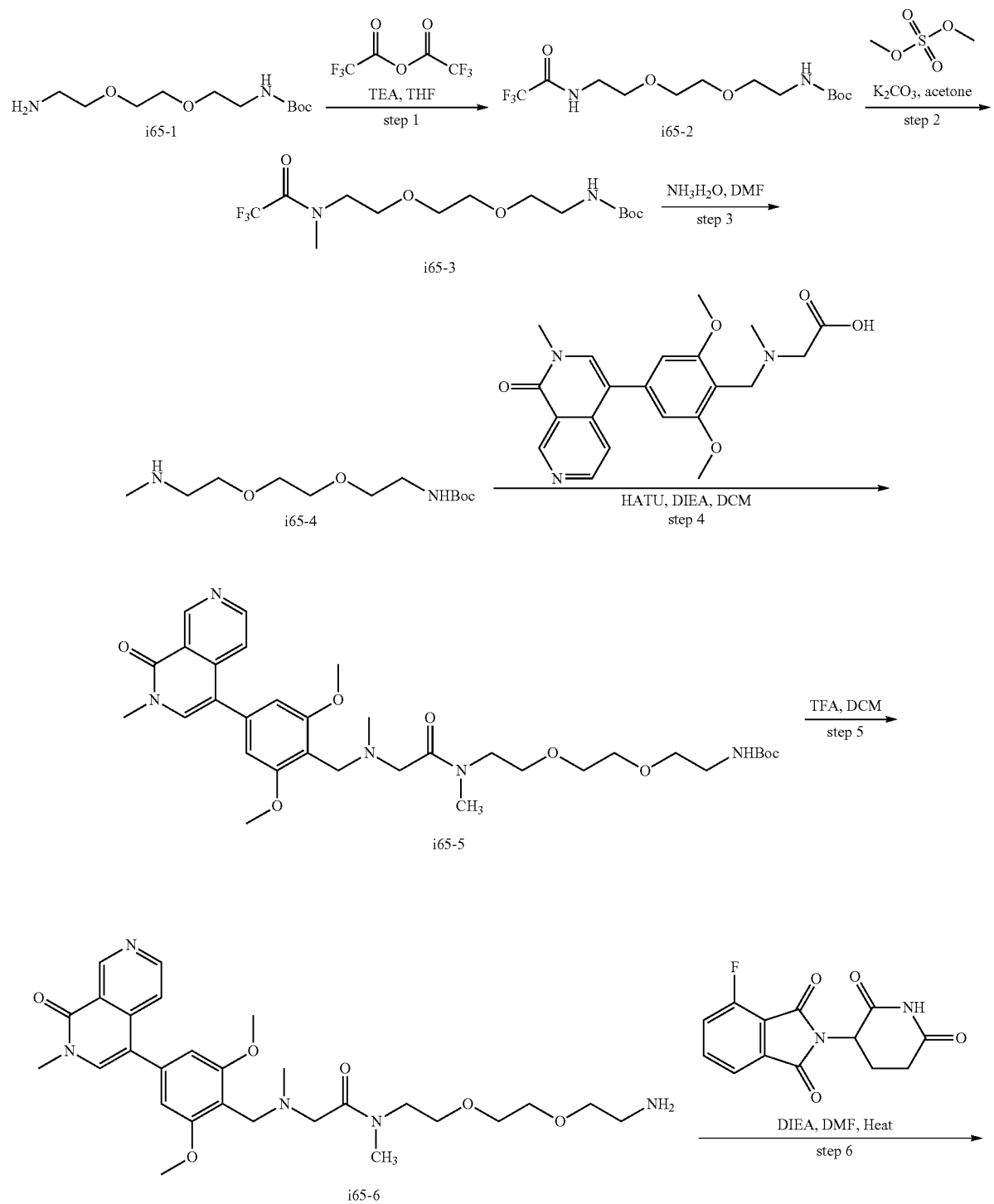

-continued

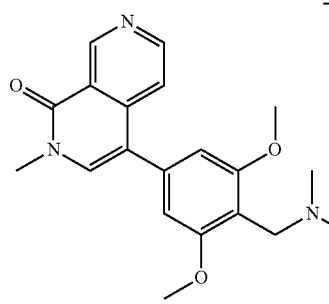 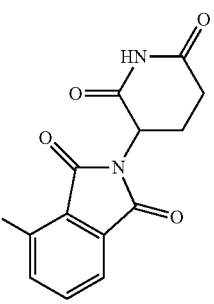

compound D13

Step 1: Preparation of tert-butyl (2-(2-(2-(2,2,2-trifluoroacetamido)ethoxy)ethoxy)ethyl)carbamate (i65-2)

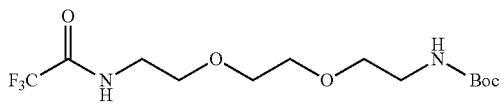

To a solution of tert-butyl N-[2-[2-(2-aminoethoxy)ethoxy] ethyl] carbamate (1.15 g, 4.631 mmol, 1.00 equiv) and TEA (0.94 g, 9.262 mmol, 2.00 equiv) in THF (12.00 mL) at 0 degree was added trifluoroacetic anhydride (1.46 g, 6.947 mmol, 1.50 equiv). The resulting solution was stirred at 25 degree for 12 hours. The resulting mixture was concentrated. The residue was applied onto a silica gel column eluted with THF/PE (40/60). Fractions containing the desired compound were evaporated to dryness to afford tert-butyl N-(2-[2-[2-(2,2,2-trifluoroacetamido)ethoxy]ethoxy]ethyl) carbamate (1.347 g, 80.0%) as a colorless oil. LCMS (ESI) m/z: [M+H]+=345.

Step 2: Preparation of tert-butyl (2-(2-(2-(2,2,2-trifluoro-N-methylacetamido)ethoxy)ethoxy)ethyl)carbamate (i65-3)

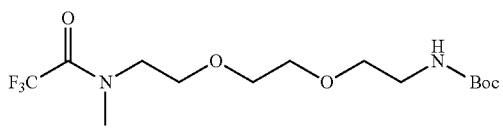

A solution of tert-butyl N-(2-[2-[2-(2,2,2-trifluoroacetamido)ethoxy]ethoxy]ethyl) carbamate (1.347 g, 3.912 mmol, 1.00 equiv) and K₂CO₃ (0.65 g, 4.694 mmol, 1.20 equiv) in acetone (15.00 mL) was stirred at 0 degree. Then dimethyl sulfate (0.74 g, 5.867 mmol, 1.51 equiv) was added to the mixture, and the resulting solution was stirred at 25 degree for 12 hours. The resulting solution was diluted with of EtOAc, and it was washed with water (3×50 mL). The organic layer was dried and evaporated to dryness to afford tert-butyl N-(2-[2-[2-(2,2,2-trifluoro-N-methylacetamido)ethoxy]ethoxy]ethyl)carbamate (1.75 g, 98.91%) as a colorless oil, which was used directly without further purification. LCMS (ESI) m/z: [M+H]+=359.

Step 3: Preparation of tert-butyl (2-(2-(2-(methylamino)ethoxy)ethoxy)ethyl)carbamate (i65-4)

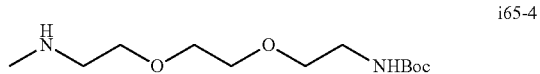 [SMILES: CNCCOCCOCCNC(=O)OC(C)(C)C]

A solution of tert-butyl N-(2-[2-[2-(2,2,2-trifluoro-N-methylacetamido)ethoxy]ethoxy]ethyl) carbamate (1.65 g) in DMF (16.00 mL) was stirred at 0 degree. Then ammonium hydroxide (16.00 mL) was added to the mixture, and the resulting solution was stirred at 25 degrees for 12 hours. The mixture was evaporated to dryness to afford crude tert-butyl N-(2-[2-[2-(methylamino) ethoxy]ethoxy]ethyl) carbamate as a colorless oil, which was used directly without further purification. LCMS (ESI) m/z: [M+H]+=263.

Step 4: Preparation of tert-butyl (1-(2,6-dimethoxy-4-(2-methyl-1-oxo-1,2-dihydro-2,7-naphthyridin-4-yl)phenyl)-2,5-dimethyl-4-oxo-8,11-dioxa-2,5-diazatridecan-13-yl)carbamate (i65-5)

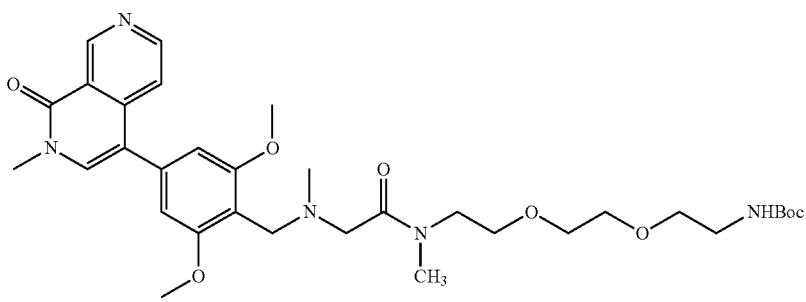

To a solution of tert-butyl N-(2-[2-[2-(methylamino)ethoxy]ethoxy]ethyl)carbamate (600.00 mg, 2.287 mmol, 1.00 equiv) and ([[2,6-dimethoxy-4-(2-methyl-1-oxo-2,7-naphthyridin-4-yl)phenyl]methyl](methyl) amino)acetic acid (1.09 g, 2.744 mmol, 1.2 equiv) in DCM (5.00 mL) was added HATU (1.30 g, 3.431 mmol, 1.5 equiv) and DIEA (886.75 mg, 6.861 mmol, 3 equiv). The resulting solution was stirred at 25 degree for 1 hour. The mixture was added H$_2$O (100 mL) and extracted with DCM (100 mL×4). The organic layer was dried over anhydrous sodium sulfate, filtered, and concentrated to give crude product that was purified by a silica gel column eluted with MeOH/DCM (5.4/94.6) to afford tert-butyl N-[2-(2-[2-[2-([[2,6-dimethoxy-4-(2-methyl-1-oxo-2,7-naphthyridin-4-yl)phenyl]methyl](methyl)amino)-N-methylacetamido] ethoxy]ethoxy) ethyl]carbamate (536 mg, 36.52%) as an off-white solid. LCMS (ESI) m/z: [M+H]+=642.

Step 5: Preparation of N-(2-(2-(2-aminoethoxy)ethoxy)ethyl)-2-((2,6-dimethoxy-4-(2-methyl-1-oxo-1,2-dihydro-2,7-naphthyridin-4-yl)benzyl)(methyl)amino)-N-methylacetamide (i65-5)

i65-6

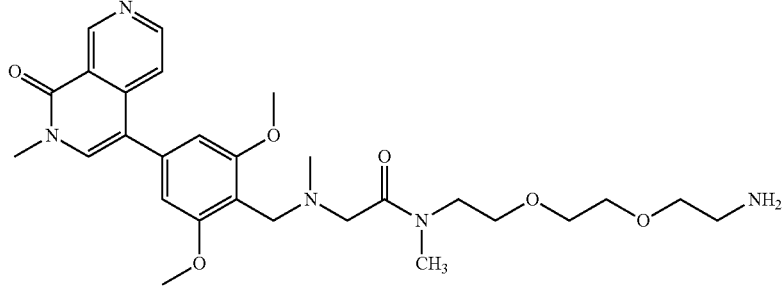

A solution of tert-butyl N-[2-(2-[2-[2-([[2,6-dimethoxy-4-(2-methyl-1-oxo-2,7-naphthyridin-4-yl)phenyl] methyl](methyl)amino)-N-methylacetamido]ethoxy]ethoxy)ethyl]carbamate (536.00 mg, 0.835 mmol, 1.00 equiv) and TFA (1.10 mL, 9.673 mmol, 17.78 equiv) in DCM (5.00 mL) was stirred at 25 degree for 1 hour. The resulting mixture were evaporated to dryness to afford N-[2-[2-(2-aminoethoxy)ethoxy]ethyl]-2-([[2,6-dimethoxy-4-(2-methyl-1-oxo-2,7-naphthyridin-4-yl)phenyl]methyl](methyl)amino)-N-methylacetamide (670 mg, crude) as a yellow oil, which was used directly without further purification. LCMS (ESI) m/z: [M+H]+=542.

Step 6: Preparation of 2-((2,6-dimethoxy-4-(2-methyl-1-oxo-1,2-dihydro-2,7-naphthyridin-4-yl)benzyl) (methyl)amino)-N-(2-(2-(2-((2-(2,6-dioxopiperidin-3-yl)-1,3-dioxoisoindolin-4-yl)amino)ethoxy)ethoxy)ethyl)-N-methylacetamide (Compound D13)

compound D13

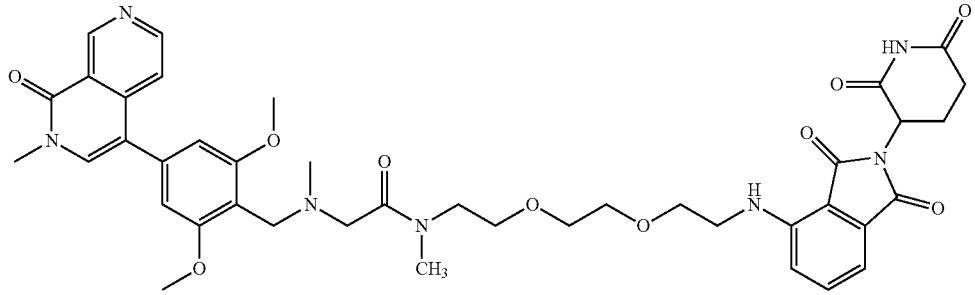

To a solution of N-[2-[2-(2-aminoethoxy)ethoxy]ethyl]-2-([[2,6-dimethoxy-4-(2-methyl-1-oxo-1,2-dihydro-2,7-naphthyridin-4-yl)phenyl]methyl](methyl)amino)-N-methylacetamide (169.42 mg, 0.313 mmol, 1.20 equiv) and 2-(2,6-dioxopiperidin-3-yl)-4-fluoro-2,3-dihydro-1H-isoindole-1,3-dione (72.00 mg, 0.261 mmol, 1.00 equiv) in NMP (2.00 mL) was added DIEA (168.44 mg, 1.303 mmol, 5.00 equiv). The resulting solution was stirred at 90 degree for 5 hours. Without any additional work-up, the mixture was purified by prep-HPLC (conditions: SunFire C18 OBD Prep Column, 100 Å, 5 μm, 19 mm×250 mm; Mobile Phase A: Water (0.1% FA), Mobile Phase B: ACN; Flow rate: 25 mL/minute; Gradient: 16% B to 22% B in 10 minutes; 254 nm; Rt: 9.3 minutes) to give 2-((2,6-dimethoxy-4-(2-methyl-1-oxo-1,2-dihydro-2,7-naphthyridin-4-yl)benzyl)(methyl)amino)-N-(2-(2-(2-((2-(2,6-dioxopiperidin-3-yl)-1,3-dioxoisoindolin-4-yl)amino)ethoxy)ethoxy)ethyl)-N-methylacetamide (7 mg, 3.37%) as a yellow solid. $^1$H NMR (400 MHz, Acetonitrile-d3) δ 9.52 (d, J=3.2 Hz, 1H), 9.09 (s, 1H), 8.70 (d, J=5.7 Hz, 1H), 7.67-7.39 (m, 3H), 7.02 (dt, J=8.5, 5.1 Hz, 2H), 6.73 (d, J=1.7 Hz, 2H), 6.52-6.38 (m, 1H), 4.94 (dd, J=12.5, 5.4 Hz, 1H), 3.97 (d, J=9.0 Hz, 2H), 3.86 (s, 6H), 3.67 (q, J=3.8, 2.3 Hz, 2H), 3.65-3.60 (m, 4H), 3.60-3.52 (m, 6H), 3.52-3.46 (m, 2H), 3.46-3.37 (m, 2H), 2.99 (s, 1H), 2.91 (s, 2H), 2.84-2.57 (m, 3H), 2.48 (d, J=3.4 Hz, 3H), 2.15-2.03 (m, 1H). LCMS (ESI) m/z: [M+H]+=798.40.

Example 66—Preparation of N-[[2,6-dimethoxy-4-(2-methyl-1-oxo-1,2-dihydro-2,7-naphthyridin-4-yl)phenyl]methyl]-3-[[2-(2,6-dioxopiperidin-3-yl)-1,3-dioxo-2,3-dihydro-1H-isoindol-4-yl]oxy]-N-methylpropanamide (Compound D14)

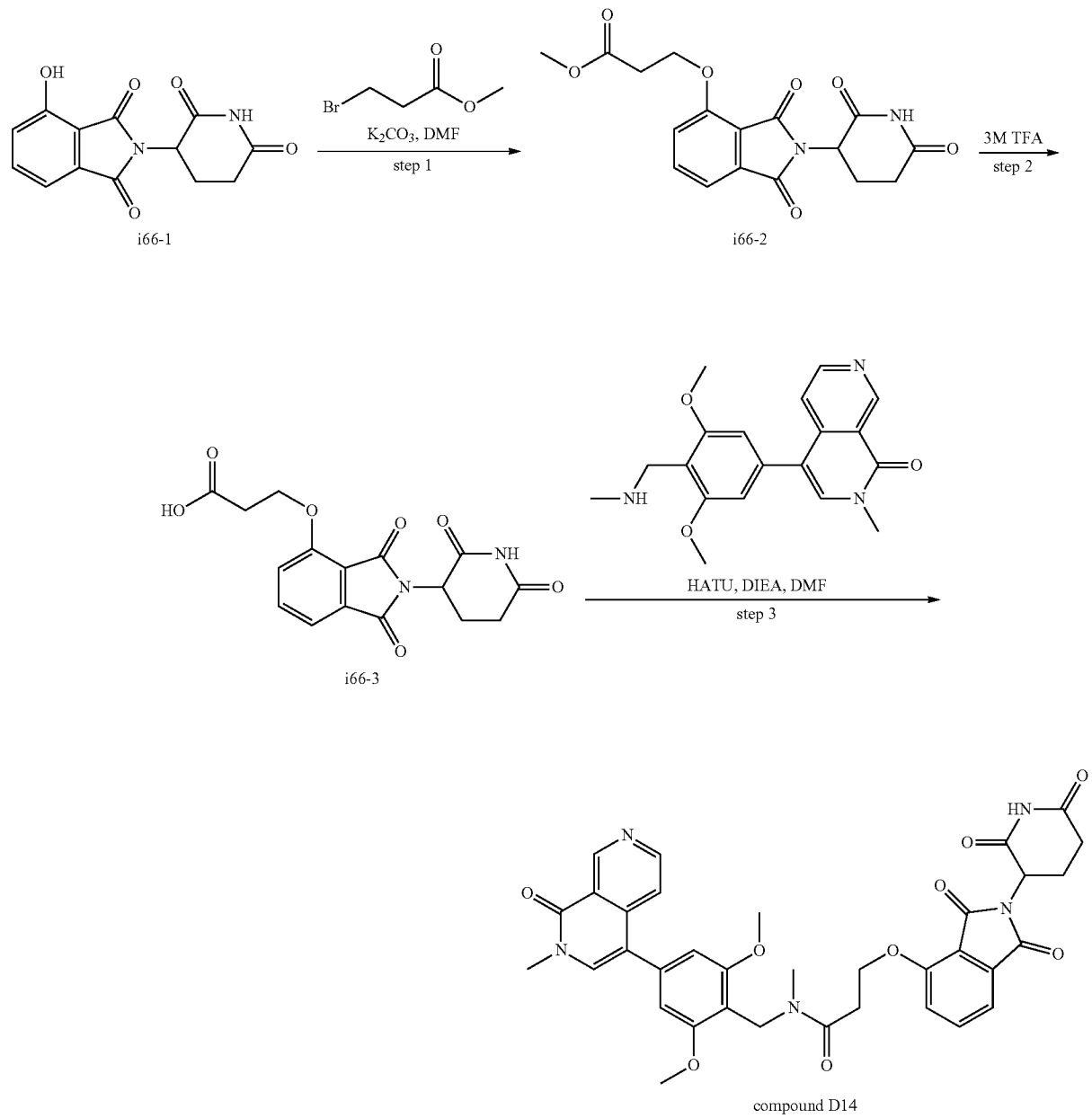

Step 1: Preparation of methyl 3-[[2-(2,6-dioxopiperidin-3-yl)-1,3-dioxoisoindol-4-yl]oxy]propanoate (i66-2)

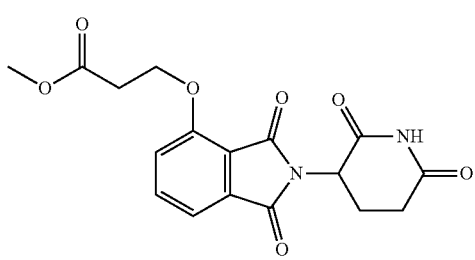

i66-2

To a stirred solution of 2-(2,6-dioxopiperidin-3-yl)-4-hydroxyisoindole-1,3-dione (500.00 mg, 1.823 mmol, 1.00 equiv) and methyl 3-bromopropanoate (395.84 mg, 2.370 mmol, 1.30 equiv) in DMF was added K$_2$CO$_3$ (755.96 mg, 5.470 mmol, 3.00 equiv). The resulting solution was stirred for 2 hours at 25° C. The solids were filtered out. The filtrate was concentrated. The residue was applied onto a silica gel column with dichloromethane/methanol (10:1). This resulted in 400 mg (60.89%) of methyl 3-[[2-(2,6-dioxopiperidin-3-yl)-1,3-dioxoisoindol-4-yl]oxy]propanoate as a green solid. LCMS (ESI) m/z: [M−H]$^+$=361.

Step 2: Preparation of 3-[[2-(2,6-dioxopiperidin-3-yl)-1,3-dioxoisoindol-4-yl]oxy]propanoic (i66-3)

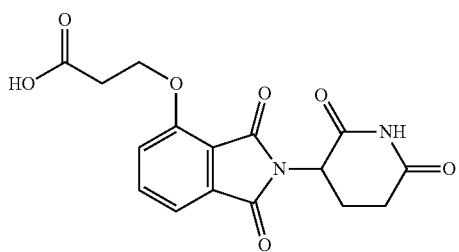

i66-3

Into a 8-mL sealed tube was added methyl 3-[[2-(2,6-dioxopiperidin-3-yl)-1,3-dioxoisoindol-4-yl]oxy]propanoate (100.00 mg, 0.278 mmol, 1.00 equiv) and TFA (3.00 mL, 3M in water). The resulting solution was stirred for 2 hours at 70° C. The resulting mixture was concentrated. This resulted in 70 mg (72.84%) of 3-[[2-(2,6-dioxopiperidin-3-yl)-1,3-dioxoisoindol-4-yl]oxy]propanoic acid as a yellow solid, which was used directly without further purification. LCMS (ESI) m/z: [M+H]$^+$=347.

Step 3: Preparation of N-[[2,6-dimethoxy-4-(2-methyl-1-oxo-1,2-dihydro-2,7-naphthyridin-4-yl)phenyl]methyl]-3-[[2-(2,6-dioxopiperidin-3-yl)-1,3-dioxo-2,3-dihydro-1H-isoindol-4-yl]oxy]-N-methylpropanamide (Compound D14)

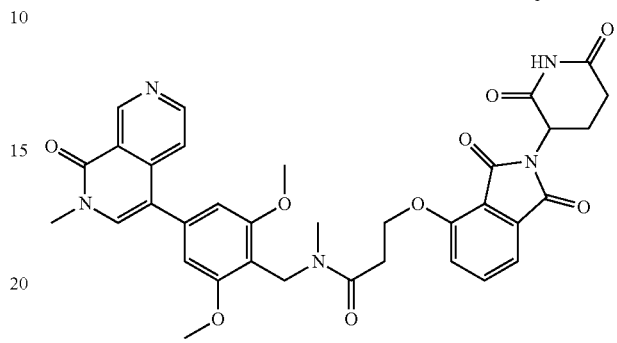

compound D14

To a solution of 3-[[2-(2,6-dioxopiperidin-3-yl)-1,3-dioxo-2,3-dihydro-1H-isoindol-4-yl]oxy]propanoic acid (60.00 mg, 0.173 mmol, 1.00 equiv) and DIEA (44.79 mg, 0.347 mmol, 2.00 equiv) in DMF (2.00 mL) was added HATU (98.82 mg, 0.260 mmol, 1.50 equiv). The reaction mixture was stirred for 10 minutes at 25° C. Then 4-[3,5-dimethoxy-4-[(methylamino)methyl]phenyl]-2-methyl-1,2-dihydro-2,7-naphthyridin-1-one (58.80 mg, 0.173 mmol, 1.00 equiv) was added to the reaction mixture. The resulting solution was stirred for 2 hours at 25° C. The crude product was purified by Prep-HPLC (conditions: SunFire C18 OBD Prep Column, 19 mm×250 mm; mobile phase, Water (0.1% FA) and ACN (26% Phase B up to 44% in 8 minutes); Detector, UV). This resulted in 28.1 mg (24.29%) of N-[[2,6-dimethoxy-4-(2-methyl-1-oxo-1,2-dihydro-2,7-naphthyridin-4-yl)phenyl]methyl]-3-[[2-(2,6-dioxopiperidin-3-yl)-1,3-dioxo-2,3-dihydro-1H-isoindol-4-yl]oxy]-N-methylpropanamide as a green solid. $^1$H NMR (400 MHz, Methanol-d4) δ 9.53 (s, 1H), 8.67 (d, J=5.9 Hz, 1H), 7.84 (s, 1H), 7.72 (d, J=6.0 Hz, 1H), 7.62 (dd, J=8.4, 7.2 Hz, 1H), 7.33 (d, J=7.1 Hz, 1H), 7.17 (d, J=8.3 Hz, 1H), 6.77 (s, 2H), 5.17 (dd, J=12.7, 5.5 Hz, 1H), 4.77-4.59 (m, 2H), 4.16-4.01 (m, 2H), 3.91 (s, 5H), 3.88 (s, 1H), 3.72 (s, 3H), 3.01-2.85 (m, 4H), 2.81 (s, 2H), 2.80-2.62 (m, 2H), 2.20-2.10 (m, 1H). LCMS (ESI) m/z: [M+H]$^+$=668.25.

Example 67—Preparation of 4-(((2,6-dimethoxy-4-(2-methyl-1-oxo-1,2-dihydro-2,7-naphthyridin-4-yl)benzyl)(methyl)amino)methyl)-2-(2,6-dioxopiperidin-3-yl)isoindoline-1,3-dione formic acid (Compound D15 Formic Acid)

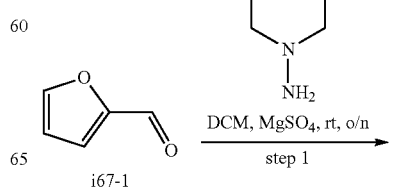

i67-1

DCM, MgSO$_4$, rt, o/n
step 1

271
-continued

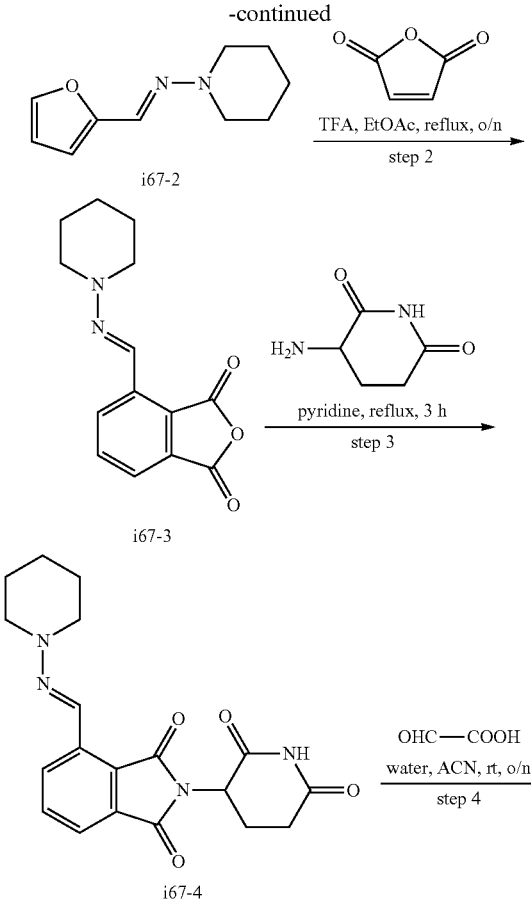

Step 1: Preparation of (E)-1-(furan-2-yl)-N-(piperidin-1-yl)methanimine (i67-2)

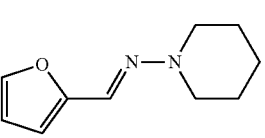

i67-2

To a mixture of furan-2-carbaldehyde (1.00 g, 10.407 mmol, 1.00 equiv) and piperidin-1-amine (1.04 g, 10.407 mmol, 1.00 equiv) in DCM (25.00 mL) was added MgSO$_4$ (2.51 g, 20.815 mmol, 2.00 equiv). The resulting mixture was stirred overnight at room temperature. The resulting mixture was concentrated under vacuum. The residue was purified by silica gel column chromatography, eluted with MeOH in DCM from 0% to 10% to afford the desired product (E)-1-(furan-2-yl)-N-(piperidin-1-yl)methanimine (1.70 g, 9.551 mmol, 82.48%) as a brown solid. LCMS (ESI) m/z: [M+H]$^+$=179.

Step 2: Preparation of (E)-4-((piperidin-1-ylimino)methyl)isobenzofuran-1,3-dione (i67-3)

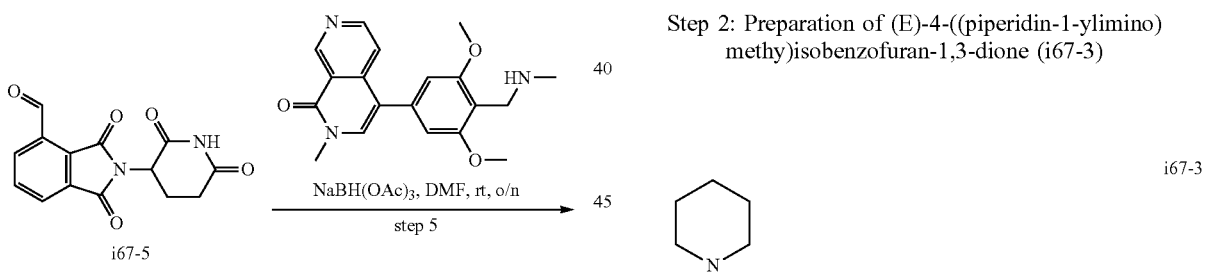

i67-3

To a solution of furan-2,5-dione (1.12 g, 11.446 mmol, 1.20 equiv) and (E)-1-(furan-2-yl)-N-(piperidin-1-yl)methanimine (1.70 g, 9.538 mmol, 1.00 equiv) in EtOAc (30 mL) was added TFA (0.20 mL). The resulting mixture was stirred overnight under reflux. The resulting mixture was concentrated under vacuum to afford the crude product (E)-4-((piperidin-1-ylimino)methyl)isobenzofuran-1,3-dione (3.10 g, crude) as a brown solid. LCMS (ESI) m/z: [M+H]$^+$=259.

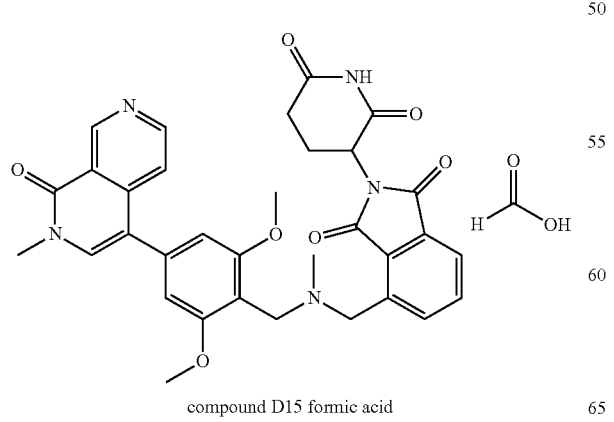

compound D15 formic acid

Step 3: Preparation of (E)-2-(2,6-dioxopiperidin-3-yl)-4-((piperidin-1-ylimino)methyl)isoindoline-1,3-dione (i67-4)

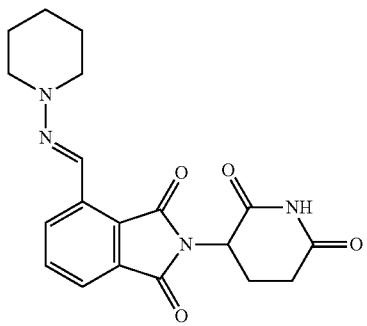

i67-4

To a mixture of 3-aminopiperidine-2,6-dione (1.54 g, 12.016 mmol, 1.00 equiv) in pyridine (15.00 mL) was added (E)-4-((piperidin-1-ylimino)methyl)isobenzofuran-1,3-dione (3.1 g, 12.016 mmol, 1.00 equiv). The resulting mixture was stirred for 3 hours under reflux. The resulting mixture was concentrated under vacuum. The residue was purified by silica gel column chromatography, eluted with EA in PE from 0% to 50% to afford (E)-2-(2,6-dioxopiperidin-3-yl)-4-((piperidin-1-ylimino)methyl)isoindoline-1,3-dione (1.00 g, 2.717 mmol, 22.62%) as a yellow solid. LCMS (ESI) m/z: [M+H]$^+$=369.

Step 3: Preparation of 2-(2,6-dioxopiperidin-3-yl)-1,3-dioxoisoindoline-4-carbaldehyde (i67-5)

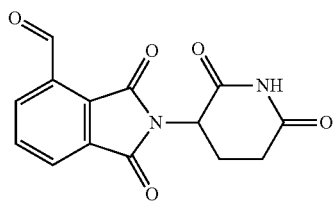

i67-5

2-oxoacetic acid (5.00 g, 0.068 mmol, 0.02 equiv) in H$_2$O (5.00 mL) was added to a solution of 2-(2,6-dioxopiperidin-3-yl)-4-[(1E)-[(piperidin-1-yl)imino]methyl]-2,3-dihydro-1H-isoindole-1,3-dione (1.00 g, 2.714 mmol, 1.00 equiv) in ACN (2.00 mL). The resulting mixture was stirred overnight at room temperature. The resulting mixture was extracted with EtOAc (3×100 mL). The combined organic layer was washed with saturated sodium bicarbonate solution (2×100 mL) and brine (1×100 mL), dried over anhydrous sodium sulfate, filtered, and concentrated under vacuum. The residue was purified by silica gel column chromatography, eluted with EtOAc in PE from 0% to 50% to afford 2-(2,6-dioxopiperidin-3-yl)-1,3-dioxo-2,3-dihydro-1H-isoindole-4-carbaldehyde (460 mg, 1.608 mmol, 59.20%) as a brown solid. LCMS (ESI) m/z: [M+H]$^+$=287.

Step 4: Preparation of 4-(((2,6-dimethoxy-4-(2-methyl-1-oxo-1,2-dihydro-2,7-naphthyridin-4-yl)benzyl)(methyl)amino)methyl)-2-(2,6-dioxopiperidin-3-yl)isoindoline-1,3-dione formic acid (Compound D4 Formic Acid)

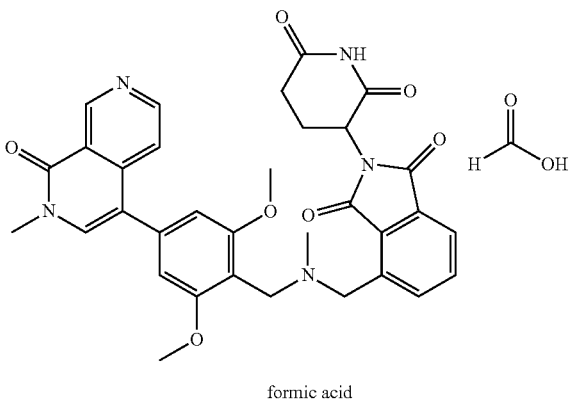

compound D15 formic acid

To a solution of 2-(2,6-dioxopiperidin-3-yl)-1,3-dioxo-2,3-dihydro-1H-isoindole-4-carbaldehyde (67.47 mg, 0.236 mmol, 1.00 equiv) in DMF (3.00 mL) was added 4-[3,5-dimethoxy-4-[(methylaminomethyl]phenyl]-2-methyl-1,2-dihydro-2,7-naphthyridin-1-one (80.00 mg, 0.236 mmol, 1.00 equiv). The mixture was stirred overnight at room temperature, and then NaBH$_3$CN (99.91 mg, 0.472 mmol, 2.00 equiv) was added. The resulting mixture was stirred for one hour at room temperature. The mixture was filtered, and the filtrate was purified by prep-HPLC (conditions: SunFire C$_{18}$ OBD Prep Column, 100 Å, 5 μm, 19 mm×250 mm; Mobile Phase A: Water (0.1% FA), Mobile Phase B: ACN; Flow rate: 25 mL/minute; Gradient: 10% B to 16% B in 14 minutes; 254 nm; Rt: 12.7 minutes) to afford 4-(((2,6-dimethoxy-4-(2-methyl-1-oxo-1,2-dihydro-2,7-naphthyridin-4-yl)benzyl)(methyl)amino)methyl)-2-(2,6-dioxopiperidin-3-yl)isoindoline-1,3-dione; formate (30.9 mg, 0.0472 mmol, 19.67%) as a light yellow solid. $^1$H NMR (300 MHz, Acetonitrile-d3) δ 9.53 (d, J=0.9 Hz, 1H), 9.03 (s, 1H), 8.70 (d, J=5.7 Hz, 1H), 8.18 (s, 0.3H, FA), 8.02 (dd, J=6.9, 1.9 Hz, 1H), 7.91-7.78 (m, 2H), 7.57-7.49 (m, 2H), 6.67 (s, 2H), 5.05 (dd, J=12.2, 5.3 Hz, 1H), 4.51 (d, J=4.5 Hz, 2H), 4.16 (s, 2H), 3.83 (s, 6H), 3.62 (s, 3H), 2.85-2.59 (m, 6H), 2.20-2.07 (m, 1H). LCMS (ESI) m/z: [M+H]$^+$=610.35.

Example 68—Preparation of 2-((2,6-dimethoxy-4-(2-methyl-1-oxo-1,2-dihydro-2,7-naphthyridin-4-yl)benzyl)(methyl)amino)-N-(2-(2-(2-((2-(2,6-dioxopiperidin-3-yl)-1,3-dioxoisoindolin-5-yl)amino)ethoxy)ethoxy)ethyl)-N-methylacetamide (Compound D16)

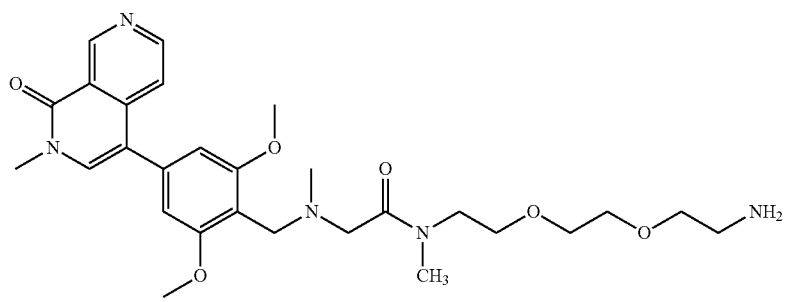
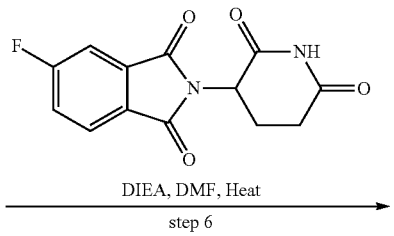

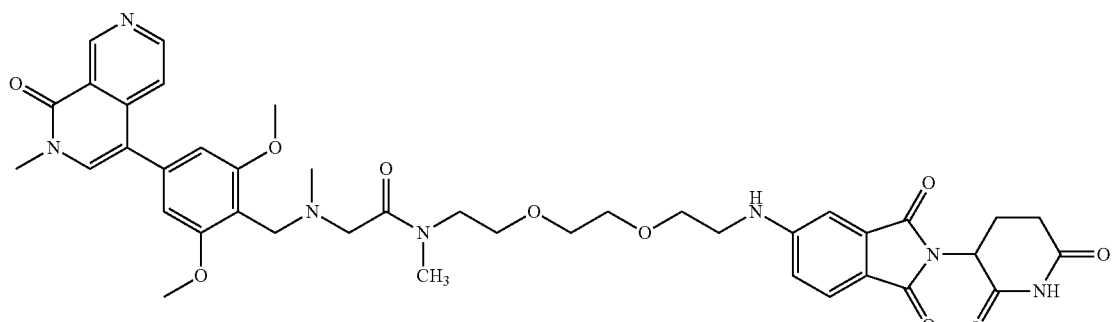

compound D16

Compound D16 was prepared in a similar manner as described for compound D13. 2-([[2,6-dimethoxy-4-(2-methyl-1-oxo-1,2-dihydro-2,7-naphthyridin-4-yl)phenyl]methyl](methyl)amino)-N-[2-[2-(2-[[2-(2,6-dioxopiperidin-3-yl)-1,3-dioxo-2,3-dihydro-1H-isoindol-5-yl]amino]ethoxy)ethoxy]ethyl]-N-methylacetamide (10 mg, 3.39%) was obtained as a yellow solid. $^1$H NMR (400 MHz, Methanol-d4) δ 9.52 (s, 1H), 8.68 (dd, J=5.7, 2.3 Hz, 1H), 8.55 (s, 0.5H, FA), 7.74 (d, J=6.3 Hz, 1H), 7.62 (dd, J=5.9, 2.7 Hz, 1H), 7.48 (dd, J=10.8, 8.4 Hz, 1H), 6.97 (d, J=2.2 Hz, 1H), 6.85-6.71 (m, 3H), 5.01 (dt, J=12.7, 4.9 Hz, 1H), 4.61 (s, 2H), 4.29 (s, 2H), 4.11 (s, 1H), 3.92 (d, J=2.9 Hz, 6H), 3.71 (d, J=1.8 Hz, 3H), 3.66 (dd, J=7.1, 3.9 Hz, 7H), 3.62-3.52 (m, 2H), 3.42-3.34 (m, 2H), 3.03 (d, J=7.0 Hz, 3H), 2.91-2.73 (m, 2H), 2.73-2.62 (m, 4H), 2.12-2.00 (m, 1H). LCMS (ESI) m/z: [M+H]+=798.40.

Example 69—Preparation of 4-[2-([[2,6-dimethoxy-4-(2-methyl-1-oxo-2,7-naphthyridin-4-yl)phenyl]methyl](methyl) amino)ethyl]-2-(2,6-dioxopiperidin-3-yl)isoindole-1,3-dione (Compound D17)

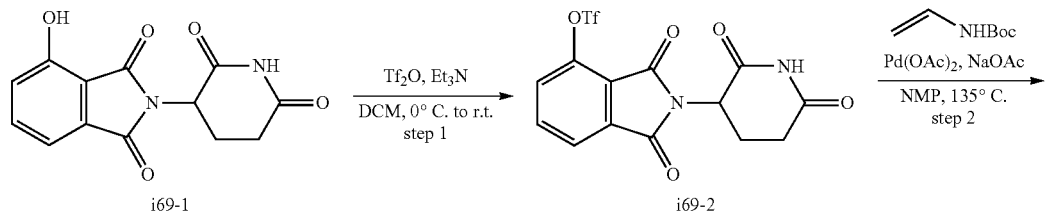

-continued
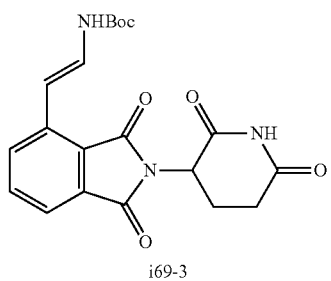
i69-3
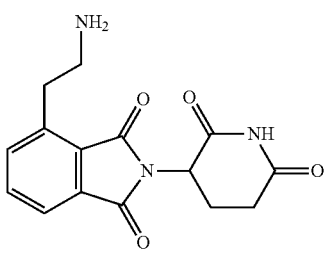
i69-4
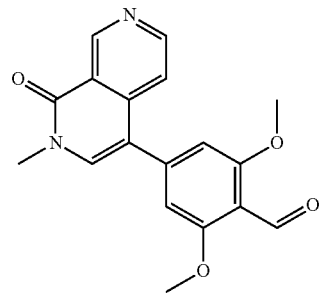
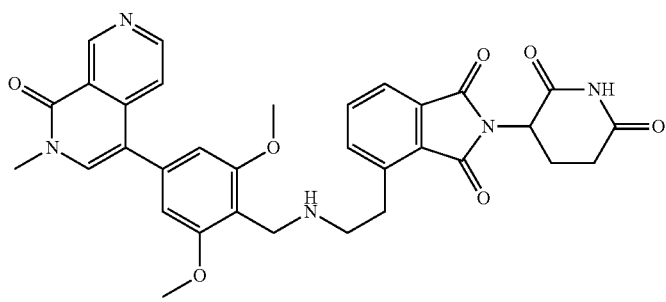
i69-5
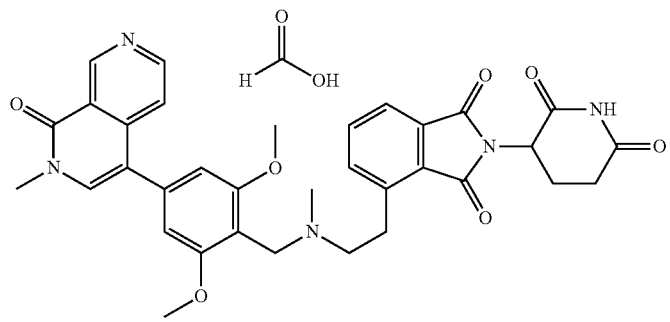
i69-6
compound D17 formic acid Step 1: 2-(2,6-dioxopiperidin-3-yl)-1,3-dioxoisoin-dol-4-yl trifluoromethanesulfonate (i69-2)

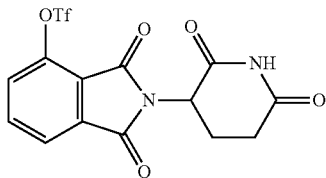

i69-2

To a stirred solution of 2-(2,6-dioxopiperidin-3-yl)-4-hydroxyisoindole-1,3-dione (0.50 g, 1.823 mmol, 1.00 equiv) in DCM (7.00 mL) was added Et$_3$N (0.76 mL, 7.513 mmol, 3.00 equiv) and pyridine (0.76 mL, 9.611 mmol, 5.18 equiv) at 0° C. Tf$_2$O (0.77 g, 2.735 mmol, 1.50 equiv) was then added dropwise at 0° C., and the mixture was stirred at this temperature for 30 minutes and then warmed to room temperature for 1 hour. The reaction was quenched by addition of sat. aq. NH$_4$Cl (5 mL). The resulting mixture was extracted with DCM (2×10 mL). The combined organic layers were dried over anhydrous Na$_2$SO$_4$. After filtration, the filtrate was concentrated under reduced pressure. The residue was suspended in 5 mL of DCM and then filtered. The light brown residue was dissolved in 40 mL of MeCN and filtered. The filtrate was concentrated in vacuo to afford 2-(2,6-dioxopiperidin-3-yl)-1,3-dioxoisoindol-4-yl trifluoromethanesulfonate (610 mg, 82.35%) as a light brown solid. LCMS (ESI) m/z: [M+H]+=407.

Step 2: tert-butyl N-[(E)-2-[2-(2,6-dioxopiperidin-3-yl)-1,3-dioxoisoindol-4-yl]ethenyl]carbamate (i69-3)

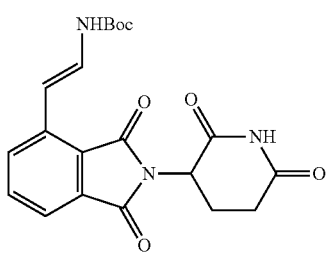

i69-3

To a mixture of 2-(2,6-dioxopiperidin-3-yl)-1,3-dioxoisoindol-4-yl trifluoromethanesulfonate (580 mg, 1.428 mmol, 1.00 equiv), AcONa (257.6 mg, 3.141 mmol, 2.20 equiv), and Pd(OAc)$_2$ (32.1 mg, 0.143 mmol, 0.10 equiv) was added tert-butyl N-ethenylcarbamate (572.3 mg, 3.997 mmol, 2.80 equiv) and NMP (5 mL) at room temperature under nitrogen atmosphere. The resulting mixture was stirred for 5 hours at 130° C. under nitrogen atmosphere. It was then diluted with EtOAc (30 mL). The resulting mixture was washed with water (3×20 mL). The organic layer was dried over anhydrous Na$_2$SO$_4$. After filtration, the filtrate was concentrated under reduced pressure. The residue was purified by Prep-TLC (PE/EtOAc 1:1) to afford tert-butyl N-[(E)-2-[2-(2,6-dioxopiperidin-3-yl)-1,3-dioxoisoindol-4-yl]ethenyl]carbamate (140 mg, 25%) as a yellow solid. LCMS (ESI) m/z: [M+H]+=400.

Step 3: tert-butyl N-[2-[2-(2,6-dioxopiperidin-3-yl)-1,3-dioxoisoindol-4-yl]ethyl]carbamate (i69-4)

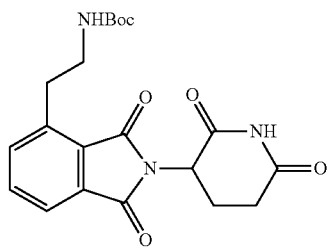

i69-4

A mixture of tert-butyl N-[(E)-2-[2-(2,6-dioxopiperidin-3-yl)-1,3-dioxoisoindol-4-yl]ethenyl]carbamate (135 mg, 0.338 mmol, 1.00 equiv) and 10% Pd/C (30 mg) in MeOH (5 mL) was stirred under an atmosphere of hydrogen at room temperature for 2 hours. The solution was filtered through a Celite pad and the pad was washed with methanol (20 mL). The filtrate was evaporated to dryness to give tert-butyl N-[2-[2-(2,6-dioxopiperidin-3-yl)-1,3-dioxoisoindol-4-yl] ethyl]carbamate (135 mg, quant.) as a light yellow oil. LCMS (ESI) m/z: [M+H]+=402.

Step 4: 4-(2-aminoethyl)-2-(2,6-dioxopiperidin-3-yl) isoindole-1,3-dione; trifluoroacetic acid (i69-5)

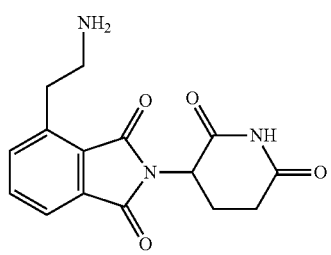

i69-5

To a stirred solution of tert-butyl N-[2-[2-(2,6-dioxopiperidin-3-yl)-1,3-dioxoisoindol-4-yl]ethyl]carbamate (125 mg, 0.311 mmol, 1.00 equiv) in DCM (3 mL) was added TFA (1 mL, 13.463 mmol, 43.23 equiv) at room temperature. The reaction solution was stirred for 30 minutes at room temperature and then concentrated in vacuo to give 4-(2-aminoethyl)-2-(2,6-dioxopiperidin-3-yl)isoindole-1,3-dione trifluoroacetic acid (129 mg, quant.) as alight brown oil. LCMS (ESI) m/z: [M+H]+=302.

Step 5: 4-[2-([[2,6-dimethoxy-4-(2-methyl-1-oxo-2,7-naphthyridin-4-yl)phenyl]methyl]amino)ethyl]-2-(2,6-dioxopiperidin-3-yl)isoindole-1,3-dione (i69-6)

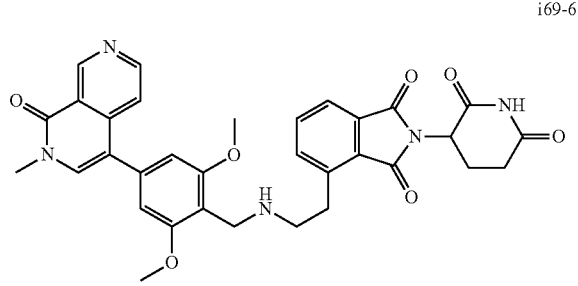 [SMILES: COc1cc(-c2cn(C)c(=O)c3cnccc23)cc(OC)c1CNCCc1cccc2c1C(=O)N(C1CCC(=O)NC1=O)C2=O]

i69-6

A solution of 4-(2-aminoethyl)-2-(2,6-dioxopiperidin-3-yl)isoindole-1,3-dione trifluoroacetic acid (120 mg, 0.289 mmol, 1.00 equiv) and 2,6-dimethoxy-4-(2-methyl-1-oxo-2,7-naphthyridin-4-yl)benzaldehyde (79.7 mg, 0.246 mmol, 0.85 equiv) in DMF (2 mL) was stirred for 45 minutes at room temperature. To the above mixture was added NaBH(OAc)$_3$ (122.47 mg, 0.578 mmol, 2.00 equiv) at room temperature. The resulting mixture was stirred for additional 1 hour at room temperature. Without any additional work-up, the mixture was purified by reverse phase flash (conditions: C18 column; mobile phase, MeCN in water (0.1% FA), 5% to 80% gradient in 30 min; detector, UV 254 nm) to afford 4-[2-([[2,6-dimethoxy-4-(2-methyl-1-oxo-2,7-naphthyridin-4-yl)phenyl]methyl]amino)ethyl]-2-(2,6-dioxopiperidin-3-yl)isoindole-1,3-dione (60 mg, 34%) as a colorless oil. LCMS (ESI) m/z: [M+H]+=610.

Step 6: 4-[2-([[2,6-dimethoxy-4-(2-methyl-1-oxo-2,7-naphthyridin-4-yl)phenyl]methyl](methyl)amino)ethyl]-2-(2,6-dioxopiperidin-3-yl)isoindole-1,3-dione (Compound D17)

compound D17

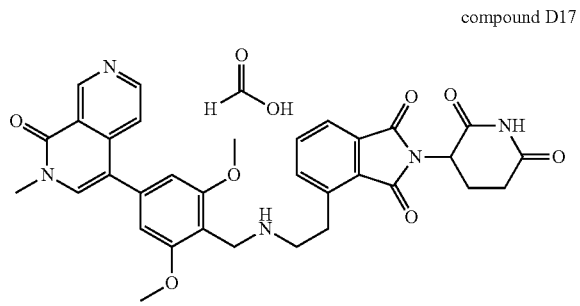

To a stirred solution of 4-[2-([[2,6-dimethoxy-4-(2-methyl-1-oxo-2,7-naphthyridin-4-yl)phenyl]methyl]amino)ethyl]-2-(2,6-dioxopiperidin-3-yl)isoindole-1,3-dione (50 mg, 0.082 mmol, 1.00 equiv) in MeOH (1.00 mL) was added HCHO (37% in water) (0.1 mL) at room temperature. The solution was stirred for 10 minutes at room temperature. Then to the above mixture was added NaBH$_3$CN (15.0 mg, 0.238 mmol, 2.90 equiv), and the resulting mixture was stirred for additional 1 hour at room temperature. The crude solution was directly purified by Prep-HPLC (conditions: SunFire C18 OBD Prep Column, 100 Å, 5 μm, 19 mm×250 mm; Mobile Phase A: Water (0.1% FA), Mobile Phase B: ACN; Flow rate: 25 mL/min; Gradient: 9% B to 19% B in 12 min; 254 nm) to afford three isomers 4-[2-([[2,6-dimethoxy-4-(2-methyl-1-oxo-2,7-naphthyridin-4-yl)phenyl]methyl](methyl)amino)ethyl]-2-(2,6-dioxopiperidin-3-yl)isoindole-1,3-dione formic acid (first peak, isomer A, 3.1 mg, 5.76%), 4-[2-([[2,6-dimethoxy-4-(2-methyl-1-oxo-2,7-naphthyridin-4-yl)phenyl]methyl](methyl)amino)ethyl]-2-(2,6-dioxopiperidin-3-yl)isoindole-1,3-dione formic acid (second peak, isomer B, 5.4 mg, 9.56%), and 4-[2-([[2,6-dimethoxy-4-(2-methyl-1-oxo-2,7-naphthyridin-4-yl)phenyl]methyl](methyl)amino)ethyl]-2-(2,6-dioxopiperidin-3-yl)isoindole-1,3-dione formic acid (third peak, isomer C, 6.7 mg, 11.94%) each as a white solid.

Isomer A: $^1$H NMR (300 MHz, Methanol-d4) δ 9.52 (d, J=0.9 Hz, 1H), 8.67 (d, J=5.8 Hz, 1H), 8.10 (t, J=4.9 Hz, 1H), 7.91 (d, J=4.6 Hz, 2H), 7.68 (s, 1H), 7.56 (dd, J=5.9, 0.9 Hz, 1H), 6.70 (s, 2H), 5.33 (br s, 1H), 5.21 (dd, J=12.5, 5.4 Hz, 1H), 4.19 (s, 2H), 3.86 (s, 6H), 3.70 (s, 3H), 2.94-2.65 (m, 6H), 2.25-2.12 (m, 1H), 1.74 (br s, 3H). LCMS (ESI) m/z: [M+H]+=624.30.

Isomer B: $^1$H NMR (300 MHz, Methanol-d4) δ 9.53 (d, J=0.9 Hz, 1H), 8.67 (d, J=5.8 Hz, 1H), 8.10 (dd, J=6.1, 2.9 Hz, 1H), 7.97 (d, J=6.1 Hz, 2H), 7.72 (s, 1H), 7.58 (dd, J=5.8, 0.9 Hz, 1H), 6.76 (s, 2H), 5.46 (br s, 1H), 5.22 (dd, J=12.5, 5.4 Hz, 1H), 4.41 (br s, 2H), 3.89 (s, 6H), 3.71 (s, 3H), 2.84 (s, 4H), 2.78-2.65 (m, 2H), 2.24-2.11 (s, 1H), 1.84 (d, J=6.9 Hz, 3H). LCMS (ESI) m/z: [M+H]+=624.35.

Isomer C: $^1$H NMR (300 MHz, Methanol-d4) δ 9.53 (d, J=0.9 Hz, 1H), 8.69 (d, J=5.8 Hz, 1H), 8.55 (s, 0.5H, FA), 7.87-7.70 (m, 4H), 7.64 (dd, J=5.8, 0.9 Hz, 1H), 6.82 (s, 2H), 5.15 (dd, J=12.2, 5.3 Hz, 1H), 4.26 (s, 2H), 3.94 (s, 6H), 3.72 (s, 3H), 3.61-3.49 (m, 2H), 3.27 (s, 2H), 2.96-2.67 (m, 6H), 2.21-2.09 (m, 1H). LCMS (ESI) m/z: [M+H]+=624.35.

Example 70—Preparation of (2S,4R)-1-[(2S)-2-[10-[2-([[2,6-dimethoxy-4-(2-methyl-1-oxo-2,7-naphthyridin-4-yl)phenyl]methyl](methyl)amino)acetamido]decanamido]-3,3-dimethylbutanoyl]-4-hydroxy-N-[[4-(4-methyl-1,3-thiazol-5-yl)phenyl]methyl]pyrrolidine-2-carboxamide (Compound D18)
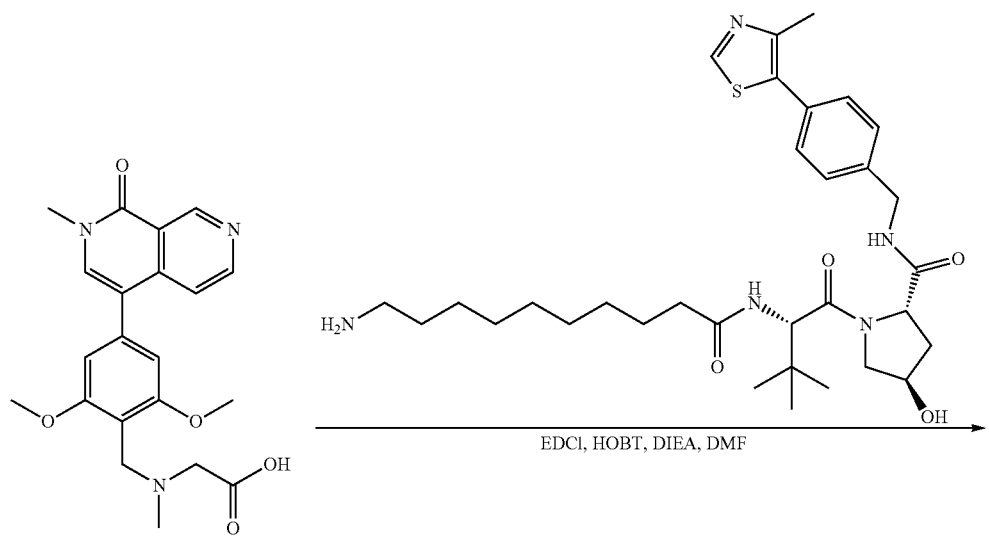
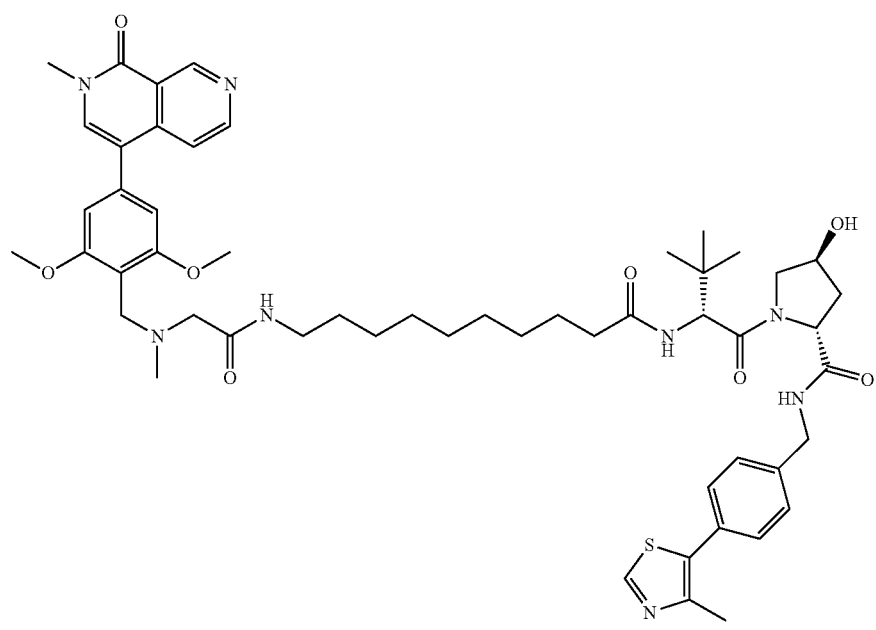
compound D18

To a stirred solution of ([[2,6-dimethoxy-4-(2-methyl-1-oxo-2,7-naphthyridin-4-yl)phenyl]methyl](methyl)amino) acetic acid (39.70 mg, 0.100 mmol, 1.00 equiv), EDCI (76.60 mg, 0.400 mmol, 4 equiv), HOBT (53.99 mg, 0.400 mmol, 4 equiv) and DIEA (129.10 mg, 0.999 mmol, 10 equiv) in DMF (1.00 mL) was added (2S,4R)-1-[(2S)-2-(10-aminodecanamido)-3,3-dimethylbutanoyl]-4-hydroxy-N-[[4-(4-methyl-1,3-thiazol-5-yl)phenyl]methyl]pyrrolidine-2-carboxamide (59.92 mg, 0.100 mmol, 1 equiv). The mixture was stirred for 5 h at room temperature under air atmosphere. Then, without any additional work-up, the resulting solution was purified by Prep-TLC (Column: XBridge Prep OBD C18 Column, 19*250 mm, 5 um; Mobile Phase A: Water (10 MMOL/L NH$_4$HCO$_3$), Mobile Phase B: ACN; Flow rate: 25 mL/min; Gradient: 35 B to 55 B in 15 min; 254/220 nm; R$_T$: 11.08 minutes) to afford (2S,4R)-1-[(2S)-2-[10-[2-([[2,6-dimethoxy-4-(2-methyl-1-oxo-2,7-naphthyridin-4-yl)phenyl]methyl](methyl) amino) acetamido]decanamido]-3,3-dimethylbutanoyl]-4-hydroxy-N-[[4-(4-methyl-1,3-thiazol-5-yl)phenyl] methyl] pyrrolidine-2-carboxamide (43 mg, 43.21%) as a white solid. $^1$H NMR (300 MHz, Methanol-d4) δ 9.54 (d, J=0.9 Hz, 1H), 8.88 (s, 1H), 8.69 (d, J=5.8 Hz, 1H), 7.75 (s, 1H), 7.63 (d, J=5.8, 1H), 7.53-7.39 (m, 4H), 6.76 (s, 2H), 4.68-4.48 (m, 4H), 4.37 (d, J=15.5 Hz, 1H), 3.93 (s, 1H), 3.90 (s, 6H), 3.81 (dd, J=11.0, 3.9 Hz, 1H), 3.76 (s, 2H), 3.71 (s, 3H), 3.21 (t, J=7.0 Hz, 2H), 3.09 (s, 2H), 2.48 (s, 3H), 2.35 (s, 3H), 2.31-2.18 (m, 3H), 2.15-2.04 (m, 1H), 1.65-1.44 (m, 4H), 1.41-1.25 (m, 10H), 1.04 (s, 9H). LCMS (ESI) m/z: [M+H]+=979.60.

Example 71—Preparation of (2S,4R)-1-[(2S)-2-[8-([[2,6-dimethoxy-4-(2-methyl-1-oxo-2,7-naphthyridin-4-yl)phenyl]methyl](methyl)amino)octanamido]-3,3-dimethylbutanoyl]-4-hydroxy-N-[[4-(4-methyl-1,3-thiazol-5-yl)phenyl]methyl]pyrrolidine-2-carboxamide (Compound D19)

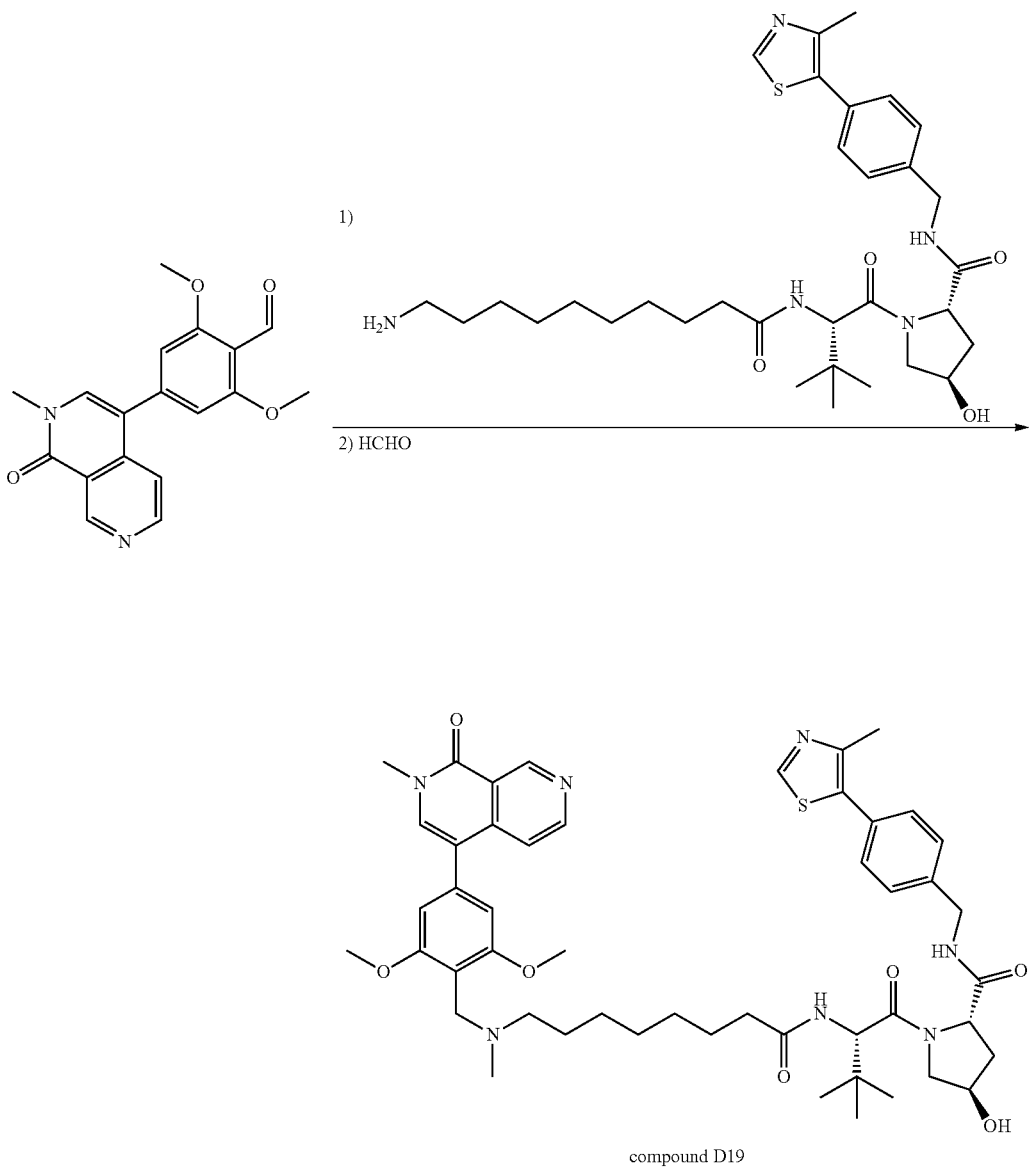

compound D19

To a stirred solution of (2S,4R)-1-[(2S)-2-[2-[2-(2-aminoethoxy)ethoxy]acetamido]-3,3-dimethylbutanoyl]-4-hydroxy-N-[[4-(4-methyl-1,3-thiazol-5-yl)phenyl]methyl]pyrrolidine-2-carboxamide (53.25 mg, 0.092 mmol, 1 equiv) in methanol was added 2,6-dimethoxy-4-(2-methyl-1-oxo-2,7-naphthyridin-4-yl)benzaldehyde (30.00 mg, 0.092 mmol, 1.00 equiv) dropwise in portions at room temperature under nitrogen atmosphere. The resulting mixture was stirred for additional 2 h at room temperature. To the above mixture was added NaBH$_3$CN (7.75 mg, 0.123 mmol, 2.00 equiv) at room temperature. The resulting mixture was stirred for additional 1 h at room temperature. To the above mixture was added NaBH$_3$CN (7.75 mg, 0.123 mmol, 2.00 equiv) and CH$_2$O at room temperature. The resulting mixture was stirred for additional 1 h at room temperature. The crude product (50.2 mg) was purified by Prep-HPLC (conditions: Xselect CSH F-Phenyl OBD column, 19*250, 5 μm; Mobile Phase A: Water (0.05% TFA), Mobile Phase B: ACN; Flow rate: 25 mL/min; Gradient: 20 B to 30 B in 12 min; 254/220 nm; R$_T$: 11.48 minutes) to afford (2S,4R)-1-[(2S)-2-[8-([[2,6-dimethoxy-4-(2-methyl-1-oxo-2,7-naphthyridin-4-yl)phenyl]methyl](methyl)amino)octanamido]-3,3-dimethylbutanoyl]-4-hydroxy-N-[[4-(4-methyl-1,3-thiazol-5-yl)phenyl]methyl]pyrrolidine-2-carboxamide as a white solid. $^1$H NMR (400 MHz, Methanol-d4) δ 1.05 (9H, s), 1.44 (6H, s), 1.67 (2H, s), 1.87 (2H, s), 2.05-2.16 (1H, m), 2.19-2.40 (3H, m), 2.50 (3H, s), 2.86 (3H, s), 3.12-3.24 (1H, m), 3.24-3.32 (1H, m), 3.76 (3H, s), 3.79-3.87 (1H, m), 3.92 (1H, d), 3.98 (6H, s), 4.31-4.42 (2H, m), 4.48-4.64 (4H, m), 4.66 (1H, s), 6.91 (2H, s), 7.40-7.52 (4H, m), 7.94 (1H, d), 8.08 (1H, s), 8.72 (1H, d), 8.99 (1H, s), 9.62 (1H, s). LCMS (ESI) m/z: [M+H]+=894.55.

Example 72—Preparation of (2S,4R)-1-[(2S)-2-(2-[2-[2-([[2,6-dimethoxy-4-(2-methyl-1-oxo-2,7-naphthyridin-4-yl)phenyl]methyl](methyl)amino)ethoxy]ethoxy]acetamido)-3,3-dimethylbutanoyl]-4-hydroxy-N-[[4-(4-methyl-1,3-thiazol-5-yl)phenyl]methyl]pyrrolidine-2-carboxamide (Compound D24)

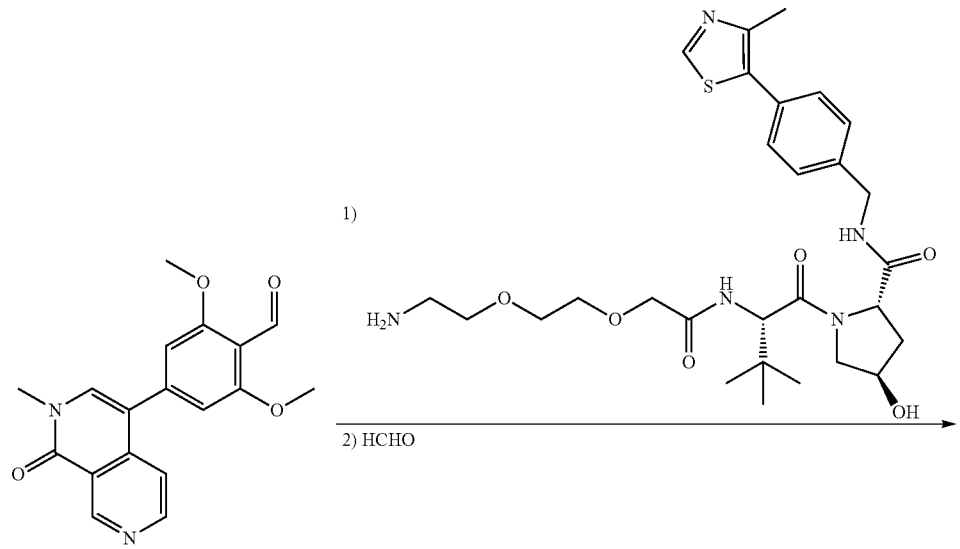

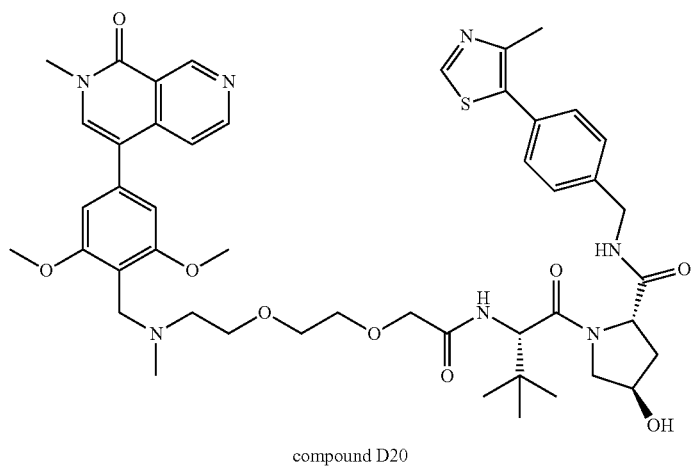

compound D20

To a stirred solution of (2S,4R)-1-[(2S)-2-[2-[2-(2-aminoethoxy)ethoxy]acetamido]-3,3-dimethylbutanoyl]-4-hydroxy-N-[[4-(4-methyl-1,3-thiazol-5-yl)phenyl]methyl]pyrrolidine-2-carboxamide (35.50 mg, 0.062 mmol, 1.00 equiv) in methanol was added 2,6-dimethoxy-4-(2-methyl-1-oxo-2,7-naphthyridin-4-yl)benzaldehyde (20.00 mg, 0.062 mmol, 1.00 equiv) dropwise in portions at room temperature under nitrogen atmosphere. The resulting mixture was stirred for additional 2 hours at room temperature. To the above mixture was added NaBH$_3$CN (7.75 mg, 0.123 mmol, 2.00 equiv) at room temperature. The resulting mixture was stirred for additional 1 h at room temperature. To the above mixture was added NaBH$_3$CN (7.75 mg, 0.123 mmol, 2.00 equiv) and CH$_2$O at room temperature. The resulting mixture was stirred for additional 1 h at room temperature. The crude product (30.5 mg) was purified by Prep-HPLC (conditions: Xselect CSH F-Phenyl OBD column, 19*250, 5 μm; Mobile Phase A: Water (0.05% TFA), Mobile Phase B: ACN; Flow rate: 25 mL/min; Gradient: 18 B to 27 B in 12 min; 254/220 nm; R$_T$: 10.97 minutes) to afford (2S,4R)-1-[(2S)-2-(2-[2-[2-([[2,6-dimethoxy-4-(2-methyl-1-oxo-2,7-naphthyridin-4-yl)phenyl]methyl](methyl)amino)ethoxy]ethoxy]acetamido)-3,3-dimethylbutanoyl]-4-hydroxy-N-[[4-(4-methyl-1,3-thiazol-5-yl)phenyl]methyl]pyrrolidine-2-carboxamide as a white solid. $^1$H NMR (400 MHz, Methanol-d4) δ 1.04-1.08 (9H, m), 2.05-2.14 (1H, m), 2.25 (1H, s), 2.49 (3H, t), 2.94 (3H, d), 3.70-3.92 (9H, m), 3.96 (8H, d), 4.02-4.17 (2H, m), 4.31-4.67 (6H, m), 4.74-4.82 (1H, m), 6.90 (2H, d), 7.39-7.49 (4H, m), 7.85-7.95 (1H, m), 8.01-8.07 (1H, m), 8.71 (1H, d), 8.92-8.99 (1H, m), 9.61 (1H, s) LCMS (ESI) m/z: [M+H]+=898.50.

Example 73—BRD9 Bromodomain TR-FRET Competition Binding Assay

This example demonstrates the ability of the compounds of the disclosure to biochemically inhibit BRD9 bromodomain in a competition binding assay.

Procedure:

His-Flag-BRD9 (P133-K239; Swiss Prot 09H8M2; SEQ ID NO:1 mgsshhhhhhenlyfq/gdykddddkgslevlfqg/PAENESTPIQQLLEHFLRQLQRKDPHGFFAFPVTDAIAPGYSMII KHPMDFGTMKDKIVANEYKSVTEFKADFKLMCDNAMTYNRPDTVYY KLAKKILHAGFKMMSK) was cloned, expressed, purified, and then treated with TEV protease. Cleaved His tag was removed by purification. The binding of a biotinylated small molecule ligand of BRD9 was assessed via the LANCE® TR-FRET platform (PerkinElmer), and the compounds were assayed for inhibitory activity against this interaction.

Results:

A mixture of biotinylated-ligand and SureLight™ Allophycocyanin-Streptavidin (APC-SA, PerkinElmer AD0201) in 50 mM HEPES (pH 7.4), 50 mM NaCl, 1 mM TCEP (pH 7), 0.01% (v/v) Tween-20, 0.01% (w/v) bovine serum albumin was added to a white 384-well PerkinElmer Proxiplate Plus plate. DMSO or 3-fold serially diluted compounds were then added to the Proxiplate followed by addition of Flag-BRD9. After a 10 minute incubation at room temperature, Eu-W1024 anti-FLAG (PerkinElmer, AD0273) was added. The final reaction mixture that contained 3.75 nM biotinylated ligand, 3 nM Flag-BRD9, 7.5 nM SureLight™ Allophycocyanin-Streptavidin, and 0.2 nM Eu-W1024 anti-FLAG was incubated at room temperature for 90 minutes.

The plates were then read on a PerkinElmer Envision plate reader to determine the ratio of emission at 665 nm over 615 nm. Data was normalized to a DMSO control (100%) and a no protein control (0%) and then fit to a four parameter, non-linear curve fit to calculate an IC$_{50}$ (μM) as shown in Table 5. As shown by the results in Table 5, a number of compounds of the present disclosure exhibit an IC$_{50}$ value of <1 μM for BRD9 binding, indicating their affinity for targeting BRD9.

TABLE 5

Bromodomain TR-FRET Binding

| Compound No. | Bromodomain TR-FRET BRD9 IC$_{50}$ (nM) |
| --- | --- |
| B1 | NT |
| B2 | +++ |
| B3 | + |
| B4 | + |
| B5 | + |
| B6 | + |
| B7 | + |
| B8 | + |
| B9 | + |
| B10 | + |
| B11 | + |
| B12 | + |
| B13 | + |
| B14 | +++ |
| B15 | +++ |
| B16 | ++ |
| B17 | ++ |
| B18 | +++ |
| B19 | ++ |
| B20 | ++++ |
| B21 | +++ |
| B22 | +++ |
| B23 | +++ |
| B24 | ++ |
| B25 | ++ |
| B26 | + |
| B27 | ++ |
| B28 | +++ |
| B29 | ++ |
| B30 | ++ |
| B31 | + |
| B32 | +++ |
| B33 | ++ |
| B34 | ++++ |
| B35 | ++++ |
| B36 | +++ |
| B37 | ++ |
| B38 | ++++ |
| B39 | ++++ |
| B40 | ++++ |
| B41 | +++ |
| B42 | + |
| B43 | ++++ |
| B44 | ++++ |
| B45 | +++ |
| B46 | +++ |
| B47 | +++ |
| B48 | ++ |
| B49 | +++ |
| B50 | +++ |
| B51 | NT |
| B52 | +++ |
| B53 | +++ |
| B54 | ++++ |
| B55 | NT |
| B56 | +++ |
| B57 | + |
| B58 | + |
| B59 | +++ |
| B60 | +++ |
| B61 | NT |
| B62 | +++ |
| B63 | +++ |
| B64 | +++ |
| B65 | +++ |
| B66 | ++ |
| B67 | +++ |

TABLE 5-continued

Bromodomain TR-FRET Binding

| Compound No. | Bromodomain TR-FRET BRD9 IC$_{50}$ (nM) |
| --- | --- |
| B68 | + |
| Compound 1 | +++ |
| D1 | +++ |
| D2 | +++ |
| D3 | +++ |
| D4 | ++++ |
| D5 | ++++ |
| D6 | +++ |
| D7 | +++ |
| D8 | +++ |
| D9 | +++ |
| D10 | +++ |
| D11 | ++++ |
| D12 | ++++ |
| D13 | +++ |
| D14 | ++++ |
| D15 | +++ |
| D16 | +++ |
| D17 | NT |
| D18 | ++++ |
| D19 | +++ |
| D20 | +++ |

"+" indicates inhibitory effect of >1000 nM;
"++" indicates inhibitory effect of 100-1000 nM;
"+++" indicates inhibitory effect of 10-100 nM;
"++++" indicates inhibitory effect of <10 nM;
"NT" indicates not tested

Example 74—SYO1 BRD9 NanoLuc Degradation Assay

This example demonstrates the ability of the compounds of the disclosure to degrade a Nanoluciferase-BRD9 fusion protein in a cell-based degradation assay.

Procedure:

A stable SYO-1 cell line expressing 3×FLAG-NLuc-BRD9 was generated. On day 0 cells were seeded in 30 µL media into each well of 384-well cell culture plates. The seeding density was 8000 cells/well. On day 1, cells were treated with 30 nL DMSO or 30 nL of 3-fold serially DMSO-diluted compounds (10 points in duplicates with 1 µM as final top dose). Subsequently plates were incubated for 6 hours in a standard tissue culture incubator and equilibrated at room temperature for 15 minutes. Nanoluciferase activity was measured by adding 15 µL of freshly prepared Nano-Glo Luciferase Assay Reagent (Promega N1130), shaking the plates for 10 minutes and reading the bioluminescence using an EnVision reader.

Results:

The Inhibition % was calculated using the following formula: % Inhibition=100×(Lum$_{HC}$−Lum$_{Sample}$)/(Lum$_{HC}$−Lum$_{LC}$). DMSO treated cells are employed as High Control (HC) and 1 µM of a known BRD9 degrader standard treated cells are employed as Low Control (LC). The data was fit to a four parameter, non-linear curve fit to calculate IC$_{50}$ (µM) values as shown in Table 6. As shown by the results in Table 6, a number of compounds of the present disclosure exhibit an IC$_{50}$ value of <1 µM for the degradation of BRD9, indicating their use as compounds for reducing the levels and/or activity of BRD9 and their potential for treating BRD9-related disorders.

TABLE 6

SYO1 BRD9-NanoLuc Degradation

| Compound No. | SYO1 BRD9-NanoLuc degradation IC50 (nM) |
| --- | --- |
| Compound 1 | ++++ |
| D1 | ++ |
| D2 | ++++ |
| D3 | +++ |
| D4 | ++++ |
| D5 | ++++ |
| D6 | ++++ |
| D7 | +++ |
| D8 | ++++ |
| D9 | ++++ |
| D10 | ++++ |
| D11 | ++++ |
| D12 | ++++ |
| D13 | +++ |
| D14 | + |
| D15 | + |
| D16 | +++ |
| D17 | + |
| D18 | ++++ |
| D19 | + |
| D20 | + |

"+" indicates inhibitory effect of >1000 nM;
"++" indicates inhibitory effect of 100-1000 nM;
"+++" indicates inhibitory effect of 10-100 nM;
"++++" indicates inhibitory effect of <10 nM;
"NT" indicates not tested

Other Embodiments

All publications, patents, and patent applications mentioned in this specification are incorporated herein by reference in their entirety to the same extent as if each individual publication, patent, or patent application was specifically and individually indicated to be incorporated by reference in its entirety.

Where a term in the present application is found to be defined differently in a document incorporated herein by reference, the definition provided herein is to serve as the definition for the term.

While the invention has been described in connection with specific embodiments thereof, it will be understood that invention is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are in the claims.

What is claimed is:

1. A method of treating synovial sarcoma in a subject in need thereof, the method comprising administering to the subject an effective amount of a compound having the structure of Formula I:

A-L-B          Formula I wherein

L is a linker;

B is a degradation moiety, which has the structure of Formula A-1:

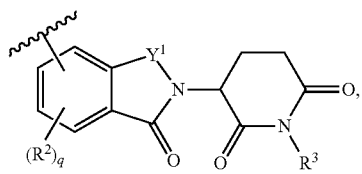

Formula A-1 wherein $Y^1$ is

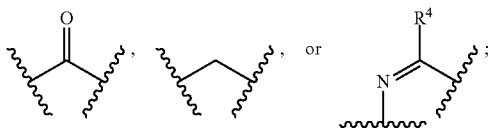

each of $R^3$ and $R^4$ is, independently, H, optionally substituted $C_1$-$C_6$ alkyl, or optionally substituted $C_1$-$C_6$ heteroalkyl;

q is 0, 1, 2, 3, or 4; and each $R^2$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxyl, —SH, or optionally substituted amino;

A has the structure of Formula E-a:

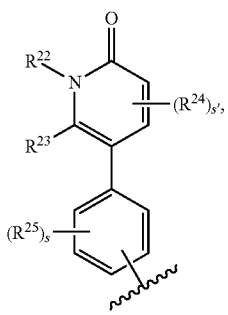

Formula E-a where $R^{22}$ is H, optionally substituted $C_1$-$C_6$ alkyl, or optionally substituted $C_1$-$C_6$ heteroalkyl;

$R^{23}$ is H, halogen, optionally substituted $C_1$-$C_6$ alkyl, or optionally substituted $C_6$-$C_{10}$ aryl;

s' is 0, 1, or 2;

each $R^{24}$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxyl, —SH, or optionally substituted amino, or two $R^{24}$ combine with the carbon atoms to which they are attached to form an optionally substituted $C_6$-$C_{10}$ aryl or optionally substituted $C_2$-$C_9$ heteroaryl;

s is 0, 1, 2, 3, or 4; and each $R^{25}$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxyl, —SH, or optionally substituted amino, or a pharmaceutically acceptable salt thereof.

2. The compound method of claim 1, wherein the linker has the structure of Formula II:

$A^1$-$(B^1)_f$-$(C^1)_g$-$(B^2)_h$-(D)-$(B^3)_i$-$(C^2)_j$-$(B^4)_k$-$A^2$        Formula II wherein $A^1$ is a bond between the linker and A;

$A^2$ is a bond between B and the linker;

each of $B^1$, $B^2$, $B^3$, and $B^4$ is, independently, optionally substituted $C_1$-$C_2$ alkyl, optionally substituted $C_1$-$C_3$ heteroalkyl, O, S, $S(O)_2$, or $NR^N$;

$R^N$ is H, optionally substituted $C_{1-4}$ alkyl, optionally substituted $C_{2-4}$ alkenyl, optionally substituted $C_{2-4}$ alkynyl, optionally substituted $C_{2-6}$ heterocyclyl, optionally substituted $C_{6-12}$ aryl, or optionally substituted $C_{1-7}$ heteroalkyl;

each of $C^1$ and $C^2$ is, independently, carbonyl, thiocarbonyl, sulphonyl, or phosphoryl;

f, g, h, l, j, and k are each, independently, 0 or 1; and

D is optionally substituted $C_{1-10}$ alkyl, optionally substituted $C_{2-10}$ alkenyl, optionally substituted $C_{2-10}$ alkynyl, optionally substituted $C_{2-6}$ heterocyclyl, optionally substituted $C_{6-12}$ aryl, optionally substituted $C_2$-$C_{10}$ polyethylene glycol, or optionally substituted $C_{1-10}$ heteroalkyl, or a chemical bond linking $A^1$-$(B^1)_f$-$(C^1)_g$-$(B^2)_h$- to -$(B^3)_i$-$(C^2)_j$-$(B^4)_k$-$A^2$.

3. The method of claim 1, wherein the compound has the structure of any of compounds:

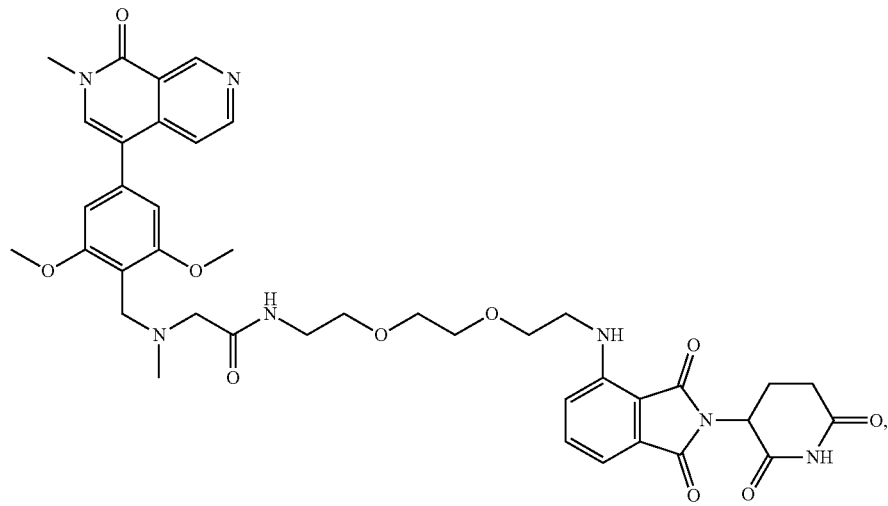
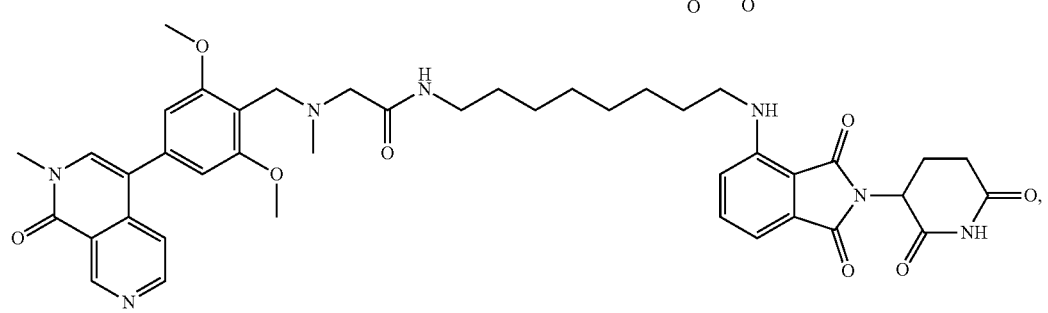
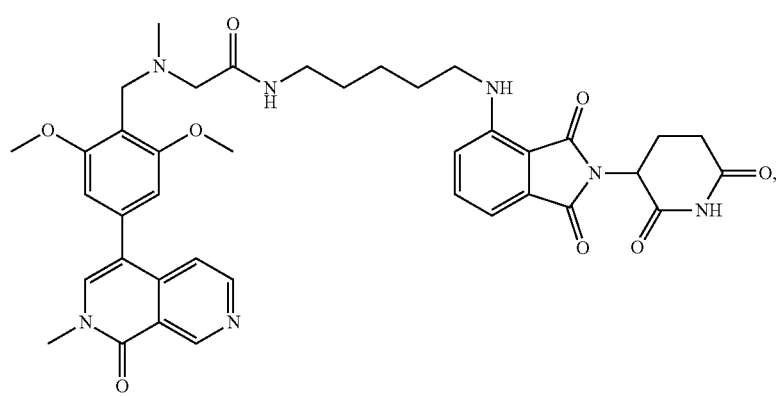
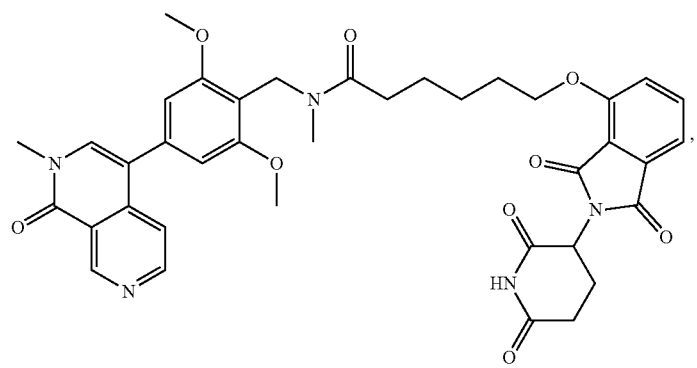

-continued
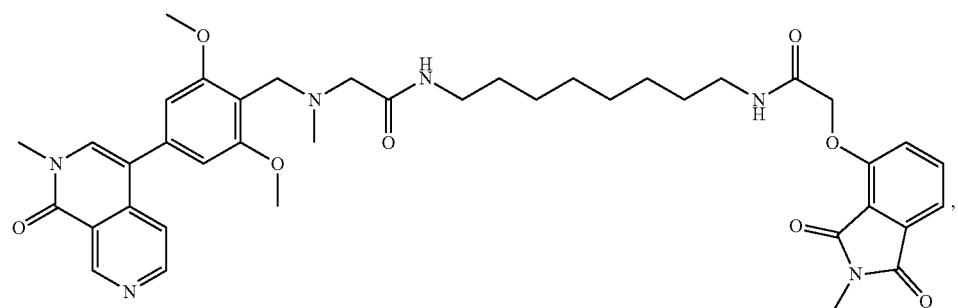
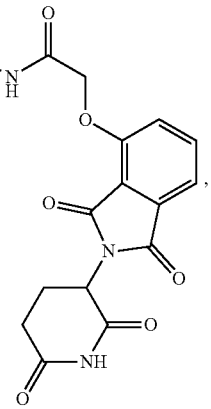
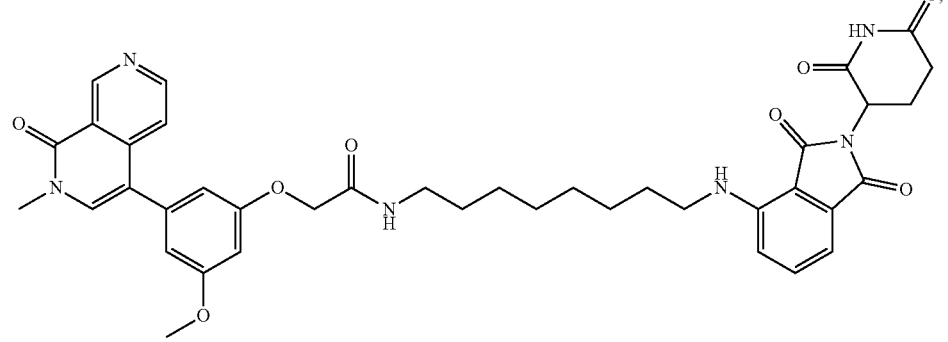
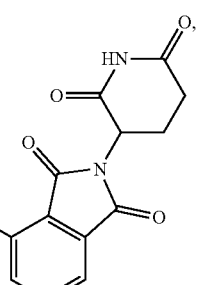
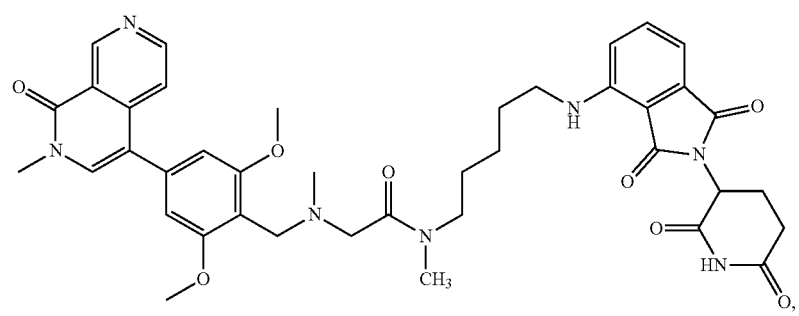
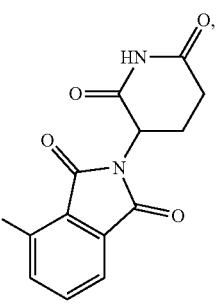
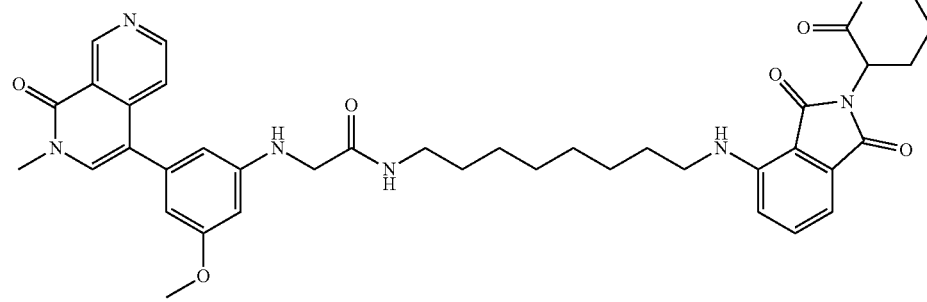

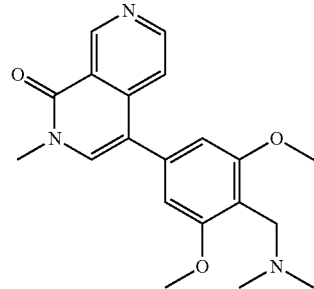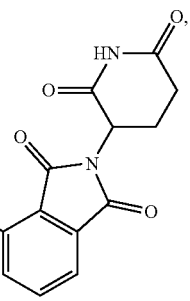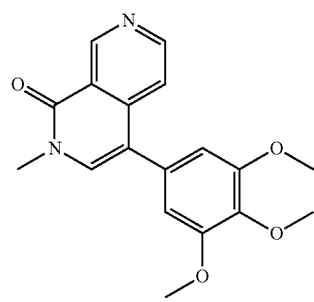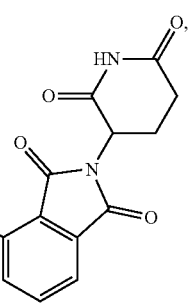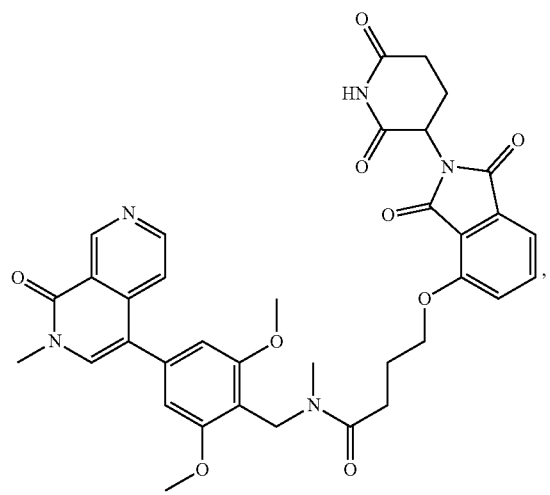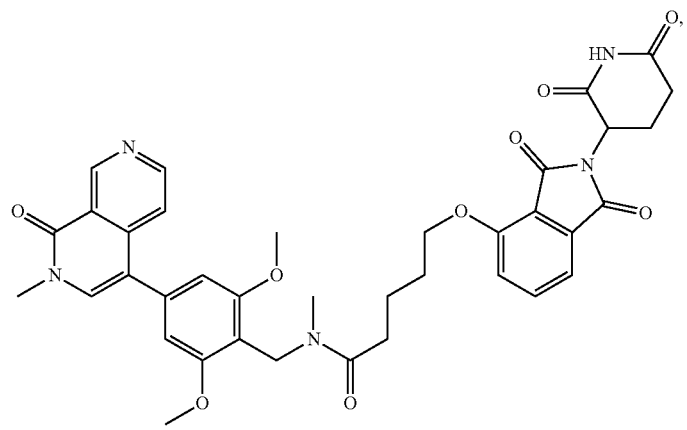

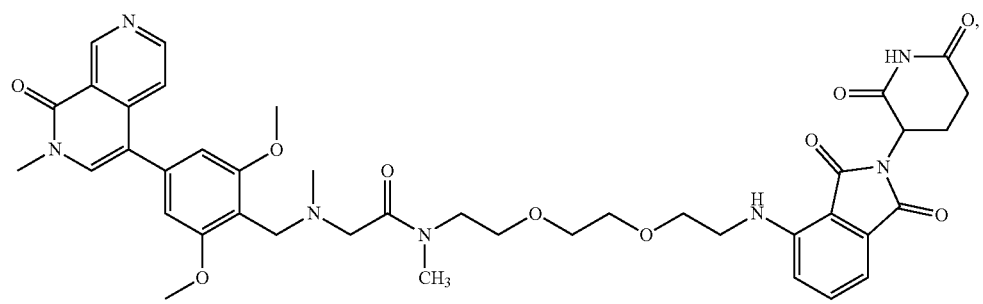
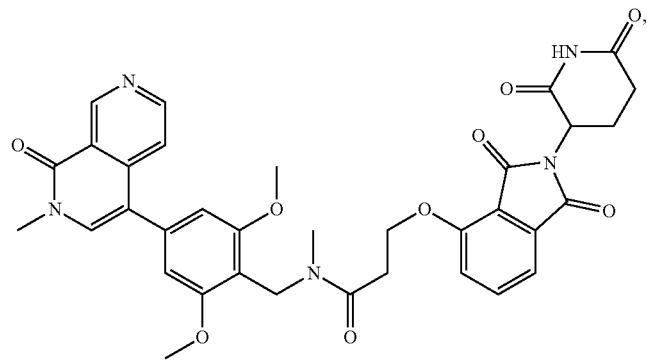
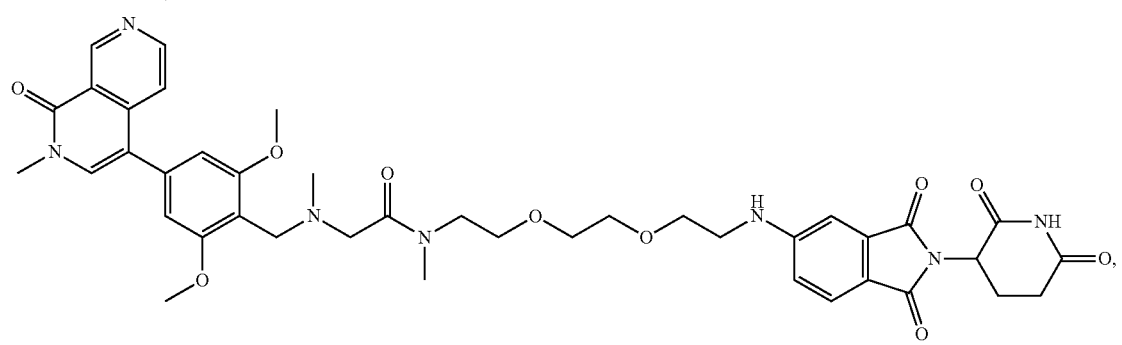
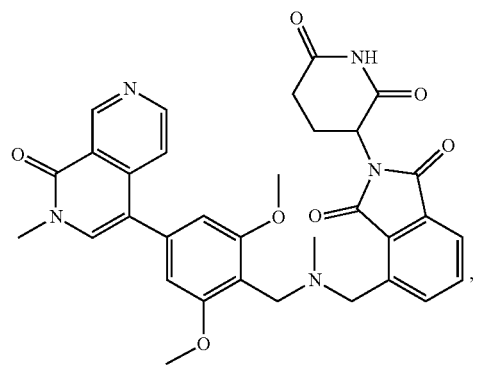
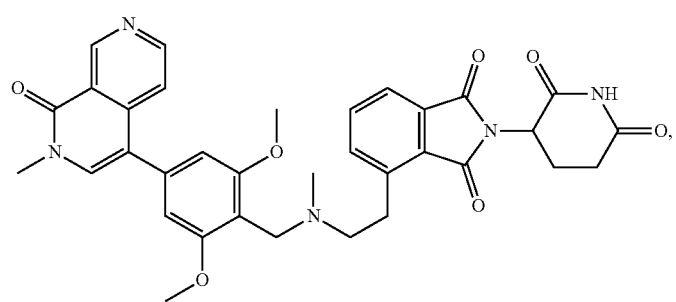

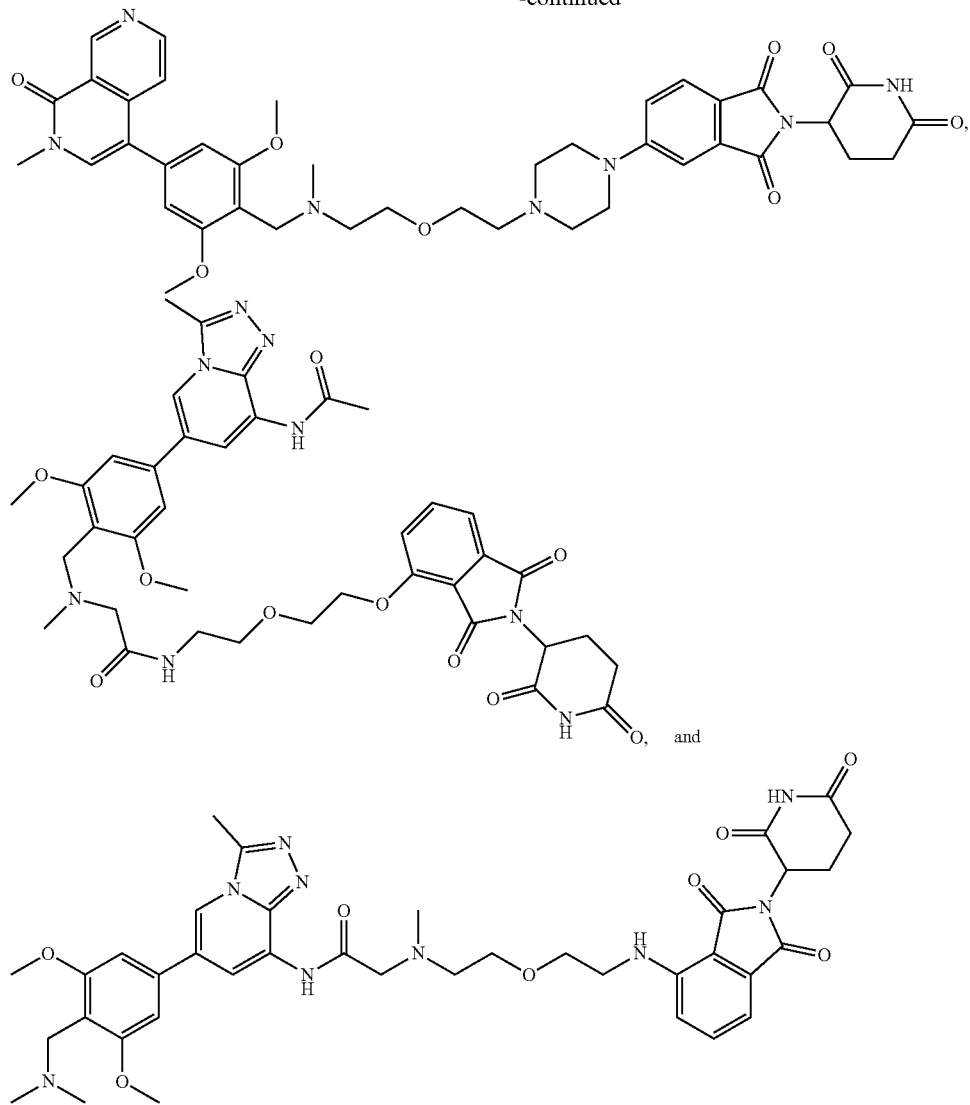

or a pharmaceutically acceptable salt thereof.

4. The method of claim 1, wherein Formula E-a has the structure of Formula E-2a:

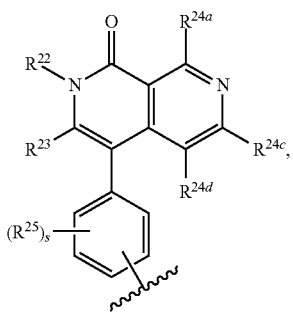

Formula E-2a where $R^{22}$ is H, optionally substituted $C_1$-$C_6$ alkyl, or optionally substituted $C_1$-$C_6$ heteroalkyl;

$R^{23}$ is H, halogen, optionally substituted $C_1$-$C_6$ alkyl, or optionally substituted $C_6$-$C_{10}$ aryl;

s is 0, 1, 2, 3, or 4;

each $R^{25}$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxyl, —SH, or optionally substituted amino;

$X^1$ is N or $CR^{24a}$;
$X^2$ is N or $CR^{24b}$;
$X^3$ is N or $CR^{24c}$;
$X^4$ is N or $CR^{24d}$; and each of $R^{24a}$, $R^{24b}$, $R^{24c}$, and $R^{24d}$ is, independently, H, halogen, hydroxyl, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxyl, —SH, or optionally substituted amino, or a pharmaceutically acceptable salt thereof.

* * * * *

SEQUENCE LISTING

<160> NUMBER OF SEQ ID NOS: 673

<210> SEQ ID NO 1
<211> LENGTH: 141
<212> TYPE: PRT

<213> ORGANISM: Artificial Sequence
<220> FEATURE:
<223> OTHER INFORMATION: Synthetic Construct

<400> SEQUENCE: 1

```
Met Gly Ser Ser His His His His His His Glu Asn Leu Tyr Phe Gln
1               5                   10                  15

Gly Asp Tyr Lys Asp Asp Asp Lys Gly Ser Leu Glu Val Leu Phe
            20                  25                  30

Gln Gly Pro Ala Glu Asn Glu Ser Thr Pro Ile Gln Gln Leu Leu Glu
        35                  40                  45

His Phe Leu Arg Gln Leu Gln Arg Lys Asp Pro His Gly Phe Phe Ala
    50                  55                  60

Phe Pro Val Thr Asp Ala Ile Ala Pro Gly Tyr Ser Met Ile Ile Lys
65                  70                  75                  80

His Pro Met Asp Phe Gly Thr Met Lys Asp Lys Ile Val Ala Asn Glu
                85                  90                  95

Tyr Lys Ser Val Thr Glu Phe Lys Ala Asp Phe Lys Leu Met Cys Asp
            100                 105                 110

Asn Ala Met Thr Tyr Asn Arg Pro Asp Thr Val Tyr Tyr Lys Leu Ala
        115                 120                 125

Lys Lys Ile Leu His Ala Gly Phe Lys Met Met Ser Lys
    130                 135                 140
```

<210> SEQ ID NO 2

<400> SEQUENCE: 2

000

<210> SEQ ID NO 3

<400> SEQUENCE: 3

000

<210> SEQ ID NO 4

<400> SEQUENCE: 4

000

<210> SEQ ID NO 5

<400> SEQUENCE: 5

000

<210> SEQ ID NO 6

<400> SEQUENCE: 6

000

<210> SEQ ID NO 7

<400> SEQUENCE: 7

000

<210> SEQ ID NO 8

<400> SEQUENCE: 8

000

<210> SEQ ID NO 9

<400> SEQUENCE: 9

000

<210> SEQ ID NO 10

<400> SEQUENCE: 10

000

<210> SEQ ID NO 11

<400> SEQUENCE: 11

000

<210> SEQ ID NO 12

<400> SEQUENCE: 12

000

<210> SEQ ID NO 13

<400> SEQUENCE: 13

000

<210> SEQ ID NO 14

<400> SEQUENCE: 14

000

<210> SEQ ID NO 15

<400> SEQUENCE: 15

000

<210> SEQ ID NO 16

<400> SEQUENCE: 16

000

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

<210> SEQ ID NO 20

<400> SEQUENCE: 20

000

<210> SEQ ID NO 21

<400> SEQUENCE: 21

000

<210> SEQ ID NO 22

<400> SEQUENCE: 22

000

<210> SEQ ID NO 23

<400> SEQUENCE: 23

000

<210> SEQ ID NO 24

<400> SEQUENCE: 24

000

<210> SEQ ID NO 25

<400> SEQUENCE: 25

000

<210> SEQ ID NO 26

<400> SEQUENCE: 26

000

<210> SEQ ID NO 27

<400> SEQUENCE: 27

000

<210> SEQ ID NO 28

<400> SEQUENCE: 28

000

<210> SEQ ID NO 29

<400> SEQUENCE: 29

000

<210> SEQ ID NO 30

<400> SEQUENCE: 30

000

```
<210> SEQ ID NO 31
<400> SEQUENCE: 31
000

<210> SEQ ID NO 32
<400> SEQUENCE: 32
000

<210> SEQ ID NO 33
<400> SEQUENCE: 33
000

<210> SEQ ID NO 34
<400> SEQUENCE: 34
000

<210> SEQ ID NO 35
<400> SEQUENCE: 35
000

<210> SEQ ID NO 36
<400> SEQUENCE: 36
000

<210> SEQ ID NO 37
<400> SEQUENCE: 37
000

<210> SEQ ID NO 38
<400> SEQUENCE: 38
000

<210> SEQ ID NO 39
<400> SEQUENCE: 39
000

<210> SEQ ID NO 40
<400> SEQUENCE: 40
000

<210> SEQ ID NO 41
<400> SEQUENCE: 41
000

<210> SEQ ID NO 42
```

<400> SEQUENCE: 42

000

<210> SEQ ID NO 43

<400> SEQUENCE: 43

000

<210> SEQ ID NO 44

<400> SEQUENCE: 44

000

<210> SEQ ID NO 45

<400> SEQUENCE: 45

000

<210> SEQ ID NO 46

<400> SEQUENCE: 46

000

<210> SEQ ID NO 47

<400> SEQUENCE: 47

000

<210> SEQ ID NO 48

<400> SEQUENCE: 48

000

<210> SEQ ID NO 49

<400> SEQUENCE: 49

000

<210> SEQ ID NO 50

<400> SEQUENCE: 50

000

<210> SEQ ID NO 51

<400> SEQUENCE: 51

000

<210> SEQ ID NO 52

<400> SEQUENCE: 52

000

<210> SEQ ID NO 53

<400> SEQUENCE: 53

000

<210> SEQ ID NO 54

<400> SEQUENCE: 54

000

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58

<400> SEQUENCE: 58

000

<210> SEQ ID NO 59

<400> SEQUENCE: 59

000

<210> SEQ ID NO 60

<400> SEQUENCE: 60

000

<210> SEQ ID NO 61

<400> SEQUENCE: 61

000

<210> SEQ ID NO 62

<400> SEQUENCE: 62

000

<210> SEQ ID NO 63

<400> SEQUENCE: 63

000

<210> SEQ ID NO 64

<400> SEQUENCE: 64

000

<210> SEQ ID NO 65
<400> SEQUENCE: 65
000

<210> SEQ ID NO 66
<400> SEQUENCE: 66
000

<210> SEQ ID NO 67
<400> SEQUENCE: 67
000

<210> SEQ ID NO 68
<400> SEQUENCE: 68
000

<210> SEQ ID NO 69
<400> SEQUENCE: 69
000

<210> SEQ ID NO 70
<400> SEQUENCE: 70
000

<210> SEQ ID NO 71
<400> SEQUENCE: 71
000

<210> SEQ ID NO 72
<400> SEQUENCE: 72
000

<210> SEQ ID NO 73
<400> SEQUENCE: 73
000

<210> SEQ ID NO 74
<400> SEQUENCE: 74
000

<210> SEQ ID NO 75
<400> SEQUENCE: 75
000

<210> SEQ ID NO 76

-continued

<400> SEQUENCE: 76

000

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81

<400> SEQUENCE: 81

000

<210> SEQ ID NO 82

<400> SEQUENCE: 82

000

<210> SEQ ID NO 83

<400> SEQUENCE: 83

000

<210> SEQ ID NO 84

<400> SEQUENCE: 84

000

<210> SEQ ID NO 85

<400> SEQUENCE: 85

000

<210> SEQ ID NO 86

<400> SEQUENCE: 86

000

<210> SEQ ID NO 87

<400> SEQUENCE: 87

000

<210> SEQ ID NO 88

<400> SEQUENCE: 88

000

<210> SEQ ID NO 89

<400> SEQUENCE: 89

000

<210> SEQ ID NO 90

<400> SEQUENCE: 90

000

<210> SEQ ID NO 91

<400> SEQUENCE: 91

000

<210> SEQ ID NO 92

<400> SEQUENCE: 92

000

<210> SEQ ID NO 93

<400> SEQUENCE: 93

000

<210> SEQ ID NO 94

<400> SEQUENCE: 94

000

<210> SEQ ID NO 95

<400> SEQUENCE: 95

000

<210> SEQ ID NO 96

<400> SEQUENCE: 96

000

<210> SEQ ID NO 97

<400> SEQUENCE: 97

000

<210> SEQ ID NO 98

<400> SEQUENCE: 98

000

<210> SEQ ID NO 99

<400> SEQUENCE: 99

000

<210> SEQ ID NO 100

<400> SEQUENCE: 100

000

<210> SEQ ID NO 101

<400> SEQUENCE: 101

000

<210> SEQ ID NO 102

<400> SEQUENCE: 102

000

<210> SEQ ID NO 103

<400> SEQUENCE: 103

000

<210> SEQ ID NO 104

<400> SEQUENCE: 104

000

<210> SEQ ID NO 105

<400> SEQUENCE: 105

000

<210> SEQ ID NO 106

<400> SEQUENCE: 106

000

<210> SEQ ID NO 107

<400> SEQUENCE: 107

000

<210> SEQ ID NO 108

<400> SEQUENCE: 108

000

<210> SEQ ID NO 109

<400> SEQUENCE: 109

000

```
<210> SEQ ID NO 110
<400> SEQUENCE: 110
000

<210> SEQ ID NO 111
<400> SEQUENCE: 111
000

<210> SEQ ID NO 112
<400> SEQUENCE: 112
000

<210> SEQ ID NO 113
<400> SEQUENCE: 113
000

<210> SEQ ID NO 114
<400> SEQUENCE: 114
000

<210> SEQ ID NO 115
<400> SEQUENCE: 115
000

<210> SEQ ID NO 116
<400> SEQUENCE: 116
000

<210> SEQ ID NO 117
<400> SEQUENCE: 117
000

<210> SEQ ID NO 118
<400> SEQUENCE: 118
000

<210> SEQ ID NO 119
<400> SEQUENCE: 119
000

<210> SEQ ID NO 120
<400> SEQUENCE: 120
000

<210> SEQ ID NO 121
```

```
<400> SEQUENCE: 121

000

<210> SEQ ID NO 122

<400> SEQUENCE: 122

000

<210> SEQ ID NO 123

<400> SEQUENCE: 123

000

<210> SEQ ID NO 124

<400> SEQUENCE: 124

000

<210> SEQ ID NO 125

<400> SEQUENCE: 125

000

<210> SEQ ID NO 126

<400> SEQUENCE: 126

000

<210> SEQ ID NO 127

<400> SEQUENCE: 127

000

<210> SEQ ID NO 128

<400> SEQUENCE: 128

000

<210> SEQ ID NO 129

<400> SEQUENCE: 129

000

<210> SEQ ID NO 130

<400> SEQUENCE: 130

000

<210> SEQ ID NO 131

<400> SEQUENCE: 131

000

<210> SEQ ID NO 132

<400> SEQUENCE: 132
```

000

<210> SEQ ID NO 133
<400> SEQUENCE: 133
000

<210> SEQ ID NO 134
<400> SEQUENCE: 134
000

<210> SEQ ID NO 135
<400> SEQUENCE: 135
000

<210> SEQ ID NO 136
<400> SEQUENCE: 136
000

<210> SEQ ID NO 137
<400> SEQUENCE: 137
000

<210> SEQ ID NO 138
<400> SEQUENCE: 138
000

<210> SEQ ID NO 139
<400> SEQUENCE: 139
000

<210> SEQ ID NO 140
<400> SEQUENCE: 140
000

<210> SEQ ID NO 141
<400> SEQUENCE: 141
000

<210> SEQ ID NO 142
<400> SEQUENCE: 142
000

<210> SEQ ID NO 143
<400> SEQUENCE: 143
000

<210> SEQ ID NO 144

<400> SEQUENCE: 144

000

<210> SEQ ID NO 145

<400> SEQUENCE: 145

000

<210> SEQ ID NO 146

<400> SEQUENCE: 146

000

<210> SEQ ID NO 147

<400> SEQUENCE: 147

000

<210> SEQ ID NO 148

<400> SEQUENCE: 148

000

<210> SEQ ID NO 149

<400> SEQUENCE: 149

000

<210> SEQ ID NO 150

<400> SEQUENCE: 150

000

<210> SEQ ID NO 151

<400> SEQUENCE: 151

000

<210> SEQ ID NO 152

<400> SEQUENCE: 152

000

<210> SEQ ID NO 153

<400> SEQUENCE: 153

000

<210> SEQ ID NO 154

<400> SEQUENCE: 154

000

<210> SEQ ID NO 155

```
<400> SEQUENCE: 155
000

<210> SEQ ID NO 156
<400> SEQUENCE: 156
000

<210> SEQ ID NO 157
<400> SEQUENCE: 157
000

<210> SEQ ID NO 158
<400> SEQUENCE: 158
000

<210> SEQ ID NO 159
<400> SEQUENCE: 159
000

<210> SEQ ID NO 160
<400> SEQUENCE: 160
000

<210> SEQ ID NO 161
<400> SEQUENCE: 161
000

<210> SEQ ID NO 162
<400> SEQUENCE: 162
000

<210> SEQ ID NO 163
<400> SEQUENCE: 163
000

<210> SEQ ID NO 164
<400> SEQUENCE: 164
000

<210> SEQ ID NO 165
<400> SEQUENCE: 165
000

<210> SEQ ID NO 166
<400> SEQUENCE: 166
```

000

<210> SEQ ID NO 167
<400> SEQUENCE: 167
000

<210> SEQ ID NO 168
<400> SEQUENCE: 168
000

<210> SEQ ID NO 169
<400> SEQUENCE: 169
000

<210> SEQ ID NO 170
<400> SEQUENCE: 170
000

<210> SEQ ID NO 171
<400> SEQUENCE: 171
000

<210> SEQ ID NO 172
<400> SEQUENCE: 172
000

<210> SEQ ID NO 173
<400> SEQUENCE: 173
000

<210> SEQ ID NO 174
<400> SEQUENCE: 174
000

<210> SEQ ID NO 175
<400> SEQUENCE: 175
000

<210> SEQ ID NO 176
<400> SEQUENCE: 176
000

<210> SEQ ID NO 177
<400> SEQUENCE: 177
000

<210> SEQ ID NO 178

<400> SEQUENCE: 178

000

<210> SEQ ID NO 179

<400> SEQUENCE: 179

000

<210> SEQ ID NO 180

<400> SEQUENCE: 180

000

<210> SEQ ID NO 181

<400> SEQUENCE: 181

000

<210> SEQ ID NO 182

<400> SEQUENCE: 182

000

<210> SEQ ID NO 183

<400> SEQUENCE: 183

000

<210> SEQ ID NO 184

<400> SEQUENCE: 184

000

<210> SEQ ID NO 185

<400> SEQUENCE: 185

000

<210> SEQ ID NO 186

<400> SEQUENCE: 186

000

<210> SEQ ID NO 187

<400> SEQUENCE: 187

000

<210> SEQ ID NO 188

<400> SEQUENCE: 188

000

```
<210> SEQ ID NO 189
<400> SEQUENCE: 189
000

<210> SEQ ID NO 190
<400> SEQUENCE: 190
000

<210> SEQ ID NO 191
<400> SEQUENCE: 191
000

<210> SEQ ID NO 192
<400> SEQUENCE: 192
000

<210> SEQ ID NO 193
<400> SEQUENCE: 193
000

<210> SEQ ID NO 194
<400> SEQUENCE: 194
000

<210> SEQ ID NO 195
<400> SEQUENCE: 195
000

<210> SEQ ID NO 196
<400> SEQUENCE: 196
000

<210> SEQ ID NO 197
<400> SEQUENCE: 197
000

<210> SEQ ID NO 198
<400> SEQUENCE: 198
000

<210> SEQ ID NO 199
<400> SEQUENCE: 199
000

<210> SEQ ID NO 200
```

```
<400> SEQUENCE: 200

000

<210> SEQ ID NO 201

<400> SEQUENCE: 201

000

<210> SEQ ID NO 202

<400> SEQUENCE: 202

000

<210> SEQ ID NO 203
<211> LENGTH: 20
<212> TYPE: RNA
<213> ORGANISM: Artificial Sequence
<220> FEATURE:
<223> OTHER INFORMATION: Synthetic Construct

<400> SEQUENCE: 203
caagaagcac aagaagcaca                                            20

<210> SEQ ID NO 204
<211> LENGTH: 20
<212> TYPE: RNA
<213> ORGANISM: Artificial Sequence
<220> FEATURE:
<223> OTHER INFORMATION: Synthetic Construct

<400> SEQUENCE: 204
cttgtgcttc ttgcccatgg                                            20

<210> SEQ ID NO 205
<211> LENGTH: 20
<212> TYPE: RNA
<213> ORGANISM: Artificial Sequence
<220> FEATURE:
<223> OTHER INFORMATION: Synthetic Construct

<400> SEQUENCE: 205
cttcttgtgc ttcttgccca                                            20

<210> SEQ ID NO 206
<211> LENGTH: 20
<212> TYPE: RNA
<213> ORGANISM: Artificial Sequence
<220> FEATURE:
<223> OTHER INFORMATION: Synthetic Construct

<400> SEQUENCE: 206
acaagaagca caaggccgag                                            20

<210> SEQ ID NO 207
<211> LENGTH: 20
<212> TYPE: RNA
<213> ORGANISM: Artificial Sequence
<220> FEATURE:
<223> OTHER INFORMATION: Synthetic Construct

<400> SEQUENCE: 207
ctcgtaggac gagcgccact                                            20
```

```
<210> SEQ ID NO 208
<211> LENGTH: 20
<212> TYPE: RNA
<213> ORGANISM: Artificial Sequence
<220> FEATURE:
<223> OTHER INFORMATION: Synthetic Construct

<400> SEQUENCE: 208
cgagtggcgc tcgtcctacg                                               20

<210> SEQ ID NO 209
<211> LENGTH: 20
<212> TYPE: RNA
<213> ORGANISM: Artificial Sequence
<220> FEATURE:
<223> OTHER INFORMATION: Synthetic Construct

<400> SEQUENCE: 209
gagtggcgct cgtcctacga                                               20

<210> SEQ ID NO 210
<211> LENGTH: 20
<212> TYPE: RNA
<213> ORGANISM: Artificial Sequence
<220> FEATURE:
<223> OTHER INFORMATION: Synthetic Construct

<400> SEQUENCE: 210
aggcttctcc aggggcttgt                                               20

<210> SEQ ID NO 211
<211> LENGTH: 20
<212> TYPE: RNA
<213> ORGANISM: Artificial Sequence
<220> FEATURE:
<223> OTHER INFORMATION: Synthetic Construct

<400> SEQUENCE: 211
agattatgcc gacaagcccc                                               20

<210> SEQ ID NO 212
<211> LENGTH: 20
<212> TYPE: RNA
<213> ORGANISM: Artificial Sequence
<220> FEATURE:
<223> OTHER INFORMATION: Synthetic Construct

<400> SEQUENCE: 212
accttcagga ctagctttag                                               20

<210> SEQ ID NO 213
<211> LENGTH: 20
<212> TYPE: RNA
<213> ORGANISM: Artificial Sequence
<220> FEATURE:
<223> OTHER INFORMATION: Synthetic Construct

<400> SEQUENCE: 213
agctttagag gcttctccag                                               20

<210> SEQ ID NO 214
<211> LENGTH: 20
<212> TYPE: RNA
<213> ORGANISM: Artificial Sequence
<220> FEATURE:
<223> OTHER INFORMATION: Synthetic Construct
```

```
<400> SEQUENCE: 214
ctagctttag aggcttctcc                                                    20

<210> SEQ ID NO 215
<211> LENGTH: 20
<212> TYPE: RNA
<213> ORGANISM: Artificial Sequence
<220> FEATURE:
<223> OTHER INFORMATION: Synthetic Construct

<400> SEQUENCE: 215
tagctttaga ggcttctcca                                                    20

<210> SEQ ID NO 216
<211> LENGTH: 20
<212> TYPE: RNA
<213> ORGANISM: Artificial Sequence
<220> FEATURE:
<223> OTHER INFORMATION: Synthetic Construct

<400> SEQUENCE: 216
ctaaagctag tcctgaaggt                                                    20

<210> SEQ ID NO 217
<211> LENGTH: 20
<212> TYPE: RNA
<213> ORGANISM: Artificial Sequence
<220> FEATURE:
<223> OTHER INFORMATION: Synthetic Construct

<400> SEQUENCE: 217
gcctctaaag ctagtcctga                                                    20

<210> SEQ ID NO 218
<211> LENGTH: 20
<212> TYPE: RNA
<213> ORGANISM: Artificial Sequence
<220> FEATURE:
<223> OTHER INFORMATION: Synthetic Construct

<400> SEQUENCE: 218
cttcacttcc tccgaccttc                                                    20

<210> SEQ ID NO 219
<211> LENGTH: 20
<212> TYPE: RNA
<213> ORGANISM: Artificial Sequence
<220> FEATURE:
<223> OTHER INFORMATION: Synthetic Construct

<400> SEQUENCE: 219
aagctagtcc tgaaggtcgg                                                    20

<210> SEQ ID NO 220
<211> LENGTH: 20
<212> TYPE: RNA
<213> ORGANISM: Artificial Sequence
<220> FEATURE:
<223> OTHER INFORMATION: Synthetic Construct

<400> SEQUENCE: 220
agtgaagtga ctgaactctc                                                    20

<210> SEQ ID NO 221
<211> LENGTH: 20
```

```
<212> TYPE: RNA
<213> ORGANISM: Artificial Sequence
<220> FEATURE:
<223> OTHER INFORMATION: Synthetic Construct

<400> SEQUENCE: 221
gtgactgaac tctcaggatc                                          20

<210> SEQ ID NO 222
<211> LENGTH: 20
<212> TYPE: RNA
<213> ORGANISM: Artificial Sequence
<220> FEATURE:
<223> OTHER INFORMATION: Synthetic Construct

<400> SEQUENCE: 222
atagtaactg gagtcgtggc                                          20

<210> SEQ ID NO 223
<211> LENGTH: 20
<212> TYPE: RNA
<213> ORGANISM: Artificial Sequence
<220> FEATURE:
<223> OTHER INFORMATION: Synthetic Construct

<400> SEQUENCE: 223
catcatagta actggagtcg                                          20

<210> SEQ ID NO 224
<211> LENGTH: 20
<212> TYPE: RNA
<213> ORGANISM: Artificial Sequence
<220> FEATURE:
<223> OTHER INFORMATION: Synthetic Construct

<400> SEQUENCE: 224
tgacctgtca tcatagtaac                                          20

<210> SEQ ID NO 225
<211> LENGTH: 20
<212> TYPE: RNA
<213> ORGANISM: Artificial Sequence
<220> FEATURE:
<223> OTHER INFORMATION: Synthetic Construct

<400> SEQUENCE: 225
actccagtta ctatgatgac                                          20

<210> SEQ ID NO 226
<211> LENGTH: 20
<212> TYPE: RNA
<213> ORGANISM: Artificial Sequence
<220> FEATURE:
<223> OTHER INFORMATION: Synthetic Construct

<400> SEQUENCE: 226
ctttgtgcct ctctcgctca                                          20

<210> SEQ ID NO 227
<211> LENGTH: 20
<212> TYPE: RNA
<213> ORGANISM: Artificial Sequence
<220> FEATURE:
<223> OTHER INFORMATION: Synthetic Construct

<400> SEQUENCE: 227
```

-continued

```
ggtcagacca tgagcgagag                                           20

<210> SEQ ID NO 228
<211> LENGTH: 20
<212> TYPE: RNA
<213> ORGANISM: Artificial Sequence
<220> FEATURE:
<223> OTHER INFORMATION: Synthetic Construct

<400> SEQUENCE: 228
gaagaagaag aagtccgaga                                           20

<210> SEQ ID NO 229
<211> LENGTH: 20
<212> TYPE: RNA
<213> ORGANISM: Artificial Sequence
<220> FEATURE:
<223> OTHER INFORMATION: Synthetic Construct

<400> SEQUENCE: 229
gtccagatgc ttctccttct                                           20

<210> SEQ ID NO 230
<211> LENGTH: 20
<212> TYPE: RNA
<213> ORGANISM: Artificial Sequence
<220> FEATURE:
<223> OTHER INFORMATION: Synthetic Construct

<400> SEQUENCE: 230
gtccgagaag gagaagcatc                                           20

<210> SEQ ID NO 231
<211> LENGTH: 20
<212> TYPE: RNA
<213> ORGANISM: Artificial Sequence
<220> FEATURE:
<223> OTHER INFORMATION: Synthetic Construct

<400> SEQUENCE: 231
ggagaagcat ctggacgatg                                           20

<210> SEQ ID NO 232
<211> LENGTH: 20
<212> TYPE: RNA
<213> ORGANISM: Artificial Sequence
<220> FEATURE:
<223> OTHER INFORMATION: Synthetic Construct

<400> SEQUENCE: 232
tgaggaaaga aggaagcgaa                                           20

<210> SEQ ID NO 233
<211> LENGTH: 20
<212> TYPE: RNA
<213> ORGANISM: Artificial Sequence
<220> FEATURE:
<223> OTHER INFORMATION: Synthetic Construct

<400> SEQUENCE: 233
atctggacga tgaggaaaga                                           20

<210> SEQ ID NO 234
<211> LENGTH: 20
<212> TYPE: RNA
<213> ORGANISM: Artificial Sequence
```

```
<220> FEATURE:
<223> OTHER INFORMATION: Synthetic Construct

<400> SEQUENCE: 234
agaagaagcg gaagcgagag                                              20

<210> SEQ ID NO 235
<211> LENGTH: 20
<212> TYPE: RNA
<213> ORGANISM: Artificial Sequence
<220> FEATURE:
<223> OTHER INFORMATION: Synthetic Construct

<400> SEQUENCE: 235
gaagaagcgg aagcgagaga                                              20

<210> SEQ ID NO 236
<211> LENGTH: 20
<212> TYPE: RNA
<213> ORGANISM: Artificial Sequence
<220> FEATURE:
<223> OTHER INFORMATION: Synthetic Construct

<400> SEQUENCE: 236
ccgcccagga agagaagaag                                              20

<210> SEQ ID NO 237
<211> LENGTH: 20
<212> TYPE: RNA
<213> ORGANISM: Artificial Sequence
<220> FEATURE:
<223> OTHER INFORMATION: Synthetic Construct

<400> SEQUENCE: 237
agagagggag cactgtgaca                                              20

<210> SEQ ID NO 238
<211> LENGTH: 20
<212> TYPE: RNA
<213> ORGANISM: Artificial Sequence
<220> FEATURE:
<223> OTHER INFORMATION: Synthetic Construct

<400> SEQUENCE: 238
agggagcact gtgacacgga                                              20

<210> SEQ ID NO 239
<211> LENGTH: 20
<212> TYPE: RNA
<213> ORGANISM: Artificial Sequence
<220> FEATURE:
<223> OTHER INFORMATION: Synthetic Construct

<400> SEQUENCE: 239
gagggagcac tgtgacacgg                                              20

<210> SEQ ID NO 240
<211> LENGTH: 20
<212> TYPE: RNA
<213> ORGANISM: Artificial Sequence
<220> FEATURE:
<223> OTHER INFORMATION: Synthetic Construct

<400> SEQUENCE: 240
gcactgtgac acggagggag                                              20
```

<210> SEQ ID NO 241
<211> LENGTH: 20
<212> TYPE: RNA
<213> ORGANISM: Artificial Sequence
<220> FEATURE:
<223> OTHER INFORMATION: Synthetic Construct

<400> SEQUENCE: 241
gaggctgacg actttgatcc                                               20

<210> SEQ ID NO 242
<211> LENGTH: 20
<212> TYPE: RNA
<213> ORGANISM: Artificial Sequence
<220> FEATURE:
<223> OTHER INFORMATION: Synthetic Construct

<400> SEQUENCE: 242
aggctgacga ctttgatcct                                               20

<210> SEQ ID NO 243
<211> LENGTH: 20
<212> TYPE: RNA
<213> ORGANISM: Artificial Sequence
<220> FEATURE:
<223> OTHER INFORMATION: Synthetic Construct

<400> SEQUENCE: 243
tccacctcca ccttcttccc                                               20

<210> SEQ ID NO 244
<211> LENGTH: 20
<212> TYPE: RNA
<213> ORGANISM: Artificial Sequence
<220> FEATURE:
<223> OTHER INFORMATION: Synthetic Construct

<400> SEQUENCE: 244
cgactttgat cctgggaaga                                               20

<210> SEQ ID NO 245
<211> LENGTH: 20
<212> TYPE: RNA
<213> ORGANISM: Artificial Sequence
<220> FEATURE:
<223> OTHER INFORMATION: Synthetic Construct

<400> SEQUENCE: 245
ctttgatcct gggaagaagg                                               20

<210> SEQ ID NO 246
<211> LENGTH: 20
<212> TYPE: RNA
<213> ORGANISM: Artificial Sequence
<220> FEATURE:
<223> OTHER INFORMATION: Synthetic Construct

<400> SEQUENCE: 246
tgatcctggg aagaaggtgg                                               20

<210> SEQ ID NO 247
<211> LENGTH: 20
<212> TYPE: RNA
<213> ORGANISM: Artificial Sequence
<220> FEATURE:
<223> OTHER INFORMATION: Synthetic Construct

```
<400> SEQUENCE: 247
tcctgggaag aaggtggagg                                                    20

<210> SEQ ID NO 248
<211> LENGTH: 20
<212> TYPE: RNA
<213> ORGANISM: Artificial Sequence
<220> FEATURE:
<223> OTHER INFORMATION: Synthetic Construct

<400> SEQUENCE: 248
cggactggcc gatctggggg                                                    20

<210> SEQ ID NO 249
<211> LENGTH: 20
<212> TYPE: RNA
<213> ORGANISM: Artificial Sequence
<220> FEATURE:
<223> OTHER INFORMATION: Synthetic Construct

<400> SEQUENCE: 249
acgctcggac tggccgatct                                                    20

<210> SEQ ID NO 250
<211> LENGTH: 20
<212> TYPE: RNA
<213> ORGANISM: Artificial Sequence
<220> FEATURE:
<223> OTHER INFORMATION: Synthetic Construct

<400> SEQUENCE: 250
aggtggagcc gcccccagat                                                    20

<210> SEQ ID NO 251
<211> LENGTH: 20
<212> TYPE: RNA
<213> ORGANISM: Artificial Sequence
<220> FEATURE:
<223> OTHER INFORMATION: Synthetic Construct

<400> SEQUENCE: 251
cgctcggact ggccgatctg                                                    20

<210> SEQ ID NO 252
<211> LENGTH: 20
<212> TYPE: RNA
<213> ORGANISM: Artificial Sequence
<220> FEATURE:
<223> OTHER INFORMATION: Synthetic Construct

<400> SEQUENCE: 252
gctcggactg gccgatctgg                                                    20

<210> SEQ ID NO 253
<211> LENGTH: 20
<212> TYPE: RNA
<213> ORGANISM: Artificial Sequence
<220> FEATURE:
<223> OTHER INFORMATION: Synthetic Construct

<400> SEQUENCE: 253
cacgctcgga ctggccgatc                                                    20

<210> SEQ ID NO 254
```

```
<211> LENGTH: 20
<212> TYPE: RNA
<213> ORGANISM: Artificial Sequence
<220> FEATURE:
<223> OTHER INFORMATION: Synthetic Construct

<400> SEQUENCE: 254
tgtgtccggc acgctcggac                                              20

<210> SEQ ID NO 255
<211> LENGTH: 20
<212> TYPE: RNA
<213> ORGANISM: Artificial Sequence
<220> FEATURE:
<223> OTHER INFORMATION: Synthetic Construct

<400> SEQUENCE: 255
ctggctgtgt ccggcacgct                                              20

<210> SEQ ID NO 256
<211> LENGTH: 20
<212> TYPE: RNA
<213> ORGANISM: Artificial Sequence
<220> FEATURE:
<223> OTHER INFORMATION: Synthetic Construct

<400> SEQUENCE: 256
atcggccagt ccgagcgtgc                                              20

<210> SEQ ID NO 257
<211> LENGTH: 20
<212> TYPE: RNA
<213> ORGANISM: Artificial Sequence
<220> FEATURE:
<223> OTHER INFORMATION: Synthetic Construct

<400> SEQUENCE: 257
cacccttgcc tggctgtgtc                                              20

<210> SEQ ID NO 258
<211> LENGTH: 20
<212> TYPE: RNA
<213> ORGANISM: Artificial Sequence
<220> FEATURE:
<223> OTHER INFORMATION: Synthetic Construct

<400> SEQUENCE: 258
cgagcgtgcc ggacacagcc                                              20

<210> SEQ ID NO 259
<211> LENGTH: 20
<212> TYPE: RNA
<213> ORGANISM: Artificial Sequence
<220> FEATURE:
<223> OTHER INFORMATION: Synthetic Construct

<400> SEQUENCE: 259
tgttccagga gttgctgaat                                              20

<210> SEQ ID NO 260
<211> LENGTH: 20
<212> TYPE: RNA
<213> ORGANISM: Artificial Sequence
<220> FEATURE:
<223> OTHER INFORMATION: Synthetic Construct

<400> SEQUENCE: 260
```
cacacctatt cagcaactcc                                                      20

<210> SEQ ID NO 261
<211> LENGTH: 20
<212> TYPE: RNA
<213> ORGANISM: Artificial Sequence
<220> FEATURE:
<223> OTHER INFORMATION: Synthetic Construct

<400> SEQUENCE: 261
gctggcggag gaagtgttcc                                                      20

<210> SEQ ID NO 262
<211> LENGTH: 20
<212> TYPE: RNA
<213> ORGANISM: Artificial Sequence
<220> FEATURE:
<223> OTHER INFORMATION: Synthetic Construct

<400> SEQUENCE: 262
tttacctctg aagctggcgg                                                      20

<210> SEQ ID NO 263
<211> LENGTH: 20
<212> TYPE: RNA
<213> ORGANISM: Artificial Sequence
<220> FEATURE:
<223> OTHER INFORMATION: Synthetic Construct

<400> SEQUENCE: 263
ccccggttta cctctgaagc                                                      20

<210> SEQ ID NO 264
<211> LENGTH: 20
<212> TYPE: RNA
<213> ORGANISM: Artificial Sequence
<220> FEATURE:
<223> OTHER INFORMATION: Synthetic Construct

<400> SEQUENCE: 264
acttcctccg ccagcttcag                                                      20

<210> SEQ ID NO 265
<211> LENGTH: 20
<212> TYPE: RNA
<213> ORGANISM: Artificial Sequence
<220> FEATURE:
<223> OTHER INFORMATION: Synthetic Construct

<400> SEQUENCE: 265
caggaaaagc aaaaaatcca                                                      20

<210> SEQ ID NO 266
<211> LENGTH: 20
<212> TYPE: RNA
<213> ORGANISM: Artificial Sequence
<220> FEATURE:
<223> OTHER INFORMATION: Synthetic Construct

<400> SEQUENCE: 266
gctttcagaa aagatcccca                                                      20

<210> SEQ ID NO 267
<211> LENGTH: 20
<212> TYPE: RNA

```
<213> ORGANISM: Artificial Sequence
<220> FEATURE:
<223> OTHER INFORMATION: Synthetic Construct

<400> SEQUENCE: 267
aggaaaagca aaaatccat                                                    20

<210> SEQ ID NO 268
<211> LENGTH: 20
<212> TYPE: RNA
<213> ORGANISM: Artificial Sequence
<220> FEATURE:
<223> OTHER INFORMATION: Synthetic Construct

<400> SEQUENCE: 268
ggaaaagcaa aaatccatg                                                    20

<210> SEQ ID NO 269
<211> LENGTH: 20
<212> TYPE: RNA
<213> ORGANISM: Artificial Sequence
<220> FEATURE:
<223> OTHER INFORMATION: Synthetic Construct

<400> SEQUENCE: 269
ggagcaattg catccgtgac                                                   20

<210> SEQ ID NO 270
<211> LENGTH: 20
<212> TYPE: RNA
<213> ORGANISM: Artificial Sequence
<220> FEATURE:
<223> OTHER INFORMATION: Synthetic Construct

<400> SEQUENCE: 270
gtcacggatg caattgctcc                                                   20

<210> SEQ ID NO 271
<211> LENGTH: 20
<212> TYPE: RNA
<213> ORGANISM: Artificial Sequence
<220> FEATURE:
<223> OTHER INFORMATION: Synthetic Construct

<400> SEQUENCE: 271
tttattatca ttgaatatcc                                                   20

<210> SEQ ID NO 272
<211> LENGTH: 20
<212> TYPE: RNA
<213> ORGANISM: Artificial Sequence
<220> FEATURE:
<223> OTHER INFORMATION: Synthetic Construct

<400> SEQUENCE: 272
aatgataata aaacatccca                                                   20

<210> SEQ ID NO 273
<211> LENGTH: 20
<212> TYPE: RNA
<213> ORGANISM: Artificial Sequence
<220> FEATURE:
<223> OTHER INFORMATION: Synthetic Construct

<400> SEQUENCE: 273 ataaacatc ccatggattt                                                    20
```

```
<210> SEQ ID NO 274
<211> LENGTH: 20
<212> TYPE: RNA
<213> ORGANISM: Artificial Sequence
<220> FEATURE:
<223> OTHER INFORMATION: Synthetic Construct

<400> SEQUENCE: 274
ttcatggtgc caaaatccat                                               20

<210> SEQ ID NO 275
<211> LENGTH: 20
<212> TYPE: RNA
<213> ORGANISM: Artificial Sequence
<220> FEATURE:
<223> OTHER INFORMATION: Synthetic Construct

<400> SEQUENCE: 275
tttcatggtg ccaaaatcca                                               20

<210> SEQ ID NO 276
<211> LENGTH: 20
<212> TYPE: RNA
<213> ORGANISM: Artificial Sequence
<220> FEATURE:
<223> OTHER INFORMATION: Synthetic Construct

<400> SEQUENCE: 276
taatgaatac aagtcagtta                                               20

<210> SEQ ID NO 277
<211> LENGTH: 20
<212> TYPE: RNA
<213> ORGANISM: Artificial Sequence
<220> FEATURE:
<223> OTHER INFORMATION: Synthetic Construct

<400> SEQUENCE: 277
caagtcagtt acggaattta                                               20

<210> SEQ ID NO 278
<211> LENGTH: 20
<212> TYPE: RNA
<213> ORGANISM: Artificial Sequence
<220> FEATURE:
<223> OTHER INFORMATION: Synthetic Construct

<400> SEQUENCE: 278
ataatgcaat gacatacaat                                               20

<210> SEQ ID NO 279
<211> LENGTH: 20
<212> TYPE: RNA
<213> ORGANISM: Artificial Sequence
<220> FEATURE:
<223> OTHER INFORMATION: Synthetic Construct

<400> SEQUENCE: 279
aacttgtagt acacggtatc                                               20

<210> SEQ ID NO 280
<211> LENGTH: 20
<212> TYPE: RNA
<213> ORGANISM: Artificial Sequence
<220> FEATURE:
```

<223> OTHER INFORMATION: Synthetic Construct

<400> SEQUENCE: 280
cttcgccaac ttgtagtaca                                       20

<210> SEQ ID NO 281
<211> LENGTH: 20
<212> TYPE: RNA
<213> ORGANISM: Artificial Sequence
<220> FEATURE:
<223> OTHER INFORMATION: Synthetic Construct

<400> SEQUENCE: 281
agataccgtg tactacaagt                                       20

<210> SEQ ID NO 282
<211> LENGTH: 20
<212> TYPE: RNA
<213> ORGANISM: Artificial Sequence
<220> FEATURE:
<223> OTHER INFORMATION: Synthetic Construct

<400> SEQUENCE: 282
gcgaagaaga tccttcacgc                                       20

<210> SEQ ID NO 283
<211> LENGTH: 20
<212> TYPE: RNA
<213> ORGANISM: Artificial Sequence
<220> FEATURE:
<223> OTHER INFORMATION: Synthetic Construct

<400> SEQUENCE: 283
tcatcttaaa gcctgcgtga                                       20

<210> SEQ ID NO 284
<211> LENGTH: 20
<212> TYPE: RNA
<213> ORGANISM: Artificial Sequence
<220> FEATURE:
<223> OTHER INFORMATION: Synthetic Construct

<400> SEQUENCE: 284
ttctcagcag gcagctcttt                                       20

<210> SEQ ID NO 285
<211> LENGTH: 20
<212> TYPE: RNA
<213> ORGANISM: Artificial Sequence
<220> FEATURE:
<223> OTHER INFORMATION: Synthetic Construct

<400> SEQUENCE: 285
caatgaagat acagctgttg                                       20

<210> SEQ ID NO 286
<211> LENGTH: 20
<212> TYPE: RNA
<213> ORGANISM: Artificial Sequence
<220> FEATURE:
<223> OTHER INFORMATION: Synthetic Construct

<400> SEQUENCE: 286
actggtacaa cttcagggac                                       20

```
<210> SEQ ID NO 287
<211> LENGTH: 20
<212> TYPE: RNA
<213> ORGANISM: Artificial Sequence
<220> FEATURE:
<223> OTHER INFORMATION: Synthetic Construct

<400> SEQUENCE: 287
cttgtactgg tacaacttca                                               20

<210> SEQ ID NO 288
<211> LENGTH: 20
<212> TYPE: RNA
<213> ORGANISM: Artificial Sequence
<220> FEATURE:
<223> OTHER INFORMATION: Synthetic Construct

<400> SEQUENCE: 288
acttgtactg gtacaacttc                                               20

<210> SEQ ID NO 289
<211> LENGTH: 20
<212> TYPE: RNA
<213> ORGANISM: Artificial Sequence
<220> FEATURE:
<223> OTHER INFORMATION: Synthetic Construct

<400> SEQUENCE: 289
ttggcagttt ctacttgtac                                               20

<210> SEQ ID NO 290
<211> LENGTH: 20
<212> TYPE: RNA
<213> ORGANISM: Artificial Sequence
<220> FEATURE:
<223> OTHER INFORMATION: Synthetic Construct

<400> SEQUENCE: 290
tacctgataa cttctctact                                               20

<210> SEQ ID NO 291
<211> LENGTH: 20
<212> TYPE: RNA
<213> ORGANISM: Artificial Sequence
<220> FEATURE:
<223> OTHER INFORMATION: Synthetic Construct

<400> SEQUENCE: 291
agccgagtag agaagttatc                                               20

<210> SEQ ID NO 292
<211> LENGTH: 20
<212> TYPE: RNA
<213> ORGANISM: Artificial Sequence
<220> FEATURE:
<223> OTHER INFORMATION: Synthetic Construct

<400> SEQUENCE: 292
agctgcatgt ttgagcctga                                               20

<210> SEQ ID NO 293
<211> LENGTH: 20
<212> TYPE: RNA
<213> ORGANISM: Artificial Sequence
<220> FEATURE:
<223> OTHER INFORMATION: Synthetic Construct
```

<400> SEQUENCE: 293
gctgcatgtt tgagcctgaa                                               20

<210> SEQ ID NO 294
<211> LENGTH: 20
<212> TYPE: RNA
<213> ORGANISM: Artificial Sequence
<220> FEATURE:
<223> OTHER INFORMATION: Synthetic Construct

<400> SEQUENCE: 294
aagctgcagg cattcccttc                                               20

<210> SEQ ID NO 295
<211> LENGTH: 20
<212> TYPE: RNA
<213> ORGANISM: Artificial Sequence
<220> FEATURE:
<223> OTHER INFORMATION: Synthetic Construct

<400> SEQUENCE: 295
ggtactgtcc gtcaagctgc                                               20

<210> SEQ ID NO 296
<211> LENGTH: 20
<212> TYPE: RNA
<213> ORGANISM: Artificial Sequence
<220> FEATURE:
<223> OTHER INFORMATION: Synthetic Construct

<400> SEQUENCE: 296
agggaatgcc tgcagcttga                                               20

<210> SEQ ID NO 297
<211> LENGTH: 20
<212> TYPE: RNA
<213> ORGANISM: Artificial Sequence
<220> FEATURE:
<223> OTHER INFORMATION: Synthetic Construct

<400> SEQUENCE: 297
cttgacggac agtaccgcag                                               20

<210> SEQ ID NO 298
<211> LENGTH: 20
<212> TYPE: RNA
<213> ORGANISM: Artificial Sequence
<220> FEATURE:
<223> OTHER INFORMATION: Synthetic Construct

<400> SEQUENCE: 298
cgccagcacg tgctcctctg                                               20

<210> SEQ ID NO 299
<211> LENGTH: 20
<212> TYPE: RNA
<213> ORGANISM: Artificial Sequence
<220> FEATURE:
<223> OTHER INFORMATION: Synthetic Construct

<400> SEQUENCE: 299
taccgcagag gagcacgtgc                                               20

<210> SEQ ID NO 300
<211> LENGTH: 20

<212> TYPE: RNA
<213> ORGANISM: Artificial Sequence
<220> FEATURE:
<223> OTHER INFORMATION: Synthetic Construct

<400> SEQUENCE: 300
agaggagcac gtgctggcgc                                         20

<210> SEQ ID NO 301
<211> LENGTH: 20
<212> TYPE: RNA
<213> ORGANISM: Artificial Sequence
<220> FEATURE:
<223> OTHER INFORMATION: Synthetic Construct

<400> SEQUENCE: 301
ggagcacgtg ctggcgctgg                                         20

<210> SEQ ID NO 302
<211> LENGTH: 20
<212> TYPE: RNA
<213> ORGANISM: Artificial Sequence
<220> FEATURE:
<223> OTHER INFORMATION: Synthetic Construct

<400> SEQUENCE: 302
agcacgcagc tgacgaagct                                         20

<210> SEQ ID NO 303
<211> LENGTH: 20
<212> TYPE: RNA
<213> ORGANISM: Artificial Sequence
<220> FEATURE:
<223> OTHER INFORMATION: Synthetic Construct

<400> SEQUENCE: 303
gcacgcagct gacgaagctc                                         20

<210> SEQ ID NO 304
<211> LENGTH: 20
<212> TYPE: RNA
<213> ORGANISM: Artificial Sequence
<220> FEATURE:
<223> OTHER INFORMATION: Synthetic Construct

<400> SEQUENCE: 304
cagctgacga agctcgggac                                         20

<210> SEQ ID NO 305
<211> LENGTH: 20
<212> TYPE: RNA
<213> ORGANISM: Artificial Sequence
<220> FEATURE:
<223> OTHER INFORMATION: Synthetic Construct

<400> SEQUENCE: 305
aagctcggga caggatcaac                                         20

<210> SEQ ID NO 306
<211> LENGTH: 20
<212> TYPE: RNA
<213> ORGANISM: Artificial Sequence
<220> FEATURE:
<223> OTHER INFORMATION: Synthetic Construct

<400> SEQUENCE: 306
ccttgccgcc tgggaggaac                                          20

<210> SEQ ID NO 307
<211> LENGTH: 20
<212> TYPE: RNA
<213> ORGANISM: Artificial Sequence
<220> FEATURE:
<223> OTHER INFORMATION: Synthetic Construct

<400> SEQUENCE: 307
aggatcaacc ggttcctccc                                          20

<210> SEQ ID NO 308
<211> LENGTH: 20
<212> TYPE: RNA
<213> ORGANISM: Artificial Sequence
<220> FEATURE:
<223> OTHER INFORMATION: Synthetic Construct

<400> SEQUENCE: 308
atcaaccggt tcctcccagg                                          20

<210> SEQ ID NO 309
<211> LENGTH: 20
<212> TYPE: RNA
<213> ORGANISM: Artificial Sequence
<220> FEATURE:
<223> OTHER INFORMATION: Synthetic Construct

<400> SEQUENCE: 309
gcactacctt gccgcctggg                                          20

<210> SEQ ID NO 310
<211> LENGTH: 20
<212> TYPE: RNA
<213> ORGANISM: Artificial Sequence
<220> FEATURE:
<223> OTHER INFORMATION: Synthetic Construct

<400> SEQUENCE: 310
agagcactac cttgccgcct                                          20

<210> SEQ ID NO 311
<211> LENGTH: 20
<212> TYPE: RNA
<213> ORGANISM: Artificial Sequence
<220> FEATURE:
<223> OTHER INFORMATION: Synthetic Construct

<400> SEQUENCE: 311
ccggttcctc ccaggcggca                                          20

<210> SEQ ID NO 312
<211> LENGTH: 20
<212> TYPE: RNA
<213> ORGANISM: Artificial Sequence
<220> FEATURE:
<223> OTHER INFORMATION: Synthetic Construct

<400> SEQUENCE: 312
tcctcttcag atagcccatc                                          20

<210> SEQ ID NO 313
<211> LENGTH: 20
<212> TYPE: RNA
<213> ORGANISM: Artificial Sequence

```
<220> FEATURE:
<223> OTHER INFORMATION: Synthetic Construct

<400> SEQUENCE: 313
atgggctatc tgaagaggaa                                          20

<210> SEQ ID NO 314
<211> LENGTH: 20
<212> TYPE: RNA
<213> ORGANISM: Artificial Sequence
<220> FEATURE:
<223> OTHER INFORMATION: Synthetic Construct

<400> SEQUENCE: 314
gggctatctg aagaggaacg                                          20

<210> SEQ ID NO 315
<211> LENGTH: 20
<212> TYPE: RNA
<213> ORGANISM: Artificial Sequence
<220> FEATURE:
<223> OTHER INFORMATION: Synthetic Construct

<400> SEQUENCE: 315
tgggctatct gaagaggaac                                          20

<210> SEQ ID NO 316
<211> LENGTH: 20
<212> TYPE: RNA
<213> ORGANISM: Artificial Sequence
<220> FEATURE:
<223> OTHER INFORMATION: Synthetic Construct

<400> SEQUENCE: 316
tatctgaaga ggaacgggga                                          20

<210> SEQ ID NO 317
<211> LENGTH: 20
<212> TYPE: RNA
<213> ORGANISM: Artificial Sequence
<220> FEATURE:
<223> OTHER INFORMATION: Synthetic Construct

<400> SEQUENCE: 317
atctgaagag gaacggggac                                          20

<210> SEQ ID NO 318
<211> LENGTH: 20
<212> TYPE: RNA
<213> ORGANISM: Artificial Sequence
<220> FEATURE:
<223> OTHER INFORMATION: Synthetic Construct

<400> SEQUENCE: 318
tgttgaccac gctgtagagc                                          20

<210> SEQ ID NO 319
<211> LENGTH: 20
<212> TYPE: RNA
<213> ORGANISM: Artificial Sequence
<220> FEATURE:
<223> OTHER INFORMATION: Synthetic Construct

<400> SEQUENCE: 319
gctctacagc gtggtcaaca                                          20
```

```
<210> SEQ ID NO 320
<211> LENGTH: 20
<212> TYPE: RNA
<213> ORGANISM: Artificial Sequence
<220> FEATURE:
<223> OTHER INFORMATION: Synthetic Construct

<400> SEQUENCE: 320
cgggagcctg ctctacagcg                                              20

<210> SEQ ID NO 321
<211> LENGTH: 20
<212> TYPE: RNA
<213> ORGANISM: Artificial Sequence
<220> FEATURE:
<223> OTHER INFORMATION: Synthetic Construct

<400> SEQUENCE: 321
cgtggtcaac acggccgagc                                              20

<210> SEQ ID NO 322
<211> LENGTH: 20
<212> TYPE: RNA
<213> ORGANISM: Artificial Sequence
<220> FEATURE:
<223> OTHER INFORMATION: Synthetic Construct

<400> SEQUENCE: 322
cccaccatca gcgtccggct                                              20

<210> SEQ ID NO 323
<211> LENGTH: 20
<212> TYPE: RNA
<213> ORGANISM: Artificial Sequence
<220> FEATURE:
<223> OTHER INFORMATION: Synthetic Construct

<400> SEQUENCE: 323
acggccgagc cggacgctga                                              20

<210> SEQ ID NO 324
<211> LENGTH: 20
<212> TYPE: RNA
<213> ORGANISM: Artificial Sequence
<220> FEATURE:
<223> OTHER INFORMATION: Synthetic Construct

<400> SEQUENCE: 324
gggcacccac catcagcgtc                                              20

<210> SEQ ID NO 325
<211> LENGTH: 20
<212> TYPE: RNA
<213> ORGANISM: Artificial Sequence
<220> FEATURE:
<223> OTHER INFORMATION: Synthetic Construct

<400> SEQUENCE: 325
gccgagccgg acgctgatgg                                              20

<210> SEQ ID NO 326
<211> LENGTH: 20
<212> TYPE: RNA
<213> ORGANISM: Artificial Sequence
<220> FEATURE:
<223> OTHER INFORMATION: Synthetic Construct
```

<400> SEQUENCE: 326
ccatgtccgt gttgcagagg                                        20

<210> SEQ ID NO 327
<211> LENGTH: 20
<212> TYPE: RNA
<213> ORGANISM: Artificial Sequence
<220> FEATURE:
<223> OTHER INFORMATION: Synthetic Construct

<400> SEQUENCE: 327
ccgagccgga cgctgatggt                                        20

<210> SEQ ID NO 328
<211> LENGTH: 20
<212> TYPE: RNA
<213> ORGANISM: Artificial Sequence
<220> FEATURE:
<223> OTHER INFORMATION: Synthetic Construct

<400> SEQUENCE: 328
cgagctcaag tccaccgggt                                        20

<210> SEQ ID NO 329
<211> LENGTH: 20
<212> TYPE: RNA
<213> ORGANISM: Artificial Sequence
<220> FEATURE:
<223> OTHER INFORMATION: Synthetic Construct

<400> SEQUENCE: 329
gcgagctcaa gtccaccggg                                        20

<210> SEQ ID NO 330
<211> LENGTH: 20
<212> TYPE: RNA
<213> ORGANISM: Artificial Sequence
<220> FEATURE:
<223> OTHER INFORMATION: Synthetic Construct

<400> SEQUENCE: 330
agagcgagct caagtccacc                                        20

<210> SEQ ID NO 331
<211> LENGTH: 20
<212> TYPE: RNA
<213> ORGANISM: Artificial Sequence
<220> FEATURE:
<223> OTHER INFORMATION: Synthetic Construct

<400> SEQUENCE: 331
gagagcgagc tcaagtccac                                        20

<210> SEQ ID NO 332
<211> LENGTH: 20
<212> TYPE: RNA
<213> ORGANISM: Artificial Sequence
<220> FEATURE:
<223> OTHER INFORMATION: Synthetic Construct

<400> SEQUENCE: 332
gaagcctggg agtagcttac                                        20

<210> SEQ ID NO 333

```
<211> LENGTH: 20
<212> TYPE: RNA
<213> ORGANISM: Artificial Sequence
<220> FEATURE:
<223> OTHER INFORMATION: Synthetic Construct

<400> SEQUENCE: 333
ctctccagta agctactccc                                               20

<210> SEQ ID NO 334
<211> LENGTH: 20
<212> TYPE: RNA
<213> ORGANISM: Artificial Sequence
<220> FEATURE:
<223> OTHER INFORMATION: Synthetic Construct

<400> SEQUENCE: 334
agcccagcgt ggtgaagcct                                               20

<210> SEQ ID NO 335
<211> LENGTH: 20
<212> TYPE: RNA
<213> ORGANISM: Artificial Sequence
<220> FEATURE:
<223> OTHER INFORMATION: Synthetic Construct

<400> SEQUENCE: 335
aagcccagcg tggtgaagcc                                               20

<210> SEQ ID NO 336
<211> LENGTH: 20
<212> TYPE: RNA
<213> ORGANISM: Artificial Sequence
<220> FEATURE:
<223> OTHER INFORMATION: Synthetic Construct

<400> SEQUENCE: 336
actcccaggc ttcaccacgc                                               20

<210> SEQ ID NO 337
<211> LENGTH: 20
<212> TYPE: RNA
<213> ORGANISM: Artificial Sequence
<220> FEATURE:
<223> OTHER INFORMATION: Synthetic Construct

<400> SEQUENCE: 337
ctcccaggct tcaccacgct                                               20

<210> SEQ ID NO 338
<211> LENGTH: 20
<212> TYPE: RNA
<213> ORGANISM: Artificial Sequence
<220> FEATURE:
<223> OTHER INFORMATION: Synthetic Construct

<400> SEQUENCE: 338
ctcgtctttg aagcccagcg                                               20

<210> SEQ ID NO 339
<211> LENGTH: 20
<212> TYPE: RNA
<213> ORGANISM: Artificial Sequence
<220> FEATURE:
<223> OTHER INFORMATION: Synthetic Construct

<400> SEQUENCE: 339
```
cactggagag aaaggtgact        20

<210> SEQ ID NO 340
<211> LENGTH: 20
<212> TYPE: RNA
<213> ORGANISM: Artificial Sequence
<220> FEATURE:
<223> OTHER INFORMATION: Synthetic Construct

<400> SEQUENCE: 340
gcactggaga gaaaggtgac        20

<210> SEQ ID NO 341
<211> LENGTH: 20
<212> TYPE: RNA
<213> ORGANISM: Artificial Sequence
<220> FEATURE:
<223> OTHER INFORMATION: Synthetic Construct

<400> SEQUENCE: 341
agtagtggca ctggagagaa        20

<210> SEQ ID NO 342
<211> LENGTH: 20
<212> TYPE: RNA
<213> ORGANISM: Artificial Sequence
<220> FEATURE:
<223> OTHER INFORMATION: Synthetic Construct

<400> SEQUENCE: 342
cgaaagcgca gtagtggcac        20

<210> SEQ ID NO 343
<211> LENGTH: 20
<212> TYPE: RNA
<213> ORGANISM: Artificial Sequence
<220> FEATURE:
<223> OTHER INFORMATION: Synthetic Construct

<400> SEQUENCE: 343
ctgcatcgaa agcgcagtag        20

<210> SEQ ID NO 344
<211> LENGTH: 20
<212> TYPE: RNA
<213> ORGANISM: Artificial Sequence
<220> FEATURE:
<223> OTHER INFORMATION: Synthetic Construct

<400> SEQUENCE: 344
atgcagaata attcagtatt        20

<210> SEQ ID NO 345
<211> LENGTH: 20
<212> TYPE: RNA
<213> ORGANISM: Artificial Sequence
<220> FEATURE:
<223> OTHER INFORMATION: Synthetic Construct

<400> SEQUENCE: 345
agtatttggc gacttgaagt        20

<210> SEQ ID NO 346
<211> LENGTH: 20
<212> TYPE: RNA

```
<213> ORGANISM: Artificial Sequence
<220> FEATURE:
<223> OTHER INFORMATION: Synthetic Construct

<400> SEQUENCE: 346
cgacttgaag tcggacgaga                                               20

<210> SEQ ID NO 347
<211> LENGTH: 20
<212> TYPE: RNA
<213> ORGANISM: Artificial Sequence
<220> FEATURE:
<223> OTHER INFORMATION: Synthetic Construct

<400> SEQUENCE: 347
gagctgctct actcagccta                                               20

<210> SEQ ID NO 348
<211> LENGTH: 20
<212> TYPE: RNA
<213> ORGANISM: Artificial Sequence
<220> FEATURE:
<223> OTHER INFORMATION: Synthetic Construct

<400> SEQUENCE: 348
cacgcctgtc tcatctccgt                                               20

<210> SEQ ID NO 349
<211> LENGTH: 20
<212> TYPE: RNA
<213> ORGANISM: Artificial Sequence
<220> FEATURE:
<223> OTHER INFORMATION: Synthetic Construct

<400> SEQUENCE: 349
tcagcctacg gagatgagac                                               20

<210> SEQ ID NO 350
<211> LENGTH: 20
<212> TYPE: RNA
<213> ORGANISM: Artificial Sequence
<220> FEATURE:
<223> OTHER INFORMATION: Synthetic Construct

<400> SEQUENCE: 350
caggcgtgca gtgtgcgctg                                               20

<210> SEQ ID NO 351
<211> LENGTH: 20
<212> TYPE: RNA
<213> ORGANISM: Artificial Sequence
<220> FEATURE:
<223> OTHER INFORMATION: Synthetic Construct

<400> SEQUENCE: 351
ccgcggcccc tctagcctgc                                               20

<210> SEQ ID NO 352
<211> LENGTH: 20
<212> TYPE: RNA
<213> ORGANISM: Artificial Sequence
<220> FEATURE:
<223> OTHER INFORMATION: Synthetic Construct

<400> SEQUENCE: 352
catccttcac aaactcctgc                                               20
```

```
<210> SEQ ID NO 353
<211> LENGTH: 20
<212> TYPE: RNA
<213> ORGANISM: Artificial Sequence
<220> FEATURE:
<223> OTHER INFORMATION: Synthetic Construct

<400> SEQUENCE: 353
tagcctgcag gagtttgtga                                              20

<210> SEQ ID NO 354
<211> LENGTH: 20
<212> TYPE: RNA
<213> ORGANISM: Artificial Sequence
<220> FEATURE:
<223> OTHER INFORMATION: Synthetic Construct

<400> SEQUENCE: 354
caggagtttg tgaaggatgc                                              20

<210> SEQ ID NO 355
<211> LENGTH: 20
<212> TYPE: RNA
<213> ORGANISM: Artificial Sequence
<220> FEATURE:
<223> OTHER INFORMATION: Synthetic Construct

<400> SEQUENCE: 355
aggagtttgt gaaggatgct                                              20

<210> SEQ ID NO 356
<211> LENGTH: 20
<212> TYPE: RNA
<213> ORGANISM: Artificial Sequence
<220> FEATURE:
<223> OTHER INFORMATION: Synthetic Construct

<400> SEQUENCE: 356
tgggagctac agcaagaaag                                              20

<210> SEQ ID NO 357
<211> LENGTH: 20
<212> TYPE: RNA
<213> ORGANISM: Artificial Sequence
<220> FEATURE:
<223> OTHER INFORMATION: Synthetic Construct

<400> SEQUENCE: 357
gagctacagc aagaaagtgg                                              20

<210> SEQ ID NO 358
<211> LENGTH: 20
<212> TYPE: RNA
<213> ORGANISM: Artificial Sequence
<220> FEATURE:
<223> OTHER INFORMATION: Synthetic Construct

<400> SEQUENCE: 358
gaaagtggtg gacgacctcc                                              20

<210> SEQ ID NO 359
<211> LENGTH: 20
<212> TYPE: RNA
<213> ORGANISM: Artificial Sequence
<220> FEATURE:
```

<223> OTHER INFORMATION: Synthetic Construct

<400> SEQUENCE: 359
cgcctgtgat ctggtccagg                                            20

<210> SEQ ID NO 360
<211> LENGTH: 20
<212> TYPE: RNA
<213> ORGANISM: Artificial Sequence
<220> FEATURE:
<223> OTHER INFORMATION: Synthetic Construct

<400> SEQUENCE: 360
ctccgcctgt gatctggtcc                                            20

<210> SEQ ID NO 361
<211> LENGTH: 20
<212> TYPE: RNA
<213> ORGANISM: Artificial Sequence
<220> FEATURE:
<223> OTHER INFORMATION: Synthetic Construct

<400> SEQUENCE: 361
gacctcctgg accagatcac                                            20

<210> SEQ ID NO 362
<211> LENGTH: 20
<212> TYPE: RNA
<213> ORGANISM: Artificial Sequence
<220> FEATURE:
<223> OTHER INFORMATION: Synthetic Construct

<400> SEQUENCE: 362
ctcctggacc agatcacagg                                            20

<210> SEQ ID NO 363
<211> LENGTH: 20
<212> TYPE: RNA
<213> ORGANISM: Artificial Sequence
<220> FEATURE:
<223> OTHER INFORMATION: Synthetic Construct

<400> SEQUENCE: 363
gctggaagag cgtcctagag                                            20

<210> SEQ ID NO 364
<211> LENGTH: 20
<212> TYPE: RNA
<213> ORGANISM: Artificial Sequence
<220> FEATURE:
<223> OTHER INFORMATION: Synthetic Construct

<400> SEQUENCE: 364
tgcagcccac ctgcttcagc                                            20

<210> SEQ ID NO 365
<211> LENGTH: 20
<212> TYPE: RNA
<213> ORGANISM: Artificial Sequence
<220> FEATURE:
<223> OTHER INFORMATION: Synthetic Construct

<400> SEQUENCE: 365
gacgctcttc cagctgaagc                                            20

```
<210> SEQ ID NO 366
<211> LENGTH: 20
<212> TYPE: RNA
<213> ORGANISM: Artificial Sequence
<220> FEATURE:
<223> OTHER INFORMATION: Synthetic Construct

<400> SEQUENCE: 366
ctcttccagc tgaagcaggt                                                     20

<210> SEQ ID NO 367
<211> LENGTH: 20
<212> TYPE: RNA
<213> ORGANISM: Artificial Sequence
<220> FEATURE:
<223> OTHER INFORMATION: Synthetic Construct

<400> SEQUENCE: 367
gctcttccag ctgaagcagg                                                     20

<210> SEQ ID NO 368
<211> LENGTH: 20
<212> TYPE: RNA
<213> ORGANISM: Artificial Sequence
<220> FEATURE:
<223> OTHER INFORMATION: Synthetic Construct

<400> SEQUENCE: 368
cctccagatg aagccaaggt                                                     20

<210> SEQ ID NO 369
<211> LENGTH: 20
<212> TYPE: RNA
<213> ORGANISM: Artificial Sequence
<220> FEATURE:
<223> OTHER INFORMATION: Synthetic Construct

<400> SEQUENCE: 369
gcttcatctg gaggcttcat                                                     20

<210> SEQ ID NO 370
<211> LENGTH: 20
<212> TYPE: RNA
<213> ORGANISM: Artificial Sequence
<220> FEATURE:
<223> OTHER INFORMATION: Synthetic Construct

<400> SEQUENCE: 370
ggcttcatct ggaggcttca                                                     20

<210> SEQ ID NO 371
<211> LENGTH: 20
<212> TYPE: RNA
<213> ORGANISM: Artificial Sequence
<220> FEATURE:
<223> OTHER INFORMATION: Synthetic Construct

<400> SEQUENCE: 371
cttaccttgg cttcatctgg                                                     20

<210> SEQ ID NO 372
<211> LENGTH: 20
<212> TYPE: RNA
<213> ORGANISM: Artificial Sequence
<220> FEATURE:
<223> OTHER INFORMATION: Synthetic Construct
```

```
<400> SEQUENCE: 372
aaacttacct tggcttcatc                                          20

<210> SEQ ID NO 373
<211> LENGTH: 20
<212> TYPE: RNA
<213> ORGANISM: Artificial Sequence
<220> FEATURE:
<223> OTHER INFORMATION: Synthetic Construct

<400> SEQUENCE: 373
gaagcctcca gatgaagcca                                          20

<210> SEQ ID NO 374
<211> LENGTH: 20
<212> TYPE: RNA
<213> ORGANISM: Artificial Sequence
<220> FEATURE:
<223> OTHER INFORMATION: Synthetic Construct

<400> SEQUENCE: 374
tcctagggtg tccccaacct                                          20

<210> SEQ ID NO 375
<211> LENGTH: 20
<212> TYPE: RNA
<213> ORGANISM: Artificial Sequence
<220> FEATURE:
<223> OTHER INFORMATION: Synthetic Construct

<400> SEQUENCE: 375
cctagggtgt ccccaacctg                                          20

<210> SEQ ID NO 376
<211> LENGTH: 20
<212> TYPE: RNA
<213> ORGANISM: Artificial Sequence
<220> FEATURE:
<223> OTHER INFORMATION: Synthetic Construct

<400> SEQUENCE: 376
gtgtctgtct ccacaggttg                                          20

<210> SEQ ID NO 377
<211> LENGTH: 20
<212> TYPE: RNA
<213> ORGANISM: Artificial Sequence
<220> FEATURE:
<223> OTHER INFORMATION: Synthetic Construct

<400> SEQUENCE: 377
tgtgtctgtc tccacaggtt                                          20

<210> SEQ ID NO 378
<211> LENGTH: 20
<212> TYPE: RNA
<213> ORGANISM: Artificial Sequence
<220> FEATURE:
<223> OTHER INFORMATION: Synthetic Construct

<400> SEQUENCE: 378
ccacaggttg gggacaccct                                          20

<210> SEQ ID NO 379
<211> LENGTH: 20
```

```
<212> TYPE: RNA
<213> ORGANISM: Artificial Sequence
<220> FEATURE:
<223> OTHER INFORMATION: Synthetic Construct

<400> SEQUENCE: 379
agagctgctg ctgtctccta                                              20

<210> SEQ ID NO 380
<211> LENGTH: 20
<212> TYPE: RNA
<213> ORGANISM: Artificial Sequence
<220> FEATURE:
<223> OTHER INFORMATION: Synthetic Construct

<400> SEQUENCE: 380
cagagctgct gctgtctcct                                              20

<210> SEQ ID NO 381
<211> LENGTH: 20
<212> TYPE: RNA
<213> ORGANISM: Artificial Sequence
<220> FEATURE:
<223> OTHER INFORMATION: Synthetic Construct

<400> SEQUENCE: 381
agacagcagc agctctgttc                                              20

<210> SEQ ID NO 382
<211> LENGTH: 20
<212> TYPE: RNA
<213> ORGANISM: Artificial Sequence
<220> FEATURE:
<223> OTHER INFORMATION: Synthetic Construct

<400> SEQUENCE: 382
atccacagaa acgtcgggat                                              20

<210> SEQ ID NO 383
<211> LENGTH: 20
<212> TYPE: RNA
<213> ORGANISM: Artificial Sequence
<220> FEATURE:
<223> OTHER INFORMATION: Synthetic Construct

<400> SEQUENCE: 383
gagatatcca cagaaacgtc                                              20

<210> SEQ ID NO 384
<211> LENGTH: 20
<212> TYPE: RNA
<213> ORGANISM: Artificial Sequence
<220> FEATURE:
<223> OTHER INFORMATION: Synthetic Construct

<400> SEQUENCE: 384
ggagatatcc acagaaacgt                                              20

<210> SEQ ID NO 385
<211> LENGTH: 20
<212> TYPE: RNA
<213> ORGANISM: Artificial Sequence
<220> FEATURE:
<223> OTHER INFORMATION: Synthetic Construct

<400> SEQUENCE: 385
```

-continued

```
gtcctatccc gacgtttctg                                          20

<210> SEQ ID NO 386
<211> LENGTH: 20
<212> TYPE: RNA
<213> ORGANISM: Artificial Sequence
<220> FEATURE:
<223> OTHER INFORMATION: Synthetic Construct

<400> SEQUENCE: 386
tctccatgct cagctctctg                                          20

<210> SEQ ID NO 387
<211> LENGTH: 20
<212> TYPE: RNA
<213> ORGANISM: Artificial Sequence
<220> FEATURE:
<223> OTHER INFORMATION: Synthetic Construct

<400> SEQUENCE: 387
ctcacccaga gagctgagca                                          20

<210> SEQ ID NO 388
<211> LENGTH: 20
<212> TYPE: RNA
<213> ORGANISM: Artificial Sequence
<220> FEATURE:
<223> OTHER INFORMATION: Synthetic Construct

<400> SEQUENCE: 388
atctccatgc tcagctctct                                          20

<210> SEQ ID NO 389
<211> LENGTH: 20
<212> TYPE: RNA
<213> ORGANISM: Artificial Sequence
<220> FEATURE:
<223> OTHER INFORMATION: Synthetic Construct

<400> SEQUENCE: 389
tatctccatg ctcagctctc                                          20

<210> SEQ ID NO 390
<211> LENGTH: 20
<212> TYPE: RNA
<213> ORGANISM: Artificial Sequence
<220> FEATURE:
<223> OTHER INFORMATION: Synthetic Construct

<400> SEQUENCE: 390
atgtcctgtt tacacaggga                                          20

<210> SEQ ID NO 391
<211> LENGTH: 20
<212> TYPE: RNA
<213> ORGANISM: Artificial Sequence
<220> FEATURE:
<223> OTHER INFORMATION: Synthetic Construct

<400> SEQUENCE: 391
ttacacaggg aaggtgaaga                                          20

<210> SEQ ID NO 392
<211> LENGTH: 20
<212> TYPE: RNA
<213> ORGANISM: Artificial Sequence
```

```
<220> FEATURE:
<223> OTHER INFORMATION: Synthetic Construct

<400> SEQUENCE: 392
agttcaaatg gctgtcgtca                                               20

<210> SEQ ID NO 393
<211> LENGTH: 20
<212> TYPE: RNA
<213> ORGANISM: Artificial Sequence
<220> FEATURE:
<223> OTHER INFORMATION: Synthetic Construct

<400> SEQUENCE: 393
tgacgacagc catttgaact                                               20

<210> SEQ ID NO 394
<211> LENGTH: 20
<212> TYPE: RNA
<213> ORGANISM: Artificial Sequence
<220> FEATURE:
<223> OTHER INFORMATION: Synthetic Construct

<400> SEQUENCE: 394
aagttcaaat ggctgtcgtc                                               20

<210> SEQ ID NO 395
<211> LENGTH: 20
<212> TYPE: RNA
<213> ORGANISM: Artificial Sequence
<220> FEATURE:
<223> OTHER INFORMATION: Synthetic Construct

<400> SEQUENCE: 395
tcgtctcatc caagttcaaa                                               20

<210> SEQ ID NO 396
<211> LENGTH: 20
<212> TYPE: RNA
<213> ORGANISM: Artificial Sequence
<220> FEATURE:
<223> OTHER INFORMATION: Synthetic Construct

<400> SEQUENCE: 396
tgagacgacg aagctcctgc                                               20

<210> SEQ ID NO 397
<211> LENGTH: 20
<212> TYPE: RNA
<213> ORGANISM: Artificial Sequence
<220> FEATURE:
<223> OTHER INFORMATION: Synthetic Construct

<400> SEQUENCE: 397
gtgcttcgtg caggtcctgc                                               20

<210> SEQ ID NO 398
<211> LENGTH: 20
<212> TYPE: RNA
<213> ORGANISM: Artificial Sequence
<220> FEATURE:
<223> OTHER INFORMATION: Synthetic Construct

<400> SEQUENCE: 398
gcaggacctg cacgaagcac                                               20
```

<210> SEQ ID NO 399
<211> LENGTH: 20
<212> TYPE: RNA
<213> ORGANISM: Artificial Sequence
<220> FEATURE:
<223> OTHER INFORMATION: Synthetic Construct

<400> SEQUENCE: 399
gctccgcctg tgcttcgtgc                                               20

<210> SEQ ID NO 400
<211> LENGTH: 20
<212> TYPE: RNA
<213> ORGANISM: Artificial Sequence
<220> FEATURE:
<223> OTHER INFORMATION: Synthetic Construct

<400> SEQUENCE: 400
ggacctgcac gaagcacagg                                               20

<210> SEQ ID NO 401
<211> LENGTH: 20
<212> TYPE: RNA
<213> ORGANISM: Artificial Sequence
<220> FEATURE:
<223> OTHER INFORMATION: Synthetic Construct

<400> SEQUENCE: 401
cacgaagcac aggcggagcg                                               20

<210> SEQ ID NO 402
<211> LENGTH: 20
<212> TYPE: RNA
<213> ORGANISM: Artificial Sequence
<220> FEATURE:
<223> OTHER INFORMATION: Synthetic Construct

<400> SEQUENCE: 402
aggcggagcg cggcggctct                                               20

<210> SEQ ID NO 403
<211> LENGTH: 20
<212> TYPE: RNA
<213> ORGANISM: Artificial Sequence
<220> FEATURE:
<223> OTHER INFORMATION: Synthetic Construct

<400> SEQUENCE: 403
agggagctga ggttggacga                                               20

<210> SEQ ID NO 404
<211> LENGTH: 20
<212> TYPE: RNA
<213> ORGANISM: Artificial Sequence
<220> FEATURE:
<223> OTHER INFORMATION: Synthetic Construct

<400> SEQUENCE: 404
gttggacagg gagctgaggt                                               20

<210> SEQ ID NO 405
<211> LENGTH: 20
<212> TYPE: RNA
<213> ORGANISM: Artificial Sequence
<220> FEATURE:
<223> OTHER INFORMATION: Synthetic Construct

```
<400> SEQUENCE: 405
aggcgttgga cagggagctg                                                 20

<210> SEQ ID NO 406
<211> LENGTH: 20
<212> TYPE: RNA
<213> ORGANISM: Artificial Sequence
<220> FEATURE:
<223> OTHER INFORMATION: Synthetic Construct

<400> SEQUENCE: 406
ccctctcgga ggcgttggac                                                 20

<210> SEQ ID NO 407
<211> LENGTH: 20
<212> TYPE: RNA
<213> ORGANISM: Artificial Sequence
<220> FEATURE:
<223> OTHER INFORMATION: Synthetic Construct

<400> SEQUENCE: 407
cctctcggag gcgttggaca                                                 20

<210> SEQ ID NO 408
<211> LENGTH: 20
<212> TYPE: RNA
<213> ORGANISM: Artificial Sequence
<220> FEATURE:
<223> OTHER INFORMATION: Synthetic Construct

<400> SEQUENCE: 408
ctggtccctc tcggaggcgt                                                 20

<210> SEQ ID NO 409
<211> LENGTH: 20
<212> TYPE: RNA
<213> ORGANISM: Artificial Sequence
<220> FEATURE:
<223> OTHER INFORMATION: Synthetic Construct

<400> SEQUENCE: 409
ccctgtccaa cgcctccgag                                                 20

<210> SEQ ID NO 410
<211> LENGTH: 20
<212> TYPE: RNA
<213> ORGANISM: Artificial Sequence
<220> FEATURE:
<223> OTHER INFORMATION: Synthetic Construct

<400> SEQUENCE: 410
cctgtccaac gcctccgaga                                                 20

<210> SEQ ID NO 411
<211> LENGTH: 20
<212> TYPE: RNA
<213> ORGANISM: Artificial Sequence
<220> FEATURE:
<223> OTHER INFORMATION: Synthetic Construct

<400> SEQUENCE: 411
gtggtgctgg tccctctcgg                                                 20

<210> SEQ ID NO 412
```

```
<211> LENGTH: 20
<212> TYPE: RNA
<213> ORGANISM: Artificial Sequence
<220> FEATURE:
<223> OTHER INFORMATION: Synthetic Construct

<400> SEQUENCE: 412
caggtggtgc tggtccctct                                              20

<210> SEQ ID NO 413
<211> LENGTH: 20
<212> TYPE: RNA
<213> ORGANISM: Artificial Sequence
<220> FEATURE:
<223> OTHER INFORMATION: Synthetic Construct

<400> SEQUENCE: 413
gcatctcacc caggtggtgc                                              20

<210> SEQ ID NO 414
<211> LENGTH: 20
<212> TYPE: RNA
<213> ORGANISM: Artificial Sequence
<220> FEATURE:
<223> OTHER INFORMATION: Synthetic Construct

<400> SEQUENCE: 414
cgagagggac cagcaccacc                                              20

<210> SEQ ID NO 415
<211> LENGTH: 20
<212> TYPE: RNA
<213> ORGANISM: Artificial Sequence
<220> FEATURE:
<223> OTHER INFORMATION: Synthetic Construct

<400> SEQUENCE: 415
gagagggacc agcaccacct                                              20

<210> SEQ ID NO 416
<211> LENGTH: 20
<212> TYPE: RNA
<213> ORGANISM: Artificial Sequence
<220> FEATURE:
<223> OTHER INFORMATION: Synthetic Construct

<400> SEQUENCE: 416
gtgggggcat ctcacccagg                                              20

<210> SEQ ID NO 417
<211> LENGTH: 20
<212> TYPE: RNA
<213> ORGANISM: Artificial Sequence
<220> FEATURE:
<223> OTHER INFORMATION: Synthetic Construct

<400> SEQUENCE: 417
ccccgacact caggcgagaa                                              20

<210> SEQ ID NO 418
<211> LENGTH: 20
<212> TYPE: RNA
<213> ORGANISM: Artificial Sequence
<220> FEATURE:
<223> OTHER INFORMATION: Synthetic Construct

<400> SEQUENCE: 418
```
tccccgacac tcaggcgaga						20

<210> SEQ ID NO 419
<211> LENGTH: 20
<212> TYPE: RNA
<213> ORGANISM: Artificial Sequence
<220> FEATURE:
<223> OTHER INFORMATION: Synthetic Construct

<400> SEQUENCE: 419
agcccttctc gcctgagtgt						20

<210> SEQ ID NO 420
<211> LENGTH: 20
<212> TYPE: RNA
<213> ORGANISM: Artificial Sequence
<220> FEATURE:
<223> OTHER INFORMATION: Synthetic Construct

<400> SEQUENCE: 420
ctggctgctc cccgacactc						20

<210> SEQ ID NO 421
<211> LENGTH: 20
<212> TYPE: RNA
<213> ORGANISM: Artificial Sequence
<220> FEATURE:
<223> OTHER INFORMATION: Synthetic Construct

<400> SEQUENCE: 421
cccttctcgc ctgagtgtcg						20

<210> SEQ ID NO 422
<211> LENGTH: 20
<212> TYPE: RNA
<213> ORGANISM: Artificial Sequence
<220> FEATURE:
<223> OTHER INFORMATION: Synthetic Construct

<400> SEQUENCE: 422
gcccttctcg cctgagtgtc						20

<210> SEQ ID NO 423
<211> LENGTH: 20
<212> TYPE: RNA
<213> ORGANISM: Artificial Sequence
<220> FEATURE:
<223> OTHER INFORMATION: Synthetic Construct

<400> SEQUENCE: 423 tagggtcgt gggtgacgtc						20

<210> SEQ ID NO 424
<211> LENGTH: 20
<212> TYPE: RNA
<213> ORGANISM: Artificial Sequence
<220> FEATURE:
<223> OTHER INFORMATION: Synthetic Construct

<400> SEQUENCE: 424
aagaaactca tagggtcgt						20

<210> SEQ ID NO 425
<211> LENGTH: 20
<212> TYPE: RNA

```
<213> ORGANISM: Artificial Sequence
<220> FEATURE:
<223> OTHER INFORMATION: Synthetic Construct

<400> SEQUENCE: 425
gaagaaactc atagggtcg                                                   20

<210> SEQ ID NO 426
<211> LENGTH: 20
<212> TYPE: RNA
<213> ORGANISM: Artificial Sequence
<220> FEATURE:
<223> OTHER INFORMATION: Synthetic Construct

<400> SEQUENCE: 426
gagactgaag aaactcatag                                                  20

<210> SEQ ID NO 427
<211> LENGTH: 20
<212> TYPE: RNA
<213> ORGANISM: Artificial Sequence
<220> FEATURE:
<223> OTHER INFORMATION: Synthetic Construct

<400> SEQUENCE: 427
ggagactgaa gaaactcata                                                  20

<210> SEQ ID NO 428
<211> LENGTH: 20
<212> TYPE: RNA
<213> ORGANISM: Artificial Sequence
<220> FEATURE:
<223> OTHER INFORMATION: Synthetic Construct

<400> SEQUENCE: 428
tggagactga agaaactcat                                                  20

<210> SEQ ID NO 429
<211> LENGTH: 20
<212> TYPE: RNA
<213> ORGANISM: Artificial Sequence
<220> FEATURE:
<223> OTHER INFORMATION: Synthetic Construct

<400> SEQUENCE: 429
tcttcagtct ccagagcctg                                                  20

<210> SEQ ID NO 430
<211> LENGTH: 20
<212> TYPE: RNA
<213> ORGANISM: Artificial Sequence
<220> FEATURE:
<223> OTHER INFORMATION: Synthetic Construct

<400> SEQUENCE: 430
ttggcagagg ccgcaggctc                                                  20

<210> SEQ ID NO 431
<211> LENGTH: 20
<212> TYPE: RNA
<213> ORGANISM: Artificial Sequence
<220> FEATURE:
<223> OTHER INFORMATION: Synthetic Construct

<400> SEQUENCE: 431
taggtcttgg cagaggccgc                                                  20
```

<210> SEQ ID NO 432
<211> LENGTH: 20
<212> TYPE: RNA
<213> ORGANISM: Artificial Sequence
<220> FEATURE:
<223> OTHER INFORMATION: Synthetic Construct

<400> SEQUENCE: 432
ctagagttag gtcttggcag                                                 20

<210> SEQ ID NO 433
<211> LENGTH: 20
<212> TYPE: RNA
<213> ORGANISM: Artificial Sequence
<220> FEATURE:
<223> OTHER INFORMATION: Synthetic Construct

<400> SEQUENCE: 433
ggtggtctag agttaggtct                                                 20

<210> SEQ ID NO 434
<211> LENGTH: 20
<212> TYPE: RNA
<213> ORGANISM: Artificial Sequence
<220> FEATURE:
<223> OTHER INFORMATION: Synthetic Construct

<400> SEQUENCE: 434
gtagcgaacg tgtccggcgt                                                 20

<210> SEQ ID NO 435
<211> LENGTH: 20
<212> TYPE: RNA
<213> ORGANISM: Artificial Sequence
<220> FEATURE:
<223> OTHER INFORMATION: Synthetic Construct

<400> SEQUENCE: 435
gaccggaacg atctcgcgta                                                 20

<210> SEQ ID NO 436
<211> LENGTH: 20
<212> TYPE: RNA
<213> ORGANISM: Artificial Sequence
<220> FEATURE:
<223> OTHER INFORMATION: Synthetic Construct

<400> SEQUENCE: 436
ggcagtcgtt cggttgatat                                                 20

<210> SEQ ID NO 437
<211> LENGTH: 20
<212> TYPE: RNA
<213> ORGANISM: Artificial Sequence
<220> FEATURE:
<223> OTHER INFORMATION: Synthetic Construct

<400> SEQUENCE: 437
gcttgagcac atacgcgaat                                                 20

<210> SEQ ID NO 438
<211> LENGTH: 20
<212> TYPE: RNA
<213> ORGANISM: Artificial Sequence
<220> FEATURE:

<223> OTHER INFORMATION: Synthetic Construct

<400> SEQUENCE: 438
gtggtagaat aacgtattac                                          20

<210> SEQ ID NO 439
<211> LENGTH: 20
<212> TYPE: RNA
<213> ORGANISM: Artificial Sequence
<220> FEATURE:
<223> OTHER INFORMATION: Synthetic Construct

<400> SEQUENCE: 439
gtcatacatg gataaggcta                                          20

<210> SEQ ID NO 440
<211> LENGTH: 20
<212> TYPE: RNA
<213> ORGANISM: Artificial Sequence
<220> FEATURE:
<223> OTHER INFORMATION: Synthetic Construct

<400> SEQUENCE: 440
gatacacgaa gcatcactag                                          20

<210> SEQ ID NO 441
<211> LENGTH: 20
<212> TYPE: RNA
<213> ORGANISM: Artificial Sequence
<220> FEATURE:
<223> OTHER INFORMATION: Synthetic Construct

<400> SEQUENCE: 441
gaacgttggc actacttcac                                          20

<210> SEQ ID NO 442
<211> LENGTH: 20
<212> TYPE: RNA
<213> ORGANISM: Artificial Sequence
<220> FEATURE:
<223> OTHER INFORMATION: Synthetic Construct

<400> SEQUENCE: 442
gatccatgta atgcgttcga                                          20

<210> SEQ ID NO 443
<211> LENGTH: 20
<212> TYPE: RNA
<213> ORGANISM: Artificial Sequence
<220> FEATURE:
<223> OTHER INFORMATION: Synthetic Construct

<400> SEQUENCE: 443
gtcgtgaagt gcattcgatc                                          20

<210> SEQ ID NO 444
<211> LENGTH: 20
<212> TYPE: RNA
<213> ORGANISM: Artificial Sequence
<220> FEATURE:
<223> OTHER INFORMATION: Synthetic Construct

<400> SEQUENCE: 444
gttcgactcg cgtgaccgta                                          20

```
<210> SEQ ID NO 445
<211> LENGTH: 20
<212> TYPE: RNA
<213> ORGANISM: Artificial Sequence
<220> FEATURE:
<223> OTHER INFORMATION: Synthetic Construct

<400> SEQUENCE: 445
gaatctaccg cagcggttcg                                              20

<210> SEQ ID NO 446
<211> LENGTH: 20
<212> TYPE: RNA
<213> ORGANISM: Artificial Sequence
<220> FEATURE:
<223> OTHER INFORMATION: Synthetic Construct

<400> SEQUENCE: 446
gaagtgacgt cgattcgata                                              20

<210> SEQ ID NO 447
<211> LENGTH: 20
<212> TYPE: RNA
<213> ORGANISM: Artificial Sequence
<220> FEATURE:
<223> OTHER INFORMATION: Synthetic Construct

<400> SEQUENCE: 447
gcggtgtatg acaaccgccg                                              20

<210> SEQ ID NO 448
<211> LENGTH: 20
<212> TYPE: RNA
<213> ORGANISM: Artificial Sequence
<220> FEATURE:
<223> OTHER INFORMATION: Synthetic Construct

<400> SEQUENCE: 448
gtaccgcgcc tgaagttcgc                                              20

<210> SEQ ID NO 449
<211> LENGTH: 20
<212> TYPE: RNA
<213> ORGANISM: Artificial Sequence
<220> FEATURE:
<223> OTHER INFORMATION: Synthetic Construct

<400> SEQUENCE: 449
gcagctcgtg tgtcgtactc                                              20

<210> SEQ ID NO 450
<211> LENGTH: 20
<212> TYPE: RNA
<213> ORGANISM: Artificial Sequence
<220> FEATURE:
<223> OTHER INFORMATION: Synthetic Construct

<400> SEQUENCE: 450
gcgccttaag agtactcatc                                              20

<210> SEQ ID NO 451
<211> LENGTH: 20
<212> TYPE: RNA
<213> ORGANISM: Artificial Sequence
<220> FEATURE:
<223> OTHER INFORMATION: Synthetic Construct
```

```
<400> SEQUENCE: 451
gagtgtcgtc gttgctccta                                              20

<210> SEQ ID NO 452
<211> LENGTH: 20
<212> TYPE: RNA
<213> ORGANISM: Artificial Sequence
<220> FEATURE:
<223> OTHER INFORMATION: Synthetic Construct

<400> SEQUENCE: 452
gcagctcgac ctcaagccgt                                              20

<210> SEQ ID NO 453
<211> LENGTH: 20
<212> TYPE: RNA
<213> ORGANISM: Artificial Sequence
<220> FEATURE:
<223> OTHER INFORMATION: Synthetic Construct

<400> SEQUENCE: 453
gtatcctgac ctacgcgctg                                              20

<210> SEQ ID NO 454
<211> LENGTH: 20
<212> TYPE: RNA
<213> ORGANISM: Artificial Sequence
<220> FEATURE:
<223> OTHER INFORMATION: Synthetic Construct

<400> SEQUENCE: 454
gtgtatctca gcacgctaac                                              20

<210> SEQ ID NO 455
<211> LENGTH: 20
<212> TYPE: RNA
<213> ORGANISM: Artificial Sequence
<220> FEATURE:
<223> OTHER INFORMATION: Synthetic Construct

<400> SEQUENCE: 455
gtcgtcatac aacggcaacg                                              20

<210> SEQ ID NO 456
<211> LENGTH: 20
<212> TYPE: RNA
<213> ORGANISM: Artificial Sequence
<220> FEATURE:
<223> OTHER INFORMATION: Synthetic Construct

<400> SEQUENCE: 456
gtcgtgcgct tccggcggta                                              20

<210> SEQ ID NO 457
<211> LENGTH: 20
<212> TYPE: RNA
<213> ORGANISM: Artificial Sequence
<220> FEATURE:
<223> OTHER INFORMATION: Synthetic Construct

<400> SEQUENCE: 457
gcggtcctca gtaagcgcgt                                              20

<210> SEQ ID NO 458
<211> LENGTH: 20
```

<212> TYPE: RNA
<213> ORGANISM: Artificial Sequence
<220> FEATURE:
<223> OTHER INFORMATION: Synthetic Construct

<400> SEQUENCE: 458
gctctgctgc ggaaggattc                                              20

<210> SEQ ID NO 459
<211> LENGTH: 20
<212> TYPE: RNA
<213> ORGANISM: Artificial Sequence
<220> FEATURE:
<223> OTHER INFORMATION: Synthetic Construct

<400> SEQUENCE: 459
gcatggagga gcgtcgcaga                                              20

<210> SEQ ID NO 460
<211> LENGTH: 20
<212> TYPE: RNA
<213> ORGANISM: Artificial Sequence
<220> FEATURE:
<223> OTHER INFORMATION: Synthetic Construct

<400> SEQUENCE: 460
gtagcgcgcg taggagtggc                                              20

<210> SEQ ID NO 461
<211> LENGTH: 20
<212> TYPE: RNA
<213> ORGANISM: Artificial Sequence
<220> FEATURE:
<223> OTHER INFORMATION: Synthetic Construct

<400> SEQUENCE: 461
gatcacctgc attcgtacac                                              20

<210> SEQ ID NO 462
<211> LENGTH: 20
<212> TYPE: RNA
<213> ORGANISM: Artificial Sequence
<220> FEATURE:
<223> OTHER INFORMATION: Synthetic Construct

<400> SEQUENCE: 462
gcacacctag atatcgaatg                                              20

<210> SEQ ID NO 463
<211> LENGTH: 20
<212> TYPE: RNA
<213> ORGANISM: Artificial Sequence
<220> FEATURE:
<223> OTHER INFORMATION: Synthetic Construct

<400> SEQUENCE: 463
gttgatcaac gcgcttcgcg                                              20

<210> SEQ ID NO 464
<211> LENGTH: 20
<212> TYPE: RNA
<213> ORGANISM: Artificial Sequence
<220> FEATURE:
<223> OTHER INFORMATION: Synthetic Construct

<400> SEQUENCE: 464

```
gcgtctcact cactccatcg                                              20

<210> SEQ ID NO 465
<211> LENGTH: 20
<212> TYPE: RNA
<213> ORGANISM: Artificial Sequence
<220> FEATURE:
<223> OTHER INFORMATION: Synthetic Construct

<400> SEQUENCE: 465
gccgaccaac gtcagcggta                                              20

<210> SEQ ID NO 466
<211> LENGTH: 20
<212> TYPE: RNA
<213> ORGANISM: Artificial Sequence
<220> FEATURE:
<223> OTHER INFORMATION: Synthetic Construct

<400> SEQUENCE: 466
ggatacggtg cgtcaatcta                                              20

<210> SEQ ID NO 467
<211> LENGTH: 20
<212> TYPE: RNA
<213> ORGANISM: Artificial Sequence
<220> FEATURE:
<223> OTHER INFORMATION: Synthetic Construct

<400> SEQUENCE: 467
gaatccagtg gcggcgacaa                                              20

<210> SEQ ID NO 468
<211> LENGTH: 20
<212> TYPE: RNA
<213> ORGANISM: Artificial Sequence
<220> FEATURE:
<223> OTHER INFORMATION: Synthetic Construct

<400> SEQUENCE: 468
gcactgtcag tgcaacgata                                              20

<210> SEQ ID NO 469
<211> LENGTH: 20
<212> TYPE: RNA
<213> ORGANISM: Artificial Sequence
<220> FEATURE:
<223> OTHER INFORMATION: Synthetic Construct

<400> SEQUENCE: 469
gcgatcctca agtatgctca                                              20

<210> SEQ ID NO 470
<211> LENGTH: 20
<212> TYPE: RNA
<213> ORGANISM: Artificial Sequence
<220> FEATURE:
<223> OTHER INFORMATION: Synthetic Construct

<400> SEQUENCE: 470
gctaatatcg acacggccgc                                              20

<210> SEQ ID NO 471
<211> LENGTH: 20
<212> TYPE: RNA
<213> ORGANISM: Artificial Sequence
```

```
<220> FEATURE:
<223> OTHER INFORMATION: Synthetic Construct

<400> SEQUENCE: 471
ggagatgcat cgaagtcgat                                          20

<210> SEQ ID NO 472
<211> LENGTH: 20
<212> TYPE: RNA
<213> ORGANISM: Artificial Sequence
<220> FEATURE:
<223> OTHER INFORMATION: Synthetic Construct

<400> SEQUENCE: 472
ggatgcactc catctcgtct                                          20

<210> SEQ ID NO 473
<211> LENGTH: 20
<212> TYPE: RNA
<213> ORGANISM: Artificial Sequence
<220> FEATURE:
<223> OTHER INFORMATION: Synthetic Construct

<400> SEQUENCE: 473
gtgccgagta ataacgcgag                                          20

<210> SEQ ID NO 474
<211> LENGTH: 20
<212> TYPE: RNA
<213> ORGANISM: Artificial Sequence
<220> FEATURE:
<223> OTHER INFORMATION: Synthetic Construct

<400> SEQUENCE: 474
gagattccga tgtaacgtac                                          20

<210> SEQ ID NO 475
<211> LENGTH: 20
<212> TYPE: RNA
<213> ORGANISM: Artificial Sequence
<220> FEATURE:
<223> OTHER INFORMATION: Synthetic Construct

<400> SEQUENCE: 475
gtcgtcacga gcaggattgc                                          20

<210> SEQ ID NO 476
<211> LENGTH: 20
<212> TYPE: RNA
<213> ORGANISM: Artificial Sequence
<220> FEATURE:
<223> OTHER INFORMATION: Synthetic Construct

<400> SEQUENCE: 476
gcgttagtca cttagctcga                                          20

<210> SEQ ID NO 477
<211> LENGTH: 20
<212> TYPE: RNA
<213> ORGANISM: Artificial Sequence
<220> FEATURE:
<223> OTHER INFORMATION: Synthetic Construct

<400> SEQUENCE: 477
gttcacacgg tgtcggatag                                          20
```

```
<210> SEQ ID NO 478
<211> LENGTH: 20
<212> TYPE: RNA
<213> ORGANISM: Artificial Sequence
<220> FEATURE:
<223> OTHER INFORMATION: Synthetic Construct

<400> SEQUENCE: 478
ggataggtga ccttagtacg                                              20

<210> SEQ ID NO 479
<211> LENGTH: 20
<212> TYPE: RNA
<213> ORGANISM: Artificial Sequence
<220> FEATURE:
<223> OTHER INFORMATION: Synthetic Construct

<400> SEQUENCE: 479
gtatgagtca agctaatgcg                                              20

<210> SEQ ID NO 480
<211> LENGTH: 20
<212> TYPE: RNA
<213> ORGANISM: Artificial Sequence
<220> FEATURE:
<223> OTHER INFORMATION: Synthetic Construct

<400> SEQUENCE: 480
gcaactattg gaatacgtga                                              20

<210> SEQ ID NO 481
<211> LENGTH: 20
<212> TYPE: RNA
<213> ORGANISM: Artificial Sequence
<220> FEATURE:
<223> OTHER INFORMATION: Synthetic Construct

<400> SEQUENCE: 481
gttaccttcg ctcgtctata                                              20

<210> SEQ ID NO 482
<211> LENGTH: 20
<212> TYPE: RNA
<213> ORGANISM: Artificial Sequence
<220> FEATURE:
<223> OTHER INFORMATION: Synthetic Construct

<400> SEQUENCE: 482
gtaccgagca ccacaggccg                                              20

<210> SEQ ID NO 483
<211> LENGTH: 20
<212> TYPE: RNA
<213> ORGANISM: Artificial Sequence
<220> FEATURE:
<223> OTHER INFORMATION: Synthetic Construct

<400> SEQUENCE: 483
gtcagccatc ggatagagat                                              20

<210> SEQ ID NO 484
<211> LENGTH: 20
<212> TYPE: RNA
<213> ORGANISM: Artificial Sequence
<220> FEATURE:
<223> OTHER INFORMATION: Synthetic Construct
```

```
<400> SEQUENCE: 484
gtacggcact cctagccgct                                                    20

<210> SEQ ID NO 485
<211> LENGTH: 20
<212> TYPE: RNA
<213> ORGANISM: Artificial Sequence
<220> FEATURE:
<223> OTHER INFORMATION: Synthetic Construct

<400> SEQUENCE: 485
ggtcctgtcg tatgcttgca                                                    20

<210> SEQ ID NO 486
<211> LENGTH: 20
<212> TYPE: RNA
<213> ORGANISM: Artificial Sequence
<220> FEATURE:
<223> OTHER INFORMATION: Synthetic Construct

<400> SEQUENCE: 486
gccgcaatat atgcggtaag                                                    20

<210> SEQ ID NO 487
<211> LENGTH: 20
<212> TYPE: RNA
<213> ORGANISM: Artificial Sequence
<220> FEATURE:
<223> OTHER INFORMATION: Synthetic Construct

<400> SEQUENCE: 487
gcgcacgtat aatcctgcgt                                                    20

<210> SEQ ID NO 488
<211> LENGTH: 20
<212> TYPE: RNA
<213> ORGANISM: Artificial Sequence
<220> FEATURE:
<223> OTHER INFORMATION: Synthetic Construct

<400> SEQUENCE: 488
gtgcacaaca cgatccacga                                                    20

<210> SEQ ID NO 489
<211> LENGTH: 20
<212> TYPE: RNA
<213> ORGANISM: Artificial Sequence
<220> FEATURE:
<223> OTHER INFORMATION: Synthetic Construct

<400> SEQUENCE: 489
gcacaatgtt gacgtaagtg                                                    20

<210> SEQ ID NO 490
<211> LENGTH: 20
<212> TYPE: RNA
<213> ORGANISM: Artificial Sequence
<220> FEATURE:
<223> OTHER INFORMATION: Synthetic Construct

<400> SEQUENCE: 490
gtaagatgct gctcaccgtg                                                    20

<210> SEQ ID NO 491
```

```
<211> LENGTH: 20
<212> TYPE: RNA
<213> ORGANISM: Artificial Sequence
<220> FEATURE:
<223> OTHER INFORMATION: Synthetic Construct

<400> SEQUENCE: 491
gtcggtgatc caacgtatcg                                                20

<210> SEQ ID NO 492
<211> LENGTH: 20
<212> TYPE: RNA
<213> ORGANISM: Artificial Sequence
<220> FEATURE:
<223> OTHER INFORMATION: Synthetic Construct

<400> SEQUENCE: 492
gagctagtag gacgcaagac                                                20

<210> SEQ ID NO 493
<211> LENGTH: 20
<212> TYPE: RNA
<213> ORGANISM: Artificial Sequence
<220> FEATURE:
<223> OTHER INFORMATION: Synthetic Construct

<400> SEQUENCE: 493
gtacgtggaa gcttgtggcc                                                20

<210> SEQ ID NO 494
<211> LENGTH: 20
<212> TYPE: RNA
<213> ORGANISM: Artificial Sequence
<220> FEATURE:
<223> OTHER INFORMATION: Synthetic Construct

<400> SEQUENCE: 494
gagaactgcc agttctcgat                                                20

<210> SEQ ID NO 495
<211> LENGTH: 20
<212> TYPE: RNA
<213> ORGANISM: Artificial Sequence
<220> FEATURE:
<223> OTHER INFORMATION: Synthetic Construct

<400> SEQUENCE: 495
gccattcggc gcggcacttc                                                20

<210> SEQ ID NO 496
<211> LENGTH: 20
<212> TYPE: RNA
<213> ORGANISM: Artificial Sequence
<220> FEATURE:
<223> OTHER INFORMATION: Synthetic Construct

<400> SEQUENCE: 496
gcacacgacc aatccgcttc                                                20

<210> SEQ ID NO 497
<211> LENGTH: 20
<212> TYPE: RNA
<213> ORGANISM: Artificial Sequence
<220> FEATURE:
<223> OTHER INFORMATION: Synthetic Construct

<400> SEQUENCE: 497
```
gaggtgatcg attaagtaca                                                    20

<210> SEQ ID NO 498
<211> LENGTH: 20
<212> TYPE: RNA
<213> ORGANISM: Artificial Sequence
<220> FEATURE:
<223> OTHER INFORMATION: Synthetic Construct

<400> SEQUENCE: 498
gtcactcgca gacgcctaac                                                    20

<210> SEQ ID NO 499
<211> LENGTH: 20
<212> TYPE: RNA
<213> ORGANISM: Artificial Sequence
<220> FEATURE:
<223> OTHER INFORMATION: Synthetic Construct

<400> SEQUENCE: 499
gcgctacgga atcatacgtt                                                    20

<210> SEQ ID NO 500
<211> LENGTH: 20
<212> TYPE: RNA
<213> ORGANISM: Artificial Sequence
<220> FEATURE:
<223> OTHER INFORMATION: Synthetic Construct

<400> SEQUENCE: 500
ggtaggacct cacggcgcgc                                                    20

<210> SEQ ID NO 501
<211> LENGTH: 20
<212> TYPE: RNA
<213> ORGANISM: Artificial Sequence
<220> FEATURE:
<223> OTHER INFORMATION: Synthetic Construct

<400> SEQUENCE: 501
gaactgcatc ttgttgtagt                                                    20

<210> SEQ ID NO 502
<211> LENGTH: 20
<212> TYPE: RNA
<213> ORGANISM: Artificial Sequence
<220> FEATURE:
<223> OTHER INFORMATION: Synthetic Construct

<400> SEQUENCE: 502
gatcctgatc cggcggcgcg                                                    20

<210> SEQ ID NO 503
<211> LENGTH: 20
<212> TYPE: RNA
<213> ORGANISM: Artificial Sequence
<220> FEATURE:
<223> OTHER INFORMATION: Synthetic Construct

<400> SEQUENCE: 503
ggtatgcgcg atcctgagtt                                                    20

<210> SEQ ID NO 504
<211> LENGTH: 20
<212> TYPE: RNA

```
<213> ORGANISM: Artificial Sequence
<220> FEATURE:
<223> OTHER INFORMATION: Synthetic Construct

<400> SEQUENCE: 504
gcggagctag agagcggtca                                                      20

<210> SEQ ID NO 505
<211> LENGTH: 20
<212> TYPE: RNA
<213> ORGANISM: Artificial Sequence
<220> FEATURE:
<223> OTHER INFORMATION: Synthetic Construct

<400> SEQUENCE: 505
gaatggcaat tacggctgat                                                      20

<210> SEQ ID NO 506
<211> LENGTH: 20
<212> TYPE: RNA
<213> ORGANISM: Artificial Sequence
<220> FEATURE:
<223> OTHER INFORMATION: Synthetic Construct

<400> SEQUENCE: 506
gtatggtgag tagtcgcttg                                                      20

<210> SEQ ID NO 507
<211> LENGTH: 20
<212> TYPE: RNA
<213> ORGANISM: Artificial Sequence
<220> FEATURE:
<223> OTHER INFORMATION: Synthetic Construct

<400> SEQUENCE: 507
gtgtaattgc gtctagtcgg                                                      20

<210> SEQ ID NO 508
<211> LENGTH: 20
<212> TYPE: RNA
<213> ORGANISM: Artificial Sequence
<220> FEATURE:
<223> OTHER INFORMATION: Synthetic Construct

<400> SEQUENCE: 508
ggtcctggcg aggagccttg                                                      20

<210> SEQ ID NO 509
<211> LENGTH: 20
<212> TYPE: RNA
<213> ORGANISM: Artificial Sequence
<220> FEATURE:
<223> OTHER INFORMATION: Synthetic Construct

<400> SEQUENCE: 509
gaagataagt cgctgtctcg                                                      20

<210> SEQ ID NO 510
<211> LENGTH: 20
<212> TYPE: RNA
<213> ORGANISM: Artificial Sequence
<220> FEATURE:
<223> OTHER INFORMATION: Synthetic Construct

<400> SEQUENCE: 510
gtcggcgttc tgttgtgact                                                      20
```

<210> SEQ ID NO 511
<211> LENGTH: 20
<212> TYPE: RNA
<213> ORGANISM: Artificial Sequence
<220> FEATURE:
<223> OTHER INFORMATION: Synthetic Construct

<400> SEQUENCE: 511
gaggcaagcc gttaggtgta                                               20

<210> SEQ ID NO 512
<211> LENGTH: 20
<212> TYPE: RNA
<213> ORGANISM: Artificial Sequence
<220> FEATURE:
<223> OTHER INFORMATION: Synthetic Construct

<400> SEQUENCE: 512
gcggatccag atctcattcg                                               20

<210> SEQ ID NO 513
<211> LENGTH: 20
<212> TYPE: RNA
<213> ORGANISM: Artificial Sequence
<220> FEATURE:
<223> OTHER INFORMATION: Synthetic Construct

<400> SEQUENCE: 513
ggaacatagg agcacgtagt                                               20

<210> SEQ ID NO 514
<211> LENGTH: 20
<212> TYPE: RNA
<213> ORGANISM: Artificial Sequence
<220> FEATURE:
<223> OTHER INFORMATION: Synthetic Construct

<400> SEQUENCE: 514
gtcatcatta tggcgtaagg                                               20

<210> SEQ ID NO 515
<211> LENGTH: 20
<212> TYPE: RNA
<213> ORGANISM: Artificial Sequence
<220> FEATURE:
<223> OTHER INFORMATION: Synthetic Construct

<400> SEQUENCE: 515
gcgactagcg ccatgagcgg                                               20

<210> SEQ ID NO 516
<211> LENGTH: 20
<212> TYPE: RNA
<213> ORGANISM: Artificial Sequence
<220> FEATURE:
<223> OTHER INFORMATION: Synthetic Construct

<400> SEQUENCE: 516
ggcgaagttc gacatgacac                                               20

<210> SEQ ID NO 517
<211> LENGTH: 20
<212> TYPE: RNA
<213> ORGANISM: Artificial Sequence
<220> FEATURE:

<223> OTHER INFORMATION: Synthetic Construct

<400> SEQUENCE: 517
gctgtcgtgt ggaggctatg                                               20

<210> SEQ ID NO 518
<211> LENGTH: 20
<212> TYPE: RNA
<213> ORGANISM: Artificial Sequence
<220> FEATURE:
<223> OTHER INFORMATION: Synthetic Construct

<400> SEQUENCE: 518
gcggagagca ttgacctcat                                               20

<210> SEQ ID NO 519
<211> LENGTH: 20
<212> TYPE: RNA
<213> ORGANISM: Artificial Sequence
<220> FEATURE:
<223> OTHER INFORMATION: Synthetic Construct

<400> SEQUENCE: 519
gactaatgga ccaagtcagt                                               20

<210> SEQ ID NO 520
<211> LENGTH: 20
<212> TYPE: RNA
<213> ORGANISM: Artificial Sequence
<220> FEATURE:
<223> OTHER INFORMATION: Synthetic Construct

<400> SEQUENCE: 520
gcggattaga ggtaatgcgg                                               20

<210> SEQ ID NO 521
<211> LENGTH: 20
<212> TYPE: RNA
<213> ORGANISM: Artificial Sequence
<220> FEATURE:
<223> OTHER INFORMATION: Synthetic Construct

<400> SEQUENCE: 521
gccgacggca atcagtacgc                                               20

<210> SEQ ID NO 522
<211> LENGTH: 20
<212> TYPE: RNA
<213> ORGANISM: Artificial Sequence
<220> FEATURE:
<223> OTHER INFORMATION: Synthetic Construct

<400> SEQUENCE: 522
gtaacctctc gagcgataga                                               20

<210> SEQ ID NO 523
<211> LENGTH: 20
<212> TYPE: RNA
<213> ORGANISM: Artificial Sequence
<220> FEATURE:
<223> OTHER INFORMATION: Synthetic Construct

<400> SEQUENCE: 523
gacttgtatg tggcttacgg                                               20

<210> SEQ ID NO 524
<211> LENGTH: 20
<212> TYPE: RNA
<213> ORGANISM: Artificial Sequence
<220> FEATURE:
<223> OTHER INFORMATION: Synthetic Construct

<400> SEQUENCE: 524
gtcactgtgg tcgaacatgt                                              20

<210> SEQ ID NO 525
<211> LENGTH: 20
<212> TYPE: RNA
<213> ORGANISM: Artificial Sequence
<220> FEATURE:
<223> OTHER INFORMATION: Synthetic Construct

<400> SEQUENCE: 525
gtactccaat ccgcgatgac                                              20

<210> SEQ ID NO 526
<211> LENGTH: 20
<212> TYPE: RNA
<213> ORGANISM: Artificial Sequence
<220> FEATURE:
<223> OTHER INFORMATION: Synthetic Construct

<400> SEQUENCE: 526
gcgttggcac gatgttacgg                                              20

<210> SEQ ID NO 527
<211> LENGTH: 20
<212> TYPE: RNA
<213> ORGANISM: Artificial Sequence
<220> FEATURE:
<223> OTHER INFORMATION: Synthetic Construct

<400> SEQUENCE: 527
gaaccagccg gctagtatga                                              20

<210> SEQ ID NO 528
<211> LENGTH: 20
<212> TYPE: RNA
<213> ORGANISM: Artificial Sequence
<220> FEATURE:
<223> OTHER INFORMATION: Synthetic Construct

<400> SEQUENCE: 528
gtatactagc taaccacacg                                              20

<210> SEQ ID NO 529
<211> LENGTH: 20
<212> TYPE: RNA
<213> ORGANISM: Artificial Sequence
<220> FEATURE:
<223> OTHER INFORMATION: Synthetic Construct

<400> SEQUENCE: 529
gaatcggaat agttgattcg                                              20

<210> SEQ ID NO 530
<211> LENGTH: 20
<212> TYPE: RNA
<213> ORGANISM: Artificial Sequence
<220> FEATURE:
<223> OTHER INFORMATION: Synthetic Construct

<400> SEQUENCE: 530
gagcacttgc atgaggcggt                                                  20

<210> SEQ ID NO 531
<211> LENGTH: 20
<212> TYPE: RNA
<213> ORGANISM: Artificial Sequence
<220> FEATURE:
<223> OTHER INFORMATION: Synthetic Construct

<400> SEQUENCE: 531
gaacggcgat gaagccagcc                                                  20

<210> SEQ ID NO 532
<211> LENGTH: 20
<212> TYPE: RNA
<213> ORGANISM: Artificial Sequence
<220> FEATURE:
<223> OTHER INFORMATION: Synthetic Construct

<400> SEQUENCE: 532
gcaaccgaga tgagaggttc                                                  20

<210> SEQ ID NO 533
<211> LENGTH: 20
<212> TYPE: RNA
<213> ORGANISM: Artificial Sequence
<220> FEATURE:
<223> OTHER INFORMATION: Synthetic Construct

<400> SEQUENCE: 533
gcaagatcaa tatgcgtgat                                                  20

<210> SEQ ID NO 534
<211> LENGTH: 20
<212> TYPE: RNA
<213> ORGANISM: Artificial Sequence
<220> FEATURE:
<223> OTHER INFORMATION: Synthetic Construct

<400> SEQUENCE: 534
acggaggcta agcgtcgcaa                                                  20

<210> SEQ ID NO 535
<211> LENGTH: 20
<212> TYPE: RNA
<213> ORGANISM: Artificial Sequence
<220> FEATURE:
<223> OTHER INFORMATION: Synthetic Construct

<400> SEQUENCE: 535
cgcttccgcg gcccgttcaa                                                  20

<210> SEQ ID NO 536
<211> LENGTH: 20
<212> TYPE: RNA
<213> ORGANISM: Artificial Sequence
<220> FEATURE:
<223> OTHER INFORMATION: Synthetic Construct

<400> SEQUENCE: 536
atcgtttccg cttaacggcg                                                  20

<210> SEQ ID NO 537
<211> LENGTH: 20

```
<212> TYPE: RNA
<213> ORGANISM: Artificial Sequence
<220> FEATURE:
<223> OTHER INFORMATION: Synthetic Construct

<400> SEQUENCE: 537
gtaggcgcgc cgctctctac                                           20

<210> SEQ ID NO 538
<211> LENGTH: 20
<212> TYPE: RNA
<213> ORGANISM: Artificial Sequence
<220> FEATURE:
<223> OTHER INFORMATION: Synthetic Construct

<400> SEQUENCE: 538
ccatatcggg gcgagacatg                                           20

<210> SEQ ID NO 539
<211> LENGTH: 20
<212> TYPE: RNA
<213> ORGANISM: Artificial Sequence
<220> FEATURE:
<223> OTHER INFORMATION: Synthetic Construct

<400> SEQUENCE: 539
tactaacgcc gctcctacag                                           20

<210> SEQ ID NO 540
<211> LENGTH: 20
<212> TYPE: RNA
<213> ORGANISM: Artificial Sequence
<220> FEATURE:
<223> OTHER INFORMATION: Synthetic Construct

<400> SEQUENCE: 540
tgaggatcat gtcgagcgcc                                           20

<210> SEQ ID NO 541
<211> LENGTH: 20
<212> TYPE: RNA
<213> ORGANISM: Artificial Sequence
<220> FEATURE:
<223> OTHER INFORMATION: Synthetic Construct

<400> SEQUENCE: 541
gggcccgcat aggatatcgc                                           20

<210> SEQ ID NO 542
<211> LENGTH: 20
<212> TYPE: RNA
<213> ORGANISM: Artificial Sequence
<220> FEATURE:
<223> OTHER INFORMATION: Synthetic Construct

<400> SEQUENCE: 542
tagacaaccg cggagaatgc                                           20

<210> SEQ ID NO 543
<211> LENGTH: 20
<212> TYPE: RNA
<213> ORGANISM: Artificial Sequence
<220> FEATURE:
<223> OTHER INFORMATION: Synthetic Construct

<400> SEQUENCE: 543
```
acgggcggct atcgctgact                                              20

<210> SEQ ID NO 544
<211> LENGTH: 20
<212> TYPE: RNA
<213> ORGANISM: Artificial Sequence
<220> FEATURE:
<223> OTHER INFORMATION: Synthetic Construct

<400> SEQUENCE: 544
cgcggaaatt ttaccgacga                                              20

<210> SEQ ID NO 545
<211> LENGTH: 20
<212> TYPE: RNA
<213> ORGANISM: Artificial Sequence
<220> FEATURE:
<223> OTHER INFORMATION: Synthetic Construct

<400> SEQUENCE: 545
cttacaatcg tcggtccaat                                              20

<210> SEQ ID NO 546
<211> LENGTH: 20
<212> TYPE: RNA
<213> ORGANISM: Artificial Sequence
<220> FEATURE:
<223> OTHER INFORMATION: Synthetic Construct

<400> SEQUENCE: 546
gcgtgcgtcc cgggttaccc                                              20

<210> SEQ ID NO 547
<211> LENGTH: 20
<212> TYPE: RNA
<213> ORGANISM: Artificial Sequence
<220> FEATURE:
<223> OTHER INFORMATION: Synthetic Construct

<400> SEQUENCE: 547
cggagtaaca agcggacgga                                              20

<210> SEQ ID NO 548
<211> LENGTH: 20
<212> TYPE: RNA
<213> ORGANISM: Artificial Sequence
<220> FEATURE:
<223> OTHER INFORMATION: Synthetic Construct

<400> SEQUENCE: 548
cgagtgttat acgcaccgtt                                              20

<210> SEQ ID NO 549
<211> LENGTH: 20
<212> TYPE: RNA
<213> ORGANISM: Artificial Sequence
<220> FEATURE:
<223> OTHER INFORMATION: Synthetic Construct

<400> SEQUENCE: 549
cgactaaccg gaaactttt                                               20

<210> SEQ ID NO 550
<211> LENGTH: 20
<212> TYPE: RNA
<213> ORGANISM: Artificial Sequence
<220> FEATURE:
<223> OTHER INFORMATION: Synthetic Construct

<400> SEQUENCE: 550
caacgggttc tcccggctac                                                    20

<210> SEQ ID NO 551
<211> LENGTH: 20
<212> TYPE: RNA
<213> ORGANISM: Artificial Sequence
<220> FEATURE:
<223> OTHER INFORMATION: Synthetic Construct

<400> SEQUENCE: 551
caggagtcgc cgatacgcgt                                                    20

<210> SEQ ID NO 552
<211> LENGTH: 20
<212> TYPE: RNA
<213> ORGANISM: Artificial Sequence
<220> FEATURE:
<223> OTHER INFORMATION: Synthetic Construct

<400> SEQUENCE: 552
ttcacgtcgt ctcgcgacca                                                    20

<210> SEQ ID NO 553
<211> LENGTH: 20
<212> TYPE: RNA
<213> ORGANISM: Artificial Sequence
<220> FEATURE:
<223> OTHER INFORMATION: Synthetic Construct

<400> SEQUENCE: 553
gtgtcggatt ccgccgctta                                                    20

<210> SEQ ID NO 554
<211> LENGTH: 20
<212> TYPE: RNA
<213> ORGANISM: Artificial Sequence
<220> FEATURE:
<223> OTHER INFORMATION: Synthetic Construct

<400> SEQUENCE: 554
cacgaactca caccgcgcga                                                    20

<210> SEQ ID NO 555
<211> LENGTH: 20
<212> TYPE: RNA
<213> ORGANISM: Artificial Sequence
<220> FEATURE:
<223> OTHER INFORMATION: Synthetic Construct

<400> SEQUENCE: 555
cgctagtacg ctcctctata                                                    20

<210> SEQ ID NO 556
<211> LENGTH: 20
<212> TYPE: RNA
<213> ORGANISM: Artificial Sequence
<220> FEATURE:
<223> OTHER INFORMATION: Synthetic Construct

<400> SEQUENCE: 556
tcgcgcttgg gttatacgct                                                    20

<210> SEQ ID NO 557
<211> LENGTH: 20
<212> TYPE: RNA
<213> ORGANISM: Artificial Sequence
<220> FEATURE:
<223> OTHER INFORMATION: Synthetic Construct

<400> SEQUENCE: 557
ctatctcgag tggtaatgcg                                               20

<210> SEQ ID NO 558
<211> LENGTH: 20
<212> TYPE: RNA
<213> ORGANISM: Artificial Sequence
<220> FEATURE:
<223> OTHER INFORMATION: Synthetic Construct

<400> SEQUENCE: 558
aatcgactcg aacttcgtgt                                               20

<210> SEQ ID NO 559
<211> LENGTH: 20
<212> TYPE: RNA
<213> ORGANISM: Artificial Sequence
<220> FEATURE:
<223> OTHER INFORMATION: Synthetic Construct

<400> SEQUENCE: 559
cccgatggac tataccgaac                                               20

<210> SEQ ID NO 560
<211> LENGTH: 20
<212> TYPE: RNA
<213> ORGANISM: Artificial Sequence
<220> FEATURE:
<223> OTHER INFORMATION: Synthetic Construct

<400> SEQUENCE: 560
acgttcgagt acgaccagct                                               20

<210> SEQ ID NO 561
<211> LENGTH: 20
<212> TYPE: RNA
<213> ORGANISM: Artificial Sequence
<220> FEATURE:
<223> OTHER INFORMATION: Synthetic Construct

<400> SEQUENCE: 561
cgcgacgact caacctagtc                                               20

<210> SEQ ID NO 562
<211> LENGTH: 20
<212> TYPE: RNA
<213> ORGANISM: Artificial Sequence
<220> FEATURE:
<223> OTHER INFORMATION: Synthetic Construct

<400> SEQUENCE: 562
ggtcaccgat cgagagctag                                               20

<210> SEQ ID NO 563
<211> LENGTH: 20
<212> TYPE: RNA
<213> ORGANISM: Artificial Sequence
<220> FEATURE:
<223> OTHER INFORMATION: Synthetic Construct

<400> SEQUENCE: 563
ctcaaccgac cgtatggtca                                               20

<210> SEQ ID NO 564
<211> LENGTH: 20
<212> TYPE: RNA
<213> ORGANISM: Artificial Sequence
<220> FEATURE:
<223> OTHER INFORMATION: Synthetic Construct

<400> SEQUENCE: 564
cgtattcgac tctcaacgcg                                               20

<210> SEQ ID NO 565
<211> LENGTH: 20
<212> TYPE: RNA
<213> ORGANISM: Artificial Sequence
<220> FEATURE:
<223> OTHER INFORMATION: Synthetic Construct

<400> SEQUENCE: 565
ctagccgccc agatcgagcc                                               20

<210> SEQ ID NO 566
<211> LENGTH: 20
<212> TYPE: RNA
<213> ORGANISM: Artificial Sequence
<220> FEATURE:
<223> OTHER INFORMATION: Synthetic Construct

<400> SEQUENCE: 566
gaatcgaccg acactaatgt                                               20

<210> SEQ ID NO 567
<211> LENGTH: 20
<212> TYPE: RNA
<213> ORGANISM: Artificial Sequence
<220> FEATURE:
<223> OTHER INFORMATION: Synthetic Construct

<400> SEQUENCE: 567
acttcagttc ggcgtagtca                                               20

<210> SEQ ID NO 568
<211> LENGTH: 20
<212> TYPE: RNA
<213> ORGANISM: Artificial Sequence
<220> FEATURE:
<223> OTHER INFORMATION: Synthetic Construct

<400> SEQUENCE: 568
gtgcgatgtc gcttcaacgt                                               20

<210> SEQ ID NO 569
<211> LENGTH: 20
<212> TYPE: RNA
<213> ORGANISM: Artificial Sequence
<220> FEATURE:
<223> OTHER INFORMATION: Synthetic Construct

<400> SEQUENCE: 569
cgcctaattt ccggatcaat                                               20

<210> SEQ ID NO 570

```
<211> LENGTH: 20
<212> TYPE: RNA
<213> ORGANISM: Artificial Sequence
<220> FEATURE:
<223> OTHER INFORMATION: Synthetic Construct

<400> SEQUENCE: 570
cgtggccgga accgtcatag                                                    20

<210> SEQ ID NO 571
<211> LENGTH: 20
<212> TYPE: RNA
<213> ORGANISM: Artificial Sequence
<220> FEATURE:
<223> OTHER INFORMATION: Synthetic Construct

<400> SEQUENCE: 571
accctccgaa tcgtaacgga                                                    20

<210> SEQ ID NO 572
<211> LENGTH: 20
<212> TYPE: RNA
<213> ORGANISM: Artificial Sequence
<220> FEATURE:
<223> OTHER INFORMATION: Synthetic Construct

<400> SEQUENCE: 572
aaacggtacg acagcgtgtg                                                    20

<210> SEQ ID NO 573
<211> LENGTH: 20
<212> TYPE: RNA
<213> ORGANISM: Artificial Sequence
<220> FEATURE:
<223> OTHER INFORMATION: Synthetic Construct

<400> SEQUENCE: 573
acatagtcga cggctcgatt                                                    20

<210> SEQ ID NO 574
<211> LENGTH: 20
<212> TYPE: RNA
<213> ORGANISM: Artificial Sequence
<220> FEATURE:
<223> OTHER INFORMATION: Synthetic Construct

<400> SEQUENCE: 574
gatggcgctt cagtcgtcgg                                                    20

<210> SEQ ID NO 575
<211> LENGTH: 20
<212> TYPE: RNA
<213> ORGANISM: Artificial Sequence
<220> FEATURE:
<223> OTHER INFORMATION: Synthetic Construct

<400> SEQUENCE: 575
ataatccgga aacgctcgac                                                    20

<210> SEQ ID NO 576
<211> LENGTH: 20
<212> TYPE: RNA
<213> ORGANISM: Artificial Sequence
<220> FEATURE:
<223> OTHER INFORMATION: Synthetic Construct

<400> SEQUENCE: 576
```
cgccgggctg acaattaacg                                             20

<210> SEQ ID NO 577
<211> LENGTH: 20
<212> TYPE: RNA
<213> ORGANISM: Artificial Sequence
<220> FEATURE:
<223> OTHER INFORMATION: Synthetic Construct

<400> SEQUENCE: 577
cgtcgccata tgccggtggc                                             20

<210> SEQ ID NO 578
<211> LENGTH: 20
<212> TYPE: RNA
<213> ORGANISM: Artificial Sequence
<220> FEATURE:
<223> OTHER INFORMATION: Synthetic Construct

<400> SEQUENCE: 578
cgggcctata acaccatcga                                             20

<210> SEQ ID NO 579
<211> LENGTH: 20
<212> TYPE: RNA
<213> ORGANISM: Artificial Sequence
<220> FEATURE:
<223> OTHER INFORMATION: Synthetic Construct

<400> SEQUENCE: 579
cgccgttccg agatacttga                                             20

<210> SEQ ID NO 580
<211> LENGTH: 20
<212> TYPE: RNA
<213> ORGANISM: Artificial Sequence
<220> FEATURE:
<223> OTHER INFORMATION: Synthetic Construct

<400> SEQUENCE: 580
cgggacgtcg cgaaaatgta                                             20

<210> SEQ ID NO 581
<211> LENGTH: 20
<212> TYPE: RNA
<213> ORGANISM: Artificial Sequence
<220> FEATURE:
<223> OTHER INFORMATION: Synthetic Construct

<400> SEQUENCE: 581
tcggcatacg ggacacacgc                                             20

<210> SEQ ID NO 582
<211> LENGTH: 20
<212> TYPE: RNA
<213> ORGANISM: Artificial Sequence
<220> FEATURE:
<223> OTHER INFORMATION: Synthetic Construct

<400> SEQUENCE: 582
agctccatcg ccgcgataat                                             20

<210> SEQ ID NO 583
<211> LENGTH: 20
<212> TYPE: RNA

```
<213> ORGANISM: Artificial Sequence
<220> FEATURE:
<223> OTHER INFORMATION: Synthetic Construct

<400> SEQUENCE: 583
atcgtatcat cagctagcgc                                                 20

<210> SEQ ID NO 584
<211> LENGTH: 20
<212> TYPE: RNA
<213> ORGANISM: Artificial Sequence
<220> FEATURE:
<223> OTHER INFORMATION: Synthetic Construct

<400> SEQUENCE: 584
tcgatcgagg ttgcattcgg                                                 20

<210> SEQ ID NO 585
<211> LENGTH: 20
<212> TYPE: RNA
<213> ORGANISM: Artificial Sequence
<220> FEATURE:
<223> OTHER INFORMATION: Synthetic Construct

<400> SEQUENCE: 585
ctcgacagtt cgtcccgagc                                                 20

<210> SEQ ID NO 586
<211> LENGTH: 20
<212> TYPE: RNA
<213> ORGANISM: Artificial Sequence
<220> FEATURE:
<223> OTHER INFORMATION: Synthetic Construct

<400> SEQUENCE: 586
cggtagtatt aatcgctgac                                                 20

<210> SEQ ID NO 587
<211> LENGTH: 20
<212> TYPE: RNA
<213> ORGANISM: Artificial Sequence
<220> FEATURE:
<223> OTHER INFORMATION: Synthetic Construct

<400> SEQUENCE: 587
tgaacgcgtg tttccttgca                                                 20

<210> SEQ ID NO 588
<211> LENGTH: 20
<212> TYPE: RNA
<213> ORGANISM: Artificial Sequence
<220> FEATURE:
<223> OTHER INFORMATION: Synthetic Construct

<400> SEQUENCE: 588
cgacgctagg taacgtagag                                                 20

<210> SEQ ID NO 589
<211> LENGTH: 20
<212> TYPE: RNA
<213> ORGANISM: Artificial Sequence
<220> FEATURE:
<223> OTHER INFORMATION: Synthetic Construct

<400> SEQUENCE: 589
cattgttgag cgggcgcgct                                                 20
```

<210> SEQ ID NO 590
<211> LENGTH: 20
<212> TYPE: RNA
<213> ORGANISM: Artificial Sequence
<220> FEATURE:
<223> OTHER INFORMATION: Synthetic Construct

<400> SEQUENCE: 590
ccgctattga aaccgcccac                                          20

<210> SEQ ID NO 591
<211> LENGTH: 20
<212> TYPE: RNA
<213> ORGANISM: Artificial Sequence
<220> FEATURE:
<223> OTHER INFORMATION: Synthetic Construct

<400> SEQUENCE: 591
agacacgtca ccggtcaaaa                                          20

<210> SEQ ID NO 592
<211> LENGTH: 20
<212> TYPE: RNA
<213> ORGANISM: Artificial Sequence
<220> FEATURE:
<223> OTHER INFORMATION: Synthetic Construct

<400> SEQUENCE: 592
tttacgatct agcggcgtag                                          20

<210> SEQ ID NO 593
<211> LENGTH: 20
<212> TYPE: RNA
<213> ORGANISM: Artificial Sequence
<220> FEATURE:
<223> OTHER INFORMATION: Synthetic Construct

<400> SEQUENCE: 593
ttcgcacgat tgcaccttgg                                          20

<210> SEQ ID NO 594
<211> LENGTH: 20
<212> TYPE: RNA
<213> ORGANISM: Artificial Sequence
<220> FEATURE:
<223> OTHER INFORMATION: Synthetic Construct

<400> SEQUENCE: 594
ggttagagac taggcgcgcg                                          20

<210> SEQ ID NO 595
<211> LENGTH: 20
<212> TYPE: RNA
<213> ORGANISM: Artificial Sequence
<220> FEATURE:
<223> OTHER INFORMATION: Synthetic Construct

<400> SEQUENCE: 595
cctccgtgct aacgcggacg                                          20

<210> SEQ ID NO 596
<211> LENGTH: 20
<212> TYPE: RNA
<213> ORGANISM: Artificial Sequence
<220> FEATURE:

<223> OTHER INFORMATION: Synthetic Construct

<400> SEQUENCE: 596
ttatcgcgta gtgctgacgt                                               20

<210> SEQ ID NO 597
<211> LENGTH: 20
<212> TYPE: RNA
<213> ORGANISM: Artificial Sequence
<220> FEATURE:
<223> OTHER INFORMATION: Synthetic Construct

<400> SEQUENCE: 597
tacgcttgcg tttagcgtcc                                               20

<210> SEQ ID NO 598
<211> LENGTH: 20
<212> TYPE: RNA
<213> ORGANISM: Artificial Sequence
<220> FEATURE:
<223> OTHER INFORMATION: Synthetic Construct

<400> SEQUENCE: 598
cgcggcccac gcgtcatcgc                                               20

<210> SEQ ID NO 599
<211> LENGTH: 20
<212> TYPE: RNA
<213> ORGANISM: Artificial Sequence
<220> FEATURE:
<223> OTHER INFORMATION: Synthetic Construct

<400> SEQUENCE: 599
agctcgccat gtcggttctc                                               20

<210> SEQ ID NO 600
<211> LENGTH: 20
<212> TYPE: RNA
<213> ORGANISM: Artificial Sequence
<220> FEATURE:
<223> OTHER INFORMATION: Synthetic Construct

<400> SEQUENCE: 600
aactagcccg agcagcttcg                                               20

<210> SEQ ID NO 601
<211> LENGTH: 20
<212> TYPE: RNA
<213> ORGANISM: Artificial Sequence
<220> FEATURE:
<223> OTHER INFORMATION: Synthetic Construct

<400> SEQUENCE: 601
cgcaaggtgt cggtaaccct                                               20

<210> SEQ ID NO 602
<211> LENGTH: 20
<212> TYPE: RNA
<213> ORGANISM: Artificial Sequence
<220> FEATURE:
<223> OTHER INFORMATION: Synthetic Construct

<400> SEQUENCE: 602
cttcgacgcc atcgtgctca                                               20

```
<210> SEQ ID NO 603
<211> LENGTH: 20
<212> TYPE: RNA
<213> ORGANISM: Artificial Sequence
<220> FEATURE:
<223> OTHER INFORMATION: Synthetic Construct

<400> SEQUENCE: 603
tcctggatac cgcgtggtta                                              20

<210> SEQ ID NO 604
<211> LENGTH: 20
<212> TYPE: RNA
<213> ORGANISM: Artificial Sequence
<220> FEATURE:
<223> OTHER INFORMATION: Synthetic Construct

<400> SEQUENCE: 604
atagccgccg ctcattactt                                              20

<210> SEQ ID NO 605
<211> LENGTH: 20
<212> TYPE: RNA
<213> ORGANISM: Artificial Sequence
<220> FEATURE:
<223> OTHER INFORMATION: Synthetic Construct

<400> SEQUENCE: 605
gtcgtccggg attacaaaat                                              20

<210> SEQ ID NO 606
<211> LENGTH: 20
<212> TYPE: RNA
<213> ORGANISM: Artificial Sequence
<220> FEATURE:
<223> OTHER INFORMATION: Synthetic Construct

<400> SEQUENCE: 606
taatgctgca cacgccgaat                                              20

<210> SEQ ID NO 607
<211> LENGTH: 20
<212> TYPE: RNA
<213> ORGANISM: Artificial Sequence
<220> FEATURE:
<223> OTHER INFORMATION: Synthetic Construct

<400> SEQUENCE: 607
tatcgcttcc gattagtccg                                              20

<210> SEQ ID NO 608
<211> LENGTH: 20
<212> TYPE: RNA
<213> ORGANISM: Artificial Sequence
<220> FEATURE:
<223> OTHER INFORMATION: Synthetic Construct

<400> SEQUENCE: 608
gtaccatacc gcgtaccctt                                              20

<210> SEQ ID NO 609
<211> LENGTH: 20
<212> TYPE: RNA
<213> ORGANISM: Artificial Sequence
<220> FEATURE:
<223> OTHER INFORMATION: Synthetic Construct
```

<400> SEQUENCE: 609
taagatccgc gggtggcaac					20

<210> SEQ ID NO 610
<211> LENGTH: 20
<212> TYPE: RNA
<213> ORGANISM: Artificial Sequence
<220> FEATURE:
<223> OTHER INFORMATION: Synthetic Construct

<400> SEQUENCE: 610
gtagacgtcg tgagcttcac					20

<210> SEQ ID NO 611
<211> LENGTH: 20
<212> TYPE: RNA
<213> ORGANISM: Artificial Sequence
<220> FEATURE:
<223> OTHER INFORMATION: Synthetic Construct

<400> SEQUENCE: 611
tcgcggacat agggctctaa					20

<210> SEQ ID NO 612
<211> LENGTH: 20
<212> TYPE: RNA
<213> ORGANISM: Artificial Sequence
<220> FEATURE:
<223> OTHER INFORMATION: Synthetic Construct

<400> SEQUENCE: 612
agcgcagata gcgcgtatca					20

<210> SEQ ID NO 613
<211> LENGTH: 20
<212> TYPE: RNA
<213> ORGANISM: Artificial Sequence
<220> FEATURE:
<223> OTHER INFORMATION: Synthetic Construct

<400> SEQUENCE: 613
gttcgcttcg taacgaggaa					20

<210> SEQ ID NO 614
<211> LENGTH: 20
<212> TYPE: RNA
<213> ORGANISM: Artificial Sequence
<220> FEATURE:
<223> OTHER INFORMATION: Synthetic Construct

<400> SEQUENCE: 614
gacccccgat aacttttgac					20

<210> SEQ ID NO 615
<211> LENGTH: 20
<212> TYPE: RNA
<213> ORGANISM: Artificial Sequence
<220> FEATURE:
<223> OTHER INFORMATION: Synthetic Construct

<400> SEQUENCE: 615
acgtccatac tgtcggctac					20

<210> SEQ ID NO 616
<211> LENGTH: 20

```
<212> TYPE: RNA
<213> ORGANISM: Artificial Sequence
<220> FEATURE:
<223> OTHER INFORMATION: Synthetic Construct

<400> SEQUENCE: 616
gtaccattgc cggctcccta                                           20

<210> SEQ ID NO 617
<211> LENGTH: 20
<212> TYPE: RNA
<213> ORGANISM: Artificial Sequence
<220> FEATURE:
<223> OTHER INFORMATION: Synthetic Construct

<400> SEQUENCE: 617
tggttccgta ggtcggtata                                           20

<210> SEQ ID NO 618
<211> LENGTH: 20
<212> TYPE: RNA
<213> ORGANISM: Artificial Sequence
<220> FEATURE:
<223> OTHER INFORMATION: Synthetic Construct

<400> SEQUENCE: 618
tctggcttga cacgaccgtt                                           20

<210> SEQ ID NO 619
<211> LENGTH: 20
<212> TYPE: RNA
<213> ORGANISM: Artificial Sequence
<220> FEATURE:
<223> OTHER INFORMATION: Synthetic Construct

<400> SEQUENCE: 619
cgctaggtcc ggtaagtgcg                                           20

<210> SEQ ID NO 620
<211> LENGTH: 20
<212> TYPE: RNA
<213> ORGANISM: Artificial Sequence
<220> FEATURE:
<223> OTHER INFORMATION: Synthetic Construct

<400> SEQUENCE: 620
agcacgtaat gtccgtggat                                           20

<210> SEQ ID NO 621
<211> LENGTH: 20
<212> TYPE: RNA
<213> ORGANISM: Artificial Sequence
<220> FEATURE:
<223> OTHER INFORMATION: Synthetic Construct

<400> SEQUENCE: 621
aaggcgcgcg aatgtggcag                                           20

<210> SEQ ID NO 622
<211> LENGTH: 20
<212> TYPE: RNA
<213> ORGANISM: Artificial Sequence
<220> FEATURE:
<223> OTHER INFORMATION: Synthetic Construct

<400> SEQUENCE: 622
```

```
actgcggagc gcccaatatc                                              20

<210> SEQ ID NO 623
<211> LENGTH: 20
<212> TYPE: RNA
<213> ORGANISM: Artificial Sequence
<220> FEATURE:
<223> OTHER INFORMATION: Synthetic Construct

<400> SEQUENCE: 623
cgtcgagtgc tcgaactcca                                              20

<210> SEQ ID NO 624
<211> LENGTH: 20
<212> TYPE: RNA
<213> ORGANISM: Artificial Sequence
<220> FEATURE:
<223> OTHER INFORMATION: Synthetic Construct

<400> SEQUENCE: 624
tcgcagcggc gtgggatcgg                                              20

<210> SEQ ID NO 625
<211> LENGTH: 20
<212> TYPE: RNA
<213> ORGANISM: Artificial Sequence
<220> FEATURE:
<223> OTHER INFORMATION: Synthetic Construct

<400> SEQUENCE: 625
atctgtccta attcggatcg                                              20

<210> SEQ ID NO 626
<211> LENGTH: 20
<212> TYPE: RNA
<213> ORGANISM: Artificial Sequence
<220> FEATURE:
<223> OTHER INFORMATION: Synthetic Construct

<400> SEQUENCE: 626
tgcggcgtaa tgcttgaaag                                              20

<210> SEQ ID NO 627
<211> LENGTH: 20
<212> TYPE: RNA
<213> ORGANISM: Artificial Sequence
<220> FEATURE:
<223> OTHER INFORMATION: Synthetic Construct

<400> SEQUENCE: 627
cgaacttaat cccgtggcaa                                              20

<210> SEQ ID NO 628
<211> LENGTH: 20
<212> TYPE: RNA
<213> ORGANISM: Artificial Sequence
<220> FEATURE:
<223> OTHER INFORMATION: Synthetic Construct

<400> SEQUENCE: 628
gccgtgttgc tggatacgcc                                              20

<210> SEQ ID NO 629
<211> LENGTH: 20
<212> TYPE: RNA
<213> ORGANISM: Artificial Sequence
```

```
<220> FEATURE:
<223> OTHER INFORMATION: Synthetic Construct

<400> SEQUENCE: 629
taccctccgg atacggactg                                               20

<210> SEQ ID NO 630
<211> LENGTH: 20
<212> TYPE: RNA
<213> ORGANISM: Artificial Sequence
<220> FEATURE:
<223> OTHER INFORMATION: Synthetic Construct

<400> SEQUENCE: 630
ccgttggact atggcgggtc                                               20

<210> SEQ ID NO 631
<211> LENGTH: 20
<212> TYPE: RNA
<213> ORGANISM: Artificial Sequence
<220> FEATURE:
<223> OTHER INFORMATION: Synthetic Construct

<400> SEQUENCE: 631
gtacggggcg atcatccaca                                               20

<210> SEQ ID NO 632
<211> LENGTH: 20
<212> TYPE: RNA
<213> ORGANISM: Artificial Sequence
<220> FEATURE:
<223> OTHER INFORMATION: Synthetic Construct

<400> SEQUENCE: 632
aagagtagta gacgcccggg                                               20

<210> SEQ ID NO 633
<211> LENGTH: 20
<212> TYPE: RNA
<213> ORGANISM: Artificial Sequence
<220> FEATURE:
<223> OTHER INFORMATION: Synthetic Construct

<400> SEQUENCE: 633
aagagcgaat cgatttcgtg                                               20

<210> SEQ ID NO 634
<211> LENGTH: 20
<212> TYPE: RNA
<213> ORGANISM: Artificial Sequence
<220> FEATURE:
<223> OTHER INFORMATION: Synthetic Construct

<400> SEQUENCE: 634
tcaacaccag tgcctgacgg                                               20

<210> SEQ ID NO 635
<211> LENGTH: 20
<212> TYPE: RNA
<213> ORGANISM: Artificial Sequence
<220> FEATURE:
<223> OTHER INFORMATION: Synthetic Construct

<400> SEQUENCE: 635
aaagtagctt cactctctcg                                               20
```

```
<210> SEQ ID NO 636
<211> LENGTH: 20
<212> TYPE: RNA
<213> ORGANISM: Artificial Sequence
<220> FEATURE:
<223> OTHER INFORMATION: Synthetic Construct

<400> SEQUENCE: 636
gagccaacca atagatgtcc                                               20

<210> SEQ ID NO 637
<211> LENGTH: 20
<212> TYPE: RNA
<213> ORGANISM: Artificial Sequence
<220> FEATURE:
<223> OTHER INFORMATION: Synthetic Construct

<400> SEQUENCE: 637
gcgccgccat gaacctagag                                               20

<210> SEQ ID NO 638
<211> LENGTH: 20
<212> TYPE: RNA
<213> ORGANISM: Artificial Sequence
<220> FEATURE:
<223> OTHER INFORMATION: Synthetic Construct

<400> SEQUENCE: 638
acaaaggttg gaacagaacc                                               20

<210> SEQ ID NO 639
<211> LENGTH: 20
<212> TYPE: RNA
<213> ORGANISM: Artificial Sequence
<220> FEATURE:
<223> OTHER INFORMATION: Synthetic Construct

<400> SEQUENCE: 639
ggtgaccggg ttattgatgt                                               20

<210> SEQ ID NO 640
<211> LENGTH: 20
<212> TYPE: RNA
<213> ORGANISM: Artificial Sequence
<220> FEATURE:
<223> OTHER INFORMATION: Synthetic Construct

<400> SEQUENCE: 640
ttagtggagg actacagagc                                               20

<210> SEQ ID NO 641
<211> LENGTH: 20
<212> TYPE: RNA
<213> ORGANISM: Artificial Sequence
<220> FEATURE:
<223> OTHER INFORMATION: Synthetic Construct

<400> SEQUENCE: 641
acatatagcc cgtaaagctg                                               20

<210> SEQ ID NO 642
<211> LENGTH: 20
<212> TYPE: RNA
<213> ORGANISM: Artificial Sequence
<220> FEATURE:
<223> OTHER INFORMATION: Synthetic Construct
```

<400> SEQUENCE: 642
cgttggcgat gatctccacg					20

<210> SEQ ID NO 643
<211> LENGTH: 20
<212> TYPE: RNA
<213> ORGANISM: Artificial Sequence
<220> FEATURE:
<223> OTHER INFORMATION: Synthetic Construct

<400> SEQUENCE: 643
tggccttttc tacctcgcgc					20

<210> SEQ ID NO 644
<211> LENGTH: 20
<212> TYPE: RNA
<213> ORGANISM: Artificial Sequence
<220> FEATURE:
<223> OTHER INFORMATION: Synthetic Construct

<400> SEQUENCE: 644
aatggagata ctcatctggg					20

<210> SEQ ID NO 645
<211> LENGTH: 20
<212> TYPE: RNA
<213> ORGANISM: Artificial Sequence
<220> FEATURE:
<223> OTHER INFORMATION: Synthetic Construct

<400> SEQUENCE: 645
gaagcccgtc cagaaagtgt					20

<210> SEQ ID NO 646
<211> LENGTH: 20
<212> TYPE: RNA
<213> ORGANISM: Artificial Sequence
<220> FEATURE:
<223> OTHER INFORMATION: Synthetic Construct

<400> SEQUENCE: 646
caatctgagg aactccacga					20

<210> SEQ ID NO 647
<211> LENGTH: 20
<212> TYPE: RNA
<213> ORGANISM: Artificial Sequence
<220> FEATURE:
<223> OTHER INFORMATION: Synthetic Construct

<400> SEQUENCE: 647
aggctgcggc gcccacgaga					20

<210> SEQ ID NO 648
<211> LENGTH: 20
<212> TYPE: RNA
<213> ORGANISM: Artificial Sequence
<220> FEATURE:
<223> OTHER INFORMATION: Synthetic Construct

<400> SEQUENCE: 648
actttgacca ggccttgcta					20

<210> SEQ ID NO 649

```
<211> LENGTH: 20
<212> TYPE: RNA
<213> ORGANISM: Artificial Sequence
<220> FEATURE:
<223> OTHER INFORMATION: Synthetic Construct

<400> SEQUENCE: 649
accttccata actgccacgc                                                   20

<210> SEQ ID NO 650
<211> LENGTH: 20
<212> TYPE: RNA
<213> ORGANISM: Artificial Sequence
<220> FEATURE:
<223> OTHER INFORMATION: Synthetic Construct

<400> SEQUENCE: 650
cgaggcgtac atacccaagg                                                   20

<210> SEQ ID NO 651
<211> LENGTH: 20
<212> TYPE: RNA
<213> ORGANISM: Artificial Sequence
<220> FEATURE:
<223> OTHER INFORMATION: Synthetic Construct

<400> SEQUENCE: 651
atggtacggc caaatcaaga                                                   20

<210> SEQ ID NO 652
<211> LENGTH: 20
<212> TYPE: RNA
<213> ORGANISM: Artificial Sequence
<220> FEATURE:
<223> OTHER INFORMATION: Synthetic Construct

<400> SEQUENCE: 652
tcttgtaatc ccatacgcgt                                                   20

<210> SEQ ID NO 653
<211> LENGTH: 20
<212> TYPE: RNA
<213> ORGANISM: Artificial Sequence
<220> FEATURE:
<223> OTHER INFORMATION: Synthetic Construct

<400> SEQUENCE: 653
attcacagga cacagagaat                                                   20

<210> SEQ ID NO 654
<211> LENGTH: 20
<212> TYPE: RNA
<213> ORGANISM: Artificial Sequence
<220> FEATURE:
<223> OTHER INFORMATION: Synthetic Construct

<400> SEQUENCE: 654
ccagggctcc atcctcaaga                                                   20

<210> SEQ ID NO 655
<211> LENGTH: 20
<212> TYPE: RNA
<213> ORGANISM: Artificial Sequence
<220> FEATURE:
<223> OTHER INFORMATION: Synthetic Construct

<400> SEQUENCE: 655
```

```
tgagctgcac caaagagacg                                                  20

<210> SEQ ID NO 656
<211> LENGTH: 20
<212> TYPE: RNA
<213> ORGANISM: Artificial Sequence
<220> FEATURE:
<223> OTHER INFORMATION: Synthetic Construct

<400> SEQUENCE: 656
atgtctgcag atgtacccct                                                  20

<210> SEQ ID NO 657
<211> LENGTH: 20
<212> TYPE: RNA
<213> ORGANISM: Artificial Sequence
<220> FEATURE:
<223> OTHER INFORMATION: Synthetic Construct

<400> SEQUENCE: 657
cgaagataac gcggatacct                                                  20

<210> SEQ ID NO 658
<211> LENGTH: 20
<212> TYPE: RNA
<213> ORGANISM: Artificial Sequence
<220> FEATURE:
<223> OTHER INFORMATION: Synthetic Construct

<400> SEQUENCE: 658
gctgcaggcc gagtacaccg                                                  20

<210> SEQ ID NO 659
<211> LENGTH: 20
<212> TYPE: RNA
<213> ORGANISM: Artificial Sequence
<220> FEATURE:
<223> OTHER INFORMATION: Synthetic Construct

<400> SEQUENCE: 659
acaagtggga ggcttacctg                                                  20

<210> SEQ ID NO 660
<211> LENGTH: 20
<212> TYPE: RNA
<213> ORGANISM: Artificial Sequence
<220> FEATURE:
<223> OTHER INFORMATION: Synthetic Construct

<400> SEQUENCE: 660
gcagcgtaca gggatgatca                                                  20

<210> SEQ ID NO 661
<211> LENGTH: 20
<212> TYPE: RNA
<213> ORGANISM: Artificial Sequence
<220> FEATURE:
<223> OTHER INFORMATION: Synthetic Construct

<400> SEQUENCE: 661
gcagtagcgc ttcaggccca                                                  20

<210> SEQ ID NO 662
<211> LENGTH: 20
<212> TYPE: RNA
```

<213> ORGANISM: Artificial Sequence
<220> FEATURE:
<223> OTHER INFORMATION: Synthetic Construct

<400> SEQUENCE: 662
caaatggtgg ggtaacagaa                                               20

<210> SEQ ID NO 663
<211> LENGTH: 20
<212> TYPE: RNA
<213> ORGANISM: Artificial Sequence
<220> FEATURE:
<223> OTHER INFORMATION: Synthetic Construct

<400> SEQUENCE: 663
gaaaggaact ggctaccgtt                                               20

<210> SEQ ID NO 664
<211> LENGTH: 20
<212> TYPE: RNA
<213> ORGANISM: Artificial Sequence
<220> FEATURE:
<223> OTHER INFORMATION: Synthetic Construct

<400> SEQUENCE: 664
agggcttccg ttacaagatg                                               20

<210> SEQ ID NO 665
<211> LENGTH: 20
<212> TYPE: RNA
<213> ORGANISM: Artificial Sequence
<220> FEATURE:
<223> OTHER INFORMATION: Synthetic Construct

<400> SEQUENCE: 665
gaacaagcaa cacctaaaag                                               20

<210> SEQ ID NO 666
<211> LENGTH: 20
<212> TYPE: RNA
<213> ORGANISM: Artificial Sequence
<220> FEATURE:
<223> OTHER INFORMATION: Synthetic Construct

<400> SEQUENCE: 666
tgaggagaag gaacggctca                                               20

<210> SEQ ID NO 667
<211> LENGTH: 20
<212> TYPE: RNA
<213> ORGANISM: Artificial Sequence
<220> FEATURE:
<223> OTHER INFORMATION: Synthetic Construct

<400> SEQUENCE: 667
ggaagaatgc agagtataag                                               20

<210> SEQ ID NO 668
<211> LENGTH: 20
<212> TYPE: RNA
<213> ORGANISM: Artificial Sequence
<220> FEATURE:
<223> OTHER INFORMATION: Synthetic Construct

<400> SEQUENCE: 668
ggaatttgag gaactcctga                                               20

<210> SEQ ID NO 669
<211> LENGTH: 20
<212> TYPE: RNA
<213> ORGANISM: Artificial Sequence
<220> FEATURE:
<223> OTHER INFORMATION: Synthetic Construct

<400> SEQUENCE: 669
gctcaccggc catccaggaa     20

<210> SEQ ID NO 670
<211> LENGTH: 20
<212> TYPE: RNA
<213> ORGANISM: Artificial Sequence
<220> FEATURE:
<223> OTHER INFORMATION: Synthetic Construct

<400> SEQUENCE: 670
actggccagg aacgatgcga     20

<210> SEQ ID NO 671
<211> LENGTH: 20
<212> TYPE: RNA
<213> ORGANISM: Artificial Sequence
<220> FEATURE:
<223> OTHER INFORMATION: Synthetic Construct

<400> SEQUENCE: 671
gcagctccaa gatcttccca     20

<210> SEQ ID NO 672
<211> LENGTH: 20
<212> TYPE: RNA
<213> ORGANISM: Artificial Sequence
<220> FEATURE:
<223> OTHER INFORMATION: Synthetic Construct

<400> SEQUENCE: 672
gaatgagtac acagaacgga     20

<210> SEQ ID NO 673
<211> LENGTH: 20
<212> TYPE: RNA
<213> ORGANISM: Artificial Sequence
<220> FEATURE:
<223> OTHER INFORMATION: Synthetic Construct

<400> SEQUENCE: 673
ggagcaggac aaggtcgggg     20